(12) United States Patent
Lee et al.

(10) Patent No.: US 7,459,532 B2
(45) Date of Patent: Dec. 2, 2008

(54) VARIANTS OF THE TRP CHANNEL FAMILY MEMBER, LTRPC3G

(75) Inventors: Ning Lee, Belle Mead, NJ (US); Jian Chen, Princeton, NJ (US); Shujian Wu, Langhorne, PA (US); Michael A. Blanar, Malvern, PA (US); Paul C. Levesque, Yardley, PA (US); Lucy Sun, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/985,981

(22) Filed: Nov. 19, 2007

(65) Prior Publication Data

US 2008/0118952 A1     May 22, 2008

Related U.S. Application Data

(62) Division of application No. 10/842,313, filed on May 10, 2004, now Pat. No. 7,344,882.

(60) Provisional application No. 60/469,894, filed on May 12, 2003.

(51) Int. Cl.
*C07K 14/435* (2006.01)
*C07K 14/705* (2006.01)
*C12P 21/02* (2006.01)
*A61K 38/17* (2006.01)

(52) U.S. Cl. .............................. 530/350; 514/2; 514/12; 536/23.5; 435/69.1

(58) Field of Classification Search ....................... None
See application file for complete search history.

(56) References Cited

U.S. PATENT DOCUMENTS

2003/0162189 A1    8/2003   Lee et al.
2003/0224450 A1   12/2003   Lee et al.
2003/0232339 A1*  12/2003   Shu et al. ....................... 435/6

FOREIGN PATENT DOCUMENTS

WO   WO01/32870   A1   5/2001
WO   WO02/46415   A2   6/2002
WO   WO02/077237  A2  10/2002
WO   WO03/012063  A2   2/2003

OTHER PUBLICATIONS

Qiu, et al., "Interaction Interface of Human Flap Endonuclease-1 with Its DNA Substrates", J. Biol. Chem., vol. 279 (23), pp. 24394-24402 (2004).
Altschul, et al., "Gapped Blast and PSI-Blast: a new generation of protein database search programs", Nucleic Acids Res., vol. 25 (17), pp. 3389-3402 (1997).
Blackshaw, et al., "Genomic Analysis of Mouse Retinal Development", PLOS Biology, vol. 2(9), pp. 1411-1431 (2004).
Carninci, et al., "[2] High-Efficiency Full-Length cDNA Cloning", Methods Enzy., vol. 303, pp. 19-44 (1999).
Carninci, et al., "Normalization and Subtraction of Cap-Trapper-Selected cDNAs to Prepare Full-Length cDNA Libraries for Rapid Discovery of New Genes", Genome Res., vol. 10, pp. 1617-1630 (2000).
Caterina, et al., "Impaired Nociception and Pain Sensation in Mice Lacking the Capsaicin Receptor", Science, vol. 288, pp. 306-313 (2000).
Caterina, et al., "A Capsaicin-Receptor Homologue with a High Threshold for Noxious Heat", Nature, vol. 398, pp. 436-441 (1999).
Dambach, et al., "Role of CCR2 in Macrophage Migration Into the Liver During Acetaminophen-Induced Hepatotoxicity in the Mouse" Hepatology, vol. 35, pp. 1093-1103 (2002).
Duncan, et al., "Down-Regulation of the Novel Gene Melastatin Correlates with Potential for Melanoma Metastasis", Cancer Research, vol. 58, pp. 1515-1520 (1998).
Eddy, Sean R., "Profile Hidden Markov Models", Bioinformatics Review, vol. 14(9), pp. 755-763 (1998).
Freichel, et al., "Lack of an Endothelial Store-Operated $Ca^{2+}$ Current Impairs Agonist-Dependent Vasorelaxation in TRP4-/- Mice", Nature Cell Biol., vol. 3, pp. 121-127 (2001).
Friedman, et al., "Cellular Calcium Transport in Renal Epithelia: Measurement, Mechanisms, and Regulation", Physiological Rev., vol. 75(3), pp. 429-471 (1995).
Grimm, et al., "Activation of the Melastatin-Related Cation Channel TRPM3 by D-*erythro*-Sphingosine", Molecular Pharm., vol. 67 (3), pp. 798-805 (2005).
Grimm, et al., "Molecular and Functional Characterization of the Melastatin-related Cation Channel TRPM3", JBC, vol. 278 (24), pp. 21493-21501 (2003).
Guo, et al., "Identification and Characterization of a Novel Polycystin Family Member, Polycystin-L2, in Mouse and Human: Sequence Expression, Alternative Splicing, and Chromosomal Localization", Genomics, vol. 64, pp. 241-251 (2000).

(Continued)

*Primary Examiner*—Christine J Saoud
*Assistant Examiner*—Jon M Lockard
(74) *Attorney, Agent, or Firm*—Stephen C. D'Amico

(57) ABSTRACT

The present invention provides novel polynucleotides encoding LTRPC3g, LTRPC3h, LTRPC3i, LTRPC3j, LTRPC3k, or LTRPC3l polypeptides, fragments and homologues thereof. Also provided are vectors, host cells, antibodies, and recombinant and synthetic methods for producing said polypeptides. The invention further relates to diagnostic and therapeutic methods for applying these novel LTRPC3g, LTRPC3h, LTRPC3i, LTRPC3j, LTRPC3k, or LTRPC3l polypeptides to the diagnosis, treatment, and/or prevention of various diseases and/or disorders related to these polypeptides. The invention further relates to screening methods for identifying agonists and antagonists of the polynucleotides and polypeptides of the present invention.

Figure 8:
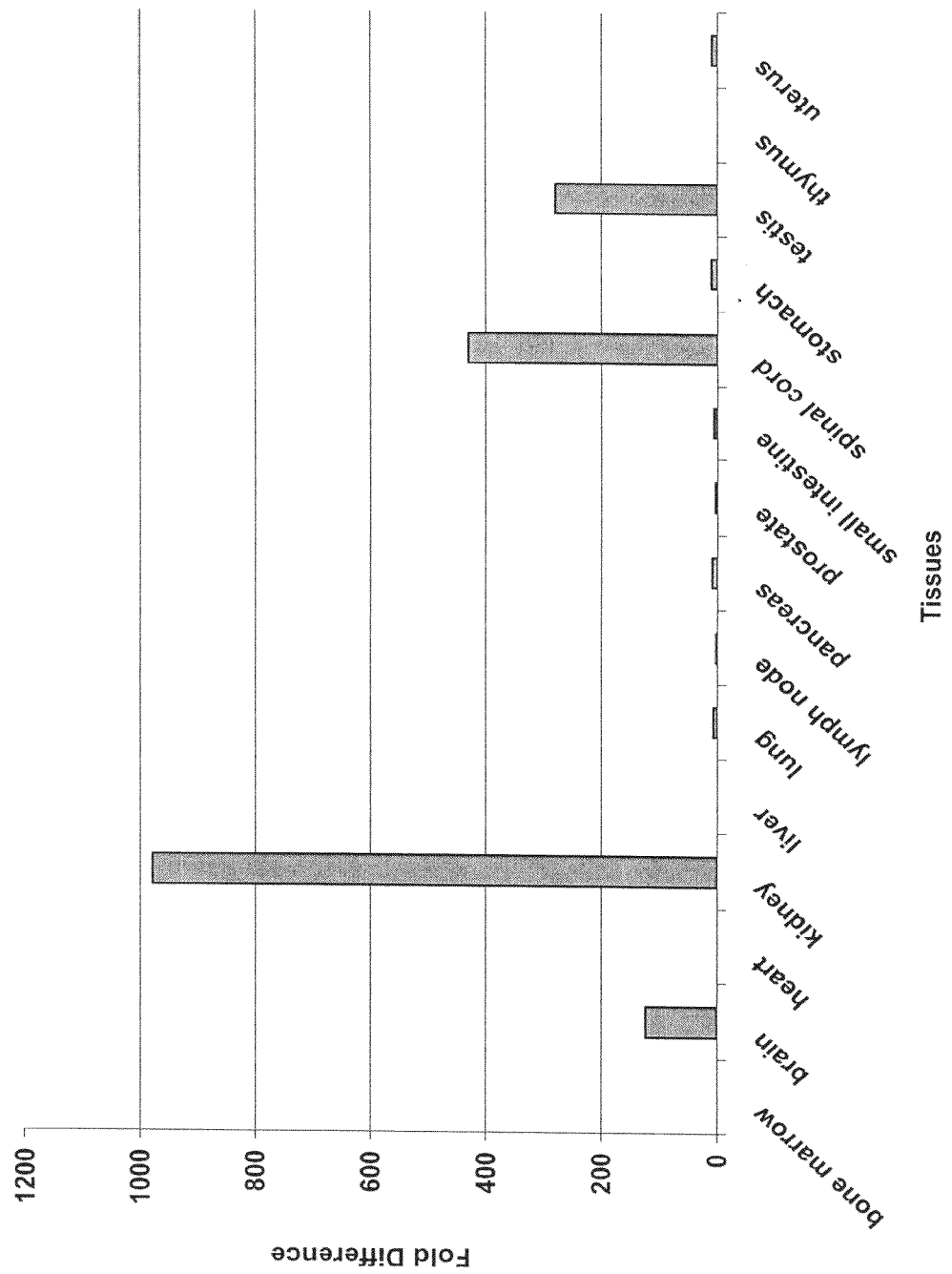

11 Claims, 63 Drawing Sheets
(2 of 63 Drawing Sheet(s) Filed in Color)

OTHER PUBLICATIONS

Hara, et al., "LTRPC2 $Ca^{2+}$-Permeable Channel Activated by Changes in Redox Status Confers Susceptibility to Cell Death", Molecular Cell., vol. 9, pp. 163-173 (2002).

Hardie, et al. "The trp Gene Is Essential for a Light-Activated $Ca^{2+}$ Channel in Drosophilia Photoreceptors", Neuron, vol. 8, pp. 643-651 (1992).

Harteneck, et al., "From worm to man: three subfamilies of TRP channels", TINS, vol. 23 (4), pp. 159-166 (2000).

Henikoff, et al., "Amino Acid Substitution Matrices From Protein Blocks", PNAS, vol. 89, pp. 10915-10919 (1992).

Henricksen, et al., "Inhibition of Flap Endonuclease 1 by Flap Secondary Structure and Relevance to Repeat Sequence Expansion", JBC, vol. 275 (22), pp. 16420-16427 (2000).

Heymann, et al., "Conformations of the rhodopsin third cytoplasmic loop grafted onto bacteriorhodopsin", Structure, vol. 8(6), pp. 643-653 (2000).

Hoenderop, et al., "Molecular Mechanism of Active $Ca^{2+}$ Reabsorption in the Distal Nephron", Annu. Rev. Physiol., vol. 64, pp. 529-549 (2002).

Hoenderop, et al., "Molecular Identification of the Apical $Ca^{2+}$ Channel in 1,25-Dihydroxyvitamin $D_3$-responsive Epithelia", J. Biol. Chem., vol. 274(13), pp. 8375-8378 (1999).

Hunter, et al., "Chromosomal Localization and Genomic Characterization of the Mouse Melastatin Gene (Mlsn1)", Genomics, vol. 54, pp. 116-123 (1998).

Inoue, et al., "The Transient Receptor Potential Protein Homologue TRP6 is the Essential Component of Vascular $α_1$-Adrenoceptor-Activated $Ca^{2+}$-Permeable Cation Channel", Circ. Res., vol. 88, pp. 325-332 (2001).

Jin, et al., "The 3'→5' Exonuclease of DNA Polymerase δ Can Substitute for the 5' Flap Endonuclease Rad27/Fen1 in Processing Okazaki Fragments and Preventing Genome Instability", PNAS, vol. 98(9), pp. 5122-5127 (2001).

Riken Genome Exploration Res. Group, "Functional annotation of a full-length mouse cDNA collection", Nature, vol. 409, pp. 685-690 (2001).

Koticha, et al., "Plasma Membrane Targeting of SNAP-25 Increases its Local Concentration and is Necessary for SNARE Complex Formation and Regulated Exocytosis", J. Cell Science, vol. 115, pp. 3341-3351 (2002).

Launay, et al., "TRPM4 Is a $Ca^{2+}$-Activated Nonselective Cation Channel Mediating Cell Membrane Depolarization", Cell. vol. 109, pp. 397-407 (2002).

Lee, et al., "Expression and Characterization of Human Transient Receptor Potential Melastatin 3 (hTRPM3)", J. Biol. Chem., vol. 278(23), pp. 20890-20897 (2003).

Liman, et al.,"TRP2: A Candidate Transduction Channel for Mammalian Pheromone Sensory Signaling", PNAS, vol. 96, pp. 5791-5796 (1999).

Ma, et al., "Single Nucleotide Polymorphism Analyses of the Human Proliferating Cell Nuclear Antigen (PCNA) and Flap Endonuclease (FEN1) Genes", Int. J. Cancer, vol. 88, pp. 938-942 (2000).

Ma, et al., "Protein Kinase C Activates Store-Operated $Ca^{2+}$ Channels in Human Glomerular Mesangial Cells", J. Biol. Chem., vol. 276(28), pp. 25759-25765 (2001).

Matsumura, et al, "Single Solitary Metastasis of the Slowly Progressive Type of Renal Cell Carcinoma to the Choroid Plexus", Neurol. Med. Chir., vol. 37, pp. 916-919 (1997).

McKemy, et al., "Identification of a cold receptor reveals a general role for TRP channels in thermosensation", Nature, vol. 416, pp. 52-58 (2002).

Missiaen, et al., "Abnormal Intracellular $Ca^{2+}$ Homeostasis and Disease", Cell Calcium, vol. 28(1), pp. 1-21 (2000).

Montell, et al., "A Unified Nomenclature for the Superfamily of TRP Cation Channels", Molec. Cell, vol. 9, pp. 229-231 (2002).

Nadler, et al., "LTRPC7 is a Mg-ATP- regulated divalent cation channel required for cell viability", Nature, vol. 411, pp. 590-595 (2001).

Nagamine, et al., "Molecular Cloning of a Novel Putative $Ca^{2+}$ Channel Protein (TRPC7) Highly Expressed in Brain", Genomics, vol. 54, pp. 124-131 (1988).

Nagase, et al., "Prediction of the Coding Sequences of Unidentified Human Genes. XVIII. The Complete Sequences of 100 New cDNA Clones from Brain Which Code for Large Proteins in vitro", DNA Res., vol. 7, pp. 273-281 (2000).

Negritto, et al., "Novel Function of Rad27 (FEN-1) in Restricting Short-Sequence Recombination", Molecular and Cellular Biology, vol. 21, (7), pp. 2349-2358 (2001).

Oberwinkler, et al., "Alternative Splicing Switches the Divalent Cation Selectivity of TRPM3 Channels", J. Biol. Chem., vol. 280(23), pp. 22540-22548 (2005).

Okada, et al., "Molecular and Functional Characterization of a Novel Mouse Transient Receptor Potential Protein Homologue TRP7", J. Biol. Chem., vol. 274(39), pp. 27359-27270 (1999).

Okazaki, et al., "Prediction of the Coding Sequences of Mouse Homologues of KIAA Gene: IV. The Complete Nucleotide Sequences of 500 Mouse KIAA-Homologous cDNAs Identified by Screening of Terminal Sequences of cDNA Clones Randomly Sampled from Size-Fractionated Libraries", DNA Res., vol. 11, pp. 205-218 (2004).

Okazaki, et al., "Analysis of the mouse transcriptome based on functional annotation of 60,700 full-length cDNAs", Nature, vol. 420, pp. 563-573 (2002).

Peier, et al., "A TRP Channel that Senses Cold Stimuli and Menthol", Cell, vol. 108, pp. 705-715 (2002).

Peng, et al., "Molecular Cloning and Characterization of a Channel-like Transporter Mediating Intestinal Calcium Absorption", JBC, vol. 274(32), pp. 22739-22746 (1999).

Perraud, et al., "ADP-ribose gating of the calcium-permeable LTRPC2 channel revealed by Nudix motif homology", Nature, vol. 411, pp. 595-599 (2001).

Philipp, et al., "A novel capacitative calcium entry channel expressed in excitable cells", EMBO J., vol. 17(15), pp. 4274-4282 (1998).

Prasad, et al., "FEN1 Stimulation of DNA Polymerase β Mediates an Excision Step in Mammalian Long Patch Base Excision Repair", The Journal of Biological Chemistry, vol. 275, No. 6, pp. 4460-4466 (2000).

Prawitt, et al., "Identification and Characterization of MTR1, a Novel Gene with Homology to Melastatin (MLSN1) and the TRP Gene Family Located in the BWS-WT2 Critical Region on Chromosome 11p15.5 and Showing Allele-Specific Expression", Hum. Molec. Genetics, vol. 9(2), pp. 203-216 (2000).

Radu, et al., "The Peptide Repeat Domain of Nucleoporin Nup98 Functions as a Docking Site in Transport across the Nuclear Pore Complex", Cell, vol. 81, pp. 215-222 (1995).

Runnels, et al., "TRP-PLIK, a Bifunctional Protein with Kinase and Ion Channel Activities", Science, vol. 291, pp. 1043-1047 (2001).

Runnels, et al., "The TRPM7 channel is inactivated by $PIP_2$ hydrolysis", Nature Cell Biol., vol. 4, pp. 329-336 (2002).

Ryazanov, et al., "Alpha-Kinases: a New Class of Protein Kinases with a Novel Catalytic Domain", Curr. Biol., vol. 9(2), R43-R45 (1999).

Sano, et al., "Immunocyte $Ca^{2+}$ Influx System Mediated by LTRPC2", Science, vol. 293, pp. 1327-1330 (2001).

Schlingmann, et al., "Hypomagnesemia with Secondary Hypocalcemia is caused by Mutations in TRPM6, a new member of the TRPM Gene Family", Nature Genetics, vol. 31, pp. 166-170 (2002).

Shibata, et al., "Riken Integrated Sequence Analysis (RISA) Systme-384-Format Sequencing Pipeline with 384 Multicapillary Sequencer", Genome Res., vol. 10, pp. 1757-1771 (2000).

Silve, et al., "The Immunosuppressant SR 31747 Blocks Cell Proliferation by Inhibiting a Steroid Isomerase in *Saccharomyces cerevisiae*", Molecular Cell Biol., vol. 16(6), pp. 2719-2727 (1996).

Strotmann, et al., "OTRPC4, a Nonselective Cation Channel that Confers Sensitivity to Extracellular Osmolarity", Nature Cell Biol., vol. 2, pp. 695-702 (2000).

Stucki, et al., "In Eukaryotic Flap Endonuclease 1, the C Terminus Is Essential for Substrate Binding", The Journal of Biological Chemistry, vol. 276, No. 11, pp. 7843-7849 (2001).

Tishkoff, et al., "A Novel Mutation Avoidance Mechanism Dependent on *S. cerevisiae RAD27* is Distinct from DNA Mismatch Repair", Cell, vol. 88, pp. 253-263 (1997).

Tom, et al., "Mechanism Whereby Proliferating Cell Nuclear Antigen Stimulates Flap Endonuclease 1", The Journal of Biological Chemistry, vol. 275(14), pp. 10498-10505 (2000).

Tsavaler, et al., "Trp-p8, a Novel Prostate -specific Gene, Is Up-Regulated in Prostate Cancer and Other Malignancies and Shares High Homology with Transient Receptor Potential Calcium Channel Proteins", Cancer Research, vol. 61, pp. 3760-3769 (2001).

Umar, et al., "DNA-Replication Fidelity, Mismatch Repair and Genome Instability in Cancer Cells", Eur. J. Biochem., vol. 238, pp. 297-307 (1996).

Walder, et al., "Familial hypomagnesemia Maps to Chromosome 9q, no to the X Chromosome: Genetic Linkage Mapping and Analysis of a balanced Translocation Breakpoint", Hum. Molec. Genetics, vol. 6(9), pp. 1491-1497 (1997).

Walder, et al., "Mutatin of TRPM6 Causes Familial Hypomagnesemia with Secondary Hypocalcemia", Nature Genetics, vol. 31, pp. 171-174 (2002).

Walker, et al., "A Drosophila Mechanosensory Transduction Channel", Science, vol. 287, pp. 2229-2234 (2000).

Warbrick, et al., "FEN1 Expression: A Novel Marker for Cell Proliferation", J. of Pathology, vol. 186, pp. 319-324 (1998).

Wes, et al., "TRPC1, a Human Homolog of a Drosophila Store-Operated Channel", PNAS, vol. 92, pp. 9652-9656 (1995).

Wiemann, et al., "Toward a Catalog of Human Genes and Proteins: Sequencing and Analysis of 500 Novel Complete Protein Coding Human cDNAs", Genome Res., vol. 11, pp. 422-435 (2001).

Wissenbach, et al., "Trp12, a Novel Trp Related Protein from Kidney", FEBS Ltrs, vol. 485, pp. 127-134 (2000).

Wissenbach, et al., Structure and mRNA Expression of a Bovine TRP Homologue Related to Mammalian TRP2 Transcripts, FEBS Ltrs., vol. 429, pp. 61-66 (1998).

Wistow, et al., "Expressed Sequence Tag Analysis of Adult Human Iris for the NEIBank Project: Steroid-response Factors and Similarities with Retinal Pigment Epithelium", Molec. Vision, vol. 8, pp. 185-195 (2002).

Xu, et al., "Regulation of Melastatin, a TRP-Related Protein, through Interaction with a Cystoplasmic Isoform", PNAS, vol. 98(19), pp. 10692-10697 (2001).

Yu, et al., "Mink-Related Peptide 1—A β Subunit for the HCN Ion Channel Subunit Family Enhances Expression and Speeds Activation", Circ. Res., vol. 88, pp. e84-e87 (2001).

Yue, et al., "CaT1 Manifests the Pore Properties of the Calcium-Release-Activated Calcium Channel", Nature, vol. 410, pp. 705-709 (2001).

Zhu, et al., "Molecular Cloning of a Widely Expressed Human Homologue for the Drosophila TRP Gene", FEBS Ltrs, vol. 373, pp. 193-198 (1995).

Zygmunt, et al., "Vanilloid Receptors on Sensory Nerves Mediate the Vasodilator Action of Anandamide", Nature, vol. 400, pp. 452-457 (1999).

NCBI Entrez Accession No. AAB50622 (gi:1911245), H. Sakura, Mar. 27, 1997.

NCBI Entrez Accession No. AAC80000 (gi:3243075), Hunter, et al., Nov. 25, 1998.

NCBI Entrez Accession No. AAD10167 (gi:4200415), Zhu, et al., Jan. 28, 1999.

NCBI Entrez Accession No. AAD17196 (gi:4324940), Vannier, et al., Mar. 15, 1999.

NCBI Entrez Accession No. AAF01468 (gi:6014703), Mori, et al., Oct. 7, 1999.

NCBI Entrez Accession No. AAF02200 (gi:6048344), Zhu, et al., Oct. 16, 1999.

NCBI Entrez Accession No. AAO49154 (gi:28626249), Lee, et al., Jun. 3, 2003.

NCBI Entrez Accession No. AJ505026 (gi:30141362), Grimm, et al., Apr. 15, 2005.

NCBI Entrez Accession No. AJ544532 (gi:59889893), Oberwinkler, et al., Jun. 9, 2005.

NCBI Entrez Accession No. AJ544533 (gi:59889895), Oberwinkler, et al., Jun. 9, 2005.

NCBI Entrez Accession No. AJ544534 (gi:59889897), Oberwinkler, et al., Jun. 9, 2005.

NCBI Entrez Accession No. AJ544536 (gi:59889901), Oberwinkler, et al., Jun. 9, 2005.

NCBI Entrez Accession No. AL136545 (gi:12052727), Poustka, et al., Jan. 20, 2005.

NCBI Entrez Accession No. AL358786 (gi:13990071), G. Laird, May 18, 2005.

NCBI Entrez Accession No. BAC31929 (gi:26336493), Carninci, et al., Oct. 4, 2006.

NCBI Entrez Accession No. BAC55102 (gi:27597205), Okabayashi, et al., Jan. 10, 2003.

NCBI Entrez Accession No. CAC14420 (gi:11065673), J.E. Sulston., Oct. 24, 2006.

NCBI Entrez Accession No. CAD43604 (gi:54632969), Harteneck, et al., Apr. 15, 2005.

NCBI Entrez Accession No. CAD67492 (gi:59889894), Oberwinkler, et al., Jun. 9, 2005.

NCBI Entrez Accession No. CAD67493 (gi:59889896), Oberwinkler, et al., Jun. 9, 2005.

NCBI Entrez Accession No. CAD67494 (gi:59889898), Oberwinkler, et al., Jun. 9, 2005.

NCBI Entrez Accession No. CAD67495 (gi:59889900), Oberwinkler, et al., Jun. 9, 2005.

NCBI Entrez Accession No. CAD67496 (gi:59889902), Oberwinkler, et al., Jun. 9, 2005.

NCBI Entrez Accession No. NP_001030316 (gi:78214526), Oberwinkler, et al., Oct. 23, 2006.

NCBI Entrez Accession No. NP_001030317 (gi:78214528), Oberwinkler, et al., Oct. 23, 2006.

NCBI Entrez Accession No. NP_001030318 (gi:78214530), Oberwinkler, et al., Oct. 23, 2006.

NCBI Entrez Accession No. NP_001030320 (gi:78214534), Oberwinkler, et al., Aug. 24, 2006.

NCBI Entrez Accession No. NM_020952 (gi:55953088)* Oberwinkler, et al., Oct. 15, 2006.

NCBI Entrez Accession No. NT_008306 (gi:14740344), NCBI Annotation Project, Jul. 16, 2001.

NCBI Entrez Accession No. NP_066003 (gi:55953089), Oberwinkler, et al., Oct. 15, 2006.

NCBI Entrez Accession No. NP_113747 (gi:13928756), Le, et al., Apr. 20, 2006.

NCBI Entrez Accession No. NP_796315 (gi:54144620), Oberwinkler, et al., Oct. 23, 2006.

NCBI Entrez Accession No. NP_996827 (gi:55953091), Oberwinkler, et al., Oct. 15, 2006.

NCBI Entrez Accession No. AAC06146 (gi:2979524), Boulay, et al., Mar. 20, 1998.

NCBI Entrez Accession No. AAD42069 (gi:5326854), Okada, et al., Sep. 21, 1999.

NCBI Entrez Accession No. BAD32496 (gi:50511021), Okazaki, et al., Mar. 1, 2005.

* cited by examiner

FIG. 1A

```
  1  CGCCCGCGGCGAGGAGCCAGCGAGAGCGCTCGGCGCTGGGCTGTTTCCCGGCCGAGGGAG    60

61  GCGAACTTCTCATGGGGAAGAAGTGGAGGGATGCGGCGGAAATGGAGCGGGGCTGCTCCG   120
  1              M  G  K  K  W  R  D  A  A  E  M  E  R  G  C  S  D    17

121  ACCGCGAGGACAACGCGGAGAGCCGCAGACGCAGCCGGAGCGCCAGCCGGGGCAGGTTTG   180
 18   R  E  D  N  A  E  S  R  R  R  S  R  S  A  S  R  G  R  F  A    37

181  CCGAGTCGTGGAAAAGGTTAAGTTCCAAGCAGGGGTCCACCAAACGCTCGGGACTCCCGT   240
 38   E  S  W  K  R  L  S  S  K  Q  G  S  T  K  R  S  G  L  P  S    57

241  CGCAGCAGACGCCGGCTCAGAAATCCTGGATAGAAGAGCATTTTATAAAGAGAATGTG    300
 58   Q  Q  T  P  A  Q  K  S  W  I  E  R  A  F  Y  K  R  E  C  V    77

301  TCCACATCATACCCAGCACCAAAGACCCCCATAGGTGTTGCTGTGGGCGTCTGATAGGCC   360
 78   H  I  I  P  S  T  K  D  P  H  R  C  C  C  G  R  L  I  G  Q    97

361  AGCATGTTGGCCTCACCCCCAGTATCTCCGTGCTTCAGAATGAGAAAAATGAAAGTCGCC   420
 98   H  V  G  L  T  P  S  I  S  V  L  Q  N  E  K  N  E  S  R  L   117

421  TCTCCCGAAATGACATCCAGTCTGAAAAGTGGTCCATCAGCAAACACACTCAACTCAGCC   480
118   S  R  N  D  I  Q  S  E  K  W  S  I  S  K  H  T  Q  L  S  P   137

481  CTACGGATGCTTTTGGGACCATTGAGTTCCAAGGAGGTGGCCATTCCAACAAAGCCATGT   540
138   T  D  A  F  G  T  I  E  F  Q  G  G  G  H  S  N  K  A  M  Y   157

541  ATGTGCGAGTATCTTTTGATACAAAACCTGATCTCCTCTTACACCTGATGACCAAGGAAT   600
158   V  R  V  S  F  D  T  K  P  D  L  L  H  L  M  T  K  E  W   177

601  GGCAGTTGGAGCTTCCCAAGCTTCTCATCTCTGTCCATGGGGCCTGCAGAACTTTGAAC    660
178   Q  L  E  L  P  K  L  L  I  S  V  H  G  G  L  Q  N  F  E  L   197

661  TCCAGCCAAAACTCAAGCAAGTCTTTGGGAAAGGGCTCATCAAAGCAGCAATGACAACTG   720
198   Q  P  K  L  K  Q  V  F  G  K  G  L  I  K  A  A  M  T  T  G   217

721  GAGCGTGGATATTCACTGGAGGGGTTAACACAGGTGTTATTCGTCATGTTGGCGATGCCT   780
218   A  W  I  F  T  G  G  V  N  T  G  V  I  R  H  V  G  D  A  L   237

781  TGAAGGATCATGCCTCTAAGTCTCGAGGAAAGATATGCACCATAGGTATTGCCCCCTGGG   840
238   K  D  H  A  S  K  S  R  G  K  I  C  T  I  G  I  A  P  W  G   257

841  GAATTGTGGAAAACCAGGAGGACCTCATTGGAAGAGATGTTGTCCGGCCATACCAGACCA   900
258   I  V  E  N  Q  E  D  L  I  G  R  D  V  V  R  P  Y  Q  T  M   277

901  TGTCCAATCCCATGAGCAAGCTCACTGTTCTCAACAGCATGCATTCCCACTTCATTCTGG   960
278   S  N  P  M  S  K  L  T  V  L  N  S  M  H  S  H  F  I  L  A   297

961  CTGACAACGGGACCACTGGAAAATATGGAGCAGAGGTGAAACTTCGAAGACAACTGGAAA  1020
298   D  N  G  T  T  G  K  Y  G  A  E  V  K  L  R  R  Q  L  E  K   317
```

FIG. 1B

```
1021 AGCATATTTCACTCCAGAAGATAAACACAAGAATCGGTCAAGGTGTTCCTGTGGTGGCAC 1080
 318   H  I  S  L  Q  K  I  N  T  R  I  G  Q  G  V  P  V  V  A  L   337

1081 TCATAGTGGAAGGAGGACCCAATGTGATCTCGATTGTTTTGGAGTACCTTCGAGACACCC 1140
 338   I  V  E  G  G  P  N  V  I  S  I  V  L  E  Y  L  R  D  T  P   357

1141 CTCCCGTGCCAGTGGTTGTCTGTGATGGGAGTGGACGGGCATCGGACATCCTGGCCTTTG 1200
 358   P  V  P  V  V  C  D  G  S  G  R  A  S  D  I  L  A  F  G   377

1201 GGCATAAATACTCAGAAGAAGGCGGACTGATAAATGAATCTTTGAGGGACCAGCTGTTGG 1260
 378   H  K  Y  S  E  E  G  G  L  I  N  E  S  L  R  D  Q  L  L  V   397

1261 TGACTATACAGAAGACTTTCACATACACTCGAACCCAAGCTCAGCATCTGTTCATCATCC 1320
 398   T  I  Q  K  T  F  T  Y  T  R  T  Q  A  Q  H  L  F  I  I  L   417

1321 TCATGGAGTGCATGAAGAAGAAGGAATTGATTACGGTATTTCGGATGGGATCAGAAGGAC 1380
 418   M  E  C  M  K  K  K  E  L  I  T  V  F  R  M  G  S  E  G  H   437

1381 ACCAGGACATTGATTTGGCTATCCTGACAGCTTTACTCAAAGGAGCCAATGCCTCGGCCC 1440
 438   Q  D  I  D  L  A  I  L  T  A  L  L  K  G  A  N  A  S  A  P   457

1441 CAGACCAACTGAGCTTAGCTTTAGCCTGGAACAGAGTCGACATCGCTCGCAGCCAGATCT 1500
 458   D  Q  L  S  L  A  L  A  W  N  R  V  D  I  A  R  S  Q  I  F   477

1501 TTATTTACGGGCAACAGTGGCCGGTGGGATCTCTGGAGCAAGCCATGTTGGATGCCTTAG 1560
 478   I  Y  G  Q  Q  W  P  V  G  S  L  E  Q  A  M  L  D  A  L  V   497

1561 TTCTGGACAGAGTGGATTTTGTGAAATTACTCATAGAGAATGGAGTAAGCATGCACCGTT 1620
 498   L  D  R  V  D  F  V  K  L  L  I  E  N  G  V  S  M  H  R  F   517

1621 TTCTCACCATCTCCAGACTAGAGGAATTGTACAATACGAGACATGGGCCCTCAAATACAT 1680
 518   L  T  I  S  R  L  E  E  L  Y  N  T  R  H  G  P  S  N  T  L   537

1681 TGTACCACTTGGTCAGGGATGTCAAAAAGGGGAACCTGCCCCCAGACTACAGAATCAGCC 1740
 538   Y  H  L  V  R  D  V  K  K  G  N  L  P  P  D  Y  R  I  S  L   557

1741 TGATTGACATCGGCCTGGTGATCGAGTACCTGATGGGCGGGGCTTATCGCTGCAACTACA 1800
 558   I  D  I  G  L  V  I  E  Y  L  M  G  G  A  Y  R  C  N  Y  T   577

1801 CGCGCAAGCGCTTCCGGACCCTCTACCACAACCTCTTCGGCCCCAAGAGGCCCAAAGCCT 1860
 578   R  K  R  F  R  T  L  Y  H  N  L  F  G  P  K  R  P  K  A  L   597

1861 TGAAACTGCTGGGAATGGAGGATGATATTCCCTTGAGGCGAGGAAGAAAGACAACCAAGA 1920
 598   K  L  L  G  M  E  D  D  I  P  L  R  R  G  R  K  T  T  K   617

1921 AACGTGAAGAAGAGGTGGACATTGACTTGGATGATCCTGAGATCAACCACTTCCCCTTCC 1980
 618   R  E  E  V  D  I  D  L  D  D  P  E  I  N  H  F  P  F  P   637

1981 CTTTCCATGAGCTCATGGTGTGGGCTGTTCTCATGAAGCGGCAGAAGATGGCCCTGTTCT 2040
 638   F  H  E  L  M  V  W  A  V  L  M  K  R  Q  K  M  A  L  F  F   657

2041 TCTGGCAGCACGGTGAGGAGGCCATGGCCAAGGCCCTGGTGGCCTGCAAGCTCTGCAAAG 2100
 658   W  Q  H  G  E  E  A  M  A  K  A  L  V  A  C  K  L  C  K  A   677
```

FIG. 1C

```
2101  CCATGGCTCATGAGGCCTCTGAGAACGACATGGTTGACGACATTTCCCAGGAGCTGAATC  2160
 678   M   A   H   E   A   S   E   N   D   M   V   D   D   I   S   Q   E   L   N   H    697

2161  ACAATTCCAGAGACTTTGGCCAGCTGGCTGTGGAGCTCCTGGACCAGTCCTACAAGCAGG  2220
 698   N   S   R   D   F   G   Q   L   A   V   E   L   L   D   Q   S   Y   K   Q   D    717

2221  ACGAACAGCTGGCCATGAAACTGCTGACGTATGAGCTGAAGAACTGGAGCAACGCCACGT  2280
 718   E   Q   L   A   M   K   L   L   T   Y   E   L   K   N   W   S   N   A   T   C    737

2281  GCCTGCAGCTTGCCGTGGCTGCCAAACACCGCGACTTCATCGCGCACACGTGCAGCCAGA  2340
 738   L   Q   L   A   V   A   A   K   H   R   D   F   I   A   H   T   C   S   Q   M    757

2341  TGCTGCTCACCGACATGTGGATGGGCCGGCTCCGCATGCGCAAGAACTCAGGCCTCAAGG  2400
 758   L   L   T   D   M   W   M   G   R   L   R   M   R   K   N   S   G   L   K   V    777

2401  TAATTCTGGGAATTCTACTTCCTCCTTCAATTCTCAGCTTGGAGTTCAAGAACAAAGACG  2460
 778   I   L   G   I   L   L   P   P   S   I   L   S   L   E   F   K   N   K   D   D    797

2461  ACATGCCCTATATGTCTCAGGCCCAGGAAATCCACCTCCAAGAGAAGGAGGCAGAAGAAC  2520
 798   M   P   Y   M   S   Q   A   Q   E   I   H   L   Q   E   K   E   A   E   E   P    817

2521  CAGAGAAGCCCACAAAGGAAAAAGAGGAAGAGGACATGGAGCTCACAGCAATGTTGGGAC  2580
 818   E   K   P   T   K   E   K   E   E   E   D   M   E   L   T   A   M   L   G   R    837

2581  GAAACAACGGGGAGTCCTCCAGGAAGAAGGATGAAGAGGAAGTTCAGAGCAAGCACCGGT  2640
 838   N   N   G   E   S   S   R   K   K   D   E   E   V   Q   S   K   H   R   L    857

2641  TAATCCCCCTCGGCAGAAAAATCTATGAATTCTACAATGCACCCATCGTGAAGTTCTGGT  2700
 858   I   P   L   G   R   K   I   Y   E   F   Y   N   A   P   I   V   K   F   W   F    877

2701  TCTACACACTGGCGTATATCGGATACCTGATGCTCTTCAACTATATCGTGTTAGTGAAGA  2760
 878   Y   T   L   A   Y   I   G   Y   L   M   L   F   N   Y   I   V   L   V   K   M    897

2761  TGGAACGCTGGCCGTCCACCCAGGAATGGATCGTAATCTCCTATATTTTCACCCTGGGAA  2820
 898   E   R   W   P   S   T   Q   E   W   I   V   I   S   Y   I   F   T   L   G    917

2821  TAGAAAAGATGAGAGAGATTCTGATGTCAGAGCCAGGGAAGTTGCTACAGAAAGTGAAGG  2880
 918   E   K   M   R   E   I   L   M   S   E   P   G   K   L   L   Q   K   V   K    937

2881  TATGGCTGCAGGAGTACTGGAATGTCACGGACCTCATCGCCATCCTTCTGTTTTCTGTCG  2940
 938   W   L   Q   E   Y   W   N   V   T   D   L   I   A   I   L   L   F   S   V   G    957

2941  GAATGATCCTTCGTCTCCAAGACCAGCCCTTCAGGAGTGACGGAGGGTCATCTACTGCG  3000
 958   M   I   L   R   L   Q   D   Q   P   F   R   S   D   G   R   V   I   Y   C   V    977

3001  TGAACATCATTTACTGGTATATCCGTCTCCTAGACATCTTCGGCGTGAACAAGTATTTGG  3060
 978   N   I   I   Y   W   Y   I   R   L   L   D   I   F   G   V   N   K   Y   L   G    997

3061  GCCCGTATGTAATGATGATTGGAAAAATGATGATAGACATGATGTACTTTGTCATCATTA  3120
 998   A   P   Y   V   M   M   I   G   K   M   M   I   D   M   M   Y   F   V   I   I   1017
```

FIG. 1D

```
3121  TGCTGGTGGTTCTGATGAGCTTTGGGGTCGCCAGGCAAGCCATCCTTTTTCCCAATGAGG  3180
1018   L  V  V  L  M  S  F  G  V  A  R  Q  A  I  L  F  P  N  E            1037

3181  AGCCATCATGGAAACTGGCCAAGAACATCTTCTACATGCCCTATTGGATGATTTATGGGG  3240
1038   S  H  H  G  N  W  P  R  T  S  S  T  C  P  I  G  *  F  M  G         1057

3241  AAGTGTTTGCGGACCAGATAGACCCTCCCTGTGGACAGAATGAGACCCGAGAGGATGGTA  3300
1058   S  V  C  G  P  D  R  P  P  L  W  T  E  *  D  P  R  G  M  V         1077

3301  AAATAATCCAGCTGCCTCCCTGCAAGACAGGAGCTTGGATCGTGCCGGCCATCATGGCCT  3360
1078   I  I  Q  L  P  P  C  K  T  G  A  W  I  V  P  A  I  M  A            1097

3361  GCTACCTCTTAGTGGCAAACATCTTGCTGGTCAACCTCCTCATTGCTGTCTTTAACAATA  3420
1098   L  L  V  A  N  I  L  L  V  N  L  L  I  A  V  F            N  N  T  1117

3421  CATTTTTTGAAGTAAAATCGATATCCAACCAAGTCTGGAAGTTTCAGAGGTATCAGCTCA  3480
1118   F  F  E  V  K  S  I  S  N  Q  V  W  K  F  Q  R  Y  Q  L  I         1137

3481  TCATGACTTTCCATGAAAGGCCAGTTCTGCCCCCACCACTGATCATCTTCAGCCACATGA  3540
1138   M  T  F  H  E  R  P  V  L  P  P  P  L  I  I  F  S  H  M            1157

3541  CCATGATATTCCAGCACCTGTGCTGCCGATGGAGGAAACACGAGAGCGACCCGGATGAAA  3600
1158   M  I  F  Q  H  L  C  C  R  W  R  K  H  E  S  D  P  D  E  R         1177

3601  GGGACTACGGCCTGAAACTCTTCATAACCGATGATGAGCTCAAGAAAGTACATGACTTTG  3660
1178   D  Y  G  L  K  L  F  I  T  D  D  E  L  K  K  V  H  D  F  E         1197

3661  AAGAGCAATGCATAGAAGAATACTTCAGAGAAAAGGATGATCGGTTCAACTCATCTAATG  3720
1198   E  Q  C  I  E  E  Y  F  R  E  K  D  D  R  F  N  S  S  N  D         1217

3721  ATGAGAGGATACGGGTGACTTCAGAAAGGGTGGAGAACATGTCTATGCGGCTGGAGGAAG  3780
1218   E  R  I  R  V  T  S  E  R  V  E  N  M  S  M  R  L  E  E  V         1237

3781  TCAACGAGAGAGAGCACTCCATGAAGGCTTCACTCCAGACCGTGGACATCCGGCTGGCGC  3840
1238   N  E  R  E  H  S  M  K  A  S  L  Q  T  V  D  I  R  L  A  Q         1257

3841  AGCTGGAAGACCTTATCGGGCGCATGGCCACGGCCCTGGAGCGCCTGACAGGTCTGGAGC  3900
1258   L  E  D  L  I  G  R  M  A  T  A  L  E  R  L  T  G  L  E  R         1277

3901  GGGCCGAGTCCAACAAAATCCGCTCGAGGACCTCGTCAGACTGCACGGACGCCGCCTACA  3960
1278   A  E  S  N  K  I  R  S  R  T  S  S  D  C  T  D  A  A  Y  I         1297

3961  TTGTCCGTCAGAGCAGCTTCAACAGCCAGGAAGGGAACACCTTCAAGCTCCAAGAGAGTA  4020
1298   V  R  Q  S  S  F  N  S  Q  E  G  N  T  F  K  L  Q  E  S  I         1317

4021  TAGACCCTGCAGGTGAGGAGACCATGTCCCCAACTTCTCCAACCTTAATGCCCCGTATGC  4080
1318   D  P  A  G  E  E  T  M  S  P  T  S  P  T  L  M  P  R  M  R         1337

4081  GAAGCCATTCTTTCTATTCAGTCAATATGAAAGACAAAGGTGGTATAGAAAAGTTGGAAA  4140
1338   S  H  S  F  Y  S  V  N  M  K  D  K  G  G  I  E  K  L  E  S         1357

4141  GTATTTTTAAAGAAAGGTCCCTGAGCCTACACCGGGCTACTAGTTCCCACTCTGTAGCAA  4200
1358   I  F  K  E  R  S  L  S  L  H  R  A  T  S  S  H  S  V  A  K         1377
```

FIG. 1E

```
4201  AAGAACCCAAAGCTCCTGCAGCCCCTGCCAACACCTTGGCCATTGTTCCTGATTCCAGAA  4260
1378   E   P   K   A   P   A   A   P   A   N   T   L   A   I   V   P   D   S   R   R    1397

4261  GACCATCATCGTGTATAGACATCTATGTCTCTGCTATGGATGAGCTCCACTGTGATATAG  4320
1398   P   S   S   C   I   D   I   Y   V   S   A   M   D   E   L   H   C   D   I   D    1417

4321  ACCCTCTGGACAATTCCGTGAACATCCTTGGGCTAGGCGAGCCAAGCTTTTCAACTCCAG  4380
1418   P   L   D   N   S   V   N   I   L   G   L   G   E   P   S   F   S   T   P   V    1437

4381  TACCTTCCACAGCCCCTTCAAGTAGTGCCTATGCAACACTTGCACCCACAGACAGACCTC  4440
1438   P   S   T   A   P   S   S   S   A   Y   A   T   L   A   P   T   D   R   P   P    1457

4441  CAAGCCGGAGCATTGATTTTGAGGACATCACCTCCATGGACACTAGATCTTTTTCTTCAG  4500
1458   S   R   S   I   D   F   E   D   I   T   S   M   D   T   R   S   F   S   S   D    1477

4501  ACTACACCCACCTCCCAGAATGCCAAAACCCCTGGGACTCAGAGCCTCCGATGTACCACA  4560
1478   Y   T   H   L   P   E   C   Q   N   P   W   D   S   E   P   P   M   Y   H   T    1497

4561  CCATTGAGCGTTCCAAAAGTAGCCGCTACCTAGCCACCACACCCTTTCTTCTAGAAGAGG  4620
1498   I   E   R   S   K   S   S   R   Y   L   A   T   T   P   F   L   L   E   E   A    1517

4621  CTCCCATTGTGAAATCTCATAGCTTTATGTTTTCCCCCTCAAGGAGCTATTATGCCAACT  4680
1518   P   I   V   K   S   H   S   F   M   F   S   P   S   R   S   Y   Y   A   N   F    1537

4681  TTGGGGTGCCTGTAAAAACAGCAGAATACACAAGTATTACAGACTGTATTGACACAAGGT  4740
1538   G   V   P   V   K   T   A   E   Y   T   S   I   T   D   C   I   D   T   R   C    1557

4741  GTGTCAATGCCCCTCAAGCAATTGCGGACAGAGCTGCCTTCCCTGGAGGTCTTGGAGACA  4800
1558   V   N   A   P   Q   A   I   A   D   R   A   A   F   P   G   G   L   G   D   K    1577

4801  AAGTGGAGGACTTAACTTGCTGCCATCCAGAGCGAGAAGCAGAACTGAGTCACCCCAGCT  4860
1578   V   E   D   L   T   C   C   H   P   E   R   E   A   E   L   S   H   P   S   S    1597

4861  CTGACAGTGAGGAGAATGAGGCCAAAGGCCGCAGAGCCACCATTGCAATATCCTCCCAGG  4920
1598   D   S   E   E   N   E   A   K   G   R   R   A   T   I   A   I   S   S   Q   E    1617

4921  AGGGTGATAACTCAGAGAGAACCCTGTCCAACAACATCACTGTTCCCAAGATAGAGCGCG  4980
1618   G   D   N   S   E   R   T   L   S   N   N   I   T   V   P   K   I   E   R   A    1637

4981  CCAACAGCTACTCGGCAGAGGAGCCAAGTGCGCCATATGCACACACCAGGAAGAGCTTCT  5040
1638   N   S   Y   S   A   E   E   P   S   A   P   Y   A   H   T   R   K   S   F   S    1657

5041  CCATCAGTGACAAACTCGACAGGCAGCGGAACACAGCAAGCCTGCAAAATCCCTTCCAGA  5100
1658   I   S   D   K   L   D   R   Q   R   N   T   A   S   L   Q   N   P   F   Q   R    1677

5101  GAAGCAAGTCCTCCAAGCCGGAGGGCCGAGGGGACAGCCTGTCCATGAGGAGACTGTCCA  5160
1678   S   K   S   S   K   P   E   G   R   G   D   S   L   S   M   R   R   L   S   R    1697

5161  GAACATCGGCTTTCCAAAGCTTTGAAAGCAAGCACACCTAA       5201
1698   T   S   A   F   Q   S   F   E   S   K   H   T           1709
```

FIG. 2A

```
  1  CGCCCGCGGCGAGGAGCCAGCGAGAGCGCTCGGCGCTGGGCTGTTTCCCGGCCGAGGGAG    60

61  GCGAACTTCTCATGGGGAAGAAGTGGAGGGATGCGGCGGAAATGGAGCGGGGCTGCTCCG   120
  1              M  G  K  K  W  R  D  A  A  E  M  E  R  G  C  S  D    17

121  ACCGCGAGGACAACGCGGAGAGCCGCAGACGCAGCCGGAGCGCCAGCCGGGCAGGTTTG    180
 18    R  E  D  N  A  E  S  R  R  R  S  R  S  A  S  R  G  R  F  A     37

181  CCGAGTCGTGGAAAAGGTTAAGTTCCAAGCAGGGGTCCACCAAACGCTCGGGACTCCCGT   240
 38    E  S  W  K  R  L  S  S  K  Q  G  S  T  K  R  S  G  L  P  S     57

241  CGCAGCAGACGCCGGCTCAGAAATCCTGGATAGAAAGAGCATTTTATAAAAGAGAATGTG   300
 58    Q  Q  T  P  A  Q  K  S  W  I  E  R  A  F  Y  K  R  E  C  V     77

301  TCCACATCATACCCAGCACCAAAGACCCCCATAGGTGTTGCTGTGGGCGTCTGATAGGCC   360
 78    H  I  I  P  S  T  K  D  P  H  R  C  C  C  G  R  L  I  G  Q     97

361  AGCATGTTGGCCTCACCCCCAGTATCTCCGTGCTTCAGAATGAGAAAAATGAAAGTCGCC   420
 98    H  V  G  L  T  P  S  I  S  V  L  Q  N  E  K  N  E  S  R  L    117

421  TCTCCCGAAATGACATCCAGTCTGAAAAGTGGTCCATCAGCAAACACACTCAACTCAGCC   480
118    S  R  N  D  I  Q  S  E  K  W  S  I  S  K  H  T  Q  L  S  P    137

481  CTACGGATGCTTTTGGGACCATTGAGTTCCAAGGAGGTGGCCATTCCAACAAAGCCATGT   540
138    T  D  A  F  G  T  I  E  F  Q  G  G  G  H  S  N  K  A  M  Y    157

541  ATGTGCGAGTATCTTTTGATACAAAACCTGATCTCCTCTTACACCTGATGACCAAGGAAT   600
158    V  R  V  S  F  D  T  K  P  D  L  L  L  H  L  M  T  K  E  W    177

601  GGCAGTTGGAGCTTCCCAAGCTTCTCATCTCTGTCCATGGGGGCCTGCAGAACTTTGAAC   660
178    Q  L  E  L  P  K  L  L  I  S  V  H  G  G  L  Q  N  F  E  L    197

661  TCCAGCCAAAACTCAAGCAAGTCTTTGGGAAAGGGCTCATCAAAGCAGCAATGACAACTG   720
198    Q  P  K  L  K  Q  V  F  G  K  G  L  I  K  A  A  M  T  T  G    217

721  GAGCGTGGATATTCACTGGAGGGGTTAACACAGGTGTTATTCGTCATGTTGGCGATGCCT   780
218    A  W  I  F  T  G  G  V  N  T  G  V  I  R  H  V  G  D  A  L    237

781  TGAAGGATCATGCCTCTAAGTCTCGAGGAAAGATATGCACCATAGGTATTGCCCCCTGGG   840
238    K  D  H  A  S  K  S  R  G  K  I  C  T  I  G  I  A  P  W  G    257

841  GAATTGTGGAAAACCAGGAGGACCTCATTGGAAGAGATGTTGTCCGGCCATACCAGACCA   900
258    I  V  E  N  Q  E  D  L  I  G  R  D  V  V  R  P  Y  Q  T  M    277

901  TGTCCAATCCCATGAGCAAGCTCACTGTTCTCAACAGCATGCATTCCCACTTCATTCTGG   960
278    S  N  P  M  S  K  L  T  V  L  N  S  M  H  S  H  F  I  L  A    297

961  CTGACAACGGGACCACTGGAAAATATGGAGCAGAGGTGAAACTTCGAAGACAACTGGAAA  1020
298    D  N  G  T  T  G  K  Y  G  A  E  V  K  L  R  R  Q  L  E  K    317
```

FIG. 2B

```
1021 AGCATATTTCACTCCAGAAGATAAACACAAGAATCGGTCAAGGTGTTCCTGTGGTGGCAC 1080
 318   H  I  S  L  Q  K  I  N  T  R  I  G  Q  G  V  P  V  V  A  L  337

1081 TCATAGTGGAAGGAGGACCCAATGTGATCTCGATTGTTTTGGAGTACCTTCGAGACACCC 1140
 338   I  V  E  G  G  P  N  V  I  S  I  V  L  E  Y  L  R  D  T  P  357

1141 CTCCCGTGCCAGTGGTTGTCTGTGATGGGAGTGGACGGGCATCGGACATCCTGGCCTTTG 1200
 358   P  V  P  V  V  C  D  G  S  G  R  A  S  D  I  L  A  F  G  377

1201 GGCATAAATACTCAGAAGAAGGCGGACTGATAAATGAATCTTTGAGGGACCAGCTGTTGG 1260
 378   H  K  Y  S  E  E  G  G  L  I  N  E  S  L  R  D  Q  L  L  V  397

1261 TGACTATACAGAAGACTTTCACATACACTCGAACCCAAGCTCAGCATCTGTTCATCATCC 1320
 398   T  I  Q  K  T  F  T  Y  T  R  T  Q  A  Q  H  L  F  I  I  L  417

1321 TCATGGAGTGCATGAAGAAGAAGGAATTGATTACGGTATTTCGGATGGGATCAGAAGGAC 1380
 418   M  E  C  M  K  K  K  E  L  I  T  V  F  R  M  G  S  E  G  H  437

1381 ACCAGGACATTGATTTGGCTATCCTGACAGCTTTACTCAAAGGAGCCAATGCCTCGGCCC 1440
 438   Q  D  I  D  L  A  I  L  T  A  L  L  K  G  A  N  A  S  A  P  457

1441 CAGACCAACTGAGCTTAGCTTTAGCCTGGAACAGAGTCGACATCGCTCGCAGCCAGATCT 1500
 458   D  Q  L  S  L  A  L  A  W  N  R  V  D  I  A  R  S  Q  I  F  477

1501 TTATTTACGGGCAACAGTGGCCGGTGGGATCTCTGGAGCAAGCCATGTTGGATGCCTTAG 1560
 478   I  Y  G  Q  Q  W  P  V  G  S  L  E  Q  A  M  L  D  A  L  V  497

1561 TTCTGGACAGAGTGGATTTTGTGAAATTACTCATAGAGAATGGAGTAAGCATGCACCGTT 1620
 498   L  D  R  V  D  F  V  K  L  L  I  E  N  G  V  S  M  H  R  F  517

1621 TTCTCACCATCTCCAGACTAGAGGAATTGTACAATACGAGACATGGGCCCTCAAATACAT 1680
 518   L  T  I  S  R  L  E  E  L  Y  N  T  R  H  G  P  S  N  T  L  537

1681 TGTACCACTTGGTCAGGGATGTCAAAAAGCGAGAGTATCCAGGTTTCGGTTGGATCTATT 1740
 538   Y  H  L  V  R  D  V  K  K  R  E  Y  P  G  F  G  W  I  Y  F  557

1741 TTAAGGGGAACCTGCCCCCAGACTACAGAATCAGCCTGATTGACATCGGCCTGGTGATCG 1800
 558   K  G  N  L  P  P  D  Y  R  I  S  L  I  D  I  G  L  V  I  E  577

1801 AGTACCTGATGGGCGGGGCTTATCGCTGCAACTACACGCGCAAGCGCTTCCGGACCCTCT 1860
 578   Y  L  M  G  G  A  Y  R  C  N  Y  T  R  K  R  F  R  T  L  Y  597

1861 ACCACAACCTCTTCGGCCCCAAGAGGCCCAAAGCCTTGAAACTGCTGGGAATGGAGGATG 1920
 598   H  N  L  F  G  P  K  R  P  K  A  L  K  L  L  G  M  E  D  D  617

1921 ATATTCCCTTGAGGCGAGGAAGAAAGACAACCAAGAAACGTGAAGAAGAGGTGGACATTG 1980
 618   I  P  L  R  R  G  R  K  T  T  K  K  R  E  E  V  D  I  D  637

1981 ACTTGGATGATCCTGAGATCAACCACTTCCCCTTCCCTTTCCATGAGCTCATGGTGTGGG 2040
 638   L  D  D  P  E  I  N  H  F  P  F  P  F  H  E  L  M  V  W  A  657
```

FIG. 2C

```
2041  CTGTTCTCATGAAGCGGCAGAAGATGGCCCTGTTCTTCTGGCAGCACGGTGAGGAGGCCA  2100
658     V  L  M  K  R  Q  K  M  A  L  F  F  W  Q  H  C  E  E  A  M   677

2101  TGGCCAAGGCCCTGGTGGCCTGCAAGCTCTGCAAAGCCATGGCTCATGAGGCCTCTGAGA  2160
678     A  K  A  L  V  A  C  K  L  C  K  A  M  A  H  E  A  S  E  N   697

2161  ACGACATGGTTGACGACATTTCCCAGGAGCTGAATCACAATTCCAGAGACTTTGGCCAGC  2220
698     D  M  V  D  D  I  S  Q  E  L  N  H  N  S  R  D  F  G  Q  L   717

2221  TGGCTGTGGAGCTCCTGGACCAGTCCTACAAGCAGGACGAACAGCTGGCCATGAAACTGC  2280
718     A  V  E  L  L  D  Q  S  Y  K  Q  D  E  Q  L  A  M  K  L  L   737

2281  TGACGTATGAGCTGAAGAACTGGAGCAACGCCACGTGCCTGCAGCTTGCCGTGGCTGCCA  2340
738     T  Y  E  L  K  N  W  S  N  A  T  C  L  Q  L  A  V  A  A  K   757

2341  AACACCGCGACTTCATCGCGCACACGTGCAGCCAGATGCTGCTCACCGACATGTGGATGG  2400
758     H  R  D  F  I  A  H  T  C  S  Q  M  L  L  T  D  M  W  M  G   777

2401  GCCGGCTCCGCATGCGCAAGAACTCAGGCCTCAAGGTAATTCTGGGAATTCTACTTCCTC  2460
778     R  L  R  M  R  K  N  S  G  L  K  V  I  L  G  I  L  L  P  P   797

2461  CTTCAATTCTCAGCTTGGACTTCAAGAACAAAGACGACATGCCCTATATGTCTCAGGCCC  2520
798     S  I  L  S  L  E  F  K  N  K  D  D  M  P  Y  M  S  Q  A  Q   817

2521  AGGAAATCCACCTCCAAGAGAAGGAGGCAGAAGAACCAGAGAAGCCCACAAAGGAAAAAG  2580
818     E  I  H  L  Q  E  K  E  A  E  E  P  E  K  P  T  K  E  K  E   837

2581  AGGAAGAGGACATGGAGCTCACAGCAATGTTGGGACGAAACAACGGGGAGTCCTCCAGGA  2640
838     E  E  D  M  E  L  T  A  M  L  G  R  N  N  G  E  S  S  R  K   857

2641  AGAAGGATGAAGAGGAAGTTCAGAGCAAGCACCGGTTAATCCCCCTCGGCAGAAAAATCT  2700
858     K  D  E  E  V  Q  S  K  H  R  L  I  P  L  G  R  K  I  Y   877

2701  ATGAATTCTACAATGCACCCATCGTGAAGTTCTGGTTCTACACACTGGCGTATATCGGAT  2760
878     E  F  Y  N  A  P  I  V  K  F  W  F  Y  T  L  A  Y  I  G  Y   897

2761  ACCTGATGCTCTTCAACTATATCGTGTTAGTGAAGATGGAACGCTGGCCGTCCACCCAGG  2820
898     L  M  L  F  N  Y  I  V  L  V  K  M  E  R  W  P  S  T  Q    917

2821  AATGGATCGTAATCTCCTATATTTTCACCCTGGGAATAGAAAAGATGAGAGAGATTCTGA  2880
918                                                                 937

2881  TGTCAGAGCCAGGGAAGTTGCTACAGAAAGTGAAGGTATGGCTGCAGGAGTACTGGAATG  2940
938                                                                 957

2941  TCACGGACCTCATCGCCATCCTTCTGTTTTCTGTCGGAATGATCCTTCGTCTCCAAGACC  3000
958                                                                 977

3001  AGCCCTTCAGGAGTGACCGGACGGTCATCTACTGCGTGAACATCATTTACTGGTATATCC  3060
978                                                                 997
```

FIG. 2D

```
3061  GTCTCCTAGACATCTTCGGCGTGAACAAGTATTTGGGCCCGTATGTAATGATGATTGGAA  3120
 998     L  D  S  F  G  V  N  K  Y  L  G  P  Y  V  M  M  I  G   1017

3121  AAATGATGATAGACATGATGTACTTTGTCATCATTATGCTGGTGGTTCTGATGAGCTTTG  3180
1018   K  M  M  I  D  M  M  Y  F  V  I  I  M  L  V  V  L  M  S  F  1037

3181  GGGTCGCCAGGCAAGCCATCCTTTTTCCCAATGAGGAGCCATCATGGAAACTGGCCAAGA  3240
1038   G  V  A  R  Q  A  S  H  P  F  P  N  E  E  P  S  W  K  L  A  K  N  1057

3241  ACATCTTCTACATGCCCTATTGGATGATTTATGGGGAAGTGTTTGCGGACCAGATAGACC  3300
1058   T  S  S  T  C  P  I  G  M  I  Y  G  E  V  F  A  D  Q  I  D  P  1077

3301  CTCCCTGTGGACAGAATGAGACCCGAGAGGATGGTAAAATAATCCAGCTGCCTCCCTGCA  3360
1078    P  C  G  Q  N  E  T  R  E  D  G  K  I  I  Q  L  P  P  C  1097

3361  AGACAGGAGCTTGGATCGTGCCGGCCATCATGGCCTGCTACCTCTTAGTGGCAAACATCT  3420
1098   R  Q  E  L  G  S  C  R  P  S  W  P  A  T  S  W  Q  T  S  1117

3421  TGCTGGTCAACCTCCTCATTGCTGTCTTTAACAATACATTTTTTGAAGTAAAATCGATAT  3480
1118   C  W  S  T  S  S  L  L  S  L  T  I  H  F  F  L  K  *   N  T  F  F  E  V  K  S  I  S  1137

3481  CCAACCAAGTCTGGAAGTTTCAGAGGTATCAGCTCATCATGACTTTCCATGAAAGGCCAG  3540
1138   N  Q  V  W  K  F  Q  R  Y  Q  L  I  M  T  F  H  E  R  P  V  1157

3541  TTCTGCCCCCACCACTGATCATCTTCAGCCACATGACCATGATATTCCAGCACCTGTGCT  3600
1158   L  P  P  P  L  I  I  F  S  H  M  T  M  I  F  Q  H  L  C  C  1177

3601  GCCGATGGAGGAAACACGAGAGCGACCCGGATGAAAGGGACTACGGCCTGAAACTCTTCA  3660
1178   R  W  R  K  H  E  S  D  P  D  E  R  D  Y  G  L  K  L  F  I  1197

3661  TAACCGATGATGAGCTCAAGAAAGTACATGACTTTGAAGAGCAATGCATAGAAGAATACT  3720
1198   T  D  D  E  L  K  K  V  H  D  F  E  E  Q  C  I  E  E  Y  F  1217

3721  TCAGAGAAAAGGATGATCGGTTCAACTCATCTAATGATGAGAGGATACGGGTGACTTCAG  3780
1218   R  E  K  D  D  R  F  N  S  S  N  D  E  R  I  R  V  T  S  E  1237

3781  AAAGGGTGGAGAACATGTCTATGCGGCTGGAGGAAGTCAACGAGAGAGAGCACTCCATGA  3840
1238   R  V  E  N  M  S  M  R  L  E  E  V  N  E  R  E  H  S  M  K  1257

3841  AGGCTTCACTCCAGACCGTGGACATCCGGCTGGCGCAGCTGGAAGACCTTATCGGGCGCA  3900
1258   A  S  L  Q  T  V  D  I  R  L  A  Q  L  E  D  L  I  G  R  M  1277

3901  TGGCCACGGCCCTGGAGCGCCTGACAGGTCTGGAGCGGGCCGAGTCCAACAAAATCCGCT  3960
1278   A  T  A  L  E  R  L  T  G  L  E  R  A  E  S  N  K  I  R  S  1297

3961  CGAGGACCTCGTCAGACTGCACGGACGCCGCCTACATTGTCCGTCAGAGCAGCTTCAACA  4020
1298   R  T  S  S  D  C  T  D  A  A  Y  I  V  R  Q  S  S  F  N  S  1317

4021  GCCAGGAAGGGAACACCTTCAAGCTCCAAGAGAGTATAGACCCTGCAGGTGAGGAGACCA  4080
1318   Q  E  G  N  T  F  K  L  Q  E  S  I  D  P  A  G  E  E  T  M  1337
```

FIG. 2E

```
4081  TGTCCCCAACTTCTCCAACCTTAATGCCCCGTATGCGAAGCCATTCTTTCTATTCAGTCA  4140
1338    S  P  T  S  P  T  L  M  P  R  M  R  S  H  S  F  Y  S  V  N   1357

4141  ATATGAAAGACAAAGGTGGTATAGAAAAGTTGGAAAGTATTTTTAAAGAAAGGTCCCTGA  4200
1358    M  K  D  K  G  G  I  E  K  L  E  S  I  F  K  E  R  S  L  S   1377

4201  GCCTACACCGGGCTACTAGTTCCCACTCTGTAGCAAAAGAACCCAAAGCTCCTGCAGCCC  4260
1378    L  H  R  A  T  S  S  H  S  V  A  K  E  P  K  A  P  A  A  P   1397

4261  CTGCCAACACCTTGGCCATTGTTCCTGATTCCAGAAGACCATCATCGTGTATAGACATCT  4320
1398    A  N  T  L  A  I  V  P  D  S  R  R  P  S  S  C  I  D  I  Y   1417

4321  ATGTCTCTGCTATGGATGAGCTCCACTGTGATATAGACCCTCTGGACAATTCCGTGAACA  4380
1418    V  S  A  M  D  E  L  H  C  D  I  D  P  L  D  N  S  V  N  I   1437

4381  TCCTTGGGCTAGGCGAGCCAAGCTTTTCAACTCCAGTACCTTCCACAGCCCCTTCAAGTA  4440
1438    L  G  L  G  E  P  S  F  S  T  P  V  P  S  T  A  P  S  S  S   1457

4441  GTGCCTATGCAACACTTGCACCCACAGACAGACCTCCAAGCCGGAGCATTGATTTTGAGG  4500
1458    A  Y  A  T  L  A  P  T  D  R  P  P  S  R  S  I  D  F  E  D   1477

4501  ACATCACCTCCATGGACACTAGATCTTTTTCTTCAGACTACACCCACCTCCCAGAATGCC  4560
1478    I  T  S  M  D  T  R  S  F  S  S  D  Y  T  H  L  P  E  C  Q   1497

4561  AAAACCCCTGGGACTCAGAGCCTCCGATGTACCACACCATTGAGCGTTCCAAAAGTAGCC  4620
1498    N  P  W  D  S  E  P  P  M  Y  H  T  I  E  R  S  K  S  S  R   1517

4621  GCTACCTAGCCACCACACCCTTTCTTCTAGAAGAGGCTCCCATTGTGAAATCTCATAGCT  4680
1518    Y  L  A  T  T  P  F  L  E  E  A  P  I  V  K  S  H  S  F   1537

4681  TTATGTTTTCCCCCTCAAGGAGCTATTATGCCAACTTTGGGGTGCCTGTAAAAACAGCAG  4740
1538    M  F  S  P  S  R  S  Y  Y  A  N  F  G  V  P  V  K  T  A  E   1557

4741  AATACACAAGTATTACAGACTGTATTGACACAAGGTGTGTCAATGCCCCTCAAGCAATTG  4800
1558    Y  T  S  I  T  D  C  I  D  T  R  C  V  N  A  P  Q  A  I  A   1577

4801  CGGACAGAGCTGCCTTCCCTGGAGGTCTTGGAGACAAAGTGGAGGACTTAACTTGCTGCC  4860
1578    D  R  A  A  F  P  G  G  L  G  D  K  V  E  D  L  T  C  C  H   1597

4861  ATCCAGAGCGAGAAGCAGAACTGAGTCACCCCAGCTCTGACAGTGAGGAGAATGAGGCCA  4920
1598    P  E  R  E  A  E  L  S  H  P  S  S  D  S  E  E  N  E  A  K   1617

4921  AAGGCCGCAGAGCCACCATTGCAATATCCTCCCAGGAGGGTGATAACTCAGAGAGAACCC  4980
1618    G  R  R  A  T  I  A  I  S  S  Q  E  G  D  N  S  E  R  T  L   1637

4981  TGTCCAACAACATCACTGTTCCCAAGATAGAGCGCGCCAACAGCTACTCGGCAGAGGAGC  5040
1638    S  N  N  I  T  V  P  K  I  E  R  A  N  S  Y  S  A  E  E  P   1657

5041  CAAGTGCGCCATATGCACACACCAGGAAGAGCTTCTCCATCAGTGACAAACTCGACAGGC  5100
1658    S  A  P  Y  A  H  T  R  K  S  F  S  I  S  D  K  L  D  R  Q   1677
```

FIG. 2F

```
5101  AGCGGAACACAGCAAGCCTGCAAAATCCCTTCCAGAGAAGCAAGTCCTCCAAGCCGGAGG  5160
1678    R  N  T  A  S  L  Q  N  P  F  Q  R  S  K  S  S  K  P  E  G    1697

5161  GCCGAGGGGACAGCCTGTCCATGAGGAGACTGTCCAGAACATCGGCTTTCCAAAGCTTTG  5220
1698    R  G  D  S  L  S  M  R  R  L  S  R  T  S  A  F  Q  S  F  E    1717

5221  AAAGCAAGCACACCTAA  5237
1718    S  K  H  T        1721
```

FIG. 3A

```
   1  CGCCCGCGGCGAGGAGCCAGCGAGAGCGCTCGGCGCTGGGCTGTTTCCCGGCCGAGGGAG    60

61  GCGAACTTCTCATGGGGAAGAAGTGGAGGGATGCGGCGGAAATGGAGCGGGGCTGCTCCG   120
   1              M   G   K   K   W   R   D   A   A   E   M   E   R   G   C   S   D    17

121  ACCGCGAGGACAACGCGGAGAGCCGCAGACGCAGCCGGAGCGCCAGCCGGGGCAGGTTTG   180
  18    R   E   D   N   A   E   S   R   R   R   S   R   S   A   S   R   G   R   F   A    37

181  CCGAGTCGTGGAAAAGGTTAAGTTCCAAGCAGGGGTCCACCAAACGCTCGGGACTCCCGT   240
  38    E   S   W   K   R   L   S   S   K   Q   G   S   T   K   R   S   G   L   P   S    57

241  CGCAGCAGACGCCGGCTCAGAAATCCTGGATAGAAAGAGCATTTTATAAAAGAGAATGTG   300
  58    Q   Q   T   P   A   Q   K   S   W   I   E   R   A   F   Y   K   R   E   C   V    77

301  TCCACATCATACCCAGCACCAAAGACCCCCATAGGTGTTGCTGTGGGCGTCTGATAGGCC   360
  78    H   I   I   P   S   T   K   D   P   H   R   C   C   C   G   R   L   I   G   Q    97

361  AGCATGTTGGCCTCACCCCCAGTATCTCCGTGCTTCAGAATGAGAAAAATGAAAGTCGCC   420
  98    H   V   G   L   T   P   S   I   S   V   L   Q   N   E   K   N   E   S   R   L   117

421  TCTCCCGAAATGACATCCAGTCTGAAAAGTGGTCCATCAGCAAACACACTCAACTCAGCC   480
 118    S   R   N   D   I   Q   S   E   K   W   S   I   S   K   H   T   Q   L   S   P   137

481  CTACGGATGCTTTTGGGACCATTGAGTTCCAAGGAGGTGGCCATTCCAACAAAGCCATGT   540
 138    T   D   A   F   G   T   I   E   F   Q   G   G   G   H   S   N   K   A   M   Y   157

541  ATGTGCGAGTATCTTTTGATACAAAACCTGATCTCCTCTTACACCTGATGACCAAGGAAT   600
 158    V   R   V   S   F   D   T   K   P   D   L   L   H   L   M   T   K   E   W   177

601  GGCAGTTGGAGCTTCCCAAGCTTCTCATCTCTGTCCATGGGGGCCTGCAGAACTTTGAAC   660
 178    Q   L   E   L   P   K   L   L   I   S   V   H   G   G   L   Q   N   F   E   L   197

661  TCCAGCCAAAACTCAAGCAAGTCTTTGGGAAAGGGCTCATCAAAGCAGCAATGACAACTG   720
 198    Q   P   K   L   K   Q   V   F   G   K   G   L   I   K   A   A   M   T   T   G   217

721  GAGCGTGGATATTCACTGGAGGGGTTAACACAGGTGTTATTCGTCATGTTGGCGATGCCT   780
 218    A   W   I   F   T   G   G   V   N   T   G   V   I   R   H   V   G   D   A   L   237

781  TGAAGGATCATGCCTCTAAGTCTCGAGGAAAGATATGCACCATAGGTATTGCCCCCTGGG   840
 238    K   D   H   A   S   K   S   R   G   K   I   C   T   I   G   I   A   P   W   G   257

841  GAATTGTGGAAAACCAGGAGGACCTCATTGGAAGAGATGTTGTCCGGCCATACCAGACCA   900
 258    I   V   E   N   Q   E   D   L   I   G   R   D   V   V   R   P   Y   Q   T   M   277

901  TGTCCAATCCCATGAGCAAGCTCACTGTTCTCAACAGCATGCATTCCCACTTCATTCTGG   960
 278    S   N   P   M   S   K   L   T   V   L   N   S   M   H   S   H   F   I   L   A   297

961  CTGACAACGGGACCACTGGAAAATATGGAGCAGAGGTGAAACTTCGAAGACAACTGGAAA  1020
 298    D   N   G   T   T   G   K   Y   G   A   E   V   K   L   R   R   Q   L   E   K   317
```

FIG. 3B

```
1021  AGCATATTTCACTCCAGAAGATAAACACAAGAATCGGTCAAGGTGTTCCTGTGGTGGCAC  1080
 318   H   I   S   L   Q   K   I   N   T   R   I   G   Q   G   V   P   V   V   A   L    337

1081  TCATAGTGGAAGGAGGACCCAATGTGATCTCGATTGTTTTGGAGTACCTTCGAGACACCC  1140
 338   I   V   E   G   G   P   N   V   I   S   I   V   L   E   Y   L   R   D   T   P    357

1141  CTCCCGTGCCAGTGGTTGTCTGTGATGGGAGTGGACGGGCATCGGACATCCTGGCCTTTG  1200
 358   P   V   P   V   V   V   C   D   G   S   G   R   A   S   D   I   L   A   F   G    377

1201  GGCATAAATACTCAGAAGAAGGCGGACTGATAAATGAATCTTTGAGGGACCAGCTGTTGG  1260
 378   H   K   Y   S   E   E   G   G   L   I   N   E   S   L   R   D   Q   L   L   V    397

1261  TGACTATACAGAAGACTTTCACATACACTCGAACCCAAGCTCAGCATCTGTTCATCATCC  1320
 398   T   I   Q   K   T   F   T   Y   T   R   T   Q   A   Q   H   L   F   I   I   L    417

1321  TCATGGAGTGCATGAAGAAGAAGGAATTGATTACGGTATTTCGGATGGGATCAGAAGGAC  1380
 418   M   E   C   M   K   K   K   E   L   I   T   V   F   R   M   G   S   E   G   H    437

1381  ACCAGGACATTGATTTGGCTATCCTGACAGCTTTACTCAAAGGAGCCAATGCCTCGGCCC  1440
 438   Q   D   I   D   L   A   I   L   T   A   L   L   K   G   A   N   A   S   A   P    457

1441  CAGACCAACTGAGCTTAGCTTTAGCCTGGAACAGAGTCGACATCGCTCGCAGCCAGATCT  1500
 458   D   Q   L   S   L   A   L   A   W   N   R   V   D   I   A   R   S   Q   I   F    477

1501  TTATTTACGGGCAACAGTGGCCGGTGGGATCTCTGGAGCAAGCCATGTTGGATGCCTTAG  1560
 478   I   Y   G   Q   Q   W   P   V   G   S   L   E   Q   A   M   L   D   A   L   V    497

1561  TTCTGGACAGAGTGGATTTTGTGAAATTACTCATAGAGAATGGAGTAAGCATGCACCGTT  1620
 498   L   D   R   V   D   F   V   K   L   L   I   E   N   G   V   S   M   H   R   F    517

1621  TTCTCACCATCTCCAGACTAGAGGAATTGTACAATACGAGACATGGGCCCTCAAATACAT  1680
 518   L   T   I   S   R   L   E   E   L   Y   N   T   R   H   G   P   S   N   T   L    537

1681  TGTACCACTTGGTCAGGGATGTCAAAAAGGGGAACCTGCCCCCAGACTACAGAATCAGCC  1740
 538   Y   H   L   V   R   D   V   K   K   G   N   L   P   P   D   Y   R   I   S   L    557

1741  TGATTGACATCGGCCTGGTGATCGAGTACCTGATGGGCGGGGCTTATCGCTGCAACTACA  1800
 558   I   D   I   G   L   V   I   E   Y   L   M   G   G   A   Y   R   C   N   Y   T    577

1801  CGCGCAAGCGCTTCCGGACCCTCTACCACAACCTCTTCGGCCCCAAGAGGCCCAAAGCCT  1860
 578   R   K   R   F   R   T   L   Y   H   N   L   F   G   P   K   R   P   K   A   L    597

1861  TGAAACTGCTGGGAATGGAGGATGATATTCCCTTGAGGCGAGGAAGAAAGACAACCAAGA  1920
 598   K   L   L   G   M   E   D   D   I   P   L   R   R   G   R   K   T   T   K    617

1921  AACGTGAAGAAGAGGTGGACATTGACTTGGATGATCCTGAGATCAACCACTTCCCCTTCC  1980
 618   R   E   E   V   D   I   D   L   D   D   P   E   I   N   H   F   P   F   P    637

1981  CTTTCCATGAGCTCATGGTGTGGGCTGTTCTCATGAAGCGGCAGAAGATGGCCCTGTTCT  2040
 638   F   H   E   L   M   V   W   A   V   L   M   K   R   Q   K   M   A   L   F   F    657
```

FIG. 3C

```
2041  TCTGGCAGCACGGTGAGGAGGCCATGGCCAAGGCCCTGGTGGCCTGCAAGCTCTGCAAAG  2100
 658    W  Q  H  G  E  E  A  M  A  K  A  L  V  A  C  K  L  C  K  A    677

2101  CCATGGCTCATGAGGCCTCTGAGAACGACATGGTTGACGACATTTCCCAGGAGCTGAATC  2160
 678    M  A  H  E  A  S  E  N  D  M  V  D  D  I  S  Q  E  L  N  H    697

2161  ACAATTCCAGAGACTTTGGCCAGCTGGCTGTGGAGCTCCTGGACCAGTCCTACAAGCAGG  2220
 698    N  S  R  D  F  G  Q  L  A  V  E  L  L  D  Q  S  Y  K  Q  D    717

2221  ACGAACAGCTGGCCATGAAACTGCTGACGTATGAGCTGAAGAACTGGAGCAACGCCACGT  2280
 718    E  Q  L  A  M  K  L  L  T  Y  E  L  K  N  W  S  N  A  T  C    737

2281  GCCTGCAGCTTGCCGTGGCTGCCAAACACCGCGACTTCATCGCGCACACGTGCAGCCAGA  2340
 738    L  Q  L  A  V  A  A  K  H  R  D  F  I  A  H  T  C  S  Q  M    757

2341  TGCTGCTCACCGACATGTGGATGGGCCGGCTCCGCATGCGCAAGAACTCAGGCCTCAAGG  2400
 758    L  L  T  D  M  W  M  G  R  L  R  M  R  K  N  S  G  L  K  V    777

2401  TAATTCTGGGAATTCTACTTCCTCCTTCAATTCTCAGCTTGGAGTTCAAGAACAAAGACG  2460
 778    I  L  G  I  L  L  P  P  S  I  L  S  L  E  F  K  N  K  D  D    797

2461  ACATGCCCTATATGTCTCAGGCCCAGGAAATCCACCTCCAAGAGAAGGAGGCAGAAGAAC  2520
 798    M  P  Y  M  S  Q  A  Q  E  I  H  L  Q  E  K  E  A  E  E  P    817

2521  CAGAGAAGCCCACAAAGGAAAAAGAGGAAGAGGACATGGAGCTCACAGCAATGTTGGGAC  2580
 818    E  K  P  T  K  E  K  E  E  E  D  M  E  L  T  A  M  L  G  R    837

2581  GAAACAACGGGGAGTCCTCCAGGAAGAAGGATGAAGAGGAAGTTCAGAGCAAGCACCGGT  2640
 838    N  N  G  E  S  S  R  K  K  D  E  E  E  V  Q  S  K  H  R  L    857

2641  TAATCCCCCTCGGCAGAAAAATCTATGAATTCTACAATGCACCCATCGTGAAGTTCTGGT  2700
 858    I  P  L  G  R  K  I  Y  E  F  Y  N  A  P  I  V  K  F  W  F    877

2701  TCTACACACTGGCGTATATCGGATACCTGATGCTCTTCAACTATATCGTGTTAGTGAAGA  2760
 878    Y  T  L  A  Y  I  G  Y  L  M  L  F  N  Y  I  V  L  V  K  M    897

2761  TGGAACGCTGGCCGTCCACCCAGGAATGGATCGTAATCTCCTATATTTTCACCCTGGGAA  2820
 898    E  R  W  P  S  T  Q  E  W  I  V  I  S  Y  I  F  T  L  G  I    917

2821  TAGAAAAGATGAGAGAGATTCTGATGTCAGAGCCAGGGAAGTTGCTACAGAAAGTGAAGG  2880
 918    E  K  M  R  E  I  L  M  S  E  P  G  K  L  L  Q  K  V  K  V    937

2881  TATGGCTGCAGGAGTACTGGAATGTCACGGACCTCATCGCCATCCTTCTGTTTTCTGTCG  2940
 938    W  L  Q  E  Y  W  N  V  T  D  L  I  A  I  L  L  F  S  V  G    957

2941  GAATGATCCTTCGTCTCCAAGACCAGCCCTTCAGGAGTGACGGGAGGGTCATCTACTGCG  3000
 958    M  I  L  R  L  Q  D  Q  P  F  R  S  D  G  R  V  I  Y  C  V    977

3001  TGAACATCATTTACTGGTATATCCGTCTCCTAGACATCTTCGGCGTGAACAAGTATTTGG  3060
 978    N  I  I  Y  W  Y  I  R  L  L  D  I  F  G  V  N  K  Y  L  G    997
```

FIG. 3D

```
3061  GCCCGTATGTAATGATGATTGGAAAAATGATGATAGACATGATGTACTTTGTCATCATTA  3120
 998                                                               1017

3121  TGCTGGTGGTTCTGATGAGCTTTGGGGTCGCCAGGCAAGCCATCCTTTTTCCCAATGAGG  3180
1018                                                              1037

3181  AGCCATCATGGAAACTGGCCAAGAACATCTTCTACATGCCCTATTCGATGATTTATGGGG  3240
1038                                                              1057

3241  AAGTGTTTGCGGACCAGATAGACCGTAAGCAAGTTTATGATTCTCATACACCAAAGTCAG  3300
1058                                                              1077

3301  CTCCCTGTGGACAGAATGAGACCCGAGAGGATGGTAAAATAATCCAGCTGCCTCCCTGCA  3360
1078                                                              1097

3361  AGACAGGAGCTTGGATCGTGCCGGCCATCATGGCCTGCTACCTCTTAGTGGCAAACATCT  3420
1098                                                              1117

3421  TGCTGGTCAACCTCCTCATTGCTGTCTTTAACAATACATTTTTTGAAGTAAAATCGATAT  3480
1118                          N  N  T  F  F  E  V  K  S  I  S    1137

3481  CCAACCAAGTCTGGAAGTTTCAGAGGTATCAGCTCATCATGACTTTCCATGAAAGGCCAG  3540
1138   N  Q  V  W  R  P  Q  R  Y  Q  L  I  M  T  F  H  E  R  P  V 1157

3541  TTCTGCCCCCACCACTGATCATCTTCAGCCACATGACCATGATATTCCAGCACCTGTGCT  3600
1158   L  P  P  P  L  I  I  F  S  H  M  T  M  I  F  Q  H  L  C  C 1177

3601  GCCGATGGAGGAAACACGAGAGCGACCCGGATGAAAGGGACTACGGCCTGAAACTCTTCA  3660
1178   R  W  R  K  H  E  S  D  P  D  E  R  D  Y  G  L  K  L  F  I 1197

3661  TAACCGATGATGAGCTCAAGAAAGTACATGACTTTGAAGAGCAATGCATAGAAGAATACT  3720
1198   T  D  D  E  L  K  K  V  H  D  F  E  E  Q  C  I  E  E  Y  F 1217

3721  TCAGAGAAAAGGATGATCGGTTCAACTCATCTAATGATGAGAGGATACGGGTGACTTCAG  3780
1218   R  E  K  D  D  R  F  N  S  S  N  D  E  R  I  R  V  T  S  E 1237

3781  AAAGGGTGGAGAACATGTCTATGCGGCTGGAGGAAGTCAACGAGAGAGACCACTCCATGA  3840
1238   R  V  E  N  M  S  M  R  L  E  E  V  N  E  R  E  H  S  M  K 1257

3841  AGGCTTCACTCCAGACCGTGGACATCCGGCTGGCGCAGCTGGAAGACCTTATCGGGCGCA  3900
1258   A  S  L  Q  T  V  D  I  R  L  A  Q  L  E  D  L  I  G  R  M 1277

3901  TGGCCACGGCCCTGGAGCGCCTGACAGGTCTGGAGCGGGCCGAGTCCAACAAAATCCGCT  3960
1278   A  T  A  L  E  R  L  T  G  L  E  R  A  E  S  N  K  I  R  S 1297

3961  CGAGGACCTCGTCAGACTGCACGGACGCCGCCTACATTGTCCGTCAGAGCAGCTTCAACA  4020
1298   R  T  S  S  D  C  T  D  A  A  Y  I  V  R  Q  S  S  F  N  S 1317

4021  GCCAGGAAGGGAACACCTTCAAGCTCCAAGAGAGTATAGACCCTGCAGGTGAGGAGACCA  4080
1318   Q  E  G  N  T  F  K  L  Q  E  S  I  D  P  A  G  E  E  T  M 1337
```

FIG. 3E

```
4081  TGTCCCCAACTTCTCCAACCTTAATGCCCCGTATGCGAAGCCATTCTTTCTATTCAGTCA  4140
1338    S   P   T   S   P   T   L   M   P   R   M   R   S   H   S   F   Y   S   V   N   1357

4141  ATATGAAAGACAAAGGTGGTATAGAAAAGTTGGAAAGTATTTTTAAAGAAAGGTCCCTGA  4200
1358    M   K   D   K   G   G   I   E   K   L   E   S   I   F   K   E   R   S   L   S   1377

4201  GCCTACACCGGGCTACTAGTTCCCACTCTGTAGCAAAAGAACCCAAAGCTCCTGCAGCCC  4260
1378    L   H   R   A   T   S   S   H   S   V   A   K   E   P   K   A   P   A   A   P   1397

4261  CTGCCAACACCTTGGCCATTGTTCCTGATTCCAGAAGACCATCATCGTGTATAGACATCT  4320
1398    A   N   T   L   A   I   V   P   D   S   R   R   P   S   S   C   I   D   I   Y   1417

4321  ATGTCTCTGCTATGGATGAGCTCCACTGTGATATAGACCCTCTGGACAATTCCGTGAACA  4380
1418    V   S   A   M   D   E   L   H   C   D   I   D   P   L   D   N   S   V   N   I   1437

4381  TCCTTGGGCTAGGCGAGCCAAGCTTTTCAACTCCAGTACCTTCCACAGCCCCTTCAAGTA  4440
1438    L   G   L   G   E   P   S   F   S   T   P   V   P   S   T   A   P   S   S   S   1457

4441  GTGCCTATGCAACACTTGCACCCACAGACAGACCTCCAAGCCGGAGCATTGATTTTGAGG  4500
1458    A   Y   A   T   L   A   P   T   D   R   P   P   S   R   S   I   D   F   E   D   1477

4501  ACATCACCTCCATGGACACTAGATCTTTTTCTTCAGACTACACCCACCTCCCAGAATGCC  4560
1478    I   T   S   M   D   T   R   S   F   S   S   D   Y   T   H   L   P   E   C   Q   1497

4561  AAACCCCTGGGACTCAGAGCCTCCGATGTACCACACCATTGAGCGTTCCAAAAGTAGCC  4620
1498    N   P   W   D   S   E   P   P   M   Y   H   T   I   E   R   S   K   S   S   R   1517

4621  GCTACCTAGCCACCACACCCTTTCTTCTAGAAGAGGCTCCCATTGTGAAATCTCATAGCT  4680
1518    Y   L   A   T   T   P   F   L   L   E   E   A   P   I   V   K   S   H   S   F   1537

4681  TTATGTTTTCCCCCTCAAGGAGCTATTATGCCAACTTTGGGGTGCCTGTAAAAACAGCAG  4740
1538    M   F   S   P   S   R   S   Y   Y   A   N   F   G   V   P   V   K   T   A   E   1557

4741  AATACACAAGTATTACAGACTGTATTGACACAAGGTGTGTCAATGCCCCTCAAGCAATTG  4800
1558    Y   T   S   I   T   D   C   I   D   T   R   C   V   N   A   P   Q   A   I   A   1577

4801  CGGACAGAGCTGCCTTCCCTGGAGGTCTTGGAGACAAAGTGGAGGACTTAACTTGCTGCC  4860
1578    D   R   A   A   F   P   G   G   L   G   D   K   V   E   D   L   T   C   C   H   1597

4861  ATCCAGAGCGAGAAGCAGAACTGAGTCACCCCAGCTCTGACAGTGAGGAGAATGAGGCCA  4920
1598    P   E   R   E   A   E   L   S   H   P   S   S   D   S   E   E   N   E   A   K   1617

4921  AAGGCCGCAGAGCCACCATTGCAATATCCTCCCAGGAGGGTGATAACTCAGAGAGAACCC  4980
1618    G   R   R   A   T   I   A   I   S   S   Q   E   G   D   N   S   E   R   T   L   1637

4981  TGTCCAACAACATCACTGTTCCCAAGATAGAGCGCGCCAACAGCTACTCGGCAGAGGAGC  5040
1638    S   N   N   I   T   V   P   K   I   E   R   A   N   S   Y   S   A   E   E   P   1657

5041  CAAGTGCGCCATATGCACACACCAGGAAGAGCTTCTCCATCAGTGACAAACTCGACAGGC  5100
1658    S   A   P   Y   A   H   T   R   K   S   F   S   I   S   D   K   L   D   R   Q   1677
```

FIG. 3F

```
5101  AGCGGAACACAGCAAGCCTGCAAAATCCCTTCCAGAGAAGCAAGTCCTCCAAGCCGGAGG   5160
1678    R   N   T   A   S   L   Q   N   P   F   Q   R   S   K   S   S   K   P   E   G   1697

5161  GCCGAGGGGACAGCCTGTCCATGAGGAGACTGTCCAGAACATCGGCTTTCCAAAGCTTTG   5220
1698    R   G   D   S   L   S   M   R   R   L   S   R   T   S   A   F   Q   S   F   E   1717

5221  AAAGCAAGCACACCTAA   5237
1718    S   K   H   T      1721
```

FIG. 4A

```
  1 CGCCCGCGGCGAGGAGCCAGCGAGAGCGCTCGGCGCTGGGCTGTTTCCCGGCCGAGGGAG   60

61 GCGAACTTCTCATGGGGAAGAAGTGGAGGGATGCGGCGGAAATGGAGCGGGGCTGCTCCG  120
  1              M  G  K  K  W  R  D  A  A  E  M  E  R  G  C  S  D   17

121 ACCGCGAGGACAACGCGGAGAGCCGCAGACGCAGCCGGAGCGCCAGCCGGGGCAGGTTTG  180
 18  R  E  D  N  A  E  S  R  R  R  S  R  S  A  S  R  G  R  F  A    37

181 CCGAGTCGTGGAAAAGGTTAAGTTCCAAGCAGGGGTCCACCAAACGCTCGGGACTCCCGT  240
 38  E  S  W  K  R  L  S  S  K  Q  G  S  T  K  R  S  G  L  P  S    57

241 CGCAGCAGACGCCGGCTCAGAAATCCTGGATAGAAAGAGCATTTTATAAAAGAGAATGTG  300
 58  Q  Q  T  P  A  Q  K  S  W  I  E  R  A  F  Y  K  R  E  C  V    77

301 TCCACATCATACCCAGCACCAAAGACCCCCATAGGTGTTGCTGTGGGCGTCTGATAGGCC  360
 78  H  I  I  P  S  T  K  D  P  H  R  C  C  G  R  L  I  G  Q       97

361 AGCATGTTGGCCTCACCCCCAGTATCTCCGTGCTTCAGAATGAGAAAAATGAAAGTCGCC  420
 98  H  V  G  L  T  P  S  I  S  V  L  Q  N  E  K  N  E  S  R  L   117

421 TCTCCCGAAATGACATCCAGTCTGAAAAGTGGTCCATCAGCAAACACACTCAACTCAGCC  480
118  S  R  N  D  I  Q  S  E  K  W  S  I  S  K  H  T  Q  L  S  P   137

481 CTACGGATGCTTTTGGGACCATTGAGTTCCAAGGAGGTGGCCATTCCAACAAAGCCATGT  540
138  T  D  A  F  G  T  I  E  F  Q  G  G  G  H  S  N  K  A  M  Y   157

541 ATGTGCGAGTATCTTTTGATACAAAACCTGATCTCCTCTTACACCTGATGACCAAGGAAT  600
158  V  R  V  S  F  D  T  K  P  D  L  L  L  H  L  M  T  K  E  W   177

601 GGCAGTTGGAGCTTCCCAAGCTTCTCATCTCTGTCCATGGGGGCCTGCAGAACTTTGAAC  660
178  Q  L  E  L  P  K  L  L  I  S  V  H  G  G  L  Q  N  F  E  L   197

661 TCCAGCCAAAACTCAAGCAAGTCTTTGGGAAAGGGCTCATCAAAGCAGCAATGACAACTG  720
198  Q  P  K  L  K  Q  V  F  G  K  G  L  I  K  A  A  M  T  T  G   217

721 GAGCGTGGATATTCACTGGAGGGGTTAACACAGCTGTTATTCGTCATGTTGGCGATGCCT  780
218  A  W  I  F  T  G  G  V  N  T  G  V  I  R  H  V  G  D  A  L   237

781 TGAAGGATCATGCCTCTAAGTCTCGAGGAAAGATATGCACCATAGGTATTGCCCCCTGGG  840
238  K  D  H  A  S  K  S  R  G  K  I  C  T  I  G  I  A  P  W  G   257

841 GAATTGTGGAAAACCAGGAGGACCTCATTGGAAGAGATGTTGTCCGGCCATACCAGACCA  900
258  I  V  E  N  Q  E  D  L  I  G  R  D  V  V  R  P  Y  Q  T  M   277

901 TGTCCAATCCCATGAGCAAGCTCACTGTTCTCAACAGCATGCATTCCCACTTCATTCTGG  960
278  S  N  P  M  S  K  L  T  V  L  N  S  M  H  S  H  F  I  L  A   297

961 CTGACAACGGGACCACTGGAAAATATGGAGCAGAGGTGAAACTTCGAAGACAACTGGAAA 1020
298  D  N  G  T  T  G  K  Y  G  A  E  V  K  L  R  R  Q  L  E  K   317
```

FIG. 4B

```
1021  AGCATATTTCACTCCAGAAGATAAACACAAGAATCGGTCAAGGTGTTCCTGTGGTGGCAC  1080
 318    H  I  S  L  Q  K  I  N  T  R  I  G  Q  G  V  P  V  V  A  L   337

1081  TCATAGTGGAAGGAGGACCCAATGTGATCTCGATTGTTTTGGAGTACCTTCGAGACACCC  1140
 338    I  V  E  G  G  P  N  V  I  S  I  V  L  E  Y  L  R  D  T  P   357

1141  CTCCCGTGCCAGTCGTTGTCTGTGATGGGAGTGGACGGGCATCGGACATCCTGGCCTTTG  1200
 358    P  V  P  V  V  V  C  D  G  S  G  R  A  S  D  I  L  A  F  G   377

1201  GGCATAAATACTCAGAAGAAGGCGGACTGATAAATGAATCTTTGAGGGACCAGCTGTTGG  1260
 378    H  K  Y  S  E  E  G  G  L  I  N  E  S  L  R  D  Q  L  L  V   397

1261  TGACTATACAGAAGACTTTCACATACACTCGAACCCAAGCTCAGCATCTGTTCATCATCC  1320
 398    T  I  Q  K  T  F  T  Y  T  R  T  Q  A  Q  H  L  F  I  I  L   417

1321  TCATGGAGTGCATGAAGAAGAAGGAATTGATTACGGTATTTCGGATGGGATCAGAAGGAC  1380
 418    M  E  C  M  K  K  K  E  L  I  T  V  F  R  M  G  S  E  G  H   437

1381  ACCAGGACATTGATTTGGCTATCCTGACAGCTTTACTCAAAGGAGCCAATGCCTCGGCCC  1440
 438    Q  D  I  D  L  A  I  L  T  A  L  L  K  G  A  N  A  S  A  P   457

1441  CAGACCAACTGAGCTTAGCTTTAGCCTGGAACAGAGTCGACATCGCTCGCAGCCAGATCT  1500
 458    D  Q  L  S  L  A  L  A  W  N  R  V  D  I  A  R  S  Q  I  F   477

1501  TTATTTACGGGCAACAGTGGCCGGTGGGATCTCTCGACCAAGCCATGTTGGATGCCTTAG  1560
 478    I  Y  G  Q  Q  W  P  V  G  S  L  E  Q  A  M  L  D  A  L  V   497

1561  TTCTGGACAGAGTGGATTTTGTGAAATTACTCATAGAGAATGGAGTAAGCATGCACCGTT  1620
 498    L  D  R  V  D  F  V  K  L  L  I  E  N  G  V  S  M  H  R  F   517

1621  TTCTCACCATCTCCAGACTAGAGGAATTGTACAATACGAGACATGGGCCCTCAAATACAT  1680
 518    L  T  I  S  R  L  E  E  L  Y  N  T  R  H  G  P  S  N  T  L   537

1681  TGTACCACTTGGTCAGGGATGTCAAAAAGGGGAACCTGCCCCAGACTACAGAATCAGCC  1740
 538    Y  H  L  V  R  D  V  K  K  G  N  L  P  P  D  Y  R  I  S  L   557

1741  TGATTGACATCGGCCTGGTGATCGAGTACCTGATGGGCGGGGCTTATCGCTGCAACTACA  1800
 558    I  D  I  G  L  V  I  E  Y  L  M  G  G  A  Y  R  C  N  Y  T   577

1801  CGCGCAAGCGCTTCCGGACCCTCTACCACAACCTCTTCGGCCCCAAGAGGGATGATATTC  1860
 578    R  K  R  F  R  T  L  Y  H  N  L  F  G  P  K  R  D  D  I  P   597

1861  CCTTGAGGCGAGGAAGAAAGACAACCAAGAAACGTGAAGAAGACGTGGACATTGACTTGG  1920
 598    L  R  R  G  R  K  T  T  K  K  R  E  E  V  D  I  D  L  D   617

1921  ATGATCCTGAGATCAACCACTTCCCCTTCCCTTTCCATGAGCTCATGGTGTGGGCTGTTC  1980
 618    D  P  E  I  N  H  F  P  F  P  F  H  E  L  M  V  W  A  V  L   637

1981  TCATGAAGCGGCAGAAGATGGCCCTGTTCTTCTGGCAGCACGGTGAGGAGGCCATGGCCA  2040
 638    M  K  R  Q  K  M  A  L  F  F  W  Q  H  G  E  E  A  M  A  K   657
```

FIG. 4C

```
2041  AGGCCCTGGTGGCCTGCAAGCTCTGCAAAGCCATGGCTCATGAGGCCTCTGAGAACGACA  2100
658     A   L   V   A   C   K   L   C   K   A   M   A   H   E   A   S   E   N   D   M    677

2101  TGGTTGACGACATTTCCCAGGAGCTGAATCACAATTCCAGAGACTTTGGCCAGCTGGCTG  2160
678     V   D   D   I   S   Q   E   L   N   H   N   S   R   D   F   G   Q   L   A   V    697

2161  TGGAGCTCCTGGACCAGTCCTACAAGCAGGACGAACAGCTGGCCATGAAACTGCTGACGT  2220
698     E   L   L   D   Q   S   Y   K   Q   D   E   Q   L   A   M   K   L   L   T   Y    717

2221  ATGAGCTGAAGAACTGGAGCAACGCCACGTGCCTGCAGCTTGCCGTGGCTGCCAAACACC  2280
718     E   L   K   N   W   S   N   A   T   C   L   Q   L   A   V   A   A   K   H   R    737

2281  GCGACTTCATCGCGCACACGTGCAGCCAGATGCTGCTCACCGACATGTGGATGGGCCGGC  2340
738     D   F   I   A   H   T   C   S   Q   M   L   L   T   D   M   W   M   G   R   L    757

2341  TCCGCATGCGCAAGAACTCAGGCCTCAAGGTAATTCTGGGAATTCTACTTCCTCCTTCAA  2400
758     R   M   R   K   N   S   G   L   K   V   I   L   G   I   L   L   P   P   S   I    777

2401  TTCTCAGCTTGGAGTTCAAGAACAAAGACGACATGCCCTATATGTCTCAGGCCCAGGAAA  2460
778     L   S   L   E   F   K   N   K   D   D   M   P   Y   M   S   Q   A   Q   E   I    797

2461  TCCACCTCCAAGAGAAGGAGGCAGAAGAACCAGAGAAGCCCACAAAGGAAAAAGAGGAAG  2520
798     H   L   Q   E   K   E   A   E   E   P   E   K   P   T   K   E   K   E   E    817

2521  AGGACATGGAGCTCACAGCAATGTTGGGACGAAACAACGGGGAGTCCTCCAGGAAGAAGG  2580
818     D   M   E   L   T   A   M   L   G   R   N   N   G   E   S   S   R   K   K   D    837

2581  ATGAAGAGGAAGTTCAGAGCAAGCACCGGTTAATCCCCCTCGGCAGAAAAATCTATGAAT  2640
838     E   E   E   V   Q   S   K   H   R   L   I   P   L   G   R   K   I   Y   E   F    857

2641  TCTACAATGCACCCATCGTGAAGTTCTGGTTCTACACACTGGCGTATATCGGATACCTGA  2700
858     Y   N   A   P   I   V   K   F   W   F   Y   T   L   A   Y   I   G   Y   L   M    877

2701  TGCTCTTCAACTATATCGTGTTAGTGAAGATGGAACGCTGGCCGTCCACCCAGGAATGGA  2760
878     L   F   N   Y   I   V   L   V   K   M   E   R   W   P   S   T   Q   E   W    897

2761  TCGTAATCTCCTATATTTTCACCCTGGGAATAGAAAAGATGAGAGAGATTCTGATGTCAG  2820
898     I   V   I   S   Y   I   F   T   L   G   I   E   K   M   R   E   I   L   M   S    917

2821  AGCCAGGGAAGTTGCTACAGAAAGTGAAGGTATGGCTGCAGGAGTACTGGAATGTCACGG  2880
918     E   P   G   K   L   L   Q   K   V   K   V   W   L   Q   E   Y   W   N   V   T    937

2881  ACCTCATCGCCATCCTTCTGTTTTCTGTCGGAATGATCCTTCGTCTCCAAGACCAGCCCT  2940
938     D   L   I   A   I   L   L   F   S   V   G   M   I   L   R   L   Q   D   Q   P    957

2941  TCAGGAGTGACGGGAGGGTCATCTACTGCGTGAACATCATTTACTGGTATATCCGTCTCC  3000
958     F   R   S   D   G   R   V   I   Y   C   V   N   I   I   Y   W   Y   I   R   L    977

3001  TAGACATCTTCGGCGTGAACAAGTATTTGGGCCCGTATGTAATGATGATTGGAAAAATGA  3060
978     L   D   I   F   G   V   N   K   Y   L   G   P   Y   V   M   M   I   G   K   M    997
```

FIG. 4D

```
3061 TGATAGACATGATGTACTTTGTCATCATTATGCTGGTGGTTCTGATGAGCTTTGGGGTCG 3120
 998  T  D  M  M  Y  F  V  I  I  M  L  V  V  L  M  S  F  G  V       1017

3121 CCAGGCAAGCCATCCTTTTTCCCAATGAGGAGCCATCATGGAAACTGGCCAAGAACATCT 3180
1018  R  Q  A  I  L  F  P  N  E  E  P  S  W  K  L  A  K  N  I       1037

3181 TCTACATGCCCTATTGGATGATTTATGGGGAAGTGTTTGCGGACCAGATAGACCCTCCCT 3240
1038  L  Y  M  P  Y  W  M  I  Y  G  E  V  F  A  D  Q  I  D  P  P    1057

3241 GTGGACAGAATGAGACCCGAGAGGATGGTAAAATAATCCAGCTGCCTCCCTGCAAGACAG 3300
1058  C  G  Q  N  E  T  R  E  D  G  K  I  I  Q  L  P  P  C  K  T    1077

3301 GAGCTTGGATCGTGCCGGCCATCATGGCCTGCTACCTCTTAGTGGCAAACATCTTGCTGG 3360
1078  G  A  W  I  V  P  A  I  M  A  C  Y  L  L  V  A  N  I  L  L    1097

3361 TCAACCTCCTCATTGCTGTCTTTAACAATACATTTTTTGAAGTAAAATCGATATCCAACC 3420
1098  V  N  L  L  I  A  V  F  N  N  T  F  F  E  V  K  S  I  S  N  Q 1117

3421 AAGTCTGGAAGTTTCAGAGGTATCAGCTCATCATGACTTTCCATGAAAGGCCAGTTCTGC 3480
1118  V  W  K  F  Q  R  Y  Q  L  I  M  T  F  H  E  R  P  V  L       1137

3481 CCCCACCACTGATCATCTTCAGCCACATGACCATGATATTCCAGCACCTGTGCTGCCGAT 3540
1138  P  P  L  I  I  F  S  H  M  T  M  I  F  Q  H  L  C  C  R  W    1157

3541 GGAGGAAACACGAGAGCGACCCGGATGAAAGGGACTACGGCCTGAAACTCTTCATAACCG 3600
1158  R  K  H  E  S  D  P  D  E  R  D  Y  G  L  K  L  F  I  T  D    1177

3601 ATGATGAGCTCAAGAAAGTACATGACTTTGAAGAGCAATGCATAGAAGAATACTTCAGAG 3660
1178  D  E  L  K  K  V  H  D  F  E  E  Q  C  I  E  E  Y  F  R  E    1197

3661 AAAAGGATGATCGGTTCAACTCATCTAATGATGAGAGGATACGGGTGACTTCAGAAAGGG 3720
1198  K  D  D  R  F  N  S  S  N  D  E  R  I  R  V  T  S  E  R  V    1217

3721 TGGAGAACATGTCTATGCGGCTGGAGGAAGTCAACGAGAGAGAGCACTCCATGAAGGCTT 3780
1218  E  N  M  S  M  R  L  E  E  V  N  E  R  E  H  S  M  K  A  S    1237

3781 CACTCCAGACCGTGGACATCCGGCTGGCGCAGCTGGAAGACCTTATCGGGCGCATGGCCA 3840
1238  L  Q  T  V  D  I  R  L  A  Q  L  E  D  L  I  G  R  M  A  T    1257

3841 CGGCCCTGGAGCGCCTGACAGGTCTGGAGCGGGCCGAGTCCAACAAAATCCGCTCGAGGA 3900
1258  A  L  E  R  L  T  G  L  E  R  A  E  S  N  K  I  R  S  R  T    1277

3901 CCTCGTCAGACTGCACGGACGCCGCCTACATTGTCCGTCAGAGCAGCTTCAACAGCCAGG 3960
1278  S  S  D  C  T  D  A  A  Y  I  V  R  Q  S  S  F  N  S  Q  E    1297

3961 AAGGGAACACCTTCAAGCTCCAAGAGAGTATAGACCCTGCAGGTGAGGAGACCATGTCCC 4020
1298  G  N  T  F  K  L  Q  E  S  I  D  P  A  G  E  E  T  M  S  P    1317

4021 CAACTTCTCCAACCTTAATGCCCCGTATGCGAAGCCATTCTTTCTATTCAGTCAATATGA 4080
1318  T  S  P  T  L  M  P  R  M  R  S  H  S  F  Y  S  V  N  M  K    1337
```

FIG. 4E

```
4081 AAGACAAAGGTGGTATAGAAAAGTTGGAAAGTATTTTTAAAGAAAGGTCCCTGAGCCTAC 4140
1338   D  K  G  G  I  E  K  L  E  S  I  F  K  E  R  S  L  S  L  H  1357

4141 ACCGGGCTACTAGTTCCCACTCTGTAGCAAAAGAACCCAAAGCTCCTGCAGCCCCTGCCA 4200
1358   R  A  T  S  S  H  S  V  A  K  E  P  K  A  P  A  A  P  A  N  1377

4201 ACACCTTGGCCATTGTTCCTGATTCCAGAAGACCATCATCGTGTATAGACATCTATGTCT 4260
1378   T  L  A  I  V  P  D  S  R  R  P  S  S  C  I  D  I  Y  V  S  1397

4261 CTGCTATGGATGAGCTCCACTGTGATATAGACCCTCTGGACAATTCCGTGAACATCCTTG 4320
1398   A  M  D  E  L  H  C  D  I  D  P  L  D  N  S  V  N  I  L  G  1417

4321 GGCTAGGCGAGCCAAGCTTTTCAACTCCAGTACCTTCCACAGCCCCTTCAAGTAGTGCCT 4380
1418   L  G  E  P  S  F  S  T  P  V  P  S  T  A  P  S  S  S  A  Y  1437

4381 ATGCAACACTTGCACCCACAGACAGACCTCCAAGCCGGAGCATTGATTTTGAGGACATCA 4440
1438   A  T  L  A  P  T  D  R  P  P  S  R  S  I  D  F  E  D  I  T  1457

4441 CCTCCATGGACACTAGATCTTTTTCTTCAGACTACACCCACCTCCCAGAATGCCAAAACC 4500
1458   S  M  D  T  R  S  F  S  S  D  Y  T  H  L  P  E  C  Q  N  P  1477

4501 CCTGGGACTCAGAGCCTCCGATGTACCACACCATTGAGCGTTCCAAAAGTAGCCGCTACC 4560
1478   W  D  S  E  P  P  M  Y  H  T  I  E  R  S  K  S  S  R  Y  L  1497

4561 TAGCCACCACACCCTTTCTTCTAGAAGAGGCTCCCATTGTGAAATCTCATAGCTTTATGT 4620
1498   A  T  T  P  F  L  L  E  E  A  P  I  V  K  S  H  S  F  M  F  1517

4621 TTTCCCCCTCAAGGAGCTATTATGCCAACTTTGGGGTGCCTGTAAAAACAGCAGAATACA 4680
1518   S  P  S  R  S  Y  Y  A  N  F  G  V  P  V  K  T  A  E  Y  T  1537

4681 CAAGTATTACAGACTGTATTGACACAAGGTGTGTCAATGCCCCTCAAGCAATTGCGGACA 4740
1538   S  I  T  D  C  I  D  T  R  C  V  N  A  P  Q  A  I  A  D  R  1557

4741 GAGCTGCCTTCCCTGGAGGTCTTGGAGACAAAGTGGAGGACTTAACTTGCTGCCATCCAG 4800
1558   A  A  F  P  G  G  L  G  D  K  V  E  D  L  T  C  C  H  P  E  1577

4801 AGCGAGAAGCAGAACTGAGTCACCCCAGCTCTGACAGTGAGGAGAATGAGGCCAAAGGCC 4860
1578   R  E  A  E  L  S  H  P  S  S  D  S  E  E  N  E  A  K  G  R  1597

4861 GCAGAGCCACCATTGCAATATCCTCCCAGGAGGGTGATAACTCAGAGAGAACCCTGTCCA 4920
1598   R  A  T  I  A  I  S  S  Q  E  G  D  N  S  E  R  T  L  S  N  1617

4921 ACAACATCACTGTTCCCAAGATAGAGCGCGCCAACAGCTACTCGGCAGAGGAGCCAAGTG 4980
1618   N  I  T  V  P  K  I  E  R  A  N  S  Y  S  A  E  E  P  S  A  1637

4981 CGCCATATGCACACACCAGGAAGAGCTTCTCCATCAGTGACAAACTCGACAGGCAGCGGA 5040
1638   P  Y  A  H  T  R  K  S  F  S  I  S  D  K  L  D  R  Q  R  N  1657

5041 ACACAGCAAGCCTGCAAAATCCCTTCCAGAGAAGCAAGTCCTCCAAGCCGGAGGGCCGAG 5100
1658   T  A  S  L  Q  N  P  F  Q  R  S  K  S  S  K  P  E  G  R  G  1677
```

FIG. 4F

```
5101  GGGACAGCCTGTCCATGAGGAGACTGTCCAGAACATCGGCTTTCCAAAGCTTTGAAAGCA  5160
1678    D   S   L   S   M   R   R   L   S   R   T   S   A   F   Q   S   F   E   S   K   1697

5161  AGCACACCTAA  5171
1698    H   T      1699
```

FIG. 5A

```
   1 CGCCCGCGGCGAGGAGCCAGCGAGAGCGCTCGGCGCTGGGCTGTTTCCCGGCCGAGGGAG    60

61 GCGAACTTCTCATGGGGAAGAAGTGGAGGGATGCGGCGGAAATGGAGCGGGGCTGCTCCG   120
   1             M  G  K  K  W  R  D  A  A  E  M  E  R  G  C  S  D   17

121 ACCGCGAGGACAACGCGGAGAGCCGCAGACGCAGCCGGAGCGCCAGCCGGGGCAGGTTTG   180
  18  R  E  D  N  A  E  S  R  R  R  S  R  S  A  S  R  G  R  F  A    37

181 CCGAGTCGTGGAAAAGGTTAAGTTCCAAGCAGGGGTCCACCAAACGCTCGGGACTCCCGT   240
  38  E  S  W  K  R  L  S  S  K  Q  G  S  T  K  R  S  G  L  P  S    57

241 CGCAGCAGACGCCGGCTCAGAAATCCTGGATAGAAAGAGCATTTTATAAAAGAGAATGTG   300
  58  Q  Q  T  P  A  Q  K  S  W  I  E  R  A  F  Y  K  R  E  C  V    77

301 TCCACATCATACCCAGCACCAAAGACCCCCATAGGTGTTGCTGTGGGCGTCTGATAGGCC   360
  78  H  I  I  P  S  T  K  D  P  H  R  C  C  C  G  R  L  I  G  Q    97

361 AGCATGTTGGCCTCACCCCCAGTATCTCCGTGCTTCAGAATGAGAAAAATGAAGTCGCC   420
  98  H  V  G  L  T  P  S  I  S  V  L  Q  N  E  K  N  E  S  R  L   117

421 TCTCCCGAAATGACATCCAGTCTGAAAAGTGGTCCATCAGCAAACACACTCAACTCAGCC   480
 118  S  R  N  D  I  Q  S  E  K  W  S  I  S  K  H  T  Q  L  S  P   137

481 CTACGGATGCTTTTGGGACCATTGAGTTCCAAGGAGGTGGCCATTCCAACAAAGCCATGT   540
 138  T  D  A  F  G  T  I  E  F  Q  G  G  G  H  S  N  K  A  M  Y   157

541 ATGTGCGAGTATCTTTTGATACAAAACCTGATCTCCTCTTACACCTGATGACCAAGGAAT   600
 158  V  R  V  S  F  D  T  K  P  D  L  L  L  H  L  M  T  K  E  W   177

601 GGCAGTTGGAGCTTCCCAAGCTTCTCATCTCTGTCCATGGGGGCCTGCAGAACTTTGAAC   660
 178  Q  L  E  L  P  K  L  L  I  S  V  H  G  G  L  Q  N  F  E  L   197

661 TCCAGCCAAAACTCAAGCAAGTCTTTGGGAAAGGGCTCATCAAAGCAGCAATGACAACTG   720
 198  Q  P  K  L  K  Q  V  F  G  K  G  L  I  K  A  A  M  T  T  G   217

721 GAGCGTGGATATTCACTGGAGGGGTTAACACAGGTGTTATTCGTCATGTTGGCGATGCCT   780
 218  A  W  I  F  T  G  G  V  N  T  G  V  I  R  H  V  G  D  A  L   237

781 TGAAGGATCATGCCTCTAAGTCTCGAGGAAAGATATGCACCATAGGTATTGCCCCCTGGG   840
 238  K  D  H  A  S  K  S  R  G  K  I  C  T  I  G  I  A  P  W  G   257

841 GAATTGTGGAAAACCAGGAGGACCTCATTGGAAGAGATGTTGTCCGGCCATACCAGACCA   900
 258  I  V  E  N  Q  E  D  L  I  G  R  D  V  V  R  P  Y  Q  T  M   277

901 TGTCCAATCCCATGAGCAAGCTCACTGTTCTCAACAGCATGCATTCCCACTTCATTCTGG   960
 278  S  N  P  M  S  K  L  T  V  L  N  S  M  H  S  H  F  I  L  A   297

961 CTGACAACGGGACCACTGGAAAATATGGAGCAGAGGTGAAACTTCGAAGACAACTGGAAA  1020
 298  D  N  G  T  T  G  K  Y  G  A  E  V  K  L  R  R  Q  L  E  K   317
```

FIG. 5B

```
1021 AGCATATTTCACTCCAGAAGATAAACACAAGAATCGGTCAAGGTGTTCCTGTGGTGGCAC 1080
 318   H  I  S  L  Q  K  I  N  T  R  I  G  Q  G  V  P  V  V  A  L    337

1081 TCATAGTGGAAGGAGGACCCAATGTGATCTCGATTGTTTTGGAGTACCTTCGAGACACCC 1140
 338   I  V  E  G  G  P  N  V  I  S  I  V  L  E  Y  L  R  D  T  P    357

1141 CTCCCGTGCCAGTGGTTGTCTGTGATGGGAGTGGACGGGCATCGGACATCCTGGCCTTTG 1200
 358   P  V  P  V  V  C  D  G  S  G  R  A  S  D  I  L  A  F  G    377

1201 GGCATAAATACTCAGAAGAAGGCGGACTGATAAATGAATCTTTGAGGGACCAGCTGTTGG 1260
 378   H  K  Y  S  E  E  G  G  L  I  N  E  S  L  R  D  Q  L  L  V    397

1261 TGACTATACAGAAGACTTTCACATACACTCGAACCCAAGCTCAGCATCTGTTCATCATCC 1320
 398   T  I  Q  K  T  F  T  Y  T  R  T  Q  A  Q  H  L  F  I  I  L    417

1321 TCATGGAGTGCATGAAGAAGAAGGAATTGATTACGGTATTTCGGATGGGATCAGAAGGAC 1380
 418   M  E  C  M  K  K  K  E  L  I  T  V  F  R  M  G  S  E  G  H    437

1381 ACCAGGACATTGATTTGGCTATCCTGACAGCTTTACTCAAAGGAGCCAATGCCTCGGCCC 1440
 438   Q  D  I  D  L  A  I  L  T  A  L  L  K  G  A  N  A  S  A  P    457

1441 CAGACCAACTGAGCTTAGCTTTAGCCTGGAACAGAGTCGACATCGCTCGCAGCCAGATCT 1500
 458   D  Q  L  S  L  A  L  A  W  N  R  V  D  I  A  R  S  Q  I  F    477

1501 TTATTTACGGGCAACAGTGGCCGGTGGGATCTCTGGAGCAAGCCATGTTGGATGCCTTAG 1560
 478   I  Y  G  Q  Q  W  P  V  G  S  L  E  Q  A  M  L  D  A  L  V    497

1561 TTCTGGACAGAGTGGATTTTGTGAAATTACTCATAGAGAATGGAGTAAGCATGCACCGTT 1620
 498   L  D  R  V  D  F  V  K  L  L  I  E  N  G  V  S  M  H  R  F    517

1621 TTCTCACCATCTCCAGACTAGAGGAATTGTACAATACGAGACATGGGCCCTCAAATACAT 1680
 518   L  T  I  S  R  L  E  E  L  Y  N  T  R  H  G  P  S  N  T  L    537

1681 TGTACCACTTGGTCAGGGATGTCAAAAAGCGAGAGTATCCAGGTTTCGGTTGGATCTATT 1740
 538   Y  H  L  V  R  D  V  K  K  R  E  Y  P  G  F  G  W  I  Y  F    557

1741 TTAAGGGGAACCTGCCCCCAGACTACAGAATCAGCCTGATTGACATCGGCCTGGTGATCG 1800
 558   K  G  N  L  P  P  D  Y  R  I  S  L  I  D  I  G  L  V  I  E    577

1801 AGTACCTGATGGGCGGGGCTTATCGCTGCAACTACACGCGCAAGCGCTTCCGGACCCTCT 1860
 578   Y  L  M  G  G  A  Y  R  C  N  Y  T  R  K  R  F  R  T  L  Y    597

1861 ACCACAACCTCTTCGGCCCCAAGAGGGATGATATTCCCTTGAGGCGAGGAAGAAAGACAA 1920
 598   H  N  L  F  G  P  K  R  D  D  I  P  L  R  R  G  R  K  T    617

1921 CCAAGAAACGTGAAGAAGAGGTGGACATTGACTTGGATGATCCTGAGATCAACCACTTCC 1980
 618   K  K  R  E  E  E  V  D  I  D  L  D  D  P  E  I  N  H  F  P    637

1981 CCTTCCCTTTCCATGAGCTCATGGTGTGGGCTGTTCTCATGAAGCGGCAGAAGATGGCCC 2040
 638   F  P  F  H  E  L  M  V  W  A  V  L  M  K  R  Q  K  M  A  L    657
```

FIG. 5C

```
2041  TGTTCTTCTGGCAGCACGGTGAGGAGGCCATGGCCAAGGCCCTGGTGGCCTGCAAGCTCT  2100
 658   F  F  W  Q  H  G  E  E  A  M  A  K  A  L  V  A  C  K  L  C    677

2101  GCAAAGCCATGGCTCATGAGGCCTCTGAGAACGACATGGTTGACGACATTTCCCAGGAGC  2160
 678   K  A  M  A  H  E  A  S  E  N  D  M  V  D  D  I  S  Q  E  L    697

2161  TGAATCACAATTCCAGAGACTTTGGCCAGCTGGCTGTGGAGCTCCTGGACCAGTCCTACA  2220
 698   N  H  N  S  R  D  F  G  Q  L  A  V  E  L  L  D  Q  S  Y  K    717

2221  AGCAGGACGAACAGCTGGCCATGAAACTGCTGACGTATGAGCTGAAGAACTGGAGCAACG  2280
 718   Q  D  E  Q  L  A  M  K  L  L  T  Y  E  L  K  N  W  S  N  A    737

2281  CCACGTGCCTGCAGCTTGCCGTGGCTGCCAAACACCGCGACTTCATCGCGCACACGTGCA  2340
 738   T  C  L  Q  L  A  V  A  A  K  H  R  D  F  I  A  H  T  C  S    757

2341  GCCAGATGCTGCTCACCGACATGTGGATGGGCCGGCTCCGCATGCGCAAGAACTCAGGCC  2400
 758   Q  M  L  L  T  D  M  W  M  G  R  L  R  M  R  K  N  S  G  L    777

2401  TCAAGGTAATTCTGGGAATTCTACTTCCTCCTTCAATTCTCAGCTTGGAGTTCAAGAACA  2460
 778   K  V  I  L  G  I  L  L  P  P  S  I  L  S  L  E  F  K  N  K    797

2461  AAGACGACATGCCCTATATGTCTCAGGCCCAGGAAATCCACCTCCAAGAGAAGGAGGCAG  2520
 798   D  D  M  P  Y  M  S  Q  A  Q  E  I  H  L  Q  E  K  E  A  E    817

2521  AAGAACCAGAGAAGCCCACAAAGGAAAAAGAGGAAGAGGACATGGAGCTCACAGCAATGT  2580
 818   E  P  E  K  P  T  K  E  K  E  E  E  D  M  E  L  T  A  M  L    837

2581  TGGGACGAAACAACGGGGAGTCCTCCAGGAAGAAGGATGAAGAGGAAGTTCAGAGCAAGC  2640
 838   G  R  N  N  G  E  S  S  R  K  K  D  E  E  V  Q  S  K  H      857

2641  ACCGGTTAATCCCCCTCGGCAGAAAAATCTATGAATTCTACAATGCACCCATCGTGAAGT  2700
 858   R  L  I  P  L  G  R  K  I  Y  E  F  Y  N  A  P  I  V  K  F    877

2701  TCTGGTTCTACACACTGGCGTATATCGGATACCTGATGCTCTTCAACTATATCGTGTTAG  2760
 878   W  F  Y  T  L  A  Y  I  G  Y  L  M  L  F  N  Y  I  V  L  V    897

2761  TGAAGATGGAACGCTGGCCGTCCACCCAGGAATGGATCGTAATCTCCTATATTTTCACCC  2820
 898   K  M  E  R  W  P  S  T  Q  E  W  I  V  I  S  Y  I  F  T      917

2821  TGGGAATAGAAAAGATCACACAGATTCTGATGTCAGAGCCAGGGAAGTTGCTACAGAAAG  2880
 918   L  G  I  E  K  I  T  Q  I  L  M  S  E  P  G  K  L  L  Q  K    937

2881  TGAAGGTATGGCTGCAGGAGTACTGGAATGTCACGGACCTCATCGCCATCCTTCTGTTTT  2940
 938   V  K  V  W  L  Q  E  Y  W  N  V  T  D  L  I  A  I  L  L  F    957

2941  CTGTCGGAATGATCCTTCGTCTCCAAGACCAGCCCTTCAGGAGTGACGGGAGGGTCATCT  3000
 958   S  V  G  M  I  L  R  L  Q  D  Q  P  F  R  S  D  G  R  V  I    977

3001  ACTGCGTGAACATCATTTACTGGTATATCCGTCTCCTAGACATCTTCGGCGTGAACAAGT  3060
 978   T  A  V  N  I  I  Y  W  Y  I  R  L  L  D  I  F  G  V  N  K    997
```

FIG. 5D

```
3061  ATTTGGGCCCGTATGTAATGATGATTGGAAAAATGATGATAGACATGATGTACTTTGTCA  3120
 998   I  G  P  Y  V  M  M  I  G  K  M  M  I  D  M  M  Y  F  V       1017

3121  TCATTATGCTGGTGGTTCTGATGAGCTTTGGGGTCGCCAGGCAAGCCATCCTTTTTCCCA  3180
1018   S  L  C  W  W  F  *  *  L  W  G  R  Q  A  S  H  P  F  P  *    1037

3181  ATGAGGAGCCATCATGGAAACTGGCCAAGAACATCTTCTACATGCCCTATTGGATGATTT  3240
1038                                                                 1057

3241  ATGGGGAAGTGTTTGCGGACCAGATAGACCCTCCCTGTGGACAGAATGAGACCCGAGAGG  3300
1058                                                                 1077

3301  ATGGTAAAATAATCCAGCTGCCTCCCTGCAAGACAGGAGCTTGGATCGTGCCGGCCATCA  3360
1078                                                                 1097

3361  TGGCCTGCTACCTCTTAGTGGCAAACATCTTGCTGGTCAACCTCCTCATTGCTGTCTTTA  3420
1098                                                     N           1117

3421  ACAATACATTTTTTGAAGTAAAATCGATATCCAACCAAGTCTGGAAGTTTCAGAGGTATC  3480
1118   N  T  F  F  E  V  K  S  I  S  N  Q  V  W  K  F  Q  R  Y  Q    1137

3481  AGCTCATCATGACTTTCCATGAAAGGCCAGTTCTGCCCCCACCACTGATCATCTTCAGCC  3540
1138   L  I  M  T  F  H  E  R  P  V  L  P  P  P  L  I  I  F  S  H    1157

3541  ACATGACCATGATATTCCAGCACCTGTGCTGCCGATGGAGGAAACACGAGAGCGACCCGG  3600
1158   M  T  M  I  F  Q  H  L  C  C  R  W  R  K  H  E  S  D  P  D    1177

3601  ATGAAAGGGACTACGGCCTGAAACTCTTCATAACCGATGATGAGCTCAAGAAAGTACATG  3660
1178   E  R  D  Y  G  L  K  L  F  I  T  D  D  E  L  K  K  V  H  D    1197

3661  ACTTTGAAGAGCAATGCATAGAAGAATACTTCAGAGAAAAGGATGATCGGTTCAACTCAT  3720
1198   F  E  E  Q  C  I  E  E  Y  F  R  E  K  D  D  R  F  N  S  S    1217

3721  CTAATGATGAGAGGATACGGGTGACTTCAGAAAGGGTGGAGAACATGTCTATGCGGCTGG  3780
1218   N  D  E  R  I  R  V  T  S  E  R  V  E  N  M  S  M  R  L  E    1237

3781  AGGAAGTCAACGAGAGAGAGCACTCCATGAAGGCTTCACTCCAGACCGTGGACATCCGGC  3840
1238   E  V  N  E  R  E  H  S  M  K  A  S  L  Q  T  V  D  I  R  L    1257

3841  TGGCGCAGCTGGAAGACCTTATCGGGCGCATGGCCACGGCCCTGGAGCGCCTGACAGGTC  3900
1258   A  Q  L  E  D  L  I  G  R  M  A  T  A  L  E  R  L  T  G  L    1277

3901  TGGAGCGGGCCGAGTCCAACAAAATCCCCTCGAGGACCTCGTCAGACTGCACGGACGCCG  3960
1278   E  R  A  E  S  N  K  I  R  S  R  T  S  S  D  C  T  D  A  A    1297

3961  CCTACATTGTCCGTCAGAGCAGCTTCAACAGCCAGGAAGGGAACACCTTCAAGCTCCAAG  4020
1298   Y  I  V  R  Q  S  S  F  N  S  Q  E  G  N  T  F  K  L  Q  E    1317

4021  AGAGTATAGACCCTGCAGGTGAGGAGACCATGTCCCCAACTTCTCCAACCTTAATGCCCC  4080
1318   S  I  D  P  A  G  E  E  T  M  S  P  T  S  P  T  L  M  P  R    1337
```

FIG. 5E

```
4081 GTATGCGAAGCCATTCTTTCTATTCAGTCAATATGAAAGACAAAGGTGGTATAGAAAAGT 4140
1338    M  R  S  H  S  F  Y  S  V  N  M  K  D  K  G  G  I  E  K  L   1357

4141 TGGAAAGTATTTTTAAAGAAAGGTCCCTGAGCCTACACCGGGCTACTAGTTCCCACTCTG 4200
1358    E  S  I  F  K  E  R  S  L  S  L  H  R  A  T  S  S  H  S  V   1377

4201 TAGCAAAAGAACCCAAAGCTCCTGCAGCCCCTGCCAACACCTTGGCCATTGTTCCTGATT 4260
1378    A  K  E  P  K  A  P  A  A  P  A  N  T  L  A  I  V  P  D  S   1397

4261 CCAGAAGACCATCATCGTGTATAGACATCTATGTCTCTGCTATGGATGAGCTCCACTGTG 4320
1398    R  R  P  S  S  C  I  D  I  Y  V  S  A  M  D  E  L  H  C  D   1417

4321 ATATAGACCCTCTGGACAATTCCGTGAACATCCTTGGGCTAGGCGAGCCAAGCTTTTCAA 4380
1418    I  D  P  L  D  N  S  V  N  I  L  G  L  G  E  P  S  F  S  T   1437

4381 CTCCAGTACCTTCCACAGCCCCTTCAAGTAGTGCCTATGCAACACTTGCACCCACAGACA 4440
1438    P  V  P  S  T  A  P  S  S  A  Y  A  T  L  A  P  T  D  R      1457

4441 GACCTCCAAGCCGGAGCATTGATTTTGAGGACATCACCTCCATGGACACTAGATCTTTTT 4500
1458    P  P  S  R  S  I  D  F  E  D  I  T  S  M  D  T  R  S  F  S   1477

4501 CTTCAGACTACACCCACCTCCCAGAATGCCAAAACCCCTGGGACTCAGAGCCTCCGATGT 4560
1478    S  D  Y  T  H  L  P  E  C  Q  N  P  W  D  S  E  P  P  M  Y   1497

4561 ACCACACCATTGAGCGTTCCAAAAGTAGCCGCTACCTAGCCACCACACCCTTTCTTCTAG 4620
1498    H  T  I  E  R  S  K  S  S  R  Y  L  A  T  T  P  F  L  L  E   1517

4621 AAGAGGCTCCCATTGTGAAATCTCATAGCTTTATGTTTTCCCCCTCAAGGAGCTATTATG 4680
1518    E  A  P  I  V  K  S  H  S  F  M  F  S  P  S  R  S  Y  Y  A   1537

4681 CCAACTTTGGGGTGCCTGTAAAAACAGCAGAATACACAAGTATTACAGACTGTATTGACA 4740
1538    N  F  G  V  P  V  K  T  A  E  Y  T  S  I  T  D  C  I  D  T   1557

4741 CAAGGTGTGTCAATGCCCCTCAAGCAATTGCGGACAGAGCTGCCTTCCCTGGAGGTCTTG 4800
1558    R  C  V  N  A  P  Q  A  I  A  D  R  A  A  F  P  G  G  L  G   1577

4801 GAGACAAAGTGGAGGACTTAACTTGCTGCCATCCAGAGCGAGAAGCAGAACTGAGTCACC 4860
1578    D  K  V  E  D  L  T  C  C  H  P  E  R  E  A  E  L  S  H  P   1597

4861 CCAGCTCTGACAGTGAGGAGAATGAGGCCAAAGGCCGCAGAGCCACCATTGCAATATCCT 4920
1598    S  S  D  S  E  E  N  E  A  K  G  R  R  A  T  I  A  I  S  S   1617

4921 CCCAGGAGGGTGATAACTCAGAGAGAACCCTGTCCAACAACATCACTGTTCCCAAGATAG 4980
1618    Q  E  G  D  N  S  E  R  T  L  S  N  N  I  T  V  P  K  I  E   1637

4981 AGCGCGCCAACAGCTACTCGGCAGAGGAGCCAAGTGCGCCATATGCACACACCAGGAAGA 5040
1638    R  A  N  S  Y  S  A  E  E  P  S  A  P  Y  A  H  T  R  K  S   1657

5041 GCTTCTCCATCAGTGACAAACTCGACAGGCAGCGGAACACAGCAAGCCTGCAAAATCCCT 5100
1658    F  S  I  S  D  K  L  D  R  Q  R  N  T  A  S  L  Q  N  P  F   1677
```

FIG. 5F

```
5101  TCCAGAGAAGCAAGTCCTCCAAGCCGGAGGGCCGAGGGGACAGCCTGTCCATGAGGAGAC  5160
1678    Q  R  S  K  S  S  K  P  E  G  R  G  D  S  L  S  M  R  R  L  1697

5161  TGTCCAGAACATCGGCTTTCCAAAGCTTTGAAAGCAAGCACACCTAA  5207
1698    S  R  T  S  A  F  Q  S  F  E  S  K  H  T        1711
```

FIG. 6A

```
  61  GCGAACTTCTCATGGGGAAGAAGTGGAGGGATGCGGCGGAAATGGAGCGGGGCTGCTCCG  120
   1            M  G  K  K  W  R  D  A  A  E  M  E  R  G  C  S  D   17

121  ACCGCGAGGACAACGCGGAGAGCCGCAGACGCAGCCGGAGCGCCAGCCGGGGCAGGTTTG  180
  18   R  E  D  N  A  E  S  R  R  R  S  R  S  A  S  R  G  R  F  A   37

181  CCGAGTCGTGGAAAAGGTTAAGTTCCAAGCAGGGGTCCACCAAACGCTCGGGACTCCCGT  240
  38   E  S  W  K  R  L  S  S  K  Q  G  S  T  K  R  S  G  L  P  S   57

241  CGCAGCAGACGCCGGCTCAGAAATCCTGGATAGAAAGAGCATTTTATAAAAGAGAATGTG  300
  58   Q  Q  T  P  A  Q  K  S  W  I  E  R  A  F  Y  K  R  E  C  V   77

301  TCCACATCATACCCAGCACCAAAGACCCCCATAGGTGTTGCTGTGGGCGTCTGATAGGCC  360
  78   H  I  I  P  S  T  K  D  P  H  R  C  C  G  R  L  I  G  Q   97

361  AGCATGTTGGCCTCACCCCCAGTATCTCCGTGCTTCAGAATGAGAAAAATGAAAGTCGCC  420
  98   H  V  G  L  T  P  S  I  S  V  L  Q  N  E  K  N  E  S  R  L  117

421  TCTCCCGAAATGACATCCAGTCTGAAAAGTGGTCCATCAGCAAACACACTCAACTCAGCC  480
 118   S  R  N  D  I  Q  S  E  K  W  S  I  S  K  H  T  Q  L  S  P  137

481  CTACGGATGCTTTTGGGACCATTGAGTTCCAAGGAGGTGGCCATTCCAACAAAGCCATGT  540
 138   T  D  A  F  G  T  I  E  F  Q  G  G  G  H  S  N  K  A  M  Y  157

541  ATGTGCGAGTATCTTTTGATACAAAACCTGATCTCCTCTTACACCTGATGACCAAGGAAT  600
 158   V  R  V  S  F  D  T  K  P  D  L  L  L  H  L  M  T  K  E  W  177

601  GGCAGTTGGAGCTTCCCAAGCTTCTCATCTCTGTCCATGGGGGCCTGCAGAACTTTGAAC  660
 178   Q  L  E  L  P  K  L  L  I  S  V  H  G  G  L  Q  N  F  E  L  197

661  TCCAGCCAAAACTCAAGCAAGTCTTTGGGAAAGGGCTCATCAAAGCAGCAATGACAACTG  720
 198   Q  P  K  L  K  Q  V  F  G  K  G  L  I  K  A  A  M  T  T  G  217

721  GAGCGTGGATATTCACTGGAGGGGTTAACACAGGTGTTATTCGTCATGTTGGCGATGCCT  780
 218   A  W  I  F  T  G  G  V  N  T  G  V  I  R  H  V  G  D  A  L  237

781  TGAAGGATCATGCCTCTAAGTCTCGAGGAAAGATATGCACCATAGGTATTGCCCCCTGGG  840
 238   K  D  H  A  S  K  S  R  G  K  I  C  T  I  G  I  A  P  W  G  257

841  GAATTGTGGAAAACCAGGAGGACCTCATTGGAAGAGATGTTGTCCGGCCATACCAGACCA  900
 258   I  V  E  N  Q  E  D  L  I  G  R  D  V  V  R  P  Y  Q  T  M  277

901  TGTCCAATCCCATGAGCAAGCTCACTGTTCTCAACAGCATGCATTCCCACTTCATTCTGG  960
 278   S  N  P  M  S  K  L  T  V  L  N  S  M  H  S  H  F  I  L  A  297

961  CTGACAACGGGACCACTGGAAAATATGGAGCAGAGGTGAAACTTCGAAGACAACTGGAAA 1020
 298   D  N  G  T  T  G  K  Y  G  A  E  V  K  L  R  R  Q  L  E  K  317

1021  AGCATATTTCACTCCAGAAGATAAACACAAGATGCCTGCCGTTTTTCTCTCTTGACTCCC 1080
 318   H  I  S  L  Q  K  I  N  T  R  C  L  P  F  F  S  L  D  S  R  337
```

FIG. 6B

```
1081 GCTTGTTTTATTCATTTTGGGGTAGTTGCCAGCTAGACTCAGTTGGAATCGGTCAAGGTG 1140
 338   L  F  Y  S  F  W  G  S  C  Q  L  D  S  V  G  I  G  Q  G  V  357

1141 TTCCTGTGGTGGCACTCATAGTGGAAGGAGGACCCAATGTGATCTCGATTGTTTTGGAGT 1200
 358   P  V  V  A  L  I  V  E  G  G  P  N  V  I  S  I  V  L  E  Y  377

1201 ACCTTCGAGACACCCCTCCCGTGCCAGTGGTTGTCTGTGATGGGAGTGGACGGGCATCGG 1260
 378   L  R  D  T  P  P  V  P  V  V  V  C  D  G  S  G  R  A  S  D  397

1261 ACATCCTGGCCTTTGGGCATAAATACTCAGAAGAAGGCGGACTGATAAATGAATCTTTGA 1320
 398   I  L  A  F  G  H  K  Y  S  E  E  G  G  L  I  N  E  S  L  R  417

1321 GGGACCAGCTGTTGGTGACTATACAGAAGACTTTCACATACACTCGAACCCAAGCTCAGC 1380
 418   D  Q  L  L  V  T  I  Q  K  T  F  T  Y  T  R  T  Q  A  Q  H  437

1381 ATCTGTTCATCATCCTCATGGAGTGCATGAAGAAGAAGGAATTGATTACGGTATTTCGGA 1440
 438   L  F  I  I  L  M  E  C  M  K  K  K  E  L  I  T  V  F  R  M  457

1441 TGGGATCAGAAGGACACCAGGACATTGATTTGGCTATCCTGACAGCTTTACTCAAAGGAG 1500
 458   G  S  E  G  H  Q  D  I  D  L  A  I  L  T  A  L  L  K  G  A  477

1501 CCAATGCCTCGGCCCCAGACCAACTGAGCTTAGCTTTAGCCTGGAACAGAGTCGACATCG 1560
 478   N  A  S  A  P  D  Q  L  S  L  A  L  A  W  N  R  V  D  I  A  497

1561 CTCGCAGCCAGATCTTTATTTACGGGCAACAGTGGCCGGTGGGATCTCTGGAGCAAGCCA 1620
 498   R  S  Q  I  F  I  Y  G  Q  Q  W  P  V  G  S  L  E  Q  A  M  517

1621 TGTTGGATGCCTTAGTTCTGGACAGAGTGGATTTTGTGAAATTACTCATAGAGAATGGAG 1680
 518   L  D  A  L  V  L  D  R  V  D  F  V  K  L  L  I  E  N  G  V  537

1681 TAAGCATGCACCGTTTTCTCACCATCTCCAGACTAGAGGAATTGTACAATACGAGACATG 1740
 538   S  M  H  R  F  L  T  I  S  R  L  E  E  L  Y  N  T  R  H  G  557

1741 GGCCCTCAAATACATTGTACCACTTGGTCAGGGATGTCAAAAAGGGGAACCTGCCCCCAG 1800
 558   P  S  N  T  L  Y  H  L  V  R  D  V  K  K  G  N  L  P  P  D  577

1801 ACTACAGAATCAGCCTGATTGACATCGGCCTGGTGATCGAGTACCTGATGGGCGGGGCTT 1860
 578   Y  R  I  S  L  I  D  I  G  L  V  I  E  Y  L  M  G  G  A  Y  597

1861 ATCGCTGCAACTACACGCGCAAGCGCTTCCGGACCCTCTACCACAACCTCTTCGGCCCCA 1920
 598   R  C  N  Y  T  R  K  R  F  R  T  L  Y  H  N  L  F  G  P  K  617

1921 AGAGGCCCAAAGCCTTGAAACTGCTGGGAATGGAGGATGATATTCCCTTGAGGCGAGGAA 1980
 618   R  P  K  A  L  K  L  L  G  M  E  D  D  I  P  L  R  R  G  R  637

1981 GAAAGACAACCAAGAAACGTGAAGAAGAGGTGGACATTGACTTGGATGATCCTGAGATCA 2040
 638   K  T  T  K  K  R  E  E  V  D  I  D  L  D  D  P  E  I  N  657

2041 ACCACTTCCCCTTCCCTTTCCATGAGCTCATGGTGTGGGCTGTTCTCATGAAGCGGCAGA 2100
 658   H  F  P  F  P  F  H  E  L  M  V  W  A  V  L  M  K  R  Q  K  677

2101 AGATGGCCCTGTTCTTCTGGCAGCACGGTGAGGAGGCCATGGCCAAGGCCCTGGTGGCCT 2160
 678   M  A  L  F  F  W  Q  H  G  E  E  A  M  A  K  A  L  V  A  C  697
```

FIG. 6C

```
2161  GCAAGCTCTGCAAAGCCATGGCTCATGAGGCCTCTGAGAACGACATGGTTGACGACATTT  2220
 698   K  L  C  K  A  M  A  H  E  A  S  E  N  D  M  V  D  D  I  S    717

2221  CCCAGGAGCTGAATCACAATTCCAGAGACTTTGGCCAGCTGGCTGTGGAGCTCCTGGACC  2280
 718   Q  E  L  N  H  N  S  R  D  F  G  Q  L  A  V  E  L  L  D  Q    737

2281  AGTCCTACAAGCAGGACGAACAGCTGGCCATCAAACTGCTGACGTATGAGCTGAAGAACT  2340
 738   S  Y  K  Q  D  E  Q  L  A  M  K  L  L  T  Y  E  L  K  N  W    757

2341  GGAGCAACGCCACGTGCCTGCAGCTTGCCGTGGCTGCCAAACACCGCGACTTCATCGCGC  2400
 758   S  N  A  T  C  Q  L  A  V  A  A  K  H  R  D  F  I  A  H       777

2401  ACACGTGCAGCCAGATGCTGCTCACCGACATGTGGATGGGCCGGCTCCGCATGCGCAAGA  2460
 778   T  C  S  Q  M  L  L  T  D  M  W  M  G  R  L  R  M  R  K  N    797

2461  ACTCAGGCCTCAAGGTAATTCTGGGAATTCTACTTCCTCCTTCAATTCTCAGCTTGGAGT  2520
 798   S  G  L  K  V  I  L  G  I  L  L  P  P  S  I  L  S  L  E  F    817

2521  TCAAGAACAAAGACGACATGCCCTATATGTCTCAGGCCCAGGAAATCCACCTCCAAGAGA  2580
 818   K  N  K  D  D  M  P  Y  M  S  Q  A  Q  E  I  H  L  Q  E  K    837

2581  AGGAGGCAGAAGAACCAGAGAAGCCCACAAAGGAAAAAGAGGAAGAGGACATGGAGCTCA  2640
 838   E  A  E  E  P  E  K  P  T  K  E  K  E  E  D  M  E  L  T       857

2641  CAGCAATGTTGGGACGAAACAACGGGGAGTCCTCCAGGAAGAAGGATGAAGAGGAAGTTC  2700
 858   A  M  L  G  R  N  N  G  E  S  S  R  K  K  D  E  E  V  Q       877

2701  AGAGCAAGCACCGGTTAATCCCCCTCGGCAGAAAAATCTATGAATTCTACAATGCACCCA  2760
 878   S  K  H  R  L  I  P  L  G  R  K  I  Y  E  F  Y  N  A  P  I    897

2761  TCGTGAAGTTCTGGTTCTACACACTGGCGTATATCGGATACCTGATGCTCTTCAACTATA  2820
 898   V  K  F  W  F  Y  T  L  A  Y  I  G  Y  L  M  L  F  N  Y  I    917

2821  TCGTGTTAGTGAAGATGGAACGCTGGCCGTCCACCCAGGAATGGATCGTAATCTCCTATA  2880
 918   V  L  V  K  M  E  R  W  P  S  Q  E  W  I  V  I  S  Y          937

2881  TTTTCACCCTGGGAATAGAAAAGATGAGAGAGATTCTGATGTCAGAGCCAGGGAAGTTGC  2940
 938   I  F  T  L  G  I  E  K  M  R  E  I  L  M  S  E  P  G  K  L    957

2941  TACAGAAAGTGAAGGTATGGCTGCAGGAGTACTGGAATGTCACGGACCTCATCGCCATCC  3000
 958   Q  K  V  K  V  W  L  Q  E  Y  W  N  V  T  D  L  I  A  I       977

3001  TTCTGTTTTCTGTCGGAATGATCCTTCGTCTCCAAGACCAGCCCTTCAGGAGTGACGGGA  3060
 978   L  F  S  V  G  M  I  L  R  L  Q  D  Q  P  F  R  S  D  G       997

3061  GGGTCATCTACTGCGTGAACATCATTTACTGGTATATCCGTCTCCTAGACATCTTCGGCG  3120
 998   V  I  Y  C  V  N  I  I  Y  W  Y  I  R  L  L  D  I  F  G       1017

3121  TGAACAAGTATTTGGGCCCGTATGTAATGATGATTGGAAAAATGATGATAGACATGATGT  3180
1018   N  K  Y  L  G  P  Y  V  M  M  I  G  K  M  M  I  D  M  M  Y   1037
```

FIG. 6D

```
3181 ACTTTGTCATCATTATGCTGGTGGTTCTGATGAGCTTTGGGGTCGCCAGGCAAGCCATCC 3240
1038   E  V  L  I  M  L  V  V  L  M  S  F  G  V  A  R  Q  A  I  L  1057

3241 TTTTTCCCAATGAGGAGCCATCATGGAAACTGGCCAAGAACATCTTCTACATGCCCTATT 3300
1058   F  P  N  E  E  P  S  W  K  L  A  K  N  I  F  Y  M  P  Y  1077

3301 GGATGATTTATGGGGAAGTGTTTGCGGACCAGATAGACCCTCCCTGTGGACAGAATGAGA 3360
1078   W  M  I  Y  G  E  V  F  A  D  Q  I  D  P  P  C  G  Q  N  E  1097

3361 CCCGAGAGGATGGTAAAATAATCCAGCTGCCTCCCTGCAAGACAGGAGCTTGGATCGTGC 3420
1098   T  R  E  D  G  K  I  I  Q  L  P  P  C  K  T  G  A  W  I  V  1117

3421 CGGCCATCATGGCCTGCTACCTCTTAGTGGCAAACATCTTGCTGGTCAACCTCCTCATTG 3480
1118   P  A  I  M  A  C  Y  L  L  V  A  N  I  L  L  V  N  L  L  I  1137

3481 CTGTCTTTAACAATACATTTTTTGAAGTAAAATCGATATCCAACCAAGTCTGGAAGTTTC 3540
1138   A  V  F  N  N  T  F  F  E  V  K  S  I  S  N  Q  V  W  K  F  1157

3541 AGAGGTATCAGCTCATCATGACTTTCCATGAAAGGCCAGTTCTGCCCCCACCACTGATCA 3600
1158   Q  R  Y  Q  L  I  M  T  F  H  E  R  P  V  L  P  P  P  L  I  1177

3601 TCTTCAGCCACATGACCATGATATTCCAGCACCTGTGCTGCCGATGGAGGAAACACGAGA 3660
1178   I  F  S  H  M  T  M  I  F  Q  H  L  C  C  R  W  R  K  H  E  1197

3661 GCGACCCGGATGAAAGGGACTACGGCCTGAAACTCTTCATAACCGATGATGAGCTCAAGA 3720
1198   S  D  P  D  E  R  D  Y  G  L  K  L  F  I  T  D  D  E  L  K  1217

3721 AAGTACATGACTTTGAAGAGCAATGCATAGAAGAATACTTCAGAGAAAAGGATGATCGGT 3780
1218   K  V  H  D  F  E  E  Q  C  I  E  E  Y  F  R  E  K  D  D  R  1237

3781 TCAACTCATCTAATGATGAGGATACGGGTGACTTCAGAAAGGGTGGAGAACATGTCTA 3840
1238   F  N  S  S  N  D  E  R  I  R  V  T  S  E  R  V  E  N  M  S  M 1257

3841 TGCGGCTGGAGGAAGTCAACGAGAGAGAGCACTCCATGAAGGCTTCACTCCAGACCGTGG 3900
1258   R  L  E  E  V  N  E  R  E  H  S  M  K  A  S  L  Q  T  V  D  1277

3901 ACATCCGGCTGGCGCAGCTGGAAGACCTTATCGGGCGCATGGCCACGGCCCTGGAGCGCC 3960
1278   I  R  L  A  Q  L  E  D  L  I  G  R  M  A  T  A  L  E  R  L  1297

3961 TGACAGGTCTGGAGCGGGCCGAGTCCAACAAAATCCGCTCGAGGACCTCGTCAGACTGCA 4020
1298   T  G  L  E  R  A  E  S  N  K  I  R  S  R  T  S  S  D  C  T  1317

4021 CGGACGCCGCCTACATTGTCCGTCAGAGCAGCTTCAACAGCCAGGAAGGGAACACCTTCA 4080
1318   D  A  A  Y  I  V  R  Q  S  S  F  N  S  Q  E  G  N  T  F  K  1337

4081 AGCTCCAAGAGAGTATAGACCCTGCAGGTGAGGAGACCATGTCCCCAACTTCTCCAACCT 4140
1338   L  Q  E  S  I  D  P  A  G  E  E  T  M  S  P  T  S  P  T  L  1357

4141 TAATGCCCCGTATGCGAAGCCATTCTTTCTATTCAGTCAATATGAAAGACAAAGGTGGTA 4200
1358   M  P  R  M  R  S  H  S  F  Y  S  V  N  M  K  D  K  G  G  I  1377
```

FIG. 6E

```
4201  TAGAAAAGTTGGAAAGTATTTTTAAAGAAAGGTCCCTGAGCCTACACCGGGCTACTAGTT  4260
1378   E  K  L  E  S  I  F  K  E  R  S  L  S  L  H  R  A  T  S  S   1397

4261  CCCACTCTGTAGCAAAAGAACCCAAAGCTCCTGCAGCCCCTGCCAACACCTTGGCCATTG  4320
1398   H  S  V  A  K  E  P  K  A  P  A  A  P  A  N  T  L  A  I  V   1417

4321  TTCCTGATTCCAGAAGACCATCATCGTGTATAGACATCTATGTCTCTGCTATGGATGAGC  4380
1418   P  D  S  R  R  P  S  S  C  I  D  I  Y  V  S  A  M  D  E  L   1437

4381  TCCACTGTGATATAGACCCTCTGGACAATTCCGTGAACATCCTTGGGCTAGGCGAGCCAA  4440
1438   H  C  D  I  D  P  L  D  N  S  V  N  I  L  G  L  G  E  P      1457

4441  GCTTTTCAACTCCAGTACCTTCCACAGCCCCTTCAAGTAGTGCCTATGCAACACTTGCAC  4500
1458   F  S  T  P  V  P  S  T  A  P  S  S  S  A  Y  A  T  L  A  P   1477

4501  CCACAGACAGACCTCCAAGCCGGAGCATTGATTTTGAGGACATCACCTCCATGGACACTA  4560
1478   T  D  R  P  P  S  R  S  I  D  F  E  D  I  T  S  M  D  T  R   1497

4561  GATCTTTTTCTTCAGACTACACCCACCTCCCAGAATGCCAAAACCCCTGGGACTCAGAGC  4620
1498   S  F  S  S  D  Y  T  H  L  P  E  C  Q  N  P  W  D  S  E  P   1517

4621  CTCCGATGTACCACACCATTGAGCGTTCCAAAAGTAGCCGCTACCTAGCCACCACACCCT  4680
1518   P  M  Y  H  T  I  E  R  S  K  S  S  R  Y  L  A  T  T  P  F   1537

4681  TTCTTCTAGAAGAGGCTCCCATTGTGAAATCTCATAGCTTTATGTTTTCCCCCTCAAGGA  4740
1538   L  L  E  E  A  P  I  V  K  S  H  S  F  M  F  S  P  S  R  S   1557

4741  GCTATTATGCCAACTTTGGGGTGCCTGTAAAAACAGCAGAATACACAAGTATTACAGACT  4800
1558   Y  Y  A  N  F  G  V  P  V  K  T  A  E  Y  T  S  I  T  D  C   1577

4801  GTATTGACACAAGGTGTGTCAATGCCCCTCAAGCAATTGCGGACAGAGCTGCCTTCCCTG  4860
1578   I  D  T  R  C  V  N  A  P  Q  A  I  A  D  R  A  A  F  P  G   1597

4861  GAGGTCTTGGAGACAAAGTGGAGGACTTAACTTGCTGCCATCCAGAGCGAGAAGCAGAAC  4920
1598   G  L  G  D  K  V  E  D  L  T  C  C  H  P  E  R  E  A  E  L   1617

4921  TGAGTCACCCCAGCTCTGACAGTGAGGAGAATGAGGCCAAAGGCCGCAGAGCCACCATTG  4980
1618   S  H  P  S  S  D  S  E  E  N  E  A  K  G  R  R  A  T  I  A   1637

4981  CAATATCCTCCCAGGAGGGTGATAACTCAGAGAGAACCCTGTCCAACAACATCACTGTTC  5040
1638   I  S  S  Q  E  G  D  N  S  E  R  T  L  S  N  N  I  T  V  P   1657

5041  CCAAGATAGAGCGCGCCAACAGCTACTCGGCAGAGGAGCCAAGTGCGCCATATGCACACA  5100
1658   K  I  E  R  A  N  S  Y  S  A  E  E  P  S  A  P  Y  A  H  T   1677

5101  CCAGGAAGAGCTTCTCCATCAGTGACAAACTCGACAGGCAGCGGAACACAGCAAGCCTGC  5160
1678   R  K  S  F  S  I  S  D  K  L  D  R  Q  R  N  T  A  S  L  Q   1697

5161  AAAATCCCTTCCAGAGAAGCAAGTCCTCCAAGCCGGAGGGCCGAGGGGACAGCCTGTCCA  5220
1698   N  P  F  Q  R  S  K  S  S  K  P  E  G  R  G  D  S  L  S  M   1717
```

FIG. 6F

```
5221  TGAGGAGACTGTCCAGAACATCGGCTTTCCAAAGCTTTGAAAGCAAGCACACCTAA  5276
1718    R  R  L  S  R  T  S  A  F  Q  S  F  E  S  K  H  T      1734
```

FIG. 7A

```
                    1                                                   50
LTRPC3g      (1)    MGKKWRDAAEMERGCSDREDNAESRRRSRSASRGRFAESWKRLSSKQGST
LTRPC3h      (1)    MGKKWRDAAEMERGCSDREDNAESRRRSRSASRGRFAESWKRLSSKQGST
LTRPC3i      (1)    MGKKWRDAAEMERGCSDREDNAESRRRSRSASRGRFAESWKRLSSKQGST
LTRPC3j      (1)    MGKKWRDAAEMERGCSDREDNAESRRRSRSASRGRFAESWKRLSSKQGST
LTRPC3k      (1)    MGKKWRDAAEMERGCSDREDNAESRRRSRSASRGRFAESWKRLSSKQGST
LTRPC3l      (1)    MGKKWRDAAEMERGCSDREDNAESRRRSRSASRGRFAESWKRLSSKQGST
melastatin1  (1)    --------------------------------------------------

51                                                  100
LTRPC3g      (51)   KRSGLPSQQTPAQKSWIERAFYKRECVHIIPSTKDPHRCCCGRLIGQHVG
LTRPC3h      (51)   KRSGLPSQQTPAQKSWIERAFYKRECVHIIPSTKDPHRCCCGRLIGQHVG
LTRPC3i      (51)   KRSGLPSQQTPAQKSWIERAFYKRECVHIIPSTKDPHRCCCGRLIGQHVG
LTRPC3j      (51)   KRSGLPSQQTPAQKSWIERAFYKRECVHIIPSTKDPHRCCCGRLIGQHVG
LTRPC3k      (51)   KRSGLPSQQTPAQKSWIERAFYKRECVHIIPSTKDPHRCCCGRLIGQHVG
LTRPC3l      (51)   KRSGLPSQQTPAQKSWIERAFYKRECVHIIPSTKDPHRCCCGRLIGQHVG
melastatin1  (1)    --------------------------------------------------

101                                                 150
LTRPC3g      (101)  LTPSISVLQNEKNESRLSRNDIQSEKWSISKHTQLSPTDAFGTIEFQGGG
LTRPC3h      (101)  LTPSISVLQNEKNESRLSRNDIQSEKWSISKHTQLSPTDAFGTIEFQGGG
LTRPC3i      (101)  LTPSISVLQNEKNESRLSRNDIQSEKWSISKHTQLSPTDAFGTIEFQGGG
LTRPC3j      (101)  LTPSISVLQNEKNESRLSRNDIQSEKWSISKHTQLSPTDAFGTIEFQGGG
LTRPC3k      (101)  LTPSISVLQNEKNESRLSRNDIQSEKWSISKHTQLSPTDAFGTIEFQGGG
LTRPC3l      (101)  LTPSISVLQNEKNESRLSRNDIQSEKWSISKHTQLSPTDAFGTIEFQGGG
melastatin1  (1)    --------------------------------------------------

151                                                 200
LTRPC3g      (151)  HSNKAMYVRVSFDTKPDLLLHLMTKEWQLELPKLLISVHGGLQNFELQPK
LTRPC3h      (151)  HSNKAMYVRVSFDTKPDLLLHLMTKEWQLELPKLLISVHGGLQNFELQPK
LTRPC3i      (151)  HSNKAMYVRVSFDTKPDLLLHLMTKEWQLELPKLLISVHGGLQNFELQPK
LTRPC3j      (151)  HSNKAMYVRVSFDTKPDLLLHLMTKEWQLELPKLLISVHGGLQNFELQPK
LTRPC3k      (151)  HSNKAMYVRVSFDTKPDLLLHLMTKEWQLELPKLLISVHGGLQNFELQPK
LTRPC3l      (151)  HSNKAMYVRVSFDTKPDLLLHLMTKEWQLELPKLLISVHGGLQNFELQPK
melastatin1  (1)    -----MYIRVSYDTKPDSLLHLMVKDWQLELPKLLISVHGGLQNFEMQPK 201                                                 250
LTRPC3g      (201)  LKQVFGKGLIKAAMTTGAWIFTGGVNTGVIRHVGDALKDHASKSRGKICT
LTRPC3h      (201)  LKQVFGKGLIKAAMTTGAWIFTGGVNTGVIRHVGDALKDHASKSRGKICT
LTRPC3i      (201)  LKQVFGKGLIKAAMTTGAWIFTGGVNTGVIRHVGDALKDHASKSRGKICT
LTRPC3j      (201)  LKQVFGKGLIKAAMTTGAWIFTGGVNTGVIRHVGDALKDHASKSRGKICT
LTRPC3k      (201)  LKQVFGKGLIKAAMTTGAWIFTGGVNTGVIRHVGDALKDHASKSRGKICT
LTRPC3l      (201)  LKQVFGKGLIKAAMTTGAWIFTGGVNTGVIRHVGDALKDHASKSRGKICT
melastatin1  (46)   LKQVFGKGLIKAAMTTGAWIFTGGVSTGVISHVGDALKDHSSKSRGRVCA 251                                                 300
LTRPC3g      (251)  IGIAPWGIVENQEDLIGRDVVRPYQTMSNPMSKLTVLNSMHSHFILADNG
LTRPC3h      (251)  IGIAPWGIVENQEDLIGRDVVRPYQTMSNPMSKLTVLNSMHSHFILADNG
LTRPC3i      (251)  IGIAPWGIVENQEDLIGRDVVRPYQTMSNPMSKLTVLNSMHSHFILADNG
LTRPC3j      (251)  IGIAPWGIVENQEDLIGRDVVRPYQTMSNPMSKLTVLNSMHSHFILADNG
LTRPC3k      (251)  IGIAPWGIVENQEDLIGRDVVRPYQTMSNPMSKLTVLNSMHSHFILADNG
LTRPC3l      (251)  IGIAPWGIVENQEDLIGRDVVRPYQTMSNPMSKLTVLNSMHSHFILADNG
melastatin1  (96)   IGIAPWGIVENREDLVGKDVTRVYQTMSNPLSKLSVLNNSHTHFILADNG
```

FIG. 7B

```
                    301                                                   350
LTRPC3g     (301)   TTGKYGAEVKLRRQLEKHISLQKINTR-----------------------
LTRPC3h     (301)   TTGKYGAEVKLRRQLEKHISLQKINTR-----------------------
LTRPC3i     (301)   TTGKYGAEVKLRRQLEKHISLQKINTR-----------------------
LTRPC3j     (301)   TTGKYGAEVKLRRQLEKHISLQKINTR-----------------------
LTRPC3k     (301)   TTGKYGAEVKLRRQLEKHISLQKINTR-----------------------
LTRPC3l     (301)   TTGKYGAEVKLRRQLEKHISLQKINTRCLPFFSLDSRLFYSFWGSCQLDS
melastatin1 (146)   TLGKYGAEVKLRRLLEKHISLQKINTR-----------------------

351                                                   400
LTRPC3g     (328)   --IGQGVPVVALIVEGGPNVISIVLEYLRDTPPVPVVVCDGSGRASDILA
LTRPC3h     (328)   --IGQGVPVVALIVEGGPNVISIVLEYLRDTPPVPVVVCDGSGRASDILA
LTRPC3i     (328)   --IGQGVPVVALIVEGGPNVISIVLEYLRDTPPVPVVVCDGSGRASDILA
LTRPC3j     (328)   --IGQGVPVVALIVEGGPNVISIVLEYLRDTPPVPVVVCDGSGRASDILA
LTRPC3k     (328)   --IGQGVPVVALIVEGGPNVISIVLEYLRDTPPVPVVVCDGSGRASDILA
LTRPC3l     (351)   VGIGQGVPVVALIVEGGPNVISIVLEYLRDTPPVPVVVCDGSGRASDILA
melastatin1 (173)   --IGQGVPLVGLVVEGGPNVVSIVLEYLQEEPDTPVVICDGSGRASDILS 401                                                                       450
LTRPC3g     (376)   FGHKYSEEGGLINESLRDQLLVTIQKTFTYTRTQAQHLFIILMECMKKKE
LTRPC3h     (376)   FGHKYSEEGGLINESLRDQLLVTIQKTFTYTRTQAQHLFIILMECMKKKE
LTRPC3i     (376)   FGHKYSEEGGLINESLRDQLLVTIQKTFTYTRTQAQHLFIILMECMKKKE
LTRPC3j     (376)   FGHKYSEEGGLINESLRDQLLVTIQKTFTYTRTQAQHLFIILMECMKKKE
LTRPC3k     (376)   FGHKYSEEGGLINESLRDQLLVTIQKTFTYTRTQAQHLFIILMECMKKKE
LTRPC3l     (401)   FGHKYSEEGGLINESLRDQLLVTIQKTFTYTRTQAQHLFIILMECMKKKE
melastatin1 (221)   FAHKYCEEGGIINESLREQLLVTIQKTFNYNKAQSHQLFAIIMECMKKKE 451                                                   500
LTRPC3g     (426)   LITVFRMGSEGHQDIDLAILTALLKGANASAPDQLSLALAWNRVDIARSQ
LTRPC3h     (426)   LITVFRMGSEGHQDIDLAILTALLKGANASAPDQLSLALAWNRVDIARSQ
LTRPC3i     (426)   LITVFRMGSEGHQDIDLAILTALLKGANASAPDQLSLALAWNRVDIARSQ
LTRPC3j     (426)   LITVFRMGSEGHQDIDLAILTALLKGANASAPDQLSLALAWNRVDIARSQ
LTRPC3k     (426)   LITVFRMGSEGHQDIDLAILTALLKGANASAPDQLSLALAWNRVDIARSQ
LTRPC3l     (451)   LITVFRMGSEGHQDIDLAILTALLKGANASAPDQLSLALAWNRVDIARSQ
melastatin1 (271)   LVTVFRMGSEGQQDIEMAILTALLKGTNVSAPDQLSLALAWNRVDIARSQ 501                                                   550
LTRPC3g     (476)   IFIYGQQWP-----------------------------------------
LTRPC3h     (476)   IFIYGQQWP-----------------------------------------
LTRPC3i     (476)   IFIYGQQWP-----------------------------------------
LTRPC3j     (476)   IFIYGQQWP-----------------------------------------
LTRPC3k     (476)   IFIYGQQWP-----------------------------------------
LTRPC3l     (501)   IFIYGQQWP-----------------------------------------
melastatin1 (321)   LFVEGPHNTPLGSLAPPTDSKATEKEKKPPMATTKGGRGKGKGKKKGKVK 551                                                   600
LTRPC3g     (485)   ----------------VGSLEQAMLDALVLDRVDFVKLLIENGVSMHRF
LTRPC3h     (485)   ----------------VGSLEQAMLDALVLDRVDFVKLLIENGVSMHRF
LTRPC3i     (485)   ----------------VGSLEQAMLDALVLDRVDFVKLLIENGVSMHRF
LTRPC3j     (485)   ----------------VGSLEQAMLDALVLDRVDFVKLLIENGVSMHRF
LTRPC3k     (485)   ----------------VGSLEQAMLDALVLDRVDFVKLLIENGVSMHRF
LTRPC3l     (510)   ----------------VGSLEQAMLDALVLDRVDFVKLLIENGVSMHRF
melastatin1 (371)   EEVEEETDPRKIELLNWVNALEQAMLDALVLDRVDFVKLLIENGVNMQHF
```

FIG. 7C

```
                    601                                                      650
LTRPC3g     (518)  LTISRLEELYNTRHGPSNTLYHLVRDVKK-----------GNLPPDYRI
LTRPC3h     (518)  LTISRLEELYNTRHGPSNTLYHLVRDVKKREYPGFGWIYFKGNLPPDYRI
LTRPC3i     (518)  LTISRLEELYNTRHGPSNTLYHLVRDVKK-----------GNLPPDYRI
LTRPC3j     (518)  LTISRLEELYNTRHGPSNTLYHLVRDVKK-----------GNLPPDYRI
LTRPC3k     (518)  LTISRLEELYNTRHGPSNTLYHLVRDVKKREYPGFGWIYFKGNLPPDYRI
LTRPC3l     (543)  LTISRLEELYNTRHGPSNTLYHLVRDVKK-----------GNLPPDYRI
melastatin1 (421)  LTIPRLEELYNTRLGPSNTLHLLVRDVKK-----------SNLPPDYHI 651                                                      700
LTRPC3g     (556)  SLIDIGLVIEYLMGGAYRCNYTRKRFRTLYHNLFGPKRPKALKLLGMEDD
LTRPC3h     (568)  SLIDIGLVIEYLMGGAYRCNYTRKRFRTLYHNLFGPKRPKALKLLGMEDD
LTRPC3i     (556)  SLIDIGLVIEYLMGGAYRCNYTRKRFRTLYHNLFGPKRPKALKLLGMEDD
LTRPC3j     (556)  SLIDIGLVIEYLMGGAYRCNYTRKRFRTLYHNLFGPKR---------DD
LTRPC3k     (568)  SLIDIGLVIEYLMGGAYRCNYTRKRFRTLYHNLFGPKR---------DD
LTRPC3l     (581)  SLIDIGLVIEYLMGGAYRCNYTRKRFRTLYHNLFGPKRPKALKLLGMEDD
melastatin1 (459)  SLIDIGLVIEYLMGGAYRCNYTRKNFRTLYNNLFGPKRPKALKLLGMEDD 701                                                      750
LTRPC3g     (606)  IPLRRGRKTTKKR-EEEVDIDLDDPEINHFPFPFHELMVWAVLMKRQKMA
LTRPC3h     (618)  IPLRRGRKTTKKR-EEEVDIDLDDPEINHFPFPFHELMVWAVLMKRQKMA
LTRPC3i     (606)  IPLRRGRKTTKKR-EEEVDIDLDDPEINHFPFPFHELMVWAVLMKRQKMA
LTRPC3j     (596)  IPLRRGRKTTKKR-EEEVDIDLDDPEINHFPFPFHELMVWAVLMKRQKMA
LTRPC3k     (608)  IPLRRGRKTTKKR-EEEVDIDLDDPEINHFPFPFHELMVWAVLMKRQKMA
LTRPC3l     (631)  IPLRRGRKTTKKR-EEEVDIDLDDPEINHFPFPFHELMVWAVLMKRQKMA
melastatin1 (509)  EPPAKGKKKKKKEEEIDIDVDDPAVSRFQYPFHELMVWAVLMKRQKMA 751                                                      800
LTRPC3g     (655)  LFFWQHGEEAMAKALVACKLCKAMAHEASENDMVDDISQELNHNSRDFGQ
LTRPC3h     (667)  LFFWQHGEEAMAKALVACKLCKAMAHEASENDMVDDISQELNHNSRDFGQ
LTRPC3i     (655)  LFFWQHGEEAMAKALVACKLCKAMAHEASENDMVDDISQELNHNSRDFGQ
LTRPC3j     (645)  LFFWQHGEEAMAKALVACKLCKAMAHEASENDMVDDISQELNHNSRDFGQ
LTRPC3k     (657)  LFFWQHGEEAMAKALVACKLCKAMAHEASENDMVDDISQELNHNSRDFGQ
LTRPC3l     (680)  LFFWQHGEEAMAKALVACKLCKAMAHEASENDMVDDISQELNHNSRDFGQ
melastatin1 (559)  VFLWQRGEESMAKALVACKLYKAMAHESSESDLVDDISQELDNNSKDFGQ 801                                                      850
LTRPC3g     (705)  LAVELLDQSYKQDEQLAMKLLTYELKNWSNATCLQLAVAAKHRDFIAHTC
LTRPC3h     (717)  LAVELLDQSYKQDEQLAMKLLTYELKNWSNATCLQLAVAAKHRDFIAHTC
LTRPC3i     (705)  LAVELLDQSYKQDEQLAMKLLTYELKNWSNATCLQLAVAAKHRDFIAHTC
LTRPC3j     (695)  LAVELLDQSYKQDEQLAMKLLTYELKNWSNATCLQLAVAAKHRDFIAHTC
LTRPC3k     (707)  LAVELLDQSYKQDEQLAMKLLTYELKNWSNATCLQLAVAAKHRDFIAHTC
LTRPC3l     (730)  LAVELLDQSYKQDEQLAMKLLTYELKNWSNATCLQLAVAAKHRDFIAHTC
melastatin1 (609)  LAVELLDQSYKHDEQLAMKLLTYELKNWSNSTCLKLAVAAKHRDFIAHTC 851                                                      900
LTRPC3g     (755)  SQMLLTDMWMGRLRMRKNSGLKVILGILLPPSILSLEFKNKDDMPYMSQA
LTRPC3h     (767)  SQMLLTDMWMGRLRMRKNSGLKVILGILLPPSILSLEFKNKDDMPYMSQA
LTRPC3i     (755)  SQMLLTDMWMGRLRMRKNSGLKVILGILLPPSILSLEFKNKDDMPYMSQA
LTRPC3j     (745)  SQMLLTDMWMGRLRMRKNSGLKVILGILLPPSILSLEFKNKDDMPYMSQA
LTRPC3k     (757)  SQMLLTDMWMGRLRMRKNSGLKVILGILLPPSILSLEFKNKDDMPYMSQA
LTRPC3l     (780)  SQMLLTDMWMGRLRMRKNSGLKVILGILLPPSILSLEFKNKDDMPYMSQA
melastatin1 (659)  SQMLLTDMWMGRLRMRKNPGLKVIMGILLPPTIILFEFRTYDDFSYQTSK
```

FIG. 7D

```
                    901                                                    950
LTRPC3g      (805)  QEIHLQEKEAEEPEKPTKEKEEEDMELTAMLGRNNGESSRKKDEEEVQSK
LTRPC3h      (817)  QEIHLQEKEAEEPEKPTKEKEEEDMELTAMLGRNNGESSRKKDEEEVQSK
LTRPC3i      (805)  QEIHLQEKEAEEPEKPTKEKEEEDMELTAMLGRNNGESSRKKDEEEVQSK
LTRPC3j      (795)  QEIHLQEKEAEEPEKPTKEKEEEDMELTAMLGRNNGESSRKKDEEEVQSK
LTRPC3k      (807)  QEIHLQEKEAEEPEKPTKEKEEEDMELTAMLGRNNGESSRKKDEEEVQSK
LTRPC3l      (830)  QEIHLQEKEAEEPEKPTKEKEEEDMELTAMLGRNNGESSRKKDEEEVQSK
melastatin1  (709)  ENEDG-----------KEKEEENTDANADAG------SRKGDEENEHKK 951                                                    1000
LTRPC3g      (855)  HRLIPLGRKIYEFYNAPIVKFWFYTLAYIGYLMLFNYIVLVKMERWPSTQ
LTRPC3h      (867)  HRLIPLGRKIYEFYNAPIVKFWFYTLAYIGYLMLFNYIVLVKMERWPSTQ
LTRPC3i      (855)  HRLIPLGRKIYEFYNAPIVKFWFYTLAYIGYLMLFNYIVLVKMERWPSTQ
LTRPC3j      (845)  HRLIPLGRKIYEFYNAPIVKFWFYTLAYIGYLMLFNYIVLVKMERWPSTQ
LTRPC3k      (857)  HRLIPLGRKIYEFYNAPIVKFWFYTLAYIGYLMLFNYIVLVKMERWPSTQ
LTRPC3l      (880)  HRLIPLGRKIYEFYNAPIVKFWFYTLAYIGYLMLFNYIVLVKMERWPSTQ
melastatin1  (741)  QRSIPIGTKICEFYNAPIVKFWFYTISYLGYLPLFNYVILVRMDGWPSLQ 1001                                                   1050
LTRPC3g      (905)  EWIVISYIFTLGIEKMREILMSEPGKLLQKVKVWLQEYWNVTDLIAILLF
LTRPC3h      (917)  EWIVISYIFTLGIEKMREILMSEPGKLLQKVKVWLQEYWNVTDLIAILLF
LTRPC3i      (905)  EWIVISYIFTLGIEKMREILMSEPGKLLQKVKVWLQEYWNVTDLIAILLF
LTRPC3j      (895)  EWIVISYIFTLGIEKMREILMSEPGKLLQKVKVWLQEYWNVTDLIAILLF
LTRPC3k      (907)  EWIVISYIFTLGIEKMREILMSEPGKLLQKVKVWLQEYWNVTDLIAILLF
LTRPC3l      (930)  EWIVISYIFTLGIEKMREILMSEPGKLLQKVKVWLQEYWNVTDLIAILLF
melastatin1  (791)  EWIVISYIVSLALEKIREILMSEPGKLSQKIKVWLQEYWNITDLVAISTF 1051                                                   1100
LTRPC3g      (955)  SVGMILRLQDQPFRSDGRVIYCVNIIYWYIRLLDIFGVNKYLGPYVMMIG
LTRPC3h      (967)  SVGMILRLQDQPFRSDGRVIYCVNIIYWYIRLLDIFGVNKYLGPYVMMIG
LTRPC3i      (955)  SVGMILRLQDQPFRSDGRVIYCVNIIYWYIRLLDIFGVNKYLGPYVMMIG
LTRPC3j      (945)  SVGMILRLQDQPFRSDGRVIYCVNIIYWYIRLLDIFGVNKYLGPYVMMIG
LTRPC3k      (957)  SVGMILRLQDQPFRSDGRVIYCVNIIYWYIRLLDIFGVNKYLGPYVMMIG
LTRPC3l      (980)  SVGMILRLQDQPFRSDGRVIYCVNIIYWYIRLLDIFGVNKYLGPYVMMIG
melastatin1  (841)  MIGAILRLQNQPYMGYGRVIYCVDIIFWYIRVLDIFGVNKYLGPYVMMIG 1101                                                   1150
LTRPC3g      (1005) KMMIDMMYFVIIMLVVLMSFGVARQAILFPNEEPSWKLAKNIFYMPYWMI
LTRPC3h      (1017) KMMIDMMYFVIIMLVVLMSFGVARQAILFPNEEPSWKLAKNIFYMPYWMI
LTRPC3i      (1005) KMMIDMMYFVIIMLVVLMSFGVARQAILFPNEEPSWKLAKNIFYMPYWMI
LTRPC3j      (995)  KMMIDMMYFVIIMLVVLMSFGVARQAILFPNEEPSWKLAKNIFYMPYWMI
LTRPC3k      (1007) KMMIDMMYFVIIMLVVLMSFGVARQAILFPNEEPSWKLAKNIFYMPYWMI
LTRPC3l      (1030) KMMIDMMYFVIIMLVVLMSFGVARQAILFPNEEPSWKLAKNIFYMPYWMI
melastatin1  (891)  KMMIDMLYFVMIMLVVLMSFGVARQAILHPEEKPSWKLARNIFYMPYWMI 1151                                                   1200
LTRPC3g      (1055) YGEVFADQID-----------PPCGQNETREDGKIIQLPPCKTGAWIVP
LTRPC3h      (1067) YGEVFADQID-----------PPCGQNETREDGKIIQLPPCKTGAWIVP
LTRPC3i      (1055) YGEVFADQIDRKQVYDSHTPKSAPCGQNETREDGKIIQLPPCKTGAWIVP
LTRPC3j      (1045) YGEVFADQID-----------PPCGQNETREDGKIIQLPPCKTGAWIVP
LTRPC3k      (1057) YGEVFADQID-----------PPCGQNETREDGKIIQLPPCKTGAWIVP
LTRPC3l      (1080) YGEVFADQID-----------PPCGQNETREDGKIIQLPPCKTGAWIVP
melastatin1  (941)  YGEVFADQIDLYAMEIN-----PPCGENLYDEEG--KRLPPCIPGAWLTP
```

FIG. 7E

```
                    1201                                                    1250
LTRPC3g    (1093)   AIMACYLLVANILLVNLLIAVFNNTFFEVKSISNQVWKFQRYQLIMTFHE
LTRPC3h    (1105)   AIMACYLLVANILLVNLLIAVFNNTFFEVKSISNQVWKFQRYQLIMTFHE
LTRPC3i    (1105)   AIMACYLLVANILLVNLLIAVFNNTFFEVKSISNQVWKFQRYQLIMTFHE
LTRPC3j    (1083)   AIMACYLLVANILLVNLLIAVFNNTFFEVKSISNQVWKFQRYQLIMTFHE
LTRPC3k    (1095)   AIMACYLLVANILLVNLLIAVFNNTFFEVKSISNQVWKFQRYQLIMTFHE
LTRPC3l    (1118)   AIMACYLLVANILLVNLLIAVFNNTFFEVKSISNQVWKFQRYQLIMTFHE
melastatin1 (984)   AIMACYLLVANILLVNLLIAVFNNTFFEVKSISNQVWKFQRYQLIMTFHD 1251                                                    1300
LTRPC3g    (1143)   RPVLPPPLIIFSHMTMIFQHLCCRWR-KHESDPDERDYGLKLFITDDELK
LTRPC3h    (1155)   RPVLPPPLIIFSHMTMIFQHLCCRWR-KHESDPDERDYGLKLFITDDELK
LTRPC3i    (1155)   RPVLPPPLIIFSHMTMIFQHLCCRWR-KHESDPDERDYGLKLFITDDELK
LTRPC3j    (1133)   RPVLPPPLIIFSHMTMIFQHLCCRWR-KHESDPDERDYGLKLFITDDELK
LTRPC3k    (1145)   RPVLPPPLIIFSHMTMIFQHLCCRWR-KHESDPDERDYGLKLFITDDELK
LTRPC3l    (1168)   RPVLPPPLIIFSHMTMIFQHLCCRWR-KHESDPDERDYGLKLFITDDELK
melastatin1 (1034)  RPVLPPPMIILSHIYIIIMRLSGRCRKKRECDQEERDRGLKLFLSDEELK 1301                                                    1350
LTRPC3g    (1192)   KVHDFEEQCIEEYFREKDDRFNSSNDERIRVTSERVENMSRLEEVNERE
LTRPC3h    (1204)   KVHDFEEQCIEEYFREKDDRFNSSNDERIRVTSERVENMSRLEEVNERE
LTRPC3i    (1204)   KVHDFEEQCIEEYFREKDDRFNSSNDERIRVTSERVENMSRLEEVNERE
LTRPC3j    (1182)   KVHDFEEQCIEEYFREKDDRFNSSNDERIRVTSERVENMSRLEEVNERE
LTRPC3k    (1194)   KVHDFEEQCIEEYFREKDDRFNSSNDERIRVTSERVENMSRLEEVNERE
LTRPC3l    (1217)   KVHDFEEQCIEEYFREKDDRFNSSNDERIRVTSERVENMSRLEEVNERE
melastatin1 (1084)  RIHPFEEQCVQEMFREKEDEQQSSSDERIRVTSERVENMSRLEEINERE 1351                                                    1400
LTRPC3g    (1242)   HSMKASLQTVDIRLAQLEDLIGRMATALERLTGLERAESNKIRSRTSSDC
LTRPC3h    (1254)   HSMKASLQTVDIRLAQLEDLIGRMATALERLTGLERAESNKIRSRTSSDC
LTRPC3i    (1254)   HSMKASLQTVDIRLAQLEDLIGRMATALERLTGLERAESNKIRSRTSSDC
LTRPC3j    (1232)   HSMKASLQTVDIRLAQLEDLIGRMATALERLTGLERAESNKIRSRTSSDC
LTRPC3k    (1244)   HSMKASLQTVDIRLAQLEDLIGRMATALERLTGLERAESNKIRSRTSSDC
LTRPC3l    (1267)   HSMKASLQTVDIRLAQLEDLIGRMATALERLTGLERAESNKIRSRTSSDC
melastatin1 (1134)  TFMKTSLQTVDLRLAQLEDLSNRMVNALENLAGIDRSDLIQARSRASSEC 1401                                                    1450
LTRPC3g    (1292)   TDAAYIVRQSSFNSQEGNTFKLQESIDPAGEETMSPTSPTLMPRMRSHSF
LTRPC3h    (1304)   TDAAYIVRQSSFNSQEGNTFKLQESIDPAGEETMSPTSPTLMPRMRSHSF
LTRPC3i    (1304)   TDAAYIVRQSSFNSQEGNTFKLQESIDPAGEETMSPTSPTLMPRMRSHSF
LTRPC3j    (1282)   TDAAYIVRQSSFNSQEGNTFKLQESIDPAGEETMSPTSPTLMPRMRSHSF
LTRPC3k    (1294)   TDAAYIVRQSSFNSQEGNTFKLQESIDPAGEETMSPTSPTLMPRMRSHSF
LTRPC3l    (1317)   TDAAYIVRQSSFNSQEGNTFKLQESIDPAGEETMSPTSPTLMPRMRSHSF
melastatin1 (1184)  EATYLLR-QSSINSADG---------------------------YSL 1451                                                    1500
LTRPC3g    (1342)   YSVNMKDKGGIEKLESIFKERSLSLHRATSSHSVAKEPKAPAAPANTLAI
LTRPC3h    (1354)   YSVNMKDKGGIEKLESIFKERSLSLHRATSSHSVAKEPKAPAAPANTLAI
LTRPC3i    (1354)   YSVNMKDKGGIEKLESIFKERSLSLHRATSSHSVAKEPKAPAAPANTLAI
LTRPC3j    (1332)   YSVNMKDKGGIEKLESIFKERSLSLHRATSSHSVAKEPKAPAAPANTLAI
LTRPC3k    (1344)   YSVNMKDKGGIEKLESIFKERSLSLHRATSSHSVAKEPKAPAAPANTLAI
LTRPC3l    (1367)   YSVNMKDKGGIEKLESIFKERSLSLHRATSSHSVAKEPKAPAAPANTLAI
melastatin1 (1203)  YRYHFNGEELLFEDTSLSTSPGTGVRKKTCSFRIKEEK----------D
```

FIG. 7F

```
              1501                                              1550
LTRPC3g  (1392) VPDSRRPSSCIDIYVSAMDELHCDIDPLDNSVNILGLGEPSFSTPVPSTA
LTRPC3h  (1404) VPDSRRPSSCIDIYVSAMDELHCDIDPLDNSVNILGLGEPSFSTPVPSTA
LTRPC3i  (1404) VPDSRRPSSCIDIYVSAMDELHCDIDPLDNSVNILGLGEPSFSTPVPSTA
LTRPC3j  (1382) VPDSRRPSSCIDIYVSAMDELHCDIDPLDNSVNILGLGEPSFSTPVPSTA
LTRPC3k  (1394) VPDSRRPSSCIDIYVSAMDELHCDIDPLDNSVNILGLGEPSFSTPVPSTA
LTRPC3l  (1417) VPDSRRPSSCIDIYVSAMDELHCDIDPLDNSVNILGLGEPSFSTPVPSTA
melastatin1 (1242) VKTHLVPECQNSLHLSLGTSTSATPDGSHLAVDDLKNAEESKLGEDIGIS 1551                                              1600
LTRPC3g  (1442) PSSSAYATLAPTDRPPSRSIDFEDITSMDTRSFSSDYTHLPECQNPWDSE
LTRPC3h  (1454) PSSSAYATLAPTDRPPSRSIDFEDITSMDTRSFSSDYTHLPECQNPWDSE
LTRPC3i  (1454) PSSSAYATLAPTDRPPSRSIDFEDITSMDTRSFSSDYTHLPECQNPWDSE
LTRPC3j  (1432) PSSSAYATLAPTDRPPSRSIDFEDITSMDTRSFSSDYTHLPECQNPWDSE
LTRPC3k  (1444) PSSSAYATLAPTDRPPSRSIDFEDITSMDTRSFSSDYTHLPECQNPWDSE
LTRPC3l  (1467) PSSSAYATLAPTDRPPSRSIDFEDITSMDTRSFSSDYTHLPECQNPWDSE
melastatin1 (1292) KEDDERQTDSKKEETISPSLNKTDVIHGQDKSDVQNTQLTVETTNIEG--

1601                                              1650
LTRPC3g  (1492) PPMYHTIERSKSSRYLATTPFLLEEAPIVKSHSFMFSPSRSYYANFGVPV
LTRPC3h  (1504) PPMYHTIERSKSSRYLATTPFLLEEAPIVKSHSFMFSPSRSYYANFGVPV
LTRPC3i  (1504) PPMYHTIERSKSSRYLATTPFLLEEAPIVKSHSFMFSPSRSYYANFGVPV
LTRPC3j  (1482) PPMYHTIERSKSSRYLATTPFLLEEAPIVKSHSFMFSPSRSYYANFGVPV
LTRPC3k  (1494) PPMYHTIERSKSSRYLATTPFLLEEAPIVKSHSFMFSPSRSYYANFGVPV
LTRPC3l  (1517) PPMYHTIERSKSSRYLATTPFLLEEAPIVKSHSFMFSPSRSYYANFGVPV
melastatin1 (1340) -TISYPLEETKITRYFP--DETINACKTMKSFSFVYSRGRKLVGGVNQDV 1651                                              1700
LTRPC3g  (1542) KTAEYTSITDCIDTRCVNAPQAIADRAAFPGGLGDKVEDLTCCHPEREAE
LTRPC3h  (1554) KTAEYTSITDCIDTRCVNAPQAIADRAAFPGGLGDKVEDLTCCHPEREAE
LTRPC3i  (1554) KTAEYTSITDCIDTRCVNAPQAIADRAAFPGGLGDKVEDLTCCHPEREAE
LTRPC3j  (1532) KTAEYTSITDCIDTRCVNAPQAIADRAAFPGGLGDKVEDLTCCHPEREAE
LTRPC3k  (1544) KTAEYTSITDCIDTRCVNAPQAIADRAAFPGGLGDKVEDLTCCHPEREAE
LTRPC3l  (1567) KTAEYTSITDCIDTRCVNAPQAIADRAAFPGGLGDKVEDLTCCHPEREAE
melastatin1 (1387) RYSSIIDQQLTTEWQCQVQKITRSHSTDIDYIVGEAAVQAEQKE------

1701                                              1750
LTRPC3g  (1592) LSHPSSDSEENEAKGRRATIAISSQEGDNSERTLSNNITVPKIERANSYS
LTRPC3h  (1604) LSHPSSDSEENEAKGRRATIAISSQEGDNSERTLSNNITVPKIERANSYS
LTRPC3i  (1604) LSHPSSDSEENEAKGRRATIAISSQEGDNSERTLSNNITVPKIERANSYS
LTRPC3j  (1582) LSHPSSDSEENEAKGRRATIAISSQEGDNSERTLSNNITVPKIERANSYS
LTRPC3k  (1594) LSHPSSDSEENEAKGRRATIAISSQEGDNSERTLSNNITVPKIERANSYS
LTRPC3l  (1617) LSHPSSDSEENEAKGRRATIAISSQEGDNSERTLSNNITVPKIERANSYS
melastatin1 (1431) --Q--FADMQDEHHVAEAIPRLPRLSLTITDRNGMENLLSVKPDQTLGFP 1751                                              1800
LTRPC3g  (1642) AEEPSAPYAHTRKSFSISDKLDRQRNTASLQNPFQRSKSSKPEGRGDSLS
LTRPC3h  (1654) AEEPSAPYAHTRKSFSISDKLDRQRNTASLQNPFQRSKSSKPEGRGDSLS
LTRPC3i  (1654) AEEPSAPYAHTRKSFSISDKLDRQRNTASLQNPFQRSKSSKPEGRGDSLS
LTRPC3j  (1632) AEEPSAPYAHTRKSFSISDKLDRQRNTASLQNPFQRSKSSKPEGRGDSLS
LTRPC3k  (1644) AEEPSAPYAHTRKSFSISDKLDRQRNTASLQNPFQRSKSSKPEGRGDSLS
LTRPC3l  (1667) AEEPSAPYAHTRKSFSISDKLDRQRNTASLQNPFQRSKSSKPEGRGDSLS
melastatin1 (1477) SLRSKSLHGHFRNVKSIQGKLDRSGHAGSVSSLVIVSGMTAEE-------
```

FIG. 7G

```
                          1801              1818
    LTRPC3g   (1692)  MRRLSRTSAFQSFESKHT
    LTRPC3h   (1704)  MRRLSRTSAFQSFESKHT
    LTRPC3i   (1704)  MRRLSRTSAFQSFESKHT
    LTRPC3j   (1682)  MRRLSRTSAFQSFESKHT
    LTRPC3k   (1694)  MRRLSRTSAFQSFESKHT
    LTRPC3l   (1717)  MRRLSRTSAFQSFESKHT
 melastatin1  (1520)  -KKVKKEKASTETEC---
```

FIG. 10

LTRPC3g

| Protein | Genbank ID | Identities | Similarities |
|---|---|---|---|
| human melastatin 1 | gi|3243075 | 65.7% | 73.5% |

LTRPC3h

| Protein | Genbank ID | Identities | Similarities |
|---|---|---|---|
| human melastatin 1 | gi|3243075 | 65.7% | 73.5% |

LTRPC3i

| Protein | Genbank ID | Identities | Similarities |
|---|---|---|---|
| human melastatin 1 | gi|3243075 | 65.4% | 73.2% |

LTRPC3j

| Protein | Genbank ID | Identities | Similarities |
|---|---|---|---|
| human melastatin 1 | gi|3243075 | 65.4% | 73.3% |

LTRPC3k

| Protein | Genbank ID | Identities | Similarities |
|---|---|---|---|
| human melastatin 1 | gi|3243075 | 65.5% | 73.3% |

LTRPC3l

| Protein | Genbank ID | Identities | Similarities |
|---|---|---|---|
| human melastatin 1 | gi|3243075 | 65.7% | 73.5% |

FIG. 11A

```
               1                                                  50
LTRPC3    (1) --------------------------------------------------
LTRPC3b   (1) --------------------------------------------------
LTRPC3c   (1) --------------------------------------------------
LTRPC3d   (1) --------------------------------------------------
LTRPC3e   (1) --------------------------------------------------
LTRPC3f   (1) --------------------------------------------------
LTRPC3g   (1) MGKKWRDAAEMERGCSDREDNAESRRRSRSASRGRFAESWKRLSSKQGST
LTRPC3h   (1) MGKKWRDAAEMERGCSDREDNAESRRRSRSASRGRFAESWKRLSSKQGST
LTRPC3i   (1) MGKKWRDAAEMERGCSDREDNAESRRRSRSASRGRFAESWKRLSSKQGST
LTRPC3j   (1) MGKKWRDAAEMERGCSDREDNAESRRRSRSASRGRFAESWKRLSSKQGST
LTRPC3k   (1) MGKKWRDAAEMERGCSDREDNAESRRRSRSASRGRFAESWKRLSSKQGST
LTRPC3l   (1) MGKKWRDAAEMERGCSDREDNAESRRRSRSASRGRFAESWKRLSSKQGST 51                                                100
LTRPC3    (1) --------------------------------------------------
LTRPC3b   (1) --------------------------------------------------
LTRPC3c   (1) --------------------------------------------------
LTRPC3d   (1) --------------------------------------------------
LTRPC3e   (1) --------------------------------------------------
LTRPC3f   (1) --------------------------------------------------
LTRPC3g  (51) KRSGLPSQQTPAQKSWIERAFYKRECVHIIPSTKDPHRCCCGRLIGQHVG
LTRPC3h  (51) KRSGLPSQQTPAQKSWIERAFYKRECVHIIPSTKDPHRCCCGRLIGQHVG
LTRPC3i  (51) KRSGLPSQQTPAQKSWIERAFYKRECVHIIPSTKDPHRCCCGRLIGQHVG
LTRPC3j  (51) KRSGLPSQQTPAQKSWIERAFYKRECVHIIPSTKDPHRCCCGRLIGQHVG
LTRPC3k  (51) KRSGLPSQQTPAQKSWIERAFYKRECVHIIPSTKDPHRCCCGRLIGQHVG
LTRPC3l  (51) KRSGLPSQQTPAQKSWIERAFYKRECVHIIPSTKDPHRCCCGRLIGQHVG 101                                               150
LTRPC3    (1) --------------------------------------------------
LTRPC3b   (1) --------------------------------------------------
LTRPC3c   (1) --------------------------------------------------
LTRPC3d   (1) --------------------------------------------------
LTRPC3e   (1) --------------------------------------------------
LTRPC3f   (1) --------------------------------------------------
LTRPC3g (101) LTPSISVLQNEKNESRLSRNDIQSEKWSISKHTQLSPTDAFGTIEFQGGG
LTRPC3h (101) LTPSISVLQNEKNESRLSRNDIQSEKWSISKHTQLSPTDAFGTIEFQGGG
LTRPC3i (101) LTPSISVLQNEKNESRLSRNDIQSEKWSISKHTQLSPTDAFGTIEFQGGG
LTRPC3j (101) LTPSISVLQNEKNESRLSRNDIQSEKWSISKHTQLSPTDAFGTIEFQGGG
LTRPC3k (101) LTPSISVLQNEKNESRLSRNDIQSEKWSISKHTQLSPTDAFGTIEFQGGG
LTRPC3l (101) LTPSISVLQNEKNESRLSRNDIQSEKWSISKHTQLSPTDAFGTIEFQGGG 151                                               200
LTRPC3    (1) -----MYVRVSFDTKPDLLHLMTKEWQLELPKLLISVHGGLQNFELQPK
LTRPC3b   (1) -----MYVRVSFDTKPDLLHLMTKEWQLELPKLLISVHGGLQNFELQPK
LTRPC3c   (1) -----MYVRVSFDTKPDLLHLMTKEWQLELPKLLISVHGGLQNFELQPK
LTRPC3d   (1) -----MYVRVSFDTKPDLLHLMTKEWQLELPKLLISVHGGLQNFELQPK
LTRPC3e   (1) -----MYVRVSFDTKPDLLHLMTKEWQLELPKLLISVHGGLQNFELQPK
LTRPC3f   (1) -----MYVRVSFDTKPDLLHLMTKEWQLELPKLLISVHGGLQNFELQPK
LTRPC3g (151) HSNKAMYVRVSFDTKPDLLHLMTKEWQLELPKLLISVHGGLQNFELQPK
LTRPC3h (151) HSNKAMYVRVSFDTKPDLLHLMTKEWQLELPKLLISVHGGLQNFELQPK
LTRPC3i (151) HSNKAMYVRVSFDTKPDLLHLMTKEWQLELPKLLISVHGGLQNFELQPK
LTRPC3j (151) HSNKAMYVRVSFDTKPDLLHLMTKEWQLELPKLLISVHGGLQNFELQPK
LTRPC3k (151) HSNKAMYVRVSFDTKPDLLHLMTKEWQLELPKLLISVHGGLQNFELQPK
LTRPC3l (151) HSNKAMYVRVSFDTKPDLLHLMTKEWQLELPKLLISVHGGLQNFELQPK
```

FIG. 11B

```
                    201                                                      250
LTRPC3     (46)   LKQVFGKGLIKAAMTTGAWIFTGGVNTGVIRHVGDALKDHASKSRGKICT
LTRPC3b    (46)   LKQVFGKGLIKAAMTTGAWIFTGGVNTGVIRHVGDALKDHASKSRGKICT
LTRPC3c    (46)   LKQVFGKGLIKAAMTTGAWIFTGGVNTGVIRHVGDALKDHASKSRGKICT
LTRPC3d    (46)   LKQVFGKGLIKAAMTTGAWIFTGGVNTGVIRHVGDALKDHASKSRGKICT
LTRPC3e    (46)   LKQVFGKGLIKAAMTTGAWIFTGGVNTGVIRHVGDALKDHASKSRGKICT
LTRPC3f    (46)   LKQVFGKGLIKAAMTTGAWIFTGGVNTGVIRHVGDALKDHASKSRGKICT
LTRPC3g   (201)   LKQVFGKGLIKAAMTTGAWIFTGGVNTGVIRHVGDALKDHASKSRGKICT
LTRPC3h   (201)   LKQVFGKGLIKAAMTTGAWIFTGGVNTGVIRHVGDALKDHASKSRGKICT
LTRPC3i   (201)   LKQVFGKGLIKAAMTTGAWIFTGGVNTGVIRHVGDALKDHASKSRGKICT
LTRPC3j   (201)   LKQVFGKGLIKAAMTTGAWIFTGGVNTGVIRHVGDALKDHASKSRGKICT
LTRPC3k   (201)   LKQVFGKGLIKAAMTTGAWIFTGGVNTGVIRHVGDALKDHASKSRGKICT
LTRPC3l   (201)   LKQVFGKGLIKAAMTTGAWIFTGGVNTGVIRHVGDALKDHASKSRGKICT 251                                                      300
LTRPC3     (96)   IGIAPWGIVENQEDLIGRDVVRPYQTMSNPMSKLTVLNSMHSHFILADNG
LTRPC3b    (96)   IGIAPWGIVENQEDLIGRDVVRPYQTMSNPMSKLTVLNSMHSHFILADNG
LTRPC3c    (96)   IGIAPWGIVENQEDLIGRDVVRPYQTMSNPMSKLTVLNSMHSHFILADNG
LTRPC3d    (96)   IGIAPWGIVENQEDLIGRDVVRPYQTMSNPMSKLTVLNSMHSHFILADNG
LTRPC3e    (96)   IGIAPWGIVENQEDLIGRDVVRPYQTMSNPMSKLTVLNSMHSHFILADNG
LTRPC3f    (96)   IGIAPWGIVENQEDLIGRDVVRPYQTMSNPMSKLTVLNSMHSHFILADNG
LTRPC3g   (251)   IGIAPWGIVENQEDLIGRDVVRPYQTMSNPMSKLTVLNSMHSHFILADNG
LTRPC3h   (251)   IGIAPWGIVENQEDLIGRDVVRPYQTMSNPMSKLTVLNSMHSHFILADNG
LTRPC3i   (251)   IGIAPWGIVENQEDLIGRDVVRPYQTMSNPMSKLTVLNSMHSHFILADNG
LTRPC3j   (251)   IGIAPWGIVENQEDLIGRDVVRPYQTMSNPMSKLTVLNSMHSHFILADNG
LTRPC3k   (251)   IGIAPWGIVENQEDLIGRDVVRPYQTMSNPMSKLTVLNSMHSHFILADNG
LTRPC3l   (251)   IGIAPWGIVENQEDLIGRDVVRPYQTMSNPMSKLTVLNSMHSHFILADNG 301                                                      350
LTRPC3    (146)   TTGKYGAEVKLRRQLEKHISLQKINT----------R-------------
LTRPC3b   (146)   TTGKYGAEVKLRRQLEKHISLQKINTR-----------------------
LTRPC3c   (146)   TTGKYGAEVKLRRQLEKHISLQKINT----------R-------------
LTRPC3d   (146)   TTGKYGAEVKLRRQLEKHISLQKINTR-----------------------
LTRPC3e   (146)   TTGKYGAEVKLRRQLEKHISLQKINTR-----------------------
LTRPC3f   (146)   TTGKYGAEVKLRRQLEKHISLQKINTRCLPFFSLDSRLFYSFWGSCQLDS
LTRPC3g   (301)   TTGKYGAEVKLRRQLEKHISLQKINTR-----------------------
LTRPC3h   (301)   TTGKYGAEVKLRRQLEKHISLQKINTR-----------------------
LTRPC3i   (301)   TTGKYGAEVKLRRQLEKHISLQKINT----------R-------------
LTRPC3j   (301)   TTGKYGAEVKLRRQLEKHISLQKINTR-----------------------
LTRPC3k   (301)   TTGKYGAEVKLRRQLEKHISLQKINTR-----------------------
LTRPC3l   (301)   TTGKYGAEVKLRRQLEKHISLQKINTRCLPFFSLDSRLFYSFWGSCQLDS 351                                                      400
LTRPC3    (173)   --IGQGVPVVALIVEGGPNVISIVLEYLRDTPPVPVVVCDGSGRASDILA
LTRPC3b   (173)   --IGQGVPVVALIVEGGPNVISIVLEYLRDTPPVPVVVCDGSGRASDILA
LTRPC3c   (173)   --IGQGVPVVALIVEGGPNVISIVLEYLRDTPPVPVVVCDGSGRASDILA
LTRPC3d   (173)   --IGQGVPVVALIVEGGPNVISIVLEYLRDTPPVPVVVCDGSGRASDILA
LTRPC3e   (173)   --IGQGVPVVALIVEGGPNVISIVLEYLRDTPPVPVVVCDGSGRASDILA
LTRPC3f   (196)   VGIGQGVPVVALIVEGGPNVISIVLEYLRDTPPVPVVVCDGSGRASDILA
LTRPC3g   (328)   --IGQGVPVVALIVEGGPNVISIVLEYLRDTPPVPVVVCDGSGRASDILA
LTRPC3h   (328)   --IGQGVPVVALIVEGGPNVISIVLEYLRDTPPVPVVVCDGSGRASDILA
LTRPC3i   (328)   --IGQGVPVVALIVEGGPNVISIVLEYLRDTPPVPVVVCDGSGRASDILA
LTRPC3j   (328)   --IGQGVPVVALIVEGGPNVISIVLEYLRDTPPVPVVVCDGSGRASDILA
LTRPC3k   (328)   --IGQGVPVVALIVEGGPNVISIVLEYLRDTPPVPVVVCDGSGRASDILA
LTRPC3l   (351)   VGIGQGVPVVALIVEGGPNVISIVLEYLRDTPPVPVVVCDGSGRASDILA
```

FIG. 11C

```
            401                                                    450
LTRPC3  (221) FGHKYSEEGGLINESLRDQLLVTIQKTFTYTRTQAQHLFIILMECMKKKE
LTRPC3b (221) FGHKYSEEGGLINESLRDQLLVTIQKTFTYTRTQAQHLFIILMECMKKKE
LTRPC3c (221) FGHKYSEEGGLINESLRDQLLVTIQKTFTYTRTQAQHLFIILMECMKKKE
LTRPC3d (221) FGHKYSEEGGLINESLRDQLLVTIQKTFTYTRTQAQHLFIILMECMKKKE
LTRPC3e (221) FGHKYSEEGGLINESLRDQLLVTIQKTFTYTRTQAQHLFIILMECMKKKE
LTRPC3f (246) FGHKYSEEGGLINESLRDQLLVTIQKTFTYTRTQAQHLFIILMECMKKKE
LTRPC3g (376) FGHKYSEEGGLINESLRDQLLVTIQKTFTYTRTQAQHLFIILMECMKKKE
LTRPC3h (376) FGHKYSEEGGLINESLRDQLLVTIQKTFTYTRTQAQHLFIILMECMKKKE
LTRPC3i (376) FGHKYSEEGGLINESLRDQLLVTIQKTFTYTRTQAQHLFIILMECMKKKE
LTRPC3j (376) FGHKYSEEGGLINESLRDQLLVTIQKTFTYTRTQAQHLFIILMECMKKKE
LTRPC3k (376) FGHKYSEEGGLINESLRDQLLVTIQKTFTYTRTQAQHLFIILMECMKKKE
LTRPC3l (401) FGHKYSEEGGLINESLRDQLLVTIQKTFTYTRTQAQHLFIILMECMKKKE 451                                                    500
LTRPC3  (271) LITVFRMGSEGHQDIDLAILTALLKGANASAPDQLSLALAWNRVDIARSQ
LTRPC3b (271) LITVFRMGSEGHQDIDLAILTALLKGANASAPDQLSLALAWNRVDIARSQ
LTRPC3c (271) LITVFRMGSEGHQDIDLAILTALLKGANASAPDQLSLALAWNRVDIARSQ
LTRPC3d (271) LITVFRMGSEGHQDIDLAILTALLKGANASAPDQLSLALAWNRVDIARSQ
LTRPC3e (271) LITVFRMGSEGHQDIDLAILTALLKGANASAPDQLSLALAWNRVDIARSQ
LTRPC3f (296) LITVFRMGSEGHQDIDLAILTALLKGANASAPDQLSLALAWNRVDIARSQ
LTRPC3g (426) LITVFRMGSEGHQDIDLAILTALLKGANASAPDQLSLALAWNRVDIARSQ
LTRPC3h (426) LITVFRMGSEGHQDIDLAILTALLKGANASAPDQLSLALAWNRVDIARSQ
LTRPC3i (426) LITVFRMGSEGHQDIDLAILTALLKGANASAPDQLSLALAWNRVDIARSQ
LTRPC3j (426) LITVFRMGSEGHQDIDLAILTALLKGANASAPDQLSLALAWNRVDIARSQ
LTRPC3k (426) LITVFRMGSEGHQDIDLAILTALLKGANASAPDQLSLALAWNRVDIARSQ
LTRPC3l (451) LITVFRMGSEGHQDIDLAILTALLKGANASAPDQLSLALAWNRVDIARSQ 501                                                    550
LTRPC3  (321) IFIYGQQWPVGSLEQAMLDALVLDRVDFVKLLIENGVSMHRFLTISRLEE
LTRPC3b (321) IFIYGQQWPVGSLEQAMLDALVLDRVDFVKLLIENGVSMHRFLTISRLEE
LTRPC3c (321) IFIYGQQWPVGSLEQAMLDALVLDRVDFVKLLIENGVSMHRFLTISRLEE
LTRPC3d (321) IFIYGQQWPVGSLEQAMLDALVLDRVDFVKLLIENGVSMHRFLTISRLEE
LTRPC3e (321) IFIYGQQWPVGSLEQAMLDALVLDRVDFVKLLIENGVSMHRFLTISRLEE
LTRPC3f (346) IFIYGQQWPVGSLEQAMLDALVLDRVDFVKLLIENGVSMHRFLTISRLEE
LTRPC3g (476) IFIYGQQWPVGSLEQAMLDALVLDRVDFVKLLIENGVSMHRFLTISRLEE
LTRPC3h (476) IFIYGQQWPVGSLEQAMLDALVLDRVDFVKLLIENGVSMHRFLTISRLEE
LTRPC3i (476) IFIYGQQWPVGSLEQAMLDALVLDRVDFVKLLIENGVSMHRFLTISRLEE
LTRPC3j (476) IFIYGQQWPVGSLEQAMLDALVLDRVDFVKLLIENGVSMHRFLTISRLEE
LTRPC3k (476) IFIYGQQWPVGSLEQAMLDALVLDRVDFVKLLIENGVSMHRFLTISRLEE
LTRPC3l (501) IFIYGQQWPVGSLEQAMLDALVLDRVDFVKLLIENGVSMHRFLTISRLEE 551                                                    600
LTRPC3  (371) LYNTRHGPSNTLYHLVRDVKK------------GNLPPDYRISLIDIGLV
LTRPC3b (371) LYNTRHGPSNTLYHLVRDVKKREYPGFGWIYFKGNLPPDYRISLIDIGLV
LTRPC3c (371) LYNTRHGPSNTLYHLVRDVKK------------GNLPPDYRISLIDIGLV
LTRPC3d (371) LYNTRHGPSNTLYHLVRDVKK------------GNLPPDYRISLIDIGLV
LTRPC3e (371) LYNTRHGPSNTLYHLVRDVKKREYPGFGWIYFKGNLPPDYRISLIDIGLV
LTRPC3f (396) LYNTRHGPSNTLYHLVRDVKK------------GNLPPDYRISLIDIGLV
LTRPC3g (526) LYNTRHGPSNTLYHLVRDVKK------------GNLPPDYRISLIDIGLV
LTRPC3h (526) LYNTRHGPSNTLYHLVRDVKKREYPGFGWIYFKGNLPPDYRISLIDIGLV
LTRPC3i (526) LYNTRHGPSNTLYHLVRDVKK------------GNLPPDYRISLIDIGLV
LTRPC3j (526) LYNTRHGPSNTLYHLVRDVKK------------GNLPPDYRISLIDIGLV
LTRPC3k (526) LYNTRHGPSNTLYHLVRDVKKREYPGFGWIYFKGNLPPDYRISLIDIGLV
LTRPC3l (551) LYNTRHGPSNTLYHLVRDVKK------------GNLPPDYRISLIDIGLV
```

FIG. 11D

```
              601                                                      650
LTRPC3  (409) IEYLMGGAYRCNYTRKRFRTLYHNLFGPKRPKALKLLGMEDDIPLRRGRK
LTRPC3b (421) IEYLMGGAYRCNYTRKRFRTLYHNLFGPKRPKALKLLGMEDDIPLRRGRK
LTRPC3c (409) IEYLMGGAYRCNYTRKRFRTLYHNLFGPKRPKALKLLGMEDDIPLRRGRK
LTRPC3d (409) IEYLMGGAYRCNYTRKRFRTLYHNLFGPKR----------DDIPLRRGRK
LTRPC3e (421) IEYLMGGAYRCNYTRKRFRTLYHNLFGPKR----------DDIPLRRGRK
LTRPC3f (434) IEYLMGGAYRCNYTRKRFRTLYHNLFGPKRPKALKLLGMEDDIPLRRGRK
LTRPC3g (564) IEYLMGGAYRCNYTRKRFRTLYHNLFGPKRPKALKLLGMEDDIPLRRGRK
LTRPC3h (576) IEYLMGGAYRCNYTRKRFRTLYHNLFGPKRPKALKLLGMEDDIPLRRGRK
LTRPC3i (564) IEYLMGGAYRCNYTRKRFRTLYHNLFGPKRPKALKLLGMEDDIPLRRGRK
LTRPC3j (564) IEYLMGGAYRCNYTRKRFRTLYHNLFGPKR----------DDIPLRRGRK
LTRPC3k (576) IEYLMGGAYRCNYTRKRFRTLYHNLFGPKR----------DDIPLRRGRK
LTRPC3l (589) IEYLMGGAYRCNYTRKRFRTLYHNLFGPKRPKALKLLGMEDDIPLRRGRK 651                                                      700
LTRPC3  (459) TTKKREEEVDIDLDDPEINHFPFPFHELMVWAVLMKRQKMALFFWQHGEE
LTRPC3b (471) TTKKREEEVDIDLDDPEINHFPFPFHELMVWAVLMKRQKMALFFWQHGEE
LTRPC3c (459) TTKKREEEVDIDLDDPEINHFPFPFHELMVWAVLMKRQKMALFFWQHGEE
LTRPC3d (449) TTKKREEEVDIDLDDPEINHFPFPFHELMVWAVLMKRQKMALFFWQHGEE
LTRPC3e (461) TTKKREEEVDIDLDDPEINHFPFPFHELMVWAVLMKRQKMALFFWQHGEE
LTRPC3f (484) TTKKREEEVDIDLDDPEINHFPFPFHELMVWAVLMKRQKMALFFWQHGEE
LTRPC3g (614) TTKKREEEVDIDLDDPEINHFPFPFHELMVWAVLMKRQKMALFFWQHGEE
LTRPC3h (626) TTKKREEEVDIDLDDPEINHFPFPFHELMVWAVLMKRQKMALFFWQHGEE
LTRPC3i (614) TTKKREEEVDIDLDDPEINHFPFPFHELMVWAVLMKRQKMALFFWQHGEE
LTRPC3j (604) TTKKREEEVDIDLDDPEINHFPFPFHELMVWAVLMKRQKMALFFWQHGEE
LTRPC3k (616) TTKKREEEVDIDLDDPEINHFPFPFHELMVWAVLMKRQKMALFFWQHGEE
LTRPC3l (639) TTKKREEEVDIDLDDPEINHFPFPFHELMVWAVLMKRQKMALFFWQHGEE 701                                                      750
LTRPC3  (509) AMAKALVACKLCKAMAHEASENDMVDDISQELNIINSRDFGQLAVELLDQS
LTRPC3b (521) AMAKALVACKLCKAMAHEASENDMVDDISQELNIINSRDFGQLAVELLDQS
LTRPC3c (509) AMAKALVACKLCKAMAHEASENDMVDDISQELNIINSRDFGQLAVELLDQS
LTRPC3d (499) AMAKALVACKLCKAMAHEASENDMVDDISQELNIINSRDFGQLAVELLDQS
LTRPC3e (511) AMAKALVACKLCKAMAHEASENDMVDDISQELNHNSRDFGQLAVELLDQS
LTRPC3f (534) AMAKALVACKLCKAMAHEASENDMVDDISQELNHNSRDFGQLAVELLDQS
LTRPC3g (664) AMAKALVACKLCKAMAHEASENDMVDDISQELNHNSRDFGQLAVELLDQS
LTRPC3h (676) AMAKALVACKLCKAMAHEASENDMVDDISQELNHNSRDFGQLAVELLDQS
LTRPC3i (664) AMAKALVACKLCKAMAHEASENDMVDDISQELNHNSRDFGQLAVELLDQS
LTRPC3j (654) AMAKALVACKLCKAMAHEASENDMVDDISQELNHNSRDFGQLAVELLDQS
LTRPC3k (666) AMAKALVACKLCKAMAHEASENDMVDDISQELNHNSRDFGQLAVELLDQS
LTRPC3l (689) AMAKALVACKLCKAMAHEASENDMVDDISQELNHNSRDFGQLAVELLDQS 751                                                      800
LTRPC3  (559) YKQDEQLAMKLLTYELKNWSNATCLQLAVAAKHRDFIAHTCSQMLLTDMW
LTRPC3b (571) YKQDEQLAMKLLTYELKNWSNATCLQLAVAAKHRDFIAHTCSQMLLTDMW
LTRPC3c (559) YKQDEQLAMKLLTYELKNWSNATCLQLAVAAKHRDFIAHTCSQMLLTDMW
LTRPC3d (549) YKQDEQLAMKLLTYELKNWSNATCLQLAVAAKHRDFIAHTCSQMLLTDMW
LTRPC3e (561) YKQDEQLAMKLLTYELKNWSNATCLQLAVAAKHRDFIAHTCSQMLLTDMW
LTRPC3f (584) YKQDEQLAMKLLTYELKNWSNATCLQLAVAAKHRDFIAHTCSQMLLTDMW
LTRPC3g (714) YKQDEQLAMKLLTYELKNWSNATCLQLAVAAKHRDFIAHTCSQMLLTDMW
LTRPC3h (726) YKQDEQLAMKLLTYELKNWSNATCLQLAVAAKHRDFIAHTCSQMLLTDMW
LTRPC3i (714) YKQDEQLAMKLLTYELKNWSNATCLQLAVAAKHRDFIAHTCSQMLLTDMW
LTRPC3j (704) YKQDEQLAMKLLTYELKNWSNATCLQLAVAAKHRDFIAHTCSQMLLTDMW
LTRPC3k (716) YKQDEQLAMKLLTYELKNWSNATCLQLAVAAKHRDFIAHTCSQMLLTDMW
LTRPC3l (739) YKQDEQLAMKLLTYELKNWSNATCLQLAVAAKHRDFIAHTCSQMLLTDMW
```

FIG. 11E

```
              801                                                   850
LTRPC3  (609) MGRLRMRKNSGLKVILGILLPPSILSLEFKNKDDMPYMSQAQEIHLQEKE
LTRPC3b (621) MGRLRMRKNSGLKVILGILLPPSILSLEFKNKDDMPYMSQAQEIHLQEKE
LTRPC3c (609) MGRLRMRKNSGLKVILGILLPPSILSLEFKNKDDMPYMSQAQEIHLQEKE
LTRPC3d (599) MGRLRMRKNSGLKVILGILLPPSILSLEFKNKDDMPYMSQAQEIHLQEKE
LTRPC3e (611) MGRLRMRKNSGLKVILGILLPPSILSLEFKNKDDMPYMSQAQEIHLQEKE
LTRPC3f (634) MGRLRMRKNSGLKVILGILLPPSILSLEFKNKDDMPYMSQAQEIHLQEKE
LTRPC3g (764) MGRLRMRKNSGLKVILGILLPPSILSLEFKNKDDMPYMSQAQEIHLQEKE
LTRPC3h (776) MGRLRMRKNSGLKVILGILLPPSILSLEFKNKDDMPYMSQAQEIHLQEKE
LTRPC3i (764) MGRLRMRKNSGLKVILGILLPPSILSLEFKNKDDMPYMSQAQEIHLQEKE
LTRPC3j (754) MGRLRMRKNSGLKVILGILLPPSILSLEFKNKDDMPYMSQAQEIHLQEKE
LTRPC3k (766) MGRLRMRKNSGLKVILGILLPPSILSLEFKNKDDMPYMSQAQEIHLQEKE
LTRPC3l (789) MGRLRMRKNSGLKVILGILLPPSILSLEFKNKDDMPYMSQAQEIHLQEKE 851                                                   900
LTRPC3  (659) AEEPEKPTKEKEEEDMELTAMLGRNNGESSRKKDEEEVQSKHRLIPLGRK
LTRPC3b (671) AEEPEKPTKEKEEEDMELTAMLGRNNGESSRKKDEEEVQSKHRLIPLGRK
LTRPC3c (659) AEEPEKPTKEKEEEDMELTAMLGRNNGESSRKKDEEEVQSKHRLIPLGRK
LTRPC3d (649) AEEPEKPTKEKEEEDMELTAMLGRNNGESSRKKDEEEVQSKHRLIPLGRK
LTRPC3e (661) AEEPEKPTKEKEEEDMELTAMLGRNNGESSRKKDEEEVQSKHRLIPLGRK
LTRPC3f (684) AEEPEKPTKEKEEEDMELTAMLGRNNGESSRKKDEEEVQSKHRLIPLGRK
LTRPC3g (814) AEEPEKPTKEKEEEDMELTAMLGRNNGESSRKKDEEEVQSKHRLIPLGRK
LTRPC3h (826) AEEPEKPTKEKEEEDMELTAMLGRNNGESSRKKDEEEVQSKHRLIPLGRK
LTRPC3i (814) AEEPEKPTKEKEEEDMELTAMLGRNNGESSRKKDEEEVQSKHRLIPLGRK
LTRPC3j (804) AEEPEKPTKEKEEEDMELTAMLGRNNGESSRKKDEEEVQSKHRLIPLGRK
LTRPC3k (816) AEEPEKPTKEKEEEDMELTAMLGRNNGESSRKKDEEEVQSKHRLIPLGRK
LTRPC3l (839) AEEPEKPTKEKEEEDMELTAMLGRNNGESSRKKDEEEVQSKHRLIPLGRK 901                                                   950
LTRPC3  (709) IYEFYNAPIVKFWFYTLAYIGYLMLFNYIVLVKMERWPSTQEWIVISYIF
LTRPC3b (721) IYEFYNAPIVKFWFYTLAYIGYLMLFNYIVLVKMERWPSTQEWIVISYIF
LTRPC3c (709) IYEFYNAPIVKFWFYTLAYIGYLMLFNYIVLVKMERWPSTQEWIVISYIF
LTRPC3d (699) IYEFYNAPIVKFWFYTLAYIGYLMLFNYIVLVKMERWPSTQEWIVISYIF
LTRPC3e (711) IYEFYNAPIVKFWFYTLAYIGYLMLFNYIVLVKMERWPSTQEWIVISYIF
LTRPC3f (734) IYEFYNAPIVKFWFYTLAYIGYLMLFNYIVLVKMERWPSTQEWIVISYIF
LTRPC3g (864) IYEFYNAPIVKFWFYTLAYIGYLMLFNYIVLVKMERWPSTQEWIVISYIF
LTRPC3h (876) IYEFYNAPIVKFWFYTLAYIGYLMLFNYIVLVKMERWPSTQEWIVISYIF
LTRPC3i (864) IYEFYNAPIVKFWFYTLAYIGYLMLFNYIVLVKMERWPSTQEWIVISYIF
LTRPC3j (854) IYEFYNAPIVKFWFYTLAYIGYLMLFNYIVLVKMERWPSTQEWIVISYIF
LTRPC3k (866) IYEFYNAPIVKFWFYTLAYIGYLMLFNYIVLVKMERWPSTQEWIVISYIF
LTRPC3l (889) IYEFYNAPIVKFWFYTLAYIGYLMLFNYIVLVKMERWPSTQEWIVISYIF 951                                                  1000
LTRPC3  (759) TLGIEKMREILMSEPGKLLQKVKVWLQEYWNVTDLIAILLFSVGMILRLQ
LTRPC3b (771) TLGIEKMREILMSEPGKLLQKVKVWLQEYWNVTDLIAILLFSVGMILRLQ
LTRPC3c (759) TLGIEKMREILMSEPGKLLQKVKVWLQEYWNVTDLIAILLFSVGMILRLQ
LTRPC3d (749) TLGIEKMREILMSEPGKLLQKVKVWLQEYWNVTDLIAILLFSVGMILRLQ
LTRPC3e (761) TLGIEKMREILMSEPGKLLQKVKVWLQEYWNVTDLIAILLFSVGMILRLQ
LTRPC3f (784) TLGIEKMREILMSEPGKLLQKVKVWLQEYWNVTDLIAILLFSVGMILRLQ
LTRPC3g (914) TLGIEKMREILMSEPGKLLQKVKVWLQEYWNVTDLIAILLFSVGMILRLQ
LTRPC3h (926) TLGIEKMREILMSEPGKLLQKVKVWLQEYWNVTDLIAILLFSVGMILRLQ
LTRPC3i (914) TLGIEKMREILMSEPGKLLQKVKVWLQEYWNVTDLIAILLFSVGMILRLQ
LTRPC3j (904) TLGIEKMREILMSEPGKLLQKVKVWLQEYWNVTDLIAILLFSVGMILRLQ
LTRPC3k (916) TLGIEKMREILMSEPGKLLQKVKVWLQEYWNVTDLIAILLFSVGMILRLQ
LTRPC3l (939) TLGIEKMREILMSEPGKLLQKVKVWLQEYWNVTDLIAILLFSVGMILRLQ
```

FIG. 11F

```
                1001                                                  1050
LTRPC3   (809) DQPFRSDGRVIYCVNIIYWYIRLLDIFGVNKYLGPYVMMIGKMMIDMMYF
LTRPC3b  (821) DQPFRSDGRVIYCVNIIYWYIRLLDIFGVNKYLGPYVMMIGKMMIDMMYF
LTRPC3c  (809) DQPFRSDGRVIYCVNIIYWYIRLLDIFGVNKYLGPYVMMIGKMMIDMMYF
LTRPC3d  (799) DQPFRSDGRVIYCVNIIYWYIRLLDIFGVNKYLGPYVMMIGKMMIDMMYF
LTRPC3e  (811) DQPFRSDGRVIYCVNIIYWYIRLLDIFGVNKYLGPYVMMIGKMMIDMMYF
LTRPC3f  (834) DQPFRSDGRVIYCVNIIYWYIRLLDIFGVNKYLGPYVMMIGKMMIDMMYF
LTRPC3g  (964) DQPFRSDGRVIYCVNIIYWYIRLLDIFGVNKYLGPYVMMIGKMMIDMMYF
LTRPC3h  (976) DQPFRSDGRVIYCVNIIYWYIRLLDIFGVNKYLGPYVMMIGKMMIDMMYF
LTRPC3i  (964) DQPFRSDGRVIYCVNIIYWYIRLLDIFGVNKYLGPYVMMIGKMMIDMMYF
LTRPC3j  (954) DQPFRSDGRVIYCVNIIYWYIRLLDIFGVNKYLGPYVMMIGKMMIDMMYF
LTRPC3k  (966) DQPFRSDGRVIYCVNIIYWYIRLLDIFGVNKYLGPYVMMIGKMMIDMMYF
LTRPC3l  (989) DQPFRSDGRVIYCVNIIYWYIRLLDIFGVNKYLGPYVMMIGKMMIDMMYF 1051                                                  1100
LTRPC3   (859) VIIMLVVLMSFGVARQAILFPNEEPSWKLAKNIFYMPYWMIYGEVFADQI
LTRPC3b  (871) VIIMLVVLMSFGVARQAILFPNEEPSWKLAKNIFYMPYWMIYGEVFADQI
LTRPC3c  (859) VIIMLVVLMSFGVARQAILFPNEEPSWKLAKNIFYMPYWMIYGEVFADQI
LTRPC3d  (849) VIIMLVVLMSFGVARQAILFPNEEPSWKLAKNIFYMPYWMIYGEVFADQI
LTRPC3e  (861) VIIMLVVLMSFGVARQAILFPNEEPSWKLAKNIFYMPYWMIYGEVFADQI
LTRPC3f  (884) VIIMLVVLMSFGVARQAILFPNEEPSWKLAKNIFYMPYWMIYGEVFADQI
LTRPC3g (1014) VIIMLVVLMSFGVARQAILFPNEEPSWKLAKNIFYMPYWMIYGEVFADQI
LTRPC3h (1026) VIIMLVVLMSFGVARQAILFPNEEPSWKLAKNIFYMPYWMIYGEVFADQI
LTRPC3i (1014) VIIMLVVLMSFGVARQAILFPNEEPSWKLAKNIFYMPYWMIYGEVFADQI
LTRPC3j (1004) VIIMLVVLMSFGVARQAILFPNEEPSWKLAKNIFYMPYWMIYGEVFADQI
LTRPC3k (1016) VIIMLVVLMSFGVARQAILFPNEEPSWKLAKNIFYMPYWMIYGEVFADQI
LTRPC3l (1039) VIIMLVVLMSFGVARQAILFPNEEPSWKLAKNIFYMPYWMIYGEVFADQI 1101                                                  1150
LTRPC3   (909) D-------------PPCGQNETREDGKIIQLPPCKTGAWIVPAIMACYLLV
LTRPC3b  (921) D-------------PPCGQNETREDGKIIQLPPCKTGAWIVPAIMACYLLV
LTRPC3c  (909) DRKQVYDSHTPKSAPCGQNETREDGKIIQLPPCKTGAWIVPAIMACYLLV
LTRPC3d  (899) D-------------PPCGQNETREDGKIIQLPPCKTGAWIVPAIMACYLLV
LTRPC3e  (911) D-------------PPCGQNETREDGKIIQLPPCKTGAWIVPAIMACYLLV
LTRPC3f  (934) D-------------PPCGQNETREDGKIIQLPPCKTGAWIVPAIMACYLLV
LTRPC3g (1064) D-------------PPCGQNETREDGKIIQLPPCKTGAWIVPAIMACYLLV
LTRPC3h (1076) D-------------PPCGQNETREDGKIIQLPPCKTGAWIVPAIMACYLLV
LTRPC3i (1064) DRKQVYDSHTPKSAPCGQNETREDGKIIQLPPCKTGAWIVPAIMACYLLV
LTRPC3j (1054) DRKQVYDSHTPKSAPCGQNETREDGKIIQLPPCKTGAWIVPAIMACYLLV
LTRPC3k (1066) D-------------PPCGQNETREDGKIIQLPPCKTGAWIVPAIMACYLLV
LTRPC3l (1089) D-------------PPCGQNETREDGKIIQLPPCKTGAWIVPAIMACYLLV 1151                                                  1200
LTRPC3   (947) ANILLVNLLIAVFNNTFFEVKSISNQVWKFQRYQLIMTFHERPVLPPPLI
LTRPC3b  (959) ANILLVNLLIAVFNNTFFEVKSISNQVWKFQRYQLIMTFHERPVLPPPLI
LTRPC3c  (959) ANILLVNLLIAVFNNTFFEVKSISNQVWKFQRYQLIMTFHERPVLPPPLI
LTRPC3d  (937) ANILLVNLLIAVFNNTFFEVKSISNQVWKFQRYQLIMTFHERPVLPPPLI
LTRPC3e  (949) ANILLVNLLIAVFNNTFFEVKSISNQVWKFQRYQLIMTFHERPVLPPPLI
LTRPC3f  (972) ANILLVNLLIAVFNNTFFEVKSISNQVWKFQRYQLIMTFHERPVLPPPLI
LTRPC3g (1102) ANILLVNLLIAVFNNTFFEVKSISNQVWKFQRYQLIMTFHERPVLPPPLI
LTRPC3h (1114) ANILLVNLLIAVFNNTFFEVKSISNQVWKFQRYQLIMTFHERPVLPPPLI
LTRPC3i (1114) ANILLVNLLIAVFNNTFFEVKSISNQVWKFQRYQLIMTFHERPVLPPPLI
LTRPC3j (1092) ANILLVNLLIAVFNNTFFEVKSISNQVWKFQRYQLIMTFHERPVLPPPLI
LTRPC3k (1104) ANILLVNLLIAVFNNTFFEVKSISNQVWKFQRYQLIMTFHERPVLPPPLI
LTRPC3l (1127) ANILLVNLLIAVFNNTFFEVKSISNQVWKFQRYQLIMTFHERPVLPPPLI
```

FIG. 11G

```
                    1201                                              1250
LTRPC3   (997)  IFSHMTMIFQHLCCRWRKHESDPDERDYGLKLFITDDELKKVHDFEEQCI
LTRPC3b  (1009) IFSHMTMIFQHLCCRWRKHESDPDERDYGLKLFITDDELKKVHDFEEQCI
LTRPC3c  (1009) IFSHMTMIFQHLCCRWRKHESDPDERDYGLKLFITDDELKKVHDFEEQCI
LTRPC3d  (987)  IFSHMTMIFQHLCCRWRKHESDPDERDYGLKLFITDDELKKVHDFEEQCI
LTRPC3e  (999)  IFSHMTMIFQHLCCRWRKHESDPDERDYGLKLFITDDELKKVHDFEEQCI
LTRPC3f  (1022) IFSHMTMIFQHLCCRWRKHESDPDERDYGLKLFITDDELKKVHDFEEQCI
LTRPC3g  (1152) IFSHMTMIFQHLCCRWRKHESDPDERDYGLKLFITDDELKKVHDFEEQCI
LTRPC3h  (1164) IFSHMTMIFQHLCCRWRKHESDPDERDYGLKLFITDDELKKVHDFEEQCI
LTRPC3i  (1164) IFSHMTMIFQHLCCRWRKHESDPDERDYGLKLFITDDELKKVHDFEEQCI
LTRPC3j  (1142) IFSHMTMIFQHLCCRWRKHESDPDERDYGLKLFITDDELKKVHDFEEQCI
LTRPC3k  (1154) IFSHMTMIFQHLCCRWRKHESDPDERDYGLKLFITDDELKKVHDFEEQCI
LTRPC3l  (1177) IFSHMTMIFQHLCCRWRKHESDPDERDYGLKLFITDDELKKVHDFEEQCI 1251                                              1300
LTRPC3   (1047) EEYFREKDDRFNSSNDERIRVTSERVENMSMRLEEVNEREHSMKASLQTV
LTRPC3b  (1059) EEYFREKDDRFNSSNDERIRVTSERVENMSMRLEEVNEREHSMKASLQTV
LTRPC3c  (1059) EEYFREKDDRFNSSNDERIRVTSERVENMSMRLEEVNEREHSMKASLQTV
LTRPC3d  (1037) EEYFREKDDRFNSSNDERIRVTSERVENMSMRLEEVNEREHSMKASLQTV
LTRPC3e  (1049) EEYFREKDDRFNSSNDERIRVTSERVENMSMRLEEVNEREHSMKASLQTV
LTRPC3f  (1072) EEYFREKDDRFNSSNDERIRVTSERVENMSMRLEEVNEREHSMKASLQTV
LTRPC3g  (1202) EEYFREKDDRFNSSNDERIRVTSERVENMSMRLEEVNEREHSMKASLQTV
LTRPC3h  (1214) EEYFREKDDRFNSSNDERIRVTSERVENMSMRLEEVNEREHSMKASLQTV
LTRPC3i  (1214) EEYFREKDDRFNSSNDERIRVTSERVENMSMRLEEVNEREHSMKASLQTV
LTRPC3j  (1192) EEYFREKDDRFNSSNDERIRVTSERVENMSMRLEEVNEREHSMKASLQTV
LTRPC3k  (1204) EEYFREKDDRFNSSNDERIRVTSERVENMSMRLEEVNEREHSMKASLQTV
LTRPC3l  (1227) EEYFREKDDRFNSSNDERIRVTSERVENMSMRLEEVNEREHSMKASLQTV 1301                                              1350
LTRPC3   (1097) DIRLAQLEDLIGRMATALERLTGLERAESNKTRSRTSSDCTDAAYIVRQS
LTRPC3b  (1109) DIRLAQLEDLIGRMATALERLTGLERAESNKTRSRTSSDCTDAAYIVRQS
LTRPC3c  (1109) DIRLAQLEDLIGRMATALERLTGLERAESNKTRSRTSSDCTDAAYIVRQS
LTRPC3d  (1087) DIRLAQLEDLIGRMATALERLTGLERAESNKTRSRTSSDCTDAAYIVRQS
LTRPC3e  (1099) DIRLAQLEDLIGRMATALERLTGLERAESNKTRSRTSSDCTDAAYIVRQS
LTRPC3f  (1122) DIRLAQLEDLIGRMATALERLTGLERAESNKTRSRTSSDCTDAAYIVRQS
LTRPC3g  (1252) DIRLAQLEDLIGRMATALERLTGLERAESNKTRSRTSSDCTDAAYIVRQS
LTRPC3h  (1264) DIRLAQLEDLIGRMATALERLTGLERAESNKTRSRTSSDCTDAAYIVRQS
LTRPC3i  (1264) DIRLAQLEDLIGRMATALERLTGLERAESNKTRSRTSSDCTDAAYIVRQS
LTRPC3j  (1242) DIRLAQLEDLIGRMATALERLTGLERAESNKTRSRTSSDCTDAAYIVRQS
LTRPC3k  (1254) DIRLAQLEDLIGRMATALERLTGLERAESNKTRSRTSSDCTDAAYIVRQS
LTRPC3l  (1277) DIRLAQLEDLIGRMATALERLTGLERAESNKTRSRTSSDCTDAAYIVRQS 1351                                              1400
LTRPC3   (1147) SFNSQEGNTFKLQESIDPAGEETMSPTSPTLMPRMRSHSFYSVNMKDKGG
LTRPC3b  (1159) SFNSQEGNTFKLQESIDPAGEETMSPTSPTLMPRMRSHSFYSVNMKDKGG
LTRPC3c  (1159) SFNSQEGNTFKLQESIDPAGEETMSPTSPTLMPRMRSHSFYSVNMKDKGG
LTRPC3d  (1137) SFNSQEGNTFKLQESIDPAGEETMSPTSPTLMPRMRSHSFYSVNMKDKGG
LTRPC3e  (1149) SFNSQEGNTFKLQESIDPAGEETMSPTSPTLMPRMRSHSFYSVNMKDKGG
LTRPC3f  (1172) SFNSQEGNTFKLQESIDPAGEETMSPTSPTLMPRMRSHSFYSVNMKDKGG
LTRPC3g  (1302) SFNSQEGNTFKLQESIDPAGEETMSPTSPTLMPRMRSHSFYSVNMKDKGG
LTRPC3h  (1314) SFNSQEGNTFKLQESIDPAGEETMSPTSPTLMPRMRSHSFYSVNMKDKGG
LTRPC3i  (1314) SFNSQEGNTFKLQESIDPAGEETMSPTSPTLMPRMRSHSFYSVNMKDKGG
LTRPC3j  (1292) SFNSQEGNTFKLQESIDPAGEETMSPTSPTLMPRMRSHSFYSVNMKDKGG
LTRPC3k  (1304) SFNSQEGNTFKLQESIDPAGEETMSPTSPTLMPRMRSHSFYSVNMKDKGG
LTRPC3l  (1327) SFNSQEGNTFKLQESIDPAGEETMSPTSPTLMPRMRSHSFYSVNMKDKGG
```

FIG. 11H

```
                    1401                                                1450
LTRPC3    (1197)   IEKLESIFKERSLSLHRATSSHSVAKEPKAPAAPANTLAIVPDSRRPSSC
LTRPC3b   (1209)   IEKLESIFKERSLSLHRATSSHSVAKEPKAPAAPANTLAIVPDSRRPSSC
LTRPC3c   (1209)   IEKLESIFKERSLSLHRATSSHSVAKEPKAPAAPANTLAIVPDSRRPSSC
LTRPC3d   (1187)   IEKLESIFKERSLSLHRATSSHSVAKEPKAPAAPANTLAIVPDSRRPSSC
LTRPC3e   (1199)   IEKLESIFKERSLSLHRATSSHSVAKEPKAPAAPANTLAIVPDSRRPSSC
LTRPC3f   (1222)   IEKLESIFKERSLSLHRATSSHSVAKEPKAPAAPANTLAIVPDSRRPSSC
LTRPC3g   (1352)   IEKLESIFKERSLSLHRATSSHSVAKEPKAPAAPANTLAIVPDSRRPSSC
LTRPC3h   (1364)   IEKLESIFKERSLSLHRATSSHSVAKEPKAPAAPANTLAIVPDSRRPSSC
LTRPC3i   (1364)   IEKLESIFKERSLSLHRATSSHSVAKEPKAPAAPANTLAIVPDSRRPSSC
LTRPC3j   (1342)   IEKLESIFKERSLSLHRATSSHSVAKEPKAPAAPANTLAIVPDSRRPSSC
LTRPC3k   (1354)   IEKLESIFKERSLSLHRATSSHSVAKEPKAPAAPANTLAIVPDSRRPSSC
LTRPC3l   (1377)   IEKLESIFKERSLSLHRATSSHSVAKEPKAPAAPANTLAIVPDSRRPSSC 1451                                                1500
LTRPC3    (1247)   IDIYVSAMDELHCDIDPLDNSVNILGLGEPSFSTPVPSTAPSSSAYATLA
LTRPC3b   (1259)   IDIYVSAMDELHCDIDPLDNSVNILGLGEPSFSTPVPSTAPSSSAYATLA
LTRPC3c   (1259)   IDIYVSAMDELHCDIDPLDNSVNILGLGEPSFSTPVPSTAPSSSAYATLA
LTRPC3d   (1237)   IDIYVSAMDELHCDIDPLDNSVNILGLGEPSFSTPVPSTAPSSSAYATLA
LTRPC3e   (1249)   IDIYVSAMDELHCDIDPLDNSVNILGLGEPSFSTPVPSTAPSSSAYATLA
LTRPC3f   (1272)   IDIYVSAMDELHCDIDPLDNSVNILGLGEPSFSTPVPSTAPSSSAYATLA
LTRPC3g   (1402)   IDIYVSAMDELHCDIDPLDNSVNILGLGEPSFSTPVPSTAPSSSAYATLA
LTRPC3h   (1414)   IDIYVSAMDELHCDIDPLDNSVNILGLGEPSFSTPVPSTAPSSSAYATLA
LTRPC3i   (1414)   IDIYVSAMDELHCDIDPLDNSVNILGLGEPSFSTPVPSTAPSSSAYATLA
LTRPC3j   (1392)   IDIYVSAMDELHCDIDPLDNSVNILGLGEPSFSTPVPSTAPSSSAYATLA
LTRPC3k   (1404)   IDIYVSAMDELHCDIDPLDNSVNILGLGEPSFSTPVPSTAPSSSAYATLA
LTRPC3l   (1427)   IDIYVSAMDELHCDIDPLDNSVNILGLGEPSFSTPVPSTAPSSSAYATLA 1501                                                1550
LTRPC3    (1297)   PTDRPPSRSIDFEDITSMDTRSFSSDYTHLPECQNPWDSEPPMYHTIERS
LTRPC3b   (1309)   PTDRPPSRSIDFEDITSMDTRSFSSDYTHLPECQNPWDSEPPMYHTIERS
LTRPC3c   (1309)   PTDRPPSRSIDFEDITSMDTRSFSSDYTHLPECQNPWDSEPPMYHTIERS
LTRPC3d   (1287)   PTDRPPSRSIDFEDITSMDTRSFSSDYTHLPECQNPWDSEPPMYHTIERS
LTRPC3e   (1299)   PTDRPPSRSIDFEDITSMDTRSFSSDYTHLPECQNPWDSEPPMYHTIERS
LTRPC3f   (1322)   PTDRPPSRSIDFEDITSMDTRSFSSDYTHLPECQNPWDSEPPMYHTIERS
LTRPC3g   (1452)   PTDRPPSRSIDFEDITSMDTRSFSSDYTHLPECQNPWDSEPPMYHTIERS
LTRPC3h   (1464)   PTDRPPSRSIDFEDITSMDTRSFSSDYTHLPECQNPWDSEPPMYHTIERS
LTRPC3i   (1464)   PTDRPPSRSIDFEDITSMDTRSFSSDYTHLPECQNPWDSEPPMYHTIERS
LTRPC3j   (1442)   PTDRPPSRSIDFEDITSMDTRSFSSDYTHLPECQNPWDSEPPMYHTIERS
LTRPC3k   (1454)   PTDRPPSRSIDFEDITSMDTRSFSSDYTHLPECQNPWDSEPPMYHTIERS
LTRPC3l   (1477)   PTDRPPSRSIDFEDITSMDTRSFSSDYTHLPECQNPWDSEPPMYHTIERS 1551                                                1600
LTRPC3    (1347)   KSSRYLATTPFLLEEAPIVKSHSFMFSPSRSYYANFGVPVKTAEYTSITD
LTRPC3b   (1359)   KSSRYLATTPFLLEEAPIVKSHSFMFSPSRSYYANFGVPVKTAEYTSITD
LTRPC3c   (1359)   KSSRYLATTPFLLEEAPIVKSHSFMFSPSRSYYANFGVPVKTAEYTSITD
LTRPC3d   (1337)   KSSRYLATTPFLLEEAPIVKSHSFMFSPSRSYYANFGVPVKTAEYTSITD
LTRPC3e   (1349)   KSSRYLATTPFLLEEAPIVKSHSFMFSPSRSYYANFGVPVKTAEYTSITD
LTRPC3f   (1372)   KSSRYLATTPFLLEEAPIVKSHSFMFSPSRSYYANFGVPVKTAEYTSITD
LTRPC3g   (1502)   KSSRYLATTPFLLEEAPIVKSHSFMFSPSRSYYANFGVPVKTAEYTSITD
LTRPC3h   (1514)   KSSRYLATTPFLLEEAPIVKSHSFMFSPSRSYYANFGVPVKTAEYTSITD
LTRPC3i   (1514)   KSSRYLATTPFLLEEAPIVKSHSFMFSPSRSYYANFGVPVKTAEYTSITD
LTRPC3j   (1492)   KSSRYLATTPFLLEEAPIVKSHSFMFSPSRSYYANFGVPVKTAEYTSITD
LTRPC3k   (1504)   KSSRYLATTPFLLEEAPIVKSHSFMFSPSRSYYANFGVPVKTAEYTSITD
LTRPC3l   (1527)   KSSRYLATTPFLLEEAPIVKSHSFMFSPSRSYYANFGVPVKTAEYTSITD
```

FIG. 11I

```
              1601                                                1650
LTRPC3  (1397) CIDTRCVNAPQAIADRAAFPGGLGDKVEDLTCCHPEREAELSHPSSDSEE
LTRPC3b (1409) CIDTRCVNAPQAIADRAAFPGGLGDKVEDLTCCHPEREAELSHPSSDSEE
LTRPC3c (1409) CIDTRCVNAPQAIADRAAFPGGLGDKVEDLTCCHPEREAELSHPSSDSEE
LTRPC3d (1387) CIDTRCVNAPQAIADRAAFPGGLGDKVEDLTCCHPEREAELSHPSSDSEE
LTRPC3e (1399) CIDTRCVNAPQAIADRAAFPGGLGDKVEDLTCCHPEREAELSHPSSDSEE
LTRPC3f (1422) CIDTRCVNAPQAIADRAAFPGGLGDKVEDLTCCHPEREAELSHPSSDSEE
LTRPC3g (1552) CIDTRCVNAPQAIADRAAFPGGLGDKVEDLTCCHPEREAELSHPSSDSEE
LTRPC3h (1564) CIDTRCVNAPQAIADRAAFPGGLGDKVEDLTCCHPEREAELSHPSSDSEE
LTRPC3i (1564) CIDTRCVNAPQAIADRAAFPGGLGDKVEDLTCCHPEREAELSHPSSDSEE
LTRPC3j (1542) CIDTRCVNAPQAIADRAAFPGGLGDKVEDLTCCHPEREAELSHPSSDSEE
LTRPC3k (1554) CIDTRCVNAPQAIADRAAFPGGLGDKVEDLTCCHPEREAELSHPSSDSEE
LTRPC3l (1577) CIDTRCVNAPQAIADRAAFPGGLGDKVEDLTCCHPEREAELSHPSSDSEE 1651                                                1700
LTRPC3  (1447) NEAKGRRATIAISSQEGDNSERTLSNNITVPKIERANSYSAEEPSAPYAH
LTRPC3b (1459) NEAKGRRATIAISSQEGDNSERTLSNNITVPKIERANSYSAEEPSAPYAH
LTRPC3c (1459) NEAKGRRATIAISSQEGDNSERTLSNNITVPKIERANSYSAEEPSAPYAH
LTRPC3d (1437) NEAKGRRATIAISSQEGDNSERTLSNNITVPKIERANSYSAEEPSAPYAH
LTRPC3e (1449) NEAKGRRATIAISSQEGDNSERTLSNNITVPKIERANSYSAEEPSAPYAH
LTRPC3f (1472) NEAKGRRATIAISSQEGDNSERTLSNNITVPKIERANSYSAEEPSAPYAH
LTRPC3g (1602) NEAKGRRATIAISSQEGDNSERTLSNNITVPKIERANSYSAEEPSAPYAH
LTRPC3h (1614) NEAKGRRATIAISSQEGDNSERTLSNNITVPKIERANSYSAEEPSAPYAH
LTRPC3i (1614) NEAKGRRATIAISSQEGDNSERTLSNNITVPKIERANSYSAEEPSAPYAH
LTRPC3j (1592) NEAKGRRATIAISSQEGDNSERTLSNNITVPKIERANSYSAEEPSAPYAH
LTRPC3k (1604) NEAKGRRATIAISSQEGDNSERTLSNNITVPKIERANSYSAEEPSAPYAH
LTRPC3l (1627) NEAKGRRATIAISSQEGDNSERTLSNNITVPKIERANSYSAEEPSAPYAH 1701                                                1750
LTRPC3  (1497) TRKSFSISDKLDRQRNTASLQNPFQRSKSSKPEGRGDSLSMRRLSRTSAF
LTRPC3b (1509) TRKSFSISDKLDRQRNTASLQNPFQRSKSSKPEGRGDSLSMRRLSRTSAF
LTRPC3c (1509) TRKSFSISDKLDRQRNTASLQNPFQRSKSSKPEGRGDSLSMRRLSRTSAF
LTRPC3d (1487) TRKSFSISDKLDRQRNTASLQNPFQRSKSSKPEGRGDSLSMRRLSRTSAF
LTRPC3e (1499) TRKSFSISDKLDRQRNTASLQNPFQRSKSSKPEGRGDSLSMRRLSRTSAF
LTRPC3f (1522) TRKSFSISDKLDRQRNTASLQNPFQRSKSSKPEGRGDSLSMRRLSRTSAF
LTRPC3g (1652) TRKSFSISDKLDRQRNTASLQNPFQRSKSSKPEGRGDSLSMRRLSRTSAF
LTRPC3h (1664) TRKSFSISDKLDRQRNTASLQNPFQRSKSSKPEGRGDSLSMRRLSRTSAF
LTRPC3i (1664) TRKSFSISDKLDRQRNTASLQNPFQRSKSSKPEGRGDSLSMRRLSRTSAF
LTRPC3j (1642) TRKSFSISDKLDRQRNTASLQNPFQRSKSSKPEGRGDSLSMRRLSRTSAF
LTRPC3k (1654) TRKSFSISDKLDRQRNTASLQNPFQRSKSSKPEGRGDSLSMRRLSRTSAF
LTRPC3l (1677) TRKSFSISDKLDRQRNTASLQNPFQRSKSSKPEGRGDSLSMRRLSRTSAF

1751
LTRPC3  (1547) QSFESKHT
LTRPC3b (1559) QSFESKHT
LTRPC3c (1559) QSFESKHT
LTRPC3d (1537) QSFESKHT
LTRPC3e (1549) QSFESKHT
LTRPC3f (1572) QSFESKHT
LTRPC3g (1702) QSFESKHT
LTRPC3h (1714) QSFESKHT
LTRPC3i (1714) QSFESKHT
LTRPC3j (1692) QSFESKHT
LTRPC3k (1704) QSFESKHT
LTRPC3l (1727) QSFESKHT
``` ated application U.S. Ser. No. 10/842,313, filed May 10, 2004, now U.S. Pat. No. 7,344,882 which claims benefit to provisional application U.S. Ser. No. 60/469,894 filed May 12, 2003; under 35 U.S.C. 119(e). The entire teachings of the referenced application are incorporated herein by reference.

VARIANTS OF THE TRP CHANNEL FAMILY MEMBER, LTRPC3G

This application is a divisional application of non-provisional application U.S. Ser. No. 10/842,313, filed May 10, 2004, now U.S. Pat. No. 7,344,882 which claims benefit to provisional application U.S. Ser. No. 60/469,894 filed May 12, 2003; under 35 U.S.C. 119(e). The entire teachings of the referenced application are incorporated herein by reference.

FIELD OF THE INVENTION

The present invention provides novel polynucleotides encoding LTRPC3 polypeptides, fragments and homologues thereof. The present invention also provides polynucleotides encoding variants of LTRPC3 polypeptides, specifically LTRPC3g, LTRPC3h, LTRPC3i, LTRPC3j, LTRPC3k, and LTRPC3l. Also provided are vectors, host cells, antibodies, and recombinant and synthetic methods for producing said polypeptides. The invention further relates to diagnostic and therapeutic methods for applying these novel LTRPC3g, LTRPC3h, LTRPC3i, LTRPC3j, LTRPC3k, and LTRPC3l polypeptides to the diagnosis, treatment, and/or prevention of various diseases and/or disorders related to these polypeptides. The invention further relates to screening methods for identifying agonists and antagonists of the polynucleotides and polypeptides of the present invention.

BACKGROUND OF THE INVENTION

Intracellular $Ca^{2+}$ plays a pivotal role in various cell functions, ranging from exocytosis and contraction to gene expression and cell differentiation, proliferation and apoptosis. $Ca^{2+}$ entry into cells, particularly in non-excitable cells, can be mediated via store-operated $Ca^{2+}$ channel (s) (SOC). Following $Ca^{2+}$ release from the intracellular stores, SOC mediate $Ca^{2+}$ influx from the extracellular space to generate sustained increases in intracellular $Ca^{2+}$ concentration and replenish the internal $Ca^{2+}$ stores. The molecular mechanism of SOC activation and the molecular identity of SOC remains elusive. Members of TRP (Transient Receptor Potential) channels, an emerging class of $Ca^{2+}$-permeable cation channel superfamily, are likely candidates for SOC (reviewed in *Trends Neurosci*, 23, 159-166, (2000)).

Human mutations in the genes involved in intracellular $Ca^{2+}$ handling result in visual defects, diabetes mellitus, disorders in the skin, skeletal-muscle, nervous, cardiac and vascular systems (reviewed by Missiaen et al., 2000). In addition to the well characterized voltage-dependent $Ca^{2+}$ channels, $Ca^{2+}$ pumps and $Ca^{2+}$-permeable ligand-gated channels, TRPC (Transient Receptor Potential Channels) is an emerging class of $Ca^{2+}$-permeable cation channel superfamily. All of the channels in this family contain a six-trans-membrane domain although various cellular mechanisms have been implicated in their functions.

Following the identification of the founding member of this family, dTRP, from the *Drosophila* mutants trp whose photoreceptors failed to generate a sustained receptor potential in response to intense sustained light (*Neuron* 8, 643-651, (1992)), mammalian homologues have been cloned and all of them contain a six-trans-membrane domain followed by a TRP motif (XWKFXR, SEQ ID NO:168), the diagnosed feature of the TRP family of proteins. The mutant fly showed a reduced $Ca^{2+}$ selectivity of the light response and the channel activity of dTRP depended on PLC activation was also demonstrated.

Based on their homology, they are divided into three subfamilies: short (s), osm (o) and long (l). New nomenclature for each subfamily has recently been proposed and is as follows: TRPC (canonical), TRPV (vanilloid), and TRPM (melastatin) (*Mol. Cell.* 9, 229-231, (2002)). The sTRPC subfamily includes TRP1-7. Although the specific physiological function of each isoform remains to be assigned, it is generally believed that they may be involved in $Ca^{2+}$ entry after activation of receptors coupling to PLC. The TRP2 is specifically expressed in vomeronasal organ and involved in pheromone sensory signaling (Liman, et al., 1999). TRP1 and TRP6 are functioned in vascular smooth muscle cells and may play a role in controlling smooth muscle tone, arteriosclerosis and neointimal hypoerplasia (Inoue et al., 2001; Xu & Beech, 2001). It has been shown that TRP4−/− mice lack an endothelial store-operated $Ca^{2+}$ current, which leads to reduced agonist-dependent vasorelaxation (Freichel et al., 2001).

The first member of oTRPC Subfamily is OSM-9 cloned from *C. elegans*. It is involved in responses to odorants, high osmotic strength, and mechanical stimulation. Recently, several mammalian homologues including vanilloid receptor (VR1) and vanilloid receptor-like receptor (VRL-1), which may have functions in pain and heat perception (Caterina, 1999; Caterina et al., 2000). VR1 has also been shown to be the receptor of anandamide and mediating its vasodilation effect (Zygmunt et al., 1999). OTRPC4 is an osmotically activated channel and a candidate osmoreceptor, may be involved in regulation of cellular volume (Strotmann et al., 2000). CaT1 & ECaC1 may be the calcium-release-activated calcium channel and involved in $Ca^{2+}$ reabsorption in intestine and kidney (Peng, et al, 1999; Yu et al., 2001).

The function of the lTRPC is less clear. The cloned mammalian lTRPC includes melastatin1/MLSN1/LTRPC1, MTR1/LTRPC5, TRPC7/LTRPC2 and TRP-P8. It is known that melastatin 1 is down regulated in metastatic melanomas (Duncan et al., 1998) and MTR1 is associated with Beckwith-Wiedemann syndrome and a predisposition to neoplasias (Prawitt et al., 2000). TRPC7 is mapped to the chromosome region linked to bipolar affective disorder, nonsyndromic hereditary deafness, Knobloch syndrome and holosencephaly (Nagamine et al., 1998). TRP-P8 is a prostate-specific gene and up-regulated in prostate cancer and other malignancies (Tsavaler et al., 2001). A recently cloned TRP-PLIK/hSOC-2/hCRAC-1 exhibits a very interesting feature in that it is a bi-functional protein with kinase and ion channel activities (Runnels et al., 2001). Additionally, a very long TRPC homologue NOMPC was found in *Drosophila* and *C. elegans*. NOMPC was identified as a mechanosensitive channel that can detect sound, pressure or movement changes (Walker et al., 2000).

Members of the TRPM subfamily are characteristic of their unusually long cytoplasmic tails at both ends of the channel domain and some of the family members contain an enzyme domain at the C-terminal region. Despite their similarities of structure, TRPMs have been implicated in a variety of biological functions. TRPM1 is found to be down-regulated in metastatic melanomas (*Cancer Res.* 58, 1515-1520, (1998)). TRPM2 is a $Ca^{2+}$-permeable channel that contains an ADP-ribose pyrophosphatase domain and can be activated by ADP-ribose, NAD (*Nature* 411, 595-599, (2001); and *Science* 293, 1327-1330, (2001)) and changes in redox status (*Mol. Cell.* 9, 163-173, (2002)). TRPM2 is mapped to the chromosome region linked to bipolar affective disorder, nonsyndromic hereditary deafness, Knobloch syndrome and holosencephaly (*Genomics* 54, 124-131, (1998)). Two splice variants of TRPM4 have been described. TRPM4a is predominantly a Ca²⁺ permeable channel (*Proc. Natl. Acad. Sci. U.S.A.* 98, 10692-10697, (2001); whereas TRPM4b conducts monovalent cations upon activation by changes in intracellular Ca²⁺ (*Cell* 109, 397-401, (2002)). TRPM5 is associated with Beckwith-Wiedemann syndrome and a predisposition to neoplasias (*Mol. Genet.* 9, 203-216, (2001)). TRPM7, another bifunctional protein, has kinase activity in additional to its ion channel activity. TRPM7 is regulated by Mg⁺-ATP and/or PIP₂, and required for cell viability (*Science* 291, 1043-1047, (2001); *Nature* 411, 690-695, (2001); and *Nat. Cell Biol.* 4, 329-36, (2002)). TRPM8 is up-regulated in prostate cancer and other malignancies (*Cancer Res.* 61, 3760-3769, (2001)). Recently, it has also been shown to be a receptor that senses cold stimuli (*Nature* 416, 52-58, (2002); and *Cell* 108, 705-715, (2002)).

As described herein, the polypeptides of the present invention are novel variants of the LTRPC3 polypeptide. The LTRPC3 polypeptide is described in co-pending U.S. Ser. No. 10/210,152, filed Aug. 1, 2002; and International Publication No. WO 03/012063, published Feb. 13, 2003; in addition to Co-pending U.S. Ser. No. 10/405,793, filed Mar. 28, 2003). which are hereby incorporated by reference in its entirety.

Characterization of the LTRPC3 polypeptide led to the determination that it is involved in the modulation of the FEN1 DNA base-excision repair/proliferation modulating protein, either directly or indirectly.

In mammalian cells, single-base lesions, such as uracil and abasic sites, appear to be repaired by at least two base excision repair (BER) subpathways: "single-nucleotide BER" requiring DNA synthesis of just one nucleotide and "long patch BER" requiring multi-nucleotide DNA synthesis. In single-nucleotide BER, DNA polymerase beta (beta-pol) accounts for both gap filling DNA synthesis and removal of the 5'-deoxyribose phosphate (dRP) of the abasic site, whereas the involvement of various DNA polymerases in long patch BER is less well understood.

Flap endonuclease 1 (Fen1) is a structure-specific metallonuclease that plays an essential function in DNA replication and DNA repair (Tom, S., Henricksen, L, A., Bambara, R, A, J. Biol, Chem., 275(14):10498-505, (2000)). It interacts like many other proteins involved in DNA metabolic events with proliferating cell nuclear antigen (PCNA), and its enzymatic activity is stimulated by PCNA in vitro by as much as 5 to 50 fold (Stucki, M., Jonsson, Z, O., Hubscher, U, J. Biol, Chem., 276(11):7843-9, (2001)). Recently, immunodepletion experiments in human lymphoid cell extracts have shown long-patch BER to be dependent upon FEN1 (Prasad, R., Dia, G, L., Bohr, V, A., Wilson, S, H, J. Biol, Chem., 275(6):4460-6, (2000)). In addition, FEN1 has also been shown to cooperate with beta-pol in long patch BER excision and is involved in determining the predominant excision product seen in cell extracts. The substrate for FEN1 is a flap formed by natural 5'-end displacement of the short intermediates of lagging strand replication. FEN1 binds to the 5'-end of the flap, tracks to the point of annealing at the base of the flap, and then cleaves the substrate (Tom, S., Henricksen, L, A., Bambara, R, A, J. Biol, Chem., 275(14):10498-505, (2000)).

The FEN1 is also referred to as Rad27. FEN1 plays a critical role in base-excision repair as evidenced by *Saccharomyces cerevisiae* FEN1 null mutants displaying an enhancement in recombination that increases as sequence length decreases (Negritto, M, C., Qiu, J., Ratay, D, O., Shen, B., Bailis, A, M, Mol, Cell, Biol., 21(7):2349-58, (2001)). The latter suggests that Rad27 preferentially restricts recombination between short sequences. Since wild-type alleles of both RAD27 and its human homologue FEN1 complement the elevated short-sequence recombination (SSR) phenotype of a rad27-null mutant, this function may be conserved from yeast to humans. Furthermore, mutant Rad27 and FEN-1 enzymes with partial flap endonuclease activity but without nick-specific exonuclease activity were shown to partially complement the SSR phenotype of the rad27-null mutant suggesting that the endonuclease activity of Rad27 (FEN-1) plays a role in limiting recombination between short sequences in eukaryotic cells. In addition, preliminary data from yeast suggests the FEN-1 deficiencies may result in genomic instability (Ma, X., Jin, Q., Forsti, A., Hemminki, K., Ku, R, Int, J. Cancer., 88(6):938-42, (2000)). More recently, FEN1 null mutants results in the expansion of repetitive sequences (Henricksen, L, A., Tom, S., Liu, Y., Bambara, R, A, J. Biol, Chem., 275(22):16420-7, (2000)).

Aside from the role of FEN1 in base-excision repair, FEN1 has also been shown to play a significant role in modulating signal transduction in proliferating cells. This role is intricately associated with the role of FEN1 in DNA replication. Of particular significance is the observation that FEN1 is a nuclear antigen, that it is expressed by cycling cells, and that it co-localizes with PCNA and polymerase alpha during S phase. Fen1 expression is topologically regulated in vivo and is associated with proliferative populations (Warbrick, E., Coates, P, J., Hall, P, A, J. Pathol., 186(3):319-24, (1998)). Antibodies have been described by Warbrick et al. that specifically bind FEN1, the assays of which are hereby incorporated herein by reference.

In addition, experiments in *S. cerevisiae* using the novel immunosuppressant agent SR 31747 have shown that SR 31747 arrests cell proliferation by directly targeting sterol isomerase and that FEN1 is required to mediate the proliferation arrest induced by ergosterol depletion (Silve, S., Leplatois, P., Josse, A., Dupuy, P, H., Lanau, C., Kaghad, M.,Dhers, C., Picard, C., Rahier, A., Taton, M., Le, Fur, G., Caput, D., Ferrara, P., Loison, G, Mol, Cell, Biol., 16(6):2719-27, (1996)).

Using the above examples, it is clear the availability of a novel cloned transient receptor potential channel family provides an opportunity for adjunct or replacement therapy, and are useful for the identification of transient receptor potential channel agonists, or stimulators (which might stimulate and/or bias transient receptor potential channel function), as well as, in the identification of transient receptor potential channel inhibitors. All of which might be therapeutically useful under different circumstances.

The present invention also relates to recombinant vectors, which include the isolated nucleic acid molecules of the present invention, and to host cells containing the recombinant vectors, as well as to methods of making such vectors and host cells, in addition to their use in the production of LTRPC3g, LTRPC3h, LTRPC3i, LTRPC3j, LTRPC3k, and LTRPC3l polypeptides using recombinant techniques. Synthetic methods for producing the polypeptides and polynucleotides of the present invention are provided. Also provided are diagnostic methods for detecting diseases, disorders, and/or conditions related to the LTRPC3g, LTRPC3h, LTRPC3i, LTRPC3j, LTRPC3k, and LTRPC3l polypeptides and polynucleotides, and therapeutic methods for treating such diseases, disorders, and/or conditions. The invention further relates to screening methods for identifying binding partners of the polypeptides.

BRIEF SUMMARY OF THE INVENTION

The present invention provides isolated nucleic acid molecules, that comprise, or alternatively consist of, a polynucleotide encoding the LTRPC3g protein having the amino acid sequence shown in FIGS. 1A-E (SEQ ID NO:2) or the amino acid sequence encoded by the cDNA clone, LTRPC3g (also referred to as TRPM3g, LTRPC3 variant g).

The present invention provides isolated nucleic acid molecules, that comprise, or alternatively consist of, a polynucleotide encoding the LTRPC3h protein having the amino acid sequence shown in FIGS. 2A-F (SEQ ID NO:4) or the amino acid sequence encoded by the cDNA clone, LTRPC3h (also referred to as TRPM3h, and/or LTRPC6 variant h).

The present invention provides isolated nucleic acid molecules, that comprise, or alternatively consist of, a polynucleotide encoding the LTRPC3i protein having the amino acid sequence shown in FIGS. 3A-F (SEQ ID NO:6) or the amino acid sequence encoded by the cDNA clone, LTRPC3i (also referred to as TRPM3i, and/or LTRPC6 variant i).

The present invention provides isolated nucleic acid molecules, that comprise, or alternatively consist of, a polynucleotide encoding the LTRPC3j protein having the amino acid sequence shown in FIGS. 4A-F (SEQ ID NO:10) or the amino acid sequence encoded by the cDNA clone, LTRPC3j (also referred to as TRPM3j, and/or LTRPC6 variant j).

The present invention provides isolated nucleic acid molecules, that comprise, or alternatively consist of, a polynucleotide encoding the LTRPC3k protein having the amino acid sequence shown in FIGS. 5A-F (SEQ ID NO:12) or the amino acid sequence encoded by the cDNA clone, LTRPC3k (also referred to as TRPM3k, and/or LTRPC6 variant k).

The present invention provides isolated nucleic acid molecules, that comprise, or alternatively consist of, a polynucleotide encoding the LTRPC3l protein having the amino acid sequence shown in FIGS. 6A-F (SEQ ID NO: 14) or the amino acid sequence encoded by the cDNA clone, LTRPC3l (also referred to as TRPM3l, and/or LTRPC6 variant l).

The present invention also relates to recombinant vectors, which include the isolated nucleic acid molecules of the present invention, and to host cells containing the recombinant vectors, as well as to methods of making such vectors and host cells, in addition to their use in the production of LTRPC3g, LTRPC3h, LTRPC3i, LTRPC3j, LTRPC3k, and LTRPC3l polynucleotides or polypeptides using recombinant techniques. Synthetic methods for producing the polypeptides and polynucleotides of the present invention are provided. Also provided are diagnostic methods for detecting diseases, disorders, and/or conditions related to the LTRPC3g, LTRPC3h, LTRPC3i, LTRPC3j, LTRPC3k, and LTRPC3l polypeptides and polynucleotides, and therapeutic methods for treating such diseases, disorders, and/or conditions. The invention further relates to screening methods for identifying binding partners of the polypeptides.

The invention further provides an isolated LTRPC3g polypeptide having an amino acid sequence encoded by a polynucleotide described herein.

The invention further provides an isolated LTRPC3h polypeptide having an amino acid sequence encoded by a polynucleotide described herein.

The invention further provides an isolated LTRPC3i polypeptide having an amino acid sequence encoded by a polynucleotide described herein.

The invention further provides an isolated LTRPC3j polypeptide having an amino acid sequence encoded by a polynucleotide described herein.

The invention further provides an isolated LTRPC3k polypeptide having an amino acid sequence encoded by a polynucleotide described herein.

The invention further provides an isolated LTRPC3l polypeptide having an amino acid sequence encoded by a polynucleotide described herein.

The invention further relates to a polynucleotide encoding a polypeptide fragment of SEQ ID NO:2, 4, 6, 8, 10 and/or 12, or a polypeptide fragment encoded by the cDNA sequence included in the deposited clone, which is hybridizable to SEQ ID NO:1, 3, 5, 7, 9 and/or 11.

The invention further relates to a polynucleotide encoding a polypeptide domain of SEQ ID NO:2, 4, 6, 8, 10 and/or 12 or a polypeptide domain encoded by the cDNA sequence included in the deposited clone, which is hybridizable to SEQ ID NO:1, 3, 5, 7, 9 and/or 11.

The invention further relates to a polynucleotide encoding a polypeptide epitope of SEQ ID NO:2, 4, 6, 8, 10 and/or 12 or a polypeptide epitope encoded by the cDNA sequence included in the deposited clone, which is hybridizable to SEQ ID NO:1,3,5,7,9 and/or 11.

The invention further relates to a polynucleotide encoding a polypeptide of SEQ ID NO:2, 4, 6, 8, 10 and/or 12 or the cDNA sequence included in the deposited clone, which is hybridizable to SEQ ID NO: 1, 3, 5, 7, 9 and/or 11, having biological activity.

The invention further relates to a polynucleotide which is a variant of SEQ ID NO:1, 3, 5, 7, 9 and/or 11.

The invention further relates to a polynucleotide which is an allelic variant of SEQ ID NO:1, 3, 5, 7, 9 and/or 11.

The invention further relates to a polynucleotide which encodes a species homologue of the SEQ ID NO:2, 4, 6, 8, 10 and/or 12.

The invention further relates to a polynucleotide which represents the complimentary sequence (antisense) of SEQ ID NO: 1, 3, 5, 7, 9 and/or 11.

The invention further relates to a polynucleotide capable of hybridizing under stringent conditions to any one of the polynucleotides specified herein, wherein said polynucleotide does not hybridize under stringent conditions to a nucleic acid molecule having a nucleotide sequence of only A residues or of only T residues.

The invention further relates to an isolated nucleic acid molecule of SEQ ID NO:2, 4, 6, 8, 10 and/or 12, wherein the polynucleotide fragment comprises a nucleotide sequence encoding an immunoglobulin protein.

The invention further relates to an isolated nucleic acid molecule of SEQ ID NO:1, 3, or 5 wherein the polynucleotide fragment comprises a nucleotide sequence encoding the sequence identified as SEQ ID NO:2, 4, 6, 8, 10 and/or 12 or the polypeptide encoded by the cDNA sequence included in the deposited clone, which is hybridizable to SEQ ID NO:1, 3, 5, 7, 9 and/or 11.

The invention further relates to an isolated nucleic acid molecule of SEQ ID NO:1, 3, or 5, wherein the polynucleotide fragment comprises the entire nucleotide sequence of SEQ ID NO:1, 3, 5, 7, 9 and/or 11 or the cDNA sequence included in the deposited clone, which is hybridizable to SEQ ID NO:1, 3, 5, 7, 9 and/or 11.

The invention further relates to an isolated nucleic acid molecule of SEQ ID NO:1, 3, 5, 7, 9 and/or 11, wherein the nucleotide sequence comprises sequential nucleotide deletions from either the C-terminus or the N-terminus.

The invention further relates to an isolated polypeptide comprising an amino acid sequence that comprises a polypeptide fragment of SEQ ID NO:2, 4, 6, 8, 10 and/or 12 or the encoded sequence included in the deposited clone.

The invention further relates to a polypeptide fragment of SEQ ID NO:2, 4, 6, 8, 10 and/or 12 or the encoded sequence included in the deposited clone, having biological activity.

The invention further relates to a polypeptide domain of SEQ ID NO:2, 4, 6, 8, 10 and/or 12 or the encoded sequence included in the deposited clone.

The invention further relates to a polypeptide epitope of SEQ ID NO:2, 4, 6, 8, and/or 12 or the encoded sequence included in the deposited clone.

The invention further relates to a full length protein of SEQ ID NO:2, 4, 6, 8, and/or 12 or the encoded sequence included in the deposited clone.

The invention further relates to a variant of SEQ ID NO:2, 4, 6, 8, 10 and/or 12.

The invention further relates to an allelic variant of SEQ ID NO:2, 4, 6, 8, 10 and/or 12.

The invention further relates to a species homologue of SEQ ID NO:2, 4, 6, 8, and/or 12.

The invention further relates to the isolated polypeptide of SEQ ID NO:2, 4, 6, 8, 10 and/or 12, wherein the full length protein comprises sequential amino acid deletions from either the C-terminus or the N-terminus.

The invention further relates to an isolated antibody that binds specifically to the isolated polypeptide of SEQ ID NO:2, 4, 6, 8, 10 and/or 12.

The invention further relates to a method for preventing, treating, or ameliorating a medical condition, comprising administering to a mammalian subject a therapeutically effective amount of the polypeptide of SEQ ID NO:2, 4, 6, 8, 10 and/or 12 or the polynucleotide of SEQ ID NO:1, 3, 5, 7, 9 and/or 11.

The invention further relates to a method of diagnosing a pathological condition or a susceptibility to a pathological condition in a subject comprising the steps of (a) determining the presence or absence of a mutation in the polynucleotide of SEQ ID NO:1, 3, 5, 7, 9 and/or 11; and (b) diagnosing a pathological condition or a susceptibility to a pathological condition based on the presence or absence of said mutation.

The invention further relates to a method of diagnosing a pathological condition or a susceptibility to a pathological condition in a subject comprising the steps of (a) determining the presence or amount of expression of the polypeptide of SEQ ID NO:2, 4, 6, 8, 10 and/or 12 in a biological sample; and (b) diagnosing a pathological condition or a susceptibility to a pathological condition based on the presence or amount of expression of the polypeptide.

The invention further relates to a method for identifying a binding partner to the polypeptide of SEQ ID NO:2, 4, 6, 8, 10 and/or 12 comprising the steps of (a) contacting the polypeptide of SEQ ID NO:2, 4, 6, 8, 10 and/or 12 with a binding partner; and (b) determining whether the binding partner effects an activity of the polypeptide.

The invention further relates to a gene corresponding to the cDNA sequence of SEQ ID NO:1,3,5,7,9 and/or 11.

The invention further relates to a method of identifying an activity in a biological assay, wherein the method comprises the steps of (a) expressing SEQ ID NO:1, 3, 5, 7, 9 and/or 11 in a cell, (b) isolating the supernatant; (c) detecting an activity in a biological assay; and (d) identifying the protein in the supernatant having the activity.

The invention further relates to a process for making polynucleotide sequences encoding gene products having altered activity selected from the group consisting of SEQ ID NO:2, 4, 6, 8, 10 and/or 12 activity comprising the steps of (a) shuffling a nucleotide sequence of SEQ ID NO:1, 3, 5, 7, 9 and/or 11, (b) expressing the resulting shuffled nucleotide sequences and, (c) selecting for altered activity selected from the group consisting of SEQ ID NO:2, 4, 6, 8, 10 and/or 12 activity as compared to the activity selected from the group consisting of SEQ ID NO:2, 4, 6, 8, 10 and/or 12 activity of the gene product of said unmodified nucleotide sequence.

The invention further relates to a shuffled polynucleotide sequence produced by a shuffling process, wherein said shuffled DNA molecule encodes a gene product having enhanced tolerance to an inhibitor of any one of the activities selected from the group consisting of SEQ ID NO:2, 4, 6, 8, 10 and/or 12 activity.

The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, wherein the medical condition is a renal disorder The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, wherein the medical condition is a neural disorder.

The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, wherein the medical condition is a disorder related to aberrant calcium regulation.

The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, wherein the medical condition is a reproductive disorder.

The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, wherein the medical condition is a neural disorder.

The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, or a modulator thereof, wherein the medical condition is a neural disorder.

The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, or a modulator thereof, wherein the medical condition is a neural disorder selected from the group consisting of: cerebellum disorders, various choroid plexus neoplasms, choroid plexus papilloma, Alzheimer's disease, prion disorders and multiple sclerosis and movement disorders that involve the cerebellum.

The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, or a modulator thereof, wherein the medical condition is a proliferative kidney or renal disorder.

The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, or a modulator thereof, wherein the medical condition is solitary metastasis of the kidney.

The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, or a modulator thereof, wherein the medical condition is renal cell carcinoma.

The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, or a modulator thereof, wherein the medical condition is ovarian cancer or related proliferative condition of the ovary.

The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, or a modulator thereof, wherein the medical condition is testicular cancer or related proliferative condition of the testis.

The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, or a modulator thereof, wherein the medical condition is kidney cancer or related proliferative condition of the kidney.

The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, or a modulator thereof, wherein the medical condition is a disorder that maps to or is associated with chromosome locus 9q21.11-21.31.

The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, or a modulator thereof, wherein the medical condition is amyotrophic lateral sclerosis with frontotemporal dementia, early-onset pulverulent cataract, infantile nephronophthisis, hypomagnesemia with secondary hypocalcemia and/or familial hemophagocytic lymphohistiocytosis.

The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, or a modulator thereof, wherein the medical condition is a disorder associated with disturbances in $Ca^{2+}$ homeostasis including osteoporosis, hypercalciuric stone disease, and chronic renal failure.

The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, or a modulator thereof, wherein the medical condition is a condition that would benefit from modulation of intracellular Ca++ ion concentrations, Ca++ ion flux, stored intracellular Ca++ ion concentrations, Ca++ ion pump activity, Ca++ ion flow into cell, Ca++ ion flow out of cells, the activation of Ca++ sensitive proteins, the activation of Ca++ sensitive signaling pathways, the activation of kinase-activatible proteins, and the activation of kinase-dependent signaling pathways.

The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, or a modulator thereof, wherein the medical condition $Ca^{2+}$ reabsorption disorders, disorders associated with aberrant luminal $Ca^{2+}$ entry via the epithelial $Ca^{2+}$ channel (ECaC), disorders associated with aberrant cytosolic diffusion of $Ca^{2+}$ bound to calbindin-D28K, disorders associated with aberrant basolateral extrusion of $Ca^{2+}$ through the Na+/Ca2+ exchanger (NCX), disorders associated with aberrant plasma membrane Ca2+-ATPase (PMCA) activity and/or activation, disorders associated with the hypocalciuric effect of diuretics, disorders associated with the hypocalciuric effect of thiazide diuretics, disorders associated with hormone insufficiencies that affect the function of the kidney, disorders associated with hormone insufficiencies that affect renal Ca2+ homeostasis, disorders associated with aberrant renal Ca2+ homeostasis as a result of vitamin D deficiency, disorders associated with aberrant renal Ca2+ homeostasis as a result of PTH deficiency, disorders associated with aberrant renal Ca2+ homeostasis as a result of vasopressin deficiency, disorders associated with aberrant renal Ca2+ homeostasis as a result of prostaglandines deficiency, disorders associated with aberrant renal Ca2+ homeostasis as a result of estrogen deficiency, disorders associated with aberrant renal Ca2+ homeostasis as a result of calcitonin deficiency, disorders associated with aberrant renal Ca2+ homeostasis as a result of parathyroid hormone deficiency, disorders associated with aberrant renal Ca2+ homeostasis as a result of atrial natriuretic peptide deficiency, calcium homeostasis-related disorders, hypercaliuric nephrolithiasis, certain forms of osteoporosis, Gitelman's disease, Bartter's syndrom, disorders associated with aberrant function of kidney tubular epithelium, disorders associated with aberrant function of kidney tubular epithelium in the medulla, disorders associated with aberrant function of kidney tubular epithelium in the medullary rays, disorders associated with aberrant function of kidney tubular epithelium in the periglomerular.

The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, or a modulator thereof, wherein the medical condition acute kidney failure, chronic kidney failure, cystic kidney disease, horseshoe kidney, hypertensive kidney disease, kidney atrophy, kidney cancer, kidney disease, kidney failure, kidney infection, kidney metastasis, kidney stone, nephrolithiasis, multicystic dysplastic kidney disease, and polycystic kidney disease.

The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, or a modulator thereof, wherein the medical condition is DNA-repair deficiencies, particularly base-excision repair deficiencies, Xeroderma pigmentosum, skin cancer, melanoma, UV senstivity, alkylation sensivity, gamma irradiation sensitivity, pyrimidine dimer sensitivity, chemical mutagenes, lymphomas, leukemias, photosensitivity, Bloom's syndrone, Fanconi's anemia, ataxia telangiectasia, chromosomal aberrations, blood vessel dilation aberrations in the skin, blood vessel dilation aberrations in the eye, conditions involving increased levels of apurinic sites, conditions involving increased levels of apyrimidinic sites, conditions involving increased levels of abasic sites, disorders related to aberrant signal transduction, proliferating disorders, and/or cancers.

The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, or a modulator thereof, wherein the medical condition is a disorder related to misregulation of FEN1 expression and/or activity.

The invention further relates to a method for preventing, treating, or ameliorating a medical condition with the polypeptide, or modulator thereof, provided as SEQ ID NO:2, 4, 6, 8, 10 and/or 12, in addition to, its encoding nucleic acid, or a modulator thereof, wherein the medical condition is a disorder that would benefit from increasing mammalian base excision repair activity, increasing mammalian single-nucleotide base excision repair activity, and/or increasing mammalian long patch base excision repair activity.

The invention further relates to a method for preventing, treating, or ameliorating a medical condition with the polypeptide, or antagonists thereof, provided as SEQ ID NO:2, 4, 6, 8, 10 and/or 12, in addition to, its encoding nucleic acid, or a modulator thereof, wherein the medical condition is a disorder that would benefit from increasing mammalian base excision repair activity, increasing mammalian single-nucleotide base excision repair activity, and/or increasing mammalian long patch base excision repair activity.

The invention further relates to a method for preventing, treating, or ameliorating a medical condition with the polypeptide, or agonists thereof, provided as SEQ ID NO:2, 4, 6, 8, 10 and/or 12, in addition to, its encoding nucleic acid, or a modulator thereof, wherein the medical condition is a disorder associated with aberrant signal transduction, proliferating disorders, and/or cancers, particularly renal cell carcinomas, testicular cancers, and/or ovarian cancers.

The invention further relates to a method for preventing, treating, or ameliorating a medical condition with the polypeptide, or agonists thereof, provided as SEQ ID NO:2, 4, 6, 8, 10 and/or 12, in addition to, its encoding nucleic acid, or a modulator thereof, wherein the medical condition is a disorder that would benefit from decreasing mammalian base excision repair activity, decreasing mammalian single-nucleotide base excision repair activity, and/or decreasing mammalian long patch base excision repair activity.

The invention further relates to a method of diagnosing a pathological condition or a susceptibility to a pathological condition in a subject comprising the steps of (a) determining the presence or amount of expression of the polypeptide of SEQ ID NO:2, 4, 6, 8, 10 and/or 12 in a biological sample; (b) and diagnosing a pathological condition or a susceptibility to a pathological condition based on the presence or amount of expression of the polypeptide relative to a control, wherein said condition is a member of the group consisting of ovarian cancer, testicular cancer, and kidney cancer.

The present invention is also directed to polynucleotides comprising at least about 465 nt of the polynucleotide sequence provided as SEQ ID NO:1, 3, 5, 7, 9, and/or 11. Specifically, the present invention is directed to a polynucleotide sequence comprising nucleotides from about nucleotide 72 to about nucleotide 536 of SEQ ID NO:1, 3, 5, 7, 9, and/or 11. In this context "about" includes the particularly recited value, a value larger or smaller by several (5, 4, 3, 2, or 1) nucleotides, at either terminus, or at both termini.

The present invention is also directed to polypeptides comprising at least about 155 amino acids of the polypeptides sequence provided as SEQ ID NO:2, 4, 6, 8, 10, and/or 12. Specifically, the present invention is directed to a polypeptides sequence comprising amino acids from about amino acid 1 to about amino acid 155 of SEQ ID NO:2, 4, 6, 8, 10, and/or 12. In this context "about" includes the particularly recited value, a value larger or smaller by several (5, 4, 3, 2, or 1) nucleotides, at either terminus, or at both termini.

The invention further relates to a method of identifying a compound that modulates the biological activity of LTRPC3g, LTRPC3h, LTRPC3i, LTRPC3j, LTRPC3k, and/or LTRPC3l, comprising the steps of, (a) combining a candidate modulator compound with LTRPC3g, LTRPC3h, LTRPC3i, LTRPC3j, LTRPC3k, and/or LTRPC3l having the sequence set forth in one or more of SEQ ID NO:2, 4, 6, 8, 10 and/or 12; and (b) measuring an effect of the candidate modulator compound on the activity of LTRPC3g, LTRPC3h, LTRPC3i, LTRPC3j, LTRPC3k, and/or LTRPC3l.

The invention further relates to a method of identifying a compound that modulates the biological activity of a transient receptor potential channel protein, comprising the steps of, (a) combining a candidate modulator compound with a host cell expressing LTRPC3g, LTRPC3h, LTRPC3i, LTRPC3j, LTRPC3k, and/or LTRPC3l having the sequence as set forth in SEQ ID NO:2, 4, 6, 8, 10 and/or 12; and, (b) measuring an effect of the candidate modulator compound on the activity of the expressed LTRPC3g, LTRPC3h, LTRPC3i, LTRPC3j, LTRPC3k, and/or LTRPC3l.

The invention further relates to a method of identifying a compound that modulates the biological activity of LTRPC3g, LTRPC3h, LTRPC3i, LTRPC3j, LTRPC3k, and/or LTRPC3l, comprising the steps of, (a) combining a candidate modulator compound with a host cell containing a vector described herein, wherein LTRPC3g, LTRPC3h, LTRPC3i, LTRPC3j, LTRPC3k, and/or LTRPC3l is expressed by the cell; and, (b) measuring an effect of the candidate modulator compound on the activity of the expressed LTRPC3g, LTRPC3h, LTRPC3i, LTRPC3j, LTRPC3k, and/or LTRPC3l.

The invention further relates to a method of screening for a compound that is capable of modulating the biological activity of LTRPC3g, LTRPC3h, LTRPC3i, LTRPC3j, LTRPC3k, and/or LTRPC3l, comprising the steps of: (a) providing a host cell described herein; (b) determining the biological activity of LTRPC3g, LTRPC3h, LTRPC3i, LTRPC3j, LTRPC3k, and/or LTRPC3l in the absence of a modulator compound; (c) contacting the cell with the modulator compound; and (d) determining the biological activity of LTRPC3g, LTRPC3h, LTRPC3i, LTRPC3j, LTRPC3k, and/or LTRPC3l in the presence of the modulator compound; wherein a difference between the activity of LTRPC3g, LTRPC3h, LTRPC3i, LTRPC3j, LTRPC3k, and/or LTRPC3l in the presence of the modulator compound and in the absence of the modulator compound indicates a modulating effect of the compound.

The invention further relates to a method of identifying a compound that modulates the biological activity of LTRPC3g, LTRPC3h, LTRPC3i, LTRPC3j, LTRPC3k, and/or LTRPC3l, comprising the steps of, (a) combining a candidate modulator compound with a host cell containing a vector described herein, wherein LTRPC3g, LTRPC3h, LTRPC3i, LTRPC3j, LTRPC3k, and/or LTRPC3l is expressed by the cell; (b) measuring an effect of the candidate modulator compound on the activity of the expressed LTRPC3g, LTRPC3h, LTRPC3i, LTRPC3j, LTRPC3k, and/or LTRPC3l; wherein step (a) optionally comprises one or more of the following additional steps: (i) incubation of said host cells in a medium lacking Ca++ ions; (ii) incubation of said host cells in a medium containing Ca++ ions; (iii) incubation of said host cells in a medium lacking Ca++ ions, followed by addition of Ca++ ion to the medium of said host cell within a period either preceding or following incubation of said candidate modulator compound; incubation of said host cells under conditions where Ca++ stores within said host cells would be expected to be at least partially depleted; incubation of said host cells with $La^{3+}$; incubation of said host cells with $Gd^{3+}$; incubation of said host cells with $La^{3+}$ in a medium lacking Ca++ ions, followed by addition of Ca++ ion to the medium of said host cell within a period either preceding or following incubation of said candidate modulator compound; incubation of said host cells with $Gd^{3+}$ in a medium lacking Ca++ ions, followed by addition of Ca++ ion to the medium of said host cell within a period either preceding or following incubation of said candidate modulator compound; incubation of said host cells with $La^{3+}$ in a medium containing Ca++ ions; incubation of said host cells with $Gd^{3+}$ in a medium containing Ca++ ions; incubation of said host cells with thapsigargin; incubation of said host cells with carbachol; incubation of said host cells with thapsigargin in a medium lacking Ca++ ions, followed by addition of Ca++ ion to the medium of said host cell within a period either preceding or following incubation of said candidate modulator compound; incubation of said host cells with carbachol in a medium lacking Ca++ ions, followed by addition of Ca++ ion to the medium of said host cell within a period either preceding or following incubation of said candidate modulator compound; incubating said host cells with Fluo-4-AM for a defined period, or other fluorescent cytoplasmic Ca++ marker amenable to measurement on a FLIPR instrument, such that said host cells are loaded with Fluo-4-AM; and/or incubating said host cells with Fluo-4-AM for a defined period, or other fluorescent cytoplasmic Ca++ marker amenable to measurement on a FLIPR instrument (or other plate reader, preferably a fluorescent plate reader), such that said host cells are loaded with Fluo-4-AM, followed by removal of extracellular Fluo-4-AM.

The invention further relates to a compound that modulates the biological activity of human LTRPC3g, LTRPC3h, LTRPC3i, LTRPC3j, LTRPC3k, and/or LTRPC3l as identified by the methods described herein.

BRIEF DESCRIPTION OF THE FIGURES/DRAWINGS

The file of this patent contains at least one Figure executed in color. Copies of this patent with color Figure(s) will be provided by the Patent and Trademark Office upon request and payment of the necessary fee.

FIGS. 1A-E show the polynucleotide sequence (SEQ ID NO:1) and deduced amino acid sequence (SEQ ID NO:2) of the novel human transient receptor potential channel member variant, LTRPC3g, of the present invention. The standard one-letter abbreviation for amino acids is used to illustrate the deduced amino acid sequence. The polynucleotide sequence contains a sequence of 5201 nucleotides (SEQ ID NO:1), encoding a polypeptide of 1709 amino acids (SEQ ID NO:2). An analysis of the LTRPC3g polypeptide determined that it comprised the following features: six transmembrane domains (TM1 thru TM6) located from about amino acid 776 to about amino acid 792 (TM1), from about amino acid 872 to about amino acid 888 (TM2), from about amino acid 945 to about amino acid 958 (TM3), from about amino acid 972 to about amino acid 989 (TM4), from about amino acid 1006 to about amino acid 1023 (TM5), and/or from about amino acid 1093 to about amino acid 1113 (TM6) of SEQ ID NO:2 represented by double underlining; a predicted TRP domain located from about amino acid 1128 to about amino acid 1133 of SEQ ID NO:2 represented by light shading; a predicted ion transport signature domain located at about amino acid 903 to about amino acid 1114 of SEQ ID NO:2 represented by dark shading; a predicted coiled-coil domain located at about amino acid 1218 to about amino acid 1273 of SEQ ID NO:2 represented by italics; and conserved cysteine residues located at amino acid 249, 364, 420, 574, 672, 737, 754, 976, 1067, 1084, 1097, 1200, 1291, and 1552 of SEQ ID NO:2 represented in bold. Conservation of cysteines at key amino acid residues is indicative of conserved structural features, which may correlate with conservation of protein function and/or activity.

FIGS. 2A-F show the polynucleotide sequence (SEQ ID NO:3) and deduced amino acid sequence (SEQ ID NO:4) of the novel human transient receptor potential channel member variant, LTRPC3h, of the present invention. The standard one-letter abbreviation for amino acids is used to illustrate the deduced amino acid sequence. The polynucleotide sequence contains a sequence of 5237 nucleotides (SEQ ID NO:3), encoding a polypeptide of 1721 amino acids (SEQ ID NO:4). An analysis of the LTRPC3h polypeptide determined that it comprised the following features: six transmembrane domains (TM1 thru TM6) located from about amino acid 787 to about amino acid 804 (TM1), from about amino acid 884 to about amino acid 901 (TM2), from about amino acid 957 to about amino acid 970 (TM3), from about amino acid 984 to about amino acid 1001 (TM4), from about amino acid 1018 to about amino acid 1035 (TM5), and/or from about amino acid 1106 to about amino acid 1125 (TM6) of SEQ ID NO:4 represented by double underlining; a predicted TRP domain located from about amino acid 1040 to about amino acid 1045 of SEQ ID NO:4 represented by light shading; a predicted ion transport signature domain located at about amino acid 915 to about amino acid 1126 of SEQ ID NO:4 represented by dark shading; a predicted coiled-coil domain located at about amino acid 1230 to about amino acid 1285 of SEQ ID NO:4 represented by italics; and conserved cysteine residues located at amino acid 249, 364, 420, 586, 749, 766, 988, 1079, 1096, 1109, 1212, 1303, and 1564 of SEQ ID NO:4 represented in bold. Conservation of cysteines at key amino acid residues is indicative of conserved structural features, which may correlate with conservation of protein function and/or activity.

FIGS. 3A-F show the polynucleotide sequence (SEQ ID NO:5) and deduced amino acid sequence (SEQ ID NO:6) of the novel human transient receptor potential channel member variant, LTRPC3i, of the present invention. The standard one-letter abbreviation for amino acids is used to illustrate the deduced amino acid sequence. The polynucleotide sequence contains a sequence of 5237 nucleotides (SEQ ID NO:5), encoding a polypeptide of 1721 amino acids (SEQ ID NO:6). An analysis of the LTRPC3l polypeptide determined that it comprised the following features: six transmembrane domains (TM1 thru TM6) located from about amino acid 775 to about amino acid 792 (TM1), from about amino acid 872 to about amino acid 888 (TM2), from about amino acid 945 to about amino acid 958 (TM3), from about amino acid 972 to about amino acid 988 (TM4), from about amino acid 1006 to about amino acid 1023 (TM5), and/or from about amino acid 1115 to about amino acid 1125 (TM6) of SEQ ID NO:6 represented by double underlining; a predicted TRP domain located from about amino acid 1140 to about amino acid 1145 of SEQ ID NO:6 represented by light shading; a predicted ion transport signature domain located at about amino acid 915 to about amino acid 1126 of SEQ ID NO:6 represented by dark shading; a predicted coiled-coil domain located at about amino acid 1230 to about amino acid 1285 of SEQ ID NO:6 represented by italics; and conserved cysteine residues located at amino acid 249, 364, 420, 574, 672, 754, 976, 1212, 1303, and 1564 of SEQ ID NO:6 represented in bold. Conservation of cysteines at key amino acid residues is indicative of conserved structural features, which may correlate with conservation of protein function and/or activity.

FIGS. 4A-F show the polynucleotide sequence (SEQ ID NO:7) and deduced amino acid sequence (SEQ ID NO:8) of the novel human transient receptor potential channel member variant, LTRPC3j, of the present invention. The standard one-letter abbreviation for amino acids is used to illustrate the deduced amino acid sequence. The polynucleotide sequence contains a sequence of 5171 nucleotides (SEQ ID NO:7), encoding a polypeptide of 1699 amino acids (SEQ ID NO:8). An analysis of the LTRPC3j polypeptide determined that it comprised the following features: six transmembrane domains (TM1 thru TM6) located from about amino acid 765 to about amino acid 782 (TM1), from about amino acid 862 to about amino acid 879 (TM2), from about amino acid 935 to about amino acid 948 (TM3), from about amino acid 962 to about amino acid 979 (TM4), from about amino acid 996 to about amino acid 1013 (TM5), and/or from about amino acid 1083 to about amino acid 1103 (TM6) of SEQ ID NO:8 represented by double underlining; a predicted TRP domain located from about amino acid 1118 to about amino acid 1123 of SEQ ID NO:8 represented by light shading; a predicted ion transport signature domain located at about amino acid 893 to about amino acid 1104 of SEQ ID NO:8 represented by dark shading; a predicted coiled-coil domain located at about amino acid 1208 to about amino acid 1263 of SEQ ID NO:8 represented by italics; and conserved cysteine residues located at amino acid 249, 364, 420, 574, 662, 727, 744, 966, 1057, 1074, 1087, 1190, 1281, and 1547 of SEQ ID NO:8 represented in bold. Conservation of cysteines at key amino acid residues is indicative of conserved structural features, which may correlate with conservation of protein function and/or activity.

FIGS. 5A-F show the polynucleotide sequence (SEQ ID NO:9) and deduced amino acid sequence (SEQ ID NO:10) of the novel human transient receptor potential channel member variant, LTRPC3k, of the present invention. The standard one-letter abbreviation for amino acids is used to illustrate the deduced amino acid sequence. The polynucleotide sequence contains a sequence of 5207 nucleotides (SEQ ID NO:9), encoding a polypeptide of 1711 amino acids (SEQ ID NO:10). An analysis of the LTRPC3e polypeptide determined that it comprised the following features: six transmembrane domains (TM1 thru TM6) located from about amino acid 777 to about amino acid 794 (TM1), from about amino acid 874 to about amino acid 891 (TM2), from about amino acid 947 to about amino acid 960 (TM3), from about amino acid 974 to about amino acid 991 (TM4), from about amino acid 1008 to about amino acid 1025 (TM5), and/or from about amino acid 1095 to about amino acid 1115 (TM6) of SEQ ID NO:10 represented by double underlining; a predicted TRP domain located from about amino acid 1130 to about amino acid 1135 of SEQ ID NO:10 represented by light shading; a predicted ion transport signature domain located at about amino acid 905 to about amino acid 1116 of SEQ ID NO:10 represented by dark shading; a predicted coiled-coil domain located at about amino acid 1220 to about amino acid 1275 of SEQ ID NO:10 represented by italics; and conserved cysteine residues located at amino acid 249, 364, 420, 586, 674, 739, 756, 978, 1069, 1086, 1099, 1202, 1293, and 1559 of SEQ ID NO:10 represented in bold. Conservation of cysteines at key amino acid residues is indicative of conserved structural features, which may correlate with conservation of protein function and/or activity.

FIGS. 6A-F show the polynucleotide sequence (SEQ ID NO:11) and deduced amino acid sequence (SEQ ID NO:12) of the novel human transient receptor potential channel member variant, LTRPC3l, of the present invention. The standard one-letter abbreviation for amino acids is used to illustrate the deduced amino acid sequence. The polynucleotide sequence contains a sequence of 5276 nucleotides (SEQ ID NO:11), encoding a polypeptide of 1734 amino acids (SEQ ID NO:12). An analysis of the LTRPC3l polypeptide determined that it comprised the following features: six transmembrane domains (TM1 thru TM6) located from about amino acid 800 to about amino acid 817 (TM1), from about amino acid 897 to about amino acid 914 (TM2), from about amino acid 970 to about amino acid 983 (TM3), from about amino acid 997 to about amino acid 1014 (TM4), from about amino acid 1031 to about amino acid 1048 (TM5), and/or from about amino acid 1118 to about amino acid 1137 (TM6) of SEQ ID NO:12 represented by double underlining; a predicted TRP domain located from about amino acid 1153 to about amino acid 1158 of SEQ ID NO:12 represented by light shading; a predicted ion transport signature domain located at about amino acid 928 to about amino acid 1136 of SEQ ID NO:12 represented by dark shading; a predicted coiled-coil domain located at about amino acid 1243 to about amino acid 1298 of SEQ ID NO:12 represented by italics; and conserved cysteine residues located at amino acid 249, 389, 599, 697, 762, 779, 1001, 1092, 1109, 1122, 1225, 1316, and 1582 of SEQ ID NO:12 represented in bold. Conservation of cysteines at key amino acid residues is indicative of conserved structural features, which may correlate with conservation of protein function and/or activity.

FIGS. 7A-G show the regions of identity and similarity between the LTRPC3g, LTRPC3h, LTRPC3i, LTRPC3j, LTRPC3k, and LTRPC3l polypeptides of the present invention to another member of human transient receptor potential channel family, specifically, the human melastatin 1 protein (Melastatin1; Genbank Accession No. gi|3243075; SEQ ID NO:13). The alignment was created using the CLUSTALW algorithm described elsewhere herein using default parameters (CLUSTALW parameters: gap opening penalty: 10; gap extension penalty: 0.5; gap separation penalty range: 8; percent identity for alignment delay: 40%; and transition, weighting: 0). The darkly shaded amino acids represent regions of matching identity. The lightly shaded amino acids represent regions of matching similarity. Dots between residues indicate gapped regions for the aligned polypeptides.

FIG. 8 shows an expression profile of a variant of the human transient receptor potential channel family members of the present invention, LTRPC3 (Co-pending U.S. Ser. No. 10/210,152, filed Aug. 1, 2002; International Publication No. WO 03/012063, published Feb. 13, 2003; SEQ ID NO:15). The figure illustrates the relative expression level of LTRPC3 amongst various mRNA tissue sources. As shown, transcripts corresponding to LTRPC3 expressed predominately in kidney tissue. The LTRPC3 polypeptide was also expressed significantly in spinal cord, testis, and brain. Expression data was obtained by measuring the steady state LTRPC3 mRNA levels by RT-PCR using the PCR primer pair provided as SEQ ID NO: 375 and 376 as described herein.

Figure 9:
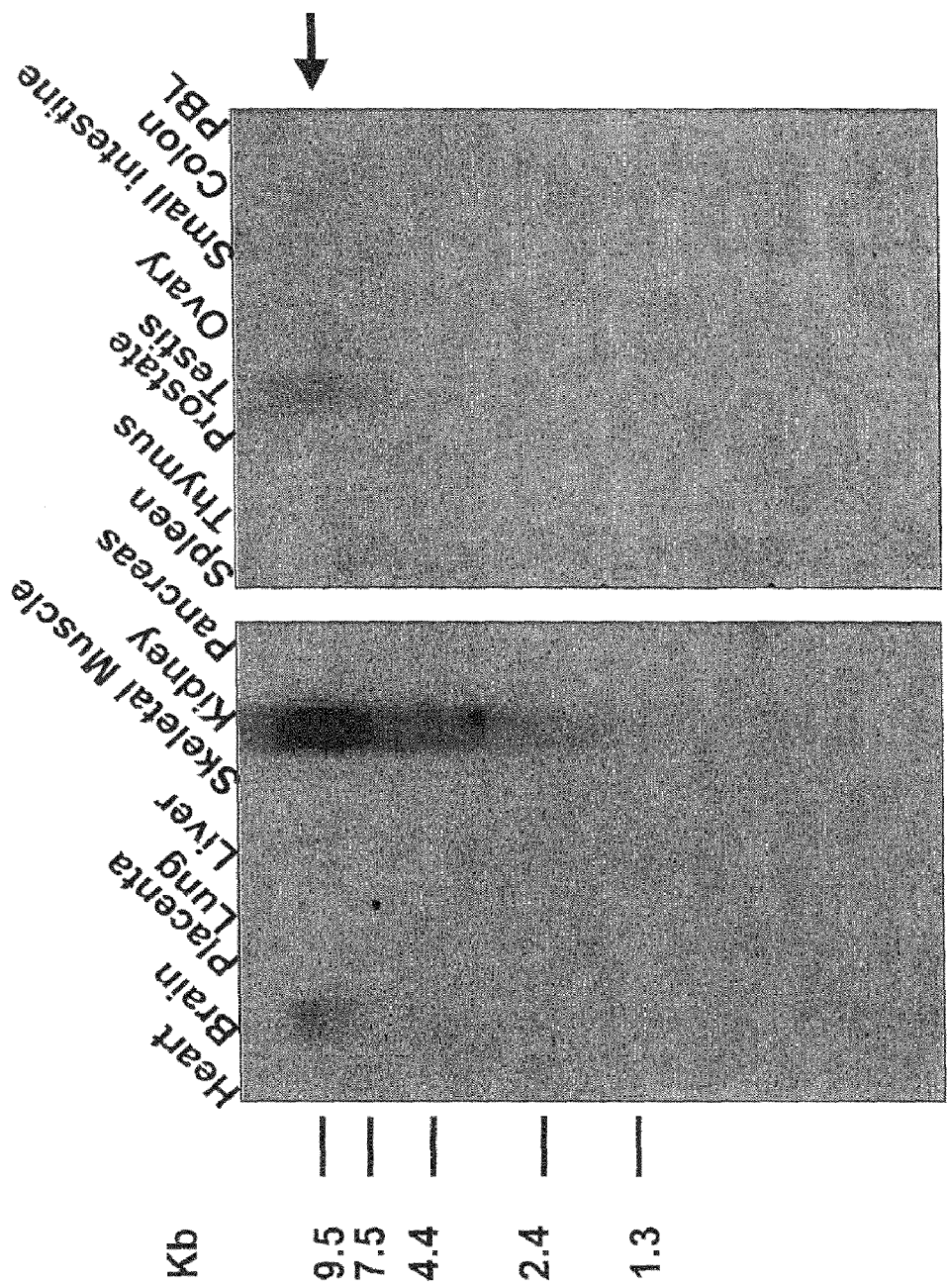

FIG. 9 shows an expression profile of a variant of the human transient receptor potential channel family members of the present invention, LTRPC3 (Co-pending U.S. Ser. No. 10/210,152, filed Aug. 1, 2002; International Publication No. WO 03/012063, published Feb. 13, 2003; SEQ ID NO:15). The figure illustrates the relative expression level of LTRPC3 amongst various mRNA tissue, and cell sources. As shown, transcripts corresponding to LTRPC3 expressed predominately in kidney tissue. The LTRPC3 polypeptide was also expressed significantly in brain, and testis. Expression data was obtained by probing a Northern blot using a LTRPC3 645-bp PCR amplified fragment from SEQ ID NO:14 as described herein.

FIG. 10 shows a table illustrating the percent identity and percent similarity between the LTRPC3g, LTRPC3h, LTRPC3i, LTRPC3j, LTRPC3k, and LTRPC3l polypeptides of the present invention with the human melastatin 1 protein (Melastatin1; Genbank Accession No. gi|3243075; SEQ ID NO:13). The percent identity and percent similarity values were determined based upon the GAP algorithm (GCG suite of programs; and Henikoff, S, and Henikoff, J. G., Proc. Natl. Acad. Sci. USA 89: 10915-10919(1992)).

FIGS. 11A-I shows the regions of identity between the LTRPC3g (SEQ ID NO:2), LTRPC3h (SEQ ID NO:4), LTRPC3l (SEQ ID NO:6), LTRPC3j (SEQ ID NO:8), LTRPC3k (SEQ ID NO:10), and LTRPC3l (SEQ ID NO:12) polypeptides of the present invention to the LTRPC3 variant (SEQ ID NO:15), in addition to splice variants of LTRPC3, including LTRPC3b (SEQ ID NO:16), LTRPC3c (SEQ ID NO:17), LTRPC3d (SEQ ID NO:18), LTRPC3e (SEQ ID NO:19), and LTRPC3f (SEQ ID NO:20). The alignment was created using the CLUSTALW algorithm described elsewhere herein using default parameters (CLUSTALW parameters: gap opening penalty: 10; gap extension penalty: 0.5; gap separation penalty range: 8; percent identity for alignment delay: 40%; and transition, weighting: 0). The darkly shaded amino acids represent regions of matching identity. The lightly shaded amino acids represent regions of matching similarity. Dots between residues indicate gapped regions for the aligned polypeptides.

Figure 12:
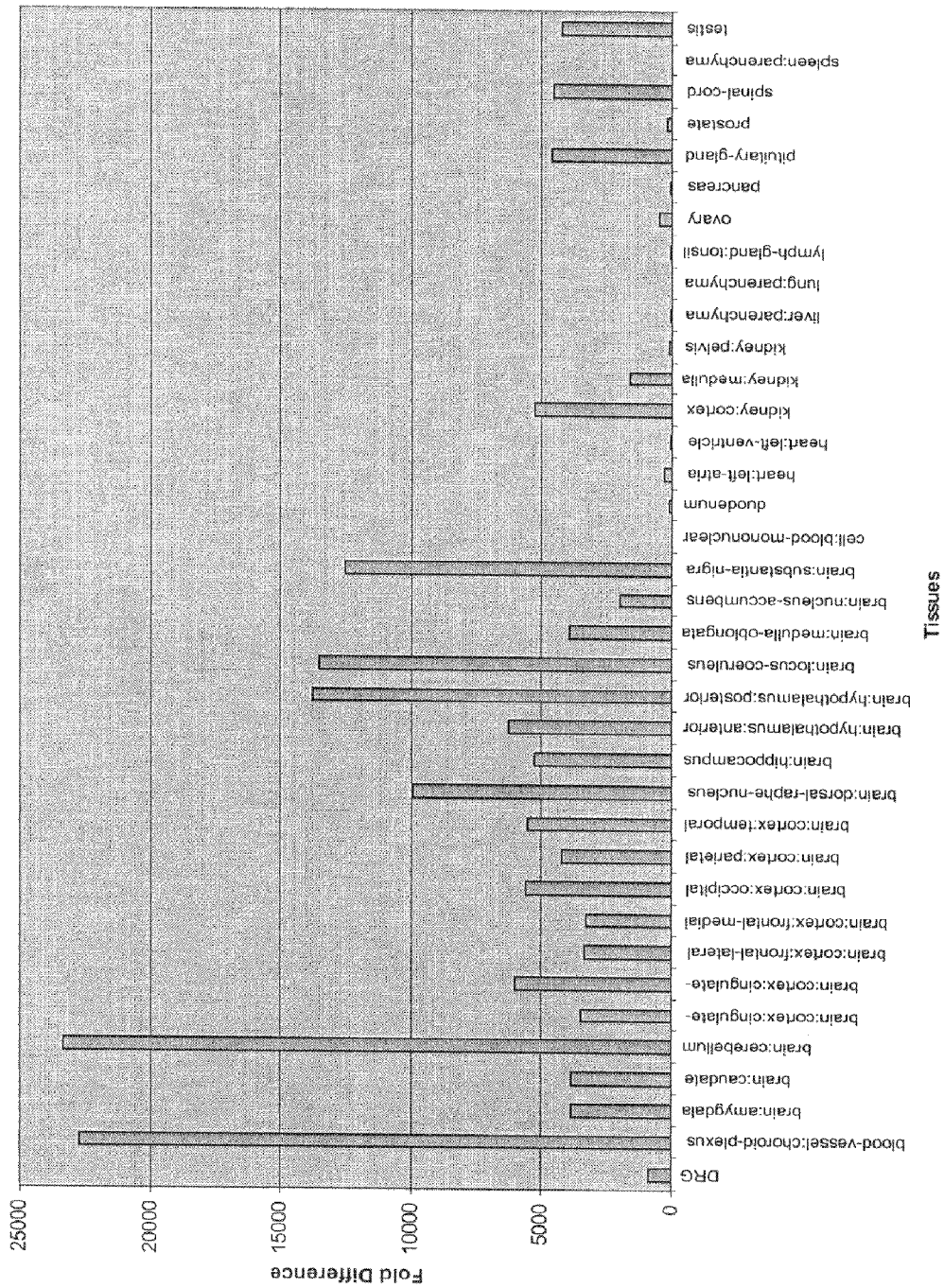

FIG. 12 shows an expanded expression profile of a variant of the human transient receptor potential channel family members of the present invention, LTRPC3 (Co-pending U.S. Ser. No. 10/210,152, filed Aug. 1, 2002; International Publication No. WO 03/012063, published Feb. 13, 2003; SEQ ID NO:15; in addition to Co-pending U.S. Ser. No. 10/405,793, filed Mar. 28, 2003). The figure illustrates the relative expression level of LTRPC3 amongst various mRNA tissue sources. As shown, the LTRPC3 polypeptide was expressed predominately in the brain, specifically the cerebellum, choroid plexus, the locus coeruleus, the posterior hypothalamus and the substantia nigra. Expression of LTRPC3 was also significantly expressed in the kidney, with higher levels observed in the cortex than in the medulla or pelvis. LTRPC3 was also significantly expressed in the spinal cord, testis, and to a lesser extent in other tissues as shown. Expression data was obtained by measuring the steady state LTRPC3 mRNA levels by quantitative PCR using the PCR primer pair provided as SEQ ID NO:306 and 307, and Taqman probe (SEQ ID NO:308) as described in Example 4 herein.

Figure 13:
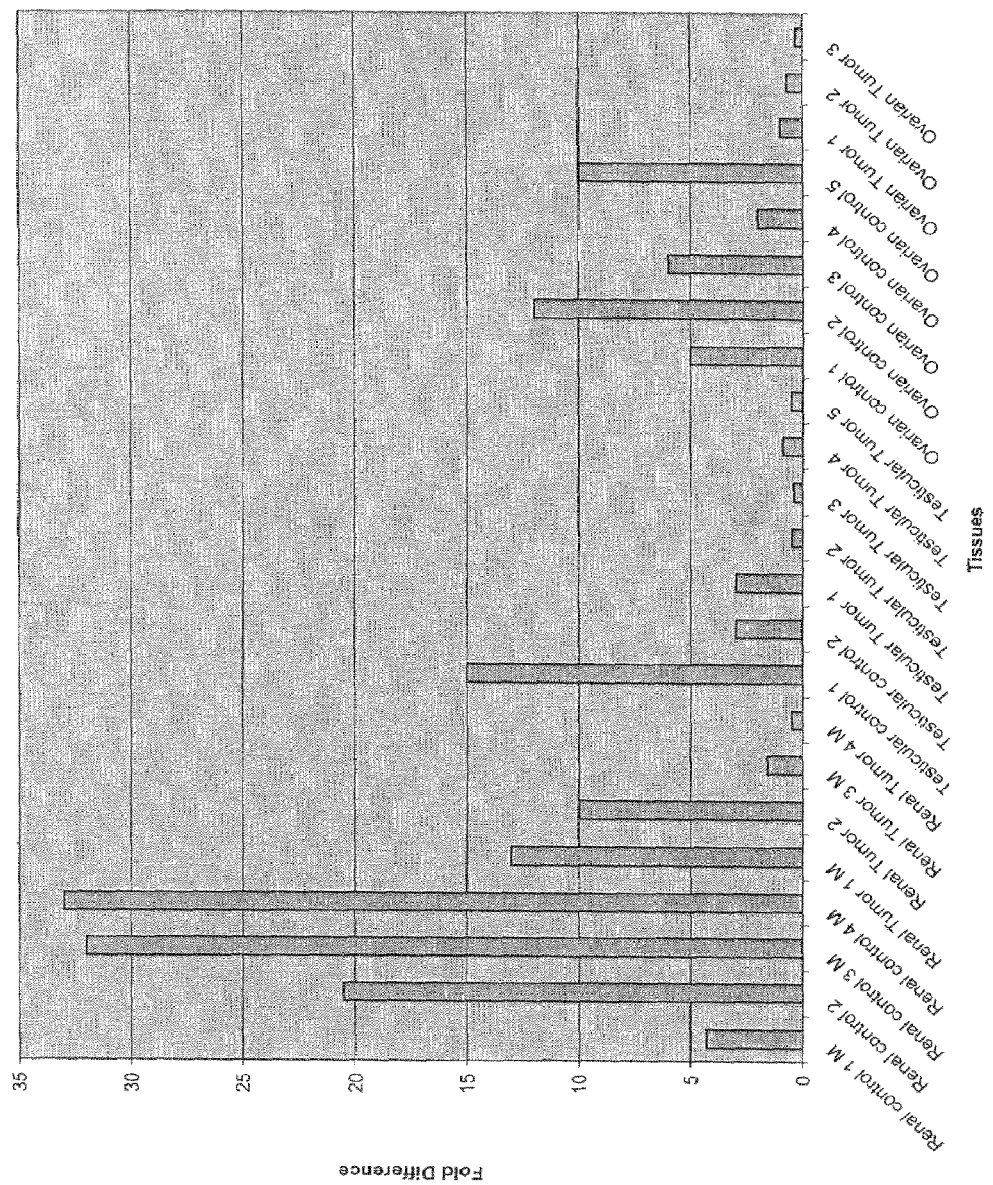

FIG. 13 shows an expanded expression profile of a variant of the human transient receptor potential channel family members of the present invention, LTRPC3 (Co-pending U.S. Ser. No. 10/210,152, filed Aug. 1, 2002; International Publication No. WO 03/012063, published Feb. 13, 2003; SEQ ID NO:15; which is hereby incorporated by reference herein in their entirety). The figure illustrates the relative expression level of LTRPC3 amongst various mRNA tissue sources isolated from normal and tumor tissues. As shown, the LTRPC3 polypeptide was differentially expressed in renal, testicular, and ovarian cancers compared to each respective normal tissue. Expression data was obtained by measuring the steady state LTRPC3 mRNA levels by quantitative PCR using the PCR primer pair provided as SEQ ID NO:306 and 307, and Taqman probe (SEQ ID NO:308) as described in Example 4 herein.

Figure 14:
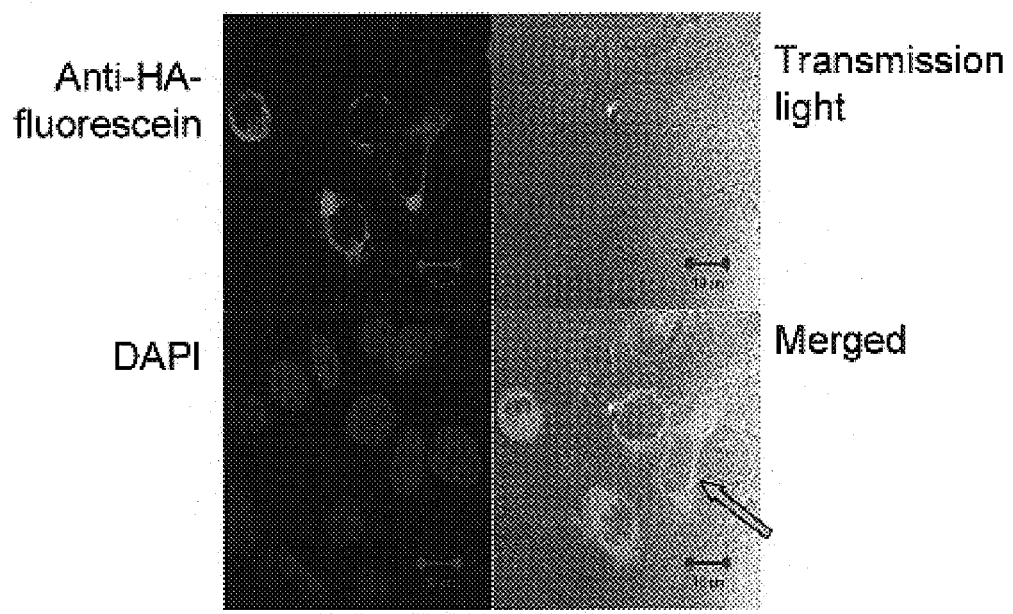

FIG. 14 shows a confocal-image of demonstrating that the LTRPC3 variant is expressed as an integral membrane protein. The left top panel shows the image obtained with a Fluorescein filter; the left bottom panel shows the image obtained with a DAPI filter; the right top panel shows the image obtained using transmitted light; and the right bottom panel is the merged picture of the above three images. One of cells expressing LTRPC3 on the plasma membrane regions is indicated by an arrow. Forty-eight hours after transfection, LTRPC3 expressing HEK 293 cells were fixed with 4% paraformaldehyde, permeabilized with 1% Triton, and labeled with fluorescein conjugated anti-HA (3F10) 48 hours post transfection. The cell nuclei were stained with DAPI. Microscopy was performed as described in Example 6 herein.

Figure 15:
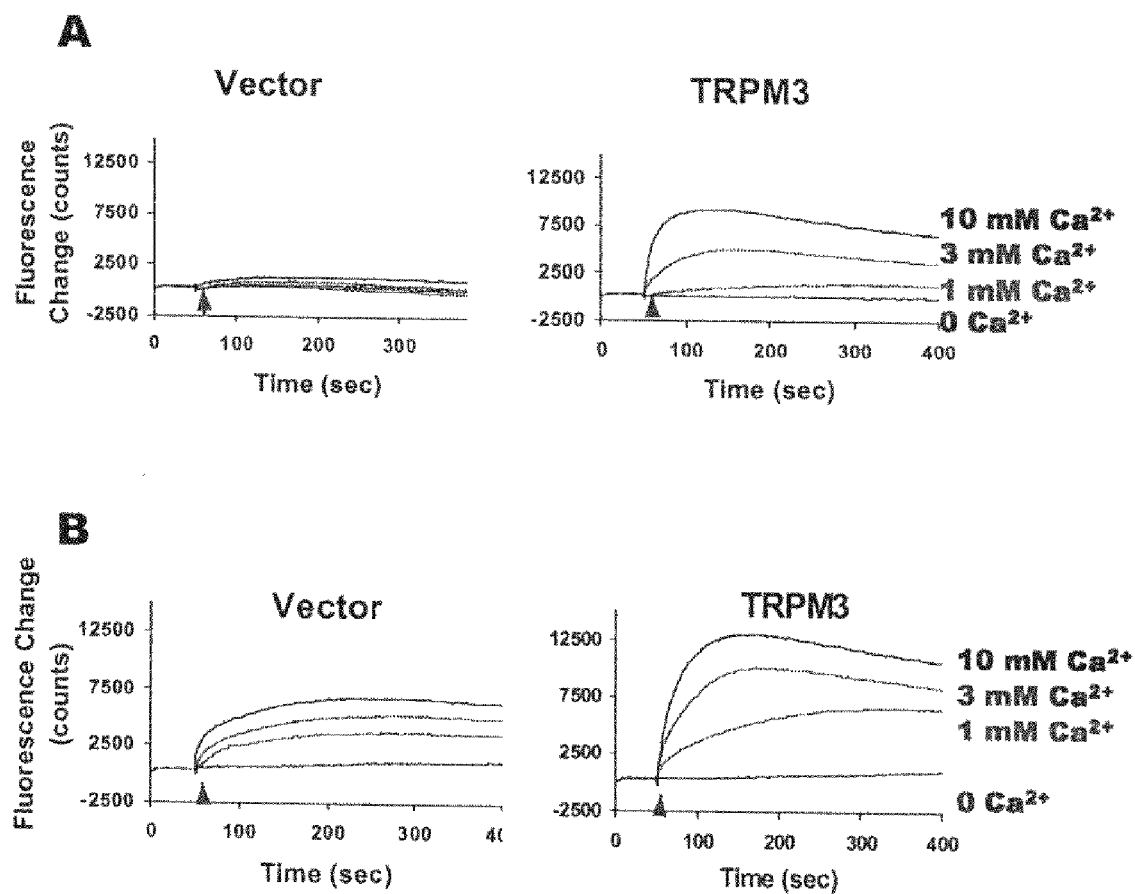

FIG. 15 shows that the LTRPC3 variant mediates concentration-dependent permeability to $Ca^{2+}$. Transfected HEK 293 cells loaded with Fluo-4 were incubated in 1 mM $Ca^{2+}$ solution (A), or a nominally $Ca^{2+}$-free solution (B), and 0, 1, 3 and 10 mM $Ca^{2+}$ solutions were added respectively to cells as indicated. The left panels represent vector-transfected control cells, and the right panels represent LTRPC3-transfected cells. Physiometric methods were performed as described in Example 7 herein.

Figure 16:
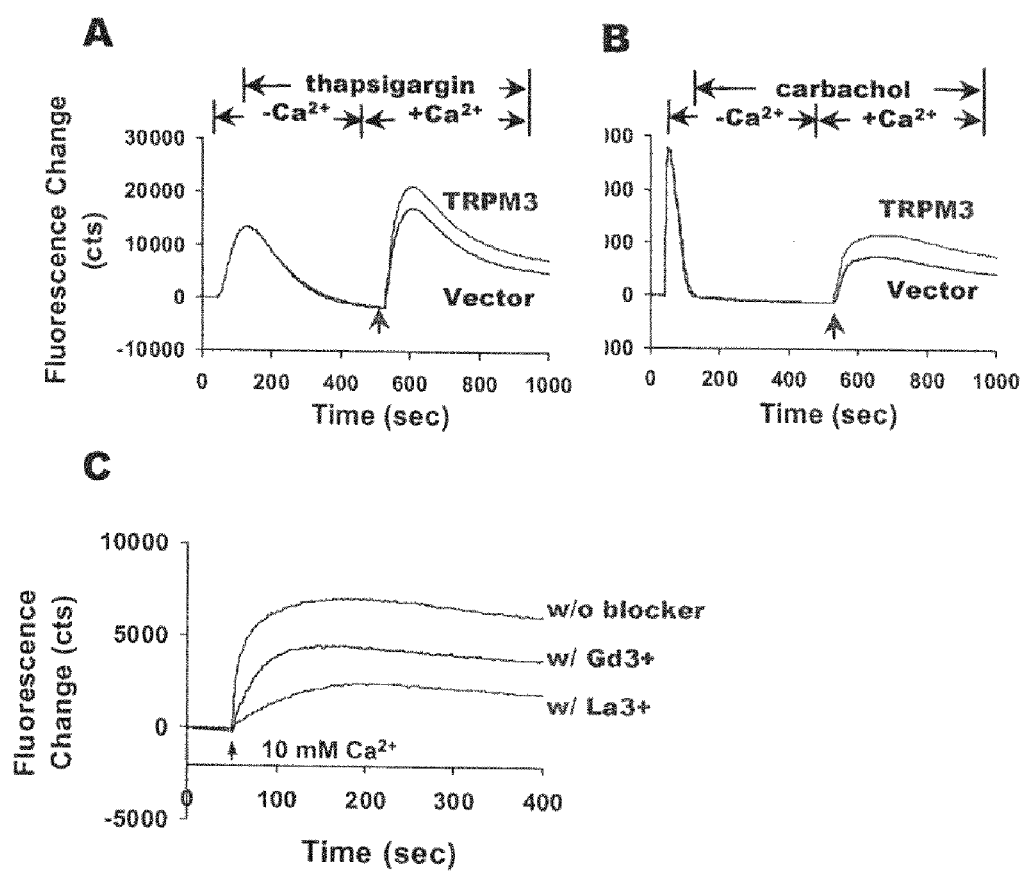

FIG. 16 shows $Ca^{2+}$ entry currents are induced upon store depletion in LTRPC3 variant expressing HEK 293 cells. 2 mM thapsigargin (A), or 50 μM carbachol (B) was first added to LTRPC3 variant expressing HEK 293 cells in the absence of external $Ca^{2+}$. After 9 minutes, 2 mM $Ca^{2+}$ solution was added to the cell medium at the indicated times. Currents for vector transfected HEK 293 cells, and LTRPC3 variant expressing HEK 293 cells are labeled accordingly. Panel (C) shows LTRPC3 variant mediated $Ca^{2+}$ currents are inhibited by $La^{3+}$ and $Gd^{3+}$. Cells loaded with Fluo-4 were incubated in 1 mM $Ca^{2+}$ solution and treated with 100 μM of $La^{3+}$ ("w/ $La^{3+}$"), $Gd^{3+}$ ("w/$Gd^{3+}$") or without blockers ("w/o blocker") for 10 min prior to the addition of 10 mM $Ca^{2+}$ to the cell medium as indicated. Curves represent averages of three independent experiments, each involving at least 8 wells per condition. Physiometric methods were performed as described in Example 7 herein.

Figure 17:
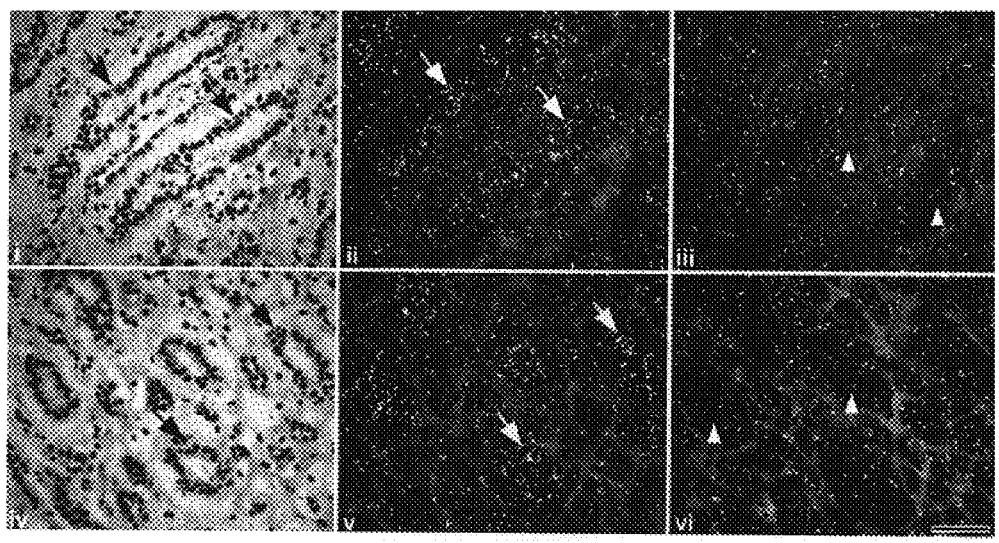

FIG. 17 shows In situ Hybridization (ISH) results of the LTRPC3 variant (see co-pending U.S. Ser. No. 10/405,793, filed Mar. 28, 2003; which is hereby incorporated by reference herein in its entirety). LTRPC3 mRNA expression was localized in the collecting tubular epithelium of human kidney medulla, medullary rays, and periglomerular regions, with the highest expression localized in medulary tubules. Bright field (i and iv) and dark field (ii and v) photomicrographs show the hybridization signal from antisense hTRMP3 riboprobe as aggregates of fine granules in the cytoplasm of the collecting tubular epithelial cells (arrows) in longitudinal (i and ii) and transverse (iv and v) sections. Low background signal is shown by the control LTRPC3 sense riboprobe in photographs iii and vi (the collecting tubules are indicated by arrowheads). Scale bar denotes 50 μm. ISH methods were performed as described in Example 8 herein.

Figure 18:
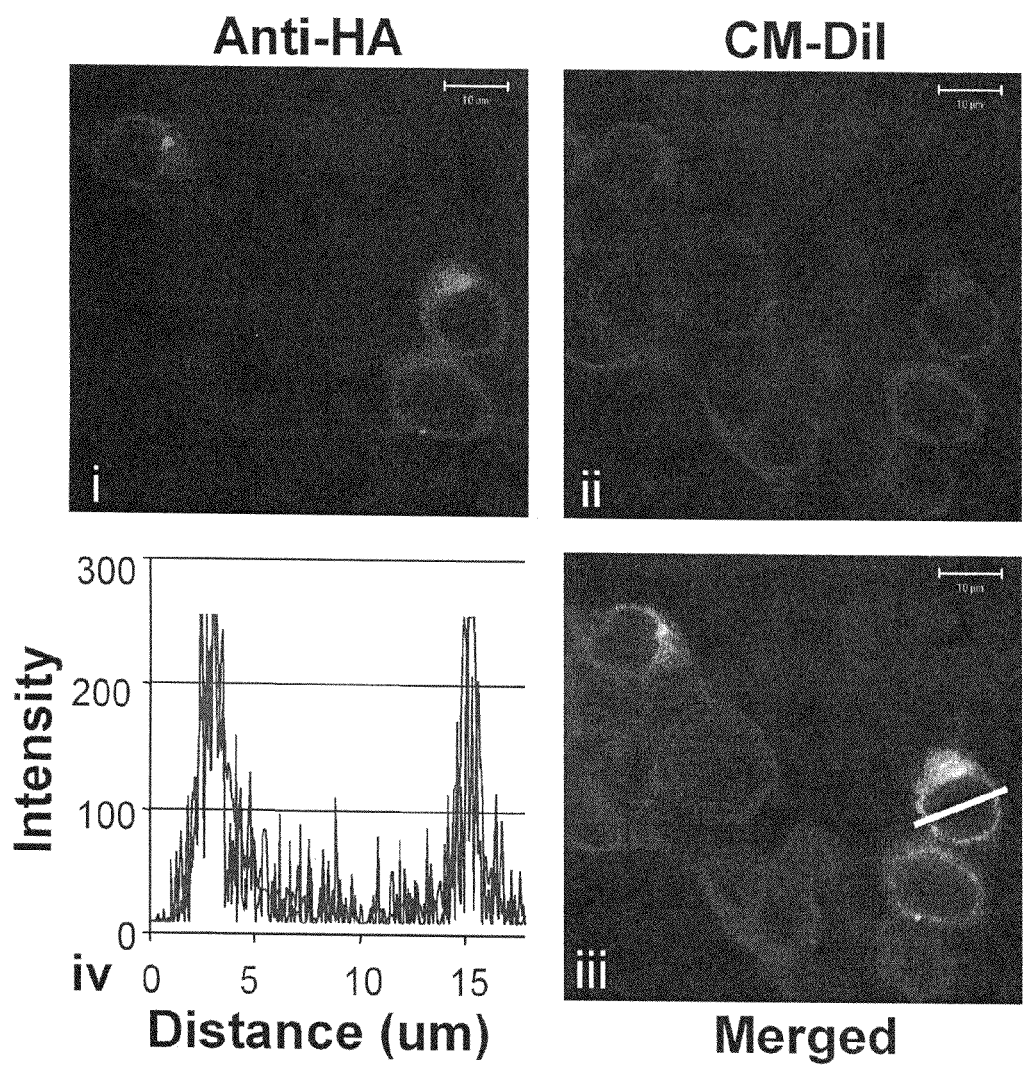

FIG. 18 shows an expanded confocal-image demonstrating that the LTRPC3 variant is expressed as an integral membrane protein (see co-pending U.S. Ser. No. 10/405,793, filed Mar. 28, 2003; which is hereby incorporated by reference herein in its entirety). The left top panel (i) shows the image obtained with anti-HA staining (green) which is specific for expressed HA-tagged LTRPC3; the right top panel (ii) shows the image obtained with CM-DiI staining (red), a lipophilic cell membrane marker; the right bottom panel (iii) shows a merged image showing anti-HA, CM-DiI, and DAPI (nuclear stain, blue), with co-localization of LTRPC3 and CM-DiI appearing as yellow; and the left bottom panel (iv) showing the intensity profiles for anti-HA staining (green) and CM-DiI staining (red) along the path indicated by the white line in panel iii, showing overlap of anti-HA staining with CM-DiI staining in a quantitative manner. Scale bar denotes 10 μm. Microscopy was performed as described in Example 9 herein.

Figure 19:
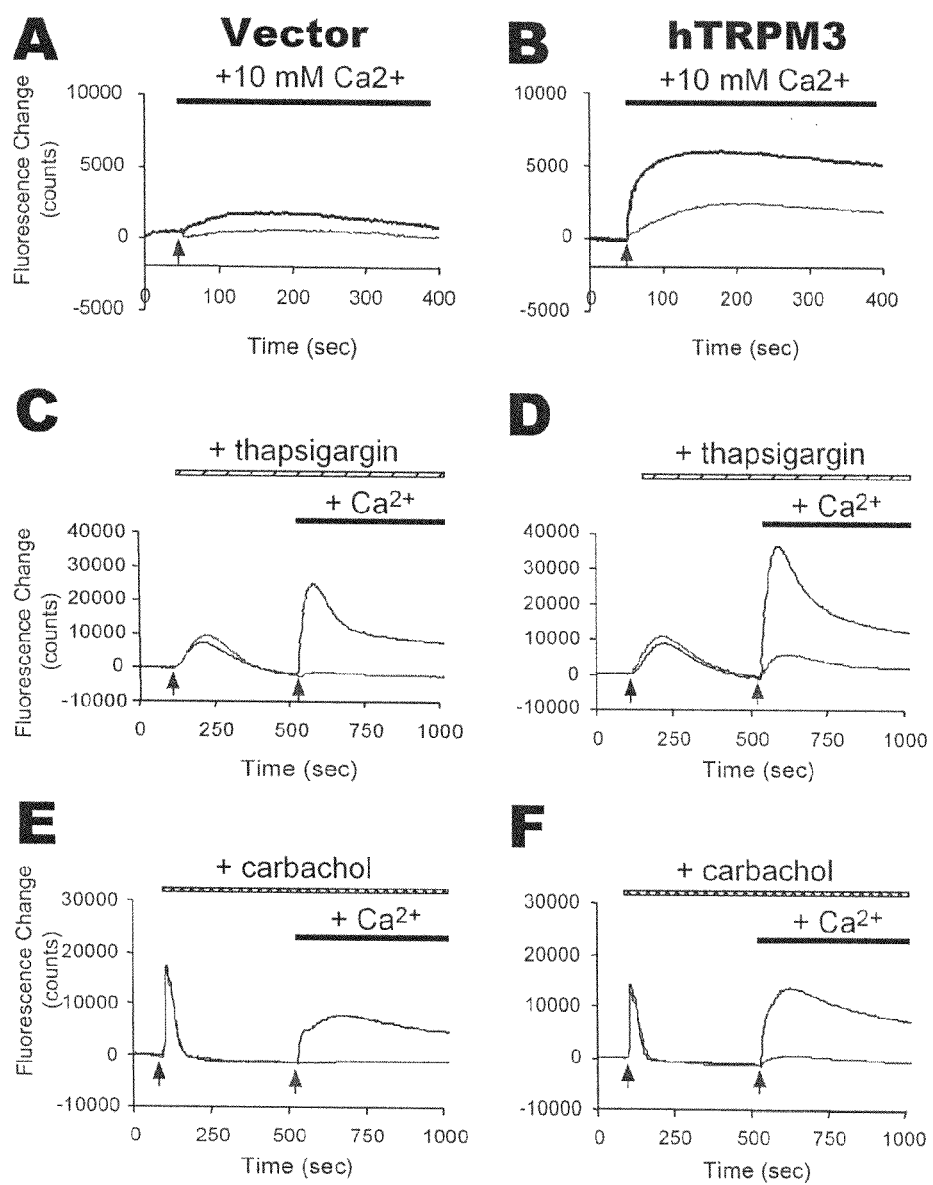

FIG. 19 shows that LTRPC3 variant ("TRPM3")-mediated $Ca^{2+}$ entry can be inhibited by $Gd^{3+}$ (see co-pending U.S. Ser. No. 10/405,793, filed Mar. 28, 2003; which is hereby incorporated by reference herein in its entirety). Panels A, C and E show results obtained for vector-transfected cells, while Panels B, D and F show results obtained for TRPM3-transfected cells. Panels A and B, show TRPM3-mediated concentration-dependent $Ca^+$ entry was partially inhibited by $Gd^{3+}$. Cells loaded with Fluo-4 were incubated in 1 mM $Ca^{2+}$ solution and treated with 100 μM of $Gd^{3+}$ (red) or without blockers (black)

for 10 min prior to the addition of 10 mM Ca$^{2+}$ to the bath solution as indicated. Panels C—F, show that both Tg (Panels C and D) and CCh (Panels E and F) induced LTRPC3 variant-mediated Ca$^{2+}$ entry can be inhibited by Gd$^{3+}$. Cells loaded with Fluo-4 were incubated in a nominally Ca$^{2+}$-free media and treated without blockers (black) or with 100 µM of Gd$^{3+}$ (red) for 10 min prior to the addition of 2 µM TG (Panels C and D, first arrow) or 50 µM CCh (Panels E and F, first arrow), Ca$^{2+}$ entry was stimulated by the bath addition of 10 mM Ca$^{2+}$ (second arrow). Representative traces from one of three independent experiments are shown; each trace is the mean of 12 wells per condition. Physiometric methods were performed as described in Example 10 herein.

Figure 20:
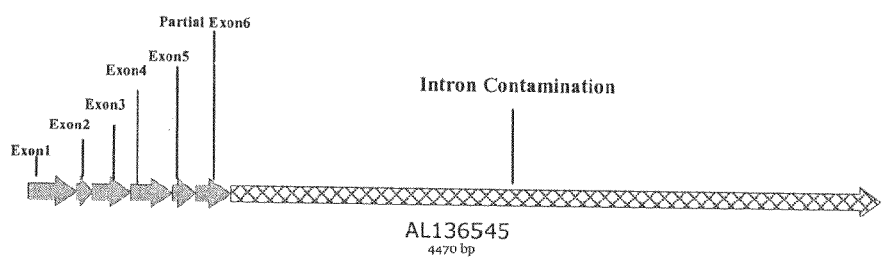

FIG. 20 shows a schematic representation of the genomic clone AL136545 that was found to contain three new exons that extend the 5' upstream region of the LTRPC3 gene. As shown, the AL136545 clone also contains exons 4, 5, part of exon 6, in addition to a significant portion containing intronic sequence. The three exons of clone AL136545 were used to extend the polynucleotide sequence of the LTRPC3 clones, and variants thereof, to arrive at the LTRPC3g-1 variant polynucleotide sequences of the present invention.

Figure 21:

FIG. 21 shows a schematic representation of the extended N-terminal portion of the polypeptide sequence of the LTRPC3g protein of the present invention (SEQ ID NO:2). Protein domain analysis of the extended N-terminal portion of the LTRPC3g polypeptide using HMMSEARCH against the Pfam protein domain database indicated that it contained one NSF domain and one Nucleoporin_FG domain. NSF domains have bee proposed to function in the regulation of intracellular traffic via fusion of two lipid bilayers(Baldini et al.). The presence of this domain is consistent with the data provided in FIGS. 14 and 18 that demonstrate that the LTRPC3 variant is a membrane protein, in addition to the data provided in FIGS. 15, 16, and 19 which demonstrate that the LTRPC3 variant suggest the LTRPC3 variant has storage-operated Ca$^{2+}$ channel activity. Nucleoporin_FG repeats are found in diverse nucleoporins and may confer function consistent with Ca$^{2+}$ channel activity.

Table I provides a summary of the novel polypeptides and their encoding polynucleotides of the present invention.

Table II illustrates the preferred hybridization conditions for the polynucleotides of the present invention. Other hybridization conditions may be known in the art or are described elsewhere herein.

Table III provides a summary of various conservative substitutions encompassed by the present invention.

DETAILED DESCRIPTION OF THE INVENTION

The present invention may be understood more readily by reference to the following detailed description of the preferred embodiments of the invention and the Examples included herein. The LTRPC3 variants of the present invention represent variants of the LTRPC3 polypeptide (Co-pending U.S. Ser. No. 10/210,152, filed Aug. 1, 2002; International Publication No. WO 03/012063, published Feb. 13, 2003; SEQ ID NO:15). Likewise, all references to "LTRPC3" shall be construed to apply to "LTRPC3", "LTRPC3g", "LTRPC3h", "LTRPC3l", "LTRPC3j", "LTRPC3k", and/or "LTRPC3l" unless otherwise specified herein.

The invention provides a novel human sequences that encode novel human transient receptor potential channel family members that are variants of the LTRPC3 polypeptide. Specifically, the present invention provides polynucleotide sequences that encode LTRPC3 variants LTRPC3g, LTRPC3h, LTRPC3i, LTRPC3j, LTRPC3k, and LTRPC3l, which all belong to the ITRPC subfamily. Each of the LTRPC3 variants of the present invention shares significant homology with other transient receptor potential channel family members, such as human melatonin receptor 1. Transcripts for the LTRPC3 variant were found predominately in kidney, spinal cord, testis, and brain suggesting that the invention potentially modulates leukocyte proliferation, differentiation, migration, and activation in these tissues. Since the polynucleotides of the present invention represent what is believed to be the full-length variants of the LTRPC3 polynucleotide, the polynucleotide variants of the present invention have been tentatively named LTRPC3g, LTRPC3h, LTRPC3i, LTRPC3j, LTRPC3k, and LTRPC3l, which are distinguished from the LTRPC3 splice variants LTRPC3b, LTRPC3c, LTRPC3d, LTRPC3e, and LTRPC3f which are also disclosed in co-pending U.S. Ser. No. 10/210,152, filed Aug. 1, 2002.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In specific embodiments, the polynucleotides of the invention are at least 15, at least 30, at least 50, at least 100, at least 125, at least 155, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As used herein, a "polynucleotide" refers to a molecule having a nucleic acid sequence contained in SEQ ID NO:1, SEQ ID NO:3, SEQ ID NO:5, SEQ ID NO:7, SEQ ID NO:9, SEQ ID NO: 11, or the cDNA contained within the clone deposited with the ATCC. For example, the polynucleotide can contain the nucleotide sequence of the full length cDNA sequence, including the 5' and 3' untranslated sequences, the coding region, with or without a signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO: 1, SEQ ID NO:3, SEQ ID NO:5, SEQ ID NO:7, SEQ ID NO:9, and SEQ ID NO:11 was often generated by overlapping sequences contained in multiple clones (contig analysis). A representative clone containing all or most of the sequence for SEQ ID NO:1, SEQ ID NO:3, SEQ ID NO:5, SEQ ID NO:7, SEQ ID NO:9, SEQ ID NO:11 was deposited with the American Type Culture Collection ("ATCC®"). As shown in Table 1, each clone is identified by a cDNA Clone ID (Identifier) and the ATCC® Deposit Number. The ATCC® is located at 10801 University Boulevard, Manassas, Virginia 20110-2209, USA. The ATCC® deposit was made pursuant to the terms of the Budapest Treaty on the international recognition of the deposit of microorganisms for purposes of patent procedure.

Unless otherwise indicated, all nucleotide sequences determined by sequencing a DNA molecule herein were determined using an automated DNA sequencer (such as the Model 373, preferably a Model 3700, from Applied Biosystems, Inc.), and all amino acid sequences of polypeptides encoded by DNA molecules determined herein were predicted by translation of a DNA sequence determined above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded bt the sequenced DNA molecule, beginning at the point of such an insertion or deletion.

Using the information provided herein, such as the nucleotide sequence in FIGS. 1A-E (SEQ ID NO:1), a nucleic acid molecule of the present invention encoding the LTRPC3g polypeptide may be obtained using standard cloning and screening procedures, such as those for cloning cDNAs using mRNA as starting material. Illustrative of the invention, the nucleic acid molecule described in FIGS. 1A-E (SEQ ID NO:1) was discovered through the application of bioinformatic methods to human genomic and EST sequences.

Using the information provided herein, such as the nucleotide sequence in FIGS. 2A-F (SEQ ID NO:3), a nucleic acid molecule of the present invention encoding the LTRPC3h polypeptide may be obtained using standard cloning and screening procedures, such as those for cloning cDNAs using mRNA as starting material. Illustrative of the invention, the nucleic acid molecule described in FIGS. 2A-F (SEQ ID NO:3) was discovered through the application of bioinformatic methods to human genomic and EST sequences.

Using the information provided herein, such as the nucleotide sequence in FIGS. 3A-F (SEQ ID NO:5), a nucleic acid molecule of the present invention encoding the LTRPC3i polypeptide may be obtained using standard cloning and screening procedures, such as those for cloning cDNAs using mRNA as starting material. Illustrative of the invention, the nucleic acid molecule described in FIGS. 3A-F (SEQ ID NO:5) was discovered through the application of bioinformatic methods to human genomic and EST sequences.

Using the information provided herein, such as the nucleotide sequence in FIGS. 4A-F (SEQ ID NO:7), a nucleic acid molecule of the present invention encoding the LTRPC3j polypeptide may be obtained using standard cloning and screening procedures, such as those for cloning cDNAs using mRNA as starting material. Illustrative of the invention, the nucleic acid molecule described in FIGS. 4A-F (SEQ ID NO:7) was discovered through the application of bioinformatic methods to human genomic and EST sequences.

Using the information provided herein, such as the nucleotide sequence in FIGS. 5A-F (SEQ ID NO:9), a nucleic acid molecule of the present invention encoding the LTRPC3k polypeptide may be obtained using standard cloning and screening procedures, such as those for cloning cDNAs using mRNA as starting material. Illustrative of the invention, the nucleic acid molecule described in FIGS. 5A-F (SEQ ID NO:7) was discovered through the application of bioinformatic methods to human genomic and EST sequences.

Using the information provided herein, such as the nucleotide sequence in FIGS. 6A-F (SEQ ID NO:11), a nucleic acid molecule of the present invention encoding the LTRPC3l polypeptide may be obtained using standard cloning and screening procedures, such as those for cloning cDNAs using mRNA as starting material. Illustrative of the invention, the nucleic acid molecule described in FIGS. 6A-F (SEQ ID NO:11) was discovered through the application of bioinformatic methods to human genomic and EST sequences.

A "polynucleotide" of the present invention also includes those polynucleotides capable of hybridizing, under stringent hybridization conditions, to sequences contained in SEQ ID NO:1, SEQ ID NO:3, SEQ ID NO:5, SEQ ID NO:7, SEQ ID NO:9, SEQ ID NO:11, the complements thereof, to polynucleotide sequences encoding the sequences contained in SEQ ID NO:2, SEQ ID NO:4, SEQ ID NO:6, SEQ ID NO:9, the complements thereof, or the cDNA within the clone deposited with the ATCC. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65 degree C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20× SSPE=3M NaCl; 0.2M NaH2PO4; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo dT as a primer).

The polynucleotide of the present invention can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure and Molecular Properties, 2nd Ed., T. E. Creighton, W. H. Freeman and Company, New York (1993); Posttranslational Covalent Modification of Proteins, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992).)

As will be appreciated by the skilled practitioner, should the amino acid fragment comprise an antigenic epitope, for example, biological function per se need not be maintained. The terms LTRPC3g, LTRPC3h, LTRPC3i, LTRPC3j, LTRPC3k, and/or LTRPC3l, polypeptide and LTRPC3g, LTRPC3h, LTRPC3i, LTRPC3j, LTRPC3k, and/or LTRPC3l protein are used interchangeably herein to refer to the encoded product of the LTRPC3g, LTRPC3h, LTRPC3i, LTRPC3j, LTRPC3k, and/or LTRPC3l nucleic acid sequence according to the present invention.

"SEQ ID NO:1", "SEQ ID NO:3", "SEQ ID NO:5", "SEQ ID NO:7", "SEQ ID NO:9", and "SEQ ID NO:11" refer to polynucleotide sequences, while "SEQ ID NO:2", "SEQ ID NO:4", "SEQ ID NO:6", "SEQ ID NO:8", "SEQ ID NO:10", and "SEQ ID NO:12" refer to polypeptide sequences, all sequences being identified by an integer specified in Table 1 herein.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about ten-fold less activity, and most preferably, not more than about three-fold less activity relative to the polypeptide of the present invention.)

The term "organism" as referred to herein is meant to encompass any organism referenced herein, though preferably to eukaryotic organisms, more preferably to mammals, and most preferably to humans.

As used herein the terms "modulate or modulates" refer to an increase or decrease in the amount, quality or effect of a particular activity, DNA, RNA, or protein.

It is another aspect of the present invention to provide modulators of the LTRPC3g, LTRPC3h, LTRPC3i, LTRPC3j, LTRPC3k, and/or LTRPC3l protein and LTRPC3g, LTRPC3h, LTRPC3i, LTRPC3j, LTRPC3k, and/or LTRPC3l peptide targets which can affect the function or activity of LTRPC3g, LTRPC3h, LTRPC3i, LTRPC3j, LTRPC3k, and/or LTRPC3l in a cell in which LTRPC3g, LTRPC3h, LTRPC3i, LTRPC3j, LTRPC3k, and/or LTRPC3l function or activity is to be modulated or affected. In addition, modulators of LTRPC3g, LTRPC3h, LTRPC3i, LTRPC3j, LTRPC3k, and/or LTRPC3l can affect downstream systems and molecules that are regulated by, or which interact with, LTRPC3g, LTRPC3h, LTRPC3i, LTRPC3j, LTRPC3k, and/or LTRPC3l in the cell. Modulators of LTRPC3g, LTRPC3h, LTRPC3i, LTRPC3j, LTRPC3k, and/or LTRPC3l include compounds, materials, agents, drugs, and the like, that antagonize, inhibit, reduce, block, suppress, diminish, decrease, or eliminate LTRPC3g, LTRPC3h, LTRPC3i, LTRPC3j, LTRPC3k, and/or LTRPC3l function and/or activity. Such compounds, materials, agents, drugs and the like can be collectively termed "antagonists". Alternatively, modulators of LTRPC3g, LTRPC3h, LTRPC3i, LTRPC3j, LTRPC3k, and/or LTRPC3l include compounds, materials, agents, drugs, and the like, that agonize, enhance, increase, augment, or amplify LTRPC3g, LTRPC3h, LTRPC3i, LTRPC3j, LTRPC3k, and/or LTRPC3l function in a cell. Such compounds, materials, agents, drugs and the like can be collectively termed "agonists".

The present invention encompasses the identification of proteins, nucleic acids, or other molecules, that bind to polypeptides and polynucleotides of the present invention (for example, in a receptor-ligand interaction). The polynucleotides of the present invention can also be used in interaction trap assays (such as, for example, that described by Ozenberger and Young (Mol. Endocrinol., 9(10):1321-9, (1995); and Ann. N.Y. Acad. Sci., 7; 766:279-81, (1995)).

The polynucleotide and polypeptides of the present invention are useful as probes for the identification and isolation of full-length cDNAs and/or genomic DNA which correspond to the polynucleotides of the present invention, as probes to hybridize and discover novel, related DNA sequences, as probes for positional cloning of this or a related sequence, as probe to "subtract-out" known sequences in the process of discovering other novel polynucleotides, as probes to quantify gene expression, and as probes for microarrays.

In addition, polynucleotides and polypeptides of the present invention may comprise one, two, three, four, five, six, seven, eight, or more membrane domains.

Also, in preferred embodiments the present invention provides methods for further refining the biological function of the polynucleotides and/or polypeptides of the present invention.

Specifically, the invention provides methods for using the polynucleotides and polypeptides of the invention to identify orthologs, homologs, paralogs, variants, and/or allelic variants of the invention. Also provided are methods of using the polynucleotides and polypeptides of the invention to identify the entire coding region of the invention, non-coding regions of the invention, regulatory sequences of the invention, and secreted, mature, pro-, prepro-, forms of the invention (as applicable).

In preferred embodiments, the invention provides methods for identifying the glycosylation sites inherent in the polynucleotides and polypeptides of the invention, and the subsequent alteration, deletion, and/or addition of said sites for a number of desirable characteristics which include, but are not limited to, augmentation of protein folding, inhibition of protein aggregation, regulation of intracellular trafficking to organelles, increasing resistance to proteolysis, modulation of protein antigenicity, and mediation of intercellular adhesion.

In further preferred embodiments, methods are provided for evolving the polynucleotides and polypeptides of the present invention using molecular evolution techniques in an effort to create and identify novel variants with desired structural, functional, and/or physical characteristics.

The present invention further provides for other experimental methods and procedures currently available to derive functional assignments. These procedures include but are not limited to spotting of clones on arrays, micro-array technology, PCR based methods (e.g., quantitative PCR), anti-sense methodology, gene knockout experiments, and other procedures that could use sequence information from clones to build a primer or a hybrid partner.

Polynucleotides and Polypeptides of the Invention

Features of the Polypeptide Encoded by Gene No: 1

The polypeptide of this gene provided as SEQ ID NO:2 (FIGS. 1A-E), encoded by the polynucleotide sequence according to SEQ ID NO:1 (FIGS. 1A-E), and/or encoded by the polynucleotide contained within the deposited clone, LTRPC3g, has significant homology at the nucleotide and amino acid level to the human melastatin 1 protein (Melastatin1; Genbank Accession No. gi|3243075; SEQ ID NO:13). An alignment of the LTRPC3g polypeptide with this protein is provided in FIGS. 7A-G.

The LTRPC3g polypeptide was determined to share 65.7% identity and 73.5% similarity with the human melastatin 1 protein (Melastatin1; Genbank Accession No. gi|3243075; SEQ ID NO:13) as shown in FIG. 10.

The LTRPC3g protein is believed to represent a member of a new class of protein kinases referred to as alpha kinases (Curr. Biol. 9 (2), R43-R45 (1999)). These kinases represent a novel type of signaling molecule comprising both a catalytic protein kinase domain, in addition to, an ion channel domain. This family is commonly referred to as the transient receptor potential channel (TRP) family. Melastatin1 defines a separate subfamily of TRP channels referred to as TRPM (melastatin1). TRPM family members are characteristic of their unusually long cytoplasmic tails at both ends of the channel domain and some of the family members contain an enzyme domain at the C-terminal region.

Specifically, the LTRPC3g (SEQ ID NO:2) polypeptide represents a novel variant of the LTRPC3 (Co-pending U.S. Ser. No. 10/210,152, filed Aug. 1, 2002; International Publication No. WO 03/012063, published Feb. 13, 2003; SEQ ID NO:15) polypeptide. The LTRPC3g represents a novel member of the TRPM subfamily.

The melastatin1 protein is believed to be negatively associated with the incidence of melanoma based upon its inverse correlative expression in highly aggressive melanomas (Genomics 54 (1), 116-123 (1998)). Thus, overexpression of melastatin1 could represent a novel therapeutic in the treatment of melanoma and potentially other cancers.

Based upon the observed homology, the polypeptide of the present invention is expected to share at least some biological activity with other transient receptor potential channel family members, more specifically with the melastatin1 protein, in addition to, other transient receptor potential channel family members referenced elsewhere herein or otherwise known in the art. Moreover, since the LTRPC3g polypeptide represents a variant of the LTRPC3 polypeptide, it is expected that it will share similar biological activity with LTRPC3, some of which is described herein.

Most of the known transient receptor potential channel family members, possess one or more transmembrane domains. Likewise, the LTRPC3g polypeptide has been determined to comprise six transmembrane domains (TM1-TM6) as shown in FIGS. 1A-E. The transmembrane domains are located from about amino acid 776 to about amino acid 792 (TM1), from about amino acid 872 to about amino acid 888 (TM2), from about amino acid 945 to about amino acid 958 (TM3), from about amino acid 972 to about amino acid 989 (TM4), from about amino acid 1006 to about amino acid 1023 (TM5), and/or from about amino acid 1093 to about amino acid 1113 to about amino acid 1062 (TM6) of SEQ ID NO:2. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following transmembrane domain polypeptides are encompassed by the present invention: LKVILGILLPPSILSLEF (SEQ ID NO:22), IVKFWFYTLAYIGYLMLF (SEQ ID NO:23), VTDLIAILLFSVGM (SEQ ID NO:24), RVIYCVNIIYWYIRLLDI (SEQ ID NO:25), MMIDMMYFVIIMLVVLMS (SEQ ID NO:26), and/or AIMACYLLVANILLVNLLIAV (SEQ ID NO:27). Polynucleotides encoding these polypeptides are also provided. The present invention also encompasses the use of the LTRPC3g transmembrane polypeptides as immunogenic and/or antigenic epitopes as described elsewhere herein.

The present invention also encompasses polypeptides corresponding to the regions between each transmembrane domain of LTRPC3g, referred to herein as inter-transmembrane domain polypeptides (inter TM1-2, inter TM2-3, inter TM3-4, inter TM4-5, and inter TM5-6). Such regions are typically solvent accessible (either extracellularly or intracellularly). Therefore, these regions are amenable to the development of agonists and/or antagonists to the LTRPC3g polypeptide, particularly for the development of antibodies specific to these regions.

In preferred embodiments, the following inter-transmembrane domain polypeptides are encompassed by the present invention: KNKDDMPYMSQAQEIHLQEKEAEEPE-KPTKEKEEEDMELTAMLGRNNGESS RKKDEEEVQSKHRLIPLGRKIYEFYNAP (SEQ ID NO:28), NYIVLVKMERWPSTQEWIVISYIFTLG-IEKMREILMSEPGKLLQKVKVWLQEY WN (SEQ ID NO:29), ILRLQDQPFRSDG (SEQ ID NO:30), FGVNKY-LGPYVMMIGK (SEQ ID NO:31), and/or FGVARQAILF-PNEEPSWKLAKNIFYMPYWMIYGEVFAD-QIDPPCGQNETRED GKIIQLPPCKTGAWIVP (SEQ ID NO:32). Polynucleotides encoding these polypeptides are also provided. The present invention also encompasses the use of the LTRPC3g inter-transmembrane polypeptides as immunogenic and/or antigenic epitopes as described elsewhere herein.

The LTRPC3g polypeptide was determined to comprise several conserved cysteines, at amino acid 249, 364, 420, 574, 672, 737, 754, 976, 1067, 1084, 1097, 1200, 1291, and 1552 of SEQ ID No: 2 (FIGS. 1A-E). Conservation of cysteines at key amino acid residues is indicative of conserved structural features, which may correlate with conservation of protein function and/or activity.

In confirmation of the LTRPC3g representing a member of the transient receptor channel family, the LTRPC3g polypeptide was determined to comprise a predicted TRP domain located from about amino acid 1128 to about amino acid 1133 8 of SEQ ID NO:2. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following TRP domain polypeptide is encompassed by the present invention: VWK-FQR (SEQ ID NO:33). Polynucleotides encoding this polypeptide are also provided. The present invention also encompasses the use of this LTRPC3g TRP domain polypeptide as an immunogenic and/or antigenic epitope as described elsewhere herein.

In further confirmation of the LTRPC3g representing a member of the transient receptor channel family, the LTRPC3g polypeptide was determined to comprise a predicted ion transport signature domain located at about amino acid 903 to about amino acid 1114 of SEQ ID NO:2. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following ion transport signature domain polypeptide is encompassed by the present invention: TQEWIVISYIFTLGIEKMREILM-SEPGKLLQKVKVWLQEYWNVTDLIAILLFSV GMIL-RLQDQPFRSDGRVIYCVNIIYWYIRLL-DIFGVNKYLGPYVMMIGKMMID MMYFVIIMLVVLMSFGVARQAILFP-NEEPSWKLAKNIFYMPYWMIYGEVFAD QIDP-PCGQNETREDGKIIQLPPCKTGAWIV-PAIMACYLLVANILLVNLLIAVF (SEQ ID NO:34). Polynucleotides encoding this polypeptide are also provided. The present invention also encompasses the use of this LTRPC3g ion transport signature domain polypeptide as an immunogenic and/or antigenic epitope as described elsewhere herein.

The LTRPC3g polypeptide was determined to comprise a predicted coiled-coil domain located at about amino acid 1218 to about amino acid 1273 of SEQ ID NO:2. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following coiled-coil domain polypeptide is encompassed by the present invention: ERIRVTSERVENMSMRLEEVNEREH-SMKASLQTVDIRLAQLEDLIGRMATAL ERLT (SEQ ID NO:35). Polynucleotides encoding this polypeptide are also provided. The present invention also encompasses the use of this LTRPC3g coiled-coil domain polypeptide as an immunogenic and/or antigenic epitope as described elsewhere herein.

LTRPC3g polypeptides and polynucleotides are useful for diagnosing diseases related to the over and/or under expression of LTRPC3g by identifying mutations in the LTRPC3g gene using LTRPC3g sequences as probes or by determining LTRPC3g protein or mRNA expression levels. LTRPC3g polypeptides will be useful in screens for compounds that affect the activity of the protein. LTRPC3g peptides can also be used for the generation of specific antibodies and as bait in yeast two hybrid screens to find proteins the specifically interact with LTRPC3g.

Consistent with LTRPC3g representing a transient receptor potential channel, immunohistochemical experiments have shown that the LTRPC3 variant (SEQ ID NO:15) localizes to the cell membrane (see FIG. 17 and Example 6). Specifically, the complete open reading frame of LTRPC3 with a C-terminal HA tag was transiently transfected into HEK 293 cells to assess its cellular localization. The HA-tagged LTRPC3 was detected using a fluorescein-conjugated anti-HA antibody and a laser scanning confocal microscope which produces a green fluorescent signal. The green fluorescent signal was exclusively detected at the subplasma membrane region of the transfected cells (see FIG. 17), which is consistent with LTRPC3 being an integral membrane protein. Under these conditions approximately ~70% of cells are expressing LTRPC3. The expression of full-length protein was accessed with immunoblot using an anti-HA antibody and detected as the expected size of ~170 kD (data not shown).

Since the LTRPC3g polypeptide represents an N-terminally extended variant of the LTRPC3 polypeptide (see polypeptide alignment provided in FIG. 11A-I), LTRPC3g is expected to have the same or similar function as the LTRPC3 polypeptide. Moreover, the LTRPC3g polypeptide is expected to localize to the cell membrane.

Additional characterization for the LTRPC3 variant protein is provided in Co-pending U.S. Ser. No. 10/405,793, filed Mar. 28, 2003; which is hereby incorporated by reference herein in its entirety).

Additionally, anti-HA staining was found to be associated with the membrane marker CM-DiI, indicating LTRPC3 protein in or near the plasmalemmal compartment of transfected cells (see FIG. 21). Plasmalemmal localization is consistent with the function of the TRP family as $Ca^{2+}$-permeable cation channels. LTRPC3 was also observed in intracellular compartments, possibly resulting from overexpression in this heterologous expression system, as observed with other ion channels (Marshall, J., et al., (1995) *Neuron* 14, 211-215.).

The LTRPC3g polypeptide is expected to also localize in or near the plasmalemmal compartment.

Moreover, physiometric studies have shown that LTRPC3 is a functional $Ca^{2+}$ permeable channel (see FIGS. 18 and 19, and Example 7). LTRPC3g function was assessed using a Fluorometric Imaging Plate Reader (FLIPR™) that measures real-time intracellular fluorescence changes. Cells transiently transfected with vector or LTRPC3-HA were loaded with the cytoplasmic $Ca^{2+}$ indicator Fluoro-4 in a 1 mM $Ca^{2+}$ solution. Addition of $Ca^{2+}$ to the media resulted in a concentration-dependent influx of $Ca^{2+}$ into LTRPC3-expressing cells (FIG. 18; right panels), indicating that LTRPC3 is a functional $Ca^{2+}$ channel. In contrast, vector-transfected cells showed minimal $Ca^{2+}$ influx under the same experimental conditions (FIG. 18, left panels). The non-transfected cells were indistinguishable from the vector-transfected cells (data not shown). Therefore, LTRPC3 is a constitutively active channel capable of mediating $Ca^{2+}$ influx.

The LTRPC3g polypeptide is also expected to be a constitutively active channel capable of mediating $Ca^{2+}$ influx.

To further address the mechanism of LTRPC3-mediated $Ca^{2+}$ entry, similar $Ca^{2+}$ addition experiments were performed on transfected cells incubated (~30 min) in a nominally $Ca^{2+}$-free solution. Previous studies have shown that lowering extracellular $Ca^{2+}$ concentration below physiological levels can deplete intracellular $Ca^{2+}$ stores in many cell types including HEK 293 (EMBO J. 17, 4274-4282, (1998)). Incubating vector-transfected HEK 293 cells in a nominally $Ca^{2+}$-free solution gave rise to $Ca^{2+}$ entry that was dependent on the concentration of $Ca^{2+}$ added to the buffers, indicating $Ca^{2+}$ influx was mediated through endogenous SOCs in HEK293 cells (FIG. 18, left panels). In LTRPC3 cells, the $Ca^{2+}$ transients triggered by similar $Ca^{2+}$ treatment were much larger (FIG. 18, right panels). This $Ca^{2+}$ entry observed in LTRPC3 cells incubated in $Ca^{2+}$-free media were greater than those observed in 1 mM $Ca^{2+}$ media, indicating that LTRPC3-mediated $Ca^{2+}$ entry can be potentiated by the store-depletion.

The LTRPC3g polypeptide is also expected to mediate $Ca^{2+}$ entry and that LTRPC3g-mediated $Ca^{2+}$ entry is expected to be potentiated by store-depletion.

The store-operated mechanism of LTRPC3-mediated $Ca^{2+}$ influx was tested further by passively depleting $Ca^{2+}$ stores with thapsigargin (TG), an inhibitor of microsomal $Ca^{2+}$ ATPases that pumps ions from the cytosol back into the stores. Addition of 2 µM thapsigargin equivalently depleted $Ca^{2+}$ stores in LTRPC3-HA- and vector-transfected cells (FIG. 19A). Following store depletion with TG, addition of $Ca^{2+}$ to the buffer induced a much larger $Ca^{2+}$ entry in LTRPC3 cells compared to the vector control cells.

Receptor-mediated $Ca^{2+}$ entry was also more pronounced in LTRPC3-HA-transfected cells. Carbachol (CCh) can activate an endogenous muscarinic receptor and trigger $IP_3$ production, leading to store-depletion in HEK 293 cells. The addition of 50 µM of CCh caused a transient and rapid intracellular $Ca^{2+}$ increase in both LTRPC3- and vector-transfected cells (FIG. 19B). After the store depletion with CCh, adding of Ca+ to the buffer induced a much larger influx of $Ca^{2+}$ into LTRPC3 cells, as compared to vector control cells. These results show that after store depletion with TG or CCh LTRPC3-transfected cells exhibit an increased $Ca^{2+}$ influx when compared to control cells.

The lanthanides, gadolinium ($Gd^{3+}$) and lanthanum ($La^{3+}$), are nonselective $Ca^{2+}$-permeable channel blockers, often used as part of the characterization of overexpressed TRP channels. Both lanthanides blocked LTRPC3 $Ca^{2+}$ conductance, although $La^{3+}$ was more potent (FIG. 19C). In the presence of 1 mM $Ca^{2+}$ in which endogenous SOCs is minimally activated (FIG. 18A), pre-treatment with 100 µM of $La^{3+}$ and $Gd^{3+}$ blocked LTRPC3 $Ca^{2+}$ currents, stimulated by adding 10 mM $Ca^{2+}$, by 67 and 39%, respectively. These results indicated that LTRPC3 mediated currents are not non-specific leak currents resulting from protein overexpression.

Additional experiments were performed to further confirm the $Ca^{2+}$ store-depleted activation of LTRPC3 using $Gd^{3+}$. The effects of 100 µM $Gd^{3+}$ on $Ca^{2+}$ permeability were tested in vector- and LTRPC3-transfected cells. The minimal $Ca^{2+}$ influx observed upon addition of 10 mM $Ca^{2+}$ to the cells (cells were incubated in the presence of 1 mM $Ca^{2+}$) in vector-transfected cells (see FIG. 22A) was strongly inhibited by 100 µM $Gd^{3+}$. In contrast, 100 µM $Gd^{3+}$ inhibited $Ca^{2+}$ entry, induced by adding 10 mM $Ca^{2+}$, by 53% in LTRPC3-transfected cells (see FIG. 22B). $Gd^{3+}$ reduced fluorescence units in vector-transfected cells from 1470±140 to −58±8 and in LTRPC3-transfected cells from 6000±322 to 2080±199 (n=12). Fluorescence values were measured 150 seconds after adding 10 mM $Ca^{2+}$ and percent blockade was calculated as 1 minus $F_{LTRPC3}$-$F_{Vector}$ in the presence of $Gd^{3+}$ divided by $FLTRPC3$-$F_{Vector}$ without blocker. The effects of $Gd^{3+}$ on LTRPC3-mediated $Ca^{2+}$ entry, induced by 10 mM $Ca^{2+}$, in the presence of thapsigargin or carbachol was also examined. Cells were incubated in nominally $Ca^{2+}$-free medium for thapsigargin and carbachol experiments. $Gd^{3+}$ inhibited $Ca^{2+}$ entry by 51% after depletion of intracellular stores with thapsigargin (see FIG. 22B). $Gd^{3+}$ reduced peak fluorescence after 10 mM $Ca^{2+}$ addition in vector-transfected cells from 26444±2410 to 1316±60 and in LTRPC3-transfected cells from 37676±2425 to 6783±250 (see FIGS. 22C and D, respectively; n=12). $Gd^{3+}$ inhibited $Ca^{2+}$ entry by 72% after depletion of intracellular stores with carbachol. $Gd^{3+}$ reduced peak $Ca^{2+}$ fluorescence in vector-transfected cells from 9327±466 to 453±15 and in LTRPC3-transfected cells from 14747±988 to 1975±79 (see FIGS. 22E and F, respectively; n=12). These results show that, under identical conditions, the endogenous $Ca^{2+}$ entry pathway was strongly blocked by application of 100 µM $Gd^{3+}$ whereas the LTRPC3-mediated pathway was partially blocked (53%, see FIGS. 22A and B). Stimulation of $Ca^{2+}$ entry in LTRPC3-transfected cells in the presence of thapsigargin or carbachol was also partially blocked by 100 µM $Gd^{3+}$. These results are consistent with the hypothesis that LTRPC3 mediates a $Ca^{2+}$ entry pathway that apparently is distinct from the endogenous $Ca^{2+}$ entry pathways present in HEK 293 cells.

The LTRPC3g polypeptide is also expected to mediate a $Ca^{2+}$ entry pathway that is distinct from the endogenous $Ca^{2+}$ entry pathways present in HEK 293 cells.

LTRPC3 is constitutively active but can be potentiated by store-depletion and is partially sensitive to $La^{3+}$ and $Gd^{3+}$ blockade. LTRPC3 is believed to represent the first member of the TRPM subfamily that exhibits this store-operated mechanism, although some members of TRPC subfamily have been considered for this role. TRPM1 and TRPM4a are constitutive $Ca^{2+}$ permeable channels but it is unclear whether they can be stimulated by store-depletion (*Proc. Natl. Acad. Sci. U.S.A.* 98, 10692-10697, (2001)). Distinct from TRPM4a, TRPM4b is directly activated by changes in intracellular $Ca^{2+}$ without significant permeation of $Ca^{2+}$ (*Cell* 109, 397-401, (2002)). TRPM2 is activated by ADP-ribose, NAD and changes in redox status (Nature 411, 595-599, (2001); Science 293, 1327-1330, (2001); and *Mol. Cell.* 9, 163-173, (2002)). TRPM7 is regulated by $Mg^{2+}$-ATP and/or $PIP_2$ (*Science* 291, 1043-1047, (2001); Nature 411, 690-695, (2001); and *Nat. Cell Biol.* 4, 329-36 (2002)). TRPM8 is activated by cold temperatures and cooling agents (*Nature* 416, 52-58, (2002); and *Cell* 108, 705-715, (2002)). Therefore, in conjunction with its fairly restricted tissue expression, which is not observed with any other family members, LTRPC3 may have a unique biological function in humans.

Expression profiling designed to measure the steady state mRNA levels encoding the LTRPC3 polypeptide showed predominately high expression levels in kidney. The LTRPC3 polypeptide was also significantly expressed in spinal cord, testis, and brain (as shown in FIG. 6).

Moreover, Northern hybridizations of the LTRPC3 mRNA confirmed the predominately high expression levels in kidney, and significant expression levels in testis, and brain (as shown in FIG. 7). The Northern hybridization was not performed on spinal cord tissue.

Expanded analysis of LTRPC3 expression levels by TaqMan™ quantitative PCR (see FIG. 12) confirmed that the LTRPC3 polypeptide is expressed in kidney, brain, testis (FIGS. 6 and 7), although higher expression levels were observed in brain than previously appreciated. LTRPC3 mRNA was expressed predominately in the brain, specifically the cerebellum, choroid plexus, the locus coeruleus, the posterior hypothalamus and the substantia nigra. Expression of LTRPC3 was also significantly expressed in the kidney, with higher levels observed in the cortex than in the medulla or pelvis. LTRPC3 was also significantly expressed in the spinal cord, testis, and to a lesser extent in other tissues as shown.

The LTRPC3g polypeptide of the present invention is expected to share the same or similar expression profile as that of the LTRPC3 polypeptide (SEQ ID NO:15).

Therefore, LTRPC3g polynucleotides and polypeptides, including modulators or fragments thereof, may be useful in treating, diagnosing, prognosing, and/or preventing a variety of neurological conditions, in particular various choroid plexus neoplasms, choroid plexus papilloma, Alzheimer's disease, prion disorders and multiple sclerosis and movement disorders that involve the cerebellum. Based upon the expression pattern of the LTRPC3 variant in kidney, the novel TRP family member LTRPC3g variant may also be the cause of solitary metastasis in the choroid plexus, a rare type of carcinoma. For example, it has been shown that out of 15 cases of solitary metastasis of the choroid plexus, five originated from renal cell carcinoma (Neurol. Med. Chir. (Tokyo) 1997 December; 37(12):916-9). Additionally, given the rather selective expression of the LTRPC3 variant in the choroid plexus and renal tissues, it may be possible that altered function of LTRPC3g may be responsible for solitary metastasis and renal carcinoma. LTRPC3g polynucleotides and polypeptides, including modulators or fragments thereof, may be useful in treating, diagnosing, prognosing, and/or preventing a variety of renal disorders, particularly solitary metastasis in the choroid plexus, and renal carcinoma.

Moreover, an additional analysis of LTRPC3 expression levels by TaqMan™ quantitative PCR (see FIG. 13) in disease cells and tissues indicated that the LTRPC3 polypeptide is differentially expressed in renal, testicular, and ovarian tumor tissues. In the renal tumor tissue results, an average of 2 out of 3 matched samples, which represent 3 out of 4 samples total, showed a significant decrease in LTRPC3 steady state RNA levels in tumor compared to control samples. In the testicular tumor tissue results, differential expression of LTRPC3 in testicular cancers was observed with all 5 tumor samples showing a significant reduction in steady-state RNA levels compared to two control samples. In the ovarian tumor tissue results, differential expression of LTRPC3 in ovarian cancers was observed with 3 tumor samples showing a significant reduction in steady-state RNA levels compared to five control samples.

The LTRPC3g polypeptide is expected to share the same or similar differential expression patterns observed for the LTRPC3 variant.

Thus, loss of LTRPC3g expression during tumor progression might contribute to the metastatic process by altering internal calcium stores in a manner that reflects a loss of cellular control on apoptosis. Restoring LTRPC3g function might provide a novel therapeutic approach to treating certain cancers. Therefore, LTRPC3g polynucleotides and polypeptides, including modulators or fragments thereof, particularly agonists of LTRPC3g activity or expression, may be useful in treating, diagnosing, prognosing, ameliorating, and/or preventing a variety of cancers and proliferative conditions, particularly of the kidney, testis, and ovaries.

An additional analysis of LTRPC3 localized expression was assessed using In situ hybridization techniques (ISH). LTRPC3 expression was localized to the cytoplasm of collecting tubular epithelium in the medulla, medullary rays, and periglomerular regions (see FIG. 20, Plates i, ii, iv and v). Tubules in the medulla exhibited the most intense expression. Other tubular epithelia, e.g., proximal convoluted tubular epithelium, exhibited minimal expression. Expression patterns were compared to LTRPC3 sense mRNA-labeled human kidney sections as negative controls (FIG. 20, Plates iii and vi) and to human lysozyme antisense mRNA labeled human kidney sections as positive controls (data not shown).

The observed for the LTRPC3 variant mRNA expression in human kidney, suggests that LTRPC3g may play a role in renal handling of calcium and other cations. The kidney plays a major role in $Ca^{2+}$ homeostasis. LTRPC3g could be involved in $Ca^{2+}$ absorption directly due to its $Ca^{2+}$ permeability. Indeed, the in situ hybridization analysis described herein demonstrates that LTRPC3 is predominantly expressed in the connecting tubule, which has frequently been implicated in active transcellular $Ca^{2+}$ reabsorption (see Hoenderop, J. G., et al., (2002) *Annu. Rev. Physiol.* 64, 529-549; which is hereby incorporated by reference herein in its entirety). Alternatively, LTRPC3g may function as an SOC that regulates $Ca^{2+}$ absorption. In the kidney, $Ca^{2+}$ absorption is regulated by agonists such as calcitonin, parathyroid hormone, and parathyroid hormone-related peptide through their respective G protein-coupled receptors, and downstream SOCs (Friedman, P. A., et al., (1995) *Physiol. Rev.* 75, 429-471; which is hereby incorporated by reference herein in its entirety).

Potentially, LTRPC3g may be involved in the pathogenesis of calcium homeostasis-related disorders such as hypercaliuric nephrolithiasis, certain forms of osteoporosis, Gitelman's disease and Bartter's syndrom.

In preferred embodiments, LTRPC3g polynucleotides and polypeptides, including fragments and modulators thereof, are useful for treating, diagnosing, and/or ameliorating $Ca^{2+}$ reabsorption disorders, disorders associated with aberrant luminal Ca2+ entry via the epithelial Ca2+ channel (ECaC), disorders associated with aberrant cytosolic diffusion of Ca2+ bound to calbindin-D28K, disorders associated with aberrant basolateral extrusion of Ca2+ through the Na+/Ca2+ exchanger (NCX), disorders associated with aberrant plasma membrane Ca2+-ATPase (PMCA) activity and/or activation, disorders associated with the hypocalciuric effect of diuretics, disorders associated with the hypocalciuric effect of thiazide diuretics, disorders associated with hormone insufficiencies that affect the function of the kidney, disorders associated with hormone insufficiencies that affect renal Ca2+ homeostasis, disorders associated with aberrant renal Ca2+ homeostasis as a result of vitamin D deficiency, disorders associated with aberrant renal Ca2+ homeostasis as a result of PTH deficiency, disorders associated with aberrant renal Ca2+ homeostasis as a result of vasopressin deficiency, disorders associated with aberrant renal Ca2+ homeostasis as a result of prostaglandines deficiency, disorders associated with aberrant renal Ca2+ homeostasis as a result of estrogen deficiency, disorders associated with aberrant renal Ca2+ homeostasis as a result of calcitonin deficiency, disorders associated with aberrant renal Ca2+ homeostasis as a result of parathyroid hormone deficiency, disorders associated with aberrant renal Ca2+ homeostasis as a result of atrial natriuretic peptide deficiency, calcium homeostasis-related disorders, hypercaliuric nephrolithiasis, certain forms of osteoporosis, Gitelman's disease, Bartter's syndrom, disorders associated with aberrant function of kidney tubular epithelium, disorders associated with aberrant function of kidney tubular epithelium in the medulla, disorders associated with aberrant function of kidney tubular epithelium in the medullary rays, disorders associated with aberrant function of kidney tubular epithelium in the periglomerular.

In preferred embodiments, LTRPC3g polynucleotides and polypeptides, including fragments and modulators thereof, are useful for treating, diagnosing, and/or ameliorating acute kidney failure, chronic kidney failure, cystic kidney disease, horseshoe kidney, hypertensive kidney disease, kidney atrophy, kidney cancer, kidney disease, kidney failure, kidney infection, kidney metastasis, kidney stone, nephrolithiasis, multicystic dysplastic kidney disease, and polycystic kidney disease.

Characterization of the LTRPC3 variant polypeptide using antisense oligonucleotides led to the determination that LTRPC3 is involved in the negative modulation of the FEN1 DNA base-excision repair/proliferation modulating protein as described in Example 5 herein.

The LTRCP3g polypeptide is expected to be able to modulate the FEN1 DNA base-excision repair/proliferation modulating protein to the same or similar extent as the LTRPC3 polypeptide.

Specifically, antisense inhibition of LTRPC3 resulted in upregulation of Fen1, a marker of proliferation. As such, LTRPC3 behaves in a manner similar to a tumor suppressor, in that loss results in increases in proliferation. While some increases in the proliferation markers p21 and IkB were also observed, they were less significant, and could be a response to the pro-proliferative effect of LTRPC3 antisense inhibition. Interestingly, expression of LTRPC3 was also observed to be significantly reduced in tumor tissues, relative to normal tissues (see FIG. 13). Specifically, renal, testicular, and ovarian tumor samples showed as much as 12 to 30 fold down regulation of LTRPC3 message levels compared to normal tissues. This reduction of LTRPC3 correlating with the tumor state is consistent with the negative FEN1 modulatory activity and suggests this gene may have antiproliferative activities. Therefore, for modulators of LTRPC3g to be useful for treating cancer, it would be necessary to increase the activity of the gene or gene product in order to have the reverse effect on cancerous cells. Thus, an agonist of LTRPC3g activity or a compound that increased LTRPC3g message levels would be a desired invention for cancer therapy.

In preferred embodiments, LTRPC3g polynucleotides and polypeptides, including fragments and modulators thereof, are useful for treating, diagnosing, and/or ameliorating DNA-repair deficiencies, particularly base-excision repair deficiencies, Xeroderma pigmentosum, skin cancer, melanoma, UV senstivity, alkylation sensivity, gamma irradiation sensitivity, pyrimidine dimer sensitivity, chemical mutagenes, lymphomas, leukemias, photosensitivity, Bloom's syndrone, Fanconi's anemia, ataxia telangiectasia, chromosomal aberrations, blood vessel dilation aberrations in the skin, blood vessel dilation aberrations in the eye, conditions involving increased levels of apurinic sites, conditions involving increased levels of apyrimidinic sites, conditions involving increased levels of abasic sites, disorders related to aberrant signal transduction, proliferating disorders, and/or cancers.

Moreover, LTRPC3g polynucleotides and polypeptides, including fragments and modulators thereof, are useful for increasing mammalian base excision repair activity, increasing mammalian single-nucleotide base excision repair activity, and/or increasing mammalian long patch base excision repair activity.

In preferred embodiments, antagonists directed against LTRPC3g are useful for treating, diagnosing, and/or ameliorating DNA-repair deficiencies, particularly base-excision repair deficiencies, Xeroderma pigmentosum, skin cancer, melanoma, UV senstivity, alkylation sensivity, gamma irradiation sensitivity, pyrimidine dimer sensitivity, chemical mutagenes, lymphomas, leukemias, photosensitivity, Bloom's syndrone, Fanconi's anemia, ataxia telangiectasia, chromosomal aberrations, blood vessel dilation aberrations in the skin, blood vessel dilation aberrations in the eye, conditions involving increased levels of apurinic sites, conditions involving increased levels of apyrimidinic sites, conditions involving increased levels of abasic sites, disorders related to, aberrant signal transduction, proliferating disorders, and/or cancers.

Moreover, antagonists directed against LTRPC3g are useful for increasing mammalian base excision repair activity, increasing mammalian single-nucleotide base excision repair activity, and/or increasing mammalian long patch base excision repair activity.

In preferred embodiments, agonists directed against LTRPC3g are useful for treating, diagnosing, and/or ameliorating, disorders related to aberrant signal transduction, proliferating disorders, and/or cancers, particularly renal cell carcinomas, testicular cancers, and/or ovarian cancers.

Moreover, agonists directed against LTRPC3g are useful for decreasing mammalian base excision repair activity, decreasing mammalian single-nucleotide base excision repair activity, and/or decreasing mammalian long patch base excision repair activity.

The strong homology to human transient receptor potential channels (TRP), combined with the predominate localized expression in kidney tissue of the LTRPC3 variant, suggests the LTRPC3g polynucleotides and polypeptides, including modulators or fragments thereof, may be useful in treating, diagnosing, prognosing, and/or preventing renal diseases and/or disorders, which include, but are not limited to: nephritis, renal failure, nephrotic syndrome, urinary tract infection, hematuria, proteinuria, oliguria, polyuria, nocturia, edema, hypertension, electrolyte disorders, sterile pyuria, renal osteodystrophy, large kidneys, renal transport defects, nephrolithiasis, azotemia, anuria, urinary retention, slowing of urinary stream, large prostate, flank tenderness, full bladder sensation after voiding, enuresis, dysuria, bacteriuria, kidney stones, glomerulonephritis, vasculitis, hemolytic uremic syndromes, thrombotic thrombocytopenic purpura, malignant hypertension, casts, tubulointerstitial kidney diseases, renal tubular acidosis, pyelonephritis, hydronephritis, nephrotic syndrome, crush syndrome, and/or renal colic, in addition to Wilm's Tumor Disease, and congenital kidney abnormalities such as horseshoe kidney, polycystic kidney, and Falconi's syndrome for example.

Several known TRP family members have been identified that are expressed significantly in kidney tissue. These TRP family members include, for example, Trp12 (Wissenbach, U., Bodding, M., Freichel, M., Flockerzi, V, Lett., 485(2-3): 127-34, (2000)); OTRPC4 (Strotmann, R., Harteneck, C., Nunnenmacher, K., Schultz, G., Plant, T, D, Nat, Cell, Biol., 2(10):695-702, (2000)); polycystin-L2 (Guo, L., Schreiber, T, H., Weremowicz, S., Morton, C, C., Lee, C., Zhou, J. Genomics., 64(3):241-51, (2000)); and EcaC (Hoenderop, J. G., van, der, Kemp, A, W., Hartog, A., van, de, Graaf, S, F., van, Os, C, H., Willems, P, H., Bindels, R, J. J. Biol, Chem., 274(13):8375-8, (1999)).

Thus, the LTRPC3g polynucleotides and polypeptides are expected to share at least some biological activity with TRP family members expressed in kidney cells and tissues, particularly those specifically referenced herein, such as LTRPC3 (SEQ ID NO:15).

The strong homology to human transient receptor potential channels (TRP) proteins, combined with the localized expression in spinal cord and brain of the LTRPC3 variant, suggests the LTRPC3g polynucleotides and polypeptides, including modulators or fragments thereof, may be useful in treating, diagnosing, prognosing, and/or preventing neurodegenerative disease states, behavioral disorders, or inflammatory conditions. Representative uses are described in the "Regeneration" and "Hyperproliferative Disorders" sections below, in the Examples, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The strong homology to human transient receptor potential channels (TRP), combined with the localized expression in testis tissue of the LTRPC3 variant emphasizes the potential utility for LTRPC3g polynucleotides and polypeptides in treating, diagnosing, prognosing, and/or preventing testicular, in addition to reproductive disorders.

In preferred embodiments, LTRPC3g polynucleotides and polypeptides including agonists and fragments thereof, have uses which include treating, diagnosing, prognosing, and/or preventing the following, non-limiting, diseases or disorders of the testis: spermatogenesis, infertility, Klinefelter's syndrome, XX male, epididymitis, genital warts, germinal cell aplasia, cryptorchidism, varicocele, immotile cilia syndrome, and viral orchitis. The LTRPC3g polynucleotides and polypeptides including agonists and fragments thereof, may also have uses related to modulating testicular development, embryogenesis, reproduction, and in ameliorating, treating, and/or preventing testicular proliferative disorders (e.g., cancers, which include, for example, choriocarcinoma, Nonseminoma, seminona, and testicular germ cell tumors).

Likewise, the localized expression in testis tissue also emphasizes the potential utility for LTRPC3g polynucleotides and polypeptides in treating, diagnosing, prognosing, and/or preventing metabolic diseases and disorders which include the following, not limiting examples: premature puberty, incomplete puberty, Kallman syndrome, Cushing's syndrome, hyperprolactinemia, hemochromatosis, congenital adrenal hyperplasia, FSH deficiency, and granulomatous disease, for example.

This gene product may also be useful in assays designed to identify binding agents, as such agents (antagonists) are useful as male contraceptive agents. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

Several known TRP family members have been identified that are expressed significantly in testis tissue. These TRP family members include, for example, polycystin-L2 (Guo, L., Schreiber, T, H., Weremowicz, S., Morton, C, C., Lee, C., Zhou, J. Genomics., 64(3):241-51, (2000)); TRP7 (Okada, T., Inoue, R., Yamazaki, K., Maeda, A., Kurosaki, T., Yamakuni, T., Tanaka, I., Shimizu, S., Ikenaka, K., Imoto, K., Mori, Y, J. Biol, Chem., 274(39):27359-70, (1999)); btrp2 (Wissenbach, U., Schroth, G., Philipp, S., Flockerzi, V, Lett., 429(1):61-6, (1998)); Htrp-1 (Zhu, X., Chu, P, B., Peyton, M., Bimbaumer, L, Lett., 373(3):193-8, (1995)); and TRPC1 (Wes, P, D., Chevesich, J., Jeromin, A., Rosenberg, C., Stetten, G., Montell, C, Proc, Natl, Acad, Sci, USA., 92(21):9652-6, (1995)).

Thus, the LTRPC3g polynucleotides and polypeptides are expected to share at least some biological activity with TRP family members expressed in testis cells and tissues, particularly those specifically referenced herein, such as the LTRPC3 variant (SEQ ID NO:15).

As described elsewhere herein, transient receptor potential channel family members have been implicated in modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity. Moreover, transient receptor potential channel family members have been implicated in disorders of the skin, skeletal-muscle, nervous, cardiac, and vascular systems, in addition to the following, non-limiting diseases and disorders, which include, for example, arteriosclerosis, neointimal hypoerplasia, metastatic melanomas, bipolar disorder, nonsyndromic hereditary deafness, Knobloch syndrome, holosencephaly, and various maligancies including prostate cancer.

In preferred embodiments, LTRPC3g polynucleotides and polypeptides of the present invention, including agonists and/or fragments thereof, have uses that include, modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity.

In more preferred embodiments, LTRPC3g polynucleotides and polypeptides of the present invention, including agonists and/or fragments thereof, have uses that include, treating, ameliorating, preventing, detecting, and/or prognosing various diseases and disorders, particularly the following, non-limiting examples, disorders of the skin, skeletal-muscle, nervous, cardiac, and vascular systems, in addition to the following, non-limiting diseases and disorders, which include, for example, arteriosclerosis, neointimal hypoerplasia, metastatic melanomas, bipolar disorder, nonsyndromic hereditary deafness, Knobloch syndrome, holosencephaly, and various malignancies including prostate cancer.

LTRPC3g polynucleotides and polypeptides of the present invention, including agonists and/or fragments may be involved in intracellular $Ca^{2+}$ homeostasis which affects various aspects of biological functions including mechano-regulation, pain transduction, vasorelaxation, gene expression, cell cycle and proliferation/apoptosis. Since the LTRPC3 variant is dominantly expressed in kidney, the LTRPC3g polypeptide may particularly play an important role in regulating cytosolic $Ca^{2+}$ in the renal system, potentially $Ca^{2+}$ absorption.

The LTRPC3g gene maps to chromosome 9q21.11-21.31 between the two markers D9S1874 and D9S1807. This region is linked to amyotrophic lateral sclerosis with frontotemporal dementia, early-onset pulverulent cataract, infantile nephronophthisis, hypomagnesemia with secondary hypocalcemia (HSH), and familial hemophagocytic lymphohistiocytosis. Therefore, agonists and/or antagonists of the novel LTRPC3g can be used to treat diseases including various forms of neuronal degeneration, neurogenic inflammation, allergy, immunodeficiency/excessive immune activation, visual defects, hearing disorder, pain, cancer, hypertension and other cardiovascular diseases. In addition, the therapeutics may be useful in the treatment of diseases associated with disturbances in $Ca^{2+}$ homeostasis including osteoporosis, hypercalciuric stone disease, and chronic renal failure.

Moreover, given the selective expression in kidney, LTRPC3g could be considered a candidate gene for HSH, since the phenotype is a renal insufficiency. LTRPC3g chromosomal location is ~600 kb downstream of a X;9 translocation breakpoint interval described for one patient with HSH (*Hum. Mol. Genet.* 6, 1491-1497, (1997)). Recently, two groups reported that a new member of the TRPM subfamily, TRPM6, expressed in both intestinal tissues and kidney, is associated with HSH (*Nat. Genet.* 31, 166-170, (2002); and Nat. Genet. 31, 171-174 (2002)). Indeed, LTRPC3g is ~4 mb 5' to TRPM6 on 9q21. Although TRPM6 is the first component identified for HSH, this should not preclude involvement of LTRPC3g in the disease. Therefore, it is possible that LTRPC3g may co-localize with TRPM6 and/or forms a heteromultimer with TRPM6 in the kidney.

The kidney plays a major role in $Ca^{2+}$ homeostasis (reviewed in *Physiol. Rev.* 75, 429-471, (1995)). LTRPC3g may play a direct role in $Ca^{2+}$ absorption due to its constitutive $Ca^{2+}$ permeability. Alternatively, LTRPC3g may be the SOC that regulates $Ca^{2+}$ absorption. In kidney, $Ca^{2+}$ absorption is regulated by agonists such as calcitonin, parathyroid hormone and parathyroid hormone-related peptide through their respective G protein-coupled receptors, and downstream SOCs. Additionally, in kidney a SOC has been described (*J. Biol. Chem.* 276, 25759-25765, (2001)) for the action of angiotensin II, a vasoactive peptide that plays a major role in regulating blood pressure.

In addition, LTRPC3g polynucleotides and polypeptides of the present invention, including agonists and/or fragments thereof, have uses that include modulating intracellular Ca++ ion concentrations, Ca++ ion flux, stored intracellular Ca++ ion concentrations, Ca++ ion pump activity, Ca++ ion flow into cell, Ca++ ion flow out of cells, the activation of Ca++ sensitive proteins, the activation of Ca++sensitive signaling pathways, the activation of kinase-activatible proteins, and the activation of kinase-dependent signaling pathways.

The LTRPC3g polynucleotides and polypeptides of the present invention, including agonists and/or fragments thereof, have uses that include modulating proliferation, differentiation, migration, and activation in various cells, tissues, and organisms, and particularly in mammalian kidney, spinal cord, testis, and brain, preferably human. LTRPC3g polynucleotides and polypeptides of the present invention, including agonists and/or fragments thereof, may be useful in diagnosing, treating, prognosing, and/or preventing renal, neural, and/or proliferative diseases or disorders, particularly of the renal system.

In addition, antagonists of the LTRPC3g polynucleotides and polypeptides, including modulators or fragments thereof, may have uses that include diagnosing, treating, prognosing, and/or preventing diseases or disorders related to transient receptor potential channel activity, which may include renal, neural, reproductive, and/or proliferative diseases or disorders.

Although it is believed the encoded polypeptide may share at least some biological activities with transient receptor potential channel family members, particularly those melastatin1, a number of methods of determining the exact biological function of this clone are either known in the art or are described elsewhere herein. Briefly, the function of this clone may be determined by applying microarray methodology. Nucleic acids corresponding to the LTRPC3g polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from tissue that has been treated with known transient potential receptor inhibitors, which include, but are not limited to the drugs listed herein or otherwise known in the art, might indicate a function in modulating transient potential receptor function, for example. In the case of LTRPC3g, kidney, spinal cord, testis, and brain, should be used to extract RNA to prepare the probe.

In addition, the function of the protein may be assessed by applying quantitative PCR methodology, for example. Real time quantitative PCR would provide the capability of following the expression of the LTRPC3g gene throughout development, for example. Quantitative PCR methodology requires only a nominal amount of tissue from each developmentally important step is needed to perform such experiements. Therefore, the application of quantitative PCR methodology to refining the biological function of this polypeptide is encompassed by the present invention. Also encompassed by the present invention are quantitative PCR probes corresponding to the polynucleotide sequence provided as SEQ ID NO:1 (FIGS. 1A-E).

The function of the protein may also be assessed through complementation assays in yeast. For example, in the case of the LTRPC3g, transforming yeast deficient in transient receptor potential channel activity with LTRPC3g and assessing their ability to grow would provide convincing evidence the LTRPC3g polypeptide has transient receptor potential channel activity. Additional assay conditions and methods that may be used in assessing the function of the polynucletides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a kidney, spinal cord, testis, and/or brain -specific promoter), or it can be expressed at a specified time of development using an inducible and/or a developmentally regulated promoter.

In the case of LTRPC3g transgenic mice or rats, if no phenotype is apparent in normal growth conditions, observing the organism under diseased conditions (renal, reproductive, neural, or proliferative disorders, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal LTRPC3g deletion polypeptides are encompassed by the present invention: M1-T1709, G2-T1709, K3-T1709, K4-T1709, W5-T1709, R6-T1709, D7-T1709, A8-T1709, A9-T1709, E10-T1709, M11-T1709, E12-T1709, R13-T1709, G14-T1709, C15-T1709, S16-T1709, D17-T1709, R18-T1709, E19-T1709, D20-T1709, N21-T1709, A22-T1709, E23-T1709, S24-T1709, R25-T1709, R26-T1709, R27-T1709, S28-T1709, R29-T1709, S30-T1709, A31-T1709, S32-T1709, R33-T1709, G34-T1709, R35-T1709, F36-T1709, A37-T1709, E38-T1709, S39-T1709, W40-T1709, K41-T1709, R42-T1709, L43-T1709, S44-T1709, S45-T1709, K46-T1709, Q47-T1709, G48-T1709, S49-T1709, T50-T1709, K51-T1709, R52-T1709, S53-T1709, G54-T1709, L55-T1709, P56-T1709, S57-T1709, Q58-T1709, Q59-T1709, T60-T1709, P61-T1709, A62-T1709, Q63-T1709, K64-T1709, S65-T1709, W66-T1709, I67-T1709, E68-T1709, R69-T1709, A70-T1709, F71-T1709, Y72-T1709, K73-T1709, R74-T1709, E75-T1709, C76-T1709, V77-T1709, H78-T1709, I79-T1709, I80-T1709, P81-T1709, S82-T1709, T83-T1709, K84-T1709, D85-T1709, P86-T1709, H87-T1709, R88-T1709, C89-T1709, C90-T1709, C91-T1709, G92-T1709, R93-T1709, L94-T1709, I95-T1709, G96-T1709, Q97-T1709, H98-T1709, V99-T1709, G100-T1709, L101-T1709, T102-T1709, P103-T1709, S104-T1709, I105-T1709, S106-T1709, V107-T1709, L108-T1709, Q109-T1709, N110-T1709, E111-T1709, K112-T1709, N113-T1709, E114-T1709, S115-T1709, R116-T1709, L117-T1709, S118-T1709, R119-T1709, N120-T1709, D121-T1709, I122-T1709, Q123-T1709, S124-T1709, E125-T1709, K126-T1709, W127-T1709, S128-T1709, I129-T1709, S130-T1709, K131-T1709, H132-T1709, T133-T1709, Q134-T1709, L135-T1709, S136-T1709, P137-T1709, T138-T1709, D139-T1709, A140-T1709, F141-T1709, G142-T1709, T143-T1709, I144-T1709, E145-T1709, F146-T1709, Q147-T1709, G148-T1709, G149-T1709, G150-T1709, H151-T1709, S152-T1709, N153-T1709, K154-T1709, and/or A155-T1709 of SEQ ID NO:2. Polynucleotide sequences encoding these polypeptides are also provided. The present invention also encompasses the use of these N-terminal LTRPC3g deletion polypeptides as immunogenic and/or antigenic epitopes as described elsewhere herein.

In preferred embodiments, the following C-terminal LTRPC3g deletion polypeptides are encompassed by the present invention: M1-T1709, M1-H1708, M1-K1707, M1-S1706, M1-E1705, M1-F1704, M1-S1703, M1-Q1702, M1-F1701, M1-A1700, M1-S1699, M1-T1698, M1-R1697, M1-S1696, M1-L1695, M1-R1694, M1-R1693, M1-M1692, M1-S1691, M1-L1690, M1-S1689, M1-D1688, M1-G1687, M1-R1686, M1-G1685, M1-E1684, M1-P1683, M1-K1682, M1-S1681, M1-S1680, M1-K1679, M1-S1678, M1-R1677, M1-Q1676, M1-F1675, M1-P1674, M1-N1673, M1-Q1672, M1-L1671, M1-S1670, M1-A1669, M1-T1668, M1-N1667, M1-R1666, M1-Q1665, M1-R1664, M1-D1663, M1-L1662, M1-K1661, M1-D1660, M1-S1659, M1-I1658, M1-S1657, M1-F1656, M1-S1655, M1-K1654, M1-R1653, M1-T1652, M1-H1651, M1-A1650, M1-Y1649, M1-P1648, M1-A1647, M1-S1646, M1-P1645, M1-E1644, M1-E1643, M1-A1642, M1-S1641, M1-Y1640, M1-S1639, M1-N1638, M1-A1637, M1-R1636, M1-E1635, M1-I1634, M1-K1633, M1-P1632, M1-V1631, M1-T1630, M1-I1629, M1-N1628, M1-N1627, M1-S1626, M1-L1625, M1-T1624, M1-R1623, M1-E1622, M1-S1621, M1-N1620, M1-D1619, M1-G1618, M1-E1617, M1-Q1616, M1-S1615, M1-S1614, M1-I1613, M1-A1612, M1-I1611, M1-T1610, M1-A1609, M1-R1608, M1-R1607, M1-G1606, M1-K1605, M1-A1604, M1-E1603, M1-N1602, M1-E1601, M1-E1600, M1-S1599, M1-D1598, M1-S1597, M1-S1596, M1-P1595, M1-H1594, M1-S1593, M1-L1592, M1-E1591, M1-A1590, M1-E1589, M1-R1588, M1-E1587, M1-P1586, M1-H1585, M1-C1584, M1-C1583, M1-T1582, M1-L1581, M1-D1580, M1-E1579, M1-V1578, M1-K1577, M1-D1576, M1-G1575, M1-L1574, M1-G1573, M1-G1572, M1-P1571, M1-F1570, M1-A1569, M1-A1568, M1-R1567, M1-D1566, M1-A1565, M1-I1564, M1-A1563, M1-Q1562, M1-P1561, M1-A1560, M1-N1559, M1-V1558, M1-C1557, M1-R1556, M1-T1555, M1-D1554, M1-I1553, M1-C1552, M1-D1551, M1-T1550, M1-I1549, M1-S1548, M1-T1547, M1-Y1546, M1-E1545, M1-A1544, M1-T1543, M1-K1542, M1-V1541, M1-P1540, M1-V1539, M1-G1538, M1-F1537, M1-N1536, M1-A1535, M1-Y1534, M1-Y1533, M1-S1532, M1-R1531, M1-S1530, M1-P1529, M1-S1528, M1-F1527, M1-M1526, M1-F1525, M1-S1524, M1-H1523, M1-S1522, M1-K1521, M1-V1520, M1-I1519, M1-P1518, M1-A1517, M1-E1516, M1-E1515, M1-L1514, M1-L1513, M1-F1512, M1-P1511, M1-T1510, M1-T1509, M1-A1508, M1-L1507, M1-Y1506, M1-R1505, M1-S1504, M1-S1503, M1-K1502, M1-S1501, M1-R1500, M1-E1499, M1-I1498, M1-T1497, M1-H1496, M1-Y1495, M1-M1494, M1-P1493, M1-P1492, M1-E1491, M1-S1490, M1-D1489, M1-W1488, M1-P1487, M1-N1486, M1-Q1485, M1-C1484, M1-E1483, M1-P1482, M1-L1481, M1-H1480, M1-T1479, M1-Y1478, M1-D1477, M1-S1476, M1-S1475, M1-F1474, M1-S1473, M1-R1472, M1-T1471, M1-D1470, M1-M1469, M1-S1468, M1-T1467, M1-I1466, M1-D1465, M1-E1464, M1-F1463, M1-D1462, M1-I1461, M1-S1460, M1-R1459, M1-S1458, M1-P1457, M1-P1456, M1-R1455, M1-D1454, M1-T1453, M1-P1452, M1-A1451, M1-L1450, M1-T1449, M1-A1448, M1-Y1447, M1-A1446, M1-S1445, M1-S1444, M1-S1443, M1-P1442, M1-A1441, M1-T1440, M1-S1439, M1-P1438, M1-V1437, M1-P1436, M1-T1435, M1-S1434, M1-F1433, M1-S1432, M1-P1431, M1-E1430, M1-G1429, M1-L1428, M1-G1427, M1-L1426, M1-I1425, M1-N1424, M1-V1423, M1-S1422, M1-N1421, M1-D1420, M1-L1419, M1-P1418, M1-D1417, M1-I1416, M1-D1415, M1-C1414, M1-H1413, M1-L1412, M1-E1411, M1-D1410, M1-M1409, M1-A1408, M1-S1407, M1-V1406, M1-Y1405, M1-I1404, M1-D1403, M1-I1402, M1-C1401, M1-S1400, M1-S1399, M1-P1398, M1-R1397, M1-R1396, M1-S1395, M1-D1394, M1-P1393, M1-V1392, M1-I1391, M1-A1390, M1-L1389, M1-T1388, M1-N1387, M1-A1386, M1-P1385, M1-A1384, M1-A1383, M1-P1382, M1-A1381, M1-K1380, M1-P1379, M1-E1378, M1-K1377, M1-A1376, M1-V1375, M1-S1374, M1-H1373, M1-S1372, M1-S1371, M1-T1370, M1-A1369, M1-R1368, M1-H1367, M1-L1366, M1-S1365, M1-L1364, M1-S1363, M1-R1362, M1-E1361, M1-K1360, M1-F1359, M1-I1358, M1-S1357, M1-E1356, M1-L1355, M1-K1354, M1-E1353, M1-L1352, M1-G1351, M1-G1350, M1-K1349, M1-D1348, M1-K1347, M1-M1346, M1-N1345, M1-V1344, M1-S1343, M1-Y1342, M1-F1341, M1-S1340, M1-H1339, M1-S1338, M1-R1337, M1-M1336, M1-R1335, M1-P1334, M1-M1333, M1-L1332, M1-T1331, M1-P1330, M1-S1329, M1-T1328, M1-P1327, M1-S1326, M1-M1325, M1-T1324, M1-E1323, M1-E1322, M1-G1321, M1-A1320, M1-P1319, M1-D1318, M1-I1317, M1-S1316, M1-E1315, M1-Q1314, M1-L1313, M1-K1312, M1-F1311, M1-T1310, M1-N1309, M1-G1308, M1-E1307, M1-Q1306, M1-S1305, M1-N1304, M1-F1303, M1-S1302, M1-S1301, M1-Q1300, M1-R1299, M1-V1298, M1-I1297, M1-Y1296, M1-A1295, M1-A1294, M1-D1293, M1-T1292, M1-C1291, M1-D1290, M1-S1289, M1-S1288, M1-T1287, M1-R1286, M1-S1285, M1-R1284, M1-I1283, M1-K1282, M1-N1281, M1-S1280, M1-E1279, M1-A1278, M1-R1277, M1-E1276, M1-L1275, M1-G1274, M1-T1273, M1-L1272, M1-R1271, M1-E1270, M1-L1269, M1-A1268, M1-T1267, M1-A1266, M1-M1265, M1-R1264, M1-G1263, M1-I1262, M1-L1261, M1-D1260, M1-E1259, M1-L1258, M1-Q1257, M1-A1256, M1-L1255, M1-R1254, M1-I1253, M1-D1252, M1-V1251, M1-T1250, M1-Q1249, M1-L1248, M1-S1247, M1-A1246, M1-K1245, M1-M1244, M1-S1243, M1-H1242, M1-E1241, M1-R1240, M1-E1239, M1-N1238, M1-V1237, M1-E1236, M1-E1235, M1-L1234, M1-R1233, M1-M1232, M1-S1231, M1-M1230, M1-N1229, M1-E1228, M1-V1227, M1-R1226, M1-E1225, M1-S1224, M1-T1223, M1-V1222, M1-R1221, M1-I1220, M1-R1219, M1-E1218, M1-D1217, M1-N1216, M1-S1215, M1-S1214, M1-N1213, M1-F1212, M1-R1211, M1-D1210, M1-D1209, M1-K1208, M1-E1207, M1-R1206, M1-F1205, M1-Y1204, M1-E1203, M1-E1202, M1-I1201, M1-C1200, M1-Q1199, M1-E1198, M1-E1197, M1-F1196, M1-D1195, M1-H1194, M1-V1193, M1-K1192, M1-K1191, M1-L1190, M1-E1189, M1-D1188, M1-D1187, M1-T1186, M1-I1185, M1-F1184, M1-L1183, M1-K1182, M1-L1181, M1-G1180, M1-Y1179, M1-D1178, M1-R1177, M1-E1176, M1-D1175, M1-P1174, M1-D1173, M1-S1172, M1-E1171, M1-H1170, M1-K1169, M1-R1168, M1-W1167, M1-R1166, M1-C1165, M1-C1164, M1-L1163, M1-H1162, M1-Q1161, M1-F1160, M1-I1159, M1-M1158, M1-T1157, M1-M1156, M1-H1155, M1-S1154, M1-F1153, M1-I1152, M1-I1151, M1-L1150, M1-P1149, M1-P1148, M1-P1147, M1-L1146, M1-V1145, M1-P1144, M1-R1143, M1-E1142, M1-H1141, M1-F1140, M1-T1139, M1-M1138, M1-I1137, M1-L1136, M1-Q1135, M1-Y1134, M1-R1133, M1-Q1132, M1-F1131, M1-K1130, M1-W1129, M1-V1128, M1-Q1127, M1-N1126, M1-S1125, M1-I1124, M1-S1123, M1-K1122, M1-V1121, M1-E1120, M1-F1119, M1-F1118, M1-T1117, M1-N1116, M1-N1115, M1-F1114, M1-V1113, M1-A1112, M1-I1111, M1-L1110, M1-L1109, M1-N1108, M1-V1107, M1-L1106, M1-L1105, M1-I1104, M1-N1103, M1-A1102, M1-V1101, M1-L1100, M1-L1099, M1-Y1098, M1-C1097, M1-A1096, M1-M1095, M1-I1094, M1-A1093, M1-P1092, M1-V1091, M1-I1090, M1-W1089, M1-A1088, M1-G1087, M1-T1086, M1-K1085, M1-C1084, M1-P1083, M1-P1082, M1-L1081, M1-Q1080, M1-I1079, M1-I1078, M1-K1077, M1-G1076, M1-D1075, M1-E1074, M1-R1073, M1-T1072, M1-E1071, M1-N1070, M1-Q1069, M1-G1068, M1-C1067, M1-P1066, M1-P1065, M1-D1064, M1-I1063, M1-Q1062, M1-E1061, M1-A1060, M1-F1059, M1-L1058, M1-E1057, M1-G1056, M1-Y1055, M1-I1054, M1-M1053, M1-W1052, M1-Y1051, M1-P1050, M1-M1049, M1-Y1048, M1-F1047, M1-I1046, M1-N1045, M1-K1044, M1-A1043, M1-L1042, M1-K1041, M1-W1040, M1-S1039, M1-P1038, M1-E1037, M1-E1036, M1-N1035, M1-P1034, M1-F1033, M1-L1032, M1-I1031, M1-A1030, M1-Q1029, M1-R1028, M1-A1027, M1-V1026, M1-G1025, M1-F1024, M1-S1023, M1-M1022, M1-L1021, M1-V1020, M1-V1019, M1-L1018, M1-M1017, M1-I1016, M1-I1015, M1-V1014, M1-F1013, M1-Y1012, M1-M1011, M1-M1010, M1-D1009, M1-I1008, M1-M1007, M1-M1006, M1-K1005, M1-G1004, M1-I1003, M1-M1002, M1-M1001, M1-V1000, M1-Y999, M1-P998, M1-G997, M1-L996, M1-Y995, M1-K994, M1-N993, M1-V992, M1-G991, M1-F990, M1-I989, M1-D988, M1-L987, M1-L986, M1-R985, M1-I984, M1-Y983, M1-W982, M1-Y981, M1-I980, M1-I979, M1-N978, M1-V977, M1-C976, M1-Y975, M1-I974, M1-V973, M1-R972, M1-G971, M1-D970, M1-S969, M1-R968, M1-F967, M1-P966, M1-Q965, M1-D964, M1-Q963, M1-L962, M1-R961, M1-L960, M1-I959, M1-M958, M1-G957, M1-V956, M1-S955, M1-F954, M1-L953, M1-L952, M1-I951, M1-A950, M1-I949, M1-L948, M1-D947, M1-T946, M1-V945, M1-N944, M1-W943, M1-Y942, M1-E941, M1-Q940, M1-L939, M1-W938, M1-V937, M1-K936, M1-V935, M1-K934, M1-M933, M1-Q932, M1-L931, M1-K930, M1-G929, M1-P928, M1-E927, M1-S926, M1-M925, M1-L924, M1-I923, M1-E922, M1-R921, M1-M920, M1-K919, M1-E918, M1-I917, M1-G916, M1-L915, M1-T914, M1-F913, M1-I912, M1-Y911, M1-S910, M-1909, M1-V908, M1-I907, M1-W906, M1-E905, M1-Q904, M1-T903, M1-S902, M1-P901, M1-W900, M1-R899, M1-E898, M1-M897, M1-K896, M1-V895, M1-L894, M1-V893, M1-I892, M1-Y891, M1-N890, M1-F889, M1-L888, M1-M887, M1-L886, M1-Y885, M1-G884, M1-I883, M1-Y882, M1-A881, M1-L880, M1-T879, M1-Y878, M1-F877, M1-W876, M1-F875, M1-K874, M1-V873, M1-I872, M1-P871, M1-A870, M1-N869, M1-Y868, M1-F867, M1-E866, M1-Y865, M1-I864, M1-K863, M1-R862, M1-G861, M1-L860, M1-P859, M1-I858, M1-L857, M1-R856, M1-H855, M1-K854, M1-S853, M1-Q852, M1-V851, M1-E850, M1-E849, M1-E848, M1-D847, M1-K846, M1-K845, M1-R844, M1-S843, M1-S842, M1-E841, M1-G840, M1-N839, M1-N838, M1-R837, M1-G836, M1-L835, M1-M834, M1-A833, M1-T832, M1-L831, M1-E830, M1-M829, M1-D828, M1-E827, M1-E826, M1-E825, M1-K824, M1-E823, M1-K822, M1-T821, M1-P820, M1-K819, M1-E818, M1-P817, M1-E816, M1-E815, M1-A814, M1-E813, M1-K812, M1-E811, M1-Q810, M1-L809, M1-H808, M1-I807, M1-E806, M1-Q805, M1-A804, M1-Q803, M1-S802, M1-M801, M1-Y800, M1-P799, M1-M798, M1-D797, M1-D796, M1-K795, M1-N794, M1-K793, M1-F792, M1-E791, M1-L790, M1-S789, M1-L788, M1-I787, M1-S786, M1-P785, M1-P784, M1-L783, M1-L782, M1-I781, M1-G780, M1-L779, M1-I778, M1-V777, M1-K776, M1-L775, M1-G774, M1-S773, M1-N772, M1-K771, M1-R770, M1-M769, M1-R768, M1-L767, M1-R766, M1-G765, M1-M764, M1-W763, M1-M762, M1-D761, M1-T760, M1-L759, M1-L758, M1-M757, M1-Q756, M1-S755, M1-C754, M1-T753, M1-H752, M1-A751, M1-I750, M1-F749, M1-D748, M1-R747, M1-H746, M1-K745, M1-A744, M1-A743, M1-V742, M1-A741, M1-L740, M1-Q739, M1-L738, M1-C737, M1-T736, M1-A735, M1-N734, M1-S733, M1-W732, M1-N731, M1-K730, M1-L729, M1-T728, M1-Y727, M1-T726, M1-L725, M1-L724, M1-K723, M1-M722, M1-A721, M1-L720, M1-Q719, M1-E718, M1-D717, M1-Q716, M1-K715, M1-Y714, M1-S713, M1-Q712, M1-D711,
M1-L710, M1-L709, M1-E708, M1-V707, M1-A706,
M1-L705, M1-Q704, M1-G703, M1-F702, M1-D701,
M1-R700, M1-N698, M1-N698, M1-H697, M1-N696,
M1-L695, M1-E694, M1-Q693, M1-S692, M1-I691,
M1-D690, M1-D689, M1-V688, M1-M687, M1-D686,
M1-N685, M1-E684, M1-S683, M1-A682, M1-E681,
M1-H680, M1-A679, M1-M678, M1-A677, M1-K676,
M1-C675, M1-L674, M1-K673, M1-C672, M1-A671,
M1-V670, M1-L669, M1-A668, M1-K667, M1-A666,
M1-M665, M1-A664, M1-E663, M1-E662, M1-G661,
M1-H660, M1-Q659, M1-W658, M1-F657, M1-F656,
M1-L655, M1-A654, M1-M653, M1-K652, M1-Q651,
M1-R650, M1-K649, M1-M648, M1-L647, M1-V646,
M1-A645, M1-W644, M1-V643, M1-M642, M1-L641,
M1-E640, M1-H639, M1-F638, M1-P637, M1-F636,
M1-P635, M1-F634, M1-H633, M1-N632, M1-I631,
M1-E630, M1-P629, M1-D628, M1-D627, M1-L626,
M1-D625, M1-I624, M1-D623, M1-V622, M1-E621,
M1-E620, M1-E619, M1-R618, M1-K617, M1-K616,
M1-T615, M1-T614, M1-K613, M1-R612, M1-G611,
M1-R610, M1-R609, M1-L608, M1-P607, M1-I606,
M1-D605, M1-D604, M1-E603, M1-M602, M1-G601,
M1-L600, M1-L599, M1-K598, M1-L597, M1-A596,
M1-K595, M1-P594, M1-R593, M1-K592, M1-P591,
M1-G590, M1-F589, M1-L588, M1-N587, M1-H586,
M1-Y585, M1-L584, M1-T583, M1-R582, M1-F581,
M1-R580, M1-K579, M1-R578, M1-T577, M1-Y576,
M1-N575, M1-C574, M1-R573, M1-Y572, M1-A571,
M1-G570, M1-G569, M1-M568, M1-L567, M1-Y566,
M1-E565, M1-I564, M1-V563, M1-L562, M1-G561,
M1-I560, M1-D559, M1-I558, M1-L557, M1-S556,
M1-I555, M1-R554, M1-Y553, M1-D552, M1-P551,
M1-P550, M1-L549, M1-N548, M1-G547, M1-K546,
M1-K545, M1-V544, M1-D543, M1-R542, M1-V541,
M1-L540, M1-H539, M1-Y538, M1-L537, M1-T536,
M1-N535, M1-S534, M1-P533, M1-G532, M1-H531,
M1-R530, M1-T529, M1-N528, M1-Y527, M1-L526,
M1-E525, M1-E524, M1-L523, M1-R522, M1-S521,
M1-I520, M1-T519, M1-L518, M1-F517, M1-R516,
M1-H515, M1-M514, M1-S513, M1-V512, M1-G511,
M1-N510, M1-E509, M1-I508, M1-L507, M1-L506,
M1-K505, M1-V504, M1-F503, M1-D502, M1-V501,
M1-R500, M1-D499, M1-L498, M1-V497, M1-L496,
M1-A495, M1-D494, M1-L493, M1-M492, M1-A491,
M1-Q490, M1-E489, M-L488, M1-S487, M1-G486,
M1-V485, M1-P484, M1-W483, M1-Q482, M1-Q481,
M1-G480, M1-Y479, M1-I478, M1-F477, M1-I476,
M1-Q475, M1-S474, M1-R473, M1-A472, M1-I471,
M1-D470, M1-V469, M1-R468, M1-N467, M1-W466,
M1-A465, M1-L464, M1-A463, M1-L462, M1-S461,
M1-L460, M1-Q459, M1-D458, M1-P457, M1-A456,
M1-S455, M1-A454, M1-N453, M1-A452, M1-G451,
M1-K450, M1-L449, M1-L448, M1-A447, M1-T446,
M1-L445, M1-I444, M1-A443, M-L442, M1-D441,
M1-I440, M1-D439, M1-Q438, M1-H437, M1-G436,
M1-E435, M1-S434, M1-G433, M1-M432, M1-R431,
M1-F430, M1-V429, M1-T428, M1-I427, M1-L426,
M1-E425, M1-K424, M1-K423, M1-K422, M1-M421,
M1-C420, M1-E419, M1-M418, M1-L417, M1-I416,
M1-I415, M1-F414, M1-L413, M1-H412, M1-Q411,
M1-A410, M1-Q409, M1-T408, M1-R407, M1-T406,
M1-Y405, M1-T404, M1-F403, M1-T402, M1-K401,
M1-Q400, M1-I399, M1-T398, M1-V397, M1-L396,
M1-L395, M1-Q394, M1-D393, M1-R392, M1-L391,
M1-S390, M1-E389, M1-N388, M1-I387, M1-L386,
M1-G385, M1-G384, M1-E383, M1-E382, M1-S381,
M1-Y380, M1-K379, M1-H378, M1-G377, M1-F376,
M1-A375, M1-L374, M1-I373, M1-D372, M1-S371,
M1-A370, M1-R369, M1-G368, M1-S367, M1-G366,
M1-D365, M1-C364, M1-V363, M1-V362, M1-V361,
M1-P360, M1-V359, M1-P358, M1-P357, M1-T356,
M1-D355, M1-R354, M1-L353, M1-Y352, M1-E351,
M1-L350, M1-V349, M1-I348, M1-S347, M1-I346,
M1-V345, M1-N344, M1-P343, M1-G342, M1-G341,
M1-E340, M1-V339, M1-I338, M1-L337, M1-A336,
M1-V335, M1-V334, M1-P333, M1-V332, M1-G331,
M1-Q330, M1-G329, M1-I328, M1-R327, M1-T326,
M1-N325, M1-I324, M1-K323, M1-Q322, M1-L321,
M1-S320, M1-I319, M1-H318, M1-K317, M1-E316,
M1-L315, M1-Q314, M1-R313, M1-R312, M1-L311,
M1-K310, M1-V309, M1-E308, M1-A307, M1-G306,
M1-Y305, M1-K304, M1-G303, M1-T302, M1-T301,
M1-G300, M1-N299, M1-D298, M1-A297, M1-L296,
M1-I295, M1-F294, M1-H293, M1-S292, M1-H291,
M1-M290, M1-S289, M1-N288, M1-L287, M1-V286,
M1-T285, M1-L284, M1-K283, M1-S282, M1-M281,
M1-P280, M1-N279, M1-S278, M1-M277, M1-T276,
M1-Q275, M1-Y274, M1-P273, M1-R272, M1-V271,
M1-V270, M1-D269, M1-R268, M1-Q267, M1-I266,
M1-L265, M1-D264, M1-E263, M1-Q262, M1-N261,
M1-E260, M1-V259, M1-I258, M1-G257, M1-W256,
M1-P255, M1-A254, M1-I253, M1-G252, M1-I251,
M1-T250, M1-C249, M1-I248, M1-K247, M1-G246,
M1-R245, M1-S244, M1-K243, M1-S242, M1-A241,
M1-H240, M1-D239, M1-K238, M1-L237, M1-A236,
M1-D235, M1-G234, M1-V233, M1-H232, M1-R231,
M1-I230, M1-V229, M1-G228, M1-T227, M1-N226,
M1-V225, M1-G224, M1-G223, M1-T222, M1-F221,
M1-I220, M1-W219, M1-A218, M1-G217, M1-T216,
M1-T215, M1-M214, M1-A213, M1-A212, M1-K211,
M1-I210, M1-L209, M1-G208, M1-K207, M1-G206,
M1-F205, M1-V204, M1-Q203, M1-K202, M1-L201,
M1-K200, M1-P199, M1-Q198, M1-L197, M1-E196,
M1-F195, M1-N194, M1-Q193, M1-L192, M1-G191,
M1-G190, M1-H189, M1-V188, M1-S187, M1-I186,
M1-L185, M1-L184, M1-K183, M1-P182, M1-L181,
M1-E180, M1-L179, M1-Q178, M1-W177, M1-E176,
M1-K175, M1-T174, M1-M173, M1-L172, M1-H171,
M1-L170, M1-L169, M1-T168, M1-D167, M1-P166,
M1-K165, M1-T164, M1-D163, M1-F162, M1-S161,
M1-V160, M1-R159, M1-V158, M1-Y157, M1-M156,
M1-A155, M1-K154, M1-N153, M1-S152, M1-H151,
M1-G150, M1-G149, M1-G148, M1-Q147, M1-F146,
M1-E145, M1-I144, M1-T143, M1-G142, M1-F141,
M1-A140, M1-D139, M1-T138, M1-P137, M1-S136,
M1-L135, M1-Q134, M1-T133, M1-H132, M1-K131,
M1-S130, M1-I129, M1-S128, M1-W127, M1-K126,
M1-E125, M1-S124, M1-Q123, M1-I122, M1-D121,
M1-N120, M1-R119, M1-S118, M1-L117, M1-R116,
M1-S115, M1-E114, M1-N113, M1-K112, M1-E111,
M1-N110, M1-Q109, M1-L108, M1-V107, M1-S106,
M1-I105, M1-S104, M1-P103, M1-T102, M1-L101,
M1-G100, M1-V99, M1-H98, M1-Q97, M1-G96, M1-I95,
M1-L94, M1-R93, M1-G92, M1-C91, M1-C90, M1-C89,
M1-R88, M1-H87, .M-P86, M1-D85, M1-K84, M1-T83,
M1-S82, M1-P81, M1-I80, M1-I79, M1-H78, M1-V77,
M1-C76, M1-E75, M1-R74, M1-K73, M1-Y72, M1-F71,
M1-A70, M1-R69, M1-E68, M1-I67, M1-W66, M1-S65,
M1-K64, M1-Q63, M1-A62, M1-P61, M1-T60, M1-Q59,
M1-Q58, M1-S57, M1-P56, M1-L55, M1-G54, M1-S53,
M1-R52, M1-K51, M1-S50, M1-S49, M1-K48, M1-Q47,
M1-K46, M1-S45, M1-S44, M1-L43, M1-R42, M1-K41,
M1-W40, M1-S39, M1-E38, M1-A37, M1-F36, M1-R35, M1-G34, M1-R33, M1-S32, M1-A31, M1-S30, M1-R29, M1-S28, M1-R27, M1-R26, M1-R25, M1-S24, M1-E23, M1-A22, M1-N21, M1-D20, M1-E19, M1-R18, M1-D17, M1-S16, M1-C15, M1-G14, M1-R13, M1-E12, M1-M11, M1-E10, M1-A9, M1-A8, and/or M1-D7 of SEQ ID NO:2. Polynucleotide sequences encoding these polypeptides are also provided. The present invention also encompasses the use of these C-terminal LTRPC3g deletion polypeptides as immunogenic and/or antigenic epitopes as described elsewhere herein.

Alternatively, preferred polypeptides of the present invention may comprise polypeptide sequences corresponding to, for example, internal regions of the LTRPC3g polypeptide (e.g., any combination of both N- and C-terminal LTRPC3g polypeptide deletions) of SEQ ID NO:2. For example, internal regions could be defined by the equation: amino acid NX to amino acid CX, wherein NX refers to any N-terminal deletion polypeptide amino acid of LTRPC3g (SEQ ID NO:2), and where CX refers to any C-terminal deletion polypeptide amino acid of LTRPC3g (SEQ ID NO:2). Polynucleotides encoding these polypeptides are also provided. The present invention also encompasses the use of these polypeptides as an immunogenic and/or antigenic epitope as described elsewhere herein.

Many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 5187 of SEQ ID NO:1, b is an integer between 15 to 5201, where both a and b correspond to the positions of nucleotide residues shown in SEQ ID NO:1, and where b is greater than or equal to a+14.

Features of the Polypeptide Encoded by Gene No:2

The polypeptide of this gene provided as SEQ ID NO:4 (FIGS. 2A-F), encoded by the polynucleotide sequence according to SEQ ID NO:3 (FIGS. 2A-F), and/or encoded by the polynucleotide contained within the deposited clone, LTRPC3h, has significant homology at the nucleotide and amino acid level to the human melastatin 1 protein (Melastatin1; Genbank Accession No. gi|3243075; SEQ ID NO:13). An alignment of the LTRPC3h polypeptide with this protein is provided in FIGS. 7A-G.

The LTRPC3h polypeptide was determined to share 65.7% identity and 73.5% similarity with the human melastatin 1 protein (Melastatin1; Genbank Accession No. gi|3243075; SEQ ID NO:13) as shown in FIG. 10.

The LTRPC3h protein is believed to represent a member of a new class of protein kinases referred to as alpha kinases (Curr. Biol. 9 (2), R43-R45 (1999)). These kinases represent a novel type of signaling molecule comprising both a catalytic protein kinase domain, in addition to, an ion channel domain. This family is commonly referred to as the transient receptor potential channel (TRP) family. Melastatin1 defines a separate subfamily of TRP channels referred to as TRPM (melastatin1). TRPM family members are characteristic of their unusually long cytoplasmic tails at both ends of the channel domain and some of the family members contain an enzyme domain at the C-terminal region.

Specifically, the LTRPC3h (SEQ ID NO:4) polypeptide represents a novel variant of the LTRPC3b (Co-pending U.S. Ser. No. 10/210,152, filed Aug. 1, 2002; International Publication No. WO 03/012063, published Feb. 13, 2003; SEQ ID NO:17; and also co-pending U.S. Ser. No. 10/405,793, filed Mar. 28, 2003; which are hereby incorporated by reference herein in their entirety) polypeptide. The LTRPC3h represents a novel member of the TRPM subfamily.

The melastatin1 protein is believed to be negatively associated with the incidence of melanoma based upon its inverse correlative expression in highly aggressive melanomas (Genomics 54 (1), 116-123 (1998)). Thus, overexpression of melastatin1 could represent a novel therapeutic in the treatment of melanoma and potentially other cancers.

Based upon the observed homology, the polypeptide of the present invention is expected to share at least some biological activity with other transient receptor potential channel family members, more specifically with the melastatin1 protein, in addition to, other transient receptor potential channel family members referenced elsewhere herein or otherwise known in the art, particularly LTRPC3b, and LTRPC3.

Most of the known transient receptor potential channel family members, possess one or more transmembrane domains. Likewise, the LTRPC3h polypeptide has been determined to comprise six transmembrane domains (TM1-TM6) as shown in FIGS. 2A-F. The transmembrane domains are located from about amino acid 787 to about amino acid 804 (TM1), from about amino acid 884 to about amino acid 901 (TM2), from about amino acid 957 to about amino acid 970 (TM3), from about amino acid 984 to about amino acid 1001 (TM4), from about amino acid 1018 to about amino acid 1035 (TM5), and/or from about amino acid 1106 to about amino acid 1125 (TM6) of SEQ ID NO:4. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following transmembrane domain polypeptides are encompassed by the present invention: LKVILGILLPPSILSLEF (SEQ ID NO:36), IVKFW-FYTLAYIGYLMLF (SEQ ID NO:37), VTDLIAILLFS-VGM (SEQ ID NO:38), RVIYCVNIIYWYIRLLDI (SEQ ID NO:39), MMIDMMYFVIIMLVVLMS (SEQ ID NO:40), and/or AIMACYLLVANILLVNLLIAV (SEQ ID NO:41). Polynucleotides encoding these polypeptides are also provided. The present invention also encompasses the use of the LTRPC3h transmembrane polypeptides as immunogenic and/or antigenic epitopes as described elsewhere herein.

The present invention also encompasses polypeptides corresponding to the regions between each transmembrane domain of LTRPC3h, referred to herein as inter-transmembrane domain polypeptides (inter TM1-2, inter TM2-3, inter TM3-4, inter TM4-5, and inter TM5-6). Such regions are typically solvent accessible (either extracellularly or intracellularly). Therefore, these regions are amenable to the development of agonists and/or antagonists to the LTRPC3h polypeptide, particularly for the development of antibodies specific to these regions.

In preferred embodiments, the following inter-transmembrane domain polypeptides are encompassed by the present invention: KNKDDMPYMSQAQEIHLQEKEAEEPE-KPTKEKEEEDMELTAMLGRNNGESS RKKDEEEVQSKHRLIPLGRKIYEFYNAP (SEQ ID NO:42), NYIVLVKMERWPSTQEWIVISYIFTLG-IEKMREILMSEPGKLLQKVKVWLQEY WN (SEQ ID NO:43), ILRLQDQPFRSDG (SEQ ID NO:44), FGVNKY-LGPYVMMIGK (SEQ ID NO:45), and/or FGVARQAILF-PNEEPSWKLAKNIFYMPYWMIYGEVFAD- QIDPPCGQNETRED GKIIQLPPCKTGAWIVP (SEQ ID NO:46). Polynucleotides encoding these polypeptides are also provided. The present invention also encompasses the use of the LTRPC3h inter-transmembrane polypeptides as immunogenic and/or antigenic epitopes as described elsewhere herein.

The LTRPC3h polypeptide was determined to comprise several conserved cysteines, at amino acid 249, 364, 420, 586, 749, 766, 988, 1079, 1096, 1109, 1212, 1303, and 1564 of SEQ ID No: 4 (FIGS. 2A-F). Conservation of cysteines at key amino acid residues is indicative of conserved structural features, which may correlate with conservation of protein function and/or activity.

In confirmation of the LTRPC3h representing a member of the transient receptor channel family, the LTRPC3h polypeptide was determined to comprise a predicted TRP domain located from about amino acid 1040 to about amino acid 1045 of SEQ ID NO:4. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following TRP domain polypeptide is encompassed by the present invention: VWKFQR (SEQ ID NO:47). Polynucleotides encoding this polypeptide are also provided. The present invention also encompasses the use of this LTRPC3h TRP domain polypeptide as an immunogenic and/or antigenic epitope as described elsewhere herein.

In further confirmation of the LTRPC3h representing a member of the transient receptor channel family, the LTRPC3h polypeptide was determined to comprise a predicted ion transport signature domain located at about amino acid 915 to about amino acid 1126 of SEQ ID NO:4. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following ion transport signature domain polypeptide is encompassed by the present invention: TQEWIVISYIFTLGIEKMREILM-SEPGKLLQKVKVWLQEYWNVTDLIAILLFSV GMIL-RLQDQPFRSDGRVIYCVNIIYWYIRLL-DIFGVNKYLGPYVMMIGKMMID MMYFVIIMLVVLMSFGVARQAILFP-NEEPSWKLAKNIFYMPYWMIYGEVFAD QIDP-PCGQNETREDGKIIQLPPCKTGAWIV-PAIMACYLLVANILLVNLLIAVF (SEQ ID NO:48). Polynucleotides encoding this polypeptide are also provided. The present invention also encompasses the use of this LTRPC3h ion transport signature domain polypeptide as an immunogenic and/or antigenic epitope as described elsewhere herein.

The LTRPC3h polypeptide was determined to comprise a predicted coiled-coil domain located at about amino acid 1230 to about amino acid 1285 of SEQ ID NO:4. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following coiled-coil domain polypeptide is encompassed by the present invention: ERIRVTSERVENMSMRLEEVNEREH-SMKASLQTVDIRLAQLEDLIGRMATAL ERL (SEQ ID NO:49). Polynucleotides encoding this polypeptide are also provided. The present invention also encompasses the use of this LTRPC3h coiled-coil domain polypeptide as an immunogenic and/or antigenic epitope as described elsewhere herein.

LTRPC3h polypeptides and polynucleotides are useful for diagnosing diseases related to the over and/or under expression of LTRPC3h by identifying mutations in the LTRPC3h gene using LTRPC3h sequences as probes or by determining LTRPC3h protein or mRNA expression levels. LTRPC3h polypeptides will be useful in screens for compounds that affect the activity of the protein. LTRPC3h peptides can also be used for the generation of specific antibodies and as bait in yeast two hybrid screens to find proteins the specifically interact with LTRPC3h.

Since the LTRPC3h polypeptide represents an N-terminally extended variant of the LTRPC3b polypeptide (see polypeptide alignment provided in FIG. 11A-I), and since the LTRPC3b (SEQ ID NO:17) polypeptide represents a splice variant of the LTRPC3 polypeptide (SEQ ID NO:15), the LTRPC3h (SEQ ID NO:4) polypeptide of the present invention is expected to have the same or similar function as the LTRPC3 polypeptide, and in particular, the LTRPC3b polypeptide. Specifically, the LTRPC3h polypeptide is expected to localize to the cell membrane.

Moreover, the LTRPC3h polypeptide is expected to also localize in or near the plasmalemmal compartment.

Moreover, the LTRPC3h polypeptide is also expected to be a constitutively active channel capable of mediating $Ca^{2+}$ influx.

Moreover, the LTRPC3h polypeptide is also expected to mediate $Ca^{2+}$ entry and that LTRPC3h-mediated $Ca^{2+}$ entry is expected to be potentiated by store-depletion.

Moreover, the LTRPC3h polypeptide is also expected to mediate a $Ca^{2+}$ entry pathway that is distinct from the endogenous $Ca^{2+}$ entry pathways present in HEK 293 cells.

Moreover, the LTRPC3h polypeptide of the present invention is expected to share the same or similar expression profile as that of the LTRPC3 polypeptide (SEQ ID NO:15).

Moreover, the LTRPC3h polypeptide is expected to share the same or similar differential expression patterns observed for the LTRPC3 variant.

Moreover, the LTRCP3g polypeptide is expected to be able to modulate the FEN1 DNA base-excision repair/proliferation modulating protein to the same or similar extent as the LTRPC3 polypeptide.

Moreover, the LTRPC3h polynucleotides and polypeptides are expected to share at least some biological activity with TRP family members expressed in kidney cells and tissues, particularly those specifically referenced herein, such as LTRPC3 (SEQ ID NO:15), and particularly as LTRPC3b (SEQ ID NO:17).

Moreover, the LTRPC3h polynucleotides and polypeptides are expected to share at least some biological activity with TRP family members expressed in testis cells and tissues, particularly those specifically referenced herein, such as the LTRPC3 variant (SEQ ID NO:15), and particularly as LTRPC3b (SEQ ID NO:17).

In preferred embodiments, LTRPC3h polynucleotides and polypeptides, including fragments and modulators thereof, are useful for treating, diagnosing, and/or ameliorating $Ca^{2+}$ reabsorption disorders, disorders associated with aberrant luminal Ca2+ entry via the epithelial Ca2+ channel (ECaC), disorders associated with aberrant cytosolic diffusion of Ca2+ bound to calbindin-D28K, disorders associated with aberrant basolateral extrusion of Ca2+ through the Na+/Ca2+ exchanger (NCX), disorders associated with aberrant plasma membrane $Ca^{2+}$-ATPase (PMCA) activity and/or activation, disorders associated with the hypocalciuric effect of diuretics, disorders associated with the hypocalciuric effect of thiazide diuretics, disorders associated with hormone insufficiencies that affect the function of the kidney, disorders associated with hormone insufficiencies that affect renal Ca2+ homeostasis, disorders associated with aberrant renal Ca2+ homeostasis as a result of vitamin D deficiency, disorders associated with aberrant renal Ca2+ homeostasis as a result of PTH deficiency, disorders associated with aberrant renal Ca2+ homeostasis as a result of vasopressin deficiency, disorders associated with aberrant renal Ca2+ homeostasis as a result of prostaglandines deficiency, disorders associated with aberrant renal Ca2+ homeostasis as a result of estrogen deficiency, disorders associated with aberrant renal Ca2+ homeostasis as a result of calcitonin deficiency, disorders associated with aberrant renal Ca2+ homeostasis as a result of parathyroid hormone deficiency, disorders associated with aberrant renal Ca2+ homeostasis as a result of atrial natriuretic peptide deficiency, calcium homeostasis-related disorders, hypercaliuric, nephrolithiasis, certain forms of osteoporosis, Gitelman's disease, Bartter's syndrom, disorders associated with aberrant function of kidney tubular epithelium, disorders associated with aberrant function of kidney tubular epithelium in the medulla, disorders associated with aberrant function of kidney tubular epithelium in the medullary rays, disorders associated with aberrant function of kidney tubular epithelium in the periglomerular.

In preferred embodiments, LTRPC3h polynucleotides and polypeptides, including fragments and modulators thereof, are useful for treating, diagnosing, and/or ameliorating acute kidney failure, chronic kidney failure, cystic kidney disease, horseshoe kidney, hypertensive kidney disease, kidney atrophy, kidney cancer, kidney disease, kidney failure, kidney infection, kidney metastasis, kidney stone, nephrolithiasis, multicystic dysplastic kidney disease, and polycystic kidney disease.

Characterization of the LTRPC3 variant polypeptide using antisense oligonucleotides led to the determination that LTRPC3 is involved in the negative modulation of the FEN1 DNA base-excision repair/proliferation modulating protein as described in Example 5 herein.

The LTRCP3g polypeptide is expected to be able to modulate the FEN1 DNA base-excision repair/proliferation modulating protein to the same or similar extent as the LTRPC3 polypeptide.

Specifically, antisense inhibition of LTRPC3 resulted in upregulation of Fen1, a marker of proliferation. As such, LTRPC3 behaves in a manner similar to a tumor suppressor, in that loss results in increases in proliferation. While some increases in the proliferation markers p21 and IkB were also observed, they were less significant, and could be a response to the pro-proliferative effect of LTRPC3 antisense inhibition. Interestingly, expression of LTRPC3 was also observed to be significantly reduced in tumor tissues, relative to normal tissues (see FIG. 13). Specifically, renal, testicular, and ovarian tumor samples showed as much as 12 to 30 fold down regulation of LTRPC3 message levels compared to normal tissues. This reduction of LTRPC3 correlating with the tumor state is consistent with the negative FEN1 modulatory activity and suggests this gene may have antiproliferative activities. Therefore, for modulators of LTRPC3h to be useful for treating cancer, it would be necessary to increase the activity of the gene or gene product in order to have the reverse effect on cancerous cells. Thus, an agonist of LTRPC3h activity or a compound that increased LTRPC3h message levels would be a desired invention for cancer therapy.

In preferred embodiments, LTRPC3h polynucleotides and polypeptides, including fragments and modulators thereof, are useful for treating, diagnosing, and/or ameliorating DNA-repair deficiencies, particularly base-excision repair deficiencies, Xeroderma pigmentosum, skin cancer, melanoma, UV senstivity, alkylation sensivity, gamma irradiation sensitivity, pyrimidine dimer sensitivity, chemical mutagenes, lymphomas, leukemias, photosensitivity, Bloom's syndrome, Fanconi's anemia, ataxia telangiectasia, chromosomal aberrations, blood vessel dilation aberrations in the skin, blood vessel dilation aberrations in the eye, conditions involving increased levels of apurinic sites, conditions involving increased levels of apyrimidinic sites, conditions involving increased levels of abasic sites, disorders related to aberrant signal transduction, proliferating disorders, and/or cancers.

Moreover, LTRPC3h polynucleotides and polypeptides, including fragments and modulators thereof, are useful for increasing mammalian base excision repair activity, increasing mammalian single-nucleotide base excision repair activity, and/or increasing mammalian long patch base excision repair activity.

In preferred embodiments, antagonists directed against LTRPC3h are useful for treating, diagnosing, and/or ameliorating DNA-repair deficiencies, particularly base-excision repair deficiencies, Xeroderma pigmentosum, skin cancer, melanoma, UV sensitivity, alkylation sensivity, gamma irradiation sensitivity, pyrimidine dimer sensitivity, chemical mutagenes, lymphomas, leukemias, photosensitivity, Bloom's syndrone, Fanconi's anemia, ataxia telangiectasia, chromosomal aberrations, blood vessel dilation aberrations in the skin, blood vessel dilation aberrations in the eye, conditions involving increased levels of apurinic sites, conditions involving increased levels of apyrimidinic sites, conditions involving increased levels of abasic sites, disorders related to aberrant signal transduction, proliferating disorders, and/or cancers.

Moreover, antagonists directed against LTRPC3h are useful for increasing mammalian base excision repair activity, increasing mammalian single-nucleotide base excision repair activity, and/or increasing mammalian long patch base excision repair activity.

In preferred embodiments, agonists directed against LTRPC3h are useful for treating, diagnosing, and/or ameliorating, disorders related to aberrant signal transduction, proliferating disorders, and/or cancers, particularly renal cell carcinomas, testicular cancers, and/or ovarian cancers.

Moreover, agonists directed against LTRPC3h are useful for decreasing mammalian base excision repair activity, decreasing mammalian single-nucleotide base excision repair activity, and/or decreasing mammalian long patch base excision repair activity.

The strong homology to human transient receptor potential channels (TRP), combined with the predominate localized expression in kidney tissue of the LTRPC3 variant, suggests the LTRPC3h polynucleotides and polypeptides, including modulators or fragments thereof, may be useful in treating, diagnosing, prognosing, and/or preventing renal diseases and/or disorders, which include, but are not limited to: nephritis, renal failure, nephrotic syndrome, urinary tract infection, hematuria, proteinuria, oliguria, polyuria, nocturia, edema, hypertension, electrolyte disorders, sterile pyuria, renal osteodystrophy, large kidneys, renal transport defects, nephrolithiasis, azotemia, anuria, urinary retention ,slowing of urinary stream, large prostate, flank tenderness, full bladder sensation after voiding, enuresis, dysuria, bacteriuria, kidney stones, glomerulonephritis, vasculitis, hemolytic uremic syndromes, thrombotic thrombocytopenic purpura, malignant hypertension, casts, tubulointerstitial kidney diseases, renal tubular acidosis, pyelonephritis, hydronephritis, nephrotic syndrome, crush syndrome, and/or renal colic, in addition to Wilm's Tumor Disease, and congenital kidney abnormalities such as horseshoe kidney, polycystic kidney, and Falconi's syndrome for example.

Several known TRP family members have been identified that are expressed significantly in kidney tissue. These TRP family members include, for example, Trp12 (Wissenbach, U., Bodding, M., Freichel, M., Flockerzi, V, Lett., 485(2-3): 127-34, (2000)); OTRPC4 (Strotmann, R., Harteneck, C., Nunnenmacher, K., Schultz, G., Plant, T, D, Nat, Cell, Biol., 2(10):695-702, (2000)); polycystin-L2 (Guo, L., Schreiber, T, H., Weremowicz, S., Morton, C, C., Lee, C., Zhou, J. Genomics., 64(3):241-51, (2000)); and EcaC (Hoenderop, J. G., van, der, Kemp, A, W., Hartog, A., van, de, Graaf, S, F., van, Os, C, H., Willems, P, H., Bindels, R, J. J. Biol, Chem., 274(13):8375-8, (1999)).

Thus, the LTRPC3h polynucleotides and polypeptides are expected to share at least some biological activity with TRP family members expressed in kidney cells and tissues, particularly those specifically referenced herein, such as LTRPC3 (SEQ ID NO:15).

The strong homology to human transient receptor potential channels (TRP) proteins, combined with the localized expression in spinal cord and brain of the LTRPC3 variant, suggests the LTRPC3h polynucleotides and polypeptides, including modulators or fragments thereof, may be useful in treating, diagnosing, prognosing, and/or preventing neurodegenerative disease states, behavioral disorders, or inflammatory conditions. Representative uses are described in the "Regeneration" and "Hyperproliferative Disorders" sections below, in the Examples, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The strong homology to human transient receptor potential channels (TRP), combined with the localized expression in testis tissue of the LTRPC3 variant emphasizes the potential utility for LTRPC3h polynucleotides and polypeptides in treating, diagnosing, prognosing, and/or preventing testicular, in addition to reproductive disorders.

In preferred embodiments, LTRPC3h polynucleotides and polypeptides including agonists and fragments thereof, have uses which include treating, diagnosing, prognosing, and/or preventing the following, non-limiting, diseases or disorders of the testis: spermatogenesis, infertility, Klinefelter's syndrome, XX male, epididymitis, genital warts, germinal cell aplasia, cryptorchidism, varicocele, immotile cilia syndrome, and viral orchitis. The LTRPC3h polynucleotides and polypeptides including agonists and fragments thereof, may also have uses related to modulating testicular development, embryogenesis, reproduction, and in ameliorating, treating, and/or preventing testicular proliferative disorders (e.g., cancers, which include, for example, choriocarcinoma, Non-seminoma, seminoma, and testicular germ cell tumors).

Likewise, the localized expression in testis tissue also emphasizes the potential utility for LTRPC3h polynucleotides and polypeptides in treating, diagnosing, prognosing, and/or preventing metabolic diseases and disorders which include the following, not limiting examples: premature puberty, incomplete puberty, Kallman syndrome, Cushing's syndrome, hyperprolactinemia, hemochromatosis, congenital adrenal hyperplasia, FSH deficiency, and granulomatous disease, for example.

This gene product may also be useful in assays designed to identify binding agents, as such agents (antagonists) are useful as male contraceptive agents. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

Several known TRP family members have been identified that are expressed significantly in testis tissue. These TRP family members include, for example, polycystin-L2 (Guo, L., Schreiber, T, H., Weremowicz, S., Morton, C, C., Lee, C., Zhou, J. Genomics., 64(3):241-51, (2000)); TRP7 (Okada, T., Inoue, R., Yamazaki, K., Maeda, A., Kurosaki, T., Yamakuni, T., Tanaka, I., Shimizu, S., Ikenaka, K., Imoto, K., Mori, Y, J. Biol, Chem., 274(39):27359-70, (1999)); btrp2 (Wissenbach, U., Schroth, G., Philipp, S., Flockerzi, V, Lett., 429(1):61-6, (1998)); Htrp-1 (Zhu, X., Chu, P, B., Peyton, M., Birnbaumer, L, Lett., 373(3):193-8, (1995)); and TRPC1 (Wes, P, D., Chevesich, J., Jeromin, A., Rosenberg, C., Stetten, G., Montell, C, Proc, Natl, Acad, Sci, U, S, A., 92(21):9652-6, (1995)).

Thus, the LTRPC3h polynucleotides and polypeptides are expected to share at least some biological activity with TRP family members expressed in testis cells and tissues, particularly those specifically referenced herein, such as the LTRPC3 variant (SEQ ID NO:15).

As described elsewhere herein, transient receptor potential channel family members have been implicated in modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity. Moreover, transient receptor potential channel family members have been implicated in disorders of the skin, skeletal-muscle, nervous, cardiac, and vascular systems, in addition to the following, non-limiting diseases and disorders, which include, for example, arteriosclerosis, neointimal hypoerplasia, metastatic melanomas, bipolar disorder, non-syndromic hereditary deafness, Knobloch syndrome, holosencephaly, and various maligancies including prostate cancer.

In preferred embodiments, LTRPC3h polynucleotides and polypeptides of the present invention, including agonists and/or fragments thereof, have uses that include, modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity.

In more preferred embodiments, LTRPC3h polynucleotides and polypeptides of the present invention, including agonists and/or fragments thereof, have uses that include, treating, ameliorating, preventing, detecting, and/or prognosing various diseases and disorders, particularly the following, non-limiting examples, disorders of the skin, skeletal-muscle, nervous, cardiac, and vascular systems, in addition to the following, non-limiting diseases and disorders, which include, for example, arteriosclerosis, neointimal hypoerplasia, metastatic melanomas, bipolar disorder, nonsyndromic hereditary deafness, Knobloch syndrome, holosencephaly, and various maligancies including prostate cancer.

LTRPC3h polynucleotides and polypeptides of the present invention, including agonists and/or fragments may be involved in intracellular $Ca^{2+}$ homeostasis which affects various aspects of biological functions including mechano-regulation, pain transduction, vasorelaxation, gene expression, cell cycle and proliferation/apoptosis. Since the LTRPC3 variant is dominantly expressed in kidney, the LTRPC3h polypeptide may particularly play an important role in regulating cytosolic Ca2+ in the renal system, potentially Ca2+ absorption.

The LTRPC3h gene maps to chromosome 9q21.11-21.31 between the two markers D9S1874 and D9S1807. This region is linked to amyotrophic lateral sclerosis with fronto-temporal dementia, early-onset pulverulent cataract, infantile nephronophthisis, hypomagnesemia with secondary hypocalcemia (HSH), and familial hemophagocytic lymphohistiocytosis. Therefore, agonists and/or antagonists of the novel LTRPC3h can be used to treat diseases including various forms of neuronal degeneration, neurogenic inflammation, allergy, immunodeficiency/excessive immune activation, visual defects, hearing disorder, pain, cancer, hypertension and other cardiovascular diseases. In addition, the therapeutics may be useful in the treatment of diseases associated with disturbances in $Ca^{2+}$ homeostasis including osteoporosis, hypercalciuric stone disease, and chronic renal failure.

Moreover, given the selective expression in kidney, LTRPC3h could be considered a candidate gene for HSH, since the phenotype is a renal insufficiency. LTRPC3h chromosomal location is ~600 kb downstream of a X;9 translocation breakpoint interval described for one patient with HSH (*Hum. Mol. Genet.* 6, 1491-1497, (1997)). Recently, two groups reported that a new member of the TRPM subfamily, TRPM6, expressed in both intestinal tissues and kidney, is associated with HSH (*Nat. Genet.* 31, 166-170, (2002); and *Nat. Genet.* 31, 171-174 (2002)). Indeed, LTRPC3h is ~4 mb 5' to TRPM6 on 9q21. Although TRPM6 is the first component identified for HSH, this should not preclude involvement of LTRPC3h in the disease. Therefore, it is possible that LTRPC3h may co-localize with TRPM6 and/or forms a heteromultimer with TRPM6 in the kidney.

The kidney plays a major role in $Ca^{2+}$ homeostasis (reviewed in *Physiol. Rev.* 75, 429-471, (1995)). LTRPC3h may play a direct role in $Ca^{2+}$ absorption due to its constitutive $Ca^{2+}$ permeability. Alternatively, LTRPC3h may be the SOC that regulates $Ca^{2+}$ absorption. In kidney, $Ca^{2+}$ absorption is regulated by agonists such as calcitonin, parathyroid hormone and parathyroid hormone-related peptide through their respective G protein-coupled receptors, and downstream SOCs. Additionally, in kidney a SOC has been described (*J. Biol. Chem.* 276, 25759-25765, (2001)) for the action of angiotensin II, a vasoactive peptide that plays a major role in regulating blood pressure.

In addition, LTRPC3h polynucleotides and polypeptides of the present invention, including agonists and/or fragments thereof, have uses that include modulating intracellular Ca++ ion concentrations, Ca++ ion flux, stored intracellular Ca++ ion concentrations, Ca++ ion pump activity, Ca++ ion flow into cell, Ca++ ion flow out of cells, the activation of Ca++ sensitive proteins, the activation of Ca++sensitive signaling pathways, the activation of kinase-activatible proteins, and the activation of kinase-dependent signaling pathways.

The LTRPC3h polynucleotides and polypeptides of the present invention, including agonists and/or fragments thereof, have uses that include modulating proliferation, differentiation, migration, and activation in various cells, tissues, and organisms, and particularly in mammalian kidney, spinal cord, testis, and brain, preferably human. LTRPC3h polynucleotides and polypeptides of the present invention, including agonists and/or fragments thereof, may be useful in diagnosing, treating, prognosing, and/or preventing renal, neural, and/or proliferative diseases or disorders, particularly of the renal system.

In addition, antagonists of the LTRPC3h polynucleotides and polypeptides, including modulators or fragments thereof, may have uses that include diagnosing, treating, prognosing, and/or preventing diseases or disorders related to transient receptor potential channel activity, which may include renal, neural, reproductive, and/or proliferative diseases or disorders.

Although it is believed the encoded polypeptide may share at least some biological activities with transient receptor potential channel family members, particularly those melastatin1, a number of methods of determining the exact biological function of this clone are either known in the art or are described elsewhere herein. Briefly, the function of this clone may be determined by applying microarray methodology. Nucleic acids corresponding to the LTRPC3h polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from tissue that has been treated with known transient potential receptor inhibitors, which include, but are not limited to the drugs listed herein or otherwise known in the art, might indicate a function in modulating transient potential receptor function, for example. In the case of LTRPC3h, kidney, spinal cord, testis, and brain, should be used to extract RNA to prepare the probe.

In addition, the function of the protein may be assessed by applying quantitative PCR methodology, for example. Real time quantitative PCR would provide the capability of following the expression of the LTRPC3h gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. Also encompassed by the present invention are quantitative PCR probes corresponding to the polynucleotide sequence provided as SEQ ID NO:1 (FIGS. 1A-E).

The function of the protein may also be assessed through complementation assays in yeast. For example, in the case of the LTRPC3h, transforming yeast deficient in transient receptor potential channel activity with LTRPC3h and assessing their ability to grow would provide convincing evidence the LTRPC3h polypeptide has transient receptor potential channel activity. Additional assay conditions and methods that may be used in assessing the function of the polynucleotides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a kidney, spinal cord, testis, and/or brain -specific promoter), or it can be expressed at a specified time of development using an inducible and/or a developmentally regulated promoter.

In the case of LTRPC3h transgenic mice or rats, if no phenotype is apparent in normal growth conditions, observing the organism under diseased conditions (renal, reproductive, neural, or proliferative disorders, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal LTRPC3h deletion polypeptides are encompassed by the present invention: M1-T1721, G2-T1721, K3-T1721, K4-T1721, W5-T1721, R6-T1721, D7-T1721, A8-T1721, A9-T1721, E10-T1721, M11-T1721, E12-T1721, R13-T1721, G14-T1721, C15-T1721, S16-T1721, D17-T1721, R18-T1721, E19-T1721, D20-T1721, N21-T1721, A22-T1721, E23-T1721, S24-T1721, R25-T1721, R26-T1721, R27-T1721, S28-T1721, R29-T1721, S30-T1721, A31-T1721, S32-T1721, R33-T1721, G34-T1721, R35-T1721, F36-T1721, A37-T1721, E38-T1721, S39-T1721, W40-T1721, K41-T1721, R42-T1721, L43-T1721, S44-T1721, S45-T1721, K46-T1721, Q47-T1721, G48-T1721, S49-T1721, T50-T1721, K51-T1721, R52-T1721, S53-T1721, G54-T1721, L55-T1721, P56-T1721, S57-T1721, Q58-T1721, Q59-T1721, T60-T1721, P61-T1721, A62-T1721, Q63-T1721, K64-T1721, S65-T1721, W66-T1721, I67-T1721, E68-T1721, R69-T1721, A70-T1721, F71-T1721, Y72-T1721, K73-T1721, R74-T1721, E75-T1721, C76-T1721, V77-T1721, H78-T1721, I79-T1721, I80-T1721, P81-T1721, S82-T1721, T83-T1721, K84-T1721, D85-T1721, P86-T1721, H87-T1721, R88-T1721, C89-T1721, C90-T1721, C91-T1721, G92-T1721, R93-T1721, L94-T1721, I95-T1721, G96-T1721, Q97-T1721, H98-T1721, V99-T1721, G100-T1721, L10-T1721, T102-T1721, P103-T1721, S104-T1721, I105-T1721, S106-T1721, V107-T1721, L108-T1721, Q109-T1721, N110-T1721, E111-T1721, K112-T1721, N113-T1721, E114-T1721, S115-T1721, R116-T1721, L117-T1721, S118-T1721, R119-T1721, N120-T1721, D121-T1721, I122-T1721, Q123-T1721, S124-T1721, E125-T1721, K126-T1721, W127-T1721, S128-T1721, I129-T1721, S130-T1721, K131-T1721, H132-T1721, T133-T1721, Q134-T1721, L135-T1721, S136-T1721, P137-T1721, T138-T1721, D139-T1721, A140-T1721, F141-T1721, G142-T1721, T143-T1721, I144-T1721, E145-T1721, F146-T1721, Q147-T1721, G148-T1721, G149-T1721, G150-T1721, H151-T1721, S152-T1721, N153-T1721, K154-T1721, and/or A155-T1721 of SEQ ID NO:4. Polynucleotide sequences encoding these polypeptides are also provided. The present invention also encompasses the use of these N-terminal LTRPC3h deletion polypeptides as immunogenic and/or antigenic epitopes as described elsewhere herein.

In preferred embodiments, the following C-terminal LTRPC3h deletion polypeptides are encompassed by the present invention: M1-T1721, M1-H1720, M1-K1719, M1-S1718, M1-E1717, M1-F1716, M1-S1715, M1-Q1714, M1-F1713, M1-A1712, M1-S1711, M1-T1710, M1-R1709, M1-S1708, M1-L1707, M1-R1706, M1-R1705, M1-M1704, M1-S1703, M1-L1702, M1-S1701, M1-D1700, M1-G1699, M1-R1698, M1-G1697, M1-E1696, M1-P1695, M1-K1694, M1-S1693, M1-S1692, M1-K1691, M1-S1690, M1-R1689, M1-Q1688, M1-F1687, M1-P1686, M1-N1685, M1-Q1684, M1-L1683, M1-S1682, M1-A1681, M1-T1680, M1-N1679, M1-R1678, M1-Q1677, M1-R1676, M1-D1675, M1-L1674, M1-K1673, M1-D1672, M1-S1671, M1-I1670, M1-S1669, M1-F1668, M1-S1667, M1-K1666, M1-R1665, M1-T1664, M1-H1663, M1-A1662, M1-Y1661, M1-P1660, M1-A1659, M1-S1658, M1-P1657, M1-E1656, M1-E1655, M1-A1654, M1-S1653, M1-Y1652, M1-S1651, M1-N1650, M1-A1649, M1-R1648, M1-E1647, M1-I1646, M1-K1645, M1-P1644, M1-V1643, M1-T1642, M1-I1641, M1-N1640, M1-N1639, M1-S1638, M1-L1637, M1-T1636, M1-R1635, M1-E1634, M1-S1633, M1-N1632, M1-D1631, M1-G1630, M1-E1629, M1-Q1628, M1-S1627, M1-S1626, M1-I1625, M1-A1624, M1-I1623, M1-T1622, M1-A1621, M1-R1620, M1-R1619, M1-G1618, M1-K1617, M1-A1616, M1-E1615, M1-N1614, M1-E1613, M1-E1612, M1-S1611, M1-D1610, M1-S1609, M1-S1608, M1-P1607, M1-H1606, M1-S1605, M1-L1604, M1-E1603, M1-A1602, M1-E1601, M1-R1600, M1-E1599, M1-P1598, M1-H1597, M1-C1596, M1-C1595, M1-T1594, M1-L1593, M1-D1592, M1-E1591, M1-V1590, M1-K1589, M1-D1588, M1-G1587, M1-L1586, M1-G1585, M1-G1584, M1-P1583, M1-F1582, M1-A1581, M1-A1580, M1-R1579, M1-D1578, M1-A1577, M1-I1576, M1-A1575, M1-Q1574, M1-P1573, M1-A1572, M1-N1571, M1-V1570, M1-C1569, M1-R1568, M1-T1567, M1-D1566, M1-I1565, M1-C1564, M1-D1563, M1-T1562, M1-I1561, M1-S1560, M1-T1559, M1-Y1558, M1-E1557, M1-A1556, M1-T1555, M1-K1554, M1-V1553, M1-P1552, M1-V1551, M1-G1550, M1-F1549, M1-N1548, M1-A1547, M1-Y1546, M1-Y1545, M1-S1544, M1-R1543, M1-S1542, M1-P1541, M1-S1540, M1-F1539, M1-M1538, M1-F1537, M1-S1536, M1-H1535, M1-S1534, M1-K1533, M1-V1532, M1-I1531, M1-P1530, M1-A1529, M1-E1528, M1-E1527, M1-L1526, M1-L1525, M1-F1524, M1-P1523, M1-T1522, M1-T1521, M1-A1520, M1-L1519, M1-Y1518, M1-R1517, M1-S1516, M1-S1515, M1-K1514, M1-S1513, M1-R1512, M1-E1511, M1-I1510, M1-T1509, M1-H1508, M1-Y1507, M1-M1506, M1-P1505, M1-P1504, M1-E1503, M1-S1502, M1-D1501, M1-W1500, M1-P1499, M1-N1498, M1-Q1497, M1-C1496, M1-E1495, M1-P1494, M1-L1493, M1-H1492, M1-T1491, M1-Y1490, M1-D1489, M1-S1488, M1-S1487, M1-F1486, M1-S1485, M1-R1484, M1-T1483, M1-D1482, M1-M1481, M1-S1480, M1-T1479, M1-I1478, M1-D1477, M1-E1476, M1-F1475, M1-D1474, M1-I1473, M1-S1472, M1-R1471, M1-S1470, M1-P1469, M1-P1468, M1-R1467, M1-D1466, M1-T1465, M1-P1464, M1-A1463, M1-L1462, M1-T1461, M1-A1460, M1-Y1459, M1-A1458, M1-S1457, M1-S1456, M1-S1455, M1-P1454, M1-A1453, M1-T1452, M1-S1451, M1-P1450, M1-V1449, M1-P1448, M1-T1447, M1-S1446, M1-F1445, M1-S1444, M1-P1443, M1-E1442, M1-G1441, M1-L1440, M1-G1439, M1-L1438, M1-I1437, M1-N1436, M1-V1435, M1-S1434, M1-N1433, M1-D1432, M1-L1431, M1-P1430, M1-D1429, M1-I1428, M1-D1427, M1-C1426, M1-H1425, M1-L1424, M1-E1423, M1-D1422, M1-M1421, M1-A1420, M1-S1419, M1-V1418, M1-Y1417, M1-I1416, M1-D1415, M1-I1414, M1-C1413, M1-S1412, M1-S1411, M1-P1410, M1-R1409, M1-R1408, M1-S1407, M1-D1406, M1-P1405, M1-V1404, M1-I1403, M1-A1402, M1-L1401, M1-T1400, M1-N1399, M1-A1398, M1-P1397, M1-A1396, M1-A1395, M1-P1394, M1-A1393, M1-K1392, M1-P1391, M1-E1390, M1-K1389, M1-A1388, M1-V1387, M1-S1386, M1-H1385, M1-S1384, M1-S1383, M1-T1382, M1-A1381, M1-R1380, M1-H1379, M1-L1378, M1-S1377, M1-L1376, M1-S1375, M1-R1374, M1-E1373, M1-K1372, M1-F1371, M1-I1370, M1-S1369, M1-E1368, M1-L1367, M1-K1366, M1-E1365, M1-I1364, M1-G1363, M1-G1362, M1-K1361, M1-D1360, M1-K1359, M1-M1358, M1-N1357, M1-V1356, M1-S1355, M1-Y1354, M1-F1353, M1-S1352, M1-H1351, M1-S1350, M1-R1349, M1-M1348, M1-R1347, M1-P1346, M1-M1345, M1-L1344, M1-T1343, M1-P1342, M1-S1341, M1-T1340, M1-P1339, M1-S1338, M1-M1337, M1-T1336, M1-E1335, M1-E1334, M1-G1333, M1-A1332, M1-P1331, M1-D1330, M1-I1329, M1-S1328, M1-E1327, M1-Q1326, M1-L1325, M1-K1324, M1-F1323, M1-T1322, M1-N1321, M1-G1320, M1-E1319, M1-Q1318, M1-S1317, M1-N1316, M1-F1315, M1-S1314, M1-S1313, M1-Q1312, M1-R1311, M1-V1310, M1-I1309, M1-Y1308, M1-A1307, M1-A1306, M1-D1305, M1-T1304, M1-C1303, M1-D1302, M1-S1301, M1-S1300, M1-T1299, M1-R1298, M1-S1297, M1-R1296, M1-I1295, M1-K1294, M1-N1293, M1-S1292, M1-E1291, M1-A1290, M1-R1289, M1-E1288, M1-L1287, M1-G1286, M1-T1285, M1-L1284, M1-R1283, M1-E1282, M1-L1281, M1-A1280, M1-T1279, M1-A1278, M1-M1277, M1-R1276, M1-G1275, M1-I1274, M1-L1273, M1-D1272, M1-E1271, M1-L1270, M1-Q1269, M1-A1268, M1-L1267, M1-R1266, M1-I1265, M1-D1264, M1-V1263, M1-T1262, M1-Q1261, M1-L1260, M1-S1259, M1-A1258, M1-K1257, M1-M1256, M1-S1255, M1-H1254, M1-E1253, M1-R1252, M1-E1251, M1-N1250, M1-V1249, M1-E1248, M1-E1247, M1-L1246, M1-R1245, M1-M1244, M1-S1243, M1-M1242, M1-N1241, M1-E1240, M1-V1239, M1-R1238, M1-E1237, M1-S1236, M1-T1235, M1-V1234, M1-R1233, M1-I1232, M1-R1231, M1-E1230, M1-D1229, M1-N1228, M1-S1227, M1-S1226, M1-N1225, M1-F1224, M1-R1223, M1-D1222, M1-D1221, M1-K1220, M1-E1219, M1-R1218, M1-F1217, M1-Y1216, M1-E1215, M1-E1214, M1-I1213, M1-C1212, M1-Q1211, M1-E1210, M1-E1209, M1-F1208, M1-D1207, M1-H1206, M1-V1205, M1-K1204, M1-K1203, M1-L1202, M1-E1201, M1-D1200, M1-D1199, M1-T1198, M1-I1197, M1-F1196, M1-L1195, M1-K1194, M1-L1193, M1-G1192, M1-Y1191, M1-D1190, M1-R1189, M1-E1188, M1-D1187, M1-P1186, M1-D1185, M1-S1184, M1-E1183, M1-H1182, M1-K1181, M1-R1180, M1-W1179, M1-R1178, M1-C1177, M1-C1176, M1-L1175, M1-H1174, M1-Q1173, M1-F1172, M1-I1171, M1-M1170, M1-T1169, M1-M1168, M1-H1167, M1-S1166, M1-F1165, M1-I1164, M1-I1163, M1-L1162, M1-P1161, M1-P1160, M1-P1159, M1-L1158, M1-V1157, M1-P1156, M1-R1155, M1-E1154, M1-H1153, M1-F1152, M1-T1151, M1-M1150, M1-I1149, M1-L1148, M1-Q1147, M1-Y1146, M1-R1145, M1-Q1144, M1-F1143, M1-K1142, M1-W1141, M1-V1140, M1-Q1139, M1-N1138, M1-S1137, M1-I1136, M1-S1135, M1-K1134, M1-V1133, M1-E1132, M1-F1131, M1-F1130, M1-T1129, M1-N1128, M1-N1127, M1-F1126, M1-V1125, M1-A1124, M1-I1123, M1-L1122, M1-L1121, M1-N1120, M1-V1119, M1-L1118, M1-L1117, M1-I1116, M1-N1115, M1-A1114, M1-V1113, M1-L1112, M1-L1111, M1-Y11101, M1-C1109, M1-A1108, M1-M1107, M1-I1106, M1-A1105, M1-P1104, M1-V1103, M1-I1102, M1-W1101, M1-A1100, M1-G1099, M1-T1098, M1-K1097, M1-C1096, M1-P1095, M1-P1094, M1-L1093, M1-Q1092, M1-I1091, M1-I1090, M1-K1089, M1-G1088, M1-D1087, M1-E1086, M1-R1085, M1-T1084, M1-E1083, M1-N1082, M1-Q1081, M1-G1080, M1-C1079, M1-P1078, M1-P1077, M1-D1076, M1-I1075, M1-Q1074, M1-D1073, M1-A1072, M1-F1071, M1-V1070, M1-E1069, M1-G1068, M1-Y1067, M1-I1066, M1-M1065, M1-W1064, M1-Y1063, M1-P1062, M1-M1061, M1-Y1060, M1-F1059, M1-I1058, M1-N1057, M1-K1056, M1-A1055, M1-L1054, M1-K1053, M1-W1052, M1-S1051, M1-P1050, M1-E1049, M1-E1048, M1-N1047, M1-P1046, M1-F1045, M1-L1044, M1-I1043, M1-A1042, M1-Q1041, M1-R1040, M1-A1039, M1-V1038, M1-G1037, M1-F1036, M1-S1035, M1-M1034, M1-L1033, M1-V1032, M1-V1031, M1-L1030, M1-M1029, M1-I1028, M1-I1027, M1-V1026, M1-F1025, M1-Y1024, M1-M1023, M1-M1022, M1-D1021, M1-I1020, M1-M1019, M1-M1018, M1-K1017, M1-G1016, M1-I1015, M1-M1014, M1-M1013, M1-V1012, M1-Y1011, M1-P1011, M1-G1009, M1-L1008, M1-Y1007, M1-K1006, M1-N1005, M1-V1004, M1-G1003, M1-F1002, M1-I1001, M1-D1000, M1-L999, M1-L998, M1-R997, M1-I996, M1-Y995, M1-W994, M1-Y993, M1-I992, M1-I991, M1-N990, M1-V989, M1-C988, M1-Y987, M1-I986, M1-V985, M1-R984, M1-G983, M1-D982, M1-S981, M1-R980, M1-F979, M1-P978, M1-Q977, M1-D976, M1-Q975, M1-L974, M1-R973, M1-L972, M1-I971, M1-M970, M1-G969, M1-V968, M1-S967, M1-F966, M1-L965, M1-L964, M1-I963, M1-A962, M1-I961, M1-L960, M1-D959, M1-T958, M1-V957, M1-N956, M1-W955, M1-Y954, M1-E953, M1-Q952, M1-L951, M1-W950, M1-V949, M1-K948, M1-V947, M1-K946, M1-Q945, M1-L944, M1-L943, M1-K942, M1-G941, M1-P940, M1-E939, M1-S938, M1-M937, M1-L936, M1-I935, M1-E934, M1-R933, M1-M932, M1-K931, M1-E930, M1-I929, M1-G928, M1-L927, M1-T926, M1-F925, M1-I924, M1-Y923, M1-S922, M1-I921, M1-V920, M1-I919, M1-W918, M1-E917, M1-Q916, M1-T915, M1-S914, M1-P913, M1-W912, M1-R911, M1-E910, M1-M909, M1-K908, M1-V907, M1-L906, M1-V905, M1-I904, M1-Y903, M1-N902, M1-F901, M1-L900, M1-M899, M1-L898, M1-Y897, M1-G896, M1-I895, M1-Y894, M1-A893, M1-L892, M1-T891, M1-Y890, M1-F889, M1-W888, M1-F887, M1-K886, M1-V885, M1-I884, M1-P883, M1-A882, M1-N881, M1-Y880, M1-F879, M1-E878, M1-Y877, M1-I876, M1-K875, M1-R874, M1-G873, M1-L872, M1-P871, M1-I870, M1-L869, M1-R868, M1-H867, M1-K866, M1-S865, M1-Q864, M1-V863, M1-E862, M1-E861, M1-E860, M1-D859, M1-K858, M1-K857, M1-R856, M1-S855, M1-S854, M1-E853, M1-G852, M1-N851, M1-N850, M1-R849, M1-G848, M1-L847, M1-M846, M1-A845, M1-T844, M1-L843, M1-E842, M1-M841, M1-D840, M1-E839, M1-E838, M1-E837, M1-K836, M1-E835, M1-K834, M1-T833, M1-P832, M1-K831, M1-E830, M1-P829, M1-E828, M1-E827, M1-A826, M1-E825, M1-K824, M1-E823, M1-Q822, M1-L821, M1-H820, M1-I819, M1-E818, M1-Q817, M1-A816, M1-Q815, M1-S814, M1-M813, M1-Y812, M1-P811, M1-M810, M1-D809, M1-D808, M1-K807, M1-N806, M1-K805, M1-F804, M1-E803, M1-M802, M1-S801, M1-K800, M1-I799, M1-S798, M1-P797, M1-P796, M1-L795, M1-L794, M1-I793, M1-G792, M1-P791, M1-I790, M1-V789, M1-K788, M1-L787, M1-G786, M1-S785, M1-N784, M1-K783, M1-R782, M1-M781, M1-R780, M1-L779, M1-R778, M1-G777, M1-M776,
M1-W775, M1-M774, M1-D773, M1-T772, M1-L771,
M1-L770, M1-M769, M1-Q768, M1-S767, M1-C766,
M1-T765, M1-H764, M1-A763, M1-I762, M1-F761,
M1-D760, M1-R759, M1-H758, M1-K757, M1-A756,
M1-A755, M1-V754, M1-A753, M1-L752, M1-Q751,
M1-L750, M1-C749, M1-T748, M1-A747, M1-N746,
M1-S745, M1-W744, M1-N743, M1-K742, M1-L741,
M1-E740, M1-Y739, M1-T738, M1-L737, M1-L736,
M1-K735, M1-M734, M1-A733, M1-L732, M1-Q731,
M1-E730, M1-D729, M1-Q728, M1-K727, M1-Y726,
M1-S725, M1-Q724, M1-D723, M1-L722, M1-L721,
M1-E720, M1-V719, M1-A718, M1-L717, M1-Q716,
M1-G715, M1-F714, M1-D713, M1-R712, M1-S711,
M1-N710, M1-H709, M1-N708, M1-L707, M1-E706,
M1-Q705, M1-S704, M1-I703, M1-D702, M1-D701,
M1-V700, M1-M699, M1-D698, M1-N697, M1-E696,
M1-S695, M1-A694, M1-E693, M1-H692, M1-A691,
M1-M690, M1-A689, M1-K688, M1-C687, M1-L686,
M1-K685, M1-C684, M1-A683, M1-V682, M1-L681,
M1-A680, M1-K679, M1-A678, M1-M677, M1-A676,
M1-E675, M1-E674, M1-G673, M1-H672, M1-Q671,
M1-W670, M1-F669, M1-F668, M1-L667, M1-A666,
M1-M665, M1-K664, M1-Q663, M1-R662, M1-K661,
M1-M660, M1-L659, M1-V658, M1-A657, M1-W656,
M1-V655, M1-M654, M1-L653, M1-E652, M1-H651,
M1-F650, M1-P649, M1-F648, M1-P647, M1-F646,
M1-H645, M1-N644, M1-I643, M1-E642, M1-P641,
M1-D640, M1-D639, M1-L638, M1-D637, M1-I636,
M1-D635, M1-V634, M1-E633, M1-E632, M1-E631,
M1-R630, M1-K629, M1-K628, M1-T627, M1-T626,
M1-K625, M1-R624, M1-G623, M1-R622, M1-R621,
M1-L620, M1-P619, M1-I618, M1-D617, M1-D616,
M1-E615, M1-M614, M1-G613, M1-L612, M1-L611,
M1-K610, M1-L609, M1-A608, M1-K607, M1-P606,
M1-R605, M1-K604, M1-P603, M1-G602, M1-F601,
M1-L600, M1-N599, M1-H598, M1-Y597, M1-L596,
M1-T595, M1-R594, M1-F593, M1-R592, M1-K591,
M1-R590, M1-T589, M1-Y588, M1-N587, M1-C586,
M1-R585, M1-Y584, M1-A583, M1-G582, M1-G581,
M1-M580, M1-L579, M1-Y578, M1-E577, M1-I576,
M1-V575, M1-L574, M1-G573, M1-I572, M1-D571,
M1-I570, M1-L569, M1-S568, M1-I567, M1-R566,
M1-Y565, M1-D564, M1-P563, M1-P562, M1-L561,
M1-N560, M1-G559, M1-K558, M1-F557, M1-Y556,
M1-I555, M1-W554, M1-G553, M1-F552, M1-G551,
M1-P550, M1-Y549, M1-E548, M1-R547, M1-K546,
M1-K545, M1-V544, M1-D543, M1-R542, M1-V541,
M1-L540, M1-H539, M1-Y538, M1-L537, M1-T536,
M1-N535, M1-S534, M1-P533, M1-G532, M1-H531,
M1-R530, M1-T529, M1-N528, M1-Y527, M1-L526,
M1-E525, M1-E524, M1-L523, M1-R522, M1-S521,
M1-I520, M1-T519, M1-L518, M1-F517, M1-R516,
M1-H515, M1-M514, M1-S513, M1-V512, M1-G511,
M1-N510, M1-E509, M1-I508, M1-L507, M1-L506,
M1-K505, M1-V504, M1-F503, M1-D502, M1-V501,
M1-R500, M1-D499, M1-L498, M1-V497, M1-L496,
M1-A495, M1-D494, M1-L493, M1-M492, M1-A491,
M1-Q490, M1-E489, M1-L488, M1-S487, M1-G486,
M1-V485, M1-P484, M1-W483, M1-Q482, M1-Q481,
M1-G480, M1-Y479, M1-I478, M1-F477, M1-I476,
M1-Q475, M1-S474, M1-R473, M1-A472, M1-I471,
M1-D470, M1-V469, M1-R468, M1-N467, M1-W466,
M1-A465, M1-L464, M1-A463, M1-L462, M1-S461,
M1-L460, M1-Q459, M1-D458, M1-P457, M1-A456,
M1-S455, M1-A454, M1-N453, M1-L452, M1-G451,
M1-K450, M1-L449, M1-L448, M1-A447, M1-T446,
M1-L445, M1-I444, M1-A443, M1-L442, M1-D441,
M1-I440, M1-D439, M1-Q438, M1-H437, M1-G436,
M1-E435, M1-S434, M1-L433, M1-W432, M1-R431,
M1-F430, M1-V429, M1-T428, M1-I427, M1-L426,
M1-E425, M1-K424, M1-K423, M1-K422, M1-M421,
M1-C420, M1-E419, M1-M418, M1-L417, M1-I416,
M1-I415, M1-F414, M1-L413, M1-H412, M1-Q411,
M1-A410, M1-Q409, M1-T408, M1-R407, M1-T406,
M1-Y405, M1-T404, M1-F403, M1-T402, M1-K401,
M1-Q400, M1-I399, M1-T398, M1-V397, M1-L396,
M1-L395, M1-Q394, M1-D393, M1-R392, M1-L391,
M1-S390, M1-E389, M1-N388, M1-I387, M1-L386,
M1-G385, M1-G384, M1-E383, M1-E382, M1-S381,
M1-Y380, M1-K379, M1-H378, M1-G377, M1-F376,
M1-A375, M1-L374, M1-I373, M1-D372, M1-S371,
M1-A370, M1-R369, M1-G368, M1-S367, M1-G366,
M1-D365, M1-C364, M1-V363, M1-V362, M1-V361,
M1-P360, M1-V359, M1-P358, M1-P357, M1-T356,
M1-D355, M1-R354, M1-L353, M1-Y352, M1-E351,
M1-L350, M1-V349, M1-I348, M1-S347, M1-I346,
M1-V345, M1-N344, M1-P343, M1-G342, M1-G341,
M1-E340, M1-V339, M1-I338, M1-L337, M1-A336,
M1-V335, M1-V334, M1-P333, M1-V332, M1-G331,
M1-Q330, M1-G329, M1-I328, M1-R327, M1-T326,
M1-N325, M1-I324, M1-K323, M1-Q322, M1-L321,
M1-S320, M1-I319, M1-H318, M1-K317, M1-E316,
M1-L315, M1-Q314, M1-R313, M1-R312, M1-L311,
M1-K310, M1-V309, M1-E308, M1-A307, M1-G306,
M1-Y305, M1-K304, M1-G303, M1-T302, M1-T301,
M1-G300, M1-N299, M1-D298, M1-A297, M1-L296,
M1-I295, M1-F294, M1-H293, M1-S292, M1-H291,
M1-M290, M1-S289, M1-N288, M1-L287, M1-V286,
M1-T285, M1-L284, M1-K283, M1-S282, M1-M281,
M1-P280, M1-N279, M1-S278, M1-M277, M1-T276,
M1-Q275, M1-Y274, M1-P273, M1-R272, M1-V271,
M1-V270, M1-D269, M1-R268, M1-G267, M1-I266,
M1-L265, M1-D264, M1-E263, M1-Q262, M1-N261,
M1-E260, M1-V259, M1-I258, M1-G257, M1-W256,
M1-P255, M1-A254, M1-I253, M1-G252, M1-I251,
M1-T250, M1-C249, M1-I248, M1-K247, M1-G246,
M1-R245, M1-S244, M1-K243, M1-S242, M1-A241,
M1-H240, M1-D239, M1-K238, M1-L237, M1-A236,
M1-D235, M1-G234, M1-V233, M1-H232, M1-R231,
M1-I230, M1-V229, M1-G228, M1-T227, M1-N226,
M1-V225, M1-G224, M1-G223, M1-T222, M1-F221,
M1-I220, M1-W219, M1-A218, M1-G217, M1-T216,
M1-T215, M1-M214, M1-A213, M1-A212, M1-K211,
M1-I210, M1-L209, M1-G208, M1-K207, M1-G206,
M1-F205, M1-V204, M1-Q203, M1-K202, M1-L201,
M1-K200, M1-P199, M1-Q198, M1-L197, M1-E196,
M1-F195, M1-N194, M1-Q193, M1-L192, M1-G191,
M1-G190, M1-H189, M1-V188, M1-S187, M1-I186,
M1-L185, M1-L184, M1-K183, M1-P182, M1-L181,
M1-E180, M1-L179, M1-Q178, M1-W177, M1-E176,
M1-K175, M1-T174, M1-M173, M1-L172, M1-H171,
M1-L170, M1-L169, M1-L168, M1-D167, M1-P166,
M1-K165, M1-T164, M1-D163, M1-F162, M1-S161,
M1-V160, M1-R159, M1-V158, M1-Y157, M1-M156,
M1-A155, M1-K154, M1-N153, M1-S152, M1-H151,
M1-G150, M1-G149, M1-G148, M1-Q147, M1-F146,
M1-E145, M1-I144, M1-T143, M1-G142, M1-F141,
M1-A140, M1-D139, M1-T138, M1-P137, M1-S136,
M1-L135, M1-Q134, M1-T133, M1-H132, M1-K131,
M1-S130, M1-I129, M1-S128, M1-W127, M1-K126,
M1-E125, M1-S124, M1-Q123, M1-I122, M1-D121,
M1-N120, M1-R119, M1-S118, M1-L117, M1-R116,
M1-S115, M1-E114, M1-N113, M1-K112, M1-E111, M1-N110, M1-Q109, M1-L108, M1-V107, M1-S106, M1-I105, M1-S104, M1-P103, M1-T102, M1-L10, M1-G100, M1-V99, M1-H98, M1-Q97, M1-G96, M1-I95, M1-L94, M1-R93, M1-G92, M1-C91, M1-C90, M1-C89, M1-R88, M1-H87, M1-P86, M1-D85, M1-K84, M1-T83, M1-S82, M1-P81, M1-I80, M1-I79, M1-H78, M1-V77, M1-C76, M1-P81, M1-E75, M1-R74, M1-K73, M1-Y72, M1-F71, M1-A70, M1-R69, M1-E68, M1-I67, M1-W66, M1-S65, M1-K64, M1-Q63, M1-A62, M1-P61, M1-T60, M1-Q59, M1-Q58, M1-S57, M1-P56, M1-L55, M1-G54, M1-S53, M1-R52, M1-K51, M1-T50, M1-S49, M1-G48, M1-Q47, M1-K46, M1-S45, M1-S44, M1-L43, M1-R42, M1-K41, M1-W40, M1-S39, M1-E38, M1-A37, M1-F36, M1-R35, M1-G34, M1-R33, M1-S32, M1-A31, M1-S30, M1-R29, M1-S28, M1-R27, M1-R26, M1-R25, M1-S24, M1-E23, M1-A22, M1-N21, M1-D20, M1-E19, M1-R18, M1-D17, M1-S16, M1-C15, M1-G14, M1-R13, M1-E12, M1-M11, M1-E10, M1-A9, M1-A8, and/or M1-D7 of SEQ ID NO:4. Polynucleotide sequences encoding these polypeptides are also provided. The present invention also encompasses the use of these C-terminal LTRPC3h deletion polypeptides as immunogenic and/or antigenic epitopes as described elsewhere herein.

Alternatively, preferred polypeptides of the present invention may comprise polypeptide sequences corresponding to, for example, internal regions of the LTRPC3h polypeptide (e.g., any combination of both N- and C-terminal LTRPC3h polypeptide deletions) of SEQ ID NO:4. For example, internal regions could be defined by the equation: amino acid NX to amino acid CX, wherein NX refers to any N-terminal deletion polypeptide amino acid of LTRPC3h (SEQ ID NO:4), and where CX refers to any C-terminal deletion polypeptide amino acid of LTRPC3h (SEQ ID NO:4). Polynucleotides encoding these polypeptides are also provided. The present invention also encompasses the use of these polypeptides as an immunogenic and/or antigenic epitope as described elsewhere herein.

Many polynucleotide sequences, such as EST sequences, are publicly available and accessible through sequence databases. Some of these sequences are related to SEQ ID NO:3 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 5223 of SEQ ID NO:3, b is an integer between 15 to 5237, where both a and b correspond to the positions of nucleotide residues shown in SEQ ID NO:3, and where b is greater than or equal to a+14.

Features of the Polypeptide Encoded by Gene No:3

The polypeptide of this gene provided as SEQ ID NO:6 (FIGS. 3A-F), encoded by the polynucleotide sequence according to SEQ ID NO:5 (FIGS. 3A-F), and/or encoded by the polynucleotide contained within the deposited clone, LTRPC3i, has significant homology at the nucleotide and amino acid level to the human melastatin 1 protein (Melastatin1; Genbank Accession No. gi|3243075; SEQ ID NO:13). An alignment of the LTRPC3i polypeptide with this protein is provided in FIGS. 7A-G.

The LTRPC3i polypeptide was determined to share 65.4% identity and 73.2% similarity with the human melastatin 1 protein (Melastatin1; Genbank Accession No. gi|3243075; SEQ ID NO:13) as shown in FIG. 10.

The LTRPC3i protein is believed to represent a member of a new class of protein kinases referred to as alpha kinases (Curr. Biol. 9 (2), R43-R45 (1999)). These kinases represent a novel type of signaling molecule comprising both a catalytic protein kinase domain, in addition to, an ion channel domain. This family is commonly referred to as the transient receptor potential channel (TRP) family. Melastatin1 defines a separate subfamily of TRP channels referred to as TRPM (melastatin1). TRPM family members are characteristic of their unusually long cytoplasmic tails at both ends of the channel domain and some of the family members contain an enzyme domain at the C-terminal region.

Specifically, the LTRPC3i (SEQ ID NO:6) polypeptide represents a novel variant of the LTRPC3c (Co-pending U.S. Ser. No. 10/210,152, filed Aug. 1, 2002; International Publication No. WO 03/012063, published Feb. 13, 2003; SEQ ID NO:18; and also co-pending U.S. Ser. No. 10/405,793, filed Mar. 28, 2003; which are hereby incorporated by reference herein in their entirety) polypeptide. The LTRPC3i represents a novel member of the TRPM subfamily.

The melastatin1 protein is believed to be negatively associated with the incidence of melanoma based upon its inverse correlative expression in highly aggressive melanomas (Genomics 54 (1), 116-123 (1998)). Thus, overexpression of melastatin1 could represent a novel therapeutic in the treatment of melanoma and potentially other cancers.

Based upon the observed homology, the polypeptide of the present invention is expected to share at least some biological activity with other transient receptor potential channel family members, more specifically with the melastatin1 protein, in addition to, other transient receptor potential channel family members referenced elsewhere herein or otherwise known in the art, particularly LTRPC3c, and LTRPC3.

Most of the known transient receptor potential channel family members, possess one or more transmembrane domains. Likewise, the LTRPC3i polypeptide has been determined to comprise six transmembrane domains (TM1-TM6) as shown in FIGS. 3A-F. The transmembrane domains are located from about amino acid 775 to about amino acid 792 (TM1), from about amino acid 872 to about amino acid 888 (TM2), from about amino acid 945 to about amino acid 958 (TM3), from about amino acid 972 to about amino acid 988 (TM4), from about amino acid 1006 to about amino acid 1023 (TM5), and/or from about amino acid 1115 to about amino acid 1125 (TM6) of SEQ ID NO:6. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following transmembrane domain polypeptides are encompassed by the present invention: LKVILGILLPPSILSLEF (SEQ ID NO:50), IVKFW-FYTLAYIGYLMLF (SEQ ID NO:51), VTDLIAILLFS-VGM (SEQ ID NO:52), RVIYCVNIIYWYIRLLDI (SEQ ID NO:53), MMIDMMYFVIIMLVVLMS (SEQ ID NO:54), and/or AIMACYLLVANILLVNLLIAV (SEQ ID NO:55). Polynucleotides encoding these polypeptides are also provided. The present invention also encompasses the use of the LTRPC3i transmembrane polypeptides as immunogenic and/or antigenic epitopes as described elsewhere herein.

The present invention also encompasses polypeptides corresponding to the regions between each transmembrane domain of LTRPC3i, referred to herein as inter-transmembrane domain polypeptides (inter TM1-2, inter TM2-3, inter TM3-4, inter TM4-5, and inter TM5-6). Such regions are typically solvent accessible (either extracellularly or intracellularly). Therefore, these regions are amenable to the development of agonists and/or antagonists to the LTRPC3i polypeptide, particularly for the development of antibodies specific to these regions.

In preferred embodiments, the following inter-transmembrane domain polypeptides are encompassed by the present invention: KNKDDMPYMSQAQEIHLQEKEAEEPE-KPTKEKEEEDMELTAMLGRNNGESS RKKDEEEVQSKHRLIPLGRKIYEFYNAP (SEQ ID NO:56), NYIVLVKMERWPSTQEWIVISYIFTLG-IEKMREILMSEPGKLLQKVKVWLQEY WN (SEQ ID NO:57), ILRLQDQPFRSDG (SEQ ID NO:58), FGVNKY-LGPYVMMIGK (SEQ ID NO:59), and/or FGVARQAILF-PNEEPSWKLAKNIFYMPYWMIYGEVFAD-QIDPPCGQNETRED GKIIQLPPCKTGAWIVP (SEQ ID NO:60). Polynucleotides encoding these polypeptides are also provided. The present invention also encompasses the use of the LTRPC3i inter-transmembrane polypeptides as immunogenic and/or antigenic epitopes as described elsewhere herein.

The LTRPC3i polypeptide was determined to comprise several conserved cysteines, at amino acid 249, 364, 420, 574, 672, 754, 976, 1212, 1303, and 1564 of SEQ ID NO:6 (FIGS. 3A-F). Conservation of cysteines at key amino acid residues is indicative of conserved structural features, which may correlate with conservation of protein function and/or activity.

In confirmation of the LTRPC3i representing a member of the transient receptor channel family, the LTRPC3i polypeptide was determined to comprise a predicted TRP domain located from about amino acid 1140 to about amino acid 1145 of SEQ ID NO:6. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following TRP domain polypeptide is encompassed by the present invention: VWK-FQR (SEQ ID NO:61). Polynucleotides encoding this polypeptide are also provided. The present invention also encompasses the use of this LTRPC3i TRP domain polypeptide as an immunogenic and/or antigenic epitope as described elsewhere herein.

In further confirmation of the LTRPC3i representing a member of the transient receptor channel family, the LTRPC3i polypeptide was determined to comprise a predicted ion transport signature domain located at about amino acid 915 to about amino acid 1126 of SEQ ID NO:6. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following ion transport signature domain polypeptide is encompassed by the present invention: TQEWIVISYIFTLGIEKMREILM-SEPGKLLQKVKVWLQEYWNVTDLIAILLFSV GMIL-RLQDQPFRSDGRVIYCVNIIYWYIRLL-DIFGVNKYLGPYVMMIGKMMID MMYFVIIMLVVLMSFGVARQAILFP-NEEPSWKLAKNIFYMPYWMIYGEVFAD QIDP-PCGQNETREDGKIIQLPPCKTGAWIV-PAIMACYLLVANILLVNLLIAVF (SEQ ID NO:62). Polynucleotides encoding this polypeptide are also provided. The present invention also encompasses the use of this LTRPC3i ion transport signature domain polypeptide as an immunogenic and/or antigenic epitope as described elsewhere herein.

The LTRPC3i polypeptide was determined to comprise a predicted coiled-coil domain located at about amino acid 1230 to about amino acid 1285 of SEQ ID NO:6. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following coiled-coil domain polypeptide is encompassed by the present invention: ERIRVTSERVENMSMRLEEVNEREH-SMKASLQTVDIRLAQLEDLIGRMATALERL (SEQ ID NO:63). Polynucleotides encoding this polypeptide are also provided. The present invention also encompasses the use of this LTRPC3i coiled-coil domain polypeptide as an immunogenic and/or antigenic epitope as described elsewhere herein.

LTRPC3i polypeptides and polynucleotides are useful for diagnosing diseases related to the over and/or under expression of LTRPC3i by identifying mutations in the LTRPC3i gene using LTRPC3i sequences as probes or by determining LTRPC3i protein or mRNA expression levels. LTRPC3i polypeptides will be useful in screens for compounds that affect the activity of the protein. LTRPC3i peptides can also be used for the generation of specific antibodies and as bait in yeast two hybrid screens to find proteins the specifically interact with LTRPC3i.

Since the LTRPC3i polypeptide represents an N-terminally extended variant of the LTRPC3c polypeptide (see polypeptide alignment provided in FIG. 11A-I), and since the LTRPC3c (SEQ ID NO: 18) polypeptide represents a splice variant of the LTRPC3 polypeptide (SEQ ID NO:15), the LTRPC3i (SEQ ID NO:6) polypeptide of the present invention is expected to have the same or similar function as the LTRPC3 polypeptide, and in particular, the LTRPC3c polypeptide. Specifically, the LTRPC3i polypeptide is expected to localize to the cell membrane.

Moreover, the LTRPC3i polypeptide is expected to also localize in or near the plasmalemmal compartment.

Moreover, the LTRPC3i polypeptide is also expected to be a constitutively active channel capable of mediating $Ca^{2+}$ influx.

Moreover, the LTRPC3i polypeptide is also expected to mediate $Ca^{2+}$ entry and that LTRPC3i-mediated $Ca^{2+}$ entry is expected to be potentiated by store-depletion.

Moreover, the LTRPC3i polypeptide is also expected to mediate a $Ca^{2+}$ entry pathway that is distinct from the endogenous $Ca^{2+}$ entry pathways present in HEK 293 cells.

Moreover, the LTRPC3i polypeptide of the present invention is expected to share the same or similar expression profile as that of the LTRPC3 polypeptide (SEQ ID NO:15).

Moreover, the LTRPC3i polypeptide is expected to share the same or similar differential expression patterns observed for the LTRPC3 variant.

Moreover, the LTRCP3g polypeptide is expected to be able to modulate the FEN1 DNA base-excision repair/proliferation modulating protein to the same or similar extent as the LTRPC3 polypeptide.

Moreover, the LTRPC3i polynucleotides and polypeptides are expected to share at least some biological activity with TRP family members expressed in kidney cells and tissues, particularly those specifically referenced herein, such as LTRPC3 (SEQ ID NO: 15), and particularly as LTRPC3c (SEQ ID NO: 18).

Moreover, the LTRPC3i polynucleotides and polypeptides are expected to share at least some biological activity with TRP family members expressed in testis cells and tissues, particularly those specifically referenced herein, such as the LTRPC3 variant (SEQ ID NO: 15), and particularly as LTRPC3c (SEQ ID NO: 18).

In preferred embodiments, LTRPC3i polynucleotides and polypeptides, including fragments and modulators thereof, are useful for treating, diagnosing, and/or ameliorating $Ca^{2+}$ reabsorption disorders, disorders associated with aberrant luminal Ca2+ entry via the epithelial Ca2+ channel (ECaC), disorders associated with aberrant cytosolic diffusion of Ca2+ bound to calbindin-D28K, disorders associated with aberrant basolateral extrusion of Ca2+ through the Na+/Ca2+ exchanger (NCX), disorders associated with aberrant plasma membrane Ca2+-ATPase (PMCA) activity and/or activation, disorders associated with the hypocalciuric effect of diuretics, disorders associated with the hypocalciuric effect of thiazide diuretics, disorders associated with hormone insufficiencies that affect the function of the kidney, disorders associated with hormone insufficiencies that affect renal Ca2+ homeostasis, disorders associated with aberrant renal Ca2+ homeostasis as a result of vitamin D deficiency, disorders associated with aberrant renal Ca2+ homeostasis as a result of PTH deficiency, disorders associated with aberrant renal Ca2+ homeostasis as a result of vasopressin deficiency, disorders associated with aberrant renal Ca2+ homeostasis as a result of prostaglandines deficiency, disorders associated with aberrant renal Ca2+ homeostasis as a result of estrogen deficiency, disorders associated with aberrant renal Ca2+ homeostasis as a result of calcitonin deficiency, disorders associated with aberrant renal Ca2+ homeostasis as a result of parathyroid hormone deficiency, disorders associated with aberrant renal Ca2+ homeostasis as a result of atrial natriuretic peptide deficiency, calcium homeostasis-related disorders, hypercaliuric nephrolithiasis, certain forms of osteoporosis, Gitelman's disease, Bartter's syndrom, disorders associated with aberrant function of kidney tubular epithelium, disorders associated with aberrant function of kidney tubular epithelium in the medulla, disorders associated with aberrant function of kidney tubular epithelium in the medullary rays, disorders associated with aberrant function of kidney tubular epithelium in the periglomerular.

In preferred embodiments, LTRPC3i polynucleotides and polypeptides, including fragments and modulators thereof, are useful for treating, diagnosing, and/or ameliorating acute kidney failure, chronic kidney failure, cystic kidney disease, horseshoe kidney, hypertensive kidney disease, kidney atrophy, kidney cancer, kidney disease, kidney failure, kidney infection, kidney metastasis, kidney stone, nephrolithiasis, multicystic dysplastic kidney disease, and polycystic kidney disease.

Characterization of the LTRPC3 variant polypeptide using antisense oligonucleotides led to the determination that LTRPC3 is involved in the negative modulation of the FEN1 DNA base-excision repair/proliferation modulating protein as described in Example 5 herein.

The LTRCP3g polypeptide is expected to be able to modulate the FEN 1DNA base-excision repair/proliferation modulating protein to the same or similar extent as the LTRPC3 polypeptide.

Specifically, antisense inhibition of LTRPC3 resulted in upregulation of Fen1, a marker of proliferation. As such, LTRPC3 behaves in a manner similar to a tumor suppressor, in that loss results in increases in proliferation. While some increases in the proliferation markers p21 and IkB were also observed, they were less significant, and could be a response to the pro-proliferative effect of LTRPC3 antisense inhibition. Interestingly, expression of LTRPC3 was also observed to be significantly reduced in tumor tissues, relative to normal tissues (see FIG. 13). Specifically, renal, testicular, and ovarian tumor samples showed as much as 12 to 30 fold down regulation of LTRPC3 message levels compared to normal tissues. This reduction of LTRPC3 correlating with the tumor state is consistent with the negative FEN1 modulatory activity and suggests this gene may have antiproliferative activities. Therefore, for modulators of LTRPC3i to be useful for treating cancer, it would be necessary to increase the activity of the gene or gene product in order to have the reverse effect on cancerous cells. Thus, an agonist of LTRPC3i activity or a compound that increased LTRPC3i message levels would be a desired invention for cancer therapy.

In preferred embodiments, LTRPC3i polynucleotides and polypeptides, including fragments and modulators thereof, are useful for treating, diagnosing, and/or ameliorating DNA-repair deficiencies, particularly base-excision repair deficiencies, Xeroderma pigmentosum, skin cancer, melanoma, UV senstivity, alkylation sensivity, gamma irradiation sensitivity, pyrimidine dimer sensitivity, chemical mutagenes, lymphomas, leukemias, photosensitivity, Bloom's syndrone, Fanconi's anemia, ataxia telangiectasia, chromosomal aberrations, blood vessel dilation aberrations in the skin, blood vessel dilation aberrations in the eye, conditions involving increased levels of apurinic sites, conditions involving increased levels of apyrimidinic sites, conditions involving increased levels of abasic sites, disorders related to aberrant signal transduction, proliferating disorders, and/or cancers.

Moreover, LTRPC3i polynucleotides and polypeptides, including fragments and modulators thereof, are useful for increasing mammalian base excision repair activity, increasing mammalian single-nucleotide base excision repair activity, and/or increasing mammalian long patch base excision repair activity.

In preferred embodiments, antagonists directed against LTRPC3i are useful for treating, diagnosing, and/or ameliorating DNA-repair deficiencies, particularly base-excision repair deficiencies, Xeroderma pigmentosum, skin cancer, melanoma, UV sensitivity, alkylation sensitivity, gamma irradiation sensitivity, pyrimidine dimer sensitivity, chemical mutagenes, lymphomas, leukemias, photosensitivity, Bloom's syndrome, Fanconi's anemia, ataxia telangiectasia, chromosomal aberrations, blood vessel dilation aberrations in the skin, blood vessel dilation aberrations in the eye, conditions involving increased levels of apurinic sites, conditions involving increased levels of apyrimidinic sites, conditions involving increased levels of abasic sites, disorders related to aberrant signal transduction, proliferating disorders, and/or cancers.

Moreover, antagonists directed against LTRPC3i are useful for increasing mammalian base excision repair activity, increasing mammalian single-nucleotide base excision repair activity, and/or increasing mammalian long patch base excision repair activity.

In preferred embodiments, agonists directed against LTRPC3i are useful for treating, diagnosing, and/or ameliorating, disorders related to aberrant signal transduction, proliferating disorders, and/or cancers, particularly renal cell carcinomas, testicular cancers, and/or ovarian cancers.

Moreover, agonists directed against LTRPC3i are useful for decreasing mammalian base excision repair activity, decreasing mammalian single-nucleotide base excision repair activity, and/or decreasing mammalian long patch base excision repair activity.

The strong homology to human transient receptor potential channels (TRP), combined with the predominate localized expression in kidney tissue of the LTRPC3 variant, suggests the LTRPC3i polynucleotides and polypeptides, including modulators or fragments thereof, may be useful in treating, diagnosing, prognosing, and/or preventing renal diseases and/or disorders, which include, but are not limited to: nephritis, renal failure, nephrotic syndrome, urinary tract infection, hematuria, proteinuria, oliguria, polyuria, nocturia, edema, hypertension, electrolyte disorders, sterile pyuria, renal osteodystrophy, large kidneys, renal transport defects, nephrolithiasis, azotemia, anuria, urinary retention ,slowing of urinary stream, large prostate, flank tenderness, full bladder sensation after voiding, enuresis, dysuria, bacteriuria, kidney stones, glomerulonephritis, vasculitis, hemolytic uremic syndromes, thrombotic thrombocytopenic purpura, malignant hypertension, casts, tubulointerstitial kidney diseases, renal tubular acidosis, pyelonephritis, hydronephritis, nephrotic syndrome, crush syndrome, and/or renal colic, in addition to Wilm's Tumor Disease, and congenital kidney abnormalities such as horseshoe kidney, polycystic kidney, and Falconi's syndrome for example.

Several known TRP family members have been identified that are expressed significantly in kidney tissue. These TRP family members include, for example, Trp12 (Wissenbach, U., Bodding, M., Freichel, M., Flockerzi, V, Lett., 485(2-3): 127-34, (2000)); OTRPC4 (Strotmann, R., Harteneck, C., Nunnenmacher, K., Schultz, G., Plant, T, D, Nat, Cell, Biol., 2(10):695-702, (2000)); polycystin-L2 (Guo, L., Schreiber, T, H., Weremowicz, S., Morton, C, C., Lee, C., Zhou, J. Genomics., 64(3):241-51, (2000)); and EcaC (Hoenderop, J. G., van, der, Kemp, A, W., Hartog, A., van, de, Graaf, S, F., van, Os, C, H.,Willems, P, H., Bindels, R, J. J. Biol, Chem., 274(13):8375-8, (1999)).

Thus, the LTRPC3i polynucleotides and polypeptides are expected to share at least some biological activity with TRP family members expressed in kidney cells and tissues, particularly those specifically referenced herein, such as LTRPC3 (SEQ ID NO:15).

The strong homology to human transient receptor potential channels (TRP) proteins, combined with the localized expression in spinal cord and brain of the LTRPC3 variant, suggests the LTRPC3i polynucleotides and polypeptides, including modulators or fragments thereof, may be useful in treating, diagnosing, prognosing, and/or preventing neurodegenerative disease states, behavioral disorders, or inflammatory conditions. Representative uses are described in the "Regeneration" and "Hyperproliferative Disorders" sections below, in the Examples, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse, formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The strong homology to human transient receptor potential channels (TRP), combined with the localized expression in testis tissue of the LTRPC3 variant emphasizes the potential utility for LTRPC3i polynucleotides and polypeptides in treating, diagnosing, prognosing, and/or preventing testicular, in addition to reproductive disorders.

In preferred embodiments, LTRPC3i polynucleotides and polypeptides including agonists and fragments thereof, have uses which include treating, diagnosing, prognosing, and/or preventing the following, non-limiting, diseases or disorders of the testis: spermatogenesis, infertility, Klinefelter's syndrome, XX male, epididymitis, genital warts, germinal cell aplasia, cryptorchidism, varicocele, immotile cilia syndrome, and viral orchitis. The LTRPC3i polynucleotides and polypeptides including agonists and fragments thereof, may also have uses related to modulating testicular development, embryogenesis, reproduction, and in ameliorating, treating, and/or preventing testicular proliferative disorders (e.g., cancers, which include, for example, choriocarcinoma, Non-seminoma, seminona, and testicular germ cell tumors).

Likewise, the localized expression in testis tissue also emphasizes the potential utility for LTRPC3i polynucleotides and polypeptides in treating, diagnosing, prognosing, and/or preventing metabolic diseases and disorders which include the following, not limiting examples: premature puberty, incomplete puberty, Kallman syndrome, Cushing's syndrome, hyperprolactinemia, hemochromatosis, congenital adrenal hyperplasia, FSH deficiency, and granulomatous disease, for example.

This gene product may also be useful in assays designed to identify binding agents, as such agents (antagonists) are useful as male contraceptive agents. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

Several known TRP family members have been identified that are expressed significantly in testis tissue. These TRP family members include, for example, polycystin-L2 (Guo, L., Schreiber, T, H., Weremowicz, S., Morton, C, C., Lee, C., Zhou, J. Genomics., 64(3):241-51, (2000)); TRP7 (Okada, T., Inoue, R., Yamazaki, K., Maeda, A., Kurosaki, T., Yamakuni, T., Tanaka, I., Shimizu, S., Ikenaka, K., Imoto, K., Mori, Y, J. Biol, Chem., 274(39):27359-70, (1999)); btrp2 (Wissenbach, U., Schroth, G., Philipp, S., Flockerzi, V, Lett., 429(1):61-6, (1998)); Htrp-1 (Zhu, X., Chu, P, B., Peyton, M., Bimbaumer, L, Lett., 373(3):193-8, (1995)); and TRPC1 (Wes, P, D., Chevesich, J., Jeromin, A., Rosenberg, C., Stetten, G., Montell, C, Proc, Natl, Acad, Sci, U, S, A., 92(21):9652-6, (1995)).

Thus, the LTRPC3i polynucleotides and polypeptides are expected to share at least some biological activity with TRP family members expressed in testis cells and tissues, particularly those specifically referenced herein, such as the LTRPC3 variant (SEQ ID NO:15).

As described elsewhere herein, transient receptor potential channel family members have been implicated in modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity. Moreover, transient receptor potential channel family members have been implicated in disorders of the skin, skeletal-muscle, nervous, cardiac, and vascular systems, in addition to the following, non-limiting diseases and disorders, which include, for example, arteriosclerosis, neointimal hypoerplasia, metastatic melanomas, bipolar disorder, non-syndromic hereditary deafness, Knobloch syndrome, holosencephaly, and various maligancies including prostate cancer.

In preferred embodiments, LTRPC3i polynucleotides and polypeptides of the present invention, including agonists and/or fragments thereof, have uses that include, modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity.

In more preferred embodiments, LTRPC3i polynucleotides and polypeptides of the present invention, including agonists and/or fragments thereof, have uses that include, treating, ameliorating, preventing, detecting, and/or prognosing various diseases and disorders, particularly the following, non-limiting examples, disorders of the skin, skeletal-muscle, nervous, cardiac, and vascular systems, in addition to the following, non-limiting diseases and disorders, which include, for example, arteriosclerosis, neointimal hypoerplasia, metastatic melanomas, bipolar disorder, nonsyndromic hereditary deafness, Knobloch syndrome, holosencephaly, and various maligancies including prostate cancer.

LTRPC3i polynucleotides and polypeptides of the present invention, including agonists and/or fragments may be involved in intracellular $Ca^{2+}$ homeostasis which affects various aspects of biological functions including mechano-regulation, pain transduction, vasorelaxation, gene expression, cell cycle and proliferation/apoptosis. Since the LTRPC3 variant is dominantly expressed in kidney, the LTRPC3i polypeptide may particularly play an important role in regulating cytosolic Ca2+ in the renal system, potentially Ca2+ absorption.

The LTRPC3i gene maps to chromosome 9q21.11-21.31 between the two markers D9S1874 and D9S1807. This region is linked to amyotrophic lateral sclerosis with frontotemporal dementia, early-onset pulverulent cataract, infantile nephronophthisis, hypomagnesemia with secondary hypocalcemia (HSH), and familial hemophagocytic lymphohistiocytosis. Therefore, agonists and/or antagonists of the novel LTRPC3i can be used to treat diseases including various forms of neuronal degeneration, neurogenic inflammation, allergy, immunodeficiency/excessive immune activation, visual defects, hearing disorder, pain, cancer, hypertension and other cardiovascular diseases. In addition, the therapeutics may be useful in the treatment of diseases associated with disturbances in $Ca^{2+}$ homeostasis including osteoporosis, hypercalciuric stone disease, and chronic renal failure.

Moreover, given the selective expression in kidney, LTRPC3i could be considered a candidate gene for HSH, since the phenotype is a renal insufficiency. LTRPC3i chromosomal location is ~600 kb downstream of a X; 9 translocation breakpoint interval described for one patient with HSH (Hum. Mol. Genet. 6, 1491-1497, (1997)). Recently, two groups reported that a new member of the TRPM subfamily, TRPM6, expressed in both intestinal tissues and kidney, is associated with HSH (Nat. Genet. 31, 166-170, (2002); and Nat. Genet. 31, 171-174 (2002)). Indeed, LTRPC3i is ~4 mb 5' to TRPM6 on 9q21. Although TRPM6 is the first component identified for HSH, this should not preclude involvement of LTRPC3i in the disease. Therefore, it is possible that LTRPC3i may co-localize with TRPM6 and/or forms a heteromultimer with TRPM6 in the kidney.

The kidney plays a major role in $Ca^{2+}$ homeostasis (reviewed in Physiol. Rev. 75, 429-471, (1995)). LTRPC3l may play a direct role in $Ca^{2+}$ absorption due to its constitutive $Ca^{2+}$ permeability. Alternatively, LTRPC3i may be the SOC that regulates $Ca^{2+}$ absorption. In kidney, $Ca^{2+}$ absorption is regulated by agonists such as calcitonin, parathyroid hormone and parathyroid hormone-related peptide through their respective G protein-coupled receptors, and downstream SOCs. Additionally, in kidney a SOC has been described (J. Biol. Chem. 276, 25759-25765, (2001)) for the action of angiotensin II, a vasoactive peptide that plays a major role in regulating blood pressure.

In addition, LTRPC3i polynucleotides and polypeptides of the present invention, including agonists and/or fragments thereof, have uses that include modulating intracellular Ca++ ion concentrations, Ca++ ion flux, stored intracellular Ca++ ion concentrations, Ca++ ion pump activity, Ca++ ion flow into cell, Ca++ ion flow out of cells, the activation of Ca++ sensitive proteins, the activation of Ca++sensitive signaling pathways, the activation of kinase-activatible proteins, and the activation of kinase-dependent signaling pathways.

The LTRPC3i polynucleotides and polypeptides of the present invention, including agonists and/or fragments thereof, have uses that include modulating proliferation, differentiation, migration, and activation in various cells, tissues, and organisms, and particularly in mammalian kidney, spinal cord, testis, and brain, preferably human. LTRPC3i polynucleotides and polypeptides of the present invention, including agonists and/or fragments thereof, may be useful in diagnosing, treating, prognosing, and/or preventing renal, neural, and/or proliferative diseases or disorders, particularly of the renal system.

In addition, antagonists of the LTRPC3i polynucleotides and polypeptides, including modulators or fragments thereof, may have uses that include diagnosing, treating, prognosing, and/or preventing diseases or disorders related to transient receptor potential channel activity, which may include renal, neural, reproductive, and/or proliferative diseases or disorders.

Although it is believed the encoded polypeptide may share at least some biological activities with transient receptor potential channel family members, particularly those melastatin1, a number of methods of determining the exact biological function of this clone are either known in the art or are described elsewhere herein. Briefly, the function of this clone may be determined by applying microarray methodology. Nucleic acids corresponding to the LTRPC3i polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from tissue that has been treated with known transient potential receptor inhibitors, which include, but are not limited to the drugs listed herein or otherwise known in the art, might indicate a function in modulating transient potential receptor function, for example. In the case of LTRPC3i, kidney, spinal cord, testis, and brain, should be used to extract RNA to prepare the probe.

In addition, the function of the protein may be assessed by applying quantitative PCR methodology, for example. Real time quantitative PCR would provide the capability of following the expression of the LTRPC3i gene throughout development, for example. Quantitative PCR methodology requires only a nominal amount of tissue from each developmentally important step is needed to perform such experiements. Therefore, the application of quantitative PCR methodology to refining the biological function of this polypeptide is encompassed by the present invention. Also encompassed by the present invention are quantitative PCR probes corresponding to the polynucleotide sequence provided as SEQ ID NO:1 (FIGS. 1A-E).

The function of the protein may also be assessed through complementation assays in yeast. For example, in the case of the LTRPC3i, transforming yeast deficient in transient receptor potential channel activity with LTRPC3i and assessing their ability to grow would provide convincing evidence the LTRPC3i polypeptide has transient receptor potential channel activity. Additional assay conditions and methods that may be used in assessing the function of the polynucleotides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a kidney, spinal cord, testis, and/or brain-specific promoter), or it can be expressed at a specified time of development using an inducible and/or a developmentally regulated promoter.

In the case of LTRPC3i transgenic mice or rats, if no phenotype is apparent in normal growth conditions, observing the organism under diseased conditions (renal, reproductive, neural, or proliferative disorders, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal LTRPC3i deletion polypeptides are encompassed by the present invention: M1-T1721, G2-T1721, K3-T1721, K4-T1721, W5-T1721, R6-T1721, D7-T1721, A8-T1721, A9-T1721, E10-T1721, M11-T1721, E12-T1721, R13-T1721, G14-T1721, C15-T1721, S16-T1721, D17-T1721, R18-T1721, E19-T1721, D20-T1721, N21-T1721, A22-T1721, E23-T1721, S24-T1721, R25-T1721, R26-T1721, R27-T1721, S28-T1721, R29-T1721, S30-T1721, A31-T1721, S32-T1721, R33-T1721, G34-T1721, R35-T1721, F36-T1721, A37-T1721, E38-T1721, S39-T1721, W40-T1721, K41-T1721, R42-T1721, L43-T1721, S44-T1721, S45-T1721, K46-T1721, Q47-T1721, G48-T1721, S49-T1721, T50-T1721, K51-T1721, R52-T1721, S53-T1721, G54-T1721, L55-T1721, P56-T1721, S57-T1721, Q58-T1721, Q59-T1721, T60-T1721, P61-T1721, A62-T1721, Q63-T1721, K64-T1721, S65-T1721, W66-T1721, I67-T1721, E68-T1721, R69-T1721, A70-T1721, F71-T1721, Y72-T1721, K73-T1721, R74-T1721, E75-T1721, C76-T1721, V77-T1721, H78-T1721, I79-T1721, I80-T1721, P81-T1721, S82-T1721, T83-T1721, K84-T1721, D85-T1721, P86-T1721, H87-T1721, R88-T1721, C89-T1721, C90-T1721, C91-T1721, G92-T1721, R93-T1721, L94-T1721, I95-T1721, G96-T1721, Q97-T1721, H98-T1721, V99-T1721, G100-T1721, L105-T1721, T102-T1721, P103-T1721, S104-T1721, I105-T1721, S106-T1721, V107-T1721, L108-T1721, Q109-T1721, N110-T1721, E111-T1721, K112-T1721, N113-T1721, E114-T1721, S115-T1721, R116-T1721, L117-T1721, S118-T1721, R119-T1721, N120-T1721, D121-T1721, I122-T1721, Q123-T1721, S124-T1721, E125-T1721, K126-T1721, W127-T1721, S128-T1721, I129-T1721, S130-T1721, K131-T1721, H132-T1721, T133-T1721, Q134-T1721, L135-T1721, S136-T1721, P137-T1721, T138-T1721, D139-T1721, A140-T1721, F141-T1721, G142-T1721, T143-T1721, I144-T1721, E145-T1721, F146-T1721, Q147-T1721, G148-T1721, G149-T1721, G150-T1721, H151-T1721, S152-T1721, N153-T1721, K154-T1721, and/or A155-T1721 of SEQ ID NO:6. Polynucleotide sequences encoding these polypeptides are also provided. The present invention also encompasses the use of these N-terminal LTRPC3i deletion polypeptides as immunogenic and/or antigenic epitopes as described elsewhere herein.

In preferred embodiments, the following C-terminal LTRPC3i deletion polypeptides are encompassed by the present invention: M1-T1721, M1-H1720, M1-K1719, M1-S1718, M1-E1717, M1-F1716, M1-S1715, M1-Q1714, M1-F1713, M1-A1712, M1-S1711, M1-T1710, M1-R1709, M1-S1708, M1-L1707, M1-R1706, M1-R1705, M1-M1704, M1-S1703, M1-L1702, M1-S1701, M1-D1700, M1-G1699, M1-R1698, M1-G1697, M1-E1696, M1-P1695, M1-K1694, M1-S1693, M1-S1692, M1-K1691, M1-S1690, M1-R1689, M1-Q1688, M1-F1687, M1-P1686, M1-N1685, M1-Q1684, M1-L1683, M1-S1682, M1-A1681, M1-T1680, M1-N1679, M1-R1678, M1-Q1677, M1-R1676, M1-D1675, M1-L1674, M1-K1673, M1-D1672, M1-S1671, M1-I1670, M1-S1669, M1-F1668, M1-S1667, M1-K1666, M1-R1665, M1-T1664, M1-H1663, M1-A1662, M1-Y1661, M1-P1660, M1-A1659, M1-S1658, M1-P1657, M1-E1656, M1-E1655, M1-A1654, M1-S1653, M1-Y1652, M1-S1651, M1-N1650, M1-A1649, M1-R1648, M1-E1647, M1-I1646, M1-K1645, M1-P1644, M1-V1643, M1-T1642, M1-I1641, M1-N1640, M1-N1639, M1-S1638, M1-L1637, M1-T1636, M1-R1635, M1-E1634, M1-S1633, M1-N1632, M1-D1631, M1-G1630, M1-E1629, M1-Q1628, M1-S1627, M1-S1626, M1-I1625, M1-A1624, M1-I1623, M1-T1622, M1-A1621, M1-R1620, M1-R1619, M1-G1618, M1-K1617, M1-A1616, M1-E1615, M1-N1614, M1-E1613, M1-E1612, M1-S1611, M1-D1610, M1-S1609, M1-S1608, M1-P1607, M1-H1606, M1-S1605, M1-L1604, M1-E1603, M1-A1602, M1-E1601, M1-R1600, M1-E1599, M1-P1598, M1-H1597, M1-C1596, M1-C1595, M1-T1594, M1-L1593, M1-D1592, M1-E1591, M1-V1590, M1-K1589, M1-D1588, M1-G1587, M1-L1586, M1-G1585, M1-G1584, M1-P1583, M1-F1582, M1-A1581, M1-A1580, M1-R1579, M1-D1578, M1-A1577, M1-I1576, M1-A1575, M1-Q1574, M1-P1573, M1-A1572, M1-N1571, M1-V1570, M1-C1569, M1-R1568, M1-T1567, M1-D1566, M1-I1565, M1-C1564, M1-D1563, M1-T1562, M1-I1561, M1-S1560, M1-T1559, M1-Y1558, M1-E1557, M1-A1556, M1-T1555, M1-K1554, M1-V1553, M1-P1552, M1-V1551, M1-G1550, M1-F1549, M1-N1548, M1-A1547, M1-Y1546, M1-Y1545, M1-S1544, M1-R1543, M1-S1542, M1-P1541, M1-S1540, M1-F1539, M1-M1538, M1-F1537, M1-S1536, M1-H1535, M1-S1534, M1-K1533, M1-V1532, M1-I1531, M1-P1530, M1-A1529, M1-E1528, M1-E1527, M1-L1526, M1-L1525, M1-F1524, M1-P1523, M1-T1522, M1-T1521, M1-A1520, M1-L1519, M1-Y1518, M1-R1517, M1-S1516, M1-S1515, M1-K1514, M1-S1513, M1-R1512, M1-E1511, M1-I1510, M1-T1509, M1-H1508, M1-Y1507, M1-M1506, M1-P1505, M1-P1504, M1-E1503, M1-S1502, M1-D1501, M1-W1500, M1-P1499, M1-N1498, M1-Q1497, M1-C1496, M1-E1495, M1-P1494, M1-L1493, M1-H1492, M1-T1491, M1-Y1490, M1-D1489, M1-S1488, M1-S1487, M1-F1486, M1-S1485, M1-R1484, M1-T1483, M1-D1482, M1-M1481, M1-S1480, M1-T1479, M1-I1478, M1-D1477, M1-E1476, M1-F1475, M1-D1474, M1-I1473, M1-S1472, M1-R1471, M1-S1470, M1-P1469, M1-P1468, M1-R1467, M1-D1466, M1-T1465, M1-P1464, M1-A1463, M1-L1462, M1-T1461, M1-A1460, M1-Y1459, M1-A1458, M1-S1457, M1-S1456, M1-S1455, M1-P1454, M1-A1453, M1-T1452, M1-S1451, M1-P1450, M1-V1449, M1-P1448, M1-T1447, M1-S1446, M1-F1445, M1-S1444, M1-P1443, M1-E1442, M1-G1441, M1-L1440, M1-G1439, M1-L1438, M1-I1437, M1-N1436, M1-V1435, M1-S1434, M1-N1433, M1-D1432, M1-L1431, M1-P1430, M1-D1429, M1-I1428, M1-D1427, M1-C1426, M1-H1425, M1-L1424, M1-E1423, M1-D1422, M1-M1421, M1-A1420, M1-S1419, M1-V1418, M1-Y1417, M1-I1416, M1-D1415, M1-I1414, M1-C1413, M1-S1412, M1-S1411, M1-P1410, M1-R1409, M1-R1408, M1-S1407, M1-D1406, M1-P1405, M1-V1404, M1-I1403, M1-A1402, M1-L1401, M1-T1400, M1-N1399, M1-A1398, M1-P1397, M1-A1396, M1-A1395, M1-P1394, M1-A1393, M1-K1392, M1-P1391, M1-E1390, M1-K1389, M1-A1388, M1-V1387, M1-S1386, M1-H1385, M1-S1384, M1-S1383, M1-T1382, M1-A1381, M1-R1380, M1-H1379, M1-L1378, M1-S1377, M1-L1376, M1-S1375, M1-R1374, M1-E1373, M1-K1372, M1-F1371, M1-I1370, M1-S1369, M1-E1368, M1-L1367, M1-K1366, M1-E1365, M1-I1364, M1-G1363, M1-G1362, M1-K1361, M1-D1360, M1-K1359, M1-M1358, M1-N1357, M1-V1356, M1-S1355, M1-Y1354, M1-F1353, M1-S1352, M1-H1351, M1-S1350, M1-R1349, M1-M1348, M1-R1347, M1-P1346, M1-M1345, M1-L1344, M1-T1343, M1-P1342, M1-S1341, M1-T1340, M1-P1339, M1-S1338, M1-M1337, M1-T1336, M1-E1335, M1-E1334, M1-G1333, M1-A1332, M1-P1331, M1-D1330, M1-I1329, M1-S1328, M1-E1327, M1-Q1326, M1-L1325, M1-K1324, M1-F1323, M1-T1322, M1-N1321, M1-G1320, M1-E1319, M1-Q1318, M1-S1317, M1-N1316, M1-F1315, M1-S1314, M1-S1313, M1-Q1312, M1-R1311, M1-V1310, M1-I1309, M1-Y1308, M1-A1307, M1-A1306, M1-D1305, M1-T1304, M1-C1303, M1-D1302, M1-S1301, M1-S1300, M1-T1299, M1-R1298, M1-S1297, M1-R1296, M1-I1295, M1-K1294, M1-N1293, M1-S1292, M1-E1291, M1-A1290, M1-R1289, M1-E1288, M1-L1287, M1-G1286, M1-T1285, M1-L1284, M1-R1283, M1-E1282, M1-L1281, M1-A1280, M1-T1279, M1-A1278, M1-M1277, M1-R1276, M1-G1275, M1-I1274, M1-L1273, M1-D1272, M1-E1271, M1-L1270, M1-Q1269, M1-A1268, M1-L1267, M1-R1266, M1-I1265, M1-D1264, M1-V1263, M1-T1262, M1-Q1261, M1-L1260, M1-S1259, M1-A1258, M1-K1257, M1-M1256, M1-S1255, M1-H1254, M1-E1253, M1-R1252, M1-E1251, M1-N1250, M1-V1249, M1-E1248, M1-E1247, M1-L1246, M1-R1245, M1-M1244, M1-S1243, M1-M1242, M1-N1241, M1-E1240, M1-V1239, M1-R1238, M1-E1237, M1-S1236, M1-T1235, M1-V1234, M1-R1233, M1-I1232, M1-R1231, M1-E1230, M1-D1229, M1-N1228, M1-S1227, M1-S1226, M1-N1225, M1-F1224, M1-R1223, M1-D1222, M1-D1221, M1-K1220, M1-E1219, M1-R1218, M1-F1217, M1-Y1216, M1-E1215, M1-E1214, M1-I1213, M1-C1212, M1-Q1211, M1-E1210, M1-E1209, M1-F1208, M1-D1207, M1-H1206, M1-V1205, M1-K1204, M1-K1203, M1-L1202, M1-E1201, M1-D1200, M1-D1199, M1-T1198, M1-I1197, M1-F1196, M1-L1195, M1-K1194, M1-L1193, M1-G1192, M1-Y1191, M1-D1190, M1-R1189, M1-E1188, M1-D1187, M1-P1186, M1-D1185, M1-S1184, M1-E1183, M1-H1182, M1-K1181, M1-R1180, M1-W1179, M1-R1178, M1-C1177, M1-C1176, M1-L1175, M1-H1174, M1-Q1173, M1-F1172, M1-I1171, M1-M1170, M1-T1169, M1-M1168, M1-H1167, M1-S1166, M1-F1165, M1-I1164, M1-I1163, M1-L1162, M1-P1161, M1-P1160, M1-P1159, M1-L1158, M1-V1157, M1-P1156, M1-R1155, M1-E1154, M1-H1153, M1-F1152, M1-T1151, M1-M1150, M1-I1149, M1-L1148, M1-Q1147, M1-Y1146, M1-R1145, M1-Q1144, M1-F1143, M1-K1142, M1-W1141, M1-V1140, M1-Q1139, M1-N1138, M1-S1137, M1-I1136, M1-S1135, M1-K1134, M1-V1133, M1-E1132, M1-F1131, M1-F1130, M1-T1129, M1-N1128, M1-N1127, M1-F1126, M1-V1125, M1-A1124, M1-I1123, M1-L1122, M1-L1121, M1-N1120, M1-V1119, M1-L1118, M1-L1117, M1-I1116, M1-N1115, M1-A1114, M1-V1113, M1-L1112, M1-L1111, M1-Y1110, M1-C1109, M1-A1108, M1-M1107, M1-I1106, M1-A1105, M1-P1104, M1-V1103, M1-I1102, M1-W1101, M1-A1100, M1-G1099, M1-T1098, M1-K1097, M1-C1096, M1-P1095, M1-P1094, M1-L1093, M1-Q1092, M1-I1091, M1-I1090, M1-K1089, M1-G1088, M1-D1087, M1-E1086, M1-R1085, M1-T1084, M1-E1083, M1-N1082, M1-Q1081, M1-G1080, M1-C1079, M1-P1078, M1-A1077, M1-S1076, M1-K1075, M1-P1074, M1-T1073, M1-H1072, M1-S1071, M1-D1070, M1-Y1069, M1-V1068, M1-Q1067, M1-K1066, M1-R1065, M1-D1064, M1-I1063, M1-Q1062, M1-D1061, M1-A1060, M1-F1059, M1-V1058, M1-E1057, M1-G1056, M1-Y1055, M1-I1054, M1-M1053, M1-W1052, M1-Y1051, M1-P1050, M1-M1049, M1-Y1048, M1-F1047, M1-I1046, M1-N1045, M1-K1044, M1-A1043, M1-L1042, M1-K1041, M1-W1040, M1-S1039, M1-P1038, M1-E1037, M1-E1036, M1-N1035, M1-P1034, M1-F1033, M1-L1032, M1-I1031, M1-A1030, M1-Q1029, M1-R1028, M1-A1027, M1-V1026, M1-G1025, M1-F1024, M1-S1023, M1-M1022, M1-L1021, M1-V1020, M1-V1019, M1-L1018, M1-M1017, M1-I1016, M1-I1015, M1-V1014, M1-F1013, M1-Y1012, M1-M1011, M1-M1010, M1-D1009, M1-I1008, M1-M1007, M1-M1006, M1-K1005, M1-G1004, M1-I1003, M1-M1002, M1-M1001, M1-V1000, M1-Y999, M1-P998, M1-G997, M1-L996, M1-Y995, M1-K994, M1-N993, M1-V992, M1-G991, M1-F990, M1-I989, M1-D988, M1-L987, M1-L986, M1-R985, M1-I984, M1-Y983, M1-W982, M1-Y981, M1-I980, M1-I979, M1-N978, M1-V977, M1-C976, M1-Y975, M1-I974, M1-V973, M1-R972, M1-G971, M1-D970, M1-S969, M1-R968, M1-F967, M1-P966, M1-Q965, M1-D964, M1-Q963, M1-L962, M1-R961, M1-L960, M1-I959, M1-M958, M1-G957, M1-V956, M1-S955, M1-F954, M1-L953, M1-L952, M1-I951, M1-A950, M1-I949, M1-L948, M1-D947, M1-T946, M1-V945, M1-N944, M1-W943, M1-Y942, M1-E941, M1-Q940, M1-L939, M1-W938, M1-V937, M1-K936, M1-V935, M1-K934, M1-Q933, M1-L932, M1-L931, M1-K930, M1-G929, M1-P928, M1-E927, M1-S926, M1-M925, M1-L924, M1-I923, M1-E922, M1-R921, M1-M920, M1-K919, M1-E918, M1-I917, M1-G916, M1-L915, M1-T914, M1-F913, M1-I912, M1-Y911, M1-S910, M1-I909, M1-V908, M1-I907, M1-W906, M1-E905, M1-Q904, M1-T903, M1-S902, M1-P901, M1-W900, M1-R899, M1-E898, M1-M897, M1-K896, M1-V895, M1-L894, M1-V893, M1-I892, M1-Y891, M1-N890, M1-F889, M1-L888, M1-M887, M1-L886, M1-Y885, M1-G884, M1-I883, M1-Y882, M1-A881, M1-L880, M1-T879, M1-Y878, M1-F877, M1-W876, M1-F875, M1-K874, M1-V873, M1-I872, M1-P871, M1-A870, M1-N869, M1-Y868, M1-F867, M1-E866, M1-Y865, M1-I864, M1-K863, M1-R862, M1-G861, M1-L860, M1-P859, M1-I858, M1-L857, M1-R856, M1-H855, M1-K854, M1-S853, M1-Q852, M1-V851, M1-E850, M1-E849, M1-E848, M1-D847, M1-K846, M1-K845, M1-R844, M1-S843, M1-S842, M1-E841, M1-G840, M1-N839, M1-N838, M1-R837, M1-G836, M1-L835, M1-M834, M1-A833, M1-T832, M1-L831, M1-E830, M1-M829, M1-D828, M1-E827, M1-E826, M1-E825, M1-K824, M1-E823, M1-K822, M1-T821, M1-P820, M1-K819, M1-E818, M1-P817, M1-E816, M1-E815, M1-A814, M1-E813, M1-K812, M1-E811, M1-Q810, M1-L809, M1-H808, M1-I807, M1-E806, M1-Q805, M1-A804, M1-Q803, M1-S802, M1-M801, M1-Y800, M1-P799, M1-M798, M1-D797, M1-D796, M1-K795, M1-N794, M1-K793, M1-F792, M1-E791, M1-L790, M1-S789, M1-L788, M1-I787, M1-S786, M1-P785, M1-P784, M1-L783, M1-L782, M1-I781, M1-G780, M1-L779, M1-I778, M1-V777, M1-K776, M1-L775, M1-G774, M1-S773, M1-N772, M1-K771, M1-R770, M1-M769, M1-R768, M1-L767, M1-R766, M1-G765, M1-M764, M1-W763, M1-M762, M1-D761, M1-T760, M1-L759, M1-L758, M1-M757, M1-Q756, M1-S755, M1-C754, M1-T753, M1-H752, M1-A751, M1-I750, M1-F749, M1-D748, M1-R747, M1-H746, M1-K745, M1-A744, M1-A743, M1-V742, M1-A741, M1-L740, M1-Q739, M1-L738, M1-C737, M1-T736, M1-A735, M1-N734, M1-S733, M1-W732, M1-N731, M1-K730, M1-L729, M1-E728, M1-Y727, M1-T726, M1-L725, M1-L724, M1-K723, M1-M722, M1-A721, M1-L720, M1-Q719, M1-E718, M1-D717, M1-Q716, M1-K715, M1-Y714, M1-S713, M1-Q712, M1-D711, M1-L710, M1-L709, M1-E708, M1-V707, M1-A706, M1-L705, M1-Q704, M1-G703, M1-F702, M1-D701, M1-R700, M1-S699, M1-N698, M1-H697, M1-N696, M1-L695, M1-E694, M1-Q693, M1-S692, M1-I691, M1-D690, M1-D689, M1-V688, M1-M687, M1-D686, M1-N685, M1-E684, M1-S683, M1-A682, M1-E681, M1-H680, M1-A679, M1-M678, M1-A677, M1-K676, M1-C675, M1-L674, M1-K673, M1-C672, M1-A671, M1-V670, M1-L669, M1-A668, M1-K667, M1-A666, M1-M665, M1-A664, M1-E663, M1-E662, M1-G661, M1-H660, M1-Q659, M1-W658, M1-F657, M1-F656, M1-L655, M1-A654, M1-M653, M1-K652, M1-Q651, M1-R650, M1-K649, M1-M648, M1-L647, M1-V646, M1-A645, M1-W644, M1-V643, M1-M642, M1-L641, M1-E640, M1-H639, M1-F638, M1-P637, M1-F636, M1-P635, M1-F634, M1-H633, M1-N632, M1-I631, M1-E630, M1-P629, M1-D628, M1-D627, M1-L626, M1-D625, M1-I624, M1-D623, M1-V622, M1-E621, M1-E620, M1-E619, M1-R618, M1-K617, M1-K616, M1-T615, M1-T614, M1-K613, M1-R612, M1-G611, M1-R610, M1-R609, M1-L608, M1-P607, M1-I606, M1-D605, M1-D604, M1-E603, M1-M602, M1-G601, M1-L600, M1-L599, M1-K598, M1-L597, M1-A596, M1-K595, M1-P594, M1-R593, M1-K592, M1-P591, M1-G590, M1-F589, M1-L588, M1-N587, M1-H586, M1-Y585, M1-L584, M1-T583, M1-R582, M1-F581, M1-R580, M1-K579, M1-R578, M1-T577, M1-Y576, M1-N575, M1-C574, M1-R573, M1-Y572, M1-A571, M1-G570, M1-G569, M1-M568, M1-L567, M1-Y566, M1-E565, M1-I564, M1-V563, M1-L562, M1-G561, M1-I560, M1-D559, M1-I558, M1-L557, M1-S556, M1-I555, M1-R554, M1-Y553, M1-D552, M1-P551, M1-P550, M1-L549, M1-N548, M1-G547, M1-K546, M1-K545, M1-V544, M1-D543, M1-R542, M1-V541, M1-L540, M1-H539, M1-Y538, M1-L537, M1-T536, M1-N535, M1-S534, M1-P533, M1-G532, M1-H531, M1-R530, M1-T529, M1-N528, M1-Y527, M1-L526, M1-E525, M1-E524, M1-L523, M1-R522, M1-S521, M1-I520, M1-T519, M1-L518, M1-F517, M1-R516, M1-H515, M1-M514, M1-S513, M1-V512, M1-G511, M1-N510, M1-E509, M1-I508, M1-L507, M1-L506, M1-K505, M1-V504, M1-F503, M1-D502, M1-V501, M1-R500, M1-D499, M1-L498, M1-V497, M1-L496, M1-A495, M1-D494, M1-L493, M1-M492, M1-A491, M1-Q490, M1-E489, M1-L488, M1-S487, M1-G486, M1-V485, M1-P484, M1-W483, M1-Q482, M1-Q481, M1-G480, M1-Y479, M1-I478, M1-F477, M1-I476, M1-Q475, M1-S474, M1-R473, M1-A472, M1-I471, M1-D470, M1-V469, M1-R468, M1-N467, M1-W466, M1-A465, M1-L464, M1-A463, M1-L462, M1-S461, M1-L460, M1-Q459, M1-D458, M1-P457, M1-A456, M1-S455, M1-A454, M1-N453, M1-A452, M1-G451, M1-K450, M1-L449, M1-L448, M1-A447, M1-T446, M1-L445, M1-I444, M1-A443, M1-L442, M1-D441, M1-I440, M1-D439, M1-Q438, M1-H437, M1-G436, M1-E435, M1-S434, M1-G433, M1-M432, M1-R431, M1-F430, M1-V429, M1-T428, M1-I427, M1-L426, M1-E425, M1-K424, M1-K423, M1-K422, M1-M421, M1-C420, M1-E419, M1-M418, M1-L417, M1-I416, M1-I415, M1-F414, M1-L413, M1-H412, M1-Q411, M1-A410, M1-Q409, M1-T408, M1-R407, M1-T406, M1-Y405, M1-T404, M1-F403, M1-T402, M1-K401, M1-Q400, M1-I399, M1-T398, M1-V397, M1-L396, M1-L395, M1-Q394, M1-D393, M1-R392, M1-L391, M1-S390, M1-E389, M1-N388, M1-I387, M1-L386, M1-G385, M1-G384, M1-E383, M1-E382, M1-S381, M1-Y380, M1-K379, M1-H378, M1-G377, M1-F376, M1-A375, M1-L374, M1-I373, M1-D372, M1-S371, M1-A370, M1-R369, M1-G368, M1-S367, M1-G366, M1-D365, M1-C364, M1-V363, M1-V362, M1-V361, M1-P360, M1-V359, M1-P358, M1-P357, M1-T356, M1-D355, M1-R354, M1-L353, M1-Y352, M1-E351, M1-L350, M1-V349, M1-I348, M1-S347, M1-I346, M1-V345, M1-N344, M1-P343, M1-G342, M1-G341, M1-E340, M1-V339, M1-I338, M1-L337, M1-A336, M1-V335, M1-V334, M1-P333, M1-V332, M1-G331, M1-Q330, M1-G329, M1-I328, M1-R327, M1-T326, M1-N325, M1-I324, M1-K323, M1-Q322, M1-L321, M1-S320, M1-I319, M1-H318, M1-K317, M1-E316, M1-L315, M1-Q314, M1-R313, M1-R312, M1-L311, M1-K310, M1-V309, M1-E308, M1-A307, M1-G306, M1-Y305, M1-K304, M1-G303, M1-T302, M1-T301, M1-G300, M1-N299, M1-D298, M1-A297, M1-L296, M1-I295, M1-F294, M1-H293, M1-S292, M1-H291, M1-M290, M1-S289, M1-N288, M1-L287, M1-V286, M1-T285, M1-L284, M1-K283, M1-S282, M1-M281, M1-P280, M1-N279, M1-S278, M1-M277, M1-T276, M1-Q275, M1-Y274, M1-P273, M1-R272, M1-V271, M1-V270, M1-R269, M1-R268, M1-G267, M1-I266, M1-L265, M1-D264, M1-E263, M1-Q262, M1-N261, M1-E260, M1-V259, M1-I258, M1-I257, M1-W256, M1-P255, M1-A254, M1-I253, M1-G252, M1-I251, M1-T250, M1-C249, M1-I248, M1-K247, M1-G246, M1-R245, M1-S244, M1-K243, M1-S242, M1-A241, M1-H240, M1-D239, M1-K238, M1-L237, M1-A236, M1-D235, M1-G234, M1-V233, M1-H232, M1-R231, M1-I230, M1-V229, M1-G228, M1-T227, M1-N226, M1-V225, M1-G224, M1-G223, M1-T222, M1-F221, M1-I220, M1-W219, M1-A218, M1-G217, M1-T216, M1-T215, M1-M214, M1-A213, M1-A212, M1-K211, M1-I210, M1-L209, M1-G208, M1-K207, M1-G206, M1-F205, M1-V204, M1-Q203, M1-K202, M1-L201, M1-K200, M1-P199, M1-Q198, M1-L197, M1-E196, M1-F195, M1-N194, M1-Q193, M1-L192, M1-G191, M1-G190, M1-H189, M1-V188, M1-S187, M1-I186, M1-L185, M1-L184, M1-K183, M1-P182, M1-L181, M1-E180, M1-L179, M1-Q178, M1-W177, M1-E176, M1-K175, M1-T174, M1-M173, M1-L172, M1-H171, M1-L170, M1-L169, M1-L168, M1-D167, M1-P166, M1-K165, M1-T164, M1-D163, M1-F162, M1-S161, M1-V160, M1-R159, M1-V158, M1-Y157, M1-M156, M1-A155, M1-K154, M1-N153, M1-S152, M1-H151, M1-G150, M1-G149, M1-G148, M1-Q147, M1-F146, M1-E145, M1-I144, M1-T143, M1-G142, M1-F141, M1-A140, M1-D139, M1-T138, M1-P137, M1-S136, M1-L135, M1-Q134, M1-T133, M1-H132, M1-K131, M1-S130, M1-I129, M1-S128, M1-W127, M1-K126, M1-E125, M1-S124, M1-Q123, M1-I122, M1-D121, M1-N120, M1-R119, M1-S118, M1-L117, M1-R116, M1-S115, M1-E114, M1-N113, M1-K112, M1-E111, M1-N111, M1-Q109, M1-L108, M1-V107, M1-S106, M1-I105, M1-S104, M1-P103, M1-T102, M1-L10, M1-G100, M1-V99, M1-H98, M1-Q97, M1-G96, M1-I95, M1-L94, M1-R93, M1-G92, M1-C91, M1-C90, M1-C89, M1-R88, M1-H87, M1-P86, M1-D85, M1-K84, M1-T83, M1-S82, M1-P81, M1-I80, M1-I79, M1-H78, M1-V77, M1-C76, M1-E75, M1-R74, M1-K73, M1-Y72, M1-F71, M1-A70, M1-R69, M1-E68, M1-I67, M1-W66, M1-S65, M1-K64, M1-Q63, M1-A62, M1-P61, M1-T60, M1-Q59, M1-Q58, M1-S57, M1-P56, M1-L55, M1-G54, M1-S53, M1-R52, M1-K51, M1-T50, M1-S49, M1-G48, M1-Q47, M1-K46, M1-S45, M1-S44, M1-L43, M1-R42, M1-K41, M1-W40, M1-S39, M1-E38, M1-A37, M1-F36, M1-R35, M1-G34, M1-R33, M1-S32, M1-A31, M1-S30, M1-R29, M1-S28, M1-R27, M1-R26, M1-R25, M1-S24, M1-E23, M1-A22, M1-N21, M1-D20, M1-E19, M1-R18, M1-D17, M1-S16, M1-C15, M1-G14, M1-R13, M1-E12, M1-M11, M1-E10, M1-A9, M1-A8, and/or M1-D7 of SEQ ID NO:6. Polynucleotide sequences encoding these polypeptides are also provided. The present invention also encompasses the use of these C-terminal LTRPC3i deletion polypeptides as immunogenic and/or antigenic epitopes as described elsewhere herein.

Alternatively, preferred polypeptides of the present invention may comprise polypeptide sequences corresponding to, for example, internal regions of the LTRPC3i polypeptide (e.g., any combination of both N- and C-terminal LTRPC3i polypeptide deletions) of SEQ ID NO:6. For example, internal regions could be defined by the equation: amino acid NX to amino acid CX, wherein NX refers to any N-terminal deletion polypeptide amino acid of LTRPC3i (SEQ ID NO:6), and where CX refers to any C-terminal deletion polypeptide amino acid of LTRPC3i (SEQ ID NO:6). Polynucleotides encoding these polypeptides are also provided. The present invention also encompasses the use of these polypeptides as an immunogenic and/or antigenic epitope as described elsewhere herein.

Many polynucleotide sequences, such as EST sequences, are publicly available and accessible through sequence databases. Some of these sequences are related to SEQ ID NO:5 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 5223 of SEQ ID NO:5, b is an integer between 15 to 5237, where both a and b correspond to the positions of nucleotide residues shown in SEQ ID NO:5, and where b is greater than or equal to a+14.

Features of the Polypeptide Encoded by Gene No:4

The polypeptide of this gene provided as SEQ ID NO:8 (FIGS. 4A-F), encoded by the polynucleotide sequence according to SEQ ID NO:7 (FIGS. 4A-F), and/or encoded by the polynucleotide contained within the deposited clone, LTRPC3j, has significant homology at the nucleotide and amino acid level to the human melastatin 1 protein (Melastatin1; Genbank Accession No. gi|3243075; SEQ ID NO:13). An alignment of the LTRPC3j polypeptide with this protein is provided in FIGS. 7A-G.

The LTRPC3j polypeptide was determined to share 65.4% identity and 73.3% similarity with the human melastatin 1 protein (Melastatin1; Genbank Accession No. gi|3243075; SEQ ID NO:13) as shown in FIG. 10.

The LTRPC3k protein is believed to represent a member of a new class of protein kinases referred to as alpha kinases (Curr. Biol. 9 (2), R43-R45 (1999)). These kinases represent a novel type of signaling molecule comprising both a catalytic protein kinase domain, in addition to, an ion channel domain. This family is commonly referred to as the transient receptor potential channel (TRP) family. Melastatin1 defines a separate subfamily of TRP channels referred to as TRPM (melastatin1). TRPM family members are characteristic of their unusually long cytoplasmic tails at both ends of the channel domain and some of the family members contain an enzyme domain at the C-terminal region.

Specifically, the LTRPC3j (SEQ ID NO:8) polypeptide represents a novel variant of the LTRPC3d (Co-pending U.S. Ser. No. 10/210,152, filed Aug. 1, 2002; International Publication No. WO 03/012063, published Feb. 13, 2003; SEQ ID NO:19; and also co-pending U.S. Ser. No. 10/405,793, filed Mar. 28, 2003; which are hereby incorporated by reference herein in their entirety) polypeptide. The LTRPC3j represents a novel member of the TRPM subfamily.

The melastatin1 protein is believed to be negatively associated with the incidence of melanoma based upon its inverse correlative expression in highly aggressive melanomas (Genomics 54 (1), 116-123 (1998)). Thus, overexpression of melastatin1 could represent a novel therapeutic in the treatment of melanoma and potentially other cancers.

Based upon the observed homology, the polypeptide of the present invention is expected to share at least some biological activity with other transient receptor potential channel family members, more specifically with the melastatin1 protein, in addition to, other transient receptor potential channel family members referenced elsewhere herein or otherwise known in the art, particularly LTRPC3d, and LTRPC3.

Most of the known transient receptor potential channel family members, possess one or more transmembrane domains. Likewise, the LTRPC3j polypeptide has been determined to comprise six transmembrane domains (TM1-TM6) as shown in FIGS. 4A-F. The transmembrane domains are located from about amino acid 775 to about amino acid 792 (TM1), from about amino acid 872 to about amino acid 888 (TM2), from about amino acid 945 to about amino acid 958 (TM3), from about amino acid 972 to about amino acid 988 (TM4), from about amino acid 1006 to about amino acid 1023 (TM5), and/or from about amino acid 1115 to about amino acid 1125 (TM6) of SEQ ID NO:8. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following transmembrane domain polypeptides are encompassed by the present invention: LKVILGILLPPSILSLEF (SEQ ID NO:64), IVKFW-FYTLAYIGYLMLF (SEQ ID NO:65), VTDLIAILLFS-VGM (SEQ ID NO:66), RVIYCVNIIYWYIRLLDI (SEQ ID NO:67), MMIDMMYFVIIMLVVLMS (SEQ ID NO:68), and/or AIMACYLLVANILLVNLLIAV (SEQ ID NO:69). Polynucleotides encoding these polypeptides are also provided. The present invention also encompasses the use of the LTRPC3j transmembrane polypeptides as immunogenic and/or antigenic epitopes as described elsewhere herein.

The present invention also encompasses polypeptides corresponding to the regions between each transmembrane domain of LTRPC3j, referred to herein as inter-transmembrane domain polypeptides (inter TM1-2, inter TM2-3, inter TM3-4, inter TM4-5, and inter TM5-6). Such regions are typically solvent accessible (either extracellularly or intracellularly). Therefore, these regions are amenable to the development of agonists and/or antagonists to the LTRPC3j polypeptide, particularly for the development of antibodies specific to these regions.

In preferred embodiments, the following inter-transmembrane domain polypeptides are encompassed by the present invention: KNKDDMPYMSQAQEIHLQEKEAEEPE-KPTKEKEEEDMELTAMLGRNNGESS RKKDEEEVQSKHRLIPLGRKIYEFYNAP (SEQ ID NO:70), NYIVLVKMERWPSTQEWIVISYIFTLG-IEKMREILMSEPGKLLQKVKVWLQEYWN (SEQ ID NO:71), ILRLQDQPFRSDG (SEQ ID NO:72), FGVNKY-LGPYVMMIGK (SEQ ID NO:73), and/or FGVARQAILF-PNEEPSWKLAKNIFYMPYWMIYGEVFAD-QIDRKQVYDSHTPK SAPCGQNETREDGKIIQLPPCKTGAWIVP (SEQ ID NO:74). Polynucleotides encoding these polypeptides are also provided. The present invention also encompasses the use of the LTRPC3j inter-transmembrane polypeptides as immunogenic and/or antigenic epitopes as described elsewhere herein.

The LTRPC3j polypeptide was determined to comprise several conserved cysteines, at amino acid 249, 364, 420, 574, 662, 727, 744, 966, 1057, 1074, 1087, 1190, 1281, and 1547 of SEQ ID NO:8 (FIGS. 4A-F). Conservation of cysteines at key amino acid residues is indicative of conserved structural features, which may correlate with conservation of protein function and/or activity.

In confirmation of the LTRPC3j representing a member of the transient receptor channel family, the LTRPC3j polypeptide was determined to comprise a predicted TRP domain located from about amino acid 1118 to about amino acid 1123 of SEQ ID NO:8. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following TRP domain polypeptide is encompassed by the present invention: VWK-FQR (SEQ ID NO:75). Polynucleotides encoding this polypeptide are also provided. The present invention also encompasses the use of this LTRPC3j TRP domain polypeptide as an immunogenic and/or antigenic epitope as described elsewhere herein.

In further confirmation of the LTRPC3j representing a member of the transient receptor channel family, the LTRPC3j polypeptide was determined to comprise a predicted ion transport signature domain located at about amino acid 893 to about amino acid 1104 of SEQ ID NO:8. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following ion transport signature domain polypeptide is encompassed by the present invention: TQEWIVISYIFTLGIEKMREILM-SEPGKLLQKVKVWLQEYWNVTDLIAILLFSV GMIL-RLQDQPFRSDGRVIYCVNIIYWYIRLL-DIFGVNKYLGPYVMMIGKMMID MMYFVIIMLVVLMSFGVARQAILFP-NEEPSWKLAKNIFYMPYWMIYGEVFAD QIDP-PCGQNETREDGKIIQLPPCKTGAWIV-PAIMACYLLVANILLVNLLIAVF (SEQ ID NO:76). Polynucleotides encoding this polypeptide are also provided. The present invention also encompasses the use of this LTRPC3j ion transport signature domain polypeptide as an immunogenic and/or antigenic epitope as described elsewhere herein.

The LTRPC3j polypeptide was determined to comprise a predicted predicted coiled-coil domain located at about amino acid 1208 to about amino acid 1263 of SEQ ID NO:8. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following coiled-coil domain polypeptide is encompassed by the present invention: ERIRVTSERVENMSMRLEEVNEREH-SMKASLQTVDIRLAQLEDLIGRMATAL ERL (SEQ ID NO:77). Polynucleotides encoding this polypeptide are also provided. The present invention also encompasses the use of this LTRPC3j coiled-coil domain polypeptide as an immunogenic and/or antigenic epitope as described elsewhere herein.

LTRPC3j polypeptides and polynucleotides are useful for diagnosing diseases related to the over and/or under expression of LTRPC3j by identifying mutations in the LTRPC3j gene using LTRPC3j sequences as probes or by determining LTRPC3k protein or mRNA expression levels. LTRPC3j polypeptides will be useful in screens for compounds that affect the activity of the protein. LTRPC3j peptides can also be used for the generation of specific antibodies and as bait in yeast two hybrid screens to find proteins the specifically interact with LTRPC3j.

Since the LTRPC3j polypeptide represents an N-terminally extended variant of the LTRPC3d polypeptide (see polypeptide alignment provided in FIG. 11A-I), and since the LTRPC3d (SEQ ID NO: 19) polypeptide represents a splice variant of the LTRPC3 polypeptide (SEQ ID NO:15), the LTRPC3j (SEQ ID NO:8) polypeptide of the present invention is expected to have the same or similar function as the LTRPC3 polypeptide, and in particular, the LTRPC3d polypeptide. Specifically, the LTRPC3j polypeptide is expected to localize to the cell membrane.

Moreover, the LTRPC3j polypeptide is expected to also localize in or near the plasmalemmal compartment.

Moreover, the LTRPC3j polypeptide is also expected to be a constitutively active channel capable of mediating $Ca^{2+}$ influx.

Moreover, the LTRPC3j polypeptide is also expected to mediate $Ca^{2+}$ entry and that LTRPC3k -mediated $Ca^{2+}$ entry is expected to be potentiated by store-depletion.

Moreover, the LTRPC3j polypeptide is also expected to mediate a $Ca^{2+}$ entry pathway that is distinct from the endogenous $Ca^{2+}$ entry pathways present in HEK 293 cells.

Moreover, the LTRPC3j polypeptide of the present invention is expected to share the same or similar expression profile as that of the LTRPC3 polypeptide (SEQ ID NO:15).

Moreover, the LTRPC3j polypeptide is expected to share the same or similar differential expression patterns observed for the LTRPC3 variant.

Moreover, the LTRCP3g polypeptide is expected to be able to modulate the FEN1 DNA base-excision repair/proliferation modulating protein to the same or similar extent as the LTRPC3 polypeptide.

Moreover, the LTRPC3j polynucleotides and polypeptides are expected to share at least some biological activity with TRP family members expressed in kidney cells and tissues, particularly those specifically referenced herein, such as LTRPC3 (SEQ ID NO:15), and particularly as LTRPC3b (SEQ ID NO:17).

Moreover, the LTRPC3j polynucleotides and polypeptides are expected to share at least some biological activity with TRP family members expressed in testis cells and tissues, particularly those specifically referenced herein, such as the LTRPC3 variant (SEQ ID NO:15), and particularly as LTRPC3d (SEQ ID NO:19).

In preferred embodiments, LTRPC3j polynucleotides and polypeptides, including fragments and modulators thereof, are useful for treating, diagnosing, and/or ameliorating $Ca^{2+}$ reabsorption disorders, disorders associated with aberrant luminal Ca2+ entry via the epithelial Ca2+ channel (ECaC), disorders associated with aberrant cytosolic diffusion of Ca2+ bound to calbindin-D28K, disorders associated with aberrant basolateral extrusion of Ca2+ through the Na+/Ca2+ exchanger (NCX), disorders associated with aberrant plasma membrane Ca2+-ATPase (PMCA) activity and/or activation, disorders associated with the hypocalciuric effect of diuretics, disorders associated with the hypocalciuric effect of thiazide diuretics, disorders associated with hormone insufficiencies that affect the function of the kidney, disorders associated with hormone insufficiencies that affect renal Ca2+ homeostasis, disorders associated with aberrant renal Ca2+ homeostasis as a result of vitamin D deficiency, disorders associated with aberrant renal Ca2+ homeostasis as a result of PTH deficiency, disorders associated with aberrant renal Ca2+ homeostasis as a result of vasopressin deficiency, disorders associated with aberrant renal Ca2+ homeostasis as a result of prostaglandines deficiency, disorders associated with aberrant renal Ca2+ homeostasis as a result of estrogen deficiency, disorders associated with aberrant renal Ca2+ homeostasis as a result of calcitonin deficiency, disorders associated with aberrant renal Ca2+ homeostasis as a result of parathyroid hormone deficiency, disorders associated with aberrant renal Ca2+ homeostasis as a result of atrial natriuretic peptide deficiency, calcium homeostasis-related disorders, hypercaliuric nephrolithiasis, certain forms of osteoporosis, Gitelman's disease, Bartter's syndrom, disorders associated with aberrant function of kidney tubular epithelium, disorders associated with aberrant function of kidney tubular epithelium in the medulla, disorders associated with aberrant function of kidney tubular epithelium in the medullary rays, disorders associated with aberrant function of kidney tubular epithelium in the periglomerular.

In preferred embodiments, LTRPC3j polynucleotides and polypeptides, including fragments and modulators thereof, are useful for treating, diagnosing, and/or ameliorating acute kidney failure, chronic kidney failure, cystic kidney disease, horseshoe kidney, hypertensive kidney disease, kidney atrophy, kidney cancer, kidney disease, kidney failure, kidney infection, kidney metastasis, kidney stone, nephrolithiasis, multicystic dysplastic kidney disease, and polycystic kidney disease.

Characterization of the LTRPC3 variant polypeptide using antisense oligonucleotides led to the determination that LTRPC3 is involved in the negative modulation of the FEN1 DNA base-excision repair/proliferation modulating protein as described in Example 5 herein.

The LTRCP3g polypeptide is expected to be able to modulate the FEN1 DNA base-excision repair/proliferation modulating protein to the same or similar extent as the LTRPC3 polypeptide.

Specifically, antisense inhibition of LTRPC3 resulted in upregulation of Fen1, a marker of proliferation. As such, LTRPC3 behaves in a manner similar to a tumor suppressor, in that loss results in increases in proliferation. While some increases in the proliferation markers p21 and IkB were also observed, they were less significant, and could be a response to the pro-proliferative effect of LTRPC3 antisense inhibition. Interestingly, expression of LTRPC3 was also observed to be significantly reduced in tumor tissues, relative to normal tissues (see FIG. 13). Specifically, renal, testicular, and ovarian tumor samples showed as much as 12 to 30 fold down regulation of LTRPC3 message levels compared to normal tissues. This reduction of LTRPC3 correlating with the tumor state is consistent with the negative FEN1 modulatory activity and suggests this gene may have antiproliferative activities. Therefore, for modulators of LTRPC3j to be useful for treating cancer, it would be necessary to increase the activity of the gene or gene product in order to have the reverse effect on cancerous cells. Thus, an agonist of LTRPC3j activity or a compound that increased LTRPC3j message levels would be a desired invention for cancer therapy.

In preferred embodiments, LTRPC3j polynucleotides and polypeptides, including fragments and modulators thereof, are useful for treating, diagnosing, and/or ameliorating DNA-repair deficiencies, particularly base-excision repair deficiencies, Xeroderma pigmentosum, skin cancer, melanoma, UV senstivity, alkylation sensivity, gamma irradiation sensitivity, pyrimidine dimer sensitivity, chemical mutagenes, lymphomas, leukemias, photosensitivity, Bloom's syndrone, Fanconi's anemia, ataxia telangiectasia, chromosomal aberrations, blood vessel dilation aberrations in the skin, blood vessel dilation aberrations in the eye, conditions involving increased levels of apurinic sites, conditions involving increased levels of apyrimidinic sites, conditions involving increased levels of abasic sites, disorders related to aberrant signal transduction, proliferating disorders, and/or cancers.

Moreover, LTRPC3j polynucleotides and polypeptides, including fragments and modulators thereof, are useful for increasing mammalian base excision repair activity, increasing mammalian single-nucleotide base excision repair activity, and/or increasing mammalian long patch base excision repair activity.

In preferred embodiments, antagonists directed against LTRPC3j are useful for treating, diagnosing, and/or ameliorating DNA-repair deficiencies, particularly base-excision repair deficiencies, Xeroderma pigmentosum, skin cancer, melanoma, UV senstivity, alkylation sensivity, gamma irradiation sensitivity, pyrimidine dimer sensitivity, chemical mutagenes, lymphomas, leukemias, photosensitivity, Bloom's syndrone, Fanconi's anemia, ataxia telangiectasia, chromosomal aberrations, blood vessel dilation aberrations in the skin, blood vessel dilation aberrations in the eye, conditions involving increased levels of apurinic sites, conditions involving increased levels of apyrimidinic sites, conditions involving increased levels of abasic sites, disorders related to aberrant signal transduction, proliferating disorders, and/or cancers.

Moreover, antagonists directed against LTRPC3j are useful for increasing mammalian base excision repair activity, increasing mammalian single-nucleotide base excision repair activity, and/or increasing mammalian long patch base excision repair activity.

In preferred embodiments, agonists directed against LTRPC3j are useful for treating, diagnosing, and/or ameliorating, disorders related to aberrant signal transduction, proliferating disorders, and/or cancers, particularly renal cell carcinomas, testicular cancers, and/or ovarian cancers.

Moreover, agonists directed against LTRPC3j are useful for decreasing mammalian base excision repair activity, decreasing mammalian single-nucleotide base excision repair activity, and/or decreasing mammalian long patch base excision repair activity.

The strong homology to human transient receptor potential channels (TRP), combined with the predominate localized expression in kidney tissue of the LTRPC3 variant, suggests the LTRPC3j polynucleotides and polypeptides, including modulators or fragments thereof, may be useful in treating, diagnosing, prognosing, and/or preventing renal diseases and/or disorders, which include, but are not limited to: nephritis, renal failure, nephrotic syndrome, urinary tract infection, hematuria, proteinuria, oliguria, polyuria, nocturia, edema, hypertension, electrolyte disorders, sterile pyuria, renal osteodystrophy, large kidneys, renal transport defects, nephrolithiasis, azotemia, anuria, urinary retention ,slowing of urinary stream, large prostate, flank tenderness, full bladder sensation after voiding, enuresis, dysuria, bacteriuria, kidney stones, glomerulonephritis, vasculitis, hemolytic uremic syndromes, thrombotic thrombocytopenic purpura, malignant hypertension, casts, tubulointerstitial kidney diseases, renal tubular acidosis, pyelonephritis, hydronephritis, nephrotic syndrome, crush syndrome, and/or renal colic, in addition to Wilm's Tumor Disease, and congenital kidney abnormalities such as horseshoe kidney, polycystic kidney, and Falconi's syndrome for example.

Several known TRP family members have been identified that are expressed significantly in kidney tissue. These TRP family members include, for example, Trp12 (Wissenbach, U., Bodding, M., Freichel, M., Flockerzi, V, Lett., 485(2-3): 127-34, (2000)); OTRPC4 (Strotmann, R., Harteneck, C., Nunnenmacher, K., Schultz, G., Plant, T, D, Nat, Cell, Biol., 2(10):695-702, (2000)); polycystin-L2 (Guo, L., Schreiber, T, H., Weremowicz, S., Morton, C, C., Lee, C., Zhou, J. Genomics., 64(3):241-51, (2000)); and EcaC (Hoenderop, J. G., van, der, Kemp, A, W., Hartog, A., van, de, Graaf, S, F., van, Os, C, H., Willems, P, H., Bindels, R, J. J. Biol, Chem., 274(13):8375-8, (1999)).

Thus, the LTRPC3j polynucleotides and polypeptides are expected to share at least some biological activity with TRP family members expressed in kidney cells and tissues, particularly those specifically referenced herein, such as LTRPC3 (SEQ ID NO:15).

The strong homology to human transient receptor potential channels (TRP) proteins, combined with the localized expression in spinal cord and brain of the LTRPC3 variant, suggests the LTRPC3j polynucleotides and polypeptides, including modulators or fragments thereof, may be useful in treating, diagnosing, prognosing, and/or preventing neurodegenerative disease states, behavioral disorders, or inflammatory conditions. Representative uses are described in the "Regeneration" and "Hyperproliferative Disorders" sections below, in the Examples, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The strong homology to human transient receptor potential channels (TRP), combined with the localized expression in testis tissue of the LTRPC3 variant emphasizes the potential utility for LTRPC3j polynucleotides and polypeptides in treating, diagnosing, prognosing, and/or preventing testicular, in addition to reproductive disorders.

In preferred embodiments, LTRPC3j polynucleotides and polypeptides including agonists and fragments thereof, have uses which include treating, diagnosing, prognosing, and/or preventing the following, non-limiting, diseases or disorders of the testis: spermatogenesis, infertility, Klinefelter's syndrome, XX male, epididymitis, genital warts, germinal cell aplasia, cryptorchidism, varicocele, immotile cilia syndrome, and viral orchitis. The LTRPC3j polynucleotides and polypeptides including agonists and fragments thereof, may also have uses related to modulating testicular development, embryogenesis, reproduction, and in ameliorating, treating, and/or preventing testicular proliferative disorders (e.g., cancers, which include, for example, choriocarcinoma, Non-seminoma, seminoma, and testicular germ cell tumors).

Likewise, the localized expression in testis tissue also emphasizes the potential utility for LTRPC3j polynucleotides and polypeptides in treating, diagnosing, prognosing, and/or preventing metabolic diseases and disorders which include the following, not limiting examples: premature puberty, incomplete puberty, Kallman syndrome, Cushing's syndrome, hyperprolactinemia, hemochromatosis, congenital adrenal hyperplasia, FSH deficiency, and granulomatous disease, for example.

This gene product may also be useful in assays designed to identify binding agents, as such agents (antagonists) are useful as male contraceptive agents. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

Several known TRP family members have been identified that are expressed significantly in testis tissue. These TRP family members include, for example, polycystin-L2 (Guo, L., Schreiber, T, H., Weremowicz, S., Morton, C, C., Lee, C., Zhou, J. Genomics., 64(3):241-51, (2000)); TRP7 (Okada, T., Inoue, R., Yamazaki, K., Maeda, A., Kurosaki, T., Yamakuni, T., Tanaka, I., Shimizu, S., Ikenaka, K., Imoto, K., Mori, Y, J. Biol, Chem., 274(39):27359-70, (1999)); btrp2 (Wissenbach, U., Schroth, G., Philipp, S., Flockerzi, V, Lett., 429(1):61-6, (1998)); Htrp-1 (Zhu, X., Chu, P, B., Peyton, M., Bimbaumer, L, Lett., 373(3):193-8, (1995)); and TRPC1 (Wes, P, D., Chevesich, J., Jeromin, A., Rosenberg, C., Stetten, G., Montell, C, Proc, Natl, Acad, Sci, U, S, A., 92(21):9652-6, (1995)).

Thus, the LTRPC3j polynucleotides and polypeptides are expected to share at least some biological activity with TRP family members expressed in testis cells and tissues, particularly those specifically referenced herein, such as the LTRPC3 variant (SEQ ID NO:15).

As described elsewhere herein, transient receptor potential channel family members have been implicated in modulating cell proliferation, differentiation, migration, activation, exocytosis, muscle contraction, gene expression, apoptosis. signalling, pheromone sensory signaling, smooth muscle tone, pain perception, heat perception, osmosentivity, and mechanosensitivity. Moreover, transient receptor potential channel family members have been implicated in disorders of the skin, skeletal-muscle, nervous, cardiac, and vascular systems, in addition to the following, non-limiting diseases and disorders, which include, for example, arteriosclerosis, neointimal hypoerplasia, metastatic melanomas, bipolar disorder, nonsyndromic hereditary deafness, Knobloch syndrome, holosencephaly, and various maligancies including prostate cancer.

In preferred embodiments, LTRPC3j polynucleotides and polypeptides of the present invention, including agonists and/or fragments thereof, have uses that include, modulating cell proliferation, differentiation, migration, activation, exocytosis, muscle contraction, gene expression, apoptosis. signalling, pheromone sensory signaling, smooth muscle tone, pain perception, heat perception, osmosentivity, and mechanosensitivity.

In more preferred embodiments, LTRPC3j polynucleotides and polypeptides of the present invention, including agonists and/or fragments thereof, have uses that include, treating, ameliorating, preventing, detecting, and/or prognosing various diseases and disorders, particularly the following, non-limiting examples, disorders of the skin, skeletal-muscle, nervous, cardiac, and vascular systems, in addition to the following, non-limiting diseases and disorders, which include, for example, arteriosclerosis, neointimal hypoerplasia, metastatic melanomas, bipolar disorder, nonsyndromic hereditary deafness, Knobloch syndrome, holosencephaly, and various maligancies including prostate cancer.

LTRPC3j polynucleotides and polypeptides of the present invention, including agonists and/or fragments may be involved in intracellular $Ca^{2+}$ homeostasis which affects various aspects of biological functions including mechano-regulation, pain transduction, vasorelaxation, gene expression, cell cycle and proliferation/apoptosis. Since the LTRPC3 variant is dominantly expressed in kidney, the LTRPC3j polypeptide may particularly play an important role in regulating cytosolic Ca2+ in the renal system, potentially Ca2+ absorption.

The LTRPC3j gene maps to chromosome 9q21.11-21.31 between the two markers D9S1874 and D9S1807. This region is linked to amyotrophic lateral sclerosis with frontotemporal dementia, early-onset pulverulent cataract, infantile nephronophthisis, hypomagnesemia with secondary hypocalcemia (HSH), and familial hemophagocytic lymphohistiocytosis. Therefore, agonists and/or antagonists of the novel LTRPC3j can be used to treat diseases including various forms of neuronal degeneration, neurogenic inflammation, allergy, immunodeficiency/excessive immune activation, visual defects, hearing disorder, pain, cancer, hypertension and other cardiovascular diseases. In addition, the therapeutics may be useful in the treatment of diseases associated with disturbances in $Ca^{2+}$ homeostasis including osteoporosis, hypercalciuric stone disease, and chronic renal failure.

Moreover, given the selective expression in kidney, LTRPC3j could be considered a candidate gene for HSH, since the phenotype is a renal insufficiency. LTRPC3j chromosomal location is ~600 kb downstream of a X; 9 translocation breakpoint interval described for one patient with HSH (*Hum. Mol. Genet.* 6, 1491-1497, (1997)). Recently, two groups reported that a new member of the TRPM subfamily, TRPM6, expressed in both intestinal tissues and kidney, is associated with HSH (*Nat. Genet.* 31, 166-170, (2002); and *Nat. Genet.* 31, 171-174 (2002)). Indeed, LTRPC3j is ~4 mb 5' to TRPM6 on 9q21. Although TRPM6 is the first component identified for HSH, this should not preclude involvement of LTRPC3j in the disease. Therefore, it is possible that LTRPC3j may co-localize with TRPM6 and/or forms a heteromultimer with TRPM6 in the kidney.

The kidney plays a major role in $Ca^{2+}$ homeostasis (reviewed in *Physiol. Rev.* 75, 429-471, (1995)). LTRPC3j may play a direct role in $Ca^{2+}$ absorption due to its constitutive $Ca^{2+}$ permeability. Alternatively, LTRPC3j may be the SOC that regulates $Ca^{2+}$ absorption. In kidney, $Ca^{2+}$ absorption is regulated by agonists such as calcitonin, parathyroid hormone and parathyroid hormone-related peptide through their respective G protein-coupled receptors, and downstream SOCs. Additionally, in kidney a SOC has been described (*J. Biol. Chem.* 276, 25759-25765, (2001)) for the action of angiotensin II, a vasoactive peptide that plays a major role in regulating blood pressure.

In addition, LTRPC3j polynucleotides and polypeptides of the present invention, including agonists and/or fragments thereof, have uses that include modulating intracellular Ca++ ion concentrations, Ca++ ion flux, stored intracellular Ca++ ion concentrations, Ca++ ion pump activity, Ca++ ion flow into cell, Ca++ ion flow out of cells, the activation of Ca++ sensitive proteins, the activation of Ca++sensitive signaling pathways, the activation of kinase-activatible proteins, and the activation of kinase-dependent signaling pathways.

The LTRPC3j polynucleotides and polypeptides of the present invention, including agonists and/or fragments thereof, have uses that include modulating proliferation, differentiation, migration, and activation in various cells, tissues, and organisms, and particularly in mammalian kidney, spinal cord, testis, and brain, preferably human. LTRPC3j polynucleotides and polypeptides of the present invention, including agonists and/or fragments thereof, may be useful in diagnosing, treating, prognosing, and/or preventing renal, neural, and/or proliferative diseases or disorders, particularly of the renal system.

In addition, antagonists of the LTRPC3j polynucleotides and polypeptides, including modulators or fragments thereof, may have uses that include diagnosing, treating, prognosing, and/or preventing diseases or disorders related to transient receptor potential channel activity, which may include renal, neural, reproductive, and/or proliferative diseases or disorders.

Although it is believed the encoded polypeptide may share at least some biological activities with transient receptor potential channel family members, particularly those melastatin1, a number of methods of determining the exact biological function of this clone are either known in the art or are described elsewhere herein. Briefly, the function of this clone may be determined by applying microarray methodology. Nucleic acids corresponding to the LTRPC3j polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from tissue that has been treated with known transient potential receptor inhibitors, which include, but are not limited to the drugs listed herein or otherwise known in the art, might indicate a function in modulating transient potential receptor function, for example. In the case of LTRPC3j, kidney, spinal cord, testis, and brain, should be used to extract RNA to prepare the probe.

In addition, the function of the protein may be assessed by applying quantitative PCR methodology, for example. Real time quantitative PCR would provide the capability of following the expression of the LTRPC3j gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. Also encompassed by the present invention are quantitative PCR probes corresponding to the polynucleotide sequence provided as SEQ ID NO:1 (FIGS. 1A-E).

The function of the protein may also be assessed through complementation assays in yeast. For example, in the case of the LTRPC3j, transforming yeast deficient in transient receptor potential channel activity with LTRPC3j and assessing their ability to grow would provide convincing evidence the LTRPC3j polypeptide has transient receptor potential channel activity. Additional assay conditions and methods that may be used in assessing the function of the polynucleotides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a kidney, spinal cord, testis, and/or brain-specific promoter), or it can be expressed at a specified time of development using an inducible and/or a developmentally regulated promoter.

In the case of LTRPC3j transgenic mice or rats, if no phenotype is apparent in normal growth conditions, observing the organism under diseased conditions (renal, reproductive, neural, or proliferative disorders, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal LTRPC3j deletion polypeptides are encompassed by the present invention: M1-T1699, G2-T1699, K3-T1699, K4-T1699, W5-T1699, R6-T1699, D7-T1699, A8-T1699, A9-T1699, E10-T1699, M11-T1699, E12-T1699, R13-T1699, G14-T1699, C15-T1699, S16-T1699, D17-T1699, R18-T1699, E19-T1699, D20-T1699, N21-T1699, A22-T1699, E23-T1699, S24-T1699, R25-T1699, R26-T1699, R27-T1699, S28-T1699, R29-T1699, S30-T1699, A31-T1699, S32-T1699, R33-T1699, G34-T1699, R35-T1699, F36-T1699, A37-T1699, E38-T1699, S39-T1699, W40-T1699, K41-T1699, R42-T1699, L43-T1699, S44-T1699, S45-T1699, K46-T1699, Q47-T1699, G48-T1699, S49-T1699, T50-T1699, K51-T1699, R52-T1699, S53-T1699, G54-T1699, L55-T1699, P56-T1699, S57-T1699, Q58-T1699, Q59-T1699, T60-T1699, P61-T1699, A62-T1699, Q63-T1699, K64-T1699, S65-T1699, W66-T1699, I67-T1699, E68-T1699, R69-T1699, A70-T1699, F71-T1699, Y72-T1699, K73-T1699, R74-T1699, E75-T1699, C76-T1699, V77-T1699, H78-T1699, I79-T1699, I80-T1699, P81-T1699, S82-T1699, T83-T1699, K84-T1699, D85-T1699, P86-T1699, H87-T1699, R88-T1699, C89-T1699, C90-T1699, C91-T1699, G92-T1699, R93-T1699, L94-T1699, I95-T1699, G96-T1699, Q97-T1699, H98-T1699, V99-T1699, G100-T1699, L10-T1699, T102-T1699, P103-T1699, S104-T1699, I105-T1699, S106-T1699, V107-T1699, L108-T1699, Q109-T1699, N110-T1699, E111-T1699, K112-T1699, N113-T1699, E114-T1699, S115-T1699, R116-T1699, L117-T1699, S118-T1699, R119-T1699, N120-T1699, D121-T1699, I122-T1699, Q123-T1699, S124-T1699, E125-T1699, K126-T1699, W127-T1699, S128-T1699, I129-T1699, S130-T1699, K131-T1699, H132-T1699, T133-T1699, Q134-T1699, L135-T1699, S136-T1699, P137-T1699, T138-T1699, D139-T1699, A140-T1699, F141-T1699, G142-T1699, T143-T1699, I144-T1699, E145-T1699, F146-T1699, Q147-T1699, G148-T1699, G149-T1699, G150-T1699, H151-T1699, S152-T1699, N153-T1699, K154-T1699, and/or A155-T1699 of SEQ ID NO:8. Polynucleotide sequences encoding these polypeptides are also provided. The present invention also encompasses the use of these N-terminal LTRPC3j deletion polypeptides as immunogenic and/or antigenic epitopes as described elsewhere herein.

In preferred embodiments, the following C-terminal LTRPC3j deletion polypeptides are encompassed by the present invention: M1-T1699, M1-H1698, M1-K1697, M1-S1696, M1-E1695, M1-F1694, M1-S1693, M1-Q1692, M1-F1691, M1-A1690, M1-S1689, M1-T1688, M1-R1687, M1-S1686, M1-L1685, M1-R1684, M1-R1683, M1-M1682, M1-S1681, M1-L1680, M1-S1679, M1-D1678, M1-G1677, M1-R1676, M1-G1675, M1-E1674, M1-P1673, M1-K1672, M1-S1671, M1-S1670, M1-K1669, M1-S1668, M1-R1667, M1-Q1666, M1-F1665, M1-P1664, M1-N1663, M1-Q1662, M1-L1661, M1-S1660, M1-A1659, M1-T1658, M1-N1657, M1-R1656, M1-Q1655, M1-R1654, M1-D1653, M1-L1652, M1-K1651, M1-D1650, M1-S1649, M1-I1648, M1-S1647, M1-F1646, M1-S1645, M1-K1644, M1-R1643, M1-T1642, M1-H1641, M1-A1640, M1-Y1639, M1-P1638, M1-A1637, M1-S1636, M1-P1635, M1-E1634, M1-E1633, M1-A1632, M1-S1631, M1-Y1630, M1-S1629, M1-N1628, M1-A1627, M1-R1626, M1-E1625, M1-I1624, M1-K1623, M1-P1622, M1-V1621, M1-T1620, M1-I1619, M1-N1618, M1-N1617, M1-S1616, M1-L1615, M1-T1614, M1-R1613, M1-E1612, M1-S1611, M1-N1610, M1-D1609, M1-G1608, M1-E1607, M1-Q1606, M1-S1605, M1-S1604, M1-I1603, M1-A1602, M1-I1601, M1-T1600, M1-A1599, M1-R1598, M1-R1597, M1-G1596, M1-K1595, M1-A1594, M1-E1593, M1-N1592, M1-E1591, M1-E1590, M1-S1589, M1-D1588, M1-S1587, M1-S1586, M1-P1585, M1-H1584, M1-S1583, M1-L1582, M1-E1581, M1-A1580, M1-E1579, M1-R1578, M1-E1577, M1-P1576, M1-H1575, M1-C1574, M1-C1573, M1-T1572, M1-L1571, M1-D1570, M1-E1569, M1-V1568, M1-K1567, M1-D1566, M1-G1565, M1-L1564, M1-G1563, M1-G1562, M1-P1561, M1-F1560, M1-A1559, M1-A1558, M1-R1557, M1-D1556, M1-A1555, M1-I1554, M1-A1553, M1-Q1552, M1-P1551, M1-A1550, M1-N1549, M1-V1548, M1-C1547, M1-R1546, M1-T1545, M1-D1544, M1-I1543, M1-C1542, M1-D1541, M1-T1540, M1-I1539, M1-S1538, M1-T1537, M1-Y1536, M1-E1535, M1-A1534, M1-T1533, M1-K1532, M1-V1531, M1-P1530, M1-V1529, M1-G1528, M1-F1527, M1-N1526, M1-A1525, M1-Y1524, M1-Y1523, M1-S1522, M1-R1521, M1-S1520, M1-P1519, M1-S1518, M1-F1517, M1-M1516, M1-F1515, M1-S1514, M1-H1513, M1-S1512, M1-K1511, M1-V1510, M1-I1509, M1-P1508, M1-A1507, M1-E1506, M1-E1505, M1-L1504, M1-L1503, M1-F1502, M1-P1501, M1-T1500, M1-T1499, M1-A1498, M1-L1497,
M1-Y1496, M1-R1495, M1-S1494, M1-S1493, M1-K1492,
M1-S1491, M1-R1490, M1-E1489, M1-I1488, M1-T1487,
M1-H1486, M1-Y1485, M1-M1484, M1-P1483, M1-P1482,
M1-E1481, M1-S1480, M1-D1479, M1-W1478, M1-P1477,
M1-N1476, M1-Q1475, M1-C1474, M1-E1473, M1-P1472,
M1-L1471, M1-H1470, M1-T1469, M1-Y1468, M1-D1467,
M1-S1466, M1-S1465, M1-F1464, M1-S1463, M1-R1462,
M1-T1461, M1-D1460, M1-M1459, M1-S1458, M1-T1457,
M1-I1456, M1-D1455, M1-E1454, M1-F1453, M1-D1452,
M1-I1451, M1-S1450, M1-R1449, M1-S1448, M1-P1447,
M1-P1446, M1-R1445, M1-D1444, M1-T1443, M1-P1442,
M1-A1441, M1-L1440, M1-T1439, M1-A1438, M1-Y1437,
M1-A1436, M1-S1435, M1-S1434, M1-S1433, M1-P1432,
M1-A1431, M1-T1430, M1-S1429, M1-P1428, M1-V1427,
M1-P1426, M1-T1425, M1-S1424, M1-F1423, M1-S1422,
M1-P1421, M1-E1420, M1-G1419, M1-L1418, M1-G1417,
M1-L1416, M1-I1415, M1-N1414, M1-V1413, M1-S1412,
M1-N1411, M1-D1410, M1-L1409, M1-P1408, M1-D1407,
M1-I1406, M1-D1405, M1-C1404, M1-H1403, M1-L1402,
M1-E1401, M1-D1400, M1-M1399, M1-A1398, M1-S1397,
M1-V1396, M1-Y1395, M1-I1394, M1-D1393, M1-I1392,
M1-C1391, M1-S1390, M1-S1389, M1-P1388, M1-R1387,
M1-R1386, M1-S1385, M1-D1384, M1-P1383, M1-V1382,
M1-I1381, M1-A1380, M1-L1379, M1-T1378, M1-N1377,
M1-A1376, M1-P1375, M1-A1374, M1-A1373, M1-P1372,
M1-A1371, M1-K1370, M1-P1369, M1-E1368, M1-K1367,
M1-A1366, M1-V1365, M1-S1364, M1-H1363, M1-S1362,
M1-S1361, M1-T1360, M1-A1359, M1-R1358, M1-H1357,
M1-L1356, M1-S1355, M1-L1354, M1-S1353, M1-R1352,
M1-E1351, M1-K1350, M1-F1349, M1-I1348, M1-S1347,
M1-E1346, M1-L1345, M1-K1344, M1-E1343, M1-I1342,
M1-G1341, M1-G1340, M1-K1339, M1-D1338,
M1-K1337, M1-M1336, M1-N1335, M1-V1334,
M1-S1333, M1-Y1332, M1-F1331, M1-S1330, M1-H1329,
M1-S1328, M1-R1327, M1-M1326, M1-R1325, M1-P1324,
M1-M1323, M1-L1322, M1-T1321, M1-P1320, M1-S1319,
M1-T1318, M1-P1317, M1-S1316, M1-M1315, M1-T1314,
M1-E1313, M1-E1312, M1-G1311, M1-A1310, M1-P1309,
M1-D1308, M1-I1307, M1-S1306, M1-E1305, M1-Q1304,
M1-L1303, M1-K1302, M1-F1301, M1-T1300, M1-N1299,
M1-G1298, M1-E1297, M1-Q1296, M1-S1295, M1-N1294,
M1-F1293, M1-S1292, M1-S1291, M1-Q1290, M1-R1289,
M1-V1288, M1-I1287, M1-Y1286, M1-L1285, M1-A1284,
M1-D1283, M1-T1282, M1-C1281, M1-D1280, M1-S1279,
M1-S1278, M1-T1277, M1-R1276, M1-S1275, M1-R1274,
M1-I1273, M1-K1272, M1-N1271, M1-S1270, M1-E1269,
M1-A1268, M1-R1267, M1-E1266, M1-L1265, M1-G1264,
M1-T1263, M1-L1262, M1-R1261, M1-E1260, M1-L1259,
M1-A1258, M1-T1257, M1-A1256, M1-M1255,
M1-R1254, M1-G1253, M1-I1252, M1-L1251, M1-D1250,
M1-E1249, M1-L1248, M1-Q1247, M1-A1246, M1-L1245,
M1-R1244, M1-I1243, M1-D1242, M1-V1241, M1-T1240,
M1-Q1239, M1-L1238, M1-S1237, M1-A1236, M1-K1235,
M1-M1234, M1-S1233, M1-H1232, M1-E1231, M1-R1230,
M1-E1229, M1-N1228, M1-V1227, M1-E1226, M1-E1225,
M1-L1224, M1-R1223, M1-M1222, M1-S1221,
M1-M1220, M1-N1219, M1-E1218, M1-V1217,
M1-R1216, M1-E1215, M1-S1214, M1-T1213, M1-V1212,
M1-R1211, M1-I1210, M1-R1209, M1-E1208, M1-D1207,
M1-N1206, M1-S1205, M1-S1204, M1-N1203, M1-F1202,
M1-R1201, M1-D1200, M1-D1199, M1-K1198, M1-E1197,
M1-R1196, M1-F1195, M1-Y1194, M1-E1193, M1-E1192,
M1-I1191, M1-C1190, M1-Q1189, M1-E1188, M1-E1187,
M1-F1186, M1-D1185, M1-H1184, M1-V1183, M1-K1182,
M1-K1181, M1-L1180, M1-E1179, M1-D1178, M1-D1177,
M1-T1176, M1-I1175, M1-F1174, M1-L1173, M1-K1172,
M1-L1171, M1-G1170, M1-Y1169, M1-D1168, M1-R1167,
M1-E1166, M1-D1165, M1-P1164, M1-D1163, M1-S1162,
M1-E1161, M1-H1160, M1-K1159, M1-R1158,
M1-W1157, M1-R1156, M1-C1155, M1-C1154,
M1-L1153, M1-H1152, M1-Q1151, M1-F1150, M1-I1149,
M1-M1148, M1-T1147, M1-M1146, M1-H1145,
M1-S1144, M1-F1143, M1-I1142, M1-I1141, M1-L1140,
M1-P1139, M1-P1138, M1-P1137, M1-L1136, M1-V1135,
M1-P1134, M1-R1133, M1-E1132, M1-H1131, M1-F1130,
M1-T1129, M1-M1128, M1-I1127, M1-L1126, M1-Q1125,
M1-Y1124, M1-R1123, M1-Q1122, M1-F1121, M1-K1120,
M1-W1119, M1-V1118, M1-Q1117, M1-N1116,
M1-S1115, M1-I1114, M1-S1113, M1-K1112, M1-V1111,
M1-E1110, M1-F0109, M1-F1108, M1-T1107, M1-N1106,
M1-N1105, M1-F1104, M1-V1103, M1-A1102, M1-I1101,
M1-L1100, M1-L1099, M1-N1098, M1-V1097, M1-L1096,
M1-L1095, M1-I1094, M1-N1093, M1-A1092, M1-V1091,
M1-L1090, M1-L1089, M1-Y1088, M1-C1087, M1-A1086,
M1-M1085, M1-I1084, M1-A1083, M1-P1082, M1-V1081,
M1-I1080, M1-W1079, M1-A1078, M1-G1077, M1-T1076,
M1-K1075, M1-C1074, M1-P1073, M1-P1072, M1-L1071,
M1-Q1070, M1-I1069, M1-I1068, M1-K1067, M1-G1066,
M1-D1065, M1-E1064, M1-R1063, M1-T1062, M1-E1061,
M1-N1060, M1-Q1059, M1-G1058, M1-C1057, M1-P1056,
M1-P1055, M1-D1054, M1-I1053, M1-Q1052, M1-D1051,
M1-A1050, M1-F1049, M1-V1048, M1-E1047, M1-G1046,
M1-Y1045, M1-I1044, M1-M1043, M1-W1042,
M1-Y1041, M1-P1040, M1-M1039, M1-Y1038, M1-F1037,
M1-I1036, M1-N1035, M1-K1034, M1-A1033, M1-L1032,
M1-K1031, M1-W1030, M1-S1029, M1-P1028, M1-E1027,
M1-E1026, M1-N1025, M1-P1024, M1-F1023, M1-L1022,
M1-I1021, M1-A1020, M1-Q1019, M1-R1018, M1-A1017,
M1-VO16, M1-G1015, M1-F1014, M1-S1013, M1-M1012,
M1-L1011, M1-V1010, M1-V1009, M1-L1008,
M1-M1007, M1-I1006, M1-I1005, M1-V1004, M1-F1003,
M1-Y1002, M1-M1001, M1-M1000, M1-D999, M1-I998,
M1-M997, M1-M996, M1-K995, M1-G994, M1-I993,
M1-M992, M1-M991, M1-V990, M1-Y989, M1-P988,
M1-G987, M1-L986, M1-Y985, M1-K984, M1-N983,
M1-V982, M1-G981, M1-F980, M1-I979, M1-D978,
M1-L977, M1-L976, M1-R975, M1-I974, M1-Y973,
M1-W972, M1-Y971, M1-I970, M1-I969, M1-N968,
M1-V967, M1-C966, M1-Y965, M1-I964, M1-V963,
M1-R962, M1-G961, M1-D960, M1-S959, M1-R958,
M1-F957, M1-P956, M1-Q955, M1-D954, M1-Q953,
M1-L952, M1-R951, M1-L950, M1-I949, M1-M948,
M1-G947, M1-V946, M1-S945, M1-F944, M1-L943,
M1-L942, M1-I941, M1-A940, M1-I939, M1-L938,
M1-D937, M1-T936, M1-V935, M1-N934, M1-W933,
M1-Y932, M1-E931, M1-Q930, M1-L929, M1-W928,
M1-V927, M1-K926, M1-V925, M1-K924, M1-Q923,
M1-L922, M1-L921, M1-K920, M1-G919, M1-P918,
M1-E917, M1-S916, M1-M915, M1-L914, M1-I913,
M1-E912, M1-R911, M1-M910, M1-K909, M1-E908,
M1-I907, M1-G906, M1-L905, M1-T904, M1-F903,
M1-I902, M1-Y901, M1-S900, M1-I899, M1-V898,
M1-I897, M1-W896, M1-E895, M1-Q894, M1-T893,
M1-S892, M1-P891, M1-W890, M1-R889, M1-E888,
M1-M887, M1-K886, M1-V885, M1-L884, M1-V883,
M1-I882, M1-Y881, M1-N880, M1-F879, M1-L878,
M1-M877, M1-L876, M1-Y875, M1-G874, M1-I873,
M1-Y872, M1-A871, M1-L870, M1-T869, M1-Y868,
M1-F867, M1-W866, M1-F865, M1-K864, M1-V863,
M1-I862, M1-P861, M1-A860, M1-N859, M1-Y858,
M1-F857, M1-E856, M1-Y855, M1-I854, M1-K853,
M1-R852, M1-G851, M1-L850, M1-P849, M1-I848,
M1-L847, M1-R846, M1-H845, M1-K844, M1-S843, M1-Q842, M1-V841, M1-E840, M1-E839, M1-E838,
M1-D837, M1-K836, M1-K835, M1-R834, M1-S833,
M1-S832, M1-E831, M1-G830, M1-N829, M1-N828,
M1-R827, M1-G826, M1-L825, M1-M824, M1-A823,
M1-T822, M1-L821, M1-E820, M1-M819, M1-D818,
M1-E817, M1-E816, M1-E815, M1-K814, M1-E813,
M1-K812, M1-T811, M1-P810, M1-K809, M1-E808,
M1-P807, M1-E806, M1-E805, M1-A804, M1-E803,
M1-K802, M1-E801, M1-Q800, M1-L799, M1-H798,
M1-I797, M1-E796, M1-Q795, M1-A794, M1-Q793,
M1-S792, M1-M791, M1-Y790, M1-P789, M1-M788,
M1-D787, M1-D786, M1-K785, M1-N784, M1-K783,
M1-F782, M1-E781, M1-L780, M1-S779, M1-L778,
M1-I777, M1-S776, M1-P775, M1-P774, M1-L773,
M1-L772, M1-I771, M1-G770, M1-L769, M1-I768,
M1-V767, M1-K766, M1-L765, M1-G764, M1-S763,
M1-N762, M1-K761, M1-R760, M1-M759, M1-R758,
M1-L757, M1-R756, M1-G755, M1-M754, M1-W753,
M1-M752, M1-D751, M1-T750, M1-L749, M1-L748,
M1-M747, M1-Q746, M1-S745, M1-C744, M1-T743,
M1-H742, M1-A741, M1-I740, M1-F739, M1-D738,
M1-R737, M1-H736, M1-K735, M1-A734, M1-A733,
M1-V732, M1-A731, M1-L730, M1-Q729, M1-L728,
M1-C727, M1-T726, M1-A725, M1-N724, M1-S723,
M1-W722, M1-N721, M1-K720, M1-L719, M1-E718,
M1-Y717, M1-T716, M1-L715, M1-L714, M1-K713,
M1-M712, M1-A711, M1-L710, M1-Q709, M1-E708,
M1-D707, M1-Q706, M1-K705, M1-Y704, M1-S703,
M1-Q702, M1-D701, M1-L700, M1-L699, M1-E698,
M1-V697, M1-A696, M1-L695, M1-Q694, M1-G693,
M1-F692, M1-D691, M1-R690, M1-S689, M1-N688,
M1-H687, M1-N686, M1-L685, M1-E684, M1-Q683,
M1-S682, M1-I681, M1-D680, M1-D679, M1-V678,
M1-M677, M1-D676, M1-N675, M1-E674, M1-S673,
M1-A672, M1-E671, M1-H670, M1-A669, M1-M668,
M1-A667, M1-K666, M1-C665, M1-L664, M1-K663,
M1-C662, M1-A661, M1-V660, M1-L659, M1-A658,
M1-K657, M1-A656, M1-M655, M1-A654, M1-E653,
M1-E652, M1-G651, M1-H650, M1-Q649, M1-W648,
M1-F647, M1-F646, M1-L645, M1-A644, M1-M643,
M1-K642, M1-Q641, M1-R640, M1-K639, M1-M638,
M1-L637, M1-V636, M1-A635, M1-W634, M1-V633,
M1-M632, M1-L631, M1-E630, M1-H629, M1-F628,
M1-P627, M1-F626, M1-P625, M1-F624, M1-H623,
M1-N622, M1-I621, M1-E620, M1-P619, M1-D618,
M1-D617, M1-L616, M1-D615, M1-I614, M1-D613,
M1-V612, M1-E611, M1-E610, M1-E609, M1-R608,
M1-K607, M1-K606, M1-T605, M1-T604, M1-K603,
M1-R602, M1-G601, M1-R600, M1-R599, M1-L598,
M1-P597, M1-I596, M1-D595, M1-D594, M1-R593,
M1-K592, M1-P591, M1-G590, M1-F589, M1-L588,
M1-N587, M1-H586, M1-Y585, M1-L584, M1-T583,
M1-R582, M1-F581, M1-R580, M1-K579, M1-R578,
M1-T577, M1-Y576, M1-N575, M1-C574, M1-R573,
M1-Y572, M1-A571, M1-G570, M1-G569, M1-M568,
M1-L567, M1-Y566, M1-E565, M1-I564, M1-V563,
M1-L562, M1-G561, M1-I560, M1-D559, M1-I558,
M1-L557, M1-S556, M1-I555, M1-R554, M1-Y553,
M1-D552, M1-P551, M1-P550, M1-L549, M1-N548,
M1-G547, M1-K546, M1-K545, M1-V544, M1-D543,
M1-R542, M1-V541, M1-L540, M1-H539, M1-Y538,
M1-L537, M1-T536, M1-N535, M1-S534, M1-P533,
M1-G532, M1-H531, M1-R530, M1-T529, M1-N528,
M1-Y527, M1-L526, M1-E525, M1-E524, M1-L523,
M1-R522, M1-S521, M1-I520, M1-T519, M1-L518,
M1-F517, M1-R516, M1-H515, M1-M514, M1-S513,
M1-V512, M1-G511, M1-N510, M1-E509, M1-I508,
M1-L507, M1-L506, M1-K505, M1-V504, M1-F503,
M1-D502, M1-V501, M1-R500, M1-D499, M1-L498,
M1-V497, M1-L496, M1-A495, M1-D494, M1-L493,
M1-M492, M1-A491, M1-Q490, M1-E489, M1-L488,
M1-S487, M1-G486, M1-V485, M1-P484, M1-W483,
M1-Q482, M1-Q481, M1-G480, M1-Y479, M1-I478,
M1-F477, M1-I476, M1-Q475, M1-S474, M1-R473,
M1-A472, M1-I471, M1-D470, M1-V469, M1-R468,
M1-N467, M1-W466, M1-A465, M1-L464, M1-A463,
M1-L462, M1-S461, M1-L460, M1-Q459, M1-D458,
M1-P457, M1-A456, M1-S455, M1-A454, M1-N453,
M1-A452, M1-G451, M1-K450, M1-L449, M1-L448,
M1-A447, M1-T446, M1-L445, M1-I444, M1-A443,
M1-L442, M1-D441, M1-I440, M1-D439, M1-Q438,
M1-H437, M1-G436, M1-E435, M1-S434, M1-G433,
M1-M432, M1-R431, M1-F430, M1-V429, M1-T428,
M1-I427, M1-L426, M1-E425, M1-K424, M1-K423,
M1-K422, M1-M421, M1-C420, M1-E419, M1-M418,
M1-L417, M1-I416, M1-I415, M1-F414, M1-L413,
M1-H412, M1-Q411, M1-A410, M1-Q409, M1-T408,
M1-R407, M1-T406, M1-Y405, M1-T404, M1-F403,
M1-T402, M1-K401, M1-Q400, M1-I399, M1-T398,
M1-V397, M1-L396, M1-L395, M1-Q394, M1-D393,
M1-R392, M1-L391, M1-S390, M1-E389, M1-N388,
M1-I387, M1-L386, M1-G385, M1-G384, M1-E383,
M1-E382, M1-S381, M1-Y380, M1-K379, M1-H378,
M1-G377, M1-F376, M1-A375, M1-L374, M1-I373,
M1-D372, M1-S371, M1-A370, M1-R369, M1-G368,
M1-S367, M1-G366, M1-D365, M1-C364, M1-V363,
M1-V362, M1-V361, M1-P360, M1-V359, M1-P358,
M1-P357, M1-T356, M1-D355, M1-R354, M1-L353,
M1-Y352, M1-E351, M1-L350, M1-V349, M1-I348,
M1-S347, M1-I346, M1-V345, M1-N344, M1-P343,
M1-G342, M1-G341, M1-E340, M1-V339, M1-I338,
M1-L337, M1-A336, M1-V335, M1-V334, M1-P333,
M1-V332, M1-G331, M1-Q330, M1-G329, M1-I328,
M1-R327, M1-T326, M1-N325, M1-I324, M1-K323,
M1-Q322, M1-L321, M1-S320, M1-I319, M1-H318,
M1-K317, M1-E316, M1-L315, M1-Q314, M1-R313,
M1-R312, M1-L311, M1-K310, M1-V309, M1-E308,
M1-A307, M1-G306, M1-Y305, M1-K304, M1-G303,
M1-T302, M1-T301, M1-G300, M1-N299, M1-D298,
M1-A297, M1-L296, M1-I295, M1-F294, M1-H293,
M1-S292, M1-M291, M1-M290, M1-S289, M1-N288,
M1-L287, M1-V286, M1-T285, M1-L284, M1-K283,
M1-S282, M1-M281, M1-P280, M1-N279, M1-S278,
M1-M277, M1-T276, M1-Q275, M1-Y274, M1-P273,
M1-R272, M1-V271, M1-V270, M1-D269, M1-R268,
M1-G267, M1-I266, M1-L265, M1-D264, M1-E263,
M1-Q262, M1-N261, M1-E260, M1-V259, M1-I258,
M1-G257, M1-W256, M1-P255, M1-A254, M1-I253,
M1-G252, M1-I251, M1-T250, M1-C249, M1-I248,
M1-K247, M1-G246, M1-R245, M1-S244, M1-K243,
M1-S242, M1-A241, M1-H240, M1-D239, M1-K238,
M1-L237, M1-A236, M1-D235, M1-G234, M1-V233,
M1-H232, M1-R231, M1-I230, M1-V229, M1-G228,
M1-T227, M1-N226, M1-V225, M1-G224, M1-G223,
M1-T222, M1-F221, M1-I220, M1-W219, M1-A218,
M1-G217, M1-T216, M1-T215, M1-M214, M1-A213,
M1-A212, M1-K211, M1-I210, M1-L209, M1-G208,
M1-K207, M1-G206, M1-F205, M1-V204, M1-Q203,
M1-K202, M1-L201, M1-K200, M1-P199, M1-Q198,
M1-L197, M1-E196, M1-F195, M1-N194, M1-Q193,
M1-L192, M1-G191, M1-G190, M1-H189, M1-V188,
M1-S187, M1-I186, M1-G185, M1-L184, M1-K183,
M1-P182, M1-L181, M1-E180, M1-L179, M1-Q178,
M1-W177, M1-E176, M1-K175, M1-T174, M1-M173, M1-L172, M1-H171, M1-L170, M1-L169, M1-L168, M1-D167, M1-P166, M1-K165, M1-T164, M1-D163, M1-F162, M1-S161, M1-V160, M1-R159, M1-V158, M1-Y157, M1-M156, M1-A155, M1-K154, M1-N153, M1-S152, M1-H151, M1-G150, M1-G149, M1-G148, M1-Q147, M1-F146, M1-E145, M1-I144, M1-T143, M1-G142, M1-F141, M1-A140, M1-D139, M1-T138, M1-P137, M1-S136, M1-L135, M1-Q134, M1-T133, M1-H132, M1-K131, M1-S130, M1-I129, M1-S128, M1-W127, M1-K126, M1-E125, M1-S124, M1-Q123, M1-I122, M1-D121, M1-N120, M1-R119, M1-S118, M1-L117, M1-R116, M1-S115, M1-E114, M1-N113, M1-K112, M1-E111, M1-N110, M1-Q109, M1-L108, M1-V107, M1-S106, M1-I105, M1-S104, M1-P103, M1-T102, M1-L10, M1-G100, M1-V99, M1-H98, M1-Q97, M1-G96, M1-I95, M1-L94, M1-R93, M1-G92, M1-C91, M1-C90, M1-C89, M1-R88, M1-H87, M1-P86, M1-D85, M1-K84, M1-T83, M1-S82, M1-P81, M1-I80, M1-I79, M1-H78, M1-V77, M1-C76, M1-E75, M1-R74, M1-K73, M1-Y72, M1-F71, M1-A70, M1-R69, M1-E68, M1-I67, M1-W66, M1-S65, M1-K64, M1-Q63, M1-A62, M1-P61, M1-T60, M1-Q59, M1-Q58, M1-S57, M1-P56, M1-L55, M1-G54, M1-S53, M1-R52, M1-K51, M1-T50, M1-S49, M1-G48, M1-Q47, M1-K46, M1-S45, M1-S44, M1-L43, M1-R42, M1-K41, M1-W40, M1-S39, M1-E38, M1-A37, M1-F36, M1-R35, M1-G34, M1-R33, M1-S32, M1-A31, M1-S30, M1-R29, M1-S28, M1-R27, M1-R26, M1-R25, M1-S24, M1-E23, M1-A22, M1-N21, M1-D20, M1-E19, M1-R18, M1-D17, M1-S16, M1-C15, M1-G14, M1-R13, M1-E12, M1-M11, M1-E10, M1-A9, M1-A8, and/or M1-D7 of SEQ ID NO:8. Polynucleotide sequences encoding these polypeptides are also provided. The present invention also encompasses the use of these C-terminal LTRPC3j deletion polypeptides as immunogenic and/or antigenic epitopes as described elsewhere herein.

Alternatively, preferred polypeptides of the present invention may comprise polypeptide sequences corresponding to, for example, internal regions of the LTRPC3j polypeptide (e.g., any combination of both N- and C-terminal LTRPC3j polypeptide deletions) of SEQ ID NO:8. For example, internal regions could be defined by the equation: amino acid NX to amino acid CX, wherein NX refers to any N-terminal deletion polypeptide amino acid of LTRPC3j (SEQ ID NO:8), and where CX refers to any C-terminal deletion polypeptide amino acid of LTRPC3j (SEQ ID NO:8). Polynucleotides encoding these polypeptides are also provided. The present invention also encompasses the use of these polypeptides as an immunogenic and/or antigenic epitope as described elsewhere herein.

Many polynucleotide sequences, such as EST sequences, are publicly available and accessible through sequence databases. Some of these sequences are related to SEQ ID NO:7 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 5157 of SEQ ID NO:7, b is an integer between 15 to 5171, where both a and b correspond to the positions of nucleotide residues shown in SEQ ID NO:7, and where b is greater than or equal to a+14.

Features of the Polypeptide Encoded by Gene No:5

The polypeptide of this gene provided as SEQ ID NO:10 (FIGS. 5A-F), encoded by the polynucleotide sequence according to SEQ ID NO:9 (FIGS. 5A-F), and/or encoded by the polynucleotide contained within the deposited clone, LTRPC3k, has significant homology at the nucleotide and amino acid level to the human melastatin 1 protein (Melastatin1; Genbank Accession No. gi|3243075; SEQ ID NO:13). An alignment of the LTRPC3k polypeptide with this protein is provided in FIGS. 7A-G.

The LTRPC3k polypeptide was determined to share 65.5% identity and 73.3% similarity with the human melastatin 1 protein (Melastatin1; Genbank Accession No. gi|3243075; SEQ ID NO:13) as shown in FIG. 10.

The LTRPC3k protein is believed to represent a member of a new class of protein kinases referred to as alpha kinases (Curr. Biol. 9 (2), R43-R45 (1999)). These kinases represent a novel type of signaling molecule comprising both a catalytic protein kinase domain, in addition to, an ion channel domain. This family is commonly referred to as the transient receptor potential channel (TRP) family. Melastatin1 defines a separate subfamily of TRP channels referred to as TRPM (melastatin1). TRPM family members are characteristic of their unusually long cytoplasmic tails at both ends of the channel domain and some of the family members contain an enzyme domain at the C-terminal region.

Specifically, the LTRPC3k (SEQ ID NO:10) polypeptide represents a novel variant of the LTRPC3e (Co-pending U.S. Ser. No. 10/210,152, filed Aug. 1, 2002; International Publication No. WO 03/012063, published Feb. 13, 2003; SEQ ID NO:20; and also co-pending U.S. Ser. No. 10/405,793, filed Mar. 28, 2003; which are hereby incorporated by reference herein in their entirety) polypeptide. The LTRPC3k represents a novel member of the TRPM subfamily.

The melastatin1 protein is believed to be negatively associated with the incidence of melanoma based upon its inverse correlative expression in highly aggressive melanomas (Genomics 54 (1), 116-123 (1998)). Thus, overexpression of melastatin1 could represent a novel therapeutic in the treatment of melanoma and potentially other cancers.

Based upon the observed homology, the polypeptide of the present invention is expected to share at least some biological activity with other transient receptor potential channel family members, more specifically with the melastatin1 protein, in addition to, other transient receptor potential channel family members referenced elsewhere herein or otherwise known in the art, particularly LTRPC3e, and LTRPC3.

Most of the known transient receptor potential channel family members, possess one or more transmembrane domains. Likewise, the LTRPC3k polypeptide has been determined to comprise six transmembrane domains (TM1-TM6) as shown in FIGS. 5A-F. The transmembrane domains are located from about amino acid 777 to about amino acid 794 (TM1), from about amino acid 874 to about amino acid 891 (TM2), from about amino acid 947 to about amino acid 960 (TM3), from about amino acid 974 to about amino acid 991 (TM4), from about amino acid 1008 to about amino acid 1025 (TM5), and/or from about amino acid 1095 to about amino acid 1115 (TM6) of SEQ ID NO:10. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following transmembrane domain polypeptides are encompassed by the present invention: LKVILGILLPPSILSLEF (SEQ ID NO:78), IVKFW-FYTLAYIGYLMLF (SEQ ID NO:79), VTDLIAILLFS- VGM (SEQ ID NO:80), RVIYCVNIIYWYIRLLDI (SEQ ID NO:81), MMIDMMYFVIIMLVVLMS (SEQ ID NO:82), and/or AIMACYLLVANILLVNLLIAV (SEQ ID NO:83). Polynucleotides encoding these polypeptides are also provided. The present invention also encompasses the use of the LTRPC3k transmembrane polypeptides as immunogenic and/or antigenic epitopes as described elsewhere herein.

The present invention also encompasses polypeptides corresponding to the regions between each transmembrane domain of LTRPC3k, referred to herein as inter-transmembrane domain polypeptides (inter TM1-2, inter TM2-3, inter TM3-4, inter TM4-5, and inter TM5-6). Such regions are typically solvent accessible (either extracellularly or intracellularly). Therefore, these regions are amenable to the development of agonists and/or antagonists to the LTRPC3k polypeptide, particularly for the development of antibodies specific to these regions.

In preferred embodiments, the following inter-transmembrane domain polypeptides are encompassed by the present invention: KNKDDMPYMSQAQEIHLQEKEAEEPE-KPTKEKEEEDMELTAMLGRNNGESS RKKDEEEVQSKHRLIPLGRKIYEFYNAP (SEQ ID NO:84), NYIVLVKMERWPSTQEWIVISYIFTLG-IEKMREILMSEPGKLLQKVKVWLQEY WN (SEQ ID NO:85), ILRLQDQPFRSDG (SEQ ID NO:86), FGVNKY-LGPYVMMIGK (SEQ ID NO:87), and/or FGVARQAILF-PNEEPSWKLAKNIFYMPYWMIYGEVFAD-QIDRKQVYDSHTPK SAPCGQNETREDGKIIQLPPCKTGAWIVP (SEQ ID NO:88). Polynucleotides encoding these polypeptides are also provided. The present invention also encompasses the use of the LTRPC3k inter-transmembrane polypeptides as immunogenic and/or antigenic epitopes as described elsewhere herein.

The LTRPC3k polypeptide was determined to comprise several conserved cysteines, at amino acid 249, 364, 420, 586, 674, 739, 756, 978, 1069, 1086, 1099, 1202, 1293, and 1559 of SEQ ID NO:10 (FIGS. 5A-F). Conservation of cysteines at key amino acid residues is indicative of conserved structural features, which may correlate with conservation of protein function and/or activity.

In confirmation of the LTRPC3k representing a member of the transient receptor channel family, the LTRPC3k polypeptide was determined to comprise a predicted TRP domain located from about amino acid 1130 to about amino acid 1135 of SEQ ID NO:10. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following TRP domain polypeptide is encompassed by the present invention: VWK-FQR (SEQ ID NO:89). Polynucleotides encoding this polypeptide are also provided. The present invention also encompasses the use of this LTRPC3k TRP domain polypeptide as an immunogenic and/or antigenic epitope as described elsewhere herein.

In further confirmation of the LTRPC3k representing a member of the transient receptor channel family, the LTRPC3k polypeptide was determined to comprise a predicted ion transport signature domain located at about amino acid 905 to about amino acid 1116 of SEQ ID NO:10. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following ion transport signature domain polypeptide is encompassed by the present invention: TQEWIVISYIFTLGIEKMREILM-SEPGKLLQKVKVWLQEYWNVTDLIAILLFSV GMIL-RLQDQPFRSDGRVIYCVNIIYWYIRLL-DIFGVNKYLGPYVMMIGKMMID MMYFVIIMLVVLMSFGVARQAILFP-NEEPSWKLAKNIFYMPYWMIYGEVFAD QIDP-PCGQNETREDGKIIQLPPCKTGAWIV-PAIMACYLLVANILLVNLLIAVF (SEQ ID NO:90). Polynucleotides encoding this polypeptide are also provided. The present invention also encompasses the use of this LTRPC3k ion transport signature domain polypeptide as an immunogenic and/or antigenic epitope as described elsewhere herein.

The LTRPC3k polypeptide was determined to comprise a predicted coiled-coil domain located at about amino acid 1220 to about amino acid 1275 of SEQ ID NO:10. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following coiled-coil domain polypeptide is encompassed by the present invention: ERIRVTSERVENMSMRLEEVNEREH-SMKASLQTVDIRLAQLEDLIGRMATAL ERL (SEQ ID NO:91). Polynucleotides encoding this polypeptide are also provided. The present invention also encompasses the use of this LTRPC3k coiled-coil domain polypeptide as an immunogenic and/or antigenic epitope as described elsewhere herein.

LTRPC3k polypeptides and polynucleotides are useful for diagnosing diseases related to the over and/or under expression of LTRPC3k by identifying mutations in the LTRPC3k gene using LTRPC3k sequences as probes or by determining LTRPC3k protein or mRNA expression levels. LTRPC3k polypeptides will be useful in screens for compounds that affect the activity of the protein. LTRPC3k peptides can also be used for the generation of specific antibodies and as bait in yeast two hybrid screens to find proteins the specifically interact with LTRPC3k.

Since the LTRPC3k polypeptide represents an N-terminally extended variant of the LTRPC3e polypeptide (see polypeptide alignment provided in FIG. 11A-I), and since the LTRPC3e (SEQ ID NO:20) polypeptide represents a splice variant of the LTRPC3 polypeptide (SEQ ID NO:15), the LTRPC3k (SEQ ID NO:10) polypeptide of the present invention is expected to have the same or similar function as the LTRPC3 polypeptide, and in particular, the LTRPC3e polypeptide. Specifically, the LTRPC3k polypeptide is expected to localize to the cell membrane.

Moreover, the LTRPC3k polypeptide is expected to also localize in or near the plasmalemmal compartment.

Moreover, the LTRPC3k polypeptide is also expected to be a constitutively active channel capable of mediating $Ca^{2+}$ influx.

Moreover, the LTRPC3k polypeptide is also expected to mediate $Ca^{2+}$ entry and that LTRPC3k-mediated $Ca^{2+}$ entry is expected to be potentiated by store-depletion.

Moreover, the LTRPC3k polypeptide is also expected to mediate a $Ca^{2+}$ entry pathway that is distinct from the endogenous $Ca^{2+}$ entry pathways present in HEK 293 cells.

Moreover, the LTRPC3k polypeptide of the present invention is expected to share the same or similar expression profile as that of the LTRPC3 polypeptide (SEQ ID NO:15).

Moreover, the LTRPC3k polypeptide is expected to share the same or similar differential expression patterns observed for the LTRPC3 variant.

Moreover, the LTRCP3g polypeptide is expected to be able to modulate the FEN1 DNA base-excision repair/proliferation modulating protein to the same or similar extent as the LTRPC3 polypeptide.

Moreover, the LTRPC3k polynucleotides and polypeptides are expected to share at least some biological activity with TRP family members expressed in kidney cells and tissues, particularly those specifically referenced herein, such as LTRPC3 (SEQ ID NO:15), and particularly as LTRPC3b (SEQ ID NO:17).

Moreover, the LTRPC3k polynucleotides and polypeptides are expected to share at least some biological activity with TRP family members expressed in testis cells and tissues, particularly those specifically referenced herein, such as the LTRPC3 variant (SEQ ID NO:15), and particularly as LTRPC3e (SEQ ID NO:20).

In preferred embodiments, LTRPC3k polynucleotides and polypeptides, including fragments and modulators thereof, are useful for treating, diagnosing, and/or ameliorating $Ca^{2+}$ reabsorption disorders, disorders associated with aberrant luminal $Ca^{2+}$ entry via the epithelial $Ca^{2+}$ channel (ECaC), disorders associated with aberrant cytosolic diffusion of $Ca^{2+}$ bound to calbindin-D28K, disorders associated with aberrant basolateral extrusion of $Ca^{2+}$ through the Na+/Ca2+ exchanger (NCX), disorders associated with aberrant plasma membrane Ca2+-ATPase (PMCA) activity and/or activation, disorders associated with the hypocalciuric effect of diuretics, disorders associated with the hypocalciuric effect of thiazide diuretics, disorders associated with hormone insufficiencies that affect the function of the kidney, disorders associated with hormone insufficiencies that affect renal Ca2+ homeostasis, disorders associated with aberrant renal Ca2+ homeostasis as a result of vitamin D deficiency, disorders associated with aberrant renal Ca2+ homeostasis as a result of PTH deficiency, disorders associated with aberrant renal Ca2+ homeostasis as a result of vasopressin deficiency, disorders associated with aberrant renal Ca2+ homeostasis as a result of prostaglandines deficiency, disorders associated with aberrant renal Ca2+ homeostasis as a result of estrogen deficiency, disorders associated with aberrant renal Ca2+ homeostasis as a result of calcitonin deficiency, disorders associated with aberrant renal Ca2+ homeostasis as a result of parathyroid hormone deficiency, disorders associated with aberrant renal Ca2+ homeostasis as a result of atrial natriuretic peptide deficiency, calcium homeostasis-related disorders, hypercaliuric nephrolithiasis, certain forms of osteoporosis, Gitelman's disease, Bartter's syndrom, disorders associated with aberrant function of kidney tubular epithelium, disorders associated with aberrant function of kidney tubular epithelium in the medulla, disorders associated with aberrant function of kidney tubular epithelium in the medullary rays, disorders associated with aberrant function of kidney tubular epithelium in the periglomerular.

In preferred embodiments, LTRPC3k polynucleotides and polypeptides, including fragments and modulators thereof, are useful for treating, diagnosing, and/or ameliorating acute kidney failure, chronic kidney failure, cystic kidney disease, horseshoe kidney, hypertensive kidney disease, kidney atrophy, kidney cancer, kidney disease, kidney failure, kidney infection, kidney metastasis, kidney stone, nephrolithiasis, multicystic dysplastic kidney disease, and polycystic kidney disease.

Characterization of the LTRPC3 variant polypeptide using antisense oligonucleotides led to the determination that LTRPC3 is involved in the negative modulation of the FEN1 DNA base-excision repair/proliferation modulating protein as described in Example 5 herein.

The LTRCP3g polypeptide is expected to be able to modulate the FEN1 DNA base-excision repair/proliferation modulating protein to the same or similar extent as the LTRPC3 polypeptide.

Specifically, antisense inhibition of LTRPC3 resulted in upregulation of Fen1, a marker of proliferation. As such, LTRPC3 behaves in a manner similar to a tumor suppressor, in that loss results in increases in proliferation. While some increases in the proliferation markers p21 and IkB were also observed, they were less significant, and could be a response to the pro-proliferative effect of LTRPC3 antisense inhibition. Interestingly, expression of LTRPC3 was also observed to be significantly reduced in tumor tissues, relative to normal tissues (see FIG. 13). Specifically, renal, testicular, and ovarian tumor samples showed as much as 12 to 30 fold down regulation of LTRPC3 message levels compared to normal tissues. This reduction of LTRPC3 correlating with the tumor state is consistent with the negative FEN1 modulatory activity and suggests this gene may have antiproliferative activities. Therefore, for modulators of LTRPC3k to be useful for treating cancer, it would be necessary to increase the activity of the gene or gene product in order to have the reverse effect on cancerous cells. Thus, an agonist of LTRPC3k activity or a compound that increased LTRPC3k message levels would be a desired invention for cancer therapy.

In preferred embodiments, LTRPC3k polynucleotides and polypeptides, including fragments and modulators thereof, are useful for treating, diagnosing, and/or ameliorating DNA-repair deficiencies, particularly base-excision repair deficiencies, Xeroderma pigmentosum, skin cancer, melanoma, UV senstivity, alkylation sensivity, gamma irradiation sensitivity, pyrimidine dimer sensitivity, chemical mutagenes, lymphomas, leukemias, photosensitivity, Bloom's syndrone, Fanconi's anemia, ataxia telangiectasia, chromosomal aberrations, blood vessel dilation aberrations in the skin, blood vessel dilation aberrations in the eye, conditions involving increased levels of apurinic sites, conditions involving increased levels of apyrimidinic sites, conditions involving increased levels of abasic sites, disorders related to aberrant signal transduction, proliferating disorders, and/or cancers.

Moreover, LTRPC3k polynucleotides and polypeptides, including fragments and modulators thereof, are useful for increasing mammalian base excision repair activity, increasing mammalian single-nucleotide base excision repair activity, and/or increasing mammalian long patch base excision repair activity.

In preferred embodiments, antagonists directed against LTRPC3k are useful for treating, diagnosing, and/or ameliorating DNA-repair deficiencies, particularly base-excision repair deficiencies, Xeroderma pigmentosum, skin cancer, melanoma, UV senstivity, alkylation sensivity, gamma irradiation sensitivity, pyrimidine dimer sensitivity, chemical mutagenes, lymphomas, leukemias, photosensitivity, Bloom's syndrone, Fanconi's anemia, ataxia telangiectasia, chromosomal aberrations, blood vessel dilation aberrations in the skin, blood vessel dilation aberrations in the eye, conditions involving increased levels of apurinic sites, conditions involving increased levels of apyrimidinic sites, conditions involving increased levels of abasic sites, disorders related to aberrant signal transduction, proliferating disorders, and/or cancers.

Moreover, antagonists directed against LTRPC3k are useful for increasing mammalian base excision repair activity, increasing mammalian single-nucleotide base excision repair activity, and/or increasing mammalian long patch base excision repair activity.

In preferred embodiments, agonists directed against LTRPC3k are useful for treating, diagnosing, and/or ameliorating, disorders related to aberrant signal transduction, proliferating disorders, and/or cancers, particularly renal cell carcinomas, testicular cancers, and/or ovarian cancers.

Moreover, agonists directed against LTRPC3k are useful for decreasing mammalian base excision repair activity, decreasing mammalian single-nucleotide base excision repair activity, and/or decreasing mammalian long patch base excision repair activity.

The strong homology to human transient receptor potential channels (TRP), combined with the predominate localized expression in kidney tissue of the LTRPC3 variant, suggests the LTRPC3k polynucleotides and polypeptides, including modulators or fragments thereof, may be useful in treating, diagnosing, prognosing, and/or preventing renal diseases and/or disorders, which include, but are not limited to: nephritis, renal failure, nephrotic syndrome, urinary tract infection, hematuria, proteinuria, oliguria, polyuria, nocturia, edema, hypertension, electrolyte disorders, sterile pyuria, renal osteodystrophy, large kidneys, renal transport defects, nephrolithiasis, azotemia, anuria, urinary retention, slowing of urinary stream, large prostate, flank tenderness, full bladder sensation after voiding, enuresis, dysuria, bacteriuria, kidney stones, glomerulonephritis, vasculitis, hemolytic uremic syndromes, thrombotic thrombocytopenic purpura, malignant hypertension, casts, tubulointerstitial kidney diseases, renal tubular acidosis, pyelonephritis, hydronephritis, nephrotic syndrome, crush syndrome, and/or renal colic, in addition to Wilm's Tumor Disease, and congenital kidney abnormalities such as horseshoe kidney, polycystic kidney, and Falconi's syndrome.for example.

Several known TRP family members have been identified that are expressed significantly in kidney tissue. These TRP family members include, for example, Trp12 (Wissenbach, U., Bodding, M., Freichel, M., Flockerzi, V, Lett., 485(2-3): 127-34, (2000)); OTRPC4 (Strotmann, R., Harteneck, C., Nunnenmacher, K., Schultz, G., Plant, T, D, Nat, Cell, Biol., 2(10):695-702, (2000)); polycystin-L2 (Guo, L., Schreiber, T, H., Weremowicz, S., Morton, C, C., Lee, C., Zhou, J. Genomics., 64(3):241-51, (2000)); and EcaC (Hoenderop, J. G., van, der, Kemp, A, W., Hartog, A., van, de, Graaf, S, F., van, Os, C, H., Willems, P, H., Bindels, R, J. J. Biol, Chem., 274(13):8375-8, (1999)).

Thus, the LTRPC3k polynucleotides and polypeptides are expected to share at least some biological activity with TRP family members expressed in kidney cells and tissues, particularly those specifically referenced herein, such as LTRPC3 (SEQ ID NO:15).

The strong homology to human transient receptor potential channels (TRP) proteins, combined with the localized expression in spinal cord and brain of the LTRPC3 variant, suggests the LTRPC3k polynucleotides and polypeptides, including modulators or fragments thereof, may be useful in treating, diagnosing, prognosing, and/or preventing neurodegenerative disease states, behavioral disorders, or inflammatory conditions. Representative uses are described in the "Regeneration" and "Hyperproliferative Disorders" sections below, in the Examples, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The strong homology to human transient receptor potential channels (TRP), combined with the localized expression in testis tissue of the LTRPC3 variant emphasizes the potential utility for LTRPC3k polynucleotides and polypeptides in treating, diagnosing, prognosing, and/or preventing testicular, in addition to reproductive disorders.

In preferred embodiments, LTRPC3k polynucleotides and polypeptides including agonists and fragments thereof, have uses which include treating, diagnosing, prognosing, and/or preventing the following, non-limiting, diseases or disorders of the testis: spermatogenesis, infertility, Klinefelter's syndrome, XX male, epididymitis, genital warts, germinal cell aplasia, cryptorchidism, varicocele, immotile cilia syndrome, and viral orchitis. The LTRPC3k polynucleotides and polypeptides including agonists and fragments thereof, may also have uses related to modulating testicular development, embryogenesis, reproduction, and in ameliorating, treating, and/or preventing testicular proliferative disorders (e.g., cancers, which include, for example, choriocarcinoma, Non-seminoma, seminona, and testicular germ cell tumors).

Likewise, the localized expression in testis tissue also emphasizes the potential utility for LTRPC3k polynucleotides and polypeptides in treating, diagnosing, prognosing, and/or preventing metabolic diseases and disorders which include the following, not limiting examples: premature puberty, incomplete puberty, Kallman syndrome, Cushing's syndrome, hyperprolactinemia, hemochromatosis, congenital adrenal hyperplasia, FSH deficiency, and granulomatous disease, for example.

This gene product may also be useful in assays designed to identify binding agents, as such agents (antagonists) are useful as male contraceptive agents. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

Several known TRP family members have been identified that are expressed significantly in testis tissue. These TRP family members include, for example, polycystin-L2 (Guo, L., Schreiber, T, H., Weremowicz, S., Morton, C, C., Lee, C., Zhou, J. Genomics., 64(3):241-51, (2000)); TRP7 (Okada, T., Inoue, R., Yamazaki, K., Maeda, A., Kurosaki, T., Yamakuni, T., Tanaka, I., Shimizu, S., Ikenaka, K., Imoto, K., Mori, Y, J. Biol, Chem., 274(39):27359-70, (1999)); btrp2 (Wissenbach, U., Schroth, G., Philipp, S., Flockerzi, V, Lett., 429(1):61-6, (1998)); Htrp-1 (Zhu, X., Chu, P, B., Peyton, M., Birnbaumer, L, Lett., 373(3):193-8, (1995)); and TRPC1 (Wes, P, D., Chevesich, J., Jeromin, A., Rosenberg, C., Stetten, G., Montell, C, Proc, Nati, Acad, Sci, U.S.A., 92(21):9652-6, (1995)).

Thus, the LTRPC3k polynucleotides and polypeptides are expected to share at least some biological activity with TRP family members expressed in testis cells and tissues, particularly those specifically referenced herein, such as the LTRPC3 variant (SEQ ID NO:15).

As described elsewhere herein, transient receptor potential channel family members have been implicated in modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity. Moreover, transient receptor potential channel family members have been implicated in disorders of the skin, skeletal-muscle, nervous, cardiac, and vascular systems, in addition to the following, non-limiting diseases and disorders, which include, for example, arteriosclerosis, neointimal hypoerplasia, metastatic melanomas, bipolar disorder, nonsyndromic hereditary deafness, Knobloch syndrome, holosencephaly, and various maligancies including prostate cancer.

In preferred embodiments, LTRPC3k polynucleotides and polypeptides of the present invention, including agonists and/or fragments thereof, have uses that include, modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity.

In more preferred embodiments, LTRPC3k polynucleotides and polypeptides of the present invention, including agonists and/or fragments thereof, have uses that include, treating, ameliorating, preventing, detecting, and/or prognosing various diseases and disorders, particularly the following, non-limiting examples, disorders of the skin, skeletal-muscle, nervous, cardiac, and vascular systems, in addition to the following, non-limiting diseases and disorders, which include, for example, arteriosclerosis, neointimal hypoerplasia, metastatic melanomas, bipolar disorder, nonsyndromic hereditary deafness, Knobloch syndrome, holosencephaly, and various maligancies including prostate cancer.

LTRPC3k polynucleotides and polypeptides of the present invention, including agonists and/or fragments may be involved in intracellular $Ca^{2+}$ homeostasis which affects various aspects of biological functions including mechano-regulation, pain transduction, vasorelaxation, gene expression, cell cycle and proliferation/apoptosis. Since the LTRPC3 variant is dominantly expressed in kidney, the LTRPC3k polypeptide may particularly play an important role in regulating cytosolic $Ca^{2+}$ in the renal system, potentially $Ca^{2+}$ absorption.

The LTRPC3k gene maps to chromosome 9q21.11-21.31 between the two markers D9S1874 and D9S1807. This region is linked to amyotrophic lateral sclerosis with frontotemporal dementia, early-onset pulverulent cataract, infantile nephronophthisis, hypomagnesemia with secondary hypocalcemia (HSH), and familial hemophagocytic lymphohistiocytosis. Therefore, agonists and/or antagonists of the novel LTRPC3k can be used to treat diseases including various forms of neuronal degeneration, neurogenic inflammation, allergy, immunodeficiency/excessive immune activation, visual defects, hearing disorder, pain, cancer, hypertension and other cardiovascular diseases. In addition, the therapeutics may be useful in the treatment of diseases associated with disturbances in $Ca^{2+}$ homeostasis including osteoporosis, hypercalciuric stone disease, and chronic renal failure.

Moreover, given the selective expression in kidney, LTRPC3k could be considered a candidate gene for HSH, since the phenotype is a renal insufficiency. LTRPC3k chromosomal location is ~600 kb downstream of a X; 9 translocation breakpoint interval described for one patient with HSH (*Hum. Mol. Genet.* 6, 1491-1497, (1997)). Recently, two groups reported that a new member of the TRPM subfamily, TRPM6, expressed in both intestinal tissues and kidney, is associated with HSH (*Nat. Genet.* 31, 166-170, (2002); and *Nat. Genet.* 31, 171-174 (2002)). Indeed, LTRPC3k is ~4 mb 5' to TRPM6 on 9q21. Although TRPM6 is the first component identified for HSH, this should not preclude involvement of LTRPC3k in the disease. Therefore, it is possible that LTRPC3k may co-localize with TRPM6 and/or forms a heteromultimer with TRPM6 in the kidney.

The kidney plays a major role in $Ca^{2+}$ homeostasis (reviewed in *Physiol. Rev.* 75, 429-471, (1995)). LTRPC3k may play a direct role in $Ca^{2+}$ absorption due to its constitutive $Ca^{2+}$ permeability. Alternatively, LTRPC3k may be the SOC that regulates $Ca^{2+}$ absorption. In kidney, $Ca^{2+}$ absorption is regulated by agonists such as calcitonin, parathyroid hormone and parathyroid hormone-related peptide through their respective G protein-coupled receptors, and downstream SOCs. Additionally, in kidney a SOC has been described (*J. Biol. Chem.* 276, 25759-25765, (2001)) for the action of angiotensin II, a vasoactive peptide that plays a major role in regulating blood pressure.

In addition, LTRPC3k polynucleotides and polypeptides of the present invention, including agonists and/or fragments thereof, have uses that include modulating intracellular Ca++ ion concentrations, Ca++ ion flux, stored intracellular Ca++ ion concentrations, Ca++ ion pump activity, Ca++ ion flow into cell, Ca++ ion flow out of cells, the activation of Ca++ sensitive proteins, the activation of Ca++sensitive signaling pathways, the activation of kinase-activatible proteins, and the activation of kinase-dependent signaling pathways.

The LTRPC3k polynucleotides and polypeptides of the present invention, including agonists and/or fragments thereof, have uses that include modulating proliferation, differentiation, migration, and activation in various cells, tissues, and organisms, and particularly in mammalian kidney, spinal cord, testis, and brain, preferably human. LTRPC3k polynucleotides and polypeptides of the present invention, including agonists and/or fragments thereof, may be useful in diagnosing, treating, prognosing, and/or preventing renal, neural, and/or proliferative diseases or disorders, particularly of the renal system.

In addition, antagonists of the LTRPC3k polynucleotides and polypeptides, including modulators or fragments thereof, may have uses that include diagnosing, treating, prognosing, and/or preventing diseases or disorders related to transient receptor potential channel activity, which may include renal, neural, reproductive, and/or proliferative diseases or disorders.

Although it is believed the encoded polypeptide may share at least some biological activities with transient receptor potential channel family members, particularly those melastatin1, a number of methods of determining the exact biological function of this clone are either known in the art or are described elsewhere herein. Briefly, the function of this clone may be determined by applying microarray methodology. Nucleic acids corresponding to the LTRPC3k polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from tissue that has been treated with known transient potential receptor inhibitors, which include, but are not limited to the drugs listed herein or otherwise known in the art, might indicate a function in modulating transient potential receptor function, for example. In the case of LTRPC3k, kidney, spinal cord, testis, and brain, should be used to extract RNA to prepare the probe.

In addition, the function of the protein may be assessed by applying quantitative PCR methodology, for example. Real time quantitative PCR would provide the capability of following the expression of the LTRPC3k gene throughout development, for example. Quantitative PCR methodology requires only a nominal amount of tissue from each developmentally important step is needed to perform such experiements. Therefore, the application of quantitative PCR methodology to refining the biological function of this polypeptide is encompassed by the present invention. Also encompassed by the present invention are quantitative PCR probes corresponding to the polynucleotide sequence provided as SEQ ID NO:1 (FIGS. 1A-E).

The function of the protein may also be assessed through complementation assays in yeast. For example, in the case of the LTRPC3k, transforming yeast deficient in transient receptor potential channel activity with LTRPC3k and assessing their ability to grow would provide convincing evidence the LTRPC3k polypeptide has transient receptor potential channel activity. Additional assay conditions and methods that may be used in assessing the function of the polynucletides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a kidney, spinal cord, testis, and/or brain -specific promoter), or it can be expressed at a specified time of development using an inducible and/or a developmentally regulated promoter.

In the case of LTRPC3k transgenic mice or rats, if no phenotype is apparent in normal growth conditions, observing the organism under diseased conditions (renal, reproductive, neural, or proliferative disorders, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal LTRPC3k deletion polypeptides are encompassed by the present invention: M1-T1711, G2-T1711, K3-T1711, K4-T1711, W5-T1711, R6-T1711, D7-T1711, A8-T1711, A9-T1711, E10-T1711, M11-T1711, E12-T1711, R13-T1711, G14-T1711, C15-T1711, S16-T1711, D17-T1711, R18-T1711, E19-T1711, D20-T1711, N21-T1711, A22-T1711, E23-T1711, S24-T1711, R25-T1711, R26-T1711, R27-T1711, S28-T1711, R29-T1711, S30-T1711, A31-T1711, S32-T1711, R33-T1711, G34-T1711, R35-T1711, F36-T1711, A37-T1711, E38-T1711, S39-T1711, W40-T1711, K41-T1711, R42-T1711, L43-T1711, S44-T1711, S45-T1711, K46-T1711, Q47-T1711, G48-T1711, S49-T1711, T50-T1711, K51-T1711, R52-T1711, S53-T1711, G54-T1711, L55-T1711, P56-T1711, S57-T1711, Q58-T1711, Q59-T1711, T60-T1711, P61-T1711, A62-T1711, Q63-T1711, K64-T1711, S65-T1711, W66-T1711, I67-T1711, E68-T1711, R69-T1711, A70-T1711, F71-T1711, Y72-T1711, K73-T1711, R74-T1711, E75-T1711, C76-T1711, V77-T1711, H78-T1711, I79-T1711, I80-T1711, P81-T1711, S82-T1711, T83-T1711, K84-T1711, D85-T1711, P86-T1711, H87-T1711, R88-T1711, C89-T1711, C90-T1711, C91-T1711, G92-T1711, R93-T1711, L94-T1711, I95-T1711, G96-T1711, Q97-T1711, H98-T1711, V99-T1711, G100-T1711, L101-T1711, T102-T1711, P103-T1711, S104-T1711, I105-T1711, S106-T1711, V107-T1711, L108-T1711, Q109-T1711, N110-T1711, E111-T1711, K112-T1711, N113-T1711, E114-T1711, S115-T1711, R116-T1711, L117-T1711, S118-T1711, R119-T1711, N120-T1711, D121-T1711, I122-T1711, Q123-T1711, S124-T1711, E125-T1711, K126-T1711, W127-T1711, S128-T1711, I129-T1711, S130-T1711, K131-T1711, H132-T1711, T133-T1711, Q134-T1711, L135-T1711, S136-T1711, P137-T1711, T138-T1711, D139-T1711, A140-T1711, F141-T1711, G142-T1711, T143-T1711, I144-T1711, E145-T1711, F146-T1711, Q147-T1711, G148-T1711, G149-T1711, G150-T1711, H151-T1711, S152-T1711, N153-T1711, K154-T1711, and/or A155-T1711 of SEQ ID NO:10. Polynucleotide sequences encoding these polypeptides are also provided. The present invention also encompasses the use of these N-terminal LTRPC3k deletion polypeptides as immunogenic and/or antigenic epitopes as described elsewhere herein.

In preferred embodiments, the following C-terminal LTRPC3k deletion polypeptides are encompassed by the present invention: M1-T1711, M1-H1710, M1-K1709, M1-S1708, M1-E1707, M1-F1706, M1-S1705, M1-Q1704, M1-F1703, M1-A1702, M1-S1701, M1-T1700, M1-R1699, M1-S1698, M1-L1697, M1-R1696, M1-R1695, M1-M1694, M1-S1693, M1-L1692, M1-S1691, M1-D1690, M1-G1689, M1-R1688, M1-G1687, M1-E1686, M1-P1685, M1-K1684, M1-S1683, M1-S1682, M1-K1681, M1-S1680, M1-R1679, M1-Q1678, M1-F1677, M1-P1676, M1-N1675, M1-Q1674, M1-L1673, M1-S1672, M1-A1671, M1-T1670, M1-N1669, M1-R1668, M1-Q1667, M1-R1666, M1-D1665, M1-L1664, M1-K1663, M1-D1662, M1-S1661, M1-I1660, M1-S1659, M1-F1658, M1-S1657, M1-K1656, M1-R1655, M1-T1654, M1-H1653, M1-A1652, M1-Y1651, M1-P1650, M1-A1649, M1-S1648, M1-P1647, M1-E1646, M1-E1645, M1-A1644, M1-S1643, M1-Y1642, M1-S1641, M1-N1640, M1-A1639, M1-R1638, M1-E1637, M1-I1636, M1-K1635, M1-P1634, M1-V1633, M1-T1632, M1-I1631, M1-N1630, M1-N1629, M1-S1628, M1-L1627, M1-T1626, M1-R1625, M1-E1624, M1-S1623, M1-N1622, M1-D1621, M1-G1620, M1-E1619, M1-Q1618, M1-S1617, M1-S1616, M1-I1615, M1-A1614, M1-I1613, M1-T1612, M1-A1611, M1-R1610, M1-R1609, M1-G1608, M1-K1607, M1-A1606, M1-E1605, M1-N1604, M1-E1603, M1-E1602, M1-S1601, M1-D1600, M1-S1599, M1-S1598, M1-P1597, M1-H1596, M1-S1595, M1-L1594, M1-E1593, M1-A1592, M1-E1591, M1-R1590, M1-E1589, M1-P1588, M1-H1587, M1-C1586, M1-C1585, M1-T1584, M1-L1583, M1-D1582, M1-E1581, M1-V1580, M1-K1579, M1-D1578, M1-G1577, M1-L1576, M1-G1575, M1-G1574, M1-P1573, M1-F1572, M1-A1571, M1-A1570, M1-R1569, M1-D1568, M1-A1567, M1-I1566, M1-A1565, M1-Q1564, M1-P1563, M1-A1562, M1-N1561, M1-V1560, M1-C1559, M1-R1558, M1-T1557, M1-D1556, M1-I1555, M1-C1554, M1-D1553, M1-T1552, M1-I1551, M1-S1550, M1-T1549, M1-Y1548, M1-E1547, M1-A1546, M1-T1545, M1-K1544, M1-V1543, M1-P1542, M1-V1541, M1-G1540, M1-F1539, M1-N1538, M1-A1537, M1-Y1536, M1-Y1535, M1-S1534, M1-R1533, M1-S1532, M1-P1531, M1-S1530, M1-F1529, M1-M1528, M1-F1527, M1-S1526, M1-H1525, M1-S1524, M1-K1523, M1-V1522, M1-I1521, M1-P1520, M1-A1519, M1-E1518, M1-E1517, M1-L1516, M1-L1515, M1-F1514, M1-P1513, M1-T1512, M1-T1511, M1-A1510, M1-L1509, M1-Y1508, M1-R1507, M1-S1506, M1-S1505, M1-K1504, M1-S1503, M1-R1502, M1-E1501, M1-I1500, M1-T1499, M1-H1498, M1-Y1497, M1-M1496, M1-P1495, M1-P1494, M1-E1493, M1-S1492, M1-D1491, M1-W1490, M1-P1489, M1-N1488, M1-Q1487, M1-C1486, M1-E1485, M1-P1484, M1-L1483, M1-H1482, M1-T1481, M1-Y1480, M1-D1479, M1-S1478, M1-S1477, M1-F1476, M1-S1475, M1-R1474, M1-T1473, M1-D1472, M1-M1471, M1-S1470, M1-T1469, M1-I1468, M1-D1467, M1-E1466, M1-F1465, M1-D1464, M1-I1463, M1-S1462, M1-R1461, M1-S1460, M1-P1459, M1-P1458, M1-R1457, M1-D1456, M1-T1455, M1-P1454, M1-A1453, M1-L1452, M1-T1451, M1-A1450, M1-Y1449, M1-A1448, M1-S1447, M1-S1446, M1-S1445, M1-P1444, M1-A1443, M1-T1442, M1-S1441, M1-P1440, M1-V1439, M1-P1438, M1-T1437, M1-S1436, M1-F1435, M1-S1434, M1-P1433, M1-E1432, M1-G1431, M1-L1430, M1-G1429, M1-L1428, M1-I1427, M1-N1426, M1-V1425, M1-S1424, M1-N1423, M1-D1422, M1-L1421, M1-P1420, M1-D1419, M1-I1418, M1-D1417, M1-C1416, M1-H1415, M1-L1414, M1-E1413, M1-D1412, M1-M1411, M1-A1410, M1-S1409, M1-V1408, M1-Y1407, M1-I1406, M1-D1405, M1-I1404, M1-C1403, M1-S1402, M1-S1401, M1-P1400, M1-R1399, M1-R1398, M1-S1397, M1-D1396, M1-P1395, M1-V1394, M1-I1393, M1-A1392, M1-L1391, M1-T1390, M1-N1389, M1-A1388, M1-P1387, M1-A1386, M1-A1385, M1-P1384, M1-A1383, M1-K1382, M1-P1381, M1-E1380, M1-K1379, M1-A1378, M1-V1377, M1-S1376, M1-H1375, M1-S1374, M1-S1373, M1-T1372, M1-A1371, M1-R1370, M1-H1369, M1-L1368, M1-S1367, M1-L1366, M1-S1365, M1-R1364, M1-E1363, M1-K1362, M1-F1361, M1-I1360, M1-S1359, M1-E1358, M1-L1357, M1-K1356, M1-E1355, M1-I1354, M1-G1353, M1-G1352, M1-K1351, M1-D1350, M1-K1349, M1-M1348, M1-M1347, M1-V1346, M1-S1345, M1-Y1344, M1-F1343, M1-S1342, M1-H1341, M1-S1340, M1-R1339, M1-M1338, M1-R1337, M1-P1336, M1-M1335, M1-L1334, M1-T1333, M1-P1332, M1-S1331, M1-T1330, M1-P1329, M1-S1328, M1-M1327, M1-T1326, M1-E1325, M1-E1324, M1-G1323, M1-A1322, M1-P1321, M1-D1320, M1-I1319, M1-S1318, M1-E1317, M1-Q1316, M1-L1315, M1-K1314, M1-F1313, M1-T1312, M1-N1311, M1-G1310, M1-E1309, M1-Q1308, M1-S1307, M1-N1306, M1-F1305, M1-S1304, M1-S1303, M1-Q1302, M1-R1301, M1-V1300, M1-I1299, M1-Y1298, M1-A1297, M1-A1296, M1-D1295, M1-T1294, M1-C1293, M1-D1292, M1-S1291, M1-S1290, M1-T1289, M1-R1288, M1-S1287, M1-R1286, M1-I1285, M1-K1284, M1-N1283, M1-S1282, M1-E1281, M1-A1280, M1-R1279, M1-E1278, M1-L1277, M1-G1276, M1-T1275, M1-L1274, M1-R1273, M1-E1272, M1-L1271, M1-A1270, M1-T1269, M1-A1268, M1-M1267, M1-R1266, M1-G1265, M1-I1264, M1-L1263, M1-D1262, M1-E1261, M1-L1260, M1-Q1259, M1-A1258, M1-L1257, M1-R1256, M1-I1255, M1-D1254, M1-V1253, M1-T1252, M1-Q1251, M1-L1250, M1-S1249, M1-A1248, M1-K1247, M1-M1246, M1-S1245, M1-H1244, M1-E1243, M1-R1242, M1-E1241, M1-N1240, M1-V1239, M1-E1238, M1-E1237, M1-L1236, M1-R1235, M1-M1234, M1-S1233, M1-M1232, M1-N1231, M1-E1230, M1-V1229, M1-R1228, M1-E1227, M1-S1226, M1-T1225, M1-V1224, M1-R1223, M1-I1222, M1-R1221, M1-E1220, M1-D1219, M1-N1218, M1-S1217, M1-S1216, M1-N1215, M1-F1214, M1-R1213, M1-D1212, M1-D1211, M1-K1210, M1-E1209, M1-R1208, M1-F1207, M1-Y1206, M1-E1205, M1-E1204, M1-I1203, M1-C1202, M1-Q1201, M1-E1200, M1-E1199, M1-F1198, M1-D1197, M1-H1196, M1-V1195, M1-K1194, M1-K1193, M1-L1192, M1-E1191, M1-D1190, M1-D1189, M1-T1188, M1-I1187, M1-F1186, M1-L1185, M1-K1184, M1-L1183, M1-G1182, M1-Y1181, M1-D1180, M1-R1179, M1-E1178, M1-D1177, M1-P1176, M1-D1175, M1-S1174, M1-E1173, M1-H1172, M1-K1171, M1-R1170, M1-W1169, M1-R1168, M1-C1167, M1-C1166, M1-L1165, M1-H11164, M1-Q1163, M1-F1162, M1-I1161, M1-M1160, M1-T1159, M1-M1158, M1-H1157, M1-S1156, M1-F1155, M1-I1154, M1-I1153, M1-L1152, M1-P1151, M1-P1150, M1-P1149, M1-L1148, M1-V1147, M1-P1146, M1-R1145, M1-E1144, M1-H1143, M1-F1142, M1-T1141, M1-M1140, M1-I1139, M1-L1138, M1-Q1137, M1-Y1136, M1-R1135, M1-Q1134, M1-F1133, M1-K1132, M1-W1131, M1-V1130, M1-Q1129, M1-N1128, M1-S1127, M1-I1126, M1-S1125, M1-K1124, M1-V1123, M1-E1122, M1-F1121, M1-F1120, M1-T1119, M1-N1118, M1-N1117, M1-F1116, M1-V1115, M1-A1114, M1-I1113, M1-L1112, M1-L1111, M1-N1110, M1-V1109, M1-L1108, M1-L1107, M1-I1106, M1-N1105, M1-A1104, M1-V1103, M1-L1102, M1-L1101, M1-Y1110, M1-C1099, M1-A1098, M1-M1097, M1-I1096, M1-A1095, M1-P1094, M1-V1093, M1-I1092, M1-W1091, M1-A1090, M1-G1089, M1-T1088, M1-K1087, M1-C1086, M1-P1085, M1-P1084, M1-L1083, M1-Q1082, M1-I1081, M1-I1080, M1-K1079, M1-G1078, M1-D1077, M1-E1076, M1-R1075, M1-T1074, M1-E1073, M1-N1072, M1-Q1071, M1-G1070, M1-C1069, M1-P1068, M1-P1067, M1-D1066, M1-I1065, M1-Q1064, M1-D1063, M1-A1062, M1-F1061, M1-V1060, M1-E1059, M1-G1058, M1-Y1057, M1-I1056, M1-M1055, M1-W1054, M1-Y1053, M1-P1052, M1-M1051, M1-Y1050, M1-F1049, M1-I1048, M1-N1047, M1-K1046, M1-A1045, M1-L1044, M1-K1043, M1-W1042, M1-S1041, M1-P1040, M1-E1039, M1-E1038, M1-N1037, M1-P1036, M1-F1035, M1-L1034, M1-I1033, M1-A1032, M1-Q1031, M1-R1030, M1-A1029, M1-V1028, M1-G1027, M1-F1026, M1-S1025, M1-M1024, M1-L1023, M1-V1022, M1-V1021, M1-L1020, M1-M1019, M1-I1018, M1-I1017, M1-V1016, M1-F1015, M1-Y1014, M1-M1013, M1-M1012, M1-D1011, M1-I1010, M1-M1009, M1-M1008, M1-K1007, M1-G1006, M1-I1005, M1-M1004, M1-M1003, M1-V1002, M1-Y1001, M1-P1000, M1-G999, M1-L998, M1-Y997, M1-K996, M1-N995, M1-V994, M1-G993, M1-F992, M1-I991, M1-D990, M1-L989, M1-L988, M1-R987, M1-I986, M1-Y985, M1-W984, M1-Y983, M1-I982, M1-I981, M1-N980, M1-V979, M1-C978, M1-Y977, M1-I976, M1-V975, M1-R974, M1-G973, M1-D972, M1-S971, M1-R970, M1-F969, M1-P968, M1-Q967, M1-D966, M1-Q965, M1-L964, M1-R963, M1-L962, M1-I961, M1-M960, M1-G959, M1-V958, M1-S957, M1-F956, M1-L955, M1-L954, M1-I953, M1-A952, M1-I951, M1-L950, M1-D949, M1-T948, M1-V947, M1-N946, M1-W945, M1-Y944, M1-E943, M1-Q942, M1-L941, M1-W940, M1-V939, M1-K938, M1-V937, M1-K936, M1-Q935, M1-L934, M1-L933, M1-K932, M1-G931, M1-P930, M1-E929, M1-S928, M1-M927, M1-L926, M1-L925, M1-E924, M1-R923, M1-M922, M1-K921, M1-E920, M1-I919, M1-G918, M1-L917, M1-T916, M1-F915, M1-I914, M1-Y913, M1-S912, M1-I911, M1-V910, M1-I909, M1-W908, M1-E907, M1-Q906, M1-T905, M1-S904, M1-P903,
M1-W902, M1-R901, M1-E900, M1-M899, M1-K898,
M1-V897, M1-L896, M1-V895, M1-I894, M1-Y893,
M1-N892, M1-F891, M1-L890, M1-M889, M1-L888,
M1-Y887, M1-G886, M1-I885, M1-Y884, M1-A883,
M1-L882, M1-T881, M1-Y880, M1-F879, M1-W878,
M1-F877, M1-K876, M1-V875, M1-I874, M1-P873,
M1-A872, M1-N871, M1-Y870, M1-F869, M1-E868,
M1-Y867, M1-I866, M1-K865, M1-R864, M1-G863,
M1-L862, M1-P861, M1-I860, M1-L859, M1-R858,
M1-H857, M1-K856, M1-S855, M1-Q854, M1-V853,
M1-E852, M1-E851, M1-E850, M1-D849, M1-K848,
M1-K847, M1-R846, M1-S845, M1-S844, M1-E843,
M1-G842, M1-N841, M1-N840, M1-R839, M1-G838,
M1-L837, M1-M836, M1-A835, M1-T834, M1-L833,
M1-E832, M1-M831, M1-D830, M1-E829, M1-E828,
M1-E827, M1-K826, M1-E825, M1-K824, M1-T823,
M1-P822, M1-K821, M1-E820, M1-P819, M1-E818,
M1-E817, M1-A816, M1-E815, M1-K814, M1-E813,
M1-Q812, M1-L811, M1-H810, M1-I809, M1-E808,
M1-Q807, M1-A806, M1-Q805, M1-S804, M1-M803,
M1-Y802, M1-P801, M1-M800, M1-D799, M1-D798,
M1-K797, M1-N796, M1-K795, M1-F794, M1-E793,
M1-L792, M1-S791, M1-L790, M1-I789, M1-S788,
M1-P787, M1-P786, M1-L785, M1-L784, M1-I783,
M1-G782, M1-L781, M1-I780, M1-V779, M1-K778,
M1-L777, M1-G776, M1-S775, M1-N774, M1-K773,
M1-R772, M1-M771, M1-R770, M1-L769, M1-R768,
M1-G767, M1-M766, M1-W765, M1-M764, M1-D763,
M1-T762, M1-L761, M1-L760, M1-M759, M1-Q758,
M1-S757, M1-C756, M1-T755, M1-H754, M1-A753,
M1-I752, M1-F751, M1-D750, M1-R749, M1-H748,
M1-K747, M1-A746, M1-A745, M1-V744, M1-A743,
M1-L742, M1-Q741, M1-L740, M1-C739, M1-T738,
M1-A737, M1-N736, M1-S735, M1-W734, M1-N733,
M1-K732, M1-L731, M1-E730, M1-Y729, M1-T728,
M1-L727, M1-L726, M1-K725, M1-M724, M1-A723,
M1-L722, M1-Q721, M1-E720, M1-D719, M1-Q718,
M1-K717, M1-Y716, M1-S715, M1-Q714, M1-D713,
M1-L712, M1-L711, M1-E710, M1-V709, M1-A708,
M1-L707, M1-Q706, M1-G705, M1-F704, M1-D703,
M1-R702, M1-S701, M1-N700, M1-H699, M1-N698,
M1-L697, M1-E696, M1-Q695, M1-S694, M1-I693,
M1-D692, M1-D691, M1-V690, M1-M689, M1-D688,
M1-N687, M1-E686, M1-S685, M1-A684, M1-E683,
M1-H682, M1-A681, M1-M680, M1-A679, M1-K678,
M1-C677, M1-L676, M1-K675, M1-C674, M1-A673,
M1-V672, M1-L671, M1-A670, M1-K669, M1-A668,
M1-M667, M1-A666, M1-E665, M1-E664, M1-G663,
M1-H662, M1-Q661, M1-W660, M1-F659, M1-F658,
M1-L657, M1-A656, M1-M655, M1-K654, M1-Q653,
M1-R652, M1-K651, M1-M650, M1-L649, M1-V648,
M1-A647, M1-W646, M1-V645, M1-M644, M1-L643,
M1-E642, M1-H641, M1-F640, M1-P639, M1-F638,
M1-P637, M1-F636, M1-H635, M1-N634, M1-I633,
M1-E632, M1-P631, M1-D630, M1-D629, M1-L628,
M1-D627, M1-I626, M1-D625, M1-V624, M1-E623,
M1-E622, M1-E621, M1-R620, M1-K619, M1-K618,
M1-T617, M1-T616, M1-K615, M1-R614, M1-G613,
M1-R612, M1-R611, M1-L610, M1-P609, M1-I608,
M1-D607, M1-D606, M1-R605, M1-K604, M1-P603,
M1-G602, M1-F601, M1-L600, M1-N599, M1-H598,
M1-Y597, M1-L596, M1-T595, M1-R594, M1-F593,
M1-R592, M1-K591, M1-R590, M1-T589, M1-Y588,
M1-N587, M1-C586, M1-R585, M1-Y584, M1-A583,
M1-G582, M1-G581, M1-M580, M1-L579, M1-Y578,
M1-E577, M1-I576, M1-V575, M1-L574, M1-G573,
M1-I572, M1-D571, M1-I570, M1-L569, M1-S568,
M1-I567, M1-R566, M1-Y565, M1-D564, M1-P563,
M1-P562, M1-L561, M1-N560, M1-G559, M1-K558,
M1-F557, M1-Y556, M1-I555, M1-W554, M1-G553,
M1-F552, M1-G551, M1-P550, M1-Y549, M1-E548,
M1-R547, M1-K546, M1-K545, M1-V544, M1-D543,
M1-R542, M1-V541, M1-L540, M1-H539, M1-Y538,
M1-L537, M1-T536, M1-N535, M1-S534, M1-P533,
M1-G532, M1-H531, M1-R530, M1-T529, M1-N528,
M1-Y527, M1-L526, M1-E525, M1-E524, M1-L523,
M1-R522, M1-S521, M1-I520, M1-T519, M1-L518,
M1-F517, M1-R516, M1-H515, M1-M514, M1-S513,
M1-V512, M1-G511, M1-N510, M1-E509, M1-I508,
M1-L507, M1-L506, M1-K505, M1-V504, M1-F503,
M1-D502, M1-V501, M1-R500, M1-D499, M1-L498,
M1-V497, M1-L496, M1-A495, M1-D494, M1-L493,
M1-M492, M1-A491, M1-Q490, M1-E489, M1-L488,
M1-S487, M1-G486, M1-V485, M1-P484, M1-W483,
M1-Q482, M1-Q481, M1-G480, M1-Y479, M1-I478,
M1-F477, M1-I476, M1-Q475, M1-S474, M1-R473,
M1-A472, M1-I471, M1-D470, M1-V469, M1-R468,
M1-N467, M1-W466, M1-A465, M1-L464, M1-A463,
M1-L462, M1-S461, M1-L460, M1-Q459, M1-D458,
M1-P457, M1-A456, M1-S455, M1-A454, M1-N453,
M1-A452, M1-G451, M1-K450, M1-L449, M1-L448,
M1-A447, M1-T446, M1-L445, M1-I444, M1-A443,
M1-L442, M1-D441, M1-I440, M1-D439, M1-Q438,
M1-H437, M1-G436, M1-E435, M1-S434, M1-G433,
M1-M432, M1-R431, M1-F430, M1-V429, M1-T428,
M1-I427, M1-L426, M1-E425, M1-K424, M1-K423,
M1-K422, M1-M421, M1-C420, M1-E419, M1-M418,
M1-L417, M1-I416, M1-I415, M1-F414, M1-L413,
M1-H412, M1-Q411, M1-A410, M1-Q409, M1-T408,
M1-R407, M1-T406, M1-Y405, M1-T404, M1-F403,
M1-T402, M1-K401, M1-Q400, M1-I399, M1-T398,
M1-V397, M1-L396, M1-L395, M1-Q394, M1-D393,
M1-R392, M1-L391, M1-S390, M1-E389, M1-N388,
M1-I387, M1-L386, M1-G385, M1-G384, M1-E383,
M1-E382, M1-S381, M1-Y380, M1-K379, M1-H378,
M1-G377, M1-F376, M1-A375, M1-L374, M1-I373,
M1-D372, M1-S371, M1-A370, M1-R369, M1-G368,
M1-S367, M1-G366, M1-D365, M1-C364, M1-V363,
M1-V362, M1-V361, M1-P360, M1-V359, M1-P358,
M1-P357, M1-T356, M1-D355, M1-R354, M1-L353,
M1-Y352, M1-E351, M1-L350, M1-V349, M1-I348,
M1-S347, M1-I346, M1-V345, M1-N344, M1-P343,
M1-G342, M1-G341, M1-E340, M1-V339, M1-I338,
M1-L337, M1-A336, M1-V335, M1-V334, M1-P333,
M1-V332, M1-G331, M1-Q330, M1-G329, M1-I328,
M1-R327, M1-T326, M1-N325, M1-I324, M1-K323,
M1-Q322, M1-L321, M1-S320, M1-I319, M1-H318,
M1-K317, M1-E316, M1-L315, M1-Q314, M1-R313,
M1-R312, M1-L311, M1-K310, M1-V309, M1-E308,
M1-A307, M1-G306, M1-Y305, M1-K304, M1-G303,
M1-T302, M1-T301, M1-G300, M1-N299, M1-D298,
M1-A297, M1-L296, M1-I295, M1-F294, M1-H293,
M1-S292, M1-H291, M1-M290, M1-S289, M1-N288,
M1-L287, M1-V286, M1-T285, M1-L284, M1-K283,
M1-S282, M1-M281, M1-P280, M1-N279, M1-S278,
M1-M277, M1-T276, M1-Q275, M1-Y274, M1-P273,
M1-R272, M1-V271, M1-V270, M1-D269, M1-R268,
M1-G267, M1-I266, M1-L265, M1-D264, M1-E263,
M1-Q262, M1-N261, M1-E260, M1-V259, M1-I258,
M1-V257, M1-W256, M1-P255, M1-A254, M1-I253,
M1-G252, M1-I251, M1-T250, M1-C249, M1-I248,
M1-K247, M1-G246, M1-R245, M1-S244, M1-K243,
M1-S242, M1-A241, M1-H240, M1-D239, M1-K238, M1-L237, M1-A236, M1-D235, M1-G234, M1-V233, M1-H232, M1-R231, M1-I230, M1-V229, M1-G228, M1-T227, M1-N226, M1-V225, M1-G224, M1-G223, M1-T222, M1-F221, M1-I220, M1-W219, M1-A218, M1-G217, M1-T216, M1-T215, M1-M214, M1-A213, M1-A212, M1-K211, M1-I210, M1-L209, M1-G208, M1-K207, M1-G206, M1-F205, M1-V204, M1-Q203, M1-K202, M1-L201, M1-K200, M1-P199, M1-Q198, M1-L197, M1-E196, M1-F195, M1-N194, M1-Q193, M1-L192, M1-G191, M1-G190, M1-H189, M1-V188, M1-S187, M1-I186, M1-L185, M1-L184, M1-K183, M1-P182, M1-L181, M1-E180, M1-L179, M1-Q178, M1-W177, M1-E176, M1-K175, M1-T174, M1-M173, M1-L172, M1-H171, M1-L170, M1-L169, M1-L168, M1-D167, M1-P166, M1-K165, M1-T164, M1-D163, M1-F162, M1-S161, M1-V160, M1-R159, M1-V158, M1-Y157, M1-M156, M1-A155, M1-K154, M1-N153, M1-S152, M1-H151, M1-G150, M1-G149, M1-G148, M1-Q147, M1-F146, M1-E145, M1-I144, M1-T143, M1-G142, M1-F141, M1-A140, M1-D139, M1-T138, M1-P137, M1-S136, M1-L135, M1-Q134, M1-T133, M1-H132, M1-K131, M1-S130, M1-I129, M1-S128, M1-W127, M1-K126, M1-E125, M1-S124, M1-Q123, M1-I122, M1-D121, M1-N120, M1-R119, M1-S118, M1-L117, M1-R116, M1-S115, M1-E114, M1-N113, M1-K112, M1-E111, M1-N110, M1-Q109, M1-L108, M1-V107, M1-S106; M1-I105, M1-S104, M1-P103, M1-T102, M1-L101, M1-G100, M1-V99, M1-H98, M1-Q97, M1-G96, M1-I95, M1-L94, M1-R93, M1-G92, M1-C91, M1-C90, M1-C89, M1-R88, M1-H87, M1-P86, M1-D85, M1-K84, M1-T83, M1-S82, M1-P81, M1-I80, M1-I79, M1-H78, M1-V77, M1-C76, M1-E75, M1-R74, M1-K73, M1-Y72, M1-F71, M1-A70, M1-R69, M1-E68, M1-I67, M1-W66, M1-S65, M1-K64, M1-Q63, M1-A62, M1-P61, M1-T60, M1-Q59, M1-Q58, M1-S57, M1-P56, M1-L55, M1-G54, M1-S53, M1-R52, M1-K51, M1-T50, M1-S49, M1-G48, M1-Q47, M1-K46, M1-S45, M1-S44, M1-L43, M1-R42, M1-K41, M1-W40, M1-S39, M1-E38, M1-A37, M1-F36, M1-R35, M1-G34, M1-R33, M1-S32, M1-A31, M1-S30, M1-R29, M1-S28, M1-R27, M1-R26, M1-R25, M1-S24, M1-E23, M1-A22, M1-N21, M1-D20, M1-E19, M1-R18, M1-D17, M1-S16, M1-C15, M1-G14, M1-R13, M1-E12, M1-M11, M1-E10, M1-A9, M1-A8, and/ or M1-D7 of SEQ ID NO:10. Polynucleotide sequences encoding these polypeptides are also provided. The present invention also encompasses the use of these C-terminal LTRPC3k deletion polypeptides as immunogenic and/or antigenic epitopes as described elsewhere herein.

Alternatively, preferred polypeptides of the present invention may comprise polypeptide sequences corresponding to, for example, internal regions of the LTRPC3k polypeptide (e.g., any combination of both N- and C-terminal LTRPC3k polypeptide deletions) of SEQ ID NO:10. For example, internal regions could be defined by the equation: amino acid NX to amino acid CX, wherein NX refers to any N-terminal deletion polypeptide amino acid of LTRPC3k (SEQ ID NO:10), and where CX refers to any C-terminal deletion polypeptide amino acid of LTRPC3k (SEQ ID NO:10). Polynucleotides encoding these polypeptides are also provided. The present invention also encompasses the use of these polypeptides as an immunogenic and/or antigenic epitope as described elsewhere herein.

Many polynucleotide sequences, such as EST sequences, are publicly available and accessible through sequence databases. Some of these sequences are related to SEQ ID NO:9 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 5193 of SEQ ID NO:9, b is an integer between 15 to 5207, where both a and b correspond to the positions of nucleotide residues shown in SEQ ID NO:9, and where b is greater than or equal to a+14.

Features of the Polypeptide Encoded by Gene No:5

The polypeptide of this gene provided as SEQ ID NO:12 (FIGS. 6A-F), encoded by the polynucleotide sequence according to SEQ ID NO:11 (FIGS. 6A-F), and/or encoded by the polynucleotide contained within the deposited clone, LTRPC3l, has significant homology at the nucleotide and amino acid level to the human melastatin 1 protein (Melastatin1; Genbank Accession No. gi|3243075; SEQ ID NO:13). An alignment of the LTRPC3l polypeptide with this protein is provided in FIGS. 7A-G.

The LTRPC3l polypeptide was determined to share 65.7% identity and 73.5% similarity with the human melastatin 1 protein (Melastatin1; Genbank Accession No. gi|3243075; SEQ ID NO:13) as shown in FIG. 10.

The LTRPC3l protein is believed to represent a member of a new class of protein kinases referred to as alpha kinases (Curr. Biol. 9 (2), R43-R45 (1999)). These kinases represent a novel type of signaling molecule comprising both a catalytic protein kinase domain, in addition to, an ion channel domain. This family is commonly referred to as the transient receptor potential channel (TRP) family. Melastatin1 defines a separate subfamily of TRP channels referred to as TRPM (melastatin1). TRPM family members are characteristic of their unusually long cytoplasmic tails at both ends of the channel domain and some of the family members contain an enzyme domain at the C-terminal region.

Specifically, the LTRPC3l (SEQ ID NO: 12) polypeptide represents a novel variant of the LTRPC3f (Co-pending U.S. Ser. No. 10/210,152, filed Aug. 1, 2002; International Publication No. WO 03/012063, published Feb. 13, 2003; SEQ ID NO:21) polypeptide. The LTRPC3l represents a novel member of the TRPM subfamily.

The melastatin1 protein is believed to be negatively associated with the incidence of melanoma based upon its inverse correlative expression in highly aggressive melanomas (Genomics 54 (1), 116-123 (1998)). Thus, overexpression of melastatin1 could represent a novel therapeutic in the treatment of melanoma and potentially other cancers.

Based upon the observed homology, the polypeptide of the present invention is expected to share at least some biological activity with other transient receptor potential channel family members, more specifically with the melastatin1 protein, in addition to, other transient receptor potential channel family members referenced elsewhere herein or otherwise known in the art, particularly LTRPC3f, and LTRPC3.

Most of the known transient receptor potential channel family members, possess one or more transmembrane domains. Likewise, the LTRPC3l polypeptide has been determined to comprise six transmembrane domains (TM1-TM6) as shown in FIGS. 6A-F. The transmembrane domains are located from about amino acid 800 to about amino acid 817 (TM1), from about amino acid 897 to about amino acid 914 (TM2), from about amino acid 970 to about amino acid 983 (TM3), from about amino acid 997 to about amino acid 1014 (TM4), from about amino acid 1031 to about amino acid 1048 (TM5), and/or from about amino acid 1118 to about amino acid 1137 (TM6) of SEQ ID NO:12. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following transmembrane domain polypeptides are encompassed by the present invention: LKVILGILLPPSILSLEF (SEQ ID NO:92), IVKFW-FYTLAYIGYLMLF (SEQ ID NO:93), VTDLIAILLFS-VGM (SEQ ID NO:94), RVIYCVNIIYWYIRLLDI (SEQ ID NO:95), MMIDMMYFVIIMLVVLMS (SEQ ID NO:96), and/or AIMACYLLVANILLVNLLIAV (SEQ ID NO:97). Polynucleotides encoding these polypeptides are also provided. The present invention also encompasses the use of the LTRPC3l transmembrane polypeptides as immunogenic and/or antigenic epitopes as described elsewhere herein.

The present invention also encompasses polypeptides corresponding to the regions between each transmembrane domain of LTRPC3l, referred to herein as inter-transmembrane domain polypeptides (inter TM1-2, inter TM2-3, inter TM3-4, inter TM4-5, and inter TM5-6). Such regions are typically solvent accessible (either extracellularly or intracellularly). Therefore, these regions are amenable to the development of agonists and/or antagonists to the LTRPC3l polypeptide, particularly for the development of antibodies specific to these regions.

In preferred embodiments, the following inter-transmembrane domain polypeptides are encompassed by the present invention: KNKDDMPYMSQAQEIHLQEKEAEEPE-KPTKEKEEEDMELTAMLGRNNGESS RKKDEEEVQSKHRLIPLGRKIYEFYNAP (SEQ ID NO:98), NYIVLVKMERWPSTQEWIVISYIFTLG-IEKMREILMSEPGKLLQKVKVWLQEY WN (SEQ ID NO:99), ILRLQDQPFRSDG (SEQ ID NO:100), FGVNKY-LGPYVMMIGK (SEQ ID NO:101), and/or FGVARQAIL-FPNEEPSWKLAKNIFYMPYWMIYGEV-FADQIDRKQVYDSHTPK SAPCGQNETREDGKIIQLPPCKTGAWIVP (SEQ ID NO:102). Polynucleotides encoding these polypeptides are also provided. The present invention also encompasses the use of the LTRPC3l inter-transmembrane polypeptides as immunogenic and/or antigenic epitopes as described elsewhere herein.

The LTRPC3l polypeptide was determined to comprise several conserved cysteines, at amino acid 249, 389, 599, 697, 762, 779, 1001, 1092, 1109, 1122, 1225, 1316, and 1582 of SEQ ID No: 12 (FIGS. 6A-F). Conservation of cysteines at key amino acid residues is indicative of conserved structural features, which may correlate with conservation of protein function and/or activity.

In confirmation of the LTRPC3l representing a member of the transient receptor channel family, the LTRPC3l polypeptide was determined to comprise a predicted TRP domain located from about amino acid 1153 to about amino acid 1158 of SEQ ID NO:12. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following TRP domain polypeptide is encompassed by the present invention: VWK-FQR (SEQ ID NO:103). Polynucleotides encoding this polypeptide are also provided. The present invention also encompasses the use of this LTRPC3l TRP domain polypeptide as an immunogenic and/or antigenic epitope as described elsewhere herein.

In further confirmation of the LTRPC3l representing a member of the transient receptor channel family, the LTRPC3l polypeptide was determined to comprise a predicted ion transport signature domain located at about amino acid 928 to about amino acid 1136 of SEQ ID NO:12. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following ion transport signature domain polypeptide is encompassed by the present invention: TQEWIVISYIFTLGIEKMREILM-SEPGKLLQKVKVWLQEYWNVTDLIAILLFSV GMIL-RLQDQPFRSDGRVIYCVNIIYWYIRLL-DIFGVNKYLGPYVMMIGKMMID MMYFVIIMLVVLMSFGVARQAILFP-NEEPSWKLAKNIFYMPYWMIYGEVFAD QIDP-PCGQNETREDGKIIQLPPCKTGAWIV-PAIMACYLLVANILLVNLLIAVF (SEQ ID NO:104). Polynucleotides encoding this polypeptide are also provided. The present invention also encompasses the use of this LTRPC3l ion transport signature domain polypeptide as an immunogenic and/or antigenic epitope as described elsewhere herein.

The LTRPC3l polypeptide was determined to comprise a predicted predicted coiled-coil domain located at about amino acid 1243 to about amino acid 1298 of SEQ ID NO:12. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following coiled-coil domain polypeptide is encompassed by the present invention: ERIRVTSERVENMSMRLEEVNEREH-SMKASLQTVDIRLAQLEDLIGRMATAL ERL (SEQ ID NO:105). Polynucleotides encoding this polypeptide are also provided. The present invention also encompasses the use of this LTRPC3l coiled-coil domain polypeptide as an immunogenic and/or antigenic epitope as described elsewhere herein.

LTRPC3l polypeptides and polynucleotides are useful for diagnosing diseases related to the over and/or under expression of LTRPC3l by identifying mutations in the LTRPC3l gene using LTRPC3l sequences as probes or by determining LTRPC3l protein or mRNA expression levels. LTRPC3l polypeptides will be useful in screens for compounds that affect the activity of the protein. LTRPC3l peptides can also be used for the generation of specific antibodies and as bait in yeast two hybrid screens to find proteins the specifically interact with LTRPC3l.

Since the LTRPC3l polypeptide represents an N-terminally extended variant of the LTRPC3f polypeptide (see polypeptide alignment provided in FIG. 11A-I), and since the LTRPC3f (SEQ ID NO:21) polypeptide represents a splice variant of the LTRPC3 polypeptide (SEQ ID NO:15), the LTRPC3l (SEQ ID NO:12) polypeptide of the present invention is expected to have the same or similar function as the LTRPC3 polypeptide, and in particular, the LTRPC3f polypeptide. Specifically, the LTRPC3l polypeptide is expected to localize to the cell membrane.

Moreover, the LTRPC3l polypeptide is expected to also localize in or near the plasmalemmal compartment.

Moreover, the LTRPC3l polypeptide is also expected to be a constitutively active channel capable of mediating $Ca^{2+}$ influx.

Moreover, the LTRPC3l polypeptide is also expected to mediate $Ca^{2+}$ entry and that LTRPC3l-mediated $Ca^{2+}$ entry is expected to be potentiated by store-depletion.

Moreover, the LTRPC3l polypeptide is also expected to mediate a $Ca^{2+}$ entry pathway that is distinct from the endogenous $Ca^{2+}$ entry pathways present in HEK 293 cells.

Moreover, the LTRPC3l polypeptide of the present invention is expected to share the same or similar expression profile as that of the LTRPC3 polypeptide (SEQ ID NO:15).

Moreover, the LTRPC3l polypeptide is expected to share the same or similar differential expression patterns observed for the LTRPC3 variant.

Moreover, the LTRCP3g polypeptide is expected to be able to modulate the FEN1 DNA base-excision repair/proliferation modulating protein to the same or similar extent as the LTRPC3 polypeptide.

Moreover, the LTRPC3l polynucleotides and polypeptides are expected to share at least some biological activity with TRP family members expressed in kidney cells and tissues, particularly those specifically referenced herein, such as LTRPC3 (SEQ ID NO:15), and particularly as LTRPC3b (SEQ ID NO:17).

Moreover, the LTRPC3l polynucleotides and polypeptides are expected to share at least some biological activity with TRP family members expressed in testis cells and tissues, particularly those specifically referenced herein, such as the LTRPC3 variant (SEQ ID NO:15), and particularly as LTRPC3f (SEQ ID NO:21).

In preferred embodiments, LTRPC3l polynucleotides and polypeptides, including fragments and modulators thereof, are useful for treating, diagnosing, and/or ameliorating $Ca^{2+}$ reabsorption disorders, disorders associated with aberrant luminal $Ca^{2+}$ entry via the epithelial $Ca^{2+}$ channel (ECaC), disorders associated with aberrant cytosolic diffusion of $Ca^{2+}$ bound to calbindin-D28K, disorders associated with aberrant basolateral extrusion of $Ca^{2+}$ through the $Na^+/Ca^{2+}$ exchanger (NCX), disorders associated with aberrant plasma membrane $Ca^{2+}$-ATPase (PMCA) activity and/or activation, disorders associated with the hypocalciuric effect of diuretics, disorders associated with the hypocalciuric effect of thiazide diuretics, disorders associated with hormone insufficiencies that affect the function of the kidney, disorders associated with hormone insufficiencies that affect renal $Ca^{2+}$ homeostasis, disorders associated with aberrant renal $Ca^{2+}$ homeostasis as a result of vitamin D deficiency, disorders associated with aberrant renal $Ca^{2+}$ homeostasis as a result of PTH deficiency, disorders associated with aberrant renal $Ca^{2+}$ homeostasis as a result of vasopressin deficiency, disorders associated with aberrant renal $Ca^{2+}$ homeostasis as a result of prostaglandines deficiency, disorders associated with aberrant renal $Ca^{2+}$ homeostasis as a result of estrogen deficiency, disorders associated with aberrant renal $Ca^{2+}$ homeostasis as a result of calcitonin deficiency, disorders associated with aberrant renal $Ca^{2+}$ homeostasis as a result of parathyroid hormone deficiency, disorders associated with aberrant renal $Ca^{2+}$ homeostasis as a result of atrial natriuretic peptide deficiency, calcium homeostasis-related disorders, hypercaliuric nephrolithiasis, certain forms of osteoporosis, Gitelman's disease, Bartter's syndrom, disorders associated with aberrant function of kidney tubular epithelium, disorders associated with aberrant function of kidney tubular epithelium in the medulla, disorders associated with aberrant function of kidney tubular epithelium in the medullary rays, disorders associated with aberrant function of kidney tubular epithelium in the periglomerular.

In preferred embodiments, LTRPC3l polynucleotides and polypeptides, including fragments and modulators thereof, are useful for treating, diagnosing, and/or ameliorating acute kidney failure, chronic kidney failure, cystic kidney disease, horseshoe kidney, hypertensive kidney disease, kidney atrophy, kidney cancer, kidney disease, kidney failure, kidney infection, kidney metastasis, kidney stone, nephrolithiasis, multicystic dysplastic kidney disease, and polycystic kidney disease.

Characterization of the LTRPC3 variant polypeptide using antisense oligonucleotides led to the determination that LTRPC3 is involved in the negative modulation of the FEN1 DNA base-excision repair/proliferation modulating protein as described in Example 5 herein.

The LTRCP3g polypeptide is expected to be able to modulate the FEN 1DNA base-excision repair/proliferation modulating protein to the same or similar extent as the LTRPC3 polypeptide.

Specifically, antisense inhibition of LTRPC3 resulted in upregulation of Fen1, a marker of proliferation. As such, LTRPC3 behaves in a manner similar to a tumor suppressor, in that loss results in increases in proliferation. While some increases in the proliferation markers p21 and IkB were also observed, they were less significant, and could be a response to the pro-proliferative effect of LTRPC3 antisense inhibition. Interestingly, expression of LTRPC3 was also observed to be significantly reduced in tumor tissues, relative to normal tissues (see FIG. 13). Specifically, renal, testicular, and ovarian tumor samples showed as much as 12 to 30 fold down regulation of LTRPC3 message levels compared to normal tissues. This reduction of LTRPC3 correlating with the tumor state is consistent with the negative FEN1 modulatory activity and suggests this gene may have antiproliferative activities. Therefore, for modulators of LTRPC3l to be useful for treating cancer, it would be necessary to increase the activity of the gene or gene product in order to have the reverse effect on cancerous cells. Thus, an agonist of LTRPC3l activity or a compound that increased LTRPC3l message levels would be a desired invention for cancer therapy.

In preferred embodiments, LTRPC3l polynucleotides and polypeptides, including fragments and modulators thereof, are useful for treating, diagnosing, and/or ameliorating DNA-repair deficiencies, particularly base-excision repair deficiencies, Xeroderma pigmentosum, skin cancer, melanoma, UV senstivity, alkylation sensivity, gamma irradiation sensitivity, pyrimidine dimer sensitivity, chemical mutagenes, lymphomas, leukemias, photosensitivity, Bloom's syndrone, Fanconi's anemia, ataxia telangiectasia, chromosomal aberrations, blood vessel dilation aberrations in the skin, blood vessel dilation aberrations in the eye, conditions involving increased levels of apurinic sites, conditions involving increased levels of apyrimidinic sites, conditions involving increased levels of abasic sites, disorders related to aberrant signal transduction, proliferating disorders, and/or cancers.

Moreover, LTRPC3l polynucleotides and polypeptides, including fragments and modulators thereof, are useful for increasing mammalian base excision repair activity, increasing mammalian single-nucleotide base excision repair activity, and/or increasing mammalian long patch base excision repair activity.

In preferred embodiments, antagonists directed against LTRPC3l are useful for treating, diagnosing, and/or ameliorating DNA-repair deficiencies, particularly base-excision repair deficiencies, Xeroderma pigmentosum, skin cancer, melanoma, UV sensitivity, alkylation sensivity, gamma irradiation sensitivity, pyrimidine dimer sensitivity, chemical mutagenes, lymphomas, leukemias, photosensitivity, Bloom's syndrone, Fanconi's anemia, ataxia telangiectasia, chromosomal aberrations, blood vessel dilation aberrations in the skin, blood vessel dilation aberrations in the eye, conditions involving increased levels of apurinic sites, conditions involving increased levels of apyrimidinic sites, conditions involving increased levels of abasic sites, disorders related to aberrant signal transduction, proliferating disorders, and/or cancers.

Moreover, antagonists directed against LTRPC3l are useful for increasing mammalian base excision repair activity, increasing mammalian single-nucleotide base excision repair activity, and/or increasing mammalian long patch base excision repair activity.

In preferred embodiments, agonists directed against LTRPC3l are useful for treating, diagnosing, and/or ameliorating, disorders related to aberrant signal transduction, proliferating disorders, and/or cancers, particularly renal cell carcinomas, testicular cancers, and/or ovarian cancers.

Moreover, agonists directed against LTRPC3l are useful for decreasing mammalian base excision repair activity, decreasing mammalian single-nucleotide base excision repair activity, and/or decreasing mammalian long patch base excision repair activity.

The strong homology to human transient receptor potential channels (TRP), combined with the predominate localized expression in kidney tissue of the LTRPC3 variant, suggests the LTRPC3l polynucleotides and polypeptides, including modulators or fragments thereof, may be useful in treating, diagnosing, prognosing, and/or preventing renal diseases and/or disorders, which include, but are not limited to: nephritis, renal failure, nephrotic syndrome, urinary tract infection, hematuria, proteinuria, oliguria, polyuria, nocturia, edema, hypertension, electrolyte disorders, sterile pyuria, renal osteodystrophy, large kidneys, renal transport defects, nephrolithiasis, azotemia, anuria, urinary retention ,slowing of urinary stream, large prostate, flank tenderness, full bladder sensation after voiding, enuresis, dysuria, bacteriuria, kidney stones, glomerulonephritis, vasculitis, hemolytic uremic syndromes, thrombotic thrombocytopenic purpura, malignant hypertension, casts, tubulointerstitial kidney diseases, renal tubular acidosis, pyelonephritis, hydronephritis, nephrotic syndrome, crush syndrome, and/or renal colic, in addition to Wilm's Tumor Disease, and congenital kidney abnormalities such as horseshoe kidney, polycystic kidney, and Falconi's syndrome for example.

Several known TRP family members have been identified that are expressed significantly in kidney tissue. These TRP family members include, for example, Trp12 (Wissenbach, U., Bodding, M., Freichel, M., Flockerzi, V, Lett., 485(2-3): 127-34, (2000)); OTRPC4 (Strotmann, R., Harteneck, C., Nunnenmacher, K., Schultz, G., Plant, T, D, Nat, Cell, Biol., 2(10):695-702, (2000)); polycystin-L2 (Guo, L., Schreiber, T, H., Weremowicz, S., Morton, C, C., Lee, C., Zhou, J. Genomics., 64(3):241-51, (2000)); and EcaC (Hoenderop, J. G., van, der, Kemp, A, W., Hartog, A., van, de, Graaf, S, F., van, Os, C, H.,Willems, P, H., Bindels, R, J. J. Biol, Chem., 274(13):8375-8, (1999)).

Thus, the LTRPC3l polynucleotides and polypeptides are expected to share at least some biological activity with TRP family members expressed in kidney cells and tissues, particularly those specifically referenced herein, such as LTRPC3 (SEQ ID NO:15).

The strong homology to human transient receptor potential channels (TRP) proteins, combined with the localized expression in spinal cord and brain of the LTRPC3 variant, suggests the LTRPC3l polynucleotides and polypeptides, including modulators or fragments thereof, may be useful in treating, diagnosing, prognosing, and/or preventing neurodegenerative disease states, behavioral disorders, or inflammatory conditions. Representative uses are described in the "Regeneration" and "Hyperproliferative Disorders" sections below, in the Examples, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The strong homology to human transient receptor potential channels (TRP), combined with the localized expression in testis tissue of the LTRPC3 variant emphasizes the potential utility for LTRPC3l polynucleotides and polypeptides in treating, diagnosing, prognosing, and/or preventing testicular, in addition to reproductive disorders.

In preferred embodiments, LTRPC3l polynucleotides and polypeptides including agonists and fragments thereof, have uses which include treating, diagnosing, prognosing, and/or preventing the following, non-limiting, diseases or disorders of the testis: spermatogenesis, infertility, Klinefelter's syndrome, XX male, epididymitis, genital warts, germinal cell aplasia, cryptorchidism, varicocele, immotile cilia syndrome, and viral orchitis. The LTRPC3l polynucleotides and polypeptides including agonists and fragments thereof, may also have uses related to modulating testicular development, embryogenesis, reproduction, and in ameliorating, treating, and/or preventing testicular proliferative disorders (e.g., cancers, which include, for example, choriocarcinoma, Non-seminoma, seminona, and testicular germ cell tumors).

Likewise, the localized expression in testis tissue also emphasizes the potential utility for LTRPC3l polynucleotides and polypeptides in treating, diagnosing, prognosing, and/or preventing metabolic diseases and disorders which include the following, not limiting examples: premature puberty, incomplete puberty, Kallman syndrome, Cushing's syndrome, hyperprolactinemia, hemochromatosis, congenital adrenal hyperplasia, FSH deficiency, and granulomatous disease, for example.

This gene product may also be useful in assays designed to identify binding agents, as such agents (antagonists) are useful as male contraceptive agents. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

Several known TRP family members have been identified that are expressed significantly in testis tissue. These TRP family members include, for example, polycystin-L2 (Guo, L., Schreiber, T, H., Weremowicz, S., Morton, C, C., Lee, C., Zhou, J. Genomics., 64(3):241-51, (2000)); TRP7 (Okada, T., Inoue, R., Yamazaki, K., Maeda, A., Kurosaki, T., Yamakuni, T., Tanaka, I., Shimizu, S., Ikenaka, K., Imoto, K., Mori, Y, J. Biol, Chem., 274(39):27359-70, (1999)); btrp2 (Wissenbach, U., Schroth, G., Philipp, S., Flockerzi, V, Lett., 429(1):61-6, (1998)); Htrp-1 (Zhu, X., Chu, P, B., Peyton, M., Bimbaumer, L, Lett., 373(3):193-8, (1995)); and TRPC1 (Wes, P, D., Chevesich, J., Jeromin, A., Rosenberg, C., Stetten, G., Montell, C, Proc, Natl, Acad, Sci, USA., 92(21):9652-6, (1995)).

Thus, the LTRPC3l polynucleotides and polypeptides are expected to share at least some biological activity with TRP family members expressed in testis cells and tissues, particularly those specifically referenced herein, such as the LTRPC3 variant (SEQ ID NO:15).

As described elsewhere herein, transient receptor potential channel family members have been implicated in modulating cell proliferation, differentiation, migration, activation, exocytosis, muscle contraction, gene expression, apoptosis. signalling, pheromone sensory signaling, smooth muscle tone, pain perception, heat perception, osmosenstivity, and mechanosensitivity. Moreover, transient receptor potential channel family members have been implicated in disorders of the skin, skeletal-muscle, nervous, cardiac, and vascular systems, in addition to the following, non-limiting diseases and disorders, which include, for example, arteriosclerosis, neointimal hypoerplasia, metastatic melanomas, bipolar disorder, non-syndromic hereditary deafness, Knobloch syndrome, holosencephaly, and various maligancies including prostate cancer.

In preferred embodiments, LTRPC3l polynucleotides and polypeptides of the present invention, including agonists and/or fragments thereof, have uses that include, modulating cell proliferation, differentiation, migration, activation, exocytosis, muscle contraction, gene expression, apoptosis signalling, pheromone sensory signaling, smooth muscle tone, pain perception, heat perception, osmosenstivity, and mechanosensitivity.

In more preferred embodiments, LTRPC3l polynucleotides and polypeptides of the present invention, including agonists and/or fragments thereof, have uses that include, treating, ameliorating, preventing, detecting, and/or prognosing various diseases and disorders, particularly the following, non-limiting examples, disorders of the skin, skeletal-muscle, nervous, cardiac, and vascular systems, in addition to the following, non-limiting diseases and disorders, which include, for example, arteriosclerosis, neointimal hypoerplasia, metastatic melanomas, bipolar disorder, nonsyndromic hereditary deafness, Knobloch syndrome, holosencephaly, and various maligancies including prostate cancer.

LTRPC3l polynucleotides and polypeptides of the present invention, including agonists and/or fragments may be involved in intracellular $Ca^{2+}$ homeostasis which affects various aspects of biological functions including mechano-regulation, pain transduction, vasorelaxation, gene expression, cell cycle and proliferation/apoptosis. Since the LTRPC3 variant is dominantly expressed in kidney, the LTRPC3l polypeptide may particularly play an important role in regulating cytosolic $Ca^{2+}$ in the renal system, potentially $Ca^{2+}$ absorption.

The LTRPC3l gene maps to chromosome 9q21.11-21.31 between the two markers D9S1874 and D9S1807. This region is linked to amyotrophic lateral sclerosis with fronto-temporal dementia, early-onset pulverulent cataract, infantile nephronophthisis, hypomagnesemia with secondary hypocalcemia (HSH), and familial hemophagocytic lymphohistiocytosis. Therefore, agonists and/or antagonists of the novel LTRPC3l can be used to treat diseases including various forms of neuronal degeneration, neurogenic inflammation, allergy, immunodeficiency/excessive immune activation, visual defects, hearing disorder, pain, cancer, hypertension and other cardiovascular diseases. In addition, the therapeutics may be useful in the treatment of diseases associated with disturbances in $Ca^{2+}$ homeostasis including osteoporosis, hypercalciuric stone disease, and chronic renal failure.

Moreover, given the selective expression in kidney, LTRPC3l could be considered a candidate gene for HSH, since the phenotype is a renal insufficiency. LTRPC3l chromosomal location is ~600 kb downstream of a X; 9 translocation breakpoint interval described for one patient with HSH (*Hum. Mol. Genet.* 6, 1491-1497, (1997)). Recently, two groups reported that a new member of the TRPM subfamily, TRPM6, expressed in both intestinal tissues and kidney, is associated with HSH (*Nat. Genet.* 31, 166-170, (2002); and *Nat. Genet.* 31, 171-174 (2002)). Indeed, LTRPC3l is ~4 mb 5' to TRPM6 on 9q21. Although TRPM6 is the first component identified for HSH, this should not preclude involvement of LTRPC3l in the disease. Therefore, it is possible that LTRPC3l may co-localize with TRPM6 and/or forms a heteromultimer with TRPM6 in the kidney.

The kidney plays a major role in $Ca^{2+}$ homeostasis (reviewed in Physiol. Rev. 75, 429-471, (1995)). LTRPC3l may play a direct role in $Ca^{2+}$ absorption due to its constitutive $Ca^{2+}$ permeability. Alternatively, LTRPC3l may be the SOC that regulates $Ca^{2+}$ absorption. In kidney, $Ca^{2+}$ absorption is regulated by agonists such as calcitonin, parathyroid hormone and parathyroid hormone-related peptide through their respective G protein-coupled receptors, and downstream SOCs. Additionally, in kidney a SOC has been described (*J. Biol. Chem.* 276, 25759-25765, (2001)) for the action of angiotensin II, a vasoactive peptide that plays a major role in regulating blood pressure.

In addition, LTRPC3l polynucleotides and polypeptides of the present invention, including agonists and/or fragments thereof, have uses that include modulating intracellular Ca++ ion concentrations, Ca++ ion flux, stored intracellular Ca++ ion concentrations, Ca++ ion pump activity, Ca++ ion flow into cell, Ca++ ion flow out of cells, the activation of Ca++ sensitive proteins, the activation of Ca++sensitive signaling pathways, the activation of kinase-activatible proteins, and the activation of kinase-dependent signaling pathways.

The LTRPC3l polynucleotides and polypeptides of the present invention, including agonists and/or fragments thereof, have uses that include modulating proliferation, differentiation, migration, and activation in various cells, tissues, and organisms, and particularly in mammalian kidney, spinal cord, testis, and brain, preferably human. LTRPC3l polynucleotides and polypeptides of the present invention, including agonists and/or fragments thereof, may be useful in diagnosing, treating, prognosing, and/or preventing renal, neural, and/or proliferative diseases or disorders, particularly of the renal system.

In addition, antagonists of the LTRPC3l polynucleotides and polypeptides, including modulators or fragments thereof, may have uses that include diagnosing, treating, prognosing, and/or preventing diseases or disorders related to transient receptor potential channel activity, which may include renal, neural, reproductive, and/or proliferative diseases or disorders.

Although it is believed the encoded polypeptide may share at least some biological activities with transient receptor potential channel family members, particularly those melastatin1, a number of methods of determining the exact biological function of this clone are either known in the art or are described elsewhere herein. Briefly, the function of this clone may be determined by applying microarray methodology. Nucleic acids corresponding to the LTRPC3l polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from tissue that has been treated with known transient potential receptor inhibitors, which include, but are not limited to the drugs listed herein or otherwise known in the art, might indicate a function in modulating transient potential receptor function, for example. In the case of LTRPC3l, kidney, spinal cord, testis, and brain, should be used to extract RNA to prepare the probe.

In addition, the function of the protein may be assessed by applying quantitative PCR methodology, for example. Real time quantitative PCR would provide the capability of following the expression of the LTRPC3l gene throughout development, for example. Quantitative PCR methodology requires only a nominal amount of tissue from each developmentally important step is needed to perform such experiements. Therefore, the application of quantitative PCR methodology to refining the biological function of this polypeptide is encompassed by the present invention. Also encompassed by the present invention are quantitative PCR probes corresponding to the polynucleotide sequence provided as SEQ ID NO:1 (FIGS. 1A-E).

The function of the protein may also be assessed through complementation assays in yeast. For example, in the case of the LTRPC3l, transforming yeast deficient in transient receptor potential channel activity with LTRPC3l and assessing their ability to grow would provide convincing evidence the LTRPC3l polypeptide has transient receptor potential channel activity. Additional assay conditions and methods that may be used in assessing the function of the polynucletides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a kidney, spinal cord, testis, and/or brain -specific promoter), or it can be expressed at a specified time of development using an inducible and/or a developmentally regulated promoter.

In the case of LTRPC3l transgenic mice or rats, if no phenotype is apparent in normal growth conditions, observing the organism under diseased conditions (renal, reproductive, neural, or proliferative disorders, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal LTRPC3l deletion polypeptides are encompassed by the present invention: M1-T1734, G2-T1734, K3-T1734, K4-T1734, W5-T1734, R6-T1734, D7-T1734, A8-T1734, A9-T1734, E10-T1734, M11-T1734, E12-T1734, R13-T1734, G14-T1734, C15-T1734, S16-T1734, D17-T1734, R18-T1734, E19-T1734, D20-T1734, N21-T1734, A22-T1734, E23-T1734, S24-T1734, R25-T1734, R26-T1734, R27-T1734, S28-T1734, R29-T1734, S30-T1734, A31-T1734, S32-T1734, R33-T1734, G34-T1734, R35-T1734, F36-T1734, A37-T1734, E38-T1734, S39-T1734, W40-T1734, K41-T1734, R42-T1734, L43-T1734, S44-T1734, S45-T1734, K46-T1734, Q47-T1734, G48-T1734, S49-T1734, T50-T1734, K51-T1734, R52-T1734, S53-T1734, G54-T1734, L55-T1734, P56-T1734, S57-T1734, Q58-T1734, Q59-T1734, T60-T1734, P61-T1734, A62-T1734, Q63-T1734, K64-T1734, S65-T1734, W66-T1734, I67-T1734, E68-T1734, R69-T1734, A70-T1734, F71-T1734, Y72-T1734, K73-T1734, R74-T1734, E75-T1734, C76-T1734, V77-T1734, H78-T1734, I79-T1734, I80-T1734, P81-T1734, S82-T1734, T83-T1734, K84-T1734, D85-T1734, P86-T1734, H87-T1734, R88-T1734, C89-T1734, C90-T1734, C91-T1734, G92-T1734, R93-T1734, L94-T1734, I95-T1734, G96-T1734, Q97-T1734, H98-T1734, V99-T1734, G100-T1734, L10-T1734, T102-T1734, P103-T1734, S104-T1734, I105-T1734, S106-T1734, V107-T1734, L108-T1734, Q109-T1734, N110-T1734, E11'-T1734, K112-T1734, N113-T1734, E114-T1734, S115-T1734, R116-T1734, L117-T1734, S118-T1734, R119-T1734, N120-T1734, D121-T1734, I122-T1734, Q123-T1734, S124-T1734, E125-T1734, K126-T1734, W127-T1734, S128-T1734, I129-T1734, S130-T1734, K131-T1734, H132-T1734, T133-T1734, Q134-T1734, L135-T1734, S136-T1734, P137-T1734, T138-T1734, D139-T1734, A140-T1734, F141-T1734, G142-T1734, T143-T1734, I144-T1734, E145-T1734, F146-T1734, Q147-T1734, G148-T1734, G149-T1734, G150-T1734, H151-T1734, S152-T1734, N153-T1734, K154-T1734, and/or A155-T1734 of SEQ ID NO:12. Polynucleotide sequences encoding these polypeptides are also provided. The present invention also encompasses the use of these N-terminal LTRPC3l deletion polypeptides as immunogenic and/or antigenic epitopes as described elsewhere herein.

In preferred embodiments, the following C-terminal LTRPC3l deletion polypeptides are encompassed by the present invention: M1-T1734, M1-H1733, M1-K1732, M1-S1731, M1-E1730, M1-F1729, M1-S1728, M1-Q1727, M1-F1726, M1-A1725, M1-S1724, M1-T1723, M1-R1722, M1-S1721, M1-L1720, M1-R1719, M1-R1718, M1-M1717, M1-S1716, M1-L1715, M1-S1714, M1-D1713, M1-G1712, M1-R1711, M1-G1710, M1-E1709, M1-P1708, M1-K1707, M1-S1706, M1-S1705, M1-K1704, M1-S1703, M1-R1702, M1-Q1701, M1-F1700, M1-P1699, M1-N1698, M1-Q1697, M1-L1696, M1-S1695, M1-A1694, M1-T1693, M1-N1692, M1-R1691, M1-Q1690, M1-R1689, M1-D1688, M1-L1687, M1-K1686, M1-D1685, M1-S1684, M1-I1683, M1-S1682, M1-F1681, M1-S1680, M1-K1679, M1-R1678, M1-T1677, M1-H1676, M1-A1675, M1-Y1674, M1-P1673, M1-A1672, M1-S1671, M1-P1670, M1-E1669, M1-E1668, M1-A1667, M1-S1666, M1-Y1665, M1-S1664, M1-N1663, M1-A1662, M1-R1661, M1-E1660, M1-I1659, M1-K1658, M1-P1657, M1-V1656, M1-T1655, M1-I1654, M1-N1653, M1-N1652, M1-S1651, M1-L1650, M1-T1649, M1-R1648, M1-E1647, M1-N1646, M1-N1645, M1-D1644, M1-G1643, M1-E1642, M1-Q1641, M1-S1640, M1-S1639, M1-I1638, M1-A1637, M1-I1636, M1-T1635, M1-A1634, M1-R1633, M1-R1632, M1-G1631, M1-K1630, M1-A1629, M1-E1628, M1-N1627, M1-E1626, M1-E1625, M1-S1624, M1-D1623, M1-S1622, M1-S1621, M1-P1620, M1-H1619, M1-S1618, M1-L1617, M1-E1616, M1-A1615, M1-E1614, M1-R1613, M1-E1612, M1-P1611, M1-H1610, M1-C1609, M1-C1608, M1-T1607, M1-L1606, M1-D1605, M1-E1604, M1-V1603, M1-K1602, M1-D1601, M1-G1600, M1-L1599, M1-G1598, M1-G1597, M1-P1596, M1-F1595, M1-A1594, M1-A1593, M1-R1592, M1-D1591, M1-A1590, M1-I1589, M1-A1588, M1-Q1587, M1-P1586, M1-A1585, M1-N1584, M1-V1583, M1-C1582, M1-R1581, M1-T1580, M1-D1579, M1-I1578, M1-C1577, M1-D1576, M1-T1575, M1-I1574, M1-S1573, M1-T1572, M1-Y1571, M1-E1570, M1-A1569, M1-T1568, M1-K1567, M1-V1566, M1-P1565, M1-V1564, M1-G1563, M1-F1562, M1-N1561, M1-A1560, M1-Y1559, M1-Y1558, M1-S1557, M1-R1556, M1-S1555, M1-P1554, M1-S1553, M1-F1552, M1-M1551, M1-F1550, M1-S1549, M1-H1548, M1-S1547, M1-K1546, M1-V1545, M1-I1544, M1-P1543, M1-A1542, M1-E1541, M1-E1540, M1-L1539, M1-L1538, M1-F1537, M1-P1536, M1-T1535, M1-T1534, M1-A1533, M1-L1532, M1-Y1531, M1-R1530, M1-S1529, M1-S1528, M1-K1527, M1-S1526, M1-R1525, M1-E1524, M1-I1523, M1-T1522, M1-H1521, M1-Y1520, M1-M1519, M1-P1518, M1-P1517, M1-E1516, M1-S1515, M1-D1514, M1-W1513, M1-P1512, M1-N1511, M1-Q1510, M1-C1509, M1-E1508, M1-P1507, M1-L1506, M1-H1505, M1-T1504, M1-Y1503, M1-D1502, M1-S1501, M1-S1500, M1-F1499, M1-S1498, M1-R1497, M1-T1496, M1-D1495, M1-M1494, M1-S1493, M1-T1492, M1-I1491, M1-D1490, M1-E1489, M1-F1488, M1-D1487, M1-I1486, M1-S1485, M1-R1484, M1-S1483, M1-P1482, M1-P1481, M1-R1480, M1-D1479, M1-T1478, M1-P1477, M1-A1476, M1-L1475, M1-T1474, M1-A1473, M1-Y1472, M1-A1471, M1-S1470, M1-S1469, M1-S1468, M1-P1467, M1-A1466, M1-T1465, M1-S1464, M1-P1463, M1-V1462, M1-P1461, M1-T1460, M1-S1459, M1-F1458, M1-S1457, M1-P1456, M1-E1455, M1-G1454, M1-L1453, M1-G1452, M1-L1451, M1-I1450, M1-N1449, M1-V1448, M1-S1447, M1-N1446, M1-D1445, M1-L1444, M1-P1443, M1-D1442, M1-I1441, M1-D1440, M1-C1439, M1-H1438, M1-L1437, M1-E1436, M1-D1435, M1-M1434, M1-A1433, M1-S1432, M1-V1431, M1-Y1430, M1-I1429, M1-D1428, M1-I1427, M1-C1426, M1-S1425, M1-S1424, M1-P1423, M1-R1422, M1-R1421, M1-S1420, M1-D1419, M1-P1418, M1-V1417, M1-I1416, M1-A1415, M1-L1414, M1-T1413, M1-N1412, M1-A1411, M1-P1410, M1-A1409, M1-A1408, M1-P1407, M1-A1406, M1-K1405, M1-P1404, M1-E1403, M1-K1402, M1-A1401, M1-V1400, M1-S1399, M1-H1398, M1-S1397, M1-S1396, M1-T1395, M1-A1394, M1-R1393, M1-H1392, M1-L1391, M1-S1390, M1-L1389, M1-S1388, M1-R1387, M1-E1386, M1-K1385, M1-F1384, M1-I1383, M1-S1382, M1-E1381, M1-L1380, M1-K1379, M1-E1378, M1-I1377, M1-G1376, M1-G1375, M1-K1374, M1-D1373, M1-K1372, M1-M1371, M1-N1370, M1-V1369, M1-S1368, M1-Y1367, M1-F1366, M1-S1365, M1-H1364, M1-S1363, M1-R1362, M1-M1361, M1-R1360, M1-P1359, M1-M1358, M1-L1357, M1-T1356, M1-P1355, M1-S1354, M1-T1353, M1-P1352, M1-S1351, M1-M1350, M1-T1349, M1-E1348, M1-E1347, M1-G1346, M1-A1345, M1-P1344, M1-D1343, M1-I1342, M1-S1341, M1-E1340, M1-Q1339, M1-L1338, M1-K1337, M1-F1336, M1-T1335, M1-N1334, M1-G1333, M1-E1332, M1-Q1331, M1-S1330, M1-N1329, M1-F1328, M1-S1327, M1-S1326, M1-Q1325, M1-R1324, M1-V1323, M1-I1322, M1-Y1321, M1-A1320, M1-A1319, M1-D1318, M1-T1317, M1-C1316, M1-D1315, M1-S1314, M1-S1313, M1-T1312, M1-R1311, M1-S1310, M1-R1309, M1-I1308, M1-K1307, M1-N1306, M1-S1305, M1-E1304, M1-A1303, M1-R1302, M1-E1301, M1-L1300, M1-G1299, M1-T1298, M1-L1297, M1-R1296, M1-E1295, M1-L1294, M1-A1293, M1-T1292, M1-A1291, M1-M1290, M1-R1289, M1-G1288, M1-I1287, M1-L1286, M1-D1285, M1-E1284, M1-L1283, M1-Q1282, M1-A1281, M1-L1280, M1-R1279, M1-I1278, M1-D1277, M1-V1276, M1-T1275, M1-Q1274, M1-L1273, M1-S1272, M1-A1271, M1-K1270, M1-M1269, M1-S1268, M1-H1267, M1-E1266, M1-R1265, M1-E1264, M1-N1263, M1-V1262, M1-E1261, M1-E1260, M1-L1259, M1-R1258, M1-M1257, M1-S1256, M1-M1255, M1-N1254, M1-E1253, M1-V1252, M1-R1251, M1-E1250, M1-S1249, M1-T1248, M1-V1247, M1-R1246, M1-I1245, M1-R1244, M1-E1243, M1-D1242, M1-N1241, M1-S1240, M1-S1239, M1-N1238, M1-F1237, M1-R1236, M1-D1235, M1-D1234, M1-K1233, M1-E1232, M1-R1231, M1-F1230, M1-Y1229, M1-E1228, M1-E1227, M1-I1226, M1-C1225, M1-Q1224, M1-E1223, M1-E1222, M1-F1221, M1-D1220, M1-H1219, M1-V1218, M1-K1217, M1-K1216, M1-L1215, M1-E1214, M1-D1213, M1-D1212, M1-T1211, M1-I1210, M1-F1209, M1-L1208, M1-K1207, M1-L1206, M1-G1205, M1-Y1204, M1-D1203, M1-R1202, M1-E1201, M1-D1200, M1-P1199, M1-D1198, M1-S1197, M1-E1196, M1-H1195, M1-K1194, M1-R1193, M1-W1192, M1-R1191, M1-C1190, M1-C1189, M1-L1188, M1-H1187, M1-Q1186, M1-F1185, M1-I1184, M1-M1183, M1-T1182, M1-M1181, M1-H1180, M1-S1179, M1-F1178, M1-I1177, M1-I1176, M1-L1175, M1-P1174, M1-P1173, M1-P1172, M1-L1171, M1-V1170, M1-P1169, M1-R1168, M1-E1167, M1-H1166, M1-F1165, M1-T1164, M1-M1163, M1-I1162, M1-L1161, M1-Q1160, M1-Y1159, M1-R1158, M1-Q1157, M1-F1156, M1-K1155, M1-W1154, M1-V1153, M1-Q1152, M1-N1151, M1-S1150, M1-I1149, M1-S1148, M1-K1147, M1-V1146, M1-E1145, M1-F1144, M1-F1143, M1-T1142, M1-N1141, M1-N1140, M1-F1139, M1-V1138, M1-A1137, M1-I1136, M1-L1135, M1-L1134, M1-N1133, M1-V1132, M1-L1131, M1-L1130, M1-I1129, M1-N1128, M1-A1127, M1-V1126, M1-L1125, M1-L1124, M1-Y1123, M1-C1122, M1-A1121, M1-M1120, M1-I1119, M1-A1118, M1-P1117, M1-V1116, M1-I1115, M1-W1114, M1-A1113, M1-G1112, M1-T1111, M1-K1110, M1-C1109, M1-P1108, M1-P1107, M1-L1106, M1-Q1105, M1-I1104, M1-I1103, M1-K1102, M1-G1101, M1-D1100, M1-E1099, M1-R1098, M1-T1097, M1-E1096, M1-N1095, M1-Q1094, M1-G1093, M1-C1092, M1-P1091, M1-P1090, M1-D1089, M1-I1088, M1-Q1087, M1-D1086, M1-A1085, M1-F1084, M1-V1083, M1-E1082, M1-G1081, M1-Y1080, M1-I1079, M1-M1078, M1-W1077, M1-Y1076, M1-P1075, M1-M1074, M1-Y1073, M1-F1072, M1-I1071, M1-N1070, M1-K1069, M1-A1068, M1-L1067, M1-K1066, M1-W1065, M1-S1064, M1-P1063, M1-E1062, M1-E1061, M1-N1060, M1-P1059, M1-F1058, M1-L1057, M1-I1056, M1-A1055, M1-Q1054, M1-R1053, M1-A1052, M1-V1051, M1-G1050, M1-F1049, M1-S1048, M1-M1047, M1-L1046, M1-V1045, M1-V1044, M1-L1043, M1-M1042, M1-I1041, M1-I1040, M1-V1039, M1-F1038, M1-Y1037, M1-M1036, M1-M1035, M1-D1034, M1-I1033, M1-M1032, M1-M1031, M1-K1030, M1-G1029, M1-I1028, M1-M1027, M1-M1026, M1-V1025, M1-Y1024, M1-P1023, M1-G1022, M1-L1021, M1-Y1020, M1-K1019, M1-N1018, M1-V1017, M1-G1016, M1-F1015, M1-I1014, M1-D1013, M1-L1012, M1-L1011, M1-R1010, M1-I1009, M1-Y1008, M1-W1007, M1-Y1006, M1-I1005, M1-I1004, M1-N1003, M1-V1002, M1-C1001, M1-Y1000, M1-I999, M1-V998, M1-R997, M1-G996, M1-D995, M1-S994, M1-R993, M1-F992, M1-P991, M1-M990, M1-D989, M1-Q988, M1-L987, M1-R986, M1-L985, M1-I984, M1-M983, M1-G982, M1-V981, M1-S980, M1-F979, M1-L978, M1-L977, M1-I976, M1-A975, M1-I974, M1-L973, M1-D972, M1-T971, M1-V970, M1-N969, M1-W968, M1-Y967,
M1-E966, M1-Q965, M1-L964, M1-W963, M1-V962,
M1-K961, M1-V960, M1-K959, M1-Q958, M1-L957,
M1-L956, M1-K955, M1-G954, M1-P953, M1-E952,
M1-S951, M1-M950, M1-L949, M1-I948, M1-E947,
M1-R946, M1-M945, M1-K944, M1-E943, M1-I942,
M1-G941, M1-L940, M1-T939, M1-F938, M1-I937,
M1-Y936, M1-S935, M1-I934, M1-V933, M1-I932,
M1-W931, M1-E930, M1-Q929, M1-T928, M1-S927,
M1-P926, M1-W925, M1-R924, M1-E923, M1-M922,
M1-K921, M1-V920, M1-L919, M1-V918, M1-I917,
M1-Y916, M1-N915, M1-F914, M1-L913, M1-M912,
M1-L911, M1-Y910, M1-G909, M1-I908, M1-Y907,
M1-A906, M1-L905, M1-T904, M1-Y903, M1-F902,
M1-W901, M1-F900, M1-K899, M1-V898, M1-I897,
M1-P896, M1-A895, M1-N894, M1-Y893, M1-F892,
M1-E891, M1-Y890, M1-I889, M1-K888, M1-R887,
M1-G886, M1-L885, M1-P884, M1-I883, M1-L882,
M1-R881, M1-H880, M1-K879, M1-S878, M1-Q877,
M1-V876, M1-E875, M1-E874, M1-E873, M1-D872,
M1-K871, M1-K870, M1-R869, M1-S868, M1-S867,
M1-E866, M1-G865, M1-N864, M1-N863, M1-R862,
M1-G861, M1-L860, M1-M859, M1-A858, M1-T857,
M1-L856, M1-E855, M1-M854, M1-D853, M1-E852,
M1-E851, M1-E850, M1-K849, M1-E848, M1-K847,
M1-T846, M1-P845, M1-K844, M1-E843, M1-P842,
M1-E841, M1-E840, M1-A839, M1-E838, M1-K837,
M1-E836, M1-Q835, M1-L834, M1-H833, M1-I832,
M1-E831, M1-Q830, M1-A829, M1-Q828, M1-S827,
M1-M826, M1-Y825, M1-P824, M1-M823, M1-D822,
M1-D821, M1-K820, M1-N819, M1-K818, M1-F817,
M1-E816, M1-L815, M1-S814, M1-L813, M1-I812,
M1-S811, M1-P810, M1-P809, M1-L808, M1-L807,
M1-I806, M1-G805, M1-L804, M1-I803, M1-V802,
M1-K801, M1-L800, M1-G799, M1-S798, M1-N797,
M1-K796, M1-R795, M1-M794, M1-R793, M1-L792,
M1-R791, M1-G790, M1-M789, M1-W788, M1-M787,
M1-D786, M1-T785, M1-L784, M1-L783, M1-M782,
M1-Q781, M1-S780, M1-C779, M1-T778, M1-H777,
M1-A776, M1-I775, M1-F774, M1-D773, M1-R772,
M1-H771, M1-K770, M1-A769, M1-A768, M1-V767,
M1-A766, M1-L765, M1-Q764, M1-L763, M1-C762,
M1-T761, M1-A760, M1-N759, M1-S758, M1-W757,
M1-N756, M1-K755, M1-L754, M1-E753, M1-Y752,
M1-T751, M1-L750, M1-L749, M1-K748, M1-M747,
M1-A746, M1-L745, M1-Q744, M1-E743, M1-D742,
M1-Q741, M1-K740, M1-Y739, M1-S738, M1-Q737,
M1-D736, M1-L735, M1-L734, M1-E733, M1-V732,
M1-A731, M1-L730, M1-Q729, M1-G728, M1-F727,
M1-D726, M1-R725, M1-S724, M1-N723, M1-H722,
M1-N721, M1-L720, M1-E719, M1-Q718, M1-S717,
M1-I716, M1-D715, M1-D714, M1-V713, M1-M712,
M1-D711, M1-N710, M1-E709, M1-S708, M1-A707,
M1-E706, M1-H705, M1-A704, M1-M703, M1-A702,
M1-K701, M1-C700, M1-L699, M1-K698, M1-C697,
M1-A696, M1-V695, M1-L694, M1-A693, M1-K692,
M1-A691, M1-M690, M1-A689, M1-E688, M1-E687,
M1-G686, M1-H685, M1-Q684, M1-W683, M1-F682,
M1-F681, M1-L680, M1-A679, M1-M678, M1-K677,
M1-Q676, M1-R675, M1-K674, M1-M673, M1-L672,
M1-V671, M1-A670, M1-W669, M1-V668, M1-M667,
M1-L666, M1-E665, M1-H664, M1-F663, M1-P662,
M1-F661, M1-P660, M1-F659, M1-H658, M1-N657,
M1-I656, M1-E655, M1-P654, M1-E653, M1-D652,
M1-L651, M1-D650, M1-I649, M1-D648, M1-V647,
M1-E646, M1-E645, M1-E644, M1-R643, M1-K642,
M1-K641, M1-T640, M1-T639, M1-K638, M1-R637,
M1-G636, M1-R635, M1-R634, M1-L633, M1-P632,
M1-I631, M1-D630, M1-D629, M1-E628, M1-M627,
M1-G626, M1-L625, M1-L624, M1-K623, M1-L622,
M1-A621, M1-K620, M1-P619, M1-R618, M1-K617,
M1-P616, M1-G615, M1-F614, M1-L613, M1-N612,
M1-H611, M1-Y610, M1-L609, M1-T608, M1-R607,
M1-F606, M1-R605, M1-K604, M1-R603, M1-T602,
M1-Y601, M1-N600, M1-C599, M1-R598, M1-Y597,
M1-A596, M1-G595, M1-G594, M1-M593, M1-L592,
M1-Y591, M1-E590, M1-I589, M1-V588, M1-L587,
M1-G586, M1-I585, M1-D584, M1-I583, M1-L582,
M1-S581, M1-I580, M1-R579, M1-Y578, M1-D577,
M1-P576, M1-P575, M1-L574, M1-N573, M1-G572,
M1-K571, M1-K570, M1-V569, M1-D568, M1-R567,
M1-V566, M1-L565, M1-H564, M1-Y563, M1-L562,
M1-T561, M1-N560, M1-S559, M1-P558, M1-G557,
M1-H556, M1-R555, M1-T554, M1-N553, M1-Y552,
M1-L551, M1-E550, M1-E549, M1-L548, M1-R547,
M1-S546, M1-I545, M1-T544, M1-L543, M1-F542,
M1-R541, M1-H540, M1-M539, M1-S538, M1-V537,
M1-G536, M1-N535, M1-E534, M1-I533, M1-L532,
M1-L531, M1-K530, M1-V529, M1-F528, M1-D527,
M1-V526, M1-R525, M1-D524, M1-L523, M1-V522,
M1-L521, M1-A520, M1-D519, M1-L518, M1-M517,
M1-A516, M1-Q515, M1-E514, M1-L513, M1-S512,
M1-G511, M1-V510, M1-P509, M1-W508, M1-Q507,
M1-Q506, M1-G505, M1-Y504, M1-I503, M1-F502,
M1-I501, M1-Q500, M1-S499, M1-R498, M1-A497,
M1-I496, M1-D495, M1-V494, M1-R493, M1-N492,
M1-W491, M1-A490, M1-L489, M1-A488, M1-L487,
M1-S486, M1-L485, M1-Q484, M1-D483, M1-P482,
M1-A481, M1-S480, M1-A479, M1-N478, M1-A477,
M1-G476, M1-K475, M1-L474, M1-L473, M1-A472,
M1-T471, M1-L470, M1-I469, M1-A468, M1-L467,
M1-D466, M1-I465, M1-D464, M1-Q463, M1-H462,
M1-G461, M1-E460, M1-S459, M1-G458, M1-M457,
M1-R456, M1-F455, M1-V454, M1-T453, M1-I452,
M1-L451, M1-E450, M1-K449, M1-K448, M1-K447,
M1-M446, M1-C445, M1-E444, M1-M443, M1-L442,
M1-I441, M1-I440, M1-F439, M1-L438, M1-H437,
M1-Q436, M1-A435, M1-Q434, M1-T433, M1-R432,
M1-T431, M1-Y430, M1-T429, M1-F428, M1-T427,
M1-K426, M1-Q425, M1-I424, M1-T423, M1-V422,
M1-L421, M1-L420, M1-Q419, M1-D418, M1-R417,
M1-L416, M1-S415, M1-E414, M1-N413, M1-I412,
M1-L411, M1-G410, M1-G409, M1-E408, M1-E407,
M1-S406, M1-Y405, M1-K404, M1-H403, M1-G402,
M1-F401, M1-A400, M1-L399, M1-I398, M1-D397,
M1-S396, M1-A395, M1-R394, M1-G393, M1-S392,
M1-G391, M1-D390, M1-C389, M1-V388, M1-V387,
M1-V386, M1-P385, M1-V384, M1-P383, M1-P382,
M1-T381, M1-D380, M1-R379, M1-L378, M1-Y377,
M1-E376, M1-L375, M1-V374, M1-I373, M1-S372,
M1-I371, M1-V370, M1-N369, M1-P368, M1-G367,
M1-G366, M1-E365, M1-V364, M1-I363, M1-L362,
M1-A361, M1-V360, M1-V359, M1-P358, M1-V357,
M1-G356, M1-Q355, M1-G354, M1-I353, M1-G352,
M1-V351, M1-S350, M1-D349, M1-L348, M1-Q347,
M1-C346, M1-S345, M1-G344, M1-W343, M1-F342,
M1-S341, M1-Y340, M1-F339, M1-L338, M1-R337,
M1-S336, M1-D335, M1-L334, M1-S333, M1-F332,
M1-F331, M1-P330, M1-L329, M1-C328, M1-R327,
M1-T326, M1-N325, M1-I324, M1-K323, M1-Q322,
M1-L321, M1-S320, M1-I319, M1-H318, M1-K317,
M1-E316, M1-L315, M1-Q314, M1-R313, M1-R312,
M1-L311, M1-K310, M1-V309, M1-E308, M1-A307,
M1-G306, M1-Y305, M1-K304, M1-G303, M1-T302, M1-T301, M1-G300, M1-N299, M1-D298, M1-A297,
M1-L296, M1-I295, M1-F294, M1-H293, M1-S292,
M1-H291, M1-M290, M1-S289, M1-N288, M1-L287,
M1-V286, M1-T285, M1-L284, M1-K283, M1-S282,
M1-M281, M1-P280, M1-N279, M1-S278, M1-M277,
M1-T276, M1-Q275, M1-Y274, M1-P273, M1-R272,
M1-V271, M1-V270, M1-D269, M1-R268, M1-G267,
M1-I266, M1-L265, M1-D264, M1-E263, M1-Q262,
M1-N261, M1-E260, M1-V259, M1-I258, M1-G257,
M1-W256, M1-P255, M1-A254, M1-I253, M1-G252,
M1-I251, M1-T250, M1-C249, M1-I248, M1-K247,
M1-G246, M1-R245, M1-S244, M1-K243, M1-S242,
M1-A241, M1-H240, M1-D239, M1-K238, M1-L237,
M1-A236, M1-D235, M1-G234, M1-V233, M1-H232,
M1-R231, M1-I230, M1-V229, M1-G228, M1-T227,
M1-N226, M1-V225, M1-G224, M1-G223, M1-T222,
M1-F221, M1-I220, M1-W219, M1-A218, M1-G217,
M1-T216, M1-T215, M1-M214, M1-A213, M1-A212,
M1-K211, M1-I210, M1-L209, M1-G208, M1-K207,
M1-G206, M1-F205, M1-V204, M1-Q203, M1-K202,
M1-L201, M1-K200, M1-P199, M1-Q198, M1-L197,
M1-E196, M1-F195, M1-N194, M1-Q193, M1-L192,
M1-G191, M1-G190, M1-H189, M1-V188, M1-S187,
M1-I186, M1-L185, M1-L184, M1-K183, M1-P182,
M1-L181, M1-E180, M1-L179, M1-Q178, M1-W177,
M1-E176, M1-K175, M1-T174, M1-M173, M1-L172,
M1-H171, M1-L170, M1-L169, M1-L168, M1-D167,
M1-P166, M1-K165, M1-T164, M1-D163, M1-F162,
M1-S161, M1-V160, M1-R159, M1-V158, M1-Y157,
M1-M156, M1-A155, M1-K154, M1-N153, M1-S152,
M1-H151, M1-G150, M1-G149, M1-G148, M1-Q147,
M1-F146, M1-E145, M1-I144, M1-T143, M1-G142,
M1-F141, M1-A140, M1-D139, M1-T138, M1-P137,
M1-S136, M1-L135, M1-Q134, M1-T133, M1-H132,
M1-K131, M1-S130, M1-I129, M1-S128, M1-W127,
M1-K126, M1-E125, M1-S124, M1-Q123, M1-I122,
M1-D121, M1-N120, M1-R119, M1-S118, M1-L117,
M1-R116, M1-S115, M1-E114, M1-N113, M1-K112,
M1-E111, M1-N110, M1-Q109, M1-L108, M1-V107,
M1-S106, M1-I105, M1-S104, M1-P103, M1-T102,
M1-L101, M1-G100, M1-V99, M1-H98, M1-Q97, M1-G96,
M1-I95, M1-L94, M1-R93, M1-G92, M1-C91, M1-C90,
M1-C89, M1-R88, M1-H87, M1-P86, M1-D85, M1-K84,
M1-T83, M1-S82, M1-P81, M1-I80, M1-I79, M1-H78,
M1-V77, M1-C76, M1-E75, M1-R74, M1-K73, M1-Y72,
M1-F71, M1-A70, M1-R69, M1-E68, M1-I67, M1-W66,
M1-S65, M1-K64, M1-Q63, M1-A62, M1-P61, M1-T60,
M1-Q59, M1-Q58, M1-S57, M1-P56, M1-L55, M1-G54,
M1-S53, M1-R52, M1-K51, M1-T50, M1-S49, M1-G48,
M1-Q47, M1-K46, M1-S45, M1-S44, M1-L43, M1-R42,
M1-K41, M1-W40, M1-S39, M1-E38, M1-A37, M1-F36,
M1-R35, M1-G34, M1-R33, M1-S32, M1-A31, M1-S30,
M1-R29, M1-S28, M1-R27, M1-R26, M1-R25, M1-S24,
M1-E23, M1-A22, M1-N21, M1-D20, M1-E19, M1-R18,
M1-D17, M1-S16, M1-C15, M1-G14, M1-R13, M1-E12,
M1-M11, M1-E10, M1-A9, M1-A8, and/or M1-D7 of SEQ ID NO:12. Polynucleotide sequences encoding these polypeptides are also provided. The present invention also encompasses the use of these C-terminal LTRPC3l deletion polypeptides as immunogenic and/or antigenic epitopes as described elsewhere herein.

Alternatively, preferred polypeptides of the present invention may comprise polypeptide sequences corresponding to, for example, internal regions of the LTRPC3l polypeptide (e.g., any combination of both N- and C-terminal LTRPC3l polypeptide deletions) of SEQ ID NO:12. For example, internal polypeptide regions could be defined by the equation: amino acid NX to amino acid CX, wherein NX refers to any N-terminal deletion polypeptide amino acid of LTRPC3l (SEQ ID NO:12), and where CX refers to any C-terminal deletion polypeptide amino acid of LTRPC3l (SEQ ID NO:12). Polynucleotides encoding these polypeptides are also provided. The present invention also encompasses the use of these polypeptides as an immunogenic and/or antigenic epitope as described elsewhere herein.

Many polynucleotide sequences, such as EST sequences, are publicly available and accessible through sequence databases. Some of these sequences are related to SEQ ID NO:11 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 5262 of SEQ ID NO:11, b is an integer between 15 to 5276, where both a and b correspond to the positions of nucleotide residues shown in SEQ ID NO:11, and where b is greater than or equal to a+14.

TABLE I

| Gene No. | CDNA CloneID | ATCC Deposit No. Z and Date | Vector | NT SEQ ID. No. X | Total NT Seq of Clone | 5' NT of Start Codon of ORF | 3' NT of ORF | AA Seq ID No. Y | Total AA of ORF |
|---|---|---|---|---|---|---|---|---|---|
| 1. | LTRPC3g (also referred to as TRPM3g, and/or LTRPC6g) | N/A | N/A | 1 | 5201 | 72 | 5198 | 2 | 1709 |
| 2 | LTRPC3h (also referred to as TRPM3h, and/or LTRPC6h) | N/A | N/A | 3 | 5237 | 72 | 5234 | 4 | 1721 |
| 3. | LTRPC3I (also referred to | N/A | N/A | 5 | 5237 | 72 | 5234 | 6 | 1721 |

TABLE I-continued

| Gene No. | CDNA CloneID | ATCC Deposit No. Z and Date | Vector | NT SEQ ID. No. X | Total NT Seq of Clone | 5' NT of Start Codon of ORF | 3' NT of ORF | AA Seq ID No. Y | Total AA of ORF |
|---|---|---|---|---|---|---|---|---|---|
| | as TRPM3I, and/or LTRPC6I) | | | | | | | | |
| 4 | LTRPC3j (also referred to as TRPM3j, and/or LTRPC6j) | N/A | N/A | 7 | 5171 | 72 | 5168 | 8 | 1699 |
| 5 | LTRPC3k (also referred to as TRPM3k, and/or LTRPC6k) | N/A | N/A | 9 | 5207 | 72 | 5204 | 10 | 1711 |
| 6 | LTRPC3l (also referred to as TRPM3l, and/or LTRPCl) | N/A | N/A | 11 | 5276 | 72 | 5273 | 12 | 1734 |

Table 1 summarizes the information corresponding to each "Gene No." described above. The nucleotide sequence identified as "NT SEQ ID NO:X" was assembled from partially homologous ("overlapping") sequences obtained from the "cDNA clone ID" identified in Table 1 and, in some cases, from additional related DNA clones. The overlapping sequences were assembled into a single contiguous sequence of high redundancy (usually several overlapping sequences at each nucleotide position), resulting in a final sequence identified as SEQ ID NO:X.

The cDNA Clone ID was deposited on the date and given the corresponding deposit number listed in "ATCC Deposit No:Z and Date." "Vector" refers to the type of vector contained in the cDNA Clone ID.

"Total NT Seq. Of Clone" refers to the total number of nucleotides in the clone contig identified by "Gene No." The deposited clone may contain all or most of the sequence of SEQ ID NO:X. The nucleotide position of SEQ ID NO:X of the putative start codon (methionine) is identified as "5' NT of Start Codon of ORF."

The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The total number of amino acids within the open reading frame of SEQ ID NO:Y is identified as "Total AA of ORF".

SEQ ID NO:X (where X may be any of the polynucleotide sequences disclosed in the sequence listing) and the translated SEQ ID NO:Y (where Y may be any of the polypeptide sequences disclosed in the sequence listing) are sufficiently accurate and otherwise suitable for a variety of uses well known in the art and described further herein. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used, for example, to generate antibodies which bind specifically to proteins containing the polypeptides and the proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides may cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO: 1, 3, 5, 7, 9 and/or 11 and the predicted translated amino acid sequence identified as SEQ ID NO:2, 4, 6, 8, 10 and/or 12, but also a sample of plasmid DNA containing a cDNA of the invention deposited with the ATCC, as set forth in Table 1. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited cDNA, collecting the protein, and determining its sequence.

The present invention also relates to the genes corresponding to SEQ ID NO:1, 3, 5, 7, 9 and/or 11, SEQ ID NO:2, 4, 6, 8, 10 and/or 12, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs, allelic variants, and/or orthologs. The skilled artisan could, using procedures well-known in the art, obtain the polynucleotide sequence corresponding to full-length genes (including, but not limited to the full-length coding region), allelic variants, splice variants, orthologs, and/or species homologues of genes corresponding to SEQ ID NO:1, 3, 5, 7, 9 and/or 11, SEQ ID NO:2, 4, 6, 8, 10 and/or 12, or a deposited clone, relying on the sequence from the sequences disclosed herein or the clones deposited with the ATCC. For example, allelic variants and/or species homologues may be isolated and identified by making suitable probes or primers which correspond to the 5', 3', or internal regions of the sequences provided herein and screening a suitable nucleic acid source for allelic variants and/or the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the protein, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, can be substantially purified using techniques described herein or otherwise known in the art, such as, for example, by the one-step method described in Smith and Johnson, Gene 67:31-40 (1988). Polypeptides of the invention also can be purified from natural, synthetic or recombinant sources using protocols described herein or otherwise known in the art, such as, for example, antibodies of the invention raised against the full-length form of the protein.

The present invention provides a polynucleotide comprising, or alternatively consisting of, the sequence identified as SEQ ID NO:1, 3, 5, 7, 9 and/or 11, and/or a cDNA provided in ATCC®Deposit No. Z:. The present invention also provides a polypeptide comprising, or alternatively consisting of, the sequence identified as SEQ ID NO:2, 4, 6, 8, 10 and/or 12. The present invention also provides polynucleotides encoding a polypeptide comprising, or alternatively consisting of the polypeptide sequence of SEQ ID NO:2, 4, 6, 8, 10 and/or 12.

Preferably, the present invention is directed to a polynucleotide comprising, or alternatively consisting of, the sequence identified as SEQ ID NO: 1, 3, 5, 7, 9 and/or 11, and/or a cDNA provided in ATCC Deposit No.: that is less than, or equal to, a polynucleotide sequence that is 5 mega basepairs, 1 mega basepairs, 0.5 mega basepairs, 0.1 mega basepairs, 50,000 basepairs, 20,000 basepairs, or 10,000 basepairs in length.

The present invention encompasses polynucleotides with sequences complementary to those of the polynucleotides of the present invention disclosed herein. Such sequences may be complementary to the sequence disclosed as SEQ ID NO:1, 3, 5, 7, 9 and/or 11, the sequence contained in a deposit, and/or the nucleic acid sequence encoding the sequence disclosed as SEQ ID NO:2, 4, 6, 8, 10 and/or 12.

The present invention also encompasses polynucleotides capable of hybridizing, preferably under reduced stringency conditions, more preferably under stringent conditions, and most preferably under highly stringent conditions, to polynucleotides described herein. Examples of stringency conditions are shown in Table 2 below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE II

| Stringency Condition | Polynucleotide Hybrid± | Hybrid Length (bp) ‡ | Hyridization Temperature and Buffer† | Wash Temperature and Buffer † |
|---|---|---|---|---|
| A | DNA:DNA | > or equal to 50 | 65° C.; 1xSSC -or- 42° C.; 1xSSC, 50% formamide | 65° C.; 0.3xSSC |
| B | DNA:DNA | <50 | Tb*; 1xSSC | Tb*; 1xSSC |
| C | DNA:RNA | > or equal to 50 | 67° C.; 1xSSC -or- 45° C.; 1xSSC, 50% formamide | 67° C.; 0.3xSSC |
| D | DNA:RNA | <50 | Td*; 1xSSC | Td*; 1xSSC |
| E | RNA:RNA | > or equal to 50 | 70° C.; 1xSSC -or- 50° C.; 1xSSC, 50% formamide | 70° C.; 0.3xSSC |
| F | RNA:RNA | <50 | Tf*; 1xSSC | Tf*; 1xSSC |
| G | DNA:DNA | > or equal to 50 | 65° C.; 4xSSC -or- 45° C.; 4xSSC, 50% formamide | 65° C.; 1xSSC |
| H | DNA:DNA | <50 | Th*; 4xSSC | Th*; 4xSSC |
| I | DNA:RNA | > or equal to 50 | 67° C.; 4xSSC -or- 45° C.; 4xSSC, 50% formamide | 67° C.; 1xSSC |
| J | DNA:RNA | <50 | Tj*; 4xSSC | Tj*; 4xSSC |
| K | RNA:RNA | > or equal to 50 | 70° C.; 4xSSC -or- 40° C.; 6xSSC, 50% formamide | 67° C.; 1xSSC |
| L | RNA:RNA | <50 | Tl*; 2xSSC | Tl*; 2xSSC |

TABLE II-continued

| Stringency Condition | Polynucleotide Hybrid± | Hybrid Length (bp) ‡ | Hyridization Temperature and Buffer† | Wash Temperature and Buffer † |
|---|---|---|---|---|
| M | DNA:DNA | > or equal to 50 | 50° C.; 4xSSC -or- 40° C. 6xSSC, 50% formamide | 50° C.; 2xSSC |
| N | DNA:DNA | <50 | Tn*; 6xSSC | Tn*; 6xSSC |
| O | DNA:RNA | > or equal to 50 | 55° C.; 4xSSC -or- 42° C.; 6xSSC, 50% formamide | 55° C.; 2xSSC |
| P | DNA:RNA | <50 | Tp*; 6xSSC | Tp*; 6xSSC |
| Q | RNA:RNA | > or equal to 50 | 60° C.; 4xSSC -or- 45° C.; 6xSSC, 50% formamide | 60° C.; 2xSSC |
| R | RNA:RNA | <50 | Tr*; 4xSSC | Tr*; 4xSSC |

‡—The "hybrid length" is the anticipated length for the hybridized region(s) of the hybridizing polynucleotides. When hybridizing a polynucleotide of unknown sequence, the hybrid is assumed to be that of the hybridizing polynucleotide of the present invention. When polynucleotides of known sequence are hybridized, the hybrid length can be determined by aligning the sequences of the polynucleotides and identifying the region or regions of optimal sequence complementarity. Methods of aligning two or more polynucleotide sequences and/or determining the percent identity between two polynucleotide sequences are well known in the art (e.g., MegAlign program of the DNA*Star suite of programs, etc).

†—SSPE (1xSSPE is 0.15M NaCl, 10 mM NaH2PO4, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete. The hybridizations and washes may additionally include 5xDenhardt's reagent, 0.5-1.0% SDS, 100 ug/ml denatured, fragmented salmon sperm DNA, 0.5% sodium pyrophosphate, and up to 50% formamide.

*Tb-Tr: The hybridization temperature for hybrids anticipated to be less than 50 base pairs in length should be 5-10° C. less than the melting temperature Tm of the hybrids there Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6($\log_{10}$[Na+])+0.41(% G+C)−(600/N), where N is the number of bases in the hybrid, and [Na+] is the concentration of sodium ions in the hybridization buffer ([NA+] for 1xSSC=0.165 M).

The present invention encompasses the substitution of any one, or more DNA or RNA hybrid partners with either a PNA, or a modified polynucleotide. Such modified polynucleotides are known in the art and are more particularly described elsewhere herein.

Additional examples of stringency conditions for polynucleotide hybridization are provided, for example, in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M., Ausubel et al., eds, John Wiley and Sons, Inc., sections 2.10 and 6.3-6.4, which are hereby incorporated by reference herein.

Preferably, such hybridizing polynucleotides have at least 70% sequence identity (more preferably, at least 80% identity; and most preferably at least 90% or 95% identity) with the polynucleotide of the present invention to which they hybridize, where sequence identity is determined by comparing the sequences of the hybridizing polynucleotides when aligned so as to maximize overlap and identity while minimizing sequence gaps. The determination of identity is well known in the art, and discussed more specifically elsewhere herein.

The invention encompasses the application of PCR methodology to the polynucleotide sequences of the present invention, the clone deposited with the ATCC, and/or the cDNA encoding the polypeptides of the present invention. PCR techniques for the amplification of nucleic acids are described in U.S. Pat. No. 4,683,195 and Saiki et al., Science, 239:487-491 (1988). PCR, for example, may include the following steps, of denaturation of template nucleic acid (if double-stranded), annealing of primer to target, and polymerization. The nucleic acid probed or used as a template in the amplification reaction may be genomic DNA, cDNA, RNA, or a PNA. PCR may be used to amplify specific sequences from genomic DNA, specific RNA sequence, and/or cDNA transcribed from mRNA. References for the general use of PCR techniques, including specific method parameters, include Mullis et al., Cold Spring Harbor Symp. Quant. Biol., 51:263, (1987), Ehrlich (ed), PCR Technology, Stockton Press, NY, 1989; Ehrlich et al., Science, 252:1643-1650, (1991); and "PCR Protocols, A Guide to Methods and Applications", Eds., Innis et al., Academic Press, New York, (1990).

Polynucleotide and Polypeptide Variants

The present invention also encompases variants (e.g., allelic variants, orthologs, etc.) of the polynucleotide sequence disclosed herein in SEQ ID NO:1, 3, 5, 7, 9 and/or 11, the complementary strand thereto, and/or the cDNA sequence contained in the deposited clone.

The present invention also encompasses variants of the polypeptide sequence, and/or fragments therein, disclosed in SEQ ID NO:2, 4, 6, 8, 10 and/or 12, a polypeptide encoded by the polunucleotide sequence in SEQ ID NO:1, 3, 5, 7, 9 and/or 11, and/or a polypeptide encoded by a cDNA in the deposited clone.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

Thus, one aspect of the invention provides an isolated nucleic acid molecule comprising, or alternatively consisting of, a polynucleotide having a nucleotide sequence selected from the group consisting of: (a) a nucleotide sequence encoding a LTRPC3 related polypeptide having an amino acid sequence as shown in the sequence listing and described in SEQ ID NO: 1, 3, 5, 7, 9 and/or 11 (b) a nucleotide sequence encoding a mature LTRPC3 related polypeptide having the amino acid sequence as shown in the sequence listing and described in SEQ ID NO:1, 3, 5, 7, 9 and/or 11(c) a nucleotide sequence encoding a biologically active fragment of a LTRPC3 related polypeptide having an amino acid sequence shown in the sequence listing and described in SEQ ID NO:1, 3, 5, 7, 9 and/or 11(d) a nucleotide sequence encoding an antigenic fragment of a LTRPC3 related polypeptide having an amino acid sequence shown in the sequence listing and described in SEQ ID NO: 1, 3, 5, 7, 9 and/or 11(e) a nucleotide sequence encoding a LTRPC3 related polypeptide comprising the complete amino acid sequence encoded by a human cDNA plasmid contained in SEQ ID NO:1, 3, 5, 7, 9 and/or 11(f) a nucleotide sequence encoding a mature LTRPC3 related polypeptide having an amino acid sequence encoded by a human cDNA plasmid contained in SEQ ID NO: 1, 3, 5, 7, 9 and/or 11(g) a nucleotide sequence encoding a biologically active fragment of a LTRPC3 related polypeptide having an amino acid sequence encoded by a human cDNA plasmid contained in SEQ ID NO:1, 3,5,7,9 and/or 11(h) a nucleotide sequence encoding an antigenic fragment of a LTRPC3 related polypeptide having an amino acid sequence encoded by a human cDNA plasmid contained in SEQ ID NO:1, 3, 5, 7, 9 and/or 11(I) a nucleotide sequence complimentary to any of the nucleotide sequences in (a), (b), (c), (d), (e), (f), (g), or (h), above.

The present invention is also directed to polynucleotide sequences which comprise, or alternatively consist of, a polynucleotide sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above. Polynucleotides encoded by these nucleic acid molecules are also encompassed by the invention. In another embodiment, the invention encompasses nucleic acid molecule which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

Another aspect of the invention provides an isolated nucleic acid molecule comprising, or alternatively, consisting of, a polynucleotide having a nucleotide sequence selected from the group consisting of: (a) a nucleotide sequence encoding a LTRPC3 related polypeptide having an amino acid sequence as shown in the sequence listing and described in Table 1; (b) a nucleotide sequence encoding a mature LTRPC3 related polypeptide having the amino acid sequence as shown in the sequence listing and described in Table 1; (c) a nucleotide sequence encoding a biologically active fragment of a LTRPC3 related polypeptide having an amino acid sequence as shown in the sequence listing and described in Table 1; (d) a nucleotide sequence encoding an antigenic fragment of a LTRPC3 related polypeptide having an amino acid sequence as shown in the sequence listing and described in Table 1; (e) a nucleotide sequence encoding a LTRPC3 related polypeptide comprising the complete amino acid sequence encoded by a human cDNA in a cDNA plasmid contained in the ATCC Deposit and described in Table 1; (f) a nucleotide sequence encoding a mature LTRPC3 related polypeptide having an amino acid sequence encoded by a human cDNA in a cDNA plasmid contained in the ATCC Deposit and described in Table 1: (g) a nucleotide sequence encoding a biologically active fragment of a LTRPC3 related polypeptide having an amino acid sequence encoded by a human cDNA in a cDNA plasmid contained in the ATCC Deposit and described in Table 1; (h) a nucleotide sequence encoding an antigenic fragment of a LTRPC3 related polypeptide having an amino acid sequence encoded by a human cDNA in a cDNA plasmid contained in the ATCC deposit and described in Table 1; (i) a nucleotide sequence complimentary to any of the nucleotide sequences in (a), (b), (c), (d), (e), (f), (g), or (h) above.

The present invention is also directed to nucleic acid molecules which comprise, or alternatively, consist of, a nucleotide sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above.

The present invention encompasses polypeptide sequences which comprise, or alternatively consist of, an amino acid sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, the following non-limited examples, the polypeptide sequence identified as SEQ ID NO:2, 4, 6, 8, 10 and/or 12, the polypeptide sequence encoded by a cDNA provided in the deposited clone, and/or polypeptide fragments of any of the polypeptides provided herein. Polynucleotides encoded by these nucleic acid molecules are also encompassed by the invention. In another embodiment, the invention encompasses nucleic acid molecule which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

The present invention is also directed to polypeptides which comprise, or alternatively consist of, an amino acid sequence which is at least about 80%, 85%, 90%, 91%, 92%, 93%, 94%, 95%, 96%, 97%, 98%, 99%, 99:1%, 99.2%, 99.3%, 99.4%, 99.5%, 99.6%, 99.7%, 99.8%, or 99.9% identical to, for example, the polypeptide sequence shown in SEQ ID NO:2, 4, 6, 8, 10 and/or 12, a polypeptide sequence encoded by the nucleotide sequence in SEQ ID NO:1, 3, 5, 7, 9 and/or 11, a polypeptide sequence encoded by the cDNA in ATCC Deposit No:PTA-4175, and/or polypeptide fragments of any of these polypeptides (e.g., those fragments described herein). Polynucleotides which hybridize to the complement of the nucleic acid molecules encoding these polypeptides under stringent hybridization conditions or alternatively, under lower stringency conditions, are also encompasses by the present invention, as are the polypeptides encoded by these polynucleotides.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence referenced in Table 1, the ORF (open reading frame), or any fragment specified as described herein.

As a practical matter, whether any particular nucleic acid molecule or polypeptide is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673-4680, (1994)), which is based on the algorithm of Higgins, D. G., et al., Computer Applications in the Biosciences (CABIOS), 8(2):189-191, (1992). In a sequence alignment the query and subject sequences are both DNA sequences. An RNA sequence can be compared by converting U's to T's. However, the CLUSTALW algorithm automatically converts U's to T's when comparing RNA sequences to DNA sequences. The result of said global sequence alignment is in percent identity. Preferred parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps:Off; Hydrophilic Residue Gap=Off; and Transition Weighting=0. The pairwise and multiple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of 5' or 3' deletions, not because of internal deletions. If only the local pairwise percent identity is required, no manual correction is needed. However, a manual correction may be applied to determine the global percent identity from a global polynucleotide alignment. Percent identity calculations based upon global polynucleotide alignments are often preferred since they reflect the percent identity between the polynucleotide molecules as a whole (i.e., including any polynucleotide overhangs, not just overlapping regions), as opposed to, only local matching polynucleotides. Manual corrections for global percent identity determinations are required since the CLUSTALW program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the CLUSTALW sequence alignment. This percentage is then subtracted from the percent identity, calculated by the above CLUSTALW program using the specified parameters, to arrive at a final percent identity score. This corrected score may be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the CLUSTALW alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the CLUSTALW program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by CLUSTALW is not manually corrected. Once again, only bases 5' and 3' of the subject sequence which are not matched/aligned with the query sequence are manually corrected for. No other manual corrections are required for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

As a practical matter, whether any particular polypeptide is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for instance, an amino acid sequence referenced in Table 1 (SEQ ID NO:2) or to the amino acid sequence encoded by cDNA contained in a deposited clone, can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673-4680, (1994)), which is based on the algorithm of Higgins, D. G., et al., Computer Applications in the Biosciences (CABIOS), 8(2):189-191, (1992). In a sequence alignment the query and subject sequences are both amino acid sequences. The result of said global sequence alignment is in percent identity. Preferred parameters used in a CLUSTALW alignment of DNA sequences to calculate percent identity via pairwise alignments are: Matrix=BLOSUM, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps:Off; Hydrophilic Residue Gap=Off; and Transition Weighting=0. The pairwise and multiple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of N- or C-terminal deletions, not because of internal deletions. If only the local pairwise percent identity is required, no manual correction is needed. However, a manual correction may be applied to determine the global percent identity from a global polypeptide alignment. Percent identity calculations based upon global polypeptide alignments are often preferred since they reflect the percent identity between the polypeptide molecules as a whole (i.e., including any polypeptide overhangs, not just overlapping regions), as opposed to, only local matching polypeptides. Manual corrections for global percent identity determinations are required since the CLUSTALW program does not account for N- and C-terminal truncations of the subject sequence when calculating percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the CLUSTALW sequence alignment. This percentage is then subtracted from the percent identity, calculated by the above CLUSTALW program using the specified parameters, to arrive at a final percent identity score. This final percent identity score is what may be used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the CLUSTALW alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the CLUSTALW program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence, which are not matched/aligned with the query. In this case the percent identity calculated by CLUSTALW is not manually corrected. Once again, only residue positions outside the N- and C-terminal ends of the subject sequence, as displayed in the CLUSTALW alignment, which are not matched/aligned with the query sequence are manually corrected for. No other manual corrections are required for the purposes of the present invention.

In addition to the above method of aligning two or more polynucleotide or polypeptide sequences to arrive at a percent identity value for the aligned sequences, it may be desirable in some circumstances to use a modified version of the CLUSTALW algorithm which takes into account known structural features of the sequences to be aligned, such as for example, the SWISS-PROT designations for each sequence. The result of such a modified CLUSTALW algorithm may provide a more accurate value of the percent identity for two polynucleotide or polypeptide sequences. Support for such a modified version of CLUSTALW is provided within the CLUSTALW algorithm and would be readily appreciated to one of skill in the art of bioinformatics.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred. Polynucleotide variants can be produced for a variety of reasons, e.g., to optimize codon expression for a particular host (change codons in the mRNA to those preferred by a bacterial host such as E. coli).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the protein without substantial loss of biological function. The authors of Ron et al., J. Biol. Chem . . . 268: 2984-2988 (1993), reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein (Dobeli et al., J. Biotechnology 7:199-216 (1988)).

Moreover, ample evidence demonstrates that variants often retain a biological activity similar to that of the naturally occurring protein. For example, Gayle and coworkers (J. Biol. Chem.. 268:22105-22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the protein will likely be retained when less than the majority of the residues of the protein are removed from the N-terminus or C-terminus. Whether a particular polypeptide lacking N- or C-terminal residues of a protein retains such immunogenic activities can readily be determined by routine methods described herein and otherwise known in the art.

Alternatively, such N-terminus or C-terminus deletions of a polypeptide of the present invention may, in fact, result in a significant increase in one or more of the biological activities of the polypeptide(s). For example, biological activity of many polypeptides are governed by the presence of regulatory domains at either one or both termini. Such regulatory domains effectively inhibit the biological activity of such polypeptides in lieu of an activation event (e.g., binding to a cognate ligand or receptor, phosphorylation, proteolytic processing, etc.). Thus, by eliminating the regulatory domain of a polypeptide, the polypeptide may effectively be rendered biologically active in the absence of an activation event.

The invention further includes polypeptide variants that show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., Science 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081-1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved.

The invention encompasses polypeptides having a lower degree of identity but having sufficient similarity so as to perform one or more of the same functions performed by the polypeptide of the present invention. Similarity is determined by conserved amino acid substitution. Such substitutions are those that substitute a given amino acid in a polypeptide by another amino acid of like characteristics (e.g., chemical properties). According to Cunningham et al above, such conservative substitutions are likely to be phenotypically silent. Additional guidance concerning which amino acid changes are likely to be phenotypically silent are found in Bowie et al., Science 247:1306-1310 (1990).

Tolerated conservative amino acid substitutions of the present invention involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and H is; replacement of the aromatic residues Phe, Tyr, and Trp, and replacement of the small-sized amino acids Ala, Ser, Thr, Met, and Gly.

In addition, the present invention also encompasses the conservative substitutions provided in Table III below.

TABLE III

| For Amino Acid | Code | Replace with any of: |
| --- | --- | --- |
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |

TABLE III-continued

| For Amino Acid | Code | Replace with any of: |
|---|---|---|
| Lysine | K | D-Lys, Arg, D-Arg, homo-Arg, D-homo-Arg, Met, D- Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L- 1- oxazolidine-4-carboxylic acid |
| Serine | S | D-Ser, Thr, D-Thr, allo-Thr, Met, D-Met, Met(O), D- Met(O), L-Cys, D-Cys |
| Threonine | T | D-Thr, Ser, D-Ser, allo-Thr, Met, D-Met, Met(O), D- Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Aside from the uses described above, such amino acid substitutions may also increase protein or peptide stability. The invention encompasses amino acid substitutions that contain, for example, one or more non-peptide bonds (which replace the peptide bonds) in the protein or peptide sequence. Also included are substitutions that include amino acid residues other than naturally occurring L-amino acids, e.g., D-amino acids or non-naturally occurring or synthetic amino acids, e.g., β or γ amino acids.

Both identity and similarity can be readily calculated by reference to the following publications: Computational Molecular Biology, Lesk, A. M., ed., Oxford University Press, New York, 1988; Biocomputing: Informatics and Genome Projects, Smith, D. W., ed., Academic Press, New York, 1993; Informatics Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991.

In addition, the present invention also encompasses substitution of amino acids based upon the probability of an amino acid substitution resulting in conservation of function. Such probabilities are determined by aligning multiple genes with related function and assessing the relative penalty of each substitution to proper gene function. Such probabilities are often described in a matrix and are used by some algorithms (e.g., BLAST, CLUSTALW, GAP, etc.) in calculating percent similarity wherein similarity refers to the degree by which one amino acid may substitute for another amino acid without lose of function. An example of such a matrix is the PAM250 or BLOSUM62 matrix.

Aside from the canonical chemically conservative substitutions referenced above, the invention also encompasses substitutions which are typically not classified as conservative, but that may be chemically conservative under certain circumstances. Analysis of enzymatic catalysis for proteases, for example, has shown that certain amino acids within the active site of some enzymes may have highly perturbed pKa's due to the unique microenvironment of the active site. Such perturbed pKa's could enable some amino acids to substitute for other amino acids while conserving enzymatic structure and function. Examples of amino acids that are known to have amino acids with perturbed pKa's are the Glu-35 residue of Lysozyme, the Ile-16 residue of Chymotrypsin, the His-159 residue of Papain, etc. The conservation of function relates to either anomalous protonation or anomalous deprotonation of such amino acids, relative to their canonical, non-perturbed pKa. The pKa perturbation may enable these amino acids to actively participate in general acid-base catalysis due to the unique ionization environment within the enzyme active site. Thus, substituting an amino acid capable of serving as either a general acid or general base within the microenvironment of an enzyme active site or cavity, as may be the case, in the same or similar capacity as the wild-type amino acid, would effectively serve as a conservative amino substitution.

Besides conservative amino acid substitution, variants of the present invention include, but are not limited to, the following: (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331-340 (1967); Robbins et al., Diabetes 36: 838-845 (1987); Cleland et al., Crit. Rev. Therapeutic Drug Carrier Systems 10:307-377 (1993).)

Moreover, the invention further includes polypeptide variants created through the application of molecular evolution ("DNA Shuffling") methodology to the polynucleotide disclosed as SEQ ID NO:1, 3, 5, 7, 9 and/or 11, the sequence of the clone submitted in a deposit, and/or the cDNA encoding the polypeptide disclosed as SEQ ID NO:2, 4, 6, 8, 10 and/or 12. Such DNA Shuffling technology is known in the art and more particularly described elsewhere herein (e.g., WPC, Stemmer, PNAS, 91:10747, (1994)), and in the Examples provided herein).

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1-5, 5-10, 5-25, 5-50, 10-50 or 50-150, conservative amino acid substitutions are preferable.

Polynucleotide and Polypeptide Fragments

The present invention is directed to polynucleotide fragments of the polynucleotides of the invention, in addition to polypeptides encoded therein by said polynucleotides and/or fragments.

In the present invention, a "polynucleotide fragment" refers to a short polynucleotide having a nucleic acid sequence which: is a portion of that contained in a deposited clone, or encoding the polypeptide encoded by the cDNA in a deposited clone; is a portion of that shown in SEQ ID NO:1, 3, 5, 7, 9 and/or 11 or the complementary strand thereto, or is a portion of a polynucleotide sequence encoding the polypeptide of SEQ ID NO:2, 4, 6, 8, 10 and/or 12. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases from the cDNA sequence contained in a deposited clone or the nucleotide sequence shown in SEQ ID NO:1, 3, 5, 7, 9 and/or 11. In this context "about" includes the particularly recited value, a value larger or smaller by several (5, 4, 3, 2, or 1) nucleotides, at either terminus, or at both termini. These nucleotide fragments have uses that include, but are not limited to, as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments comprising, or alternatively consisting of, a sequence from about nucleotide number 1-50, 51-100, 101-150, 151-200, 201-250, 251-300, 301-350, 351-400, 401-450, 451-500, 501-550, 551-600, 651-700, 701-750, 751-800, 800-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, or 2001 to the end of SEQ ID NO:1, 3, 5, 7, 9 and/or 11, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Also encompassed by the present invention are polynucleotides which hybridize to these nucleic acid molecules under stringent hybridization conditions or lower stringency conditions, as are the polypeptides encoded by these polynucleotides.

In the present invention, a "polypeptide fragment" refers to an amino acid sequence which is a portion of that contained in SEQ ID NO:2, 4, 6, 8, 10 and/or 12 or encoded by the cDNA contained in a deposited clone. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1-20, 21-40, 41-60, 61-80, 81-100, 102-120, 12'-140, 141-160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are, also encompassed by the invention.

Preferred polypeptide fragments include the full-length protein. Further preferred polypeptide fragments include the full-length protein having a continuous series of deleted residues from the amino or the carboxy terminus, or both. For example, any number of amino acids, ranging from 1-60, can be deleted from the amino terminus of the full-length polypeptide. Similarly, any number of amino acids, ranging from 1-30, can be deleted from the carboxy terminus of the full-length protein. Furthermore, any combination of the above amino and carboxy terminus deletions are preferred. Similarly, polynucleotides encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:2, 4, 6, 8, 10 and/or 12 falling within conserved domains are specifically contemplated by the present invention. Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

In a preferred embodiment, the functional activity displayed by a polypeptide encoded by a polynucleotide fragment of the invention may be one or more biological activities typically associated with the full-length polypeptide of the invention. Illustrative of these biological activities includes the fragments ability to bind to at least one of the same antibodies which bind to the full-length protein, the fragments ability to interact with at lease one of the same proteins which bind to the full-length, the fragments ability to elicit at least one of the same immune responses as the full-length protein (i.e., to cause the immune system to create antibodies specific to the same epitope, etc.), the fragments ability to bind to at least one of the same polynucleotides as the full-length protein, the fragments ability to bind to a receptor of the full-length protein, the fragments ability to bind to a ligand of the full-length protein, and the fragments ability to multimerize with the full-length protein. However, the skilled artisan would appreciate that some fragments may have biological activities which are desirable and directly inapposite to the biological activity of the full-length protein. The functional activity of polypeptides of the invention, including fragments, variants, derivatives, and analogs thereof can be determined by numerous methods available to the skilled artisan, some of which are described elsewhere herein.

The present invention encompasses polypeptides comprising, or alternatively consisting of, an epitope of the polypeptide having an amino acid sequence of SEQ ID NO:2, 4, 6, 8, 10 and/or 12, or an epitope of the polypeptide sequence encoded by a polynucleotide sequence contained in ATCC deposit No. Z or encoded by a polynucleotide that hybridizes to the complement of the sequence of SEQ ID NO:1, 3, 5, 7, 9 and/or 11 or contained in ATCC deposit No. Z under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998-4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131-5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length, or longer.

Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767-778 (1984); Sutcliffe et al., Science 219:660-666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724-33 (1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety). In one embodiment, alteration of polynucleotides corresponding to SEQ ID NO:1, 3, 5, 7, 9 and/or 11 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a polypeptide, polypeptide fragment, or variant of SEQ ID NO:2, 4, 6, 8, 10 and/or 12, and/or an epitope, of the present invention (as determined by immunoassays well known in the art for assaying specific antibody-antigen binding). Antibodies of the invention include, but are not limited to, polyclonal, monoclonal, monovalent, bispecific, heteroconjugate, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (Mab) is meant to include intact molecules, as well as, antibody fragments (such as, for example, Fab and F(ab')2 fragments) which are capable of specifically binding to protein. Fab and F(ab')2 fragments lack the Fc fragment of intact antibody, clear more rapidly from the circulation of the animal or plant, and may have less non-specific tissue binding than an intact antibody (Wahl et al., J. Nucl. Med. 24:316-325 (1983)). Thus, these fragments are preferred, as well as the products of a FAB or other immunoglobulin expression library. Moreover, antibodies of the present invention include chimeric, single chain, and humanized antibodies.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al. The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homologue of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologues of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161(4): 1786-1794 (1998); Zhu et al., Cancer Res. 58(15):3209-3214 (1998); Yoon et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/ blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art.

The antibodies of the present invention may comprise polyclonal antibodies. Methods of preparing polyclonal antibodies are known to the skilled artisan (Harlow, et al., Antibodies: A Laboratory Manual, (Cold spring Harbor Laboratory Press, $2^{nd}$ ed. (1988); and Current Protocols, Chapter 2; which are hereby incorporated herein by reference in its entirety). In a preferred method, a preparation of the LTRPC3g, LTRPC3h, LTRPC3i, LTRPC3j, LTRPC3k, and/or LTRPC3l protein is prepared and purified to render it substantially free of natural contaminants. Such a preparation is then introduced into an animal in order to produce polyclonal antisera of greater specific activity. For example, a polypeptide of the invention can be administered to various host animals including, but not limited to, rabbits, mice, rats, etc. to induce the production of sera containing polyclonal antibodies specific for the antigen. The administration of the polypeptides of the present invention may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art. For the purposes of the invention, "immunizing agent" may be defined as a polypeptide of the invention, including fragments, variants, and/or derivatives thereof, in addition to fusions with heterologous polypeptides and other forms of the polypeptides described herein.

Typically, the immunizing agent and/or adjuvant will be injected in the mammal by multiple subcutaneous or intraperitoneal injections, though they may also be given intramuscularly, and/or through IV). The immunizing agent may include polypeptides of the present invention or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivitizing active chemical functional groups to both the polypeptide of the present invention and the immunogenic protein such that a covalent bond is formed, or through fusion-protein based methodology, or other methods known to the skilled artisan. Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Additional examples of adjuvants which may be employed includes the MPL-TDM adjuvant (monophosphoryl lipid A, synthetic trehalose dicorynomycolate). The immunization protocol may be selected by one skilled in the art without undue experimentation.

The antibodies of the present invention may comprise monoclonal antibodies. Monoclonal antibodies may be prepared using hybridoma methods, such as those described by Kohler and Milstein, Nature, 256:495 (1975) and U.S. Pat. No. 4,376,110, by Harlow, et al., Antibodies: A Laboratory Manual, (Cold spring Harbor Laboratory Press, $2^{nd}$ ed. (1988), by Hammerling, et al., Monoclonal Antibodies and T-Cell Hybridomas (Elsevier, N.Y., pp. 563-681 (1981); Köhler et al., Eur. J. Immunol. 6:511 (1976); Köhler et al., Eur. J. Immunol. 6:292 (1976), or other methods known to the artisan. Other examples of methods which may be employed for producing monoclonal antibodies includes, but are not limited to, the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mabs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include polypeptides of the present invention or a fusion protein thereof. Preferably, the immunizing agent consists of an LTRPC3g, LTRPC3h, LTRPC3i, LTRPC3j, LTRPC3k, and/or LTRPC3l polypeptide or, more preferably, with a LTRPC3g, LTRPC3h, LTRPC3i, LTRPC3j, LTRPC3k, and/or LTRPC3l polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. More preferred are the parent myeloma cell line (SP20) as provided by the ATCC. As inferred throughout the specification, human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the polypeptides of the present invention. Preferably, the binding specificity of monoclonal antibodies produced by the hybridoma cells is determined by immunoprecipitation or by an in vitro binding assay, such as radioimmunoassay (RIA) or enzyme-linked immunoabsorbant assay (ELISA). Such techniques are known in the art and within the skill of the artisan. The binding affinity of the monoclonal antibody can, for example, be determined by the Scatchard analysis of Munson and Pollart, Anal. Biochem., 107:220 (1980).

After the desired hybridoma cells are identified, the clones may be subcloned by limiting dilution procedures and grown by standard methods (Goding, supra, and/or according to Wands et al. (Gastroenterology 80:225-232 (1981)). Suitable culture media for this purpose include, for example, Dulbecco's Modified Eagle's Medium and RPMI-1640. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the invention is not limited to their sole production in hydridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). The hydridoma cells of the invention serve as a preferred source of such DNA. Once isolated, the DNA may be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples described herein. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240: 1038-1040 (1988).

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; Cabilly et al., Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985); U.S. Pat. Nos. 5,807, 715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592, 106; EP 519,596; Padlan, Molecular Immunology 28(4/5): 489-498 (1991); Studnicka et al., Protein Engineering 7(6): 805-814 (1994); Roguska. et al., PNAS 91:969-973 (1994)), and chain shuffling (U.S. Pat. No. 5,565,332). Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones et al., Nature, 321:522-525 (1986); Reichmann et al., Nature, 332:323-327 (1988); Verhoeyen et al., Science, 239: 1534-1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature 332:323-329 (1988)1 and Presta, Curr. Op. Struct. Biol., 2:593-596 (1992).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. The techniques of cole et al., and Boerder et al., are also available for the preparation of human monoclonal antibodies (cole et al., Monoclonal Antibodies and Cancer Therapy, Alan R. Riss, (1985); and Boerner et al., J. Immunol., 147(1):86-95, (1991)).

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and creation of an antibody repertoire. This approach is described, for example, in U.S. Pat. Nos. 5,545,807; 5,545,806; 5,569,825; 5,625,126; 5,633,425; 5,661,106, and in the following scientific publications: Marks et al., Biotechnol., 10:779-783 (1992); Lonberg et al., Nature 368:856-859 (1994); Fishwild et al., Nature Biotechnol., 14:845-51 (1996); Neuberger, Nature Biotechnol., 14:826 (1996); Lonberg and Huszar, Intern. Rev. Immunol., 13:65-93 (1995).

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Such anti-idiotypic antibodies capable of binding to the LTRPC3g, LTRPC3h, LTRPC3i, LTRPC3j, LTRPC3k, and/or LTRPC3l polypeptide can be produced in a two-step procedure. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

The antibodies of the present invention may be bispecific antibodies. Bispecific antibodies are monoclonal, Preferably human or humanized, antibodies that have binding specificities for at least two different antigens. In the present invention, one of the binding specificities may be directed towards a polypeptide of the present invention, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details of generating bispecific antibodies see, for example Suresh et al., Meth. In Enzym., 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980), and for the treatment of HIV infection (WO 91/00360; WO 92/20373; and EP03089). It is contemplated that the antibodies may be prepared in vitro using known methods in synthetic protein chemistry, including those involving crosslinking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2, 4, 6, 8, 10 and/or 12.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties ), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., Science 242:1038-1041 (1988)).

More preferably, a clone encoding an antibody of the present invention may be obtained according to the method described in the Example section herein.

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, 1993, TIB TECH 11(5):155-215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341 (1992) (said references incorporated by reference in their entireties).

As discussed, supra, the polypeptides corresponding to a polypeptide, polypeptide fragment, or a variant of SEQ ID NO:2, 4, 6, 8, 10 and/or 12 may be fused or conjugated to the above antibody portions to increase the in vivo half life of the polypeptides or for use in immunoassays using methods known in the art. Further, the polypeptides corresponding to SEQ ID NO:2, 4, 6, 8, 10 and/or 12 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958-3964 (1995)). In many cases, the Fc part in a fusion protein is beneficial in therapy and diagnosis, and thus can result in, for example, improved pharmacokinetic properties. (EP A 232, 262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52-58 (1995); Johanson et al., J. Biol. Chem. 270: 9459-9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

The present invention also encompasses the creation of synthetic antibodies directed against the polypeptides of the present invention. One example of synthetic antibodies is described in Radrizzani, M., et al., Medicina, (Aires), 59(6): 753-8, (1999)). Recently, a new class of synthetic antibodies has been described and are referred to as molecularly imprinted polymers (MIPs) (Semorex, Inc.). Antibodies, peptides, and enzymes are often used as molecular recognition elements in chemical and biological sensors. However, their lack of stability and signal transduction mechanisms limits their use as sensing devices. Molecularly imprinted polymers (MIPs) are capable of mimicking the function of biological receptors but with less stability constraints. Such polymers provide high sensitivity and selectivity while maintaining excellent thermal and mechanical stability. MIPs have the ability to bind to small molecules and to target molecules such as organics and proteins' with equal or greater potency than that of natural antibodies. These "super" MIPs have higher affinities for their target and thus require lower concentrations for efficacious binding.

During synthesis, the MIPs are imprinted so as to have complementary size, shape, charge and functional groups of the selected target by using the target molecule itself (such as a polypeptide, antibody, etc.), or a substance having a very similar structure, as its "print" or "template." MIPs can be derivatized with the same reagents afforded to antibodies. For example, fluorescent 'super' MIPs can be coated onto beads or wells for use in highly sensitive separations or assays, or for use in high throughput screening of proteins.

Moreover, MIPs based upon the structure of the polypeptide(s) of the present invention may be useful in screening for compounds that bind to the polypeptide(s) of the invention. Such a MIP would serve the role of a synthetic "receptor" by minimicking the native architecture of the polypeptide. In fact, the ability of a MIP to serve the role of a synthetic receptor has already been demonstrated for the estrogen receptor (Ye, L., Yu, Y., Mosbach, K, Analyst., 126(6):760-5, (2001); Dickert, F, L., Hayden, O., Halikias, K, P, Analyst., 126(6):766-71, (2001)). A synthetic receptor may either be mimicked in its entirety (e.g., as the entire protein), or mimicked as a series of short peptides corresponding to the protein (Rachkov, A., Minoura, N, Biochim, Biophys, Acta., 1544(1-2):255-66, (2001)). Such a synthetic receptor MIPs may be employed in any one or more of the screening methods described elsewhere herein.

MIPs have also been shown to be useful in "sensing" the presence of its mimicked molecule (Cheng, Z., Wang, E., Yang, X, Biosens, Bioelectron., 16(3):179-85, (2001); Jenkins, A, L., Yin, R., Jensen, J. L, Analyst., 126(6):798-802, (2001); Jenkins, A, L., Yin, R., Jensen, J. L, Analyst., 126(6): 798-802, (2001)). For example, a MIP designed using a polypeptide of the present invention may be used in assays designed to identify, and potentially quantitate, the level of said polypeptide in a sample. Such a MIP may be used as a substitute for any component described in the assays, or kits, provided herein (e.g., ELISA, etc.).

A number of methods may be employed to create MIPs to a specific receptor, ligand, polypeptide, peptide, organic molecule. Several preferred methods are described by Esteban et al in J. Anal, Chem., 370(7):795-802, (2001), which is hereby incorporated herein by reference in its entirety in addition to any references cited therein. Additional methods are known in the art and are encompassed by the present invention, such as for example, Hart, B, R., Shea, K, J. J. Am. Chem., Soc., 123(9):2072-3, (2001); and Quaglia, M., Chenon, K., Hall, A, J., De, Lorenzi, E., Sellergren, B, J. Am. Chem., Soc., 123 (10):2146-54, (2001); which are hereby incorporated by reference in their entirety herein.

Uses for Antibodies Directed Against Polypeptides of the Invention

The antibodies of the present invention have various utilities. For example, such antibodies may be used in diagnostic assays to detect the presence or quantification of the polypeptides of the invention in a sample. Such a diagnostic assay may be comprised of at least two steps. The first, subjecting a sample with the antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (e.g., See Arenkov P, et al., Anal Biochem., 278(2):123-131 (2000)), or a chromatography column, etc. And a second step involving the quantification of antibody bound to the substrate. Alternatively, the method may additionally involve a first step of attaching the antibody, either covalently, electrostatically, or reversibly, to a solid support, and a second step of subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp147-158). The antibodies used in the diagnostic assays can be labeled with a detectable moiety. The detectable moiety should be capable of producing, either directly or indirectly, a detectable signal. For example, the detectable moiety may be a radioisotope, such as $^{2}H$, $^{14}C$, $^{32}P$, or $^{125}I$, a florescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety may be employed, including those methods described by Hunter et al., Nature, 144:945 (1962); Dafvid et al., Biochem., 13:1014 (1974); Pain et al., J. Immunol. Metho., 40:219 (1981); and Nygren, J. Histochem. And Cytochem., 30:407 (1982).

Antibodies directed against the polypeptides of the present invention are useful for the affinity purification of such polypeptides from recombinant cell culture or natural sources. In this process, the antibodies against a particular polypeptide are immobilized on a suitable support, such as a Sephadex resin or filter paper, using methods well known in the art. The immobilized antibody then is contacted with a sample containing the polypeptides to be purified, and thereafter the support is washed with a suitable solvent that will remove substantially all the material in the sample except for the desired polypeptides, which are bound to the immobilized antibody. Finally, the support is washed with another suitable solvent that will release the desired polypeptide from the antibody.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737-49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays For Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses of Antibodies

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, and $10^{-15}$ M.

Antibodies directed against polypeptides of the present invention are useful for inhibiting allergic reactions in animals. For example, by administering a therapeutically acceptable dose of an antibody, or antibodies, of the present invention, or a cocktail of the present antibodies, or in combination with other antibodies of varying sources, the animal may not elicit an allergic response to antigens.

Likewise, one could envision cloning the gene encoding an antibody directed against a polypeptide of the present invention, said polypeptide having the potential to elicit an allergic and/or immune response in an organism, and transforming the organism with said antibody gene such that it is expressed (e.g., constitutively, inducibly, etc.) in the organism. Thus, the organism would effectively become resistant to an allergic response resulting from the ingestion or presence of such an immune/allergic reactive polypeptide. Moreover, such a use of the antibodies of the present invention may have particular utility in preventing and/or ameliorating autoimmune diseases and/or disorders, as such conditions are typically a result of antibodies being directed against endogenous proteins. For example, in the instance where the polypeptide of the present invention is responsible for modulating the immune response to auto-antigens, transforming the organism and/or individual with a construct comprising any of the promoters disclosed herein or otherwise known in the art, in addition, to a polynucleotide encoding the antibody directed against the polypeptide of the present invention could effective inhibit the organisms immune system from eliciting an immune response to the auto-antigen(s). Detailed descriptions of therapeutic and/or gene therapy applications of the present invention are provided elsewhere herein.

Alternatively, antibodies of the present invention could be produced in a plant (e.g., cloning the gene of the antibody directed against a polypeptide of the present invention, and transforming a plant with a suitable vector comprising said gene for constitutive expression of the antibody within the plant), and the plant subsequently ingested by an animal, thereby conferring temporary immunity to the animal for the specific antigen the antibody is directed towards (See, for example, U.S. Pat. Nos. 5,914,123 and 6,034,298).

In another embodiment, antibodies of the present invention, preferably polyclonal antibodies, more preferably monoclonal antibodies, and most preferably single-chain antibodies, can be used as a means of inhibiting gene expression of a particular gene, or genes, in a human, mammal, and/or other organism. See, for example, International Publication Number WO 00/05391, published Feb. 3, 2000, to Dow Agrosciences LLC. The application of such methods for the antibodies of the present invention are known in the art, and are more particularly described elsewhere herein.

In yet another embodiment, antibodies of the present invention may be useful for multimerizing the polypeptides of the present invention. For example, certain proteins may confer enhanced biological activity when present in a multimeric state (i.e., such enhanced activity may be due to the increased effective concentration of such proteins whereby more protein is available in a localized location).

Antibody-Based Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains nucleic acid sequences encoding an antibody of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytesu, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973-985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Compositions

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem . . . 262: 4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228: 190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E.W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging With Antibodies

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et-al., J. Cell . Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because certain proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Peptide moieties may be added to the polypeptide to facilitate purification. Such regions may be removed prior to final preparation of the polypeptide. Similarly, peptide cleavage sites can be introduced in-between such peptide moieties, which could additionally be subjected to protease activity to remove said peptide(s) from the protein of the present invention. The addition of peptide moieties, including peptide cleavage sites, to facilitate handling of polypeptides are familiar and routine techniques in the art.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84-86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958-3964 (1995).)

Similarly, EP-A-0 464 533 (Canadian counterpart 2045869) discloses fusion proteins comprising various portions of the constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52-58 (1995); K. Johanson et al., J. Biol. Chem. . . . 270:9459-9471 (1995).)

Moreover, the polypeptides of the present invention can be fused to marker sequences (also referred to as "tags"). Due to the availability of antibodies specific to such "tags", purification of the fused polypeptide of the invention, and/or its identification is significantly facilitated since antibodies specific to the polypeptides of the invention are not required. Such purification may be in the form of an affinity purification whereby an anti-tag antibody or another type of affinity matrix (e.g., anti-tag antibody attached to the matrix of a flow-thru column) that binds to the epitope tag is present. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984)).

The skilled artisan would acknowledge the existence of other "tags" which could be readily substituted for the tags referred to supra for purification and/or identification of polypeptides of the present invention (Jones C., et al., J Chromatogr A. 707(1):3-22 (1995)). For example, the c-myc tag and the 8F9, 3C7, 6E10, G4m B7 and 9E10 antibodies thereto (Evan et al., Molecular and Cellular Biology 5:3610-3616 (1985)); the Herpes Simplex virus glycoprotein D (gD) tag and its antibody (Paborsky et al., Protein Engineering, 3(6): 547-553 (1990), the Flag-peptide—i.e., the octapeptide sequence DYKDDDDK (SEQ ID NO: 16), (Hopp et al., Biotech. 6:1204-1210 (1988); the KT3 epitope peptide (Martin et al., Science, 255:192-194 (1992)); a-tubulin epitope peptide (Skinner et al., J. Biol. Chem., 266:15136-15166, (1991)); the T7 gene 10 protein peptide tag (Lutz-Freyermuth et al., Proc. Natl. Sci. USA, 87:6363-6397 (1990)), the FITC epitope (Zymed, Inc.), the GFP epitope (Zymed, Inc.), and the Rhodamine epitope (Zymed, Inc.).

The present invention also encompasses the attachment of up to nine codons encoding a repeating series of up to nine arginine amino acids to the coding region of a polynucleotide of the present invention. The invention also encompasses chemically derivitizing a polypeptide of the present invention with a repeating series of up to nine arginine amino acids. Such a tag, when attached to a polypeptide, has recently been shown to serve as a universal pass, allowing compounds access to the interior of cells without additional derivitization or manipulation (Wender, P., et al., unpublished data).

Protein fusions involving polypeptides of the present invention, including fragments and/or variants thereof, can be used for the following, non-limiting examples, subcellular localization of proteins, determination of protein-protein interactions via immunoprecipitation, purification of proteins via affinity chromatography, functional and/or structural characterization of protein. The present invention also encompasses the application of hapten specific antibodies for any of the uses referenced above for epitope fusion proteins. For example, the polypeptides of the present invention could be chemically derivatized to attach hapten molecules (e.g., DNP, (Zymed, Inc.)). Due to the availability of monoclonal antibodies specific to such haptens, the protein could be readily purified using immunoprecipation, for example.

Polypeptides of the present invention, including fragments and/or variants thereof, in addition to, antibodies directed against such polypeptides, fragments, and/or variants, may be fused to any of a number of known, and yet to be determined, toxins, such as ricin, saporin (Mashiba H, et al., Ann. N.Y. Acad. Sci. 1999; 886:233-5), or HC toxin (Tonukari N J, et al., Plant Cell. 2000 February; 12(2):237-248), for example. Such fusions could be used to deliver the toxins to desired tissues for which a ligand or a protein capable of binding to the polypeptides of the invention exists.

The invention encompasses the fusion of antibodies directed against polypeptides of the present invention, including variants and fragments thereof, to said toxins for delivering the toxin to specific locations in a cell, to specific tissues, and/or to specific species. Such bifunctional antibodies are known in the art, though a review describing additional advantageous fusions, including citations for methods of production, can be found in P. J. Hudson, Curr. Opp. In. 1 mm. 11:548-557, (1999); this publication, in addition to the references cited therein, are hereby incorporated by reference in their entirety herein. In this context, the term "toxin" may be expanded to include any heterologous protein, a small molecule, radionucleotides, cytotoxic drugs, liposomes, adhesion molecules, glycoproteins, ligands, cell or tissue-specific ligands, enzymes, of bioactive agents, biological response modifiers, anti-fungal agents, hormones, steroids, vitamins, peptides, peptide analogs, anti-allergenic agents, anti-tubercular agents, anti-viral agents, antibiotics, anti-protozoan agents, chelates, radioactive particles, radioactive ions, X-ray contrast agents, monoclonal antibodies, polyclonal antibodies and genetic material. In view of the present disclosure, one skilled in the art could determine whether any particular "toxin" could be used in the compounds of the present invention. Examples of suitable "toxins" listed above are exemplary only and are not intended to limit the "toxins" that may be used in the present invention.

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli, streptomyces* and *Salmonella typhimurium* cells; fungal cells, such as yeast cells (e.g., *Saccharomyces cerevisiae* or *Pichia pastoris* (ATCC Accession No. 201178)); insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSW2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlsbad, Calif.). Other suitable vectors will be readily apparent to the skilled artisan.

Introduction of the construct into the host cell that can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast *Pichia pastoris* is used to express the polypeptide of the present invention in a eukaryotic system. *Pichia pastoris* is a methylotrophic yeast which can metabolize methanol as its sole carbon source. A main step in the methanol metabolization pathway is the oxidation of methanol to formaldehyde using O2. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for O2. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See, Ellis, S. B., et al., Mol. Cell. Biol. 5:1111-21 (1985); Koutz, P. J, et al., Yeast 5:167-77 (1989); Tschopp, J. F., et al., Nucl. Acids Res. 15:3859-76 (1987). Thus, a heterologous coding sequence, such as, for example, a polynucleotide of the present invention, under the transcriptional regulation of all or part of the AOX1 regulatory sequence is expressed at exceptionally high levels in *Pichia* yeast grown in the presence of methanol.

In one example, the plasmid vector pPIC9K is used to express DNA encoding a polypeptide of the invention, as set forth herein, in a Pichea yeast system essentially as described in "*Pichia* Protocols: Methods in Molecular Biology," D. R. Higgins and J. Cregg, eds. The Humana Press, Totowa, N.J., 1998. This expression vector allows expression and secretion of a protein of the invention by virtue of the strong AOX1 promoter linked to the *Pichia pastoris* alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG, as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932-8935 (1989); and Zijistra et al., Nature 342:435-438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W.H. Freeman & Co., N.Y., and Hunkapiller et al., Nature, 310:105-111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the protein, the addition of epitope tagged peptide fragments (e.g., FLAG, HA, GST, thioredoxin, maltose binding protein, etc.), attachment of affinity tags such as biotin and/or streptavidin, the covalent attachment of chemical moieties to the amino acid backbone, N- or C-terminal processing of the polypeptides ends (e.g., proteolytic processing), deletion of the N-terminal methionine residue, etc.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The invention further encompasses chemical derivitization of the polypeptides of the present invention, preferably where the chemical is a hydrophilic polymer residue. Exemplary hydrophilic polymers, including derivatives, may be those that include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates.

The molecular weight of the hydrophilic polymers may vary, and is generally about 50 to about 5,000,000, with polymers having a molecular weight of about 100 to about 50,000 being preferred. The polymers may be branched or unbranched. More preferred polymers have a molecular weight of about 150 to about 10,000, with molecular weights of 200 to about 8,000 being even more preferred.

For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

Additional preferred polymers which may be used to derivatize polypeptides of the invention, include, for example, poly(ethylene glycol) (PEG), poly(vinylpyrrolidine), polyoxomers, polysorbate and poly(vinyl alcohol), with PEG polymers being particularly preferred. Preferred among the PEG polymers are PEG polymers having a molecular weight of from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers, in addition to those exemplified above, will be readily apparent to one skilled in the art based on the present disclosure. Generally, the polymers used may include polymers that can be attached to the polypeptides of the invention via alkylation or acylation reactions.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactiye group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As with the various polymers exemplified above, it is contemplated that the polymeric residues may contain functional groups in addition, for example, to those typically involved in linking the polymeric residues to the polypeptides of the present invention. Such functionalities include, for example, carboxyl, amine, hydroxy and thiol groups. These functional groups on the polymeric residues can be further reacted, if desired, with materials that are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins, and nucleosides.

In addition to residues of hydrophilic polymers, the chemical used to derivatize the polypeptides of the present invention can be a saccharide residue. Exemplary saccharides which can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure. Generally, saccharides which may be used for derivitization include saccharides that can be attached to the polypeptides of the invention via alkylation or acylation reactions.

Moreover, the invention also encompasses derivitization of the polypeptides of the present invention, for example, with lipids (including cationic, anionic, polymerized, charged, synthetic, saturated, unsaturated, and any combination of the above, etc.). stabilizing agents.

The invention encompasses derivitization of the polypeptides of the present invention, for example, with compounds that may serve a stabilizing function (e.g., to increase the polypeptides half-life in solution, to make the polypeptides more water soluble, to increase the polypeptides hydrophilic or hydrophobic character, etc.). Polymers useful as stabilizing materials may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin, polyalginates, and polylactide-coglycolide polymers. Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, hydroxyapatites, fluoroapatite polymers, polyethylenes (such as, for example, polyethylene glycol (including for example, the class of compounds referred to as Pluronics.RTM., commercially available from BASF, Parsippany, N.J.), polyoxyethylene, and polyethylene terephthlate), polypropylenes. (such as, for example, polypropylene glycol), polynrethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of derivatized polypeptides of the invention which employ polymers as stabilizing compounds will be readily apparent to one skilled in the art, in view of the present disclosure, when coupled with information known in the art, such as that described and referred to in Unger, U.S. Pat. No. 5,205,290, the disclosure of which is hereby incorporated by reference herein in its entirety.

Moreover, the invention encompasses additional modifications of the polypeptides of the present invention. Such additional modifications are known in the art, and are specifically provided, in addition to methods of derivitization, etc., in U.S. Pat. No. 6,028,066, which is hereby incorporated in its entirety herein.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:2, 4, 6, 8, 10 and/or 12 or encoded by the cDNA contained in a deposited clone (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, osteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide sequence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hydrophobic or signal peptide) and which can be incorporated by membrane reconstitution techniques into liposomes (see, e.g., U.S. Pat. No. 5,478,925, which is herein incorporated by reference in its entirety).

In addition, the polynucleotide insert of the present invention could be operatively linked to "artificial" or chimeric promoters and transcription factors. Specifically, the artificial promoter could comprise, or alternatively consist, of any combination of cis-acting DNA sequence elements that are recognized by trans-acting transcription factors. Preferably, the cis acting DNA sequence elements and trans-acting transcription factors are operable in mammals. Further, the transacting transcription factors of such "artificial" promoters could also be "artificial" or chimeric in design themselves and could act as activators or repressors to said "artificial" promoter.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15-25 bp) from the sequences shown in SEQ ID NO:1, 3, 5, 7, 9 and/or 11. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:1, 3, 5, 7, 9 and/or 11 will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000-4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. Disease mapping data are known in the art. Assuming 1 megabase mapping resolution and one gene per 20 kb, a cDNA precisely localized to a chromosomal region associated with the disease could be one of 50-500 potential causative genes.

Thus, once coinheritance is established, differences in the polynucleotide and the corresponding gene between affected and unaffected organisms can be examined. First, visible structural alterations in the chromosomes, such as deletions or translocations, are examined in chromosome spreads or by PCR. If no structural alterations exist, the presence of point mutations are ascertained. Mutations observed in some or all affected organisms, but not in normal organisms, indicates that the mutation may cause the disease. However, complete sequencing of the polypeptide and the corresponding gene from several normal organisms is required to distinguish the mutation from a polymorphism. If a new polymorphism is identified, this polymorphic polypeptide can be used for further linkage analysis.

Furthermore, increased or decreased expression of the gene in affected organisms as compared to unaffected organisms can be assessed using polynucleotides of the present invention. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an organism and comparing the measured gene expression level with a standard level of polynucleotide expression level, whereby an increase or decrease in the gene expression level compared to the standard is indicative of a disorder.

By "measuring the expression level of a polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of organisms not having a disorder. As will be appreciated in the art, once a standard polypeptide level or mRNA level is known, it can be used repeatedly as a standard for comparison.

By "biological sample" is intended any biological sample obtained from an organism, body fluids, cell line, tissue culture, or other source which contains the polypeptide of the present invention or mRNA. As indicated, biological samples include body fluids (such as the following non-limiting examples, sputum, amniotic fluid, urine, saliva, breast milk, secretions, interstitial fluid, blood, serum, spinal fluid, etc.) which contain the polypeptide of the present invention, and other tissue sources found to express the polypeptide of the present invention. Methods for obtaining tissue biopsies and body fluids from organisms are well known in the art. Where the biological sample is to include mRNA, a tissue biopsy is the preferred source.

The method(s) provided above may Preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including proliferative diseases and conditions. Such a method is described in U.S. Pat. Nos. 5,858,659 and 5,856,104. The US patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L.Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the stronger binding characteristics of PNA:DNA hybrids. In addition, it is more likely that single base mismatches can be determined with PNA/DNA hybridization because a single mismatch in a PNA/DNA 15-mer lowers the melting point (T.sub.m) by 8°-20° C., vs. 4°-16° C. for the DNA/DNA 15-mer duplex. Also, the absence of charge groups in PNA means that hybridization can be done at low ionic strengths and reduce possible interference by salt during the analysis.

In addition to the foregoing, a polynucleotide can be used to control gene expression through triple helix formation or antisense DNA or RNA. Antisense techniques are discussed, for example, in Okano, J. Neurochem. 56: 560 (1991); "Oligodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense -Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat or prevent disease.

The present invention encompasses the addition of a nuclear localization signal, operably linked to the 5' end, 3' end, or any location therein, to any of the oligonucleotides, antisense oligonucleotides, triple helix oligonucleotides, ribozymes, PNA oligonucleotides, and/or polynucleotides, of the present invention. See, for example, G. Cutrona, et al., Nat. Biotech., 18:300-303, (2000); which is hereby incorporated herein by reference.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell. In one example, polynucleotide sequences of the present invention may be used to construct chimeric RNA/DNA oligonucleotides corresponding to said sequences, specifically designed to induce host cell mismatch repair mechanisms in an organism upon systemic injection, for example (Bartlett, R. J., et al., Nat. Biotech, 18:615-622 (2000), which is hereby incorporated by reference herein in its entirety). Such RNA/DNA oligonucleotides could be designed to correct genetic defects in certain host strains, and/or to introduce desired phenotypes in the host (e.g., introduction of a specific polymorphism within an endogenous gene corresponding to a polynucleotide of the present invention that may ameliorate and/or prevent a disease symptom and/or disorder, etc.). Alternatively, the polynucleotide sequence of the present invention may be used to construct duplex oligonucleotides corresponding to said sequence, specifically designed to correct genetic defects in certain host strains, and/or to introduce desired phenotypes into the host (e.g., introduction of a specific polymorphism within an endogenous gene corresponding to a polynucleotide of the present invention that may ameliorate and/or prevent a disease symptom and/or disorder, etc). Such methods of using duplex oligonucleotides are known in the art and are encompassed by the present invention (see EP1007712, which is hereby incorporated by reference herein in its entirety).

The polynucleotides are also useful for identifying organisms from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an organisms genome. These sequences can be used to prepare PCR primers for amplifying and isolating such selected DNA, which can then be sequenced. Using this technique, organisms can be identified because each organism will have a unique set of DNA sequences. Once an unique ID database is established for an organism, positive identification of that organism, living or dead, can be made from extremely small tissue samples. Similarly, polynucleotides of the present invention can be used as polymorphic markers, in addition to, the identification of transformed or non-transformed cells and/or tissues.

There is also a need for reagents capable of identifying the source of a particular tissue. Such need arises, for example, when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination. Moreover, as mentioned above, such reagents can be used to screen and/or identify transformed and non-transformed cells and/or tissues.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976-985 (1985); Jalkanen, M., et al., J. Cell . Biol. 105:3087-3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99 mTc), and fluorescent labels, such as fluorescein and rhodamine, and biotin.

In addition to assaying protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, polypeptides of the present invention can be used to treat, prevent, and/or diagnose disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor suppressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to a polypeptide of the present invention can also be used to treat, prevent, and/or diagnose disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Gene Therapy Methods

Another aspect of the present invention is to gene therapy methods for treating or preventing disorders, diseases and conditions. The gene therapy methods relate to the introduction of nucleic acid (DNA, RNA and antisense DNA or RNA) sequences into an animal to achieve expression of a polypeptide of the present invention. This method requires a polynucleotide which codes for a polypeptide of the invention that operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a polynucleotide of the invention ex vivo, with the engineered cells then being provided to a patient to be treated with the polypeptide. Such methods are well-known in the art. For example, see Belldegrun et al., J. Natl. Cancer Inst., 85:207-216 (1993); Ferrantini et al., Cancer Research, 53:107-1112 (1993); Ferrantini et al., J. Immunology 153: 4604-4615 (1994); Kaido, T., et al., Int. J. Cancer 60: 221-229 (1995); Ogura et al., Cancer Research 50: 5102-5106 (1990); Santodonato, et al., Human Gene Therapy 7:1-10 (1996); Santodonato, et al., Gene Therapy 4:1246-1255 (1997); and Zhang, et al., Cancer Gene Therapy 3: 31-38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the polynucleotide constructs can be delivered by any method that delivers injectable materials to the cells of an animal, such as, injection into the interstitial space of tissues (heart, muscle, skin, lung, liver, and the like). The polynucleotide constructs may be delivered in a pharmaceutically acceptable liquid or aqueous carrier.

In one embodiment, the polynucleotide of the invention is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotides of the invention can also be delivered in liposome formulations and lipofectin formulations and the like can be prepared by methods well known to those skilled in the art. Such methods are described, for example, in U.S. Pat. Nos. 5,593,972, 5,589, 466, and 5,580,859, which are herein incorporated by reference.

The polynucleotide vector constructs of the invention used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of polynucleotide sequence of the invention. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for the polynucleotides of the invention.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct of the invention can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the polynucleotide constructs of the invention are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA, 84:7413-7416 (1987), which is herein incorporated by reference); mRNA (Malone et al., Proc. Natl. Acad. Sci. USA, 86:6077-6081 (1989), which is herein incorporated by reference); and purified transcription factors (Debs et al., J. Biol. Chem. . . . , 265:10189-10192 (1990), which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl. Acad. Sci. USA, 84:7413-7416 (1987), which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication NO: WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., Felgner et al., Proc. Natl. Acad. Sci. USA, 84:7413-7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology, 101:512-527 (1983), which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include Ca2+-EDTA chelation (Papahadjopoulos et al., Biochim. Biophys. Acta, 394: 483 (1975); Wilson et al., Cell, 17:77 (1979)); ether injection (Deamer et al., Biochim. Biophys. Acta, 443:629 (1976); Ostro et al., Biochem. Biophys. Res. Commun., 76:836 (1977); Fraley et al., Proc. Natl. Acad. Sci. USA, 76:3348 (1979)); detergent dialysis (Enoch et al., Proc. Natl. Acad. Sci. USA , 76:145 (1979)); and reverse-phase evaporation (REV) (Fraley et al., J. Biol. Chem. . . . , 255:10431 (1980); Szoka et al., Proc. Natl. Acad. Sci. USA , 75:145 (1978); Schaefer-Ridder et al., Science, 215:166 (1982)), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication NO: WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding polypeptides of the invention. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, Human Gene Therapy , 1:5-14 (1990), which is incorporated herein by reference in its entirety. The vector may transduce the packaging cells through any means known in the art. Such means include, but are not limited to, electroporation, the use of liposomes, and CaPO4 precipitation. In one alternative, the retroviral plasmid vector may be encapsulated into a liposome, or coupled to a lipid, and then administered to a host.

The producer cell line generates infectious retroviral vector particles which include polynucleotide encoding polypeptides of the invention. Such retroviral vector particles then may be employed, to transduce eukaryotic cells, either in vitro or in vivo. The transduced eukaryotic cells will express polypeptides of the invention.

In certain other embodiments, cells are engineered, ex vivo or in vivo, with polynucleotides of the invention contained in an adenovirus vector. Adenovirus can be manipulated such that it encodes and expresses polypeptides of the invention, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz et al., Am. Rev. Respir. Dis., 109:233-238 (1974)). Finally, adenovirus mediated gene transfer has been demonstrated in a number of instances including transfer of alpha-1-antitrypsin and CFTR to the lungs of cotton rats (Rosenfeld et al., Science, 252:431-434 (1991); Rosenfeld et al., Cell, 68:143-155 (1992)). Furthermore, extensive studies to attempt to establish adenovirus as a causative agent in human cancer were uniformly negative (Green et al. Proc. Natl. Acad. Sci. USA, 76:6606 (1979)).

Suitable adenoviral vectors useful in the present invention are described, for example, in Kozarsky and Wilson, Curr. Opin. Genet. Devel., 3:499-503 (1993); Rosenfeld et al., Cell, 68:143-155 (1992); Engelhardt et al., Human Genet. Ther., 4:759-769 (1993); Yang et al., Nature Genet., 7:362-369 (1994); Wilson et al., Nature, 365:691-692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, Curr. Topics in Microbiol. Immunol., 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The polynucleotide construct containing polynucleotides of the invention is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct of the invention. These viral particles are then used to transduce eukaryotic cells, either ex vivo or in vivo. The transduced cells will contain the polynucleotide construct integrated into its genome, and will express the desired gene product.

Another method of gene therapy involves operably associating heterologous control regions and endogenous polynucleotide sequences (e.g. encoding the polypeptide sequence of interest) via homologous recombination (see, e.g., U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932-8935 (1989); and Zijlstra et al., Nature, 342:435-438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

The polynucleotides encoding polypeptides of the present invention may be administered along with other polynucleotides encoding angiogenic proteins. Angiogenic proteins include, but are not limited to, acidic and basic fibroblast growth factors, VEGF-1, VEGF-2 (VEGF-C), VEGF-3 (VEGF-B), epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding a polypeptide of the invention contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers. (Kaneda et al., Science, 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA, 189: 11277-11281 (1992), which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian. Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Biological Activities

The polynucleotides or polypeptides, or agonists or antagonists of the present invention can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists could be used to treat the associated disease.

Immune Activity

The polynucleotides or polypeptides, or agonists or antagonists of the present invention may be useful in treating, preventing, and/or diagnosing diseases, disorders, and/or conditions of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer or some autoimmune diseases, disorders, and/or conditions, acquired (e.g., by chemotherapy or toxins), or infectious. Moreover, a polynucleotides or polypeptides, or agonists or antagonists of the present invention can be used as a marker or detector of a particular immune system disease or disorder.

A polynucleotides or polypeptides, or agonists or antagonists of the present invention may be useful in treating, preventing, and/or diagnosing diseases, disorders, and/or conditions of hematopoietic cells. A polynucleotides or polypeptides, or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polynucleotides or polypeptides, or agonists or antagonists of the present invention could also be used to modulate hemostatic (the stopping of bleeding) or thrombolytic activity (clot formation). For example, by increasing hemostatic or thrombolytic activity, a polynucleotides or polypeptides, or agonists or antagonists of the present invention could be used to treat or prevent blood coagulation diseases, disorders, and/or conditions (e.g., afibrinogenemia, factor deficiencies), blood platelet diseases, disorders, and/or conditions (e.g. thrombocytopenia), or wounds resulting from trauma, surgery, or other causes. Alternatively, a polynucleotides or polypeptides, or agonists or antagonists of the present invention that can decrease hemostatic or thrombolytic activity could be used to inhibit or dissolve clotting. These molecules could be important in the treatment or prevention of heart attacks (infarction), strokes, or scarring.

A polynucleotides or polypeptides, or agonists or antagonists of the present invention may also be useful in treating, preventing, and/or diagnosing autoimmune diseases, disorders, and/or conditions. Many autoimmune diseases, disorders, and/or conditions result from inappropriate recognition of self as foreign material by immune cells. This inappropriate recognition results in an immune response leading to the destruction of the host tissue. Therefore, the administration of a polynucleotides or polypeptides, or agonists or antagonists of the present invention that inhibits an immune response, particularly the proliferation, differentiation, or chemotaxis of T-cells, may be an effective therapy in preventing autoimmune diseases, disorders, and/or conditions.

Examples of autoimmune diseases, disorders, and/or conditions that can be treated, prevented, and/or diagnosed or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated, prevented, and/or diagnosed by polynucleotides or polypeptides, or agonists or antagonists of the present invention. Moreover, these molecules can be used to treat anaphylaxis, hypersensitivity to an antigenic molecule, or blood group incompatibility.

A polynucleotides or polypeptides, or agonists or antagonists of the present invention may also be used to treat, prevent, and/or diagnose organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polynucleotides or polypeptides, or agonists or antagonists of the present invention that inhibits an immune response, particularly the proliferation, differentiation, or chemotaxis of T-cells, may be an effective therapy in preventing organ rejection or GVHD.

Similarly, a polynucleotides or polypeptides, or agonists or antagonists of the present invention may also be used to modulate inflammation. For example, the polypeptide or polynucleotide or agonists or antagonist may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polynucleotides or polypeptides, or agonists or antagonists of the invention can be used to treat, prevent, and/or diagnose hyperproliferative diseases, disorders, and/or conditions, including neoplasms. A polynucleotides or polypeptides, or agonists or antagonists of the present invention may inhibit the proliferation of the disorder through direct or indirect interactions. Alternatively, a polynucleotides or polypeptides, or agonists or antagonists of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative diseases, disorders, and/or conditions can be treated, prevented, and/or diagnosed. This immune response may be increased by either enhancing an existing immune response, or by initiating a new immune response. Alternatively, decreasing an immune response may also be a method of treating, preventing, and/or diagnosing hyperproliferative diseases, disorders, and/or conditions, such as a chemotherapeutic agent.

Examples of hyperproliferative diseases, disorders, and/or conditions that can be treated, prevented, and/or diagnosed by polynucleotides or polypeptides, or agonists or antagonists of the present invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative diseases, disorders, and/or conditions can also be treated, prevented, and/or diagnosed by a polynucleotides or polypeptides, or agonists or antagonists of the present invention. Examples of such hyperproliferative diseases, disorders, and/or conditions include, but are not limited to: hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating or preventing cell proliferative diseases, disorders, and/or conditions by inserting into an abnormally proliferating cell a polynucleotide of the present invention, wherein said polynucleotide represses said expression.

Another embodiment of the present invention provides a method of treating or preventing cell-proliferative diseases, disorders, and/or conditions in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the polynucleotides of the present invention is inserted into cells to be treated utilizing a retrovirus, or more Preferably an adenoviral vector (See G J. Nabel, et. al., PNAS 1999 96:324-326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic genes or antigens. By "repressing expression of the oncogenic genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell. Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating, preventing, and/or diagnosing one or more of the described diseases, disorders, and/or conditions. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating, preventing, and/or diagnosing a subject having or developing cell proliferative and/or differentiation diseases, disorders, and/or conditions as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of diseases, disorders, and/or conditions related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Moreover, polypeptides of the present invention may be useful in inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (See Joseph I B, et al. J Natl Cancer Inst, 90(21):1648-53 (1998), which is hereby incorporated by reference). Antibodies directed to polypeptides or polynucleotides of the present invention may also result in inhibition of angiogenesis directly, or indirectly (See Witte L, et al., Cancer Metastasis Rev. 17(2):155-61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et al., Eur J Biochem 254(3):439-59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuvants, such as apoptonin, galectins, thioredoxins, antiinflammatory proteins (See for example, Mutat. Res. 400(1-2):447-55 (1998), Med. Hypotheses. 50(5):423-33 (1998), Chem. Biol. Interact. April 24; 111-112:23-34 (1998), J Mol. Med. 76(6):402-12 (1998), Int. J. Tissue React. 20(1):3-15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewhere herein, or indirectly, such as activating the expression of proteins known to inhibit metastasis, for example alpha 4 integrins, (See, e.g., Curr Top Microbiol Immunol 1998; 231: 125-41, which is hereby incorporated by reference). Such therapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodies associated with heterologous polypeptides, heterologous nucleic acids, toxins, or prodrugs) to targeted cells expressing the polypeptide of the present invention. Polypeptides or polypeptide antibodies of the invention may be associated with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Cardiovascular Disorders

Polynucleotides or polypeptides, or agonists or antagonists of the invention may be used to treat, prevent, and/or diagnose cardiovascular diseases, disorders, and/or conditions, including peripheral artery disease, such as limb ischemia.

Cardiovascular diseases, disorders, and/or conditions include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, criss-cross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular diseases, disorders, and/or conditions also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular diseases, disorders, and/or conditions, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular diseases, disorders, and/or conditions include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Polynucleotides or polypeptides, or agonists or antagonists of the invention, are especially effective for the treatment of critical limb ischemia and coronary disease.

Polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Polypeptides of the invention may be administered as part of a Therapeutic, described in more detail below. Methods of delivering polynucleotides of the invention are described in more detail herein.

Anti-Angiogenesis Activity

The naturally occurring balance between endogenous stimulators and inhibitors of angiogenesis is one in which inhibitory influences predominate. Rastinejad et al., Cell 56:345-355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye diseases, disorders, and/or conditions, and psoriasis. See, e.g., reviews by Moses et al., Biotech. 9:630-634 (1991); Folkman et al., N. Engl. J. Med., 333:1757-1763 (1995); Auerbach et al., J. Microvasc. Res. 29:401-411 (1985); Folkman, Advances in Cancer Research, eds. Klein and Weinhouse, Academic Press, New York, pp. 175-203 (1985); Patz, Am. J. Opthalmol. 94:715-743 (1982); and Folkman et al., Science 221:719-725 (1983).

In a number of pathological conditions, the process of angiogenesis contributes to the disease state. For example, significant data have accumulated which suggest that the growth of solid tumors is dependent on angiogenesis. Folkman and Klagsbrun, Science 235:442-447 (1987).

The present invention provides for treatment of diseases, disorders, and/or conditions associated with neovascularization by administration of the polynucleotides and/or polypeptides of the invention, as well as agonists or antagonists of the present invention. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)).Thus, the present invention provides a method of treating, preventing, and/or diagnosing an angiogenesis-related disease and/or disorder, comprising administering to an individual in need thereof a therapeutically effective amount of a polynucleotide, polypeptide, antagonist and/or agonist of the invention. For example, polynucleotides, polypeptides, antagonists and/or agonists may be utilized in a variety of additional methods in order to therapeutically treat or prevent a cancer or tumor. Cancers which may be treated, prevented, and/or diagnosed with polynucleotides, polypeptides, antagonists and/or agonists include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemias. For example, polynucleotides, polypeptides, antagonists and/or agonists may be delivered topically, in order to treat or prevent cancers such as skin cancer, head and neck tumors, breast tumors, and Kaposi's sarcoma.

Within yet other aspects, polynucleotides, polypeptides, antagonists and/or agonists may be utilized to treat superficial forms of bladder cancer by, for example, intravesical administration. Polynucleotides, polypeptides, antagonists and/or agonists may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

Polynucleotides, polypeptides, antagonists and/or agonists may be useful in treating, preventing, and/or diagnosing other diseases, disorders, and/or conditions, besides cancers, which involve angiogenesis. These diseases, disorders, and/or conditions include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

For example, within one aspect of the present invention methods are provided for treating, preventing, and/or diagnosing hypertrophic scars and keloids, comprising the step of administering a polynucleotide, polypeptide, antagonist and/or agonist of the invention to a hypertrophic scar or keloid.

Within one embodiment of the present invention polynucleotides, polypeptides, antagonists and/or agonists are directly injected into a hypertrophic scar or keloid, in order to prevent the progression of these lesions. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development. As noted above, the present invention also provides methods for treating, preventing, and/or diagnosing neovascular diseases of the eye, including for example, corneal neovascularization, neovascular glaucoma, proliferative diabetic retinopathy, retrolental fibroplasia and macular degeneration.

Moreover, Ocular diseases, disorders, and/or conditions associated with neovascularization which can be treated, prevented, and/or diagnosed with the polynucleotides and polypeptides of the present invention (including agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., Am. J. Ophthal. 85:704-710 (1978) and Gartner et al., Surv. Ophthal. 22:291-312 (1978).

Thus, within one aspect of the present invention methods are provided for treating or preventing neovascular diseases of the eye such as corneal neovascularization (including corneal graft neovascularization), comprising the step of administering to a patient a therapeutically effective amount of a compound (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of diseases, disorders, and/or conditions can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali burns, trauma, inflammation (of any cause), toxic and nutritional deficiency states, and as a complication of wearing contact lenses.

Within particularly preferred embodiments of the invention, may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a muco-adhesive polymer which binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2-3 times per year. A steroid could also be added to the injection solution to reduce inflammation resulting from the injection itself.

Within another aspect of the present invention, methods are provided for treating or preventing neovascular glaucoma, comprising the step of administering to a patient a therapeutically effective amount of a polynucleotide, polypeptide, antagonist and/or agonist to the eye, such that the formation of blood vessels is inhibited. In one embodiment, the compound may be administered topically to the eye in order to treat or prevent early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating or preventing proliferative diabetic retinopathy, comprising the step of administering to a patient a therapeutically effective amount of a polynucleotide, polypeptide, antagonist and/or agonist to the eyes, such that the formation of blood vessels is inhibited.

Within particularly preferred embodiments of the invention, proliferative diabetic retinopathy may be treated by injection into the aqueous humor or the vitreous, in order to increase the local concentration of the polynucleotide, polypeptide, antagonist and/or agonist in the retina. Preferably, this treatment should be initiated prior to the acquisition of severe disease requiring photocoagulation.

Within another aspect of the present invention, methods are provided for treating or preventing retrolental fibroplasia, comprising the step of administering to a patient a therapeutically effective amount of a polynucleotide, polypeptide, antagonist and/or agonist to the eye, such that the formation of blood vessels is inhibited. The compound may be administered topically, via intravitreous injection and/or via intraocular implants.

Additionally, diseases, disorders, and/or conditions which can be treated, prevented, and/or diagnosed with the polynucleotides, polypeptides, agonists and/or agonists include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, diseases, disorders, and/or conditions and/or states, which can be treated, prevented, and/or diagnosed with the polynucleotides, polypeptides, agonists and/or agonists include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uveitis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (Rochele minalia quintosa), ulcers (*Helicobacter pylori*), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method. Polynucleotides, polypeptides, agonists and/or agonists may also be used in controlling menstruation or administered as either a peritoneal lavage fluid or for peritoneal implantation in the treatment of endometriosis.

Polynucleotides, polypeptides, agonists and/or agonists of the present invention may be incorporated into surgical sutures in order to prevent stitch granulomas.

Polynucleotides, polypeptides, agonists and/or agonists may be utilized in a wide variety of surgical procedures. For example, within one aspect of the present invention a compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiogenesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a polynucleotide, polypeptide, agonist and/or agonist to the resection margins of a tumor subsequent to excision, such that the local recurrence of cancer and the formation of new blood vessels at the site is inhibited. Within one embodiment of the invention, the anti-angiogenic compound is administered directly to the tumor excision site (e.g., applied by swabbing, brushing or otherwise coating the resection margins of the tumor with the anti-angiogenic compound). Alternatively, the anti-angiogenic compounds may be incorporated into known surgical pastes prior to administration. Within particularly preferred embodiments of the invention, the anti-angiogenic compounds are applied after hepatic resections for malignancy, and after neurosurgical operations.

Within one aspect of the present invention, polynucleotides, polypeptides, agonists and/or agonists may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The polynucleotides, polypeptides, agonists and/or agonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22-26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321-17326, 1992); Chymostatin (Tomkinson et al., Biochem J. 286:475-480, 1992); Cyclodextrin Tetradecasulfate; Eponemycin; Camptothecin; Fumagillin (Ingber et al., Nature 348:555-557, 1990); Gold Sodium Thiomalate ("GST"; Matsubara and Ziff, J. Clin. Invest. 79:1440-1446, 1987); anticollagenase-serum; alpha2-antiplasmin (Holmes et al., J. Biol. Chem. . . . 262(4):1659-1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312-316, 1992); Thalidomide; Angostatic steroid; AGM-1470; carboxynaminolmidazole; and metalloproteinase inhibitors such as BB94.

Diseases at the Cellular Level

Diseases associated with increased cell survival or the inhibition of apoptosis that could be treated, prevented, and/or diagnosed by the polynucleotides or polypeptides and/or antagonists or agonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, the polynucleotides or polypeptides, and/or agonists or antagonists of the invention are used to inhibit growth, progression, and/or metastasis of cancers, in particular those listed above.

Additional diseases or conditions associated with increased cell survival that could be treated, prevented or diagnosed by the polynucleotides or polypeptides, or agonists or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated, prevented, and/or diagnosed by the polynucleotides or polypeptides, and/or agonists or antagonists of the invention, include AIDS; neurodegenerative diseases, disorders, and/or conditions (such as Alzheimer's disease, Parkinson's disease, Amyotrophic lateral sclerosis, Retinitis pigmentosa, Cerebellar degeneration and brain tumor or prior associated disease); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing the polynucleotides or polypeptides, and/or agonists or antagonists of the invention, for therapeutic purposes, for example, to stimulate epithelial cell proliferation and basal keratinocytes for the purpose of wound healing, and to stimulate hair follicle production and healing of dermal wounds. Polynucleotides or polypeptides, as well as agonists or antagonists of the invention, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. Polynucleotides or polypeptides, and/or agonists or antagonists of the invention, could be used to promote dermal reestablishment subsequent to dermal loss.

The polynucleotides or polypeptides, and/or agonists or antagonists of the invention, could be used to increase the adherence of skin grafts to a wound bed and to stimulate re-epithelialization from the wound bed. The following are a non-exhaustive list of grafts that polynucleotides or polypeptides, agonists or antagonists of the invention, could be used to increase adherence to a wound bed: autografts, artificial skin, allografts, autodermic graft, autoepidermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. The polynucleotides or polypeptides, and/or agonists or antagonists of the invention, can be used to promote skin strength and to improve the appearance of aged skin.

It is believed that the polynucleotides or polypeptides, and/or agonists or antagonists of the invention, will also produce changes in hepatocyte proliferation, and epithelial cell proliferation in the lung, breast, pancreas, stomach, small intestine, and large intestine. The polynucleotides or polypeptides, and/or agonists or antagonists of the invention, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. The polynucleotides or polypeptides, and/or agonists or antagonists of the invention, may promote proliferation of endothelial cells, keratinocytes, and basal keratinocytes.

The polynucleotides or polypeptides, and/or agonists or antagonists of the invention, could also be used to reduce the side effects of gut toxicity that result from radiation, chemotherapy treatments or viral infections. The polynucleotides or polypeptides, and/or agonists or antagonists of the invention, may have a cytoprotective effect on the small intestine mucosa. The polynucleotides or polypeptides, and/or agonists or antagonists of the invention, may also stimulate healing of mucositis (mouth ulcers) that result from chemotherapy and viral infections.

The polynucleotides or polypeptides, and/or agonists or antagonists of the invention, could further be used in full regeneration of skin in full and partial thickness skin defects, including burns, (i.e., repopulation of hair follicles, sweat glands, and sebaceous glands), treatment of other skin defects such as psoriasis. The polynucleotides or polypeptides, and/or agonists or antagonists of the invention, could be used to treat epidermolysis bullosa, a defect in adherence of the epidermis to the underlying dermis which results in frequent, open and painful blisters by accelerating reepithelialization of these lesions. The polynucleotides or polypeptides, and/or agonists or antagonists of the invention, could also be used to treat gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, the polynucleotides or polypeptides, and/or agonists or antagonists of the invention, could be used to promote the resurfacing of the mucosal surface to aid more rapid healing and to prevent progression of inflammatory bowel disease. Treatment with the polynucleotides or polypeptides, and/or agonists or antagonists of the invention, is expected to have a significant effect on the production of mucus throughout the gastrointestinal tract and could be used to protect the intestinal mucosa from injurious substances that are ingested or following surgery. The polynucleotides or polypeptides, and/or agonists or antagonists of the invention, could be used to treat diseases associate with the under expression of the polynucleotides of the invention.

Moreover, the polynucleotides or polypeptides, and/or agonists or antagonists of the invention, could be used to prevent and heal damage to the lungs due to various pathological states. A growth factor such as the polynucleotides or polypeptides, and/or agonists or antagonists of the invention, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated, prevented, and/or diagnosed using the polynucleotides or polypeptides, and/or agonists or antagonists of the invention. Also, the polynucleotides or polypeptides, and/or agonists or antagonists of the invention, could be used to stimulate the proliferation of and differentiation of type II pneumocytes, which may help treat or prevent disease such as hyaline membrane diseases, such as infant respiratory distress syndrome and bronchopulmonary displasia, in premature infants.

The polynucleotides or polypeptides, and/or agonists or antagonists of the invention, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, the polynucleotides or polypeptides, and/or agonists or antagonists of the invention, could be used treat or prevent the onset of diabetes mellitus. In patients with newly diagnosed Types I and II diabetes, where some islet cell function remains, the polynucleotides or polypeptides, and/or agonists or antagonists of the invention, could be used to maintain the islet function so as to alleviate, delay or prevent permanent manifestation of the disease. Also, the polynucleotides or polypeptides, and/or agonists or antagonists of the invention, could be used as an auxiliary in islet cell transplantation to improve or promote islet cell function.

Neurological Diseases

Nervous system diseases, disorders, and/or conditions, which can be treated, prevented, and/or diagnosed with the compositions of the invention (e.g., polypeptides, polynucleotides, and/or agonists or antagonists), include, but are not limited to, nervous system injuries, and diseases, disorders, and/or conditions which result in either a disconnection of axons, a diminution or degeneration of neurons, or demyelination. Nervous system lesions which may be treated, prevented, and/or diagnosed in a patient (including human and non-human mammalian patients) according to the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In a preferred embodiment, the polypeptides, polynucleotides, or agonists or antagonists of the invention are used to protect neural cells from the damaging effects of cerebral hypoxia. According to this embodiment, the compositions of the invention are used to treat, prevent, and/or diagnose neural cell injury associated with cerebral hypoxia. In one aspect of this embodiment, the polypeptides, polynucleotides, or agonists or antagonists of the invention are used to treat, prevent, and/or diagnose neural cell injury associated with cerebral ischemia. In another aspect of this embodiment, the polypeptides, polynucleotides, or agonists or antagonists of the invention are used to treat, prevent, and/or diagnose neural cell injury associated with cerebral infarction. In another aspect of this embodiment, the polypeptides, polynucleotides, or agonists or antagonists of the invention are used to treat, prevent, and/or diagnose or prevent neural cell injury associated with a stroke. In a further aspect of this embodiment, the polypeptides, polynucleotides, or agonists or antagonists of the invention are used to treat, prevent, and/or diagnose neural cell injury associated with a heart attack.

The compositions of the invention which are useful for treating or preventing a nervous system disorder may be selected by testing for biological activity in promoting the survival or differentiation of neurons. For example, and not by way of limitation, compositions of the invention which elicit any of the following effects may be useful according to the invention: (1) increased survival time of neurons in culture; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, the method set forth in Arakawa et al. (J. Neurosci. 10:3507-3515 (1990)); increased sprouting of neurons may be detected by methods known in the art, such as, for example, the methods set forth in Pestronk et al. (Exp. Neurol. 70:65-82 (1980)) or Brown et al. (Ann. Rev. Neurosci. 4:17-42 (1981)); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron diseases, disorders, and/or conditions that may be treated, prevented, and/or diagnosed according to the invention include, but are not limited to, diseases, disorders, and/or conditions such as infarction, infection, exposure to toxin, trauma, surgical damage, degenerative disease or malignancy that may affect motor neurons as well as other components of the nervous system, as well as diseases, disorders, and/or conditions that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Infectious Disease

A polypeptide or polynucleotide and/or agonist or antagonist of the present invention can be used to treat, prevent, and/or diagnose infectious agents. For example, by increasing the immune response, particularly increasing the proliferation and differentiation of B and/or T cells, infectious diseases may be treated, prevented, and/or diagnosed. The immune response may be increased by either enhancing an existing immune response, or by initiating a new immune response. Alternatively, polypeptide or polynucleotide and/or agonist or antagonist of the present invention may also directly inhibit the infectious agent, without necessarily eliciting an immune response.

Viruses are one example of an infectious agent that can cause disease or symptoms that can be treated, prevented, and/or diagnosed by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Bimaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxyiridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat, prevent, and/or diagnose AIDS.

Similarly, bacterial or fungal agents that can cause disease or symptoms and that can be treated, prevented, and/or diagnosed by a polynucleotide or polypeptide and/or agonist or antagonist of the present invention include, but not limited to, include, but not limited to, the following Gram-Negative and Gram-positive bacteria and bacterial families and fungi: Actinomycetales (e.g., *Corynebacterium, Mycobacterium, Norcardia*), *Cryptococcus neoformans*, Aspergillosis, Bacillaceae (e.g., Anthrax, *Clostridium*), Bacteroidaceae, Blastomycosis, *Bordetella, Borrelia* (e.g., *Borrelia burgdorferi*), Brucellosis, Candidiasis, *Campylobacter, Coccidioidomycosis, Cryptococcosis, Dermatocycoses, E. coli* (e.g., Enterotoxigenic *E. coli* and Enterohemorrhagic *E. coli*), Enterobacteriaceae (Klebsiella, *Salmonella* (e.g., *Salmonella typhi*, and *Salmonella paratyphi*), *Serratia, Yersinia*), *Erysipelothrix, Helicobacter*, Legionellosis, Leptospirosis, *Listeria, Mycoplasmatales, Mycobacterium leprae, Vibrio cholerae*, Neisseriaceae (e.g., *Acinetobacter, Gonorrhea, Menigococcal*), *Meisseria meningitidis*, Pasteurellacea Infections (e.g., *Actinobacillus, Heamophilus* (e.g., *Heamophilus influenza* type B), *Pasteurella*), *Pseudomonas*, Rickettsiaceae, Chlamydiaceae, Syphilis, *Shigella* spp., Staphylococcal, Meningiococcal, Pneumococcal and Streptococcal (e.g., *Streptococcus pneumoniae* and Group B *Streptococcus*). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), *Chlamydia*, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, *dermatocycoses*), toxemia, urinary tract infections, wound infections. Polynucleotides or polypeptides, agonists or antagonists of the invention, can be used to treat, prevent, and/or diagnose any of these symptoms or diseases. In specific embodiments, polynucleotides, polypeptides, agonists or antagonists of the invention are used to treat, prevent, and/or diagnose: tetanus, Diptheria, botulism, and/or meningitis type B.

Moreover, parasitic agents causing disease or symptoms that can be treated, prevented, and/or diagnosed by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose malaria.

Preferably, treatment or prevention using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide and/or agonist or antagonist of the present invention can be used to differentiate, proliferate, and attract cells, leading to the regeneration of tissues. (See, Science 276:59-87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide and/or agonist or antagonist of the present invention may increase regeneration of tissues difficult to heal. For example, increased tendon/ligament regeneration would quicken recovery time after damage. A polynucleotide or polypeptide and/or agonist or antagonist of the present invention could also be used prophylactically in an effort to avoid damage. Specific diseases that could be treated, prevented, and/or diagnosed include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide and/or agonist or antagonist of the present invention to proliferate and differentiate nerve cells. Diseases that could be treated, prevented, and/or diagnosed using this method include central and peripheral nervous system diseases, neuropathies, or mechanical and traumatic diseases, disorders, and/or conditions (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated, prevented, and/or diagnosed using the polynucleotide or polypeptide and/or agonist or antagonist of the present invention.

Chemotaxis

A polynucleotide or polypeptide and/or agonist or antagonist of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide and/or agonist or antagonist of the present invention may increase chemotaxic activity of particular cells. These chemotactic molecules can then be used to treat, prevent, and/or diagnose inflammation, infection, hyperproliferative diseases, disorders, and/or conditions, or any immune system disorder by increasing the number of cells targeted to a particular location in the body. For example, chemotaxic molecules can be used to treat, prevent, and/or diagnose wounds and other trauma to tissues by attracting immune cells to the injured location. Chemotactic molecules of the present invention can also attract fibroblasts, which can be used to treat, prevent, and/or diagnose wounds.

It is also contemplated that a polynucleotide or polypeptide and/or agonist or antagonist of the present invention may inhibit chemotactic activity. These molecules could also be used to treat, prevent, and/or diagnose diseases, disorders, and/or conditions. Thus, a polynucleotide or polypeptide and/or agonist or antagonist of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2): Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, Drosophila, or E. coli. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which a polypeptide of the invention binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labeled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of polypeptides of the invention thereby effectively generating agonists and antagonists of polypeptides of the invention. See generally, U.S. Pat. Nos. 5,605, 793, 5,811,238, 5,830,721, 5,834,252, and 5,837,458, and Patten, P. A., et al., Curr. Opinion Biotechnol. 8:724-33 (1997); Harayama, S. Trends Biotechnol. 16(2):76-82 (1998); Hansson, L. O., et al., J. Mol. Biol. 287:265-76 (1999); and Lorenzo, M. M. and Blasco, R. Biotechniques 24(2):308-13 (1998) (each of these patents and publications are hereby incorporated by reference). In one embodiment, alteration of polynucleotides and corresponding polypeptides of the invention may be achieved by DNA shuffling. DNA shuffling involves the assembly of two or more DNA segments into a desired polynucleotide sequence of the invention molecule by homologous, or site-specific, recombination. In another embodiment, polynucleotides and corresponding polypeptides of the invention may be altered by being subjected to random mutagenesis by error-prone PCR, random nucleotide insertion or other methods prior to recombination. In another embodiment, one or more components, motifs, sections, parts, domains, fragments, etc., of the polypeptides of the invention may be recombined with one or more components, motifs, sections, parts, domains, fragments, etc. of one or more heterologous molecules. In preferred embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active fragments of the polypeptides of the invention. Biologically active fragments are those exhibiting activity similar, but not necessarily identical, to an activity of the polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and 3-[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3-[H] thymidine in each case. The amount of fibroblast cell proliferation is measured by liquid scintillation chromatography which measures the incorporation of 3-[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues. Therefore, the invention includes a method of identifying compounds which bind to the polypeptides of the invention comprising the steps of: (a) incubating a candidate binding compound with the polypeptide; and (b) determining if binding has occurred. Moreover, the invention includes a method of identifying agonists/antagonists comprising the steps of: (a) incubating a candidate compound with the polypeptide, (b) assaying a biological activity, and (c) determining if a biological activity of the polypeptide has been altered.

Also, one could identify molecules bind a polypeptide of the invention experimentally by using the beta-pleated sheet regions contained in the polypeptide sequence of the protein. Accordingly, specific embodiments of the invention are directed to polynucleotides encoding polypeptides which comprise, or alternatively consist of, the amino acid sequence of each beta pleated sheet regions in a disclosed polypeptide sequence. Additional embodiments of the invention are directed to polynucleotides encoding polypeptides which comprise, or alternatively consist of, any combination or all of contained in the polypeptide sequences of the invention. Additional preferred embodiments of the invention are directed to polypeptides which comprise, or alternatively consist of, the amino acid sequence of each of the beta pleated sheet regions in one of the polypeptide sequences of the invention. Additional embodiments of the invention are directed to polypeptides which comprise, or alternatively consist of, any combination or all of the beta pleated sheet regions in one of the polypeptide sequences of the invention.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. By "cytotoxic prodrug" is meant a nontoxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

The human LTRPC3 polypeptides and/or peptides of the present invention, or immunogenic fragments or oligopeptides thereof, can be used for screening therapeutic drugs or compounds in a variety of drug screening techniques. The fragment employed in such a screening assay may be free in solution, affixed to a solid support, borne on a cell surface, or located intracellularly. The reduction or abolition of activity of the formation of binding complexes between the ion channel protein and the agent being tested can be measured. Thus, the present invention provides a method for screening or assessing a plurality of compounds for their specific binding affinity with a LTRPC3 polypeptide, or a bindable peptide fragment, of this invention, comprising providing a plurality of compounds, combining the LTRPC3 polypeptide, or a bindable peptide fragment, with each of a plurality of compounds for a time sufficient to allow binding under suitable conditions and detecting binding of the LTRPC3 polypeptide or peptide to each of the plurality of test compounds, thereby identifying the compounds that specifically bind to the LTRPC3 polypeptide or peptide.

Methods of identifying compounds that modulate the activity of the novel human LTRPC3 polypeptides and/or peptides are provided by the present invention and comprise combining a potential or candidate compound or drug modulator of immunoglobulin biological activity with an LTRPC3 polypeptide or peptide, for example, the LTRPC3 amino acid sequence as set forth in SEQ ID NOS:2, 41, or 43, and measuring an effect of the candidate compound or drug modulator on the biological activity of the LTRPC3 polypeptide or peptide. Such measurable effects include, for example, physical binding interaction; the ability to cleave a suitable immunoglobulin substrate; effects on native and cloned LTRPC3-expressing cell line; and effects of modulators or other immunoglobulin-mediated physiological measures.

Another method of identifying compounds that modulate the biological activity of the novel LTRPC3 polypeptides of the present invention comprises combining a potential or candidate compound or drug modulator of a immunoglobulin biological activity with a host cell that expresses the LTRPC3 polypeptide and measuring an effect of the candidate compound or drug modulator on the biological activity of the LTRPC3 polypeptide. The host cell can also be capable of being induced to express the LTRPC3 polypeptide, e.g., via inducible expression. Physiological effects of a given modulator candidate on the LTRPC3 polypeptide can also be measured. Thus, cellular assays for particular immunoglobulin modulators may be either direct measurement or quantification of the physical biological activity of the LTRPC3 polypeptide, or they may be measurement or quantification of a physiological effect. Such methods preferably employ a LTRPC3 polypeptide as described herein, or an overexpressed recombinant LTRPC3 polypeptide in suitable host cells containing an expression vector as described herein, wherein the LTRPC3 polypeptide is expressed, overexpressed, or undergoes upregulated expression.

Another aspect of the present invention embraces a method of screening for a compound that is capable of modulating the biological activity of a LTRPC3 polypeptide, comprising providing a host cell containing an expression vector harboring a nucleic acid sequence encoding a LTRPC3 polypeptide, or a functional peptide or portion thereof (e.g., SEQ ID NOS:2, 41, or 43); determining the biological activity of the expressed LTRPC3 polypeptide in the absence of a modulator compound; contacting the cell with the modulator compound and determining the biological activity of the expressed LTRPC3 polypeptide in the presence of the modulator compound. In such a method, a difference between the activity of the LTRPC3 polypeptide in the presence of the modulator compound and in the absence of the modulator compound indicates a modulating effect of the compound.

Essentially any chemical compound can be employed as a potential modulator or ligand in the assays according to the present invention. Compounds tested as immunoglobulin modulators can be any small chemical compound, or biological entity (e.g., protein, sugar, nucleic acid, lipid). Test compounds will typically be small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. Also, compounds may be synthesized by methods known in the art.

High throughput screening methodologies are particularly envisioned for the detection of modulators of the novel LTRPC3 polynucleotides and polypeptides described herein. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, *Int. J. Pept. Prot. Res.,* 37:487-493; and Houghton et al., 1991, *Nature,* 354:84-88). Other chemistries for generating chemical diversity libraries can also be used. Nonlimiting examples of chemical diversity library chemistries include, peptides (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, *Proc. Natl. Acad. Sci. USA,* 90:6909-6913), vinylogous polypeptides (Hagihara et al., 1992, *J. Amer. Chem. Soc.,* 114:6568), non-peptidal peptidomimetics with glucose scaffolding (Hirschmann et al., 1992, *J. Amer. Chem. Soc.,* 114:9217-9218), analogous organic synthesis of small compound libraries (Chen et al., 1994, *J. Amer. Chem. Soc.,* 116:2661), oligocarbamates (Cho et al., 1993, *Science,* 261:1303), and/or peptidyl phosphonates (Campbell et al., 1994, *J. Org. Chem.,* 59:658), nucleic acid libraries (see Ausubel, Berger and Sambrook, all supra), peptide nucleic acid libraries (U.S. Pat. No. 5,539,083), antibody libraries (e.g., Vaughn et al., 1996, *Nature Biotechnology,* 14(3):309-314) and PCT/US96/10287), carbohydrate libraries (e.g., Liang et al., 1996, *Science,* 274-1520-1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

In one embodiment, the invention provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000-20,000 different compounds are possible using the described integrated systems.

In another of its aspects, the present invention encompasses screening and small molecule (e.g., drug) detection assays which involve the detection or identification of small molecules that can bind to a given protein, i.e., a LTRPC3 polypeptide or peptide. Particularly preferred are assays suitable for high throughput screening methodologies.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, *Gen. Eng. News,* 20(8)). The assay allows the detection of small molecules (e.g., drugs, ligands) that bind to expressed, and preferably purified, ion channel polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

To purify a LTRPC3 polypeptide or peptide to measure a biological binding or ligand binding activity, the source may be a whole cell lysate that can be prepared by successive freeze-thaw cycles (e.g., one to three) in the presence of standard protease inhibitors. The LTRPC3 polypeptide may be partially or completely purified by standard protein purification methods, e.g., affinity chromatography using specific antibody described infra, or by ligands specific for an epitope tag engineered into the recombinant LTRPC3 polypeptide molecule, also as described herein. Binding activity can then be measured as described.

Compounds which are identified according to the methods provided herein, and which modulate or regulate the biological activity or physiology of the LTRPC3 polypeptides according to the present invention are a preferred embodiment of this invention. It is contemplated that such modulatory compounds may be employed in treatment and therapeutic methods for treating a condition that is mediated by the novel LTRPC3 polypeptides by administering to an individual in need of such treatment a therapeutically effective amount of the compound identified by the methods described herein.

In addition, the present invention provides methods for treating an individual in need of such treatment for a disease, disorder, or condition that is mediated by the LTRPC3 polypeptides of the invention, comprising administering to the individual a therapeutically effective amount of the LTRPC3-modulating compound identified by a method provided herein.

Antisense and Ribozyme (Antagonists)

In specific embodiments, antagonists according to the present invention are nucleic acids corresponding to the sequences contained in SEQ ID NO:1, 3, 5, 7, 9 and/or 11, or the complementary strand thereof, and/or to nucleotide sequences contained a deposited clone. In one embodiment, antisense sequence is generated internally by the organism, in another embodiment, the antisense sequence is separately administered (see, for example, O'Connor, Neurochem., 56:560 (1991). Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, Neurochem., 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research, 6:3073 (1979); Cooney et al., Science, 241:456 (1988); and Dervan et al., Science, 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoRI site on the 5 end and a HindIII site on the 3 end. Next, the pair of oligonucleotides is heated at 90° C. for one minute and then annealed in 2× ligation buffer (20 mM TRIS HCl pH 7.5, 10 mM $MgCl_2$, 10 mM dithiothreitol (DTT) and 0.2 mM ATP) and then ligated to the EcoRI/Hind III site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the antisense nucleic acid of the invention. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding a polypeptide of the invention, or fragments thereof, can be by any promoter known in the art to act in vertebrate, preferably human cells. Such promoters can be inducible or constitutive. Such promoters include, but are not limited to, the SV40 early promoter region (Bemoist and Chambon, Nature, 29:304-310 (1981), the promoter contained in the 3' long terminal repeat of Rous sarcoma virus (Yamamoto et al., Cell, 22:787-797 (1980), the herpes thymidine promoter (Wagner et al., Proc. Natl. Acad. Sci. U.S.A., 78:1441-1445 (1981), the regulatory sequences of the metallothionein gene (Brinster et al., Nature, 296:39-42 (1982)), etc.

The antisense nucleic acids of the invention comprise a sequence complementary to at least a portion of an RNA transcript of a gene of interest. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded antisense nucleic acids of the invention, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a RNA sequence of the invention it may contain and still form a stable duplex (or triplex as the case may be). One skilled in the art can ascertain a tolerable degree of mismatch by use of standard procedures to determine the melting point of the hybridized complex.

Antisense oligonucleotides may be single or double stranded. Double stranded RNA's may be designed based upon the teachings of Paddison et al., Proc. Nat. Acad. Sci., 99:1443-1448 (2002); and International Publication Nos. WO 01/29058, and WO 99/32619; which are hereby incorporated herein by reference.

SiRNA reagents are specifically contemplated by the present invention. Such reagents are useful for inhibiting expression of the polynucleotides of the present invention and may have therapeutic efficacy. Several methods are known in the art for the therapeutic treatment of disorders by the administration of siRNA reagents. One such method is described by Tiscomia et al (PNAS, 100(4):1844-1848 (2003)); WO0409769, filed July 18, 2003; and Reich S J et al., Mol. Vis. 2003 May 30; 9:210-6, which are incorporated by reference herein in its entirety.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., Nature, 372:333-335 (1994). Thus, oligonucleotides complementary to either the 5'- or 3'-non-translated, non-coding regions of a polynucleotide sequence of the invention could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553-6556 (1989); Lemaitre et al., Proc. Natl. Acad. Sci., 84:648-652 (1987); PCT Publication NO: WO88/09810, published Dec. 15, 1988) or the blood-brain barrier (see, e.g., PCT Publication NO: WO89/10134, published Apr. 25, 1988), hybridization-triggered cleavage agents. (See, e.g., Krol et al., BioTechniques, 6:958-976 (1988)) or intercalating agents. (See, e.g., Zon, Pharm. Res., 5:539-549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., Nucl. Acids Res., 15:6625-6641 (1987)). The oligonucleotide is a 2-0-methylribonucleotide (Inoue et al., Nucl. Acids Res., 15:6131-6148 (1987)), or a chimeric RNA-DNA analogue (Inoue et al., FEBS Lett. 215:327-330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res., 16:3209 (1988)), methylphosphonate oligonucleotides can be prepared by use of controlled pore glass polymer supports (Sarin et al., Proc. Natl. Acad. Sci. U.S.A., 85:7448-7451 (1988)), etc.

While antisense nucleotides complementary to the coding region sequence of the invention could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science, 247:1222-1225 (1990). While ribozymes that cleave mRNA at site specific recognition sequences can be used to destroy mRNAs corresponding to the polynucleotides of the invention, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature, 334:585-591 (1988). There are numerous potential hammerhead ribozyme cleavage sites within each nucleotide sequence disclosed in the sequence listing. Preferably, the ribozyme is engineered so that the cleavage recognition site is located near the 5' end of the mRNA corresponding to the polynucleotides of the invention; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express the polynucleotides of the invention in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat, prevent, and/or diagnose the diseases described herein.

Thus, the invention provides a method of treating or preventing diseases, disorders, and/or conditions, including but not limited to the diseases, disorders, and/or conditions listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

Biotic Associations

A polynucleotide or polypeptide and/or agonist or antagonist of the present invention may increase the organisms ability, either directly or indirectly, to initiate and/or maintain biotic associations with other organisms. Such associations may be symbiotic, nonsymbiotic, endosymbiotic, macrosymbiotic, and/or microsymbiotic in nature. In general, a polynucleotide or polypeptide and/or agonist or antagonist of the present invention may increase the organisms ability to form biotic associations with any member of the fungal, bacterial, lichen, mycorrhizal, cyanobacterial, dinoflaggellate, and/or algal, kingdom, phylums, families, classes, genuses, and/or species.

The mechanism by which a polynucleotide or polypeptide and/or agonist or antagonist of the present invention may increase the host organisms ability, either directly or indirectly, to initiate and/or maintain biotic associations is variable, though may include, modulating osmolarity to desirable levels for the symbiont, modulating pH to desirable levels for the symbiont, modulating secretions of organic acids, modulating the secretion of specific proteins, phenolic compounds, nutrients, or the increased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL. Roberts, Cambridge University Press, Cambridge, (1999); which is hereby incorporated herein by reference).

In an alternative embodiment, a polynucleotide or polypeptide and/or agonist or antagonist of the present invention may decrease the host organisms ability to form biotic associations with another organism, either directly or indirectly. The mechanism by which a polynucleotide or polypeptide and/or agonist or antagonist of the present invention may decrease the host organisms ability, either directly or indirectly, to initiate and/or maintain biotic associations with another organism is variable, though may include, modulating osmolarity to undesirable levels, modulating pH to undesirable levels, modulating secretions of organic acids, modulating the secretion of specific proteins, phenolic compounds, nutrients, or the decreased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL. Roberts, Cambridge University Press, Cambridge, (1999); which is hereby incorporated herein by reference).

The hosts ability to maintain biotic associations with a particular pathogen has significant implications for the overall health and fitness of the host. For example, human hosts have symbiosis with enteric bacteria in their gastrointestinal tracts, particularly in the small and large intestine. In fact, bacteria counts in feces of the distal colon often approach $10^{12}$ per milliliter of feces. Examples of bowel flora in the gastrointestinal tract are members of the Enterobacteriaceae, *Bacteriodes*, in addition to a-hemolytic streptococci, *E. coli, Bifobacteria, Anaerobic cocci, Eubacteria, Costridia, lactobacilli*, and yeasts. Such bacteria, among other things, assist the host in the assimilation of nutrients by breaking down food stuffs not typically broken down by the hosts digestive system, particularly in the hosts bowel. Therefore, increasing the hosts ability to maintain such a biotic association would help assure proper nutrition for the host.

Aberrations in the enteric bacterial population of mammals, particularly humans, has been associated with the following disorders: diarrhea, ileus, chronic inflammatory disease, bowel obstruction, duodenal diverticula, biliary calculous disease, and malnutrition. A polynucleotide or polypeptide and/or agonist or antagonist of the present invention are useful for treating, detecting, diagnosing, prognosing, and/or ameliorating, either directly or indirectly, and of the above mentioned diseases and/or disorders associated with aberrant enteric flora population.

The composition of the intestinal flora, for example, is based upon a variety of factors, which include, but are not limited to, the age, race, diet, malnutrition, gastric acidity, bile salt excretion, gut motility, and immune mechanisms. As a result, the polynucleotides and polypeptides, including agonists, antagonists, and fragments thereof, may modulate the ability of a host to form biotic associations by affecting, directly or indirectly, at least one or more of these factors.

Although the predominate intestinal flora comprises anaerobic organisms, an underlying percentage represents aerobes (e.g., *E. coli*). This is significant as such aerobes rapidly become the predominate organisms in intraabdominal infections -effectively becoming opportunistic early in infection pathogenesis. As a result, there is an intrinsic need to control aerobe populations, particularly for immune compromised individuals.

In a preferred embodiment, a polynucleotides and polypeptides, including agonists, antagonists, and fragments thereof, are useful for inhibiting biotic associations with specific enteric symbiont organisms in an effort to control the population of such organisms.

Biotic associations occur not only in the gastrointestinal tract, but also on an in the integument. As opposed to the gastrointestinal flora, the cutaneous flora is comprised almost equally with aerobic and anaerobic organisms. Examples of cutaneous flora are members of the gram-positive cocci (e.g., *S. aureus*, coagulase-negative staphylococci, *micrococcus, M. sedentarius*), gram-positive bacilli (e.g., *Corynebacterium* species, *C. minutissimum, Brevibacterium* species, *Propoionibacterium* species, *P. acnes*), gram-negative bacilli (e.g., *Acinebacter* species), and fungi (*Pityrosporum orbiculare*). The relatively low number of flora associated with the integument is based upon the inability of many organisms to adhere to the skin. The organisms referenced above have acquired this unique ability. Therefore, the polynucleotides and polypeptides of the present invention may have uses which include modulating the population of the cutaneous flora, either directly or indirectly.

Aberrations in the cutaneous flora are associated with a number of significant diseases and/or disorders, which include, but are not limited to the following: impetigo, ecthyma, blistering distal dactulitis, pustules, folliculitis, cutaneous abscesses, pitted keratolysis, trichomycosis axcillaris, dermatophytosis complex, axillary odor, erthyrasma, cheesy foot odor, acne, tinea versicolor, seborrheic dermititis, and *Pityrosporum folliculitis*, to name a few. A polynucleotide or polypeptide and/or agonist or antagonist of the present invention are useful for treating, detecting, diagnosing, prognosing, and/or ameliorating, either directly or indirectly, and of the above mentioned diseases and/or disorders associated with aberrant cutaneous flora population.

Additional biotic associations, including diseases and disorders associated with the aberrant growth of such associations, are known in the art and are encompassed by the invention. See, for example, "Infectious Disease", Second Edition, Eds., S. L., Gorbach, J. G., Bartlett, and N. R., Blacklow, W. B. Saunders Company, Philadelphia, (1998); which is hereby incorporated herein by reference).

Pheromones

In another embodiment, a polynucleotide or polypeptide and/or agonist or antagonist of the present invention may increase the organisms ability to synthesize, release, and/or respond to a pheromone, either directly or indirectly. Such a pheromone may, for example, alter the organisms behavior and/or metabolism.

A polynucleotide or polypeptide and/or agonist or antagonist of the present invention may modulate the biosynthesis and/or release of pheromones, the organisms ability to respond to pheromones (e.g., behaviorally, and/or metabolically), and/or the organisms ability to detect pheromones, either directly or indirectly. Preferably, any of the pheromones, and/or volatiles released from the organism, or induced, by a polynucleotide or polypeptide and/or agonist or antagonist of the invention have behavioral effects on the organism.

For example, recent studies have shown that administration of picogram quantities of androstadienone, the most prominent androstene present on male human axillary hair and on the male axillary skin, to the female vomeronasal organ resulted in a significant reduction of nervousness, tension and other negative feelings in the female recipients (Grosser-BI, et al., Psychoneuroendocrinology, 25(3): 289-99 (2000)).

Other Activities

The polypeptide of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. These polypeptide may also be employed to stimulate angiogenesis and limb regeneration, as discussed above.

The polypeptide may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat, prevent, and/or diagnose neuronal damage which occurs in certain neuronal disorders or neuro-degenerative conditions such as Alzheimer's disease, Parkinson's disease, and AIDS-related complex. The polypeptide of the invention may have the ability to stimulate chondrocyte growth, therefore, they may be employed to enhance bone and periodontal regeneration and aid in tissue transplants or bone grafts.

The polypeptide of the invention may also be employed to maintain organs before transplantation or for supporting cell culture of primary tissues.

The polypeptide of the present invention may also be employed for inducing tissue of mesodermal origin to differentiate in early embryos.

The polypeptide or polynucleotides and/or agonist or antagonists of the present invention may also increase or decrease the differentiation or proliferation of embryonic stem cells, besides, as discussed above, hematopoietic lineage.

The polypeptide or polynucleotides and/or agonist or antagonists of the present invention may also be used to modulate mammalian characteristics, such as body height, weight, hair color, eye color, skin, percentage of adipose tissue, pigmentation, size, and shape (e.g., cosmetic surgery). Similarly, polypeptides or polynucleotides and/or agonist or antagonists of the present invention may be used to modulate mammalian metabolism affecting catabolism, anabolism, processing, utilization, and storage of energy.

Polypeptide or polynucleotides and/or agonist or antagonists of the present invention may be used to change a mammal's mental state or physical state by influencing biorhythms, caricadic rhythms, depression (including depressive diseases, disorders, and/or conditions), tendency for violence, tolerance for pain, reproductive capabilities (preferably by Activin or Inhibin-like activity), hormonal or endocrine levels, appetite, libido, memory, stress, or other cognitive qualities.

Polypeptide or polynucleotides and/or agonist or antagonists of the present invention may also be used as a food additive or preservative, such as to increase or decrease storage capabilities, fat content, lipid, protein, carbohydrate, vitamins, minerals, cofactors or other nutritional components.

Polypeptide or polynucleotides and/or agonist or antagonists of the present invention may also be used to increase the efficacy of a pharmaceutical composition, either directly or indirectly. Such a use may be administered in simultaneous conjunction with said pharmaceutical, or separately through either the same or different route of administration (e.g., intravenous for the polynucleotide or polypeptide of the present invention, and orally for the pharmaceutical, among others described herein.).

Also preferred is a method of treatment of an individual in need of an increased level of a protein activity, which method comprises administering to such an individual a pharmaceutical composition comprising an amount of an isolated polypeptide, polynucleotide, or antibody of the claimed invention effective to increase the level of said protein activity in said individual.

Polypeptide or polynucleotides and/or agonist or antagonists of the present invention may also be used to prepare individuals for extraterrestrial travel, low gravity environments, prolonged exposure to extraterrestrial radiation levels, low oxygen levels, reduction of metabolic activity, exposure to extraterrestrial pathogens, etc. Such a use may be administered either prior to an extraterrestrial event, during an extraterrestrial event, or both. Moreover, such a use may result in a number of beneficial changes in the recipient, such as, for example, any one of the following, non-limiting, effects: an increased level of hematopoietic cells, particularly red blood cells which would aid the recipient in coping with low oxygen levels; an increased level of B-cells, T-cells, antigen presenting cells, and/or macrophages, which would aid the recipient in coping with exposure to extraterrestrial pathogens, for example; a temporary (i.e., reversible) inhibition of hematopoietic cell production which would aid the recipient in coping with exposure to extraterrestrial radiation levels; increase and/or stability of bone mass which would aid the recipient in coping with low gravity environments; and/or decreased metabolism which would effectively facilitate the recipients ability to prolong their extraterrestrial travel by any one of the following, non-limiting means: (i) aid the recipient by decreasing their basal daily energy requirements; (ii) effectively lower the level of oxidative and/or metabolic stress in recipient (i.e., to enable recipient to cope with increased extraterrestial radiation levels by decreasing the level of internal oxidative/metabolic damage acquired during normal basal energy requirements; and/or (iii) enabling recipient to subsist at a lower metabolic temperature (i.e., cryogenic, and/or sub-cryogenic environment).

Having generally described the invention, the same will be more readily understood by reference to the following examples, which are provided by way of illustration and are not intended as limiting.

REFERENCES

Baldini G., Mccarthy E. E., Koticha D. K. Plasma membrane targeting of SNAP-25 increases its local concentration and is necessary for SNARE complex formation and regulated exocytosis. *J. Cell Sci.* 115: 3341-3351 (2002).

Caterina, M. J., Leffler, A, Malmberg, A. B., Martin, W. J., Trafton, J, Petersen-Zeitz, K. R., Koltzenburg, M, Basbaum, A. I. & Julius, D. Impaired nociception and pain sensation in mice lacking the capsaicin receptor. *Science.* 288, 306-313 (2000).

Caterina, M. J., Rosen, T. A., Tominaga, M., Brake, A. J. & Julius, D. A capsaicin-receptor homologue with a high threshold for noxious heat. *Nature.* 398, 436-41 (1999).

Duncan, L. M., Deeds, J., Hunter, J., Shao, J., Holmgren, L. M., Woolf, E. A., Tepper, R. I. & Shyjan, A. W. Down-regulation of the novel gene melastatin correlates with potential for melanoma metastasis. *Cancer Res.* 58, 1515-1520 (1998).

Eddy S. Profile hidden Markov models. *Bioinformatics* 14:755-763 (1998).

Freichel, M., Suh, S. H., Pfeifer, A., Schweig, U., Trost, C., Weissgerber, P., Biel, M., Philipp, S., Freise, D., Droogmans, G., Hofmann, F., Flockerzi, V. & Nilius, B. Lack of an endothelial store-operated Ca2+ current impairs agonist-dependent vasorelaxation in TRP4−/− mice. *Nat. Cell Biol.* 3, 121-127 (2001).

Harteneck, C., Plant T. D. & Schultz, G. From worm to man: three subfamilies of TRP channels. *Trends Neurosci.* 23, 159-166 (2000).

Inoue, R., Okada, T., Onoue, H., Hara, Y., Shimizu, S., Naitoh, S., Ito, Y. & Mori, Y. The transient receptor potential protein homologue TRP6 is the essential component of vascular alpha(1)-adrenoceptor-activated Ca(2+)-permeable cation channel. *Circ Res.* 88, 325-332 (2001).

Lee N, Chen J, Wu S, Sun L, Huang M, Levesque PC, Rich A, Feder J N, Gray, K R, Lin J H, Janovitz E B, Blanar M A. Expression and characterization of human TRPM3. *J Biol. Chem.* (2003).

Liman, E. R., Corey, D. P. & Dulac, C. TRP2: a candidate transduction channel for mammalian pheromone sensory signaling. *Proc Natl Acad Sci USA.* 96, 5791-5796 (1999).

Missiaen, L., Robberecht, W., van den Bosch, L., Callewaert, G., Parys, J. B., Wuytack, F., Raeymaekers, L., Nilius, B., Eggermont, J. & De Smedt, H. Abnormal intracellular $Ca^{2+}$ homeostasis and disease. *Cell Calcium.* 28, 1-21 (2000).

Nagamine, K., Kudoh, J., Minoshima, S., Kawasaki, K., Asakawa, S., Ito F. & Shimizu, N. Molecular cloning of a novel putative Ca2+ channel protein (TRPC7) highly expressed in brain. *Genomics* 54, 124-131 (1998).

Peng, J. B., Chen, X. Z., Berger, U.V., Vassilev, P. M., Tsukaguchi, H., Brown, E. M. & Hediger, M. A. Molecular cloning and characterization of a channel-like transporter mediating intestinal calcium absorption. *J. Biol. Chem.* 274, 22739-22746 (1999).

Prawitt, D., Enklaar, T., Klemm, G., Gartner, B., Spangenberg, C., Winterpacht, A., Higgins, M., Pelletier, J. & Zabel, B. Identification and characterization of MTR1, a novel gene with homology to melastatin (MLSN1) and the trp family located in the BWS-WT2 critical region on chromosome 11p15.5 and showing allele-specific expression. *Hum Mol. Genet.* 9, 203-16 (2000).

Radu A, Moore M S, Blobel G. The peptide repeat domain of nucleoporin Nup98 functions as a docking site in transport across the nuclear pore complex. *Cell* 81:215-222 (1995).

Runnels, L. W., Yue, L. & Clapham, D. E. TRP-PLIK, a bifunctional protein kinase and ion channel activities. *Science* 291, 1043-1047 (2001).

Strotmann, R., Harteneck, C., Nunnenmacher, K., Schultz, G. & Plant, T. D. OTRPC4, a nonselective cation channel that confers sensitivity to extracellular osmolarity. *Nat. Cell Biol.* 2, 695-702 (2000).

Tsavaler, L., Shapero, M. H., Morkowski, S. & Laus R. TRP-P8, a novel prostate-specific gene, is up-regulated in prostate cancer and other malignancies and shares high homology with transient receptor potential calcium channel proteins. *Cancer Res.* 61, 3760-3769 (2001).

Walker, R. G., Willingham, A. T. & Zuker, C. S. A *Drosophila* mechanosensory transduction channel. *Science.* 287, 2229-34 (2000).

Xu, S. Z. & Beech, D. J. TrpC1 is a membrane-spanning subunit of store-operated $Ca^{2+}$ channels in native vascular smooth muscle. *Circ Res.* 88, 84-7 (2001).

Yue, L., Peng, J. B., Hediger, M. A., Clapham, D. E. CaT1 manifests the pore properties of the calcium-release-activated calcium channel. *Nature.* 410, 705-709 (2001).

Zygmunt, P. M., Petersson, J., Andersson, D. A., Chuang, H., Sorgard, M., Di Marzo V., Julius, D. & Hogestatt, E. D. Vanilloid receptors on sensory nerves mediate the vasodilator action of anandamide. *Nature.* 400, 452-457 (1999).

EXAMPLES

Description of the Preferred Embodiments

Example 1

Method Used to Identify the Novel LTRPC3g, LTRPC3h, LTRPC3i, LTRPC3j, LTRPC3k, LTRPC3l Polynucleotides of the Present Invention—Bioinformatics Analysis The polynucleotide sequence of the LTRPC3 variant (SEQ ID NO:14; co-pending U.S. Ser. No. 10/210,152, filed Aug. 1, 2002; International Publication No. WO 03/012063, published Feb. 13, 2003) was used as a probe to BLAST the GenBank human cDNA database using TBLASTN program. mRNA sequence gi|AL136545 (SEQ ID NO:106) was found to further extend the 5' end of the LTRPC3 variant polynucleotide sequence (SEQ ID NO:14) by an addition of 534 bases. The nucleotide sequence of this 5' extension is provided as SEQ ID NO:107. The new elongated 5' end of the LTRPC3 variant was mapped to the human genomic sequence (NCBI version 31) using software BLIS (Biotique Local Integration System). These 534 bases represent 3 exons in the 5' upstream region of the original TRPM3 (i.e., LTRPC3) gene (see FIG. 20).

Protein domain analysis of the new 5' end of the LTRPC3 variant using HMMSEARCH (Eddy S.) against the Pfam protein domain database suggests that this portion of the extended LTRPC3 variant protein contains one NSF domain and one Nucleoporin_FG domain, as shown in FIG. 21. NSF domain was proposed to function in regulation of intracellular traffic via fusion of two lipid bilayers(Baldini et al.). Our previous publication(Lee et al.) on the LTRPC3 variant suggest the LTRPC3 variant is a membrane protein with storage-operated $Ca^{2+}$ channel activity. The NSF domain on the LTRPC3 variant protein may function to guide the localization of the LTRPC3 variant carrying intracellular membrane. Nucleoporin_FG repeats are found in diverse nucleoporins (Radu et al.). It has been suggested that these repeats mediate interactions with substrates to be transported through the nuclear pore. The function of Nucleoporin_FG domain in the LTRPC3 variant is unknown.

The extended polynucleotide sequence of the gi|AL136545 sequence (SEQ ID NO:106) was used to extend the coding region of the LTRPC3 polynucleotide sequence (SEQ ID NO:14) which resulted in the LTRPC3g variant of the present invention (SEQ ID NO:1). The same sequence was also used to extend the LTRCP3b, LTRCP3c, LTRCP3d, LTRCP3e, and LTRCP3f sequences as well which resulted in the LTRPC3h (SEQ ID NO:3), LTRPC3l (SEQ ID NO:5), LTRPC3j (SEQ ID NO:7), LTRPC3k (SEQ ID NO:9), and LTRPC3l (SEQ ID NO: 11) variants of the present invention.

The full-length polynucleotide sequences of the LTRPC3g (SEQ ID NO:1), LTRPC3h (SEQ ID NO:3), LTRPC3l (SEQ ID NO:5), LTRPC3j (SEQ ID NO:7), LTRPC3k (SEQ ID NO:9), and LTRPC3l (SEQ ID NO:11) variants are provided in FIGS. 1A-E, FIGS. 2A-F, FIGS. 3A-F, FIGS. 4A-F, FIGS. 5A-F, and FIGS. 6A-F, respectively.

Example 2

Cloning the Novel Transient Receptor Potential Channel Member, LTRPC3

A number of methods may be employed to clone the full-length polynucleotides of the present invention. Specifically, the polynucleotides of the present invention may be PCR amplified using the primers provided below. The oligonucleotide primers may be used used to amplify fragments from the human kidney Marathon-Ready cDNA library (Clontech). The reaction mixture in 50 ul containing 5 ul cDNA library, 0.5 mM each primer, 5 mM dNTPs (1.25 mM each), 5 ul of 10× PCR and 0.5 unit of TaqPlus Precision polymerase (Stratagene) can be used. The reaction can be repeated for 30 cycles (94° C. for 45 seconds, 55° C. for 45 seconds, and 72° C. for 4 minutes). The amplified fragments can then be cloned into the sequencing vector pCR4 Blunt-TOPO (Invitrogen) for sequence analysis.

| PrimerName | Primer Sequence | |
|---|---|---|
| TRPM3-1C | ATGGGGAAGAAGTGG AGGGATGCGG | (SEQ ID NO:169) |
| TRPM3-2C | GCTCAGAAATCCTGG ATAGAAAGAG | (SEQ ID NO:170) |
| 86-N2-NC | TGTATCAAAAGATAC TCGCACATACAT | (SEQ ID NO:171) |

The TRPM3-1C and TRPM3-2C are forward primers. Either of the latter could be used in conjunction with the reverse 86-N2-NC primer to clone the LTRPC3g, LTRPC3h, LTRPC3i, LTRPC3j, LTRPC3k, or LTRPC3l polynucleotides of the present invention.

Example 3

Expression Profiling of the Transient Receptor Potential Channel Member. LTRPC3

The following protocol was used to elucidate the expression profile of the LTRPC3 polypeptide (SEQ ID NO:15) and is described in co-pending U.S. Ser. No. 10/210,152, filed Aug. 1, 2002 and International Publication No. WO 03/012063, published Feb. 13, 2003. The same protocol may be employed to elucidate the expression profile of the LTRPC3g-l variants of the present invention using primer pairs specific for these variants. The LTRPC3 expression profile is provided here for representative purposes only although it is expected that the LTRPC3g-l variants will have similar expression patterns as the LTRPC3 polypeptide since the LTRPC3g-l variants represent longer N-terminally extended versions of LTRPC3.

RT-PCR

A PCR primer pair was designed to measure the steady state levels of the LTRPC3 mRNA by quantitative RT-PCR.

| LTRP6.tpls | CGCAGCTGGAAGACCTTATC | (SEQ ID NO:109) |
|---|---|---|
| LTRP6.tpla | AAGCTGCTCTGACGGACAAT | (SEQ ID NO:110) |

Briefly, first strand cDNA was made from commercially available mRNA. The relative amount of cDNA used in each assay was determined by performing a parallel experiment using a primer pair for a gene expressed in equal amounts in all tissues, cyclophilin. The cyclophilin primer pair detected small variations in the amount of cDNA in each sample and these data were used for normalization of the data obtained with the primer pair for the LTRPC3 transcript. The PCR data was converted into a relative assessment of the difference in transcript abundance amongst the tissues tested and the data is presented in FIG. 8. Transcripts corresponding to the LTRPC3 transcript were found to be highly expressed in the kidney; and significantly in spinal cord, testis, and brain.

Northern Blot Analysis

Human tissue Northern blots (Clontech) were probed with an RNA probe derived from a 645-bp DNA fragment amplified from the primer pair 86-1-C (SEQ ID NO: 111) and 86-5-NC (5'-AGGGAAGGGGAAGTGGTTGATCTC-3', SEQ ID NO:112). Hybridization of the blot was performed at 68° C. in ExpressHyb (Clontech) for 6 hours, with 1×10⁶ cpm/ml of $^{32}$P-labeled probe. Autoradiography was performed for 1 week at −70° C.

The results of the Northern hybridization are shown in FIG. 9. As shown, Transcripts corresponding to the LTRPC3 transcript were found to be highly expressed in kidney, and to a lesser extent in brain, and testis.

Example 4

Method of Assessing the Expression Profile of the LTRPC3 Polypeptides of the Present Invention Using Expanded mRNA Tissue and Cell Sources The following protocol was used to elucidate the expanded expression profile of the LTRPC3 polypeptide (SEQ ID NO:15) and is described in co-pending U.S. Ser. No. 10/210, 152, filed Aug. 1, 2002 and International Publication No. WO 03/012063, published Feb. 13, 2003. The same protocol may be employed to elucidate the expanded expression profile of the LTRPC3g-1 variants of the present invention using primer pairs specific for these variants. The expanded LTRPC3 expression profile is provided here for representative purposes only although it is expected that the LTRPC3g-1 variants have similar expanded expression patterns as the LTRPC3 polypeptide since the LTRPC3g-1 variants represent N-terminally extended versions of LTRPC3.

Total RNA from tissues was isolated using the TriZol protocol (Invitrogen) and quantified by determining its absorbance at 260 nM. An assessment of the 18s and 28s ribosomal RNA bands was made by denaturing gel electrophoresis to determine RNA integrity.

The specific sequence to be measured was aligned with related genes found in GenBank to identify regions of significant sequence divergence to maximize primer and probe specificity. Gene-specific primers and probes were designed using the ABI primer express software to amplify small amplicons (150 base pairs or less) to maximize the likelihood that the primers function at 100% efficiency. All primer/probe sequences were searched against Public Genbank databases to ensure target specificity. Primers and probes were obtained from ABI.

For LTRPC3, the primer probe sequences were as follows

```
Forward Primer
5'-TCAGAGAATGGGCCAACAAGA-3'        (SEQ ID NO:113)

Reverse Primer
5'-CGAAAACGCTCGAGGAATGA-3'         (SEQ ID NO:114)

TaqMan Probe
5'-CAGGCCTAGGTTCCTCCTCTCGGAAA-3'   (SEQ ID NO:115)
```

DNA Contamination

To access the level of contaminating genomic DNA in the RNA, the RNA was divided into 2 aliquots and one half was treated with Rnase-free Dnase (Invitrogen). Samples from both the Dnase-treated and non-treated were then subjected to reverse transcription reactions with (RT+) and without (RT−) the presence of reverse transcriptase. TaqMan assays were carried out with gene-specific primers (see above) and the contribution of genomic DNA to the signal detected was evaluated by comparing the threshold cycles obtained with the RT+/RT− non-Dnase treated RNA to that on the RT+/RT− Dnase treated RNA. The amount of signal contributed by genomic DNA in the Dnased RT− RNA must be less that 10% of that obtained with Dnased RT+ RNA. If not the RNA was not used in actual experiments.

Reverse Transcription Reaction and Sequence Detection 100 ng of Dnase-treated total RNA was annealed to 2.5 µM of the respective gene-specific reverse primer in the presence of 5.5 mM Magnesium Chloride by heating the sample to 72° C. for 2 min and then cooling to 55° C. for 30 min. 1.25 U/µl of MuLv reverse transcriptase and 500 µM of each dNTP was added to the reaction and the tube was incubated at 37° C. for 30 min. The sample was then heated to 90° C. for 5 min to denature enzyme.

Quantitative sequence detection was carried out on an ABI PRISM 7700 by adding to the reverse transcribed reaction 2.5 µM forward and reverse primers, 500 µM of each dNTP, buffer and 5 U AmpliTaq Gold™. The PCR reaction was then held at 94° C. for 12 min, followed by 40 cycles of 94° C. for 15 sec and 60° C. for 30 sec.

Data Handling

The threshold cycle (Ct) of the lowest expressing tissue (the highest Ct value) was used as the baseline of expression and all other tissues were expressed as the relative abundance to that tissue by calculating the difference in Ct value between the baseline and the other tissues and using it as the exponent in $2^{(\Delta Ct)}$ The expanded expression profile of the LTRPC3 polypeptide is provided in FIGS. 12 and 13 and described elsewhere herein.

Example 5

Complementary Oligonucleotides to the LTRPC3 Polynucleotide

The following protocol was used to elucidate the association of the LTRPC3 polypeptide (SEQ ID NO:15) to regulation of FEN1 and is described in co-pending U.S. Ser. No. 10/210,152, filed Aug. 1, 2002 and International Publication No. WO 03/012063, published Feb. 13, 2003. The same protocol may be employed to demonstrate an association to the regulation of FEN1 for the LTRPC3g-1 variants of the present invention using antisense oligos specific for these variants. The FEN1 association data for LTRPC3 is provided here for representative purposes only although it is expected that the LTRPC3g-1 variants have a similar FEN1 association as the LTRPC3 polypeptide since the LTRPC3g-1 variants represent N-terminally extended versions of LTRPC3.

Antisense molecules or nucleic acid sequences complementary to the LTRPC3 protein-encoding sequence, or any part thereof, was used to decrease or to inhibit the expression of naturally occurring LTRPC3. Although the use of antisense or complementary oligonucleotides comprising about 15 to 35 base-pairs is described, essentially the same procedure is used with smaller or larger nucleic acid sequence fragments. An oligonucleotide based on the coding sequence of LTRPC3 protein as depicted in SEQ ID NO:14, for example, is used to inhibit expression of naturally occurring LTRPC3. The complementary oligonucleotide is typically designed from the most unique 5' sequence and is used either to inhibit transcription by preventing promoter binding to the coding sequence, or to inhibit translation by preventing the ribosome from binding to the LTRPC3 protein-encoding transcript. However, other regions may also be targeted.

Using an appropriate portion of a 5' sequence of SEQ ID NO:14, an effective antisense oligonucleotide includes any of about 15-35 nucleotides spanning the region which translates into the signal or 5' coding sequence, among other regions, of the polypeptide as shown in SEQ ID NO:15. Appropriate oligonucleotides are designed using OLIGO 4.06 software and the LTRPC3 protein coding sequence (SEQ ID NO:14). Preferred oligonucleotides are deoxynucleotide, or chimeric deoxynucleotide/ribonucleotide based and are provided below. The oligonucleotides were synthesized using chemistry essentially as described in U.S. Pat. No. 5,849,902; which is hereby incorporated herein by reference in its entirety.

| ID # | Sequence |
|---|---|
| 15737 | CCAUGGACAGAGAUGAGAAGCUUGGU (SEQ ID NO:119) |
| 15738 | AGUGGUCCCGUUGUCAGCCAGAAUGU (SEQ ID NO:120) |
| 15739 | CCUUCCACUAUGAGUGCCACCACAGU (SEQ ID NO:121) |
| 15740 | GUGUCCUUCUGAUCCCAUCCGAAAUU (SEQ ID NO:122) |
| 15741 | UGGUAUGGCCGGACAACAUCUCUUCU (SEQ ID NO:123) |

The LTRPC3 polypeptide has been shown to be involved in the regulation of mammalian base-excision repair. Subjecting cells with an effective amount of a pool of all five of the above antisense oligoncleotides resulted in a significant increase in FEN1 expression/activity providing convincing evidence that LTRPC3 at least regulates the activity and/or expression of FEN1 either directly, or indirectly. Moreover, the results suggest that LTRPC3 is involved in the negative regulation of FEN1 activity and/or expression, either directly or indirectly. The FEN1 assay used is described below and was based upon the analysis of FEN1 activity as a downstream marker for proliferative signal transduction events.

Transfection of Post-Quiescent A549 Cells with AntiSense Oligonucleotides Materials Needed A549 cells maintained in DMEM with high glucose (Gibco-BRL) supplemented with 10% Fetal Bovine Serum, 2 mM L-Glutamine, and 1×penicillin/streptomycin.
Opti-MEM (Gibco-BRL)
Lipofectamine 2000 (Invitrogen)
Antisense oligomers (Sequitur)
Polystyrene tubes.
Tissue culture treated plates.
Quiescent cells were prepared as follows:
Day 0: 300,000 A549 cells were seeded in a T75 tissue culture flask in 10 ml of A549 media (as specified above), and incubated in at 37° C., 5% $CO_2$ in a humidified incubator for 48 hours.
Day 2: The T75 flasks were rocked to remove any loosely adherent cells, and the A549 growth media removed and replenished with 10 ml of fresh A549 media. The cells were cultured for six days without changing the media to create a quiescent cell population.
Day 8: Quiescent cells were plated in multi-well format and transfected with antisense oligonucleotides.
A549 cells were transfected according to the following:
1. Trypsinize T75 flask containing quiescent population of A549 cells.
2. Count the cells and seed 24-well plates with 60K quiescent A549 cells per well.
3. Allow the cells to adhere to the tissue culture plate (approximately 4 hours).
4. Transfect the cells with antisense and control oligonucleotides according to the following:
   a. A 10× stock of lipofectamine 2000 (10 ug/ml is 10×) was prepared, and diluted lipid was allowed to stand at RT for 15 minutes.
   b. Stock solution of lipofectamine 2000 was 1 mg/ml.
   c. 10× solution for transfection was 10 ug/ml.
To prepare 10× solution, dilute 10 ul of lipofectamine 2000 stock per 1 ml of Opti-MEM (serum free media).
   a. A 10× stock of each oligomer was prepared to be used in the transfection.
   b. Stock solutions of oligomers were at 100 uM in 20 mM HEPES, pH 7.5.
   c. 10× concentration of oligomer was 0.25 uM.
To prepare the 10× solutions, dilute 2.5 ul of oligomer per 1 ml of Opti-MEM.
   a. Equal volumes of the 10× lipofectamine 2000 stock and the 10× oligomer solutions were mixed well, and incubated for 15 minutes at RT to allow complexation of the oligomer and lipid. The resulting mixture was 5×.
   b. After the 15 minute complexation, 4 volumes of full growth media was added to the oligomer/lipid complexes (solution was 1×).
   c. The media was aspirated from the cells, and 0.5 ml of the 1× oligomer/lipid complexes added to each well.
   d. The cells were incubated for 16-24 hours at 37° C. in a humidified $CO_2$ incubator.
   e. Cell pellets were harvested for RNA isolation and TaqMan analysis of downstream marker genes.

TaqMan Reactions

Quantitative RT-PCR analysis was performed on total RNA preps that had been treated with DNaseI or poly A selected RNA. The Dnase treatment may be performed using methods known in the art, though preferably using a Qiagen Rneasy kit to purify the RNA samples, wherein DNAse I treatment is performed on the column.
Briefly, a master mix of reagents was prepared according to the following table:

| Dnase I Treatment | |
|---|---|
| Reagent | Per r'xn (in uL) |
| 10x Buffer | 2.5 |
| Dnase I (1 unit/ul @1 unit per ug sample) | 2 |
| DEPC $H_2O$ | 0.5 |
| RNA sample @ 0.1 ug/ul (2-3 ug total) | 20 |
| Total | 25 |

Next, 5 ul of master mix was aliquoted per well of a 96-well PCR reaction plate (PE part # N801-0560). RNA samples were adjusted to 0.1 ug/ul with DEPC treated $H_2O$ (if necessary), and 20 ul was added to the aliquoted master mix for a final reaction volume of 25 ul.
The wells were capped using strip well caps (PE part # N801-0935), placed in a plate, and briefly spun in a plate centrifuge (Beckman) to collect all volume in the bottom of the tubes. Generally, a short spin up to 500 rpm in a Sorvall RT is sufficient.
The plates were incubated at 37° C. for 30 mins. Then, an equal volume of 0.1 mM EDTA in 10 mM Tris was added to each well, and heat inactivated at 70° C. for 5 min. The plates were stored at −80° C. upon completion.

RT Reaction

A master mix of reagents was prepared according to the following table:

RT reaction

| Reagent | RT Per Rx'n (in ul) | No RT Per Rx'n (in ul) |
|---|---|---|
| 10x RT buffer | 5 | 2.5 |
| MgCl$_2$ | 11 | 5.5 |
| DNTP mixture | 10 | 5 |
| Random Hexamers | 2.5 | 1.25 |
| Rnase inhibitors | 1.25 | 0.625 |
| RT enzyme | 1.25 | — |
| Total RNA 500 ng (100 ng no RT) | 19.0 max | 10.125 max |
| DEPC H$_2$O | — | — |
| Total | 50 uL | 25 uL |

Samples were adjusted to a concentration so that 500 ng of RNA was added to each RT rx'n (100 ng for the no RT). A maximum of 19 ul can be added to the RT rx'n mixture (10.125 ul for the no RT.) Any remaining volume up to the maximum values was filled with DEPC treated H$_2$O, so that the total reaction volume was 50 ul (RT) or 25 ul (no RT).

On a 96-well PCR reaction plate (PE part # N801-0560), 37.5 ul of master mix was aliquoted (22.5 ul of no RT master mix), and the RNA sample added for a total reaction volume of 50 ul (25 ul, no RT). Control samples were loaded into two or even three different wells in order to have enough template for generation of a standard curve.

The wells were capped using strip well caps (PE part # N801-0935), placed in a plate, and spin briefly in a plate centrifuge (Beckman) to collect all volume in the bottom of the tubes. Generally, a short spin up to 500 rpm in a Sorvall RT is sufficient.

For the RT-PCR reaction, the following thermal profile was used:
25C for 10 min
48° C. for 30 min
95° C. for 5 min
4° C. hold (for 1 hour)
Store plate @−20° C. or lower upon completion.

TaqMan Reaction

Template Comes from RT Plate

A master mix was prepared according to the following table:

TaqMan reaction (per well)

| Reagent | Per Rx'n (in ul) |
|---|---|
| TaqMan Master Mix | 4.17 |
| 100 uM Probe (SEQ ID NO: 118) | .025 |
| 100 uM Forward primer (SEQ ID NO: 116) | .05 |
| 100 uM Reverse primer (SEQ ID NO: 117) | .05 |
| Template | — |
| DEPC H$_2$O | 18.21 |
| Total | 22.5 |

The primers used for the RT-PCR reaction is as follows:

```
FEN1 primer and probes
                                    (SEQ ID NO:116)
    Forward Primer:     CCACCTGATGGGCATGTTCT (SEQ ID NO:117)
    Reverse Primer:     CGGCTTGCCATCAAAGACATA (SEQ ID NO:118)
    TaqMan Probe:       CCGCACCATTCGCATGATGGAG
```

Using a Gilson P-10 repeat pipetter, 22.5 ul of master mix was aliquouted per well of a 96-well optical plate. Then, using P-10 pipetter, 2.5 ul of sample was added to individual wells. Generally, RT samples are run in triplicate with each primer/probe set used, and no RT samples are run once and only with one primer/probe set, often gapdh (or other internal control).

A standard curve is then constructed and loaded onto the plate. The curve has five points plus one no template control (NTC, =DEPC treated H$_2$O). The curve was made with a high point of 50 ng of sample (twice the amount of RNA in unknowns), and successive samples of 25, 10, 5, and 1 ng. The curve was made from a control sample(s) (see above).

The wells were capped using optical strip well caps (PE part # N801-0935), placed in a plate, and spun in a centrifuge to collect all volume in the bottom of the tubes. Generally, a short spin up to 500 rpm in a Sorvall RT is sufficient.

Plates were loaded onto a PE 5700 sequence detector making sure the plate is aligned properly with the notch in the upper right hand corner. The lid was tightened down and run using the 5700 and 5700 quantitation programes and the SYBR probe using the following thermal profile:
50° C. for 2 min
95° C. for 10 min
and the following for 40 cycles:
   95° C. for 15 sec
   60° C. for 1 min
Change the reaction volume to 25 ul.

Once the reaction was complete, a manual threshold of around 0.1 was set to minimize the background signal. Additional information relative to operation of the GeneAmp 5700 machine may be found in reference to the following manuals: "GeneAmp 5700 Sequence Detection System Operator Training CD"; and the "User's Manual for 5700 Sequence Detection System"; available from Perkin-Elmer and hereby incorporated by reference herein in their entirety.

Example 6

Method of Assessing the Cellular Localization of the LTRPC3 Polypeptide

The following protocol was used to confirm the cellular localization of the LTRPC3 polypeptide (SEQ ID NO:15) and is described in co-pending U.S. Ser. No. 10/210,152, filed Aug. 1, 2002 and International Publication No. WO 03/012063, published Feb. 13, 2003. The same protocol may be employed to demonstrate the cellular localization of the LTRPC3g-l variants of the present invention. The cellular localization data for LTRPC3 is provided here for representative purposes only although it is expected that the LTRPC3g-l variants are also localized to the cellular membrane since the LTRPC3g-l variants represent N-terminally extended versions of LTRPC3.

HEK 293 cells were cultured in Dulbecco's modified medium containing 10% heat-inactivated fetal bovine serum and grown on the poly-D-lysine-coated glass coverslips. The cells were transiently transfected with the pcDNA3.1/Hygro-LTRPC3-HA vector with Fugene (Roche). Forty-eight hours later, cells were fixed with 4% paraformaldehyde in PBS, permeabilized with 0.1% Triton X-100, blocked in PBS containing 5% FBS and 5% normal goat serum, and stained with 10 µg/ml Fluorescein-conjugated anti-HA High Affinity antibody (3F10, Roche) and DAPI (0.5 µg/ml; Molecular Probes). Immunostained cell cultures were examined using a laser scanning confocal microscope (ZEISS LSM510). A 63× oil immersion objective was used with appropriate filter sets. Images were reconstructed from confocal stacks of Z-series scans of 10-20 optical sections through a depth of 5-15 µM.

The cellular localization of HA-tagged LTRPC3 was exclusively detected at the subplasma membrane region of the transfected cells (see FIG. 18), which is consistent with LTRPC3 being an integral membrane protein. Under these conditions approximately ~70% of cells were expressing LTRPC3.

Example 7

Method of Assessing the Ion Channel Activity of the LTRPC3 Polypeptide

The following protocol was used to demonstrate the putative ion channel activity of the LTRPC3 polypeptide (SEQ ID NO:15) and is described in co-pending U.S. Ser. No. 10/210,152, filed Aug. 1, 2002 and International Publication No. WO 03/012063, published Feb. 13, 2003. The same protocol may be employed to demonstrate the putative ion channel activity of the LTRPC3g-l variants of the present invention. The ion channel activity data for LTRPC3 is provided here for representative purposes only since it is expected that the LTRPC3g-l variants also have the same or similar ion channel activity as LTRPC3 since the LTRPC3g-l variants represent N-terminally extended versions of LTRPC3.

The cytoplasmic $Ca^{2+}$ indicator Fluo-4-AM (Molecular Probe) and the Fluorometric Imaging Plate Reader (FLIPR™, Molecular Devices) instrument were used to detect changes in intracellular $Ca^{2+}$. The pcDNA3.1/Hygro-LTRPC3-HA transfected cells were seeded on PDL-coated 96-well plates at a density of 70,000 cells/well 24 hours after transfection and used 24 hours after plating. Transfected cells were loaded with 4 µM Fluo-4-AM at 37° C. for 30 min in a nominally $Ca^{2+}$-free or 1 mM $CaCl_2$ buffer containing 140 mM NaCl, 4.7 mM KCl, 1 mM $MgCl_2$, 10 mM HEPES, 10 mM Glucose, and 2.5 mM Probenecid (Sigma), pH 7.4. Extracellular Fluo-4-AM was removed and cells were maintained in either $Ca^{2+}$-free buffer or buffer containing 1 mM $Ca^{2+}$ at room temperature prior to the experiments, which were conducted within 30 min after dye removal. Fluo-4 was excited at 488 nm using an argon laser and emitted light was selected using a 510-570 nm bandpass filter. Baseline intracellular fluorescence was established during the initial 50 seconds of the FLIPR read, then 1, 3 or 10 mM $Ca^{2+}$ was added to each well and subsequent changes in the intracellular $Ca^{2+}$ were monitored for 8 minutes. For store-depletion studies, 2 µM thapsigargin or 100 µM carbachol was added to Fluo-4-loaded cells in $Ca^{2+}$-free buffer before adding $Ca^{2+}$ on FLIPR. For pharmacology studies, 100 µM $LaCl_3$ or 100 µM $GdCl_3$ were added to Fluo-4-loaded cells in 1 mM $Ca^{2+}$ buffer before adding $Ca^{2+}$ on FLIPR. Experiments were carried out at room temperature. The results of these physiometric studies are shown in FIGS. 18 and 19.

The addition of $Ca^{2+}$ to the media resulted in a concentration-dependent influx of $Ca^{2+}$ into LTRPC3-expressing cells (as shown in FIG. 18, right panels), indicating that LTRPC3 is a functional $Ca^{2+}$ channel. In contrast, vector-transfected cells showed minimal $Ca^{2+}$ influx under the same experimental conditions (as shown in FIG. 18, left panels). The non-transfected cells were indistinguishable from the vector-transfected cells (data not shown). Therefore, LTRPC3 is a constitutively active channel capable of mediating $Ca^{2+}$ influx.

To further address the mechanism of LTRPC3-mediated $Ca^{2+}$ entry, similar $Ca^{2+}$ addition experiments were performed on transfected cells incubated (~30 min) in a nominally $Ca^{2+}$-free solution. Previous studies have shown that lowering extracellular $Ca^{2+}$ concentration below physiological levels can deplete intracellular $Ca^{2+}$ stores in many cell types including HEK 293 (*EMBO J.* 17, 4274-4282 (1998)). Incubating vector-transfected HEK 293 cells in a nominally $Ca^{2+}$-free solution gave rise to $Ca^{2+}$ entry that was dependent on the concentration of $Ca^{2+}$ added to the buffers, indicating $Ca^{2+}$ influx was mediated through endogenous SOCs in HEK293 cells (as shown in FIG. 19; left panel). In LTRPC3 cells, the $Ca^{2+}$ transients triggered by similar $Ca^{2+}$ treatment were much larger (as shown in FIG. 19, right panel). This $Ca^{2+}$ entry observed in LTRPC3 cells incubated in $Ca^{2+}$-free media were greater than in 1 mM $Ca^{2+}$ media, indicating that LTRPC3-mediated $Ca^{2+}$ entry can be potentiated by the store-depletion.

Example 8

Method of Assessing the Expression Profile of the LTRPC3 Polypeptide Using In Situ Hybridization The following protocol was used to demonstrate the expression profile of the LTRPC3 polypeptide (SEQ ID NO:15) using In situ hybridization and is described in co-pending U.S. Ser. No. 10/210,152, filed Aug. 1, 2002 and International Publication No. WO 03/012063, published Feb. 13, 2003. The same protocol may be employed to demonstrate the In situ hybridization expression profile of the LTRPC3g-l variants of the present invention using appropriate primer pairs. The In situ hybridization expression data for LTRPC3 is provided here for representative purposes only since it is expected that the LTRPC3g-l variants also have the same or similar In situ hybridization expression profile as LTRPC3 since the LTRPC3g-l variants represent N-terminally extended versions of LTRPC3.

Human Kidney was collected and received from the National Disease Research Interchange (Philadelphia, Pa.) according to IRB approved protocol. Tissue sections were embedded in OCT compound (Miles) and snap-frozen by immersion in 2-methylbutane cooled in dry ice and subsequently stored at −70° C.

Templates for LTRPC3 cRNA probes were derived from a 678-bp LTRPC3 fragment, cloned in a pCR-BluntII-TOPO vector (Invitrogen) utilizing the primer pair: (forward: 5'-CAGCTGGAAGACCTTATCGGG-3' (SEQ ID NO:124); reverse: 5'-TGGGAGGTGGGTGTAGTCTGAAGA-3' (SEQ ID NO:125)). The template for positive control cRNA human lysozyme probe was derived from a 638 bp EST (Incyte Genomics, GenBank Accession No:AA588081). $^{35}$S-labeled riboprobes were synthesized via in vitro transcription utilizing the Riboprobe® Combination System (Promega) where T7 and Sp6 RNA polymerase yielded sense and antisense probes respectively for LTRPC3 while T7 and T3 RNA polymerases yielded antisense and sense probes respectively for human lysozyme. Cryostat tissue sections cut at 10 µm and fixed in 4.0% formalin were used for in situ hybridization as previously described (Dambach, D. M., et al., (2002)

*Hepatology* 35, 1093-1103.): Briefly, tissue sections were acetylated; dehydrated in a graded ethanol series; immersed in chloroform; alcohol rinsed; air dried and then hybridized with sense and antisense $^{35}$S RNA probes (1.5×106 cpm/slide) for 16-20 hours at 60° C. Following hybridization, slides were rinsed in 4×SSC/50% formamide and 4×SSC; treated with RNAse A (20 µg/ml; Invitrogen) at 37° C.; washed through increasing stringent solutions to final high stringency wash in 0.1×SSC at 60° C.; dehydrated; air dried and then coated with NTB-2 emulsion (Eastman Kodak). Slides were placed in a dark box with desiccant at 4° C. and developed after one and four weeks exposure. Sections were stained with hematoxylin and eosin, and coverslipped. Expression signals were detected by dark phase microscopy. Cellular phenotype identification was by bright field microscopy.

The In situ hybridization results of the LTRPC3 polypeptide is provided in FIG. 17 and described elsewhere herein.

Example 9

Method of Further Assessing Cellular Localization of the LTRPC3 Polypeptide

The following protocol was used to further assess the cellular localization of the LTRPC3 polypeptide (SEQ ID NO:15) and is described in co-pending U.S. Ser. No. 10/210, 152, filed Aug. 1, 2002 and International Publication No. WO 03/012063, published Feb. 13, 2003. The same protocol may be employed to further assess the cellular localization of the LTRPC3g-l variants of the present invention. The cellular localization data for LTRPC3 is provided here for representative purposes only since it is expected that the LTRPC3g-l variants are also localized to the cellular membrane since the LTRPC3g-l variants represent N-terminally extended versions of LTRPC3.

HEK 293 cells were cultured in Dulbecco's Modified Eagle Medium (DMEM) containing 10% heat-inactivated fetal bovine serum and grown on poly-D-lysine-coated (PDL) glass coverslips. The cells were transiently transfected with hLTRPC3-HA with FuGENE 6 (Roche Molecular Biochemicals). Forty-eight hours later, cells were stained in culture media with the membrane probe Vybrant™ CM-DiI (5 µl/ml; Molecular Probes) at 37° C. for 5 min and 4° C. for 15 min. After washing with PBS, cells were fixed with 4% paraformaldehyde in PBS, permeabilized with 0.1% Triton X-100, blocked in PBS containing 5% FBS and 5% normal goat serum, and stained with 10 µg/ml Fluorescein-conjugated anti-HA High Affinity antibody (3F10; Roche Molecular Biochemicals) and DAPI (0.5 pg/ml; Molecular Probes). Immunostained cell cultures were examined using a laser scanning confocal microscope (ZEISS LSM510), a 63× oil immersion objective, and appropriate filter sets. Images shown are of a single optical section approximately 1 µm thick.

The expanded confocal microscopy results of the LTRPC3 polypeptide is provided in FIG. 18 and described elsewhere herein.

Example 10

Method of Further Assessing the Ion Channel Activity of the LTRPC3 Polypeptide

The following protocol was used to further assess the ion channel activity of the LTRPC3 polypeptide (SEQ ID NO:15) and is described in co-pending U.S. Ser. No. 10/210,152, filed Aug. 1, 2002 and International Publication No. WO 03/012063, published Feb. 13, 2003. The same protocol may be employed to further assess the ion channel activity of the LTRPC3g-l variants of the present invention. The ion channel activity data for LTRPC3 is provided here for representative purposes only since it is expected that the LTRPC3g-l variants also have the same or similar ion channel activity as LTRPC3 since the LTRPC3g-l variants represent N-terminally extended versions of LTRPC3.

The cytoplasmic $Ca^{2+}$ indicator Fluo-4-AM (Molecular Probes) and a Fluorometric Imaging Plate Reader (FLIPR™; Molecular Devices) instrument were used to detect changes in intracellular $Ca^{2+}$ concentration. The hLTRPC3-transfected cells were seeded on PDL-coated 96-well plates at a density of 70,000 cells/well 24 hours after transfection and used 24 hours after plating. Cells were loaded with 4 µM Fluo-4-AM at 37° C. for 30 min in a nominally $Ca^{2+}$-free or 1 mM $CaCl_2$ buffer containing (in mM): 140 NaCl, 4.7 KCl, 1 $MgCl_2$, 10 HEPES, 10 Glucose, and 2.5 Probenecid (Sigma), pH 7.4. Extracellular Fluo-4-AM was removed and cells were maintained in either $Ca^{2+}$-free buffer or buffer containing 1 mM $Ca^{2+}$ at room temperature prior to the experiments, which were conducted within 30 min after dye removal. Fluo-4 was excited at 488 nm using an argon laser and emitted light was selected using a 510-570 nm bandpass filter. Baseline intracellular fluorescence was established during the initial 50 seconds of the FLIPR read, then 1, 3, or 10 mM $Ca^{2+}$ was added to each well and subsequent changes in the intracellular $Ca^{2+}$ were monitored for 8 minutes. For store-depletion or receptor activation studies, 2 µM thapsigargin or 50 µM carbachol, respectively, was added to Fluo-4-loaded cells in $Ca^{2+}$-free buffer before adding 2 mM $Ca^{2+}$ on FLIPR. For pharmacology studies, 100 µM $GdCl_3$ was added to Fluo-4-loaded cells in 0 or 1 mM $Ca^{2+}$ buffer, as described in herein, prior to the start of the FLIPR recordings. Experiments were carried out at room temperature.

The results of the expanded physiometric experiments are provided in FIG. 19 and described herein.

Example 11

Method of Assessing the Putative Kinase Activity of the LTRPC3 Polypeptide

A number of methods may be employed to assess the potental kinase activity of the LTRPC3g, LTRPC3h, LTRPC3i, LTRPC3j, LTRPC3k, and LTRPC3l polypeptides. One preferred method is described below. A fusion construct is made whereby the LTRPC3g-, LTRPC3h-, LTRPC3l-, LTRPC3j-, LTRPC3k-, or LTRPC3l-encoding polynucleotide is operably linked to the coding region of the HA protein. CHO-K1 or HEK-293 cells grown on 100-mm dishes are transiently transfected with 8 µg of novel LTRPC3(g, h, I, j, k, or l)-HA cDNA construct in the pTracer-CMV2 (Invitrogen) vector with LipofectAMINE 2000 (Gibco). Cells are harvested after 48 hours with 3 ml of RIPA buffer [50 mM Tris (pH 7.4), 150 mM NaCl, 1 mM EDTA, 1% IGEPAL CA-630, 0.5% (w/v) deoxycholate, 0.1% (w/v) SDS, and 10 mM iodoacetamide]. LTRPC3(g, h, I, j, k, or l)-HA is immunoprecipitated with mouse monoclonal immunoglobulin G2a (IgG2a) HA probe (F-7) coupled to agarose (Santa Cruz Biotechnology). The agarose is sedimented and washed three times with RIPA buffer, and 2× SDS sample buffer is added. The samples may be resolved by SDS-PAGE and Western blotting following standard methods. HA probe Y-11 antibody could be the primary antibody (Santa Cruz Biotechnology), and horseradish peroxidase-linked antibody to rabbit Ig (Amersham Pharmacia Biotech) could be the secondary antibody. The SuperSignal West Dura substrate may be used for chemiluminescent detection (Pierce)

For phosphorylation experiments, purified GST-kinase fusion proteins and mutants are incubated at 37° C. for 30 min in the presence or absence of MBP as a test substrate in a 50-ul reaction. These reactions are performed in KIN buffer {50 mM Mops (pH 7.2), 100 mM NaCl, 20 mM $MgCl_2$, 0.5 mM ATP, and 2 µCi of [−32P]ATP}. Immunokinase reactions containing immunopurified LTRPC3(g, h, I, j, k, or l)-HA are incubated at 37° C. for 30 min in a 50-µl reaction containing KIN buffer with 75 mM n-octyl-D-glucopyranoside. The reactions are terminated by the addition of 2× SDS sample buffer, and the proteins were resolved by SDS-PAGE and Coomassie staining for the GST-kinase experiment or by SDS-PAGE and Western blotting for the immunokinase assay. The gels are dried, and 32P incorporation is visualized by autoradiography for the GST-kinase experiment. For the immunokinase experiment, 32P incorporation may be visualized by autoradiography of the transferred proteins on polyvinylidene difluoride membrane (Bio-Rad) before Western blotting.

Example 12

Method of Assessing Ability of LTRPC3 Polypeptides to Associate with Other Proteins Using the Yeast Two-Hybrid System In an effort to determine whether the LTRPC3g, LTRPC3h, LTRPC3i, LTRPC3j, LTRPC3k, or LTRPC3l polypeptides of the present invention are capable of functioning as an ion channel or kinase protein, it would be important to effectively test the interaction between LTRPC3g, LTRPC3h, LTRPC3i, LTRPC3j, LTRPC3k, or LTRPC3l and various portions of other proteins, particularly known ion channel proteins, for example, in a yeast two-hybrid system. Such a system could be created using methods known in the art (see, for example, S. Fields and O, Song, Nature, 340:245-246 (1989); and Gaston-SM and Loughlin-KR, Urology, 53(4): 835-42 (1999); which are hereby incorporated herein by reference in their entirety, including the articles referenced therein).

Cytoplasmic NH and COOH terminal domains of different proteins, preferably ion channel proteins (such as those referenced herein), could be subcloned and expressed as fusion proteins of the GAL4 DNA binding (DB) domain using molecular biology techniques within the skill of the artisan.

Exemplary subunits which could be used in the two-hybrid system to assess the ability of LTRPC3g, LTRPC3h, LTRPC3i, LTRPC3j, LTRPC3k, or LTRPC3l to associate with other ion channel proteins include, but are not limited to, the NH and/or C-terminal domain TRP1, TRP2, TRP3, TRP4, TRP5, TRP6, TRP7, signalling proteins, etc.

Example 13

Method of Assessing Ability of LTRPC3g, LTRPC3h, LTRPC3i, LTRPC3j, LTRPC3k, or LTRPC3l Polypeptides to Form Oligomeric Complexes with Itself or Other Ion Channel Proteins in Solution Aside from determining whether the LTRPC3g, LTRPC3h, LTRPC3i, LTRPC3j, LTRPC3k, or LTRPC3l polypeptides are capable of interacting with other proteins, preferably ion channel proteins, in a yeast two-hybrid assay, it would be an important next step to assess its ability to form oligomeric complexes with itself, in addition to other proteins, preferably ion channel proteins, in solution. Such a finding would be significant as it would provide convincing evidence that LTRPC3g, LTRPC3h, LTRPC3i, LTRPC3j, LTRPC3k, or LTRPC3l could serve as an ion channel protein.

A number of methods could be used to that are known in the art, for example, the method described by Sanguinetti, M. C., et al., Nature, 384:80-83 (1996) could be adapted using methods within the skill of the artisan.

Example 14

Method of Identifying the Cognate Ligand of the LTRPC3g, LTRPC3h, LTRPC3i, LTRPC3j, LTRPC3k, or LTRPC3l Polypeptide A number of methods are known in the art for identifying the cognate binding partner of a particular polypeptide. For example, the encoding LTRPC3g, LTRPC3h, LTRPC3i, LTRPC3j, LTRPC3k, or LTRPC3l polynucleotide could be engineered to comprise an epitope tag. The epitope could be any epitope known in the art or disclosed elsewhere herein. Once created, the epitope tagged LTRPC3g, LTRPC3h, LTRPC3i, LTRPC3j, LTRPC3k, or LTRPC3l encoding polynucleotide could be cloned into an expression vector and used to transfect a variety of cell lines representing different tissue origins (e.g., brain, testis, kidney, testis, liver, etc.). The transfected cell lines could then be induced to overexpress the LTRPC3g, LTRPC3h, LTRPC3i, LTRPC3j, LTRPC3k, or LTRPC3l polypeptide. The presence of the LTRPC3g, LTRPC3h, LTRPC3i, LTRPC3j, LTRPC3k, or LTRPC3l polypeptide on the cell surface could be determined by fractionating whole cell lysates into cellular and membrane protein fractions and performing immunoprecipitation using the antibody directed against the epitope engineered into the LTRPC3g, LTRPC3h, LTRPC3i, LTRPC3j, LTRPC3k, or LTRPC3l polypeptide. Monoclonal or polyclonal antibodies directed against the LTRPC3g, LTRPC3h, LTRPC3i, LTRPC3j, LTRPC3k, or LTRPC3l polypeptide could be created and used in place of the antibodies directed against the epitope.

Alternatively, the cell surface proteins could be distinguished from cellular proteins by biotinylating the surface proteins and then performing immunoprecipitations with antibody specific to the LTRPC3g, LTRPC3h, LTRPC3i, LTRPC3j, LTRPC3k, or LTRPC3l protein. After electrophoretic separation, the biotinylated protein could be detected with streptavidin-HRP (using standard methods known to those skilled in the art). Identification of the proteins bound to LTRPC3g, LTRPC3h, LTRPC3i, LTRPC3j, LTRPC3k, or LTRPC3l could be made in those cells by immunoprecipitation, followed by one-dimensional electrophoresis, followed by various versions of mass spectrometry. Such mass-spectrometry methods are known in the art, such as for example the methods taught by Ciphergen Biosystems Inc. (see U.S. Pat. No. 5,792,664; which is hereby incorporated herein by reference).

Example 15

Isolation of a Specific Clone from the Deposited Sample

The deposited material in the sample assigned the ATCC Deposit Number cited in Table 1 for any given cDNA clone also may contain one or more additional plasmids, each comprising a cDNA clone different from that given clone. Thus, deposits sharing the same ATCC Deposit Number contain at least a plasmid for each cDNA clone identified in Table 1. Typically, each ATCC deposit sample cited in Table 1 comprises a mixture of approximately equal amounts (by weight) of about 1-10 plasmid DNAs, each containing a different cDNA clone and/or partial cDNA clone; but such a deposit sample may include plasmids for more or less than 2 cDNA clones.

Two approaches can be used to isolate a particular clone from the deposited sample of plasmid DNA(s) cited for that clone in Table 1. First, a plasmid is directly isolated by screening the clones using a polynucleotide probe corresponding to SEQ ID NO:1, 3, 5, 8, 317 or 318.

Particularly, a specific polynucleotide with 30-40 nucleotides is synthesized using an Applied Biosystems DNA synthesizer according to the sequence reported. The oligonucleotide is labeled, for instance, with 32P-(-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17-20 nucleotides derived from both ends of the SEQ ID NO:1, 3, 5, 7, 9, or 11 (i.e., within the region of SEQ ID NO:1, 3, 5, 7, 9, or 11 bounded by the 5' NT and the 3' NT of the clone defined in Table 1) are synthesized and used to amplify the desired cDNA using the deposited cDNA plasmid as a template. The polymerase chain reaction is carried out under routine conditions, for instance, in 25 ul of reaction mixture with 0.5 ug of the above cDNA template. A convenient reaction mixture is 1.5-5 mM MgCl2, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94 degree C. for 1 min; annealing at 55 degree C. for 1 min; elongation at 72 degree C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

The polynucleotide(s) of the present invention, the polynucleotide encoding the polypeptide of the present invention, or the polypeptide encoded by the deposited clone may represent partial, or incomplete versions of the complete coding region (i.e., full-length gene). Several methods are known in the art for the identification of the 5' or 3' non-coding and/or coding portions of a gene which may not be present in the deposited clone. The methods that follow are exemplary and should not be construed as limiting the scope of the invention. These methods include but are not limited to, filter probing, clone enrichment using specific probes, and protocols similar or identical to 5' and 3, "RACE" protocols that are well known in the art. For instance, a method similar to 5' RACE is available for generating the missing 5' end of a desired full-length transcript. (Fromont-Racine et al., Nucleic Acids Res. 21(7):1683-1684 (1993)).

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full-length gene.

This above method starts with total RNA isolated from the desired source, although poly-A+ RNA can be used. The RNA preparation can then be treated with phosphatase if necessary to eliminate 5' phosphate groups on degraded or damaged RNA that may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene. Moreover, it may be advantageous to optimize the RACE protocol to increase the probability of isolating additional 5' or 3' coding or non-coding sequences. Various methods of optimizing a RACE protocol are known in the art, though a detailed description summarizing these methods can be found in B. C. Schaefer, Anal. Biochem., 227:255-273, (1995).

An alternative method for carrying out 5' or 3' RACE for the identification of coding or non-coding sequences is provided by Frohman, M. A., et al., Proc. Nat'l. Acad. Sci. USA, 85:8998-9002 (1988). Briefly, a cDNA clone missing either the 5' or 3' end can be reconstructed to include the absent base pairs extending to the translational start or stop codon, respectively. In some cases, cDNAs are missing the start of translation, therefor. The following briefly describes a modification of this original 5' RACE procedure. Poly A+ or total RNAs reverse transcribed with Superscript II (Gibco/BRL) and an antisense or I complementary primer specific to the cDNA sequence. The primer is removed from the reaction with a Microcon Concentrator (Amicon). The first-strand cDNA is then tailed with dATP and terminal deoxynucleotide transferase (Gibco/BRL). Thus, an anchor sequence is produced which is needed for PCR amplification. The second strand is synthesized from the dA-tail in PCR buffer, Taq DNA polymerase (Perkin-Elmer Cetus), an oligo-dT primer containing three adjacent restriction sites (XhoIJ Sail and ClaI) at the 5' end and a primer containing just these restriction sites. This double-stranded cDNA is PCR amplified for 40 cycles with the same primers as well as a nested cDNA-specific antisense primer. The PCR products are size-separated on an ethidium bromide-agarose gel and the region of gel containing cDNA products the predicted size of missing protein-coding DNA is removed. cDNA is purified from the agarose with the Magic PCR Prep kit (Promega), restriction digested with XhoI or SalI, and ligated to a plasmid such as pBluescript SKII (Stratagene) at XhoI and EcoRV sites. This DNA is transformed into bacteria and the plasmid clones sequenced to identify the correct protein-coding inserts. Correct 5' ends are confirmed by comparing this sequence with the putatively identified homologue and overlap with the partial cDNA clone. Similar methods known in the art and/or commercial kits are used to amplify and recover 3' ends.

Several quality-controlled kits are commercially available for purchase. Similar reagents and methods to those above are supplied in kit form from Gibco/BRL for both 5' and 3' RACE for recovery of full length genes. A second kit is available from Clontech which is a modification of a related technique, SLIC (single-stranded ligation to single-stranded cDNA), developed by Dumas et al., Nucleic Acids Res., 19:5227-32 (1991). The major differences in procedure are that the RNA is alkaline hydrolyzed after reverse transcription and RNA ligase is used to join a restriction site-containing anchor primer to the first-strand cDNA. This obviates the necessity for the dA-tailing reaction which results in a polyT stretch that is difficult to sequence past.

An alternative to generating 5' or 3' cDNA from RNA is to use cDNA library double-stranded DNA. An asymmetric PCR-amplified antisense cDNA strand is synthesized with an antisense cDNA-specific primer and a plasmid-anchored primer. These primers are removed and a symmetric PCR reaction is performed with a nested cDNA-specific antisense primer and the plasmid-anchored primer.

RNA Ligase Protocol for Generating the 5' or 3' End Sequences to Obtain Full Length Genes Once a gene of interest is identified, several methods are available for the identification of the 5' or 3' portions of the gene which may not be present in the original cDNA plasmid. These methods include, but are not limited to, filter probing, clone enrichment using specific probes and protocols similar and identical to 5' and 3'RACE. While the full-length gene may be present in the library and can be identified by probing, a useful method for generating the 5' or 3' end is to use the existing sequence information from the original cDNA to generate the missing information. A method similar to 5'RACE is available for generating the missing 5' end of a desired full-length gene. (This method was published by Fromont-Racine et al., Nucleic Acids Res., 21(7): 1683-1684 (1993)). Briefly, a specific RNA oligonucleotide is ligated to the 5' ends of a population of RNA presumably 30 containing full-length gene RNA transcript and a primer set containing a primer specific to the ligated RNA oligonucleotide and a primer specific to a known sequence of the gene of interest, is used to PCR amplify the 5' portion of the desired full length gene which may then be sequenced and used to generate the full length gene. This method starts with total RNA isolated from the desired source, poly A RNA may be used but is not a prerequisite for this procedure. The RNA preparation may then be treated with phosphatase if necessary to eliminate 5' phosphate groups on degraded or damaged RNA which may interfere with the later RNA ligase step. The phosphatase if used is then inactivated and the RNA is treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase. This modified RNA preparation can then be used as a template for first strand cDNA synthesis using a gene specific oligonucleotide. The first strand synthesis reaction can then be used as a template for PCR amplification of the desired 5' end using a primer specific to the ligated RNA oligonucleotide and a primer specific to the known sequence of the apoptosis related of interest. The resultant product is then sequenced and analyzed to confirm that the 5' end sequence belongs to the relevant apoptosis related.

Example 16

Chromosomal Mapping of the Polynucleotides

An oligonucleotide primer set is designed according to the sequence at the 5' end of SEQ ID NO:1, 3, 5, 7, 9, or 11. This primer preferably spans about 100 nucleotides. This primer set is then used in a polymerase chain reaction under the following set of conditions: 30 seconds, 95 degree C.; 1 minute, 56 degree C.; 1 minute, 70 degree C. This cycle is repeated 32 times followed by one 5 minute cycle at 70 degree C. Mammalian DNA, preferably human DNA, is used as template in addition to a somatic cell hybrid panel containing individual chromosomes or chromosome fragments (Bios, Inc). The reactions are analyzed on either 8% polyacrylamide gels or 3.5% agarose gels. Chromosome mapping is determined by the presence of an approximately 100 bp PCR fragment in the particular somatic cell hybrid.

Example 17

Bacterial Expression of a Polypeptide

A polynucleotide encoding a polypeptide of the present invention is amplified using PCR oligonucleotide primers corresponding to the 5' and 3' ends of the DNA sequence, as outlined in Example 15, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Ampr), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the E. coli strain M15/rep4 (Qiagen, Inc.) which contains multiple copies of the plasmid pREP4, that expresses the lacI repressor and also confers kanamycin resistance (Kanr). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.600) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3-4 hours at 4 degree C. The cell debris is removed by centrifugation, and the supernatant containing the polypeptide is loaded onto a nickel-nitrilo-triacetic acid ("Ni-NTA") affinity resin column (available from QIAGEN, Inc., supra). Proteins with a 6× His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM imidazole. Imidazole is removed by a final dialyzing step against PBS or 50 mM sodium acetate pH 6 buffer plus 200 mM NaCl. The purified protein is stored at 4 degree C. or frozen at −80 degree C.

Example 18

Purification of a Polypeptide from an Inclusion Body

The following alternative method can be used to purify a polypeptide expressed in *E coli* when it is present in the form of inclusion bodies. Unless otherwise specified, all of the following steps are conducted at 4-10 degree C.

Upon completion of the production phase of the *E. coli* fermentation, the cell culture is cooled to 4-10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfluidics, Corp. or APV Gaulin, Inc.) twice at 4000-6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2-4 hours. After 7000×g centrifugation for 15 min., the pellet is discarded and the polypeptide containing supernatant is incubated at 4 degree C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4 degree C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., Poros HS-50, Perceptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perceptive Biosystems) and weak anion (Poros CM-20, Perceptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant A280 monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Coomassie blue stained 16% SDS-PAGE gel when 5 ug of purified protein is loaded. The purified protein can also be tested for endotoxin/LPS contamination, and typically the LPS content is less than 0.1 ng/ml according to LAL assays.

Example 19

Cloning and Expression of a Polypeptide in a Baculovirus Expression System

In this example, the plasmid shuttle vector pAc373 is used to insert a polynucleotide into a baculovirus to express a polypeptide. A typical baculovirus expression vector contains the strong polyhedrin promoter of the *Autographa californica* nuclear polyhedrosis virus (AcMNPV) followed by convenient restriction sites, which may include, for example BamHI, Xba I and Asp718. The polyadenylation site of the simian virus 40 ("SV40") is often used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31-39 (1989).

A polynucleotide encoding a polypeptide of the present invention is amplified using PCR oligonucleotide primers corresponding to the 5' and 3' ends of the DNA sequence, as outlined in Example 15, to synthesize insertion fragments. The primers used to amplify the cDNA insert should preferably contain restriction sites at the 5' end of the primers in order to clone the amplified product into the expression vector. Specifically, the cDNA sequence contained in the deposited clone, including the AUG initiation codon and the naturally associated leader sequence identified elsewhere herein (if applicable), is amplified using the PCR protocol described in Example 15. If the naturally occurring signal sequence is used to produce the protein, the vector used does not need a second signal peptide. Alternatively, the vector can be modified to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transformed with 1.0 ug of a commercially available linearized baculovirus DNA ("BaculoGoldtm baculovirus DNA", Pharmingen, San Diego, Calif.), using the lipofection method described by Felgner et al., Proc. Natl. Acad. Sci. USA 84:7413-7417 (1987). One ug of BaculoGoldtm virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of 35S-methionine and 5 uCi 35S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 20

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transformation with a selectable marker such as dhfr, gpt, neomycin, hygromycin allows the identification and isolation of the transformed cells.

The transformed gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. . . . 253:1357-1370 (1978); Hamlin, J. L. and Ma, C., Biochem. et Biophys. Acta, 1097:107-143 (1990); Page, M. J. and Sydenham, M. A., Biotechnology 9:64-68 (1991).) Another useful selection marker is the enzyme glutamine synthase (GS) (Murphy et al., Biochem J. 227:277-279 (1991); Bebbington et al., Bio/Technology 10:169-175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

A polynucleotide of the present invention is amplified according to the protocol outlined in herein. If the naturally occurring signal sequence is used to produce the protein, the vector does not need a second signal peptide. Alternatively, if the naturally occurring signal sequence is not used, the vector can be modified to include a heterologous signal sequence. (See, e.g., WO 96/34891.) The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transformation. Five μg of an expression plasmid is cotransformed with 0.5 ug of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mm). The same procedure is repeated until clones are obtained which grow at a concentration of 100-200 uM. Expression of the desired gene product is analyzed, for instance, by SDS-PAGE and Western blot or by reversed phase HPLC analysis.

Example 21

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example described herein; see also EP A 394,827; Traunecker, et al., Nature 331:84-86 (1988).) Similarly, fusion to IgG-1, IgG-3, and albumin increases the half-life time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector. Note that the polynucleotide is cloned without a stop codon, otherwise a fusion protein will not be produced.

The naturally occurring signal sequence may be used to produce the protein (if applicable). Alternatively, if the naturally occurring signal sequence is not used, the vector can be modified to include a heterologous signal sequence. (See, e.g., WO 96/34891 and/or U.S. Pat. No. 6,066,781, supra.)

Human IgG Fc Region (SEQ ID NO:108)
GGGATCCGGAGCCCAAATCTTCTGACAAAACTCACACATGCCCACCGTGC

CCAGCACCTGAATTCGAGGGTGCACCGTCAGTCTTCCTCTTCCCCCCAAA

ACCCAAGGACACCCTCATGATCTCCCGGACTCCTGAGGTCACATGCGTGG

TGGTGGACGTAAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCAAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAATGAGTGCGACGGCCGCGACTCTAGAGGAT

Example 22

Method of Creating N- and C-Terminal Deletion Mutants Corresponding to the LTRPC3g, LTRPC3h, LTRPC3i, LTRPC3j, LTRPC3k, or LTRPC3l Polypeptide of the Present Invention As described elsewhere herein, the present invention encompasses the creation of N- and C-terminal deletion mutants, in addition to any combination of N- and C-terminal deletions thereof, corresponding to the LTRPC3g, LTRPC3h, LTRPC3i, LTRPC3j, LTRPC3k, or LTRPC3l polypeptide of the present invention. A number of methods are available to one skilled in the art for creating such mutants. Such methods may include a combination of PCR amplification and gene cloning methodology. Although one of skill in the art of molecular biology, through the use of the teachings provided or referenced herein, and/or otherwise known in the art as standard methods, could readily create each deletion mutant of the present invention, exemplary methods are described below.

Briefly, using the isolated cDNA clone encoding the full-length LTRPC3g, LTRPC3h, LTRPC3i, LTRPC3j, LTRPC3k, or LTRPC3l polypeptide sequence (as described in Example 15, for example), appropriate primers of about 15-25 nucleotides derived from the desired 5' and 3' positions of SEQ ID NO:1, SEQ ID NO:3, SEQ ID NO:5, SEQ ID NO:7, SEQ ID NO:9, or SEQ ID NO:11, may be designed to PCR amplify, and subsequently clone, the intended N- and/or C-terminal deletion mutant. Such primers could comprise, for example, an inititation and stop codon for the 5' and 3' primer, respectively. Such primers may also comprise restriction sites to facilitate cloning of the deletion mutant post amplification.

Moreover, the primers may comprise additional sequences, such as, for example, flag-tag sequences, kozac sequences, or other sequences discussed and/or referenced herein.

For example, in the case of the L775 to T1709 LTRPC3g N-terminal deletion mutant, the following primers could be used to amplify a cDNA fragment corresponding to this deletion mutant:

```
5' Primer                              (SEQ ID NO:126)
5'-GCAGCA GCGGCCGC CTCAAGGTAATTCTGGGAATTCTAC-3'
          NotI 3' Primer                              (SEQ ID NO:127)
5'-GCAGCA GTCGAC GGTGTGCTTGCTTTCAAAGCTTTGG-3'
          SalI
```

For example, in the case of the M1 to N1150 LTRPC3g C-terminal deletion mutant, the following primers could be used to amplify a cDNA fragment corresponding to this deletion mutant:

```
5' Primer                              (SEQ ID NO:128)
5'-GCAGCA GCGGCCGC ATGTATGTGCGAGTATCTTTTG-3'
          NotI 3' Primer                              (SEQ ID NO:129)
5'-GCAGCA GTCGAC GTTAAAGACAGCAATGAGGAGGTTG-3'
          SalI
```

The resulting C-terminal deletion mutant could be used as a potential, membrane bound, LTRPC3g decoy receptor.

For example, in the case of the M1 to N1216 LTRPC3g C-terminal deletion mutant, the following primers could be used to amplify a cDNA fragment corresponding to this deletion mutant:

```
5' Primer                              (SEQ ID NO:130)
5'-GCAGCA GCGGCCGC ATGTATGTGCGAGTATCTTTTG-3'
          NotI 3' Primer                              (SEQ ID NO:131)
5'-GCAGCA GTCGAC ATTAGATGAGTTGAACCGATCATCC-3'
          SalI
```

The resulting C-terminal deletion mutant could be used as a potential, membrane bound, LTRPC3g decoy receptor.

Representative PCR amplification conditions are provided below, although the skilled artisan would appreciate that other conditions may be required for efficient amplification. A 100 ul PCR reaction mixture may be prepared using long of the template DNA (cDNA clone of LTRPC3), 200 uM 4dNTPs, 1 uM primers, 0.25 U Taq DNA polymerase (PE), and standard Taq DNA polymerase buffer. Typical PCR cycling condition are as follows:

| | |
|---|---|
| 20-25 cycles: | 45 sec, 93 degrees |
| | 2 min, 50 degrees |
| | 2 min, 72 degrees |
| 1 cycle: | 10 min, 72 degrees |

After the final extension step of PCR, 5 U Klenow Fragment may be added and incubated for 15 min at 30 degrees.

Upon digestion of the fragment with the NotI and SalI restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances.

The digested fragment and vector are then ligated using a DNA ligase, and then used to transform competent *E. coli* cells using methods provided herein and/or otherwise known in the art.

The 5' primer sequence for amplifying any additional N-terminal deletion mutants may be determined by reference to the following formula: $(S+(X * 3))$ to $((S+(X * 3))+25)$, wherein 'S' is equal to the nucleotide position of the initiating start codon of the LTRPC3g, LTRPC3h, LTRPC3i, LTRPC3j, LTRPC3k, or LTRPC3l gene (SEQ ID NO:1, 3, 5, 7, 9, or 11), and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand of SEQ ID NO:1, SEQ ID NO:3, SEQ ID NO:5, SEQ ID NO:7, SEQ ID NO:9, or SEQ ID NO:11. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula: $(S+(X * 3))$ to $((S+(X * 3))-25)$, wherein 'S' is equal to the nucleotide position of the initiating start codon of the LTRPC3g, LTRPC3h, LTRPC3i, LTRPC3j, LTRPC3k, or LTRPC3l gene (SEQ ID NO:1, 3, 5, 7, 9, or 11), and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ ID NO:1, SEQ ID NO:3, SEQ ID NO:5, SEQ ID NO:7, SEQ ID NO:9, or SEQ ID NO:11. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions, may be necessary for optimizing PCR amplification.

Example 23

Regulation of Protein Expression Via Controlled Aggregation in the Endoplasmic Reticulum As described more particularly herein, proteins regulate diverse cellular processes in higher organisms, ranging from rapid metabolic changes to growth and differentiation. Increased production of specific proteins could be used to prevent certain diseases and/or disease states. Thus, the ability to modulate the expression of specific proteins in an organism would provide significant benefits.

Numerous methods have been developed to date for introducing foreign genes, either under the control of an inducible, constitutively active, or endogenous promoter, into organisms. Of particular interest are the inducible promoters (see, M. Gossen, et al., Proc. Natl. Acad. Sci. USA., 89:5547 (1992); Y. Wang, et al., Proc. Natl. Acad. Sci. USA, 91:8180 (1994), D. No., et al., Proc. Natl. Acad. Sci. USA, 93:3346 (1996); and V. M. Rivera, et al., Nature Med, 2:1028 (1996); in addition to additional examples disclosed elsewhere herein). In one example, the gene for erthropoietin (Epo) was transferred into mice and primates under the control of a small molecule inducer for expression (e.g., tetracycline or rapamycin) (see, D. Bohl, et al., Blood, 92:1512, (1998); K. G. Rendahl, et al., Nat. Biotech, 16:757, (1998); V. M. Rivera, et al., Proc. Natl. Acad. Sci. USA, 96:8657 (1999); and X. Ye et al., Science, 283:88 (1999). Although such systems enable efficient induction of the gene of interest in the organism upon addition of the inducing agent (i.e., tetracycline, rapamycin, etc.), the levels of expression tend to peak at 24 hours and trail off to background levels after 4 to 14 days. Thus, controlled transient expression is virtually impossible using these systems, though such control would be desirable.

A new alternative method of controlling gene expression levels of a protein from a transgene (i.e., includes stable and transient transformants) has recently been elucidated (V. M. Rivera., et al., Science, 287:826-830, (2000)). This method does not control gene expression at the level of the mRNA like the aforementioned systems. Rather, the system controls the level of protein in an active secreted form. In the absence of the inducing agent, the protein aggregates in the ER and is not secreted. However, addition of the inducing agent results in dis-aggregation of the protein and the subsequent secretion from the ER. Such a system affords low basal secretion, rapid, high level secretion in the presence of the inducing agent, and rapid cessation of secretion upon removal of the inducing agent. In fact, protein secretion reached a maximum level within 30 minutes of induction, and a rapid cessation of secretion within 1 hour of removing the inducing agent. The method is also applicable for controlling the level of production for membrane proteins.

Detailed methods are presented in V.M. Rivera., et al., Science, 287:826-830, (2000)), briefly:

Fusion protein constructs are created using polynucleotide sequences of the present invention with one or more copies (preferably at least 2, 3, 4, or more) of a conditional aggregation domain (CAD) a domain that interacts with itself in a ligand-reversible manner (i.e., in the presence of an inducing agent) using molecular biology methods known in the art and discussed elsewhere herein. The CAD domain may be the mutant domain isolated from the human FKBP12 (Phe$^{36}$ to Met) protein (as disclosed in V.M. Rivera., et al., Science, 287:826-830, (2000), or alternatively other proteins having domains with similar ligand-reversible, self-aggregation properties. As a principle of design the fusion protein vector would contain a furin cleavage sequence operably linked between the polynucleotides of the present invention and the CAD domains. Such a cleavage site would enable the proteolytic cleavage of the CAD domains from the polypeptide of the present invention subsequent to secretion from the ER and upon entry into the trans-Golgi (J. B. Denault, et al., FEBS Lett., 379:113, (1996)). Alternatively, the skilled artisan would recognize that any proteolytic cleavage sequence could be substituted for the furin sequence provided the substituted sequence is cleavable either endogenously (e.g., the furin sequence) or exogenously (e.g., post secretion, post purification, post production, etc.). The preferred sequence of each feature of the fusion protein construct, from the 5' to 3' direction with each feature being operably linked to the other, would be a promoter, signal sequence, "X" number of (CAD)x domains, the furin sequence (or other proteolytic sequence), and the coding sequence of the polypeptide of the present invention. The artisan would appreciate that the promotor and signal sequence, independent from the other, could be either the endogenous promotor or signal sequence of a polypeptide of the present invention, or alternatively, could be a heterologous signal sequence and promotor.

The specific methods described herein for controlling protein secretion levels through controlled ER aggregation are not meant to be limiting are would be generally applicable to any of the polynucleotides and polypeptides of the present invention, including variants, homologues, orthologs, and fragments therein.

Example 24

Alteration of Protein Glycosylation Sites to Enhance Characteristics of Polypeptides of the Invention Many eukaryotic cell surface and proteins are post-translationally processed to incorporate N-linked and O-linked carbohydrates (Kornfeld and Kornfeld (1985) Annu. Rev. Biochem. 54:631-64; Rademacher et al., (1988) Annu. Rev. Biochem. 57:785-838). Protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion (Fieldler and Simons (1995) Cell, 81:309-312; Helenius (1994) Mol. Biol. Of the Cell 5:253-265; Olden et al., (1978) Cell, 13:461-473; Caton et al., (1982) Cell, 37:417-427; Alexamnder and Elder (1984), Science, 226:1328-1330; and Flack et al., (1994), J. Biol. Chem. . . . , 269:14015-14020). In higher organisms, the nature and extent of glycosylation can markedly affect the circulating half-life and bio-availability of proteins by mechanisms involving receptor mediated uptake and clearance (Ashwell and Morrell, (1974), Adv. Enzymol., 41:99-128; Ashwell and Harford (1982), Ann. Rev. Biochem., 51:531-54). Receptor systems have been identified that are thought to play a major role in the clearance of serum proteins through recognition of various carbohydrate structures on the glycoproteins (Stockert (1995), Physiol. Rev., 75:591-609; Kery et al., (1992), Arch. Biochem. Biophys., 298:49-55). Thus, production strategies resulting in incomplete attachment of terminal sialic acid residues might provide a means of shortening the bioavailability and half-life of glycoproteins. Conversely, expression strategies resulting in saturation of terminal sialic acid attachment sites might lengthen protein bioavailability and half-life.

In the development of recombinant glycoproteins for use as pharmaceutical products, for example, it has been speculated that the pharmacodynamics of recombinant proteins can be modulated by the addition or deletion of glycosylation sites from a glycoproteins primary structure (Berman and Lasky (1985a) Trends in Biotechnol., 3:51-53). However, studies have reported that the deletion of N-linked glycosylation sites often impairs intracellular transport and results in the intracellular accumulation of glycosylation site variants (Machamer and Rose (1988), J. Biol. Chem., 263:5955-5960; Gallagher et al., (1992), J. Virology., 66:7136-7145; Collier et al., (1993), Biochem., 32:7818-7823; Claffey et al., (1995) Biochemica et Biophysica Acta, 1246:1-9; Dube et al., (1988), J. Biol. Chem. . . . 263:17516-17521). While glycosylation site variants of proteins can be expressed intracellularly, it has proved difficult to recover useful quantities from growth conditioned cell culture medium.

Moreover, it is unclear to what extent a glycosylation site in one species will be recognized by another species glycosylation machinery. Due to the importance of glycosylation in protein metabolism, particularly the secretion and/or expression of the protein, whether a glycosylation signal is recognized may profoundly determine a proteins ability to be expressed, either endogenously or recombinately, in another organism (i.e., expressing a human protein in *E. coli*, yeast, or viral organisms; or an *E. coli*, yeast, or viral protein in human, etc.). Thus, it may be desirable to add, delete, or modify a glycosylation site, and possibly add a glycosylation site of one species to a protein of another species to improve the proteins functional, bioprocess purification, and/or structural characteristics (e.g., a polypeptide of the present invention).

A number of methods may be employed to identify the location of glycosylation sites within a protein. One preferred method is to run the translated protein sequence through the PROSITE computer program (Swiss Institute of Bioinformatics). Once identified, the sites could be systematically deleted, or impaired, at the level of the DNA using mutagenesis methodology known in the art and available to the skilled artisan, Preferably using PCR-directed mutagenesis (See Maniatis, Molecular Cloning: A Laboratory Manual, Cold Spring Harbor Press, Cold Spring, N.Y. (1982)). Similarly, glycosylation sites could be added, or modified at the level of the DNA using similar methods, preferably PCR methods (See, Maniatis, supra). The results of modifying the glycosylation sites for a particular protein (e.g., solubility, secretion potential, activity, aggregation, proteolytic resistance, etc.) could then be analyzed using methods know in the art.

Example 25

Method of Enhancing the Biological Activity/Functional Characteristics of Invention Through Molecular Evolution Although many of the most biologically active proteins known are highly effective for their specified function in an organism, they often possess characteristics that make them undesirable for transgenic, therapeutic, and/or industrial applications. Among these traits, a short physiological half-life is the most prominent problem, and is present either at the level of the protein, or the level of the proteins mRNA. The ability to extend the half-life, for example, would be particularly important for a proteins use in gene therapy, transgenic animal production, the bioprocess production and purification of the protein, and use of the protein as a chemical modulator among others. Therefore, there is a need to identify novel variants of isolated proteins possessing characteristics which enhance their application as a therapeutic for treating diseases of animal origin, in addition to the proteins applicability to common industrial and pharmaceutical applications.

Thus, one aspect of the present invention relates to the ability to enhance specific characteristics of invention through directed molecular evolution. Such an enhancement may, in a non-limiting example, benefit the inventions utility as an essential component in a kit, the inventions physical attributes such as its solubility, structure, or codon optimization, the inventions specific biological activity, including any associated enzymatic activity, the proteins enzyme kinetics, the proteins Ki, Kcat, Km, Vmax, Kd, protein-protein activity, protein-DNA binding activity, antagonist/inhibitory activity (including direct or indirect interaction), agonist activity (including direct or indirect interaction), the proteins antigenicity (e.g., where it would be desirable to either increase or decrease the antigenic potential of the protein), the immunogenicity of the protein, the ability of the protein to form dimers, trimers, or multimers with either itself or other proteins, the antigenic efficacy of the invention, including its subsequent use a preventative treatment for disease or disease states, or as an effector for targeting diseased genes. Moreover, the ability to enhance specific characteristics of a protein may also be applicable to changing the characterized activity of an enzyme to an activity completely unrelated to its initially characterized activity. Other desirable enhancements of the invention would be specific to each individual protein, and would thus be well known in the art and contemplated by the present invention.

For example, an engineered transient potential receptor may be constitutively active upon binding of its cognate ligand. Alternatively, an engineered transient potential receptor may be constitutively active in the absence of ligand binding. In yet another example, an engineered transient potential receptor may be capable of being activated with less than all of the regulatory factors and/or conditions typically required for transient potential receptor activation (e.g., ligand binding, phosphorylation, conformational changes, etc.). Such transient potential receptors would be useful in screens to identify transient potential receptor modulators, among other uses described herein.

Directed evolution is comprised of several steps. The first step is to establish a library of variants for the gene or protein of interest. The most important step is to then select for those variants that entail the activity you wish to identify. The design of the screen is essential since your screen should be selective enough to eliminate non-useful variants, but not so stringent as to eliminate all variants. The last step is then to repeat the above steps using the best variant from the previous screen. Each successive cycle, can then be tailored as necessary, such as increasing the stringency of the screen, for example.

Over the years, there have been a number of methods developed to introduce mutations into macromolecules. Some of these methods include, random mutagenesis, "error-prone" PCR, chemical mutagenesis, site-directed mutagenesis, and other methods well known in the art (for a comprehensive listing of current mutagenesis methods, see Maniatis, Molecular Cloning: A Laboratory Manual, Cold Spring Harbor Press, Cold Spring, N.Y. (1982)). Typically, such methods have been used, for example, as tools for identifying the core functional region(s) of a protein or the function of specific domains of a protein (if a multi-domain protein). However, such methods have more recently been applied to the identification of macromolecule variants with specific or enhanced characteristics.

Random mutagenesis has been the most widely recognized method to date. Typically, this has been carried out either through the use of "error-prone" PCR (as described in Moore, J., et al, Nature Biotechnology 14:458, (1996), or through the application of randomized synthetic oligonucleotides corresponding to specific regions of interest (as described by Derbyshire, K. M. et al, Gene, 46:145-152, (1986), and Hill, D E, et al, Methods Enzymol., 55:559-568, (1987). Both approaches have limits to the level of mutagenesis that can be obtained. However, either approach enables the investigator to effectively control the rate of mutagenesis. This is particularly important considering the fact that mutations beneficial to the activity of the enzyme are fairly rare. In fact, using too high a level of mutagenesis may counter or inhibit the desired benefit of a useful mutation.

While both of the aforementioned methods are effective for creating randomized pools of macromolecule variants, a third method, termed "DNA Shuffling", or "sexual PCR" (WPC, Stemmer, PNAS, 91:10747, (1994)) has recently been elucidated. DNA shuffling has also been referred to as "directed molecular evolution", "exon-shuffling", "directed enzyme evolution", "in vitro evolution", and "artificial evolution". Such reference terms are known in the art and are encompassed by the invention. This new, preferred, method apparently overcomes the limitations of the previous methods in that it not only propagates positive traits, but simultaneously eliminates negative traits in the resulting progeny.

DNA shuffling accomplishes this task by combining the principal of in vitro recombination, along with the method of "error-prone" PCR. In effect, you begin with a randomly digested pool of small fragments of your gene, created by Dnase I digestion, and then introduce said random fragments into an "error-prone" PCR assembly reaction. During the PCR reaction, the randomly sized DNA fragments not only hybridize to their cognate strand, but also may hybridize to other DNA fragments corresponding to different regions of the polynucleotide of interest—regions not typically accessible via hybridization of the entire polynucleotide. Moreover, since the PCR assembly reaction utilizes "error-prone" PCR reaction conditions, random mutations are introduced during the DNA synthesis step of the PCR reaction for all of the fragments -further diversifying the potential hybridization sites during the annealing step of the reaction.

A variety of reaction conditions could be utilized to carry-out the DNA shuffling reaction. However, specific reaction conditions for DNA shuffling are provided, for example, in PNAS, 91:10747, (1994). Briefly:

Prepare the DNA substrate to be subjected to the DNA shuffling reaction. Preparation may be in the form of simply purifying the DNA from contaminating cellular material, chemicals, buffers, oligonucleotide primers, deoxynucleotides, RNAs, etc., and may entail the use of DNA purification kits as those provided by Qiagen, Inc., or by the Promega, Corp., for example.

Once the DNA substrate has been purified, it would be subjected to Dnase I digestion. About 2-4-ug of the DNA substrate(s) would be digested with 0.0015 units of Dnase I (Sigma) per ul in 100 ul of 50 mM Tris-HCL, pH 7.4/1 mM MgCl2 for 10-20 min. at room temperature. The resulting fragments of 10-50 bp could then be purified by running them through a 2% low-melting point agarose gel by electrophoresis onto DE81 ion-exchange paper (Whatmann) or could be purified using Microcon concentrators (Amicon) of the appropriate molecular weight cutoff, or could use oligonucleotide purification columns (Qiagen), in addition to other methods known in the art. If using DE81 ion-exchange paper, the 10-50 bp fragments could be eluted from said paper using 1 M NaCl, followed by ethanol precipitation.

The resulting purified fragments would then be subjected to a PCR assembly reaction by re-suspension in a PCR mixture containing: 2 mM of each dNTP, 2.2 mM MgCl2, 50 mM KCl, 10 mM Tris.HCL, pH 9.0, and 0.1% Triton X-100, at a final fragment concentration of 10-30 ng/ul. No primers are added at this point. Taq DNA polymerase (Promega) would be used at 2.5 units per 100 ul of reaction mixture. A PCR program of 94 C for 60s; 94 C for 30s, 50-55 C for 30s, and 72 C for 30s using 30-45 cycles, followed by 72 C for 5 min using an MJ Research (Cambridge, Mass.) PTC-150 thermocycler. After the assembly reaction is completed, a 1:40 dilution of the resulting primerless product would then be introduced into a PCR mixture (using the same buffer mixture used for the assembly reaction) containing 0.8 um of each primer and subjecting this mixture to 15 cycles of PCR (using 94 C for 30 s, 50 C for 30 s, and 72 C for 30 s). The referred primers would be primers corresponding to the nucleic acid sequences of the polynucleotide(s) utilized in the shuffling reaction. Said primers could consist of modified nucleic acid base pairs using methods known in the art and referred to else where herein, or could contain additional sequences (i.e., for adding restriction sites, mutating specific base-pairs, etc.).

The resulting shuffled, assembled, and amplified product can be purified using methods well known in the art (e.g., Qiagen PCR purification kits) and then subsequently cloned using appropriate restriction enzymes.

Although a number of variations of DNA shuffling have been published to date, such variations would be obvious to the skilled artisan and are encompassed by the invention. The DNA shuffling method can also be tailored to the desired level of mutagenesis using the methods described by Zhao, et al. (Nucl Acid Res., 25(6): 1307-1308, (1997).

As described above, once the randomized pool has been created, it can then be subjected to a specific screen to identify the variant possessing the desired characteristic(s). Once the variant has been identified, DNA corresponding to the variant could then be used as the DNA substrate for initiating another round of DNA shuffling. This cycle of shuffling, selecting the optimized variant of interest, and then re-shuffling, can be repeated until the ultimate variant is obtained. Examples of model screens applied to identify variants created using DNA shuffling technology may be found in the following publications: J. C., Moore, et al., J. Mol. Biol., 272:336-347, (1997), F. R., Cross, et al., Mol. Cell. Biol., 18:2923-2931, (1998), and A. Crameri., et al., Nat. Biotech., 15:436-438, (1997).

DNA shuffling has several advantages. First, it makes use of beneficial mutations. When combined with screening, DNA shuffling allows the discovery of the best mutational combinations and does not assume that the best combination contains all the mutations in a population. Secondly, recombination occurs simultaneously with point mutagenesis. An effect of forcing DNA polymerase to synthesize full-length genes from the small fragment DNA pool is a background mutagenesis rate. In combination with a stringent selection method, enzymatic activity has been evolved up to 16000 fold increase over the wild-type form of the enzyme. In essence, the background mutagenesis yielded the genetic variability on which recombination acted to enhance the activity.

A third feature of recombination is that it can be used to remove deleterious mutations. As discussed above, during the process of the randomization, for every one beneficial mutation, there may be at least one or more neutral or inhibitory mutations. Such mutations can be removed by including in the assembly reaction an excess of the wild-type random-size fragments, in addition to the random-size fragments of the selected mutant from the previous selection. During the next selection, some of the most active variants of the polynucleotide/polypeptide/enzyme, should have lost the inhibitory mutations.

Finally, recombination enables parallel processing. This represents a significant advantage since there are likely multiple characteristics that would make a protein more desirable (e.g. solubility, activity, etc.). Since it is increasingly difficult to screen for more than one desirable trait at a time, other methods of molecular evolution tend to be inhibitory. However, using recombination, it would be possible to combine the randomized fragments of the best representative variants for the various traits, and then select for multiple properties at once.

DNA shuffling can also be applied to the polynucleotides and polypeptides of the present invention to decrease their immunogenicity in a specified host. For example, a particular variant of the present invention may be created and isolated using DNA shuffling technology. Such a variant may have all of the desired characteristics, though may be highly immunogenic in a host due to its novel intrinsic structure. Specifically, the desired characteristic may cause the polypeptide to have a non-native structure which could no longer be recognized as a "self" molecule, but rather as a "foreign", and thus activate a host immune response directed against the novel variant. Such a limitation can be overcome, for example, by including a copy of the gene sequence for a xenobiotic ortholog of the native protein in with the gene sequence of the novel variant gene in one or more cycles of DNA shuffling. The molar ratio of the ortholog and novel variant DNAs could be varied accordingly. Ideally, the resulting hybrid variant identified would contain at least some of the coding sequence which enabled the xenobiotic protein to evade the host immune system, and additionally, the coding sequence of the original novel variant that provided the desired characteristics.

Likewise, the invention encompasses the application of DNA shuffling technology to the evolution of polynucleotides and polypeptides of the invention, wherein one or more cycles of DNA shuffling include, in addition to the gene template DNA, oligonucleotides coding for known allelic sequences, optimized codon sequences, known variant sequences, known polynucleotide polymorphism sequences, known ortholog sequences, known homologue sequences, additional homologous sequences, additional non-homologous sequences, sequences from another species, and any number and combination of the above.

In addition to the described methods above, there are a number of related methods that may also be applicable, or desirable in certain cases. Representative among these are the methods discussed in PCT applications WO 98/31700, and WO 98/32845, which are hereby incorporated by reference. Furthermore, related methods can also be applied to the polynucleotide sequences of the present invention in order to evolve invention for creating ideal variants for use in gene therapy, protein engineering, evolution of whole cells containing the variant, or in the evolution of entire enzyme pathways containing polynucleotides of the invention as described in PCT applications WO 98/13485, WO 98/13487, WO 98/27230, WO 98/31837, and Crameri, A., et al., Nat. Biotech., 15:436-438, (1997), respectively.

Additional methods of applying "DNA Shuffling" technology to the polynucleotides and polypeptides of the present invention, including their proposed applications, may be found in U.S. Pat. No. 5,605,793; PCT Application No. WO 95/22625; PCT Application No. WO 97/20078; PCT Application No. WO 97/35966; and PCT Application No. WO 98/42832; PCT Application No. WO 00/09727 specifically provides methods for applying DNA shuffling to the identification of herbicide selective crops which could be applied to the polynucleotides and polypeptides of the present invention; additionally, PCT Application No. WO 00/12680 provides methods and compositions for generating, modifying, adapting, and optimizing polynucleotide sequences that confer detectable phenotypic properties on plant species; each of the above are hereby incorporated in their entirety herein for all purposes.

Example 26

Method of Determining Alterations in a Gene Corresponding to a Polynucleotide

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95 degrees C. for 30 seconds; 60-120 seconds at 52-58 degrees C.; and 60-120 seconds at 70 degrees C., using buffer solutions described in Sidransky et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products are cloned into T-tailed vectors as described in Holton et al., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 15 are nick-translated with digoxigenindeoxy-uridine 5'-triphosphate (Boehringer Manheim), and FISH performed as described in Johnson et al., Methods Cell Biol. 35:73-99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 27

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described elsewhere herein. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25-400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 28

Formulation

The invention also provides methods of treatment and/or prevention diseases, disorders, and/or conditions (such as, for example, any one or more of the diseases or disorders disclosed herein) by administration to a subject of an effective amount of a Therapeutic. By therapeutic is meant a polynucleotides or polypeptides of the invention (including fragments and variants), agonists or antagonists thereof, and/or antibodies thereto, in combination with a pharmaceutically acceptable carrier type (e.g., a sterile carrier).

The Therapeutic will be formulated and dosed in a fashion consistent with good medical practice, taking into account the clinical condition of the individual patient (especially the side effects of treatment with the Therapeutic alone), the site of delivery, the method of administration, the scheduling of administration, and other factors known to practitioners. The "effective amount" for purposes herein is thus determined by such considerations.

As a general proposition, the total pharmaceutically effective amount of the Therapeutic administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Therapeutic is typically administered at a dose rate of about 1 ug/kg/hour to about 50 ug/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Therapeutics can be administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrasternal, subcutaneous and intraarticular injection and infusion.

In yet an additional embodiment, the Therapeutics of the invention are delivered orally using the drug delivery technology described in U.S. Pat. No. 6,258,789, which is hereby incorporated by reference herein.

Therapeutics of the invention are also suitably administered by sustained-release systems. Suitable examples of sustained-release Therapeutics are administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Therapeutics of the invention may also be suitably administered by sustained-release systems. Suitable examples of sustained-release Therapeutics include suitable polymeric materials (such as, for example, semi-permeable polymer matrices in the form of shaped articles, e.g., films, or microcapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547-556 (1983)), poly (2-hydroxyethyl methacrylate) (Langer et al., J. Biomed. Mater. Res. 15:167-277 (1981), and Langer, Chem. Tech. 12:98-105 (1982)), ethylene vinyl acetate (Langer et al., Id.) or poly-D-(-)-3-hydroxybutyric acid (EP 133,988).

Sustained-release Therapeutics also include liposomally entrapped Therapeutics of the invention (see, generally, Langer, Science 249:1527-1533 (1990); Treat et al., in Liposomes in the Therapy of Infectious Disease and Cancer, Lopez-Berestein and Fidler (eds.), Liss, N.Y., pp. 317-327 and 353-365 (1989)). Liposomes containing the Therapeutic are prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal Therapeutic.

In yet an additional embodiment, the Therapeutics of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (Science 249:1527-1533 (1990)).

For parenteral administration, in one embodiment, the Therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the Therapeutic.

Generally, the formulations are prepared by contacting the Therapeutic uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The Therapeutic will typically be formulated in such vehicles at a concentration of about 0.1 mg/ml to 100 mg/ml, preferably 1-10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Therapeutic solution, and the resulting mixture is lyophilized. The infusion solution is prepared by reconstituting the lyophilized Therapeutic using bacteriostatic Water-for-Injection.

The invention also provides a pharmaceutical pack or kit comprising one or more containers filled with one or more of the ingredients of the Therapeutics of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the Therapeutics may be employed in conjunction with other therapeutic compounds.

The Therapeutics of the invention may be administered alone or in combination with adjuvants. Adjuvants that may be administered with the Therapeutics of the invention include, but are not limited to, alum, alum plus deoxycholate (ImmunoAg), MTP-PE (Biocine Corp.), QS21 (Genentech, Inc.), BCG, and MPL. In a specific embodiment, Therapeutics of the invention are administered in combination with alum. In another specific embodiment, Therapeutics of the invention are administered in combination with QS-21. Further adjuvants that may be administered with the Therapeutics of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the Therapeutics of the invention include, but are not limited to, vaccines directed toward protection against MMR (measles, mumps, rubella), polio, varicella, tetanus/diptheria, hepatitis A, hepatitis B, *haemophilus influenzae* B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The Therapeutics of the invention may be administered alone or in combination with other therapeutic agents. Therapeutic agents that may be administered in combination with the Therapeutics of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the Therapeutics of the invention are administered in combination with members of the TNF family. TNF, TNF-related or TNF-like molecules that may be administered with the Therapeutics of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12, and soluble forms CD154, CD70, and CD153.

In certain embodiments, Therapeutics of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the Therapeutics of the invention, include, but are not limited to, RETROVIR (zidovudine/AZT), VIDEX (didanosine/ddI), HIVID (zalcitabine/ddC), ZERIT (stavudine/d4T), EPIVIR (lamivudine/3TC), and COMBIVIR (zidovudine/lamivudine). Non-nucleoside reverse transcriptase inhibitors that may be administered in combination with the Therapeutics of the invention, include, but are not limited to, VIRAMUNE (nevirapine), RESCRIPTOR (delavirdine), and SUSTIVA (efavirenz). Protease inhibitors that may be administered in combination with the Therapeutics of the invention, include, but are not limited to, CRIXIVAN (indinavir), NORVIR (ritonavir), INVIRASE (saquinavir), and VIRACEPT (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In other embodiments, Therapeutics of the invention may be administered in combination with anti-opportunistic infection agents. Anti-opportunistic agents that may be administered in combination with the Therapeutics of the invention, include, but are not limited to, TRIMETHOPRIM-SULFAMETHOXAZOLE, DAPSONE, PENTAMIDINE, ATOVAQUONE, ISONIAZID, RIFAMPIN, PYRAZINAMIDE, ETHAMBUTOL, RIFABUTIN, CLARITHROMYCIN, AZITHROMYCIN, GANCICLBVIR, FOSCARNET, CIDOFOVIR, FLUCONAZOLE, ITRACONAZOLE, KETOCONAZOLE, ACYCLOVIR, FAMCICOLVIR, PYRIMETHAMINE, LEUCOVORIN, NEUPOGEN (filgrastim/G-CSF), and LEUKINE (sargramostim/GM-CSF). In a specific embodiment, Therapeutics of the invention are used in any combination with TRIMETHOPRIM-SULFAMETHOXAZOLE, DAPSONE, PENTAMIDINE, and/or ATOVAQUONE to prophylactically treat or prevent an opportunistic *Pneumocystis carinii* pneumonia infection. In another specific embodiment, Therapeutics of the invention are used in any combination with ISONIAZID, RIFAMPIN, PYRAZINAMIDE, and/or ETHAMBUTOL to prophylactically treat or prevent an opportunistic *Mycobacterium avium* complex infection. In another specific embodiment, Therapeutics of the invention are used in any combination with RIFABUTIN, CLARITHROMYCIN, and/or AZITHROMYCIN to prophylactically treat or prevent an opportunistic *Mycobacterium tuberculosis* infection. In another specific embodiment, Therapeutics of the invention are used in any combination with GANCICLOVIR, FOSCARNET, and/or CIDOFOVIR to prophylactically treat or prevent an opportunistic cytomegalovirus infection. In another specific embodiment, Therapeutics of the invention are used in any combination with FLUCONAZOLE, ITRACONAZOLE, and/or KETOCONAZOLE to prophylactically treat or prevent an opportunistic fungal infection. In another specific embodiment, Therapeutics of the invention are used in any combination with ACYCLOVIR and/or FAMCICOLVIR to prophylactically treat or prevent an opportunistic herpes simplex virus type I and/or type II infection. In another specific embodiment, Therapeutics of the invention are used in any combination with PYRIMETHAMINE and/or LEUCOVORIN to prophylactically treat or prevent an opportunistic *Toxoplasma gondii* infection. In another specific embodiment, Therapeutics of the invention are used in any combination with LEUCOVORIN and/or NEUPOGEN to prophylactically treat or prevent an opportunistic bacterial infection.

In a further embodiment, the Therapeutics of the invention are administered in combination with an antiviral agent. Antiviral agents that may be administered with the Therapeutics of the invention include, but are not limited to, acyclovir, ribavirin, amantadine, and remantidine.

In a further embodiment, the Therapeutics of the invention are administered in combination with an antibiotic agent. Antibiotic agents that may be administered with the Therapeutics of the invention include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the Therapeutics of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, Therapeutics of the invention are administered in combination with immunosuppressants. Immunosuppressants preparations that may be administered with the Therapeutics of the invention include, but are not limited to, ORTHOCLONE (OKT3), SANDIMMUNE/NEORAL/SANGDYA (cyclosporin), PROGRAF (tacrolimus), CELLCEPT (mycophenolate), Azathioprine, glucorticosteroids, and RAPAMUNE (sirolimus). In a specific embodiment, immunosuppressants may be used to prevent rejection of organ or bone marrow transplantation.

In an additional embodiment, Therapeutics of the invention are administered alone or in combination with one or more intravenous immune globulin preparations. Intravenous immune globulin preparations that may be administered with the Therapeutics of the invention include, but not limited to, GAMMAR, IVEEGAM, SANDOGLOBULIN, GAMMA-GARD S/D, and GAMIMUNE. In a specific embodiment, Therapeutics of the invention are administered in combination with intravenous immune globulin preparations in transplantation therapy (e.g., bone marrow transplant).

In an additional embodiment, the Therapeutics of the invention are administered alone or in combination with an anti-inflammatory agent. Anti-inflammatory agents that may be administered with the Therapeutics of the invention include, but are not limited to, glucocorticoids and the non-steroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the Therapeutics of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, Therapeutics of the invention are administered in combination with CHOP (cyclophosphamide, doxorubicin, vincristine, and prednisone) or any combination of the components of CHOP. In another embodiment, Therapeutics of the invention are administered in combination with Rituximab. In a further embodiment, Therapeutics of the invention are administered with Rituxmab and CHOP, or Rituxmab and any combination of the components of CHOP.

In an additional embodiment, the Therapeutics of the invention are administered in combination with cytokines. Cytokines that may be administered with the Therapeutics of the invention include, but are not limited to, IL2, IL3, IL4, IL5, IL6, IL7, IL10, IL12, IL13, IL15, anti-CD40, CD40L, IFN-gamma and TNF-alpha. In another embodiment, Therapeutics of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21.

In an additional embodiment, the Therapeutics of the invention are administered in combination with angiogenic proteins. Angiogenic proteins that may be administered with the Therapeutics of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., Growth Factors, 4:259-268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the Therapeutics of the invention are administered in combination with hematopoietic growth factors. Hematopoietic growth factors that may be administered with the Therapeutics of the invention include, but are not limited to, LEUKINE (SARGRAMOSTIM) and NEUPOGEN (FILGRASTIM).

In an additional embodiment, the Therapeutics of the invention are administered in combination with Fibroblast Growth Factors. Fibroblast Growth Factors that may be administered with the Therapeutics of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In an additional embodiment, the Therapeutics of the invention are administered in combination with other immune factors. Immune factors that may be administered with the Therapeutics of the invention include, but are not limited to, Ly9, CD2, CD48, CD58, 2B4, CD84, CDw15O, CTLA4, CTLA4Ig, Bsl1, Bsl2, Bsl3, BLYS, TRAIL, APRIL, B7, B7 antagonists, B7 agonists, and Ret16.

In a specific embodiment, formulations of the present invention may further comprise antagonists of P-glycoprotein (also referred to as the multiresistance protein, or PGP), including antagonists of its encoding polynucleotides (e.g., antisense oligonucleotides, ribozymes, zinc-finger proteins, etc.). P-glycoprotein is well known for decreasing the efficacy of various drug administrations due to its ability to export intracellular levels of absorbed drug to the cell exterior. While this activity has been particularly pronounced in cancer cells in response to the administration of chemotherapy regimens, a variety of other cell types and the administration of other drug classes have been noted (e.g., T-cells and anti-HIV drugs). In fact, certain mutations in the PGP gene significantly reduces PGP function, making it less able to force drugs out of cells. People who have two versions of the mutated gene—one inherited from each parent—have more than four times less PGP than those with two normal versions of the gene. People may also have one normal gene and one mutated one. Certain ethnic populations have increased incidence of such PGP mutations. Among individuals from Ghana, Kenya, the Sudan, as well as African Americans, frequency of the normal gene ranged from 73% to 84%. In contrast, the frequency was 34% to 59% among British whites, Portuguese, Southwest Asian, Chinese, Filipino and Saudi populations. As a result, certain ethnic populations may require increased administration of PGP antagonist in the formulation of the present invention to arrive at the an efficacious dose of the therapeutic (e.g., those from African descent). Conversely, certain ethnic populations, particularly those having increased frequency of the mutated PGP (e.g., of Caucasian descent, or non-African descent) may require less pharmaceutical compositions in the formulation due to an effective increase in efficacy of such compositions as a result of the increased effective absorption (e.g., less PGP activity) of said composition.

Moreover, in another specific embodiment, formulations of the present invention may further comprise antagonists of OATP2 (also referred to as the multiresistance protein, or MRP2), including antagonists of its encoding polynucleotides (e.g., antisense oligonucleotides, ribozymes, zinc-finger proteins, etc.). The invention also further comprises any additional antagonists known to inhibit proteins thought to be attributable to a multidrug resistant phenotype in proliferating cells.

Preferred antagonists that formulations of the present may comprise include the potent P-glycoprotein inhibitor elacridar, and/or LY-335979. Other P-glycoprotein inhibitors known in the art are also encompassed by the present invention.

In additional embodiments, the Therapeutics of the invention are administered in combination with other therapeutic or prophylactic regimens, such as, for example, radiation therapy.

Example 29

Method of Treating Decreased Levels Of the Polypeptide

The present invention relates to a method for treating an individual in need of an increased level of a polypeptide of the invention in the body comprising administering to such an individual a composition comprising a therapeutically effective amount of an agonist of the invention (including polypeptides of the invention). Moreover, it will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a Therapeutic comprising an amount of the polypeptide to increase the activity level of the polypeptide in such an individual.

For example, a patient with decreased levels of a polypeptide receives a daily dose 0.1-100 ug/kg of the polypeptide for six consecutive days. Preferably, the polypeptide is in the secreted form. The exact details of the dosing scheme, based on administration and formulation, are provided herein.

Example 30

Method of Treating Increased Levels Of the Polypeptide

The present invention also relates to a method of treating an individual in need of a decreased level of a polypeptide of the invention in the body comprising administering to such an individual a composition comprising a therapeutically effective amount of an antagonist of the invention (including polypeptides and antibodies of the invention).

In one example, antisense technology is used to inhibit production of a polypeptide of the present invention. This technology is one example of a method of decreasing levels of a polypeptide, preferably a secreted form, due to a variety of etiologies, such as cancer. For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided herein.

Example 31

Method of Treatment Using Gene Therapy-Ex Vivo

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219-25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 15 using primers and having appropriate restriction sites and initiation/stop codons, if necessary. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 32

Gene Therapy Using Endogenous Genes Corresponding to Polynucleotides of the Invention Another method of gene therapy according to the present invention involves operably associating the endogenous polynucleotide sequence of the invention with a promoter via homologous recombination as described, for example, in U.S. Pat. No. 5,641,670, issued Jun. 24, 1997; International Publication NO: WO 96/29411, published Sep. 26, 1996; International Publication NO: WO 94/12650, published Aug.

4, 1994; Koller et al., Proc. Natl. Acad. Sci. USA, 86:8932-8935 (1989); and Zijlstra et al., Nature, 342:435-438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous polynucleotide sequence, flanking the promoter. The targeting sequence will be sufficiently near the 5' end of the polynucleotide sequence so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous polynucleotide sequence. This results in the expression of polynucleotide corresponding to the polynucleotide in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2 HPO4, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the locus corresponding to the polynucleotide of the invention, plasmid pUC18 (MBI Fermentas, Amherst, N.Y.) is digested with HindIII. The CMV promoter is amplified by PCR with an XbaI site on the 5' end and a BamHI site on the 3' end. Two non-coding sequences are amplified via PCR: one non-coding sequence (fragment 1) is amplified with a HindIII site at the 5' end and an Xba site at the 3' end; the other non-coding sequence (fragment 2) is amplified with a BamHI site at the 5' end and a HindIII site at the 3' end. The CMV promoter and the fragments (1 and 2) are digested with the appropriate enzymes (CMV promoter—XbaI and BamHI; fragment 1—XbaI; fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 pg/ml. 0.5 ml of the cell suspension (containing approximately $1.5 \times 10^6$ cells) is then added to the cuvette, and the cell suspension and DNA solutions are gently mixed. Electroporation is performed with a Gene-Pulser apparatus (Bio-Rad). Capacitance and voltage are set at 960 µF and 250-300 V, respectively. As voltage increases, cell survival decreases, but the percentage of surviving cells that stably incorporate the introduced DNA into their genome increases dramatically. Given these parameters, a pulse time of approximately 14-20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16-24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 33

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide. The polynucleotide of the present invention may be operatively linked to a promoter or any other genetic elements necessary for the expression of the polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata et al., Cardiovasc. Res. 35(3):470-479 (1997); Chao et al., Pharmacol. Res. 35(6): 517-522 (1997); Wolff, Neuromuscul. Disord. 7(5):314-318 (1997); Schwartz et al., Gene Ther. 3(5):405-411 (1996); Tsurumi et al., Circulation 94(12):3281-3290 (1996) (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. NY Acad. Sci. 772:126-139 and Abdallah B. et al. (1995) Biol. Cell 85(1):1-7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 34

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691-698 (1994); Carver et al., Biotechnology (NY) 11:1263-1270 (1993); Wright et al., Biotechnology (NY) 9:830-834 (1991); and Hoppe et al., U.S. Pat. No. 4,873,191 (1989)); retrovirus mediated gene transfer into germ lines (Van der Putten et al., Proc. Natl. Acad. Sci., USA 82:6148-6152 (1985)), blastocysts or embryos; gene targeting in embryonic stem cells (Thompson et al., Cell 56:313-321 (1989)); electroporation of cells or embryos (Lo, 1983, Mol. Cell. Biol. 3:1803-1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717-723 (1989); etc. For a review of such techniques, see Gordon, "Transgenic Animals," Intl. Rev. Cytol. 115:171-229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64-66 (1996); Wilmut et al., Nature 385:810-813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232-6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265: 103-106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (RT-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 35

Knock-Out Animals

Endogenous gene expression can also be reduced by inactivating or "knocking out" the gene and/or its promoter using targeted homologous recombination. (E.g., see Smithies et al., Nature 317:230-234 (1985); Thomas & Capecchi, Cell 51:503-512 (1987); Thompson et al., Cell 5:313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 36

Method of Isolating Antibody Fragments Directed Against LTRPC3g, LTRPC3h, LTRPC3i, LTRPC3j, LTRPC3k, or LTRPC3l from a Library of scFvs Naturally occurring V-genes isolated from human PBLs are constructed into a library of antibody fragments which contain reactivities against LTRPC3g, LTRPC3h, LTRPC3l, LTRPC3j, LTRPC3k, or LTRPC3l to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 E. coli harboring the phagemid are used to inoculate 50 ml of 2×TY containing 1% glucose and 100 pg/ml of ampicillin (2×TY-AMP-GLU) and grown to an O.D. of 0.8 with shaking. Five ml of this culture is used to inoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 µg/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 µg ampicillin/ml and 25 pg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 µm filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 pg/ml or 10 µg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 µg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Moreover, in another preferred method, the antibodies directed against the polypeptides of the present invention may be produced in plants. Specific methods are disclosed in U.S. Pat. Nos. 5,959,177, and 6,080,560, which are hereby incorporated in their entirety herein. The methods not only describe methods of expressing antibodies, but also the means of assembling foreign multimeric proteins in plants (i.e., antibodies, etc,), and the subsequent secretion of such antibodies from the plant.

Example 37

Identification and Cloning of VH and VL Domains of Antibodies Directed Against the LTRPC3g, LTRPC3h, LTRPC3l, LTRPC3j, LTRPC3k, or LTRPC3l Polypeptide VH and VL domains may be identified and cloned from cell lines expressing an antibody directed against a LTRPC3g, LTRPC3h, LTRPC3i, LTRPC3j, LTRPC3k, or LTRPC3l epitope by performing PCR with VH and VL specific primers on cDNA made from the antibody expressing cell lines. Briefly, RNA is isolated from the cell lines and used as a template for RT-PCR designed to amplify the VH and VL domains of the antibodies expressed by the EBV cell lines. Cells may be lysed using the TRIzol reagent (Life Technologies, Rockville, Md.) and extracted with one fifth volume of chloroform. After addition of chloroform, the solution is allowed to incubate at room temperature for 10 minutes, and then centrifuged at 14,000 rpm for 15 minutes at 4 C in a tabletop centrifuge. The supernatant is collected and RNA is precipitated using an equal volume of isopropanol. Precipitated RNA is pelleted by centrifuging at 14,000 rpm for 15 minutes at 4 C in a tabletop centrifuge.

Following centrifugation, the supernatant is discarded and washed with 75% ethanol. Following the wash step, the RNA is centrifuged again at 800 rpm for 5-minutes at 4 C. The supernatant is discarded and the pellet allowed to air dry. RNA is the dissolved in DEPC water and heated to 60 C for 10 minutes. Quantities of RNA can be determined using optical density measurements. cDNA may be synthesized, according to methods well-known in the art and/or described herein, from 1.5-2.5 micrograms of RNA using reverse transcriptase and random hexamer primers. cDNA is then used as a template for PCR amplification of VH and VL domains.

Primers used to amplify VH and VL genes are shown below. Typically a PCR reaction makes use of a single 5'primer and a single 3'primer. Sometimes, when the amount of available RNA template is limiting, or for greater efficiency, groups of 5' and/or 3'primers may be used. For example, sometimes all five VH-5'primers and all JH3'primers are used in a single PCR reaction. The PCR reaction is carried out in a 50 microliter volume containing 1×PCR buffer, 2 mM of each dNTP, 0.7 units of High Fidelity Taq polymerse, 5'primer mix, 3'primer mix and 7.5 microliters of cDNA. The 5' and 3'primer mix of both VH and VL can be made by pooling together 22 pmole and 28 pmole, respectively, of each of the individual primers. PCR conditions are: 96 C for 5 minutes ; followed by 25 cycles of 94 C for 1 minute, 50 C for 1 minute, and 72 C for 1 minute ; followed by an extension cycle of 72 C for 10 minutes. After the reaction has been completed, sample tubes may be stored at 4 C.

Primer Sequences Used to Amplify VH domains

| Primer name | Primer Sequence | SEQ ID NO: |
|---|---|---|
| Hu VH1-5' | CAGGTGCAGCTGGTGCAGTCTGG | 132 |
| Hu VH2-5' | CAGGTCAACTTAAGGGAGTCTGG | 133 |
| Hu VH3-5' | GAGGTGCAGCTGGTGGAGTCTGG | 134 |
| Hu VH4-5' | CAGGTGCAGCTGCAGGAGTCGGG | 135 |
| Hu VH5-5' | GAGGTGCAGCTGTTGCAGTCTGC | 136 |
| Hu VH6-5' | CAGGTACAGCTGCAGCAGTCAGG | 137 |
| Hu JH1-5' | TGAGGAGACGGTGACCAGGGTGCC | 138 |
| Hu JH3-5' | TGAAGAGACGGTGACCATTGTCCC | 139 |
| Hu JH4-5' | TGAGGAGACGGTGACCAGGGTTCC | 140 |
| Hu JH6-5' | TGAGGAGACGGTGACCGTGGTCCC | 141 |

Primer Sequences Used to Amplify VL domains

| Primer name | Primer Sequence | SEQ ID NO: |
|---|---|---|
| Hu Vkappa1-5' | GACATCCAGATGACCCAGTCTCC | 142 |
| Hu Vkappa2a-5' | GATGTTGTGATGACTCAGTCTCC | 143 |
| Hu Vkappa2b-5' | GATATTGTGATGACTCAGTCTCC | 144 |
| Hu Vkappa3-5' | GAAATTGTGTTGACGCAGTCTCC | 145 |
| Hu Vkappa4-5' | GACATCGTGATGACCCAGTCTCC | 146 |
| Hu Vkappa5-5' | GAAACGACACTCACGCAGTCTCC | 147 |
| Hu Vkappa6-5' | GAAATTGTGCTGACTCAGTCTCC | 148 |
| Hu Vlambda1-5' | CAGTCTGTGTTGACGCAGCCGCC | 149 |
| Hu Vlambda2-5' | CAGTCTGCCCTGACTCAGCCTGC | 150 |
| Hu Vlambda3-5' | TCCTATGTGCTGACTCAGCCACC | 151 |
| Hu Vlambda3b-5' | TCTTCTGAGCTGACTCAGGACCC | 152 |
| Hu Vlambda4-5' | CACGTTATACTGACTCAACCGCC | 153 |
| Hu Vlambda5-5' | CAGGCTGTGCTCACTCAGCCGTC | 154 |
| Hu Vlambda6-5' | AATTTTATGCTGACTCAGCCCCA | 155 |
| Hu Jkappa1-3' | ACGTTTGATTTCCACCTTGGTCCC | 156 |
| Hu Jkappa2-3' | ACGTTTGATCTCCAGCTTGGTCCC | 157 |
| Hu Jkappa3-3' | ACGTTTGATATCCACTTTGGTCCC | 158 |
| Hu Jkappa4-3' | ACGTTTGATCTCCACCTTGGTCCC | 159 |
| Hu Jkappa5-3' | ACGTTTAATCTCCAGTCGTGTCCC | 160 |
| Hu Vlambda1-3' | CAGTCTGTGTTGACGCAGCCGCC | 161 |
| Hu Vlambda2-3' | CAGTCTGCCCTGACTCAGCCTGC | 162 |
| Hu Vlambda3-3' | TCCTATGTGCTGACTCAGCCACC | 163 |
| Hu Vlambda3b-3' | TCTTCTGAGCTGACTCAGGACCC | 164 |
| Hu Vlambda4-3' | CACGTTATACTGACTCAACCGCC | 165 |
| Hu Vlambda5-3' | CAGGCTGTGCTCACTCAGCCGTC | 166 |
| Hu Vlambda6-3' | AATTTTATGCTGACTCAGCCCCA | 167 |

PCR samples are then electrophoresed on a 1.3% agarose gel. DNA bands of the expected sizes (−506 base pairs for VH domains, and 344 base pairs for VL domains) can be cut out of the gel and purified using methods well known in the art and/or described herein.

Purified PCR products can be ligated into a PCR cloning vector (TA vector from Invitrogen Inc., Carlsbad, Calif.). Individual cloned PCR products can be isolated after transfection of *E. coli* and blue/white color selection. Cloned PCR products may then be sequenced using methods commonly known in the art and/or described herein.

The PCR bands containing the VH domain and the VL domains can also be used to create full-length Ig expression vectors. VH and VL domains can be cloned into vectors containing the nucleotide sequences of a heavy (e.g., human IgG1 or human IgG4) or light chain (human kappa or human ambda) constant regions such that a complete heavy or light chain molecule could be expressed from these vectors when transfected into an appropriate host cell. Further, when cloned heavy and light chains are both expressed in one cell line (from either one or two vectors), they can assemble into a complete functional antibody molecule that is secreted into the cell culture medium. Methods using polynucleotides encoding VH and VL antibody domain to generate expression vectors that encode complete antibody molecules are well known within the art.

Example 38

Biological Effects of Polypeptides Of the Invention

Astrocyte and Neuronal Assays

Recombinant polypeptides of the invention, expressed in *Escherichia coli* and purified as described above, can be tested for activity in promoting the survival, neurite outgrowth, or phenotypic differentiation of cortical neuronal cells and for inducing the proliferation of glial fibrillary acidic protein immunopositive cells, astrocytes. The selection of cortical cells for the bioassay is based on the prevalent expression of FGF-1 and FGF-2 in cortical structures and on the previously reported enhancement of cortical neuronal survival resulting from FGF-2 treatment. A thymidine incorporation assay, for example, can be used to elucidate a polypeptide of the invention's activity on these cells.

Moreover, previous reports describing the biological effects of FGF-2 (basic FGF) on cortical or hippocampal neurons in vitro have demonstrated increases in both neuron survival and neurite outgrowth (Walicke et al., "Fibroblast growth factor promotes survival of dissociated hippocampal neurons and enhances neurite extension." Proc. Natl. Acad. Sci. USA 83:3012-3016. (1986), assay herein incorporated by reference in its entirety). However, reports from experiments done on PC-12 cells suggest that these two responses are not necessarily synonymous and may depend on not only which FGF is being tested but also on which receptor(s) are expressed on the target cells. Using the primary cortical neuronal culture paradigm, the ability of a polypeptide of the invention to induce neurite outgrowth can be compared to the response achieved with FGF-2 using, for example, a thymidine incorporation assay.

Fibroblast and Endothelial Cell Assays

Human lung fibroblasts are obtained from Clonetics (San Diego, Calif.) and maintained in growth media from Clonetics. Dermal microvascular endothelial cells are obtained from Cell Applications (San Diego, Calif.). For proliferation assays, the human lung fibroblasts and dermal microvascular endothelial cells can be cultured at 5,000 cells/well in a 96-well plate for one day in growth medium. The cells are then incubated for one day in 0.1% BSA basal medium. After replacing the medium with fresh 0.1% BSA medium, the cells are incubated with the test proteins for 3 days. Alamar Blue (Alamar Biosciences, Sacramento, Calif.) is added to each well to a final concentration of 10%. The cells are incubated for 4 hr. Cell viability is measured by reading in a CytoFluor fluorescence reader. For the PGE2 assays, the human lung fibroblasts are cultured at 5,000 cells/well in a 96-well plate for one day. After a medium change to 0.1% BSA basal medium, the cells are incubated with FGF-2 or polypeptides of the invention with or without IL-1 (for 24 hours. The supernatants are collected and assayed for PGE2 by EIA kit (Cayman, Ann Arbor, Mich.). For the IL-6 assays, the human lung fibroblasts are cultured at 5,000 cells/well in a 96-well plate for one day. After a medium change to 0.1% BSA basal medium, the cells are incubated with FGF-2 or with or without polypeptides of the invention IL-1(for 24 hours. The supernatants are collected and assayed for IL-6 by ELISA kit (Endogen, Cambridge, Mass.).

Human lung fibroblasts are cultured with FGF-2 or polypeptides of the invention for 3 days in basal medium before the addition of Alamar Blue to assess effects on growth of the fibroblasts. FGF-2 should show a stimulation at 10-2500 ng/ml which can be used to compare stimulation with polypeptides of the invention.

Parkinson Models

The loss of motor function in Parkinson's disease is attributed to a deficiency of striatal dopamine resulting from the degeneration of the nigrostriatal dopaminergic projection neurons. An animal model for Parkinson's that has been extensively characterized involves the systemic administration of 1-methyl-4 phenyl 1,2,3,6-tetrahydropyridine (MPTP). In the CNS, MPTP is taken-up by astrocytes and catabolized by monoamine oxidase B to 1-methyl-4-phenyl pyridine (MPP+) and released. Subsequently, MPP+ is actively accumulated in dopaminergic neurons by the high-affinity reuptake transporter for dopamine. MPP+ is then concentrated in mitochondria by the electrochemical gradient and selectively inhibits nicotidamide adenine disphosphate: ubiquinone oxidoreductionase (complex I), thereby interfering with electron transport and eventually generating oxygen radicals.

It has been demonstrated in tissue culture paradigms that FGF-2 (basic FGF) has trophic activity towards nigral dopaminergic neurons (Ferrari et al., Dev. Biol. 1989). Recently, Dr. Unsicker's group has demonstrated that administering FGF-2 in gel foam implants in the striatum results in the near complete protection of nigral dopaminergic neurons from the toxicity associated with MPTP exposure (Otto and Unsicker, J. Neuroscience, 1990).

Based on the data with FGF-2, polypeptides of the invention can be evaluated to determine whether it has an action similar to that of FGF-2 in enhancing dopaminergic neuronal survival in vitro and it can also be tested in vivo for protection of dopaminergic neurons in the striatum from the damage associated with MPTP treatment. The potential effect of a polypeptide of the invention is first examined in vitro in a dopaminergic neuronal cell culture paradigm. The cultures are prepared by dissecting the midbrain floor plate from gestation day 14 Wistar rat embryos. The tissue is dissociated with trypsin and seeded at a density of 200,000 cells/cm2 on polyorthinine-laminin coated glass coverslips. The cells are maintained in Dulbecco's Modified Eagle's medium and F12 medium containing hormonal supplements (N1). The cultures are fixed with paraformaldehyde after 8 days in vitro and are processed for tyrosine hydroxylase, a specific marker for dopaminergic neurons, immunohistochemical staining. Dissociated cell cultures are prepared from embryonic rats. The culture medium is changed every third day and the factors are also added at that time.

Since the dopaminergic neurons are isolated from animals at gestation day 14, a developmental time which is past the stage when the dopaminergic precursor cells are proliferating, an increase in the number of tyrosine hydroxylase immunopositive neurons would represent an increase in the number of dopaminergic neurons surviving in vitro. Therefore, if a polypeptide of the invention acts to prolong the survival of dopaminergic neurons, it would suggest that the polypeptide may be involved in Parkinson's Disease.

One skilled in the art could easily modify the exemplified studies to test the activity of polynucleotides of the invention (e.g., gene therapy), agonists, and/or antagonists of polynucleotides or polypeptides of the invention.

Example 39

The Effect of Polypeptides of the Invention on The Growth of Vascular Endothelial Cells On day 1, human umbilical vein endothelial cells (HUVEC) are seeded at 2-5×104 cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. A polypeptide having the amino acid sequence of SEQ ID NO:2, and positive controls, such as VEGF and basic FGF (bFGF) are added, at varying concentrations. On days 4 and 6, the medium is replaced. On day 8, cell number is determined with a Coulter Counter.

An increase in the number of HUVEC cells indicates that the polypeptide of the invention may proliferate vascular endothelial cells.

One skilled in the art could easily modify the exemplified studies to test the activity of polynucleotides of the invention (e.g., gene therapy), agonists, and/or antagonists of polynucleotides or polypeptides of the invention.

Example 40

Stimulatory Effect of Polypeptides of the Invention on the Proliferation of Vascular Endothelial Cells For evaluation of mitogenic activity of growth factors, the colorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) was performed (CellTiter 96 AQ, Promega). Cells are seeded in a 96-well plate (5,000 cells/well) in 0.1 mL serum-supplemented medium and are allowed to attach overnight. After serum-starvation for 12 hours in 0.5% FBS, conditions (bFGF, VEGF165 or a polypeptide of the invention in 0.5% FBS) with or without Heparin (8 U/ml) are added to wells for 48 hours. 20 mg of MTS/PMS mixture (1:0.05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. In Vitro Cell. Dev. Biol. 30A:512-518 (1994).

One skilled in the art could easily modify the exemplified studies to test the activity of polynucleotides of the invention (e.g., gene therapy), agonists, and/or antagonists of polynucleotides or polypeptides of the invention.

Example 41

Suppression of TNF Alpha-Induced Adhesion Molecule Expression by a Polypeptide of the Invention The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-a), a potent proinflammatory cytokine, is a stimulator of all three CAMs on endothelial cells and may be involved in a wide variety of inflammatory responses, often resulting in a pathological outcome.

The potential of a polypeptide of the invention to mediate a suppression of TNF-a induced CAM expression can be examined. A modified ELISA assay which uses ECs as a solid phase absorbent is employed to measure the amount of CAM expression on TNF-a treated ECs when co-stimulated with a member of the FGF family of proteins.

To perform the experiment, human umbilical vein endothelial cell (HUVEC) cultures are obtained from pooled cord harvests and maintained in growth medium (EGM-2; Clonetics, San Diego, Calif.) supplemented with 10% FCS and 1% penicillin/streptomycin in a 37 degree C. humidified incubator containing 5% CO2. HUVECs are seeded in 96-well plates at concentrations of 1×104 cells/well in EGM medium at 37 degree C. for 18-24 hrs or until confluent. The monolayers are subsequently washed 3 times with a serum-free solution of RPMI-1640 supplemented with 100 U/ml penicillin and 100 mg/ml streptomycin, and treated with a given cytokine and/or growth factor(s) for 24 h at 37 degree C. Following incubation, the cells are then evaluated for CAM expression.

Human Umbilical Vein Endothelial cells (HUVECs) are grown in a standard 96 well plate to confluence. Growth medium is removed from the cells and replaced with 90 ul of 199 Medium (10% FBS). Samples for testing and positive or negative controls are added to the plate in triplicate (in 10 ul volumes). Plates are incubated at 37 degree C. for either 5 h (selectin and integrin expression) or 24 h (integrin expression only). Plates are aspirated to remove medium and 100 µl of 0.1% paraformaldehyde-PBS(with Ca++ and Mg++) is added to each well. Plates are held at 4° C. for 30 min.

Fixative is then removed from the wells and wells are washed 1× with PBS(+Ca,Mg)+0.5% BSA and drained. Do not allow the wells to dry. Add 10 µl of diluted primary antibody to the test and control wells. Anti-ICAM-1-Biotin, Anti-VCAM-1-Biotin and Anti-E-selectin-Biotin are used at a concentration of 10 pg/ml (1:10 dilution of 0.1 mg/ml stock antibody). Cells are incubated at 37° C. for 30 min. in a humidified environment. Wells are washed ×3 with PBS(+Ca, Mg)+0.5% BSA.

Then add 20 µl of diluted ExtrAvidin-Alkaline Phosphatase (1:5,000 dilution) to each well and incubated at 37° C. for 30 min. Wells are washed ×3 with PBS(+Ca,Mg)+0.5% BSA. 1 tablet of p-Nitrophenol Phosphate pNPP is dissolved in 5 ml of glycine buffer (pH 10.4). 100 µl of pNPP substrate in glycine buffer is added to each test well. Standard wells in triplicate are prepared from the working dilution of the ExtrAvidin-Alkaline Phosphatase in glycine buffer: 1:5,000 (100)>10-0.5>10-1>10-1.5. 5 µl of each dilution is added to triplicate wells and the resulting AP content in each well is 5.50 ng, 1.74 ng, 0.55 ng, 0.18 ng. 100 µl of pNNP reagent must then be added to each of the standard wells. The plate must be incubated at 37° C. for 4 h. A volume of 50 µl of 3M NaOH is added to all wells. The results are quantified on a plate reader at 405 nm. The background subtraction option is used on blank wells filled with glycine buffer only. The template is set up to indicate the concentration of AP-conjugate in each standard well [5.50 ng; 1.74 ng; 0.55 ng; 0.18 ng]. Results are indicated as amount of bound AP-conjugate in each sample.

One skilled in the art could easily modify the exemplified studies to test the activity of polynucleotides of the invention (e.g., gene therapy), agonists, and/or antagonists of polynucleotides or polypeptides of the invention.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

---

What is claimed is:

1. An isolated polypeptide comprising a polypeptide selected from the group consisting of:
   (a) an isolated polypeptide comprising amino acids 1 to 1709 of SEQ ID NO:2;
   (b) an isolated polypeptide comprising amino acids 2 to 1709 of SEQ ID NO:2;
   (c) an isolated polypeptide encoded by nucleotides 72 to 5198 of SEQ ID NO:1; and
   (d) an isolated polypeptide encoded by nucleotides 75 to 5198 of SEQ ID NO:1.

2. The isolated polypeptide of claim 1, wherein said polypeptide is (a).

3. The isolated polypeptide of claim 1, wherein said polypeptide is (b).

4. The isolated polypeptide of claim 1, wherein said polypeptide is (c).

5. The isolated polypeptide of claim 1, wherein said polypeptide is (d).

6. An isolated polypeptide produced by a method comprising:
   (a) culturing an isolated recombinant host cell comprising a vector that comprises the coding region encoding the polypeptide of claim 1 under conditions such that the polypeptide of claim 1 is expressed; and
   (b) recovering said polypeptide.

7. The isolated polypeptide of claim 1 further comprising a heterologous polypeptide.

8. The isolated polypeptide of claim 7 wherein said heterologous polypeptide is the Fc domain of immunoglobulin.

9. An isolated polypeptide having at least 95.0% identity to amino acids 1 to 1709 of SEQ ID NO:2, wherein percent identity is calculated using a CLUSTALW global sequence alignment using default parameters, and wherein said polypeptide has storage-operated $Ca^{2+}$ channel activity.

10. An isolated polypeptide comprising at least 1555 contiguous amino acids of SEQ ID NO:2, and wherein said polypeptide has storage-operated $Ca^{2+}$ channel activity.

11. An isolated polypeptide comprising a polypeptide selected from the group consisting of:
   (a) an isolated polypeptide comprising amino acids 155 to 1709 of SEQ ID NO:2; and
   (b) an isolated polypeptide comprising amino acids 1 to 1555 of SEQ ID NO:2, wherein said polypeptide has storage-operated $Ca^{2+}$ channel activity.

* * * * *

UNITED STATES PATENT AND TRADEMARK OFFICE
CERTIFICATE OF CORRECTION

PATENT NO. : 7,459,532 B2  Page 1 of 1
APPLICATION NO. : 11/985981
DATED : December 2, 2008
INVENTOR(S) : Lee Ning et al.

It is certified that error appears in the above-identified patent and that said Letters Patent is hereby corrected as shown below:

Column 135, Line 52
Delete ", a polypeptide sequence encoded by the cDNA in ATCC Deposit No:PTA-4175"

Signed and Sealed this

Eighteenth Day of May, 2010

David J. Kappos
*Director of the United States Patent and Trademark Office*

SEQUENCE LISTING

<160> NUMBER OF SEQ ID NOS: 171

<210> SEQ ID NO 1
<211> LENGTH: 5201
<212> TYPE: DNA
<213> ORGANISM: Homo sapiens
<220> FEATURE:
<221> NAME/KEY: CDS
<222> LOCATION: (72)..(5198)

<400> SEQUENCE: 1

```
cgcccgcggc gaggagccag cgagagcgct cggcgctggg ctgtttcccg gccgagggag        60
gcgaacttct c atg ggg aag aag tgg agg gat gcg gcg gaa atg gag cgg       110
            Met Gly Lys Lys Trp Arg Asp Ala Ala Glu Met Glu Arg
            1               5                   10 ggc tgc tcc gac cgc gag gac aac gcg gag agc cgc aga cgc agc cgg        158
Gly Cys Ser Asp Arg Glu Asp Asn Ala Glu Ser Arg Arg Arg Ser Arg
15                  20                  25 agc gcc agc cgg ggc agg ttt gcc gag tcg tgg aaa agg tta agt tcc        206
Ser Ala Ser Arg Gly Arg Phe Ala Glu Ser Trp Lys Arg Leu Ser Ser
30                  35                  40                  45 aag cag ggg tcc acc aaa cgc tcg gga ctc ccg tcg cag cag acg ccg        254
Lys Gln Gly Ser Thr Lys Arg Ser Gly Leu Pro Ser Gln Gln Thr Pro
50                  55                  60 gct cag aaa tcc tgg ata gaa aga gca ttt tat aaa aga gaa tgt gtc        302
Ala Gln Lys Ser Trp Ile Glu Arg Ala Phe Tyr Lys Arg Glu Cys Val
65                  70                  75 cac atc ata ccc agc acc aaa gac ccc cat agg tgt tgc tgt ggg cgt        350
His Ile Ile Pro Ser Thr Lys Asp Pro His Arg Cys Cys Cys Gly Arg
80                  85                  90 ctg ata ggc cag cat gtt ggc ctc acc ccc agt atc tcc gtg ctt cag        398
Leu Ile Gly Gln His Val Gly Leu Thr Pro Ser Ile Ser Val Leu Gln
95                  100                 105 aat gag aaa aat gaa agt cgc ctc tcc cga aat gac atc cag tct gaa        446
Asn Glu Lys Asn Glu Ser Arg Leu Ser Arg Asn Asp Ile Gln Ser Glu
110                 115                 120                 125 aag tgg tcc atc agc aaa cac act caa ctc agc cct acg gat gct ttt        494
Lys Trp Ser Ile Ser Lys His Thr Gln Leu Ser Pro Thr Asp Ala Phe
130                 135                 140 ggg acc att gag ttc caa gga ggt ggc cat tcc aac aaa gcc atg tat        542
Gly Thr Ile Glu Phe Gln Gly Gly Gly His Ser Asn Lys Ala Met Tyr
145                 150                 155 gtg cga gta tct ttt gat aca aaa cct gat ctc ctc tta cac ctg atg        590
Val Arg Val Ser Phe Asp Thr Lys Pro Asp Leu Leu Leu His Leu Met
160                 165                 170 acc aag gaa tgg cag ttg gag ctt ccc aag ctt ctc atc tct gtc cat        638
Thr Lys Glu Trp Gln Leu Glu Leu Pro Lys Leu Leu Ile Ser Val His
175                 180                 185 ggg ggc ctg cag aac ttt gaa ctc cag cca aaa ctc aag caa gtc ttt        686
Gly Gly Leu Gln Asn Phe Glu Leu Gln Pro Lys Leu Lys Gln Val Phe
190                 195                 200                 205 ggg aaa ggg ctc atc aaa gca gca atg aca act gga gcg tgg ata ttc        734
Gly Lys Gly Leu Ile Lys Ala Ala Met Thr Thr Gly Ala Trp Ile Phe
210                 215                 220
```

```
act gga ggg gtt aac aca ggt gtt att cgt cat gtt ggc gat gcc ttg       782
Thr Gly Gly Val Asn Thr Gly Val Ile Arg His Val Gly Asp Ala Leu
225                 230                 235 aag gat cat gcc tct aag tct cga gga aag ata tgc acc ata ggt att       830
Lys Asp His Ala Ser Lys Ser Arg Gly Lys Ile Cys Thr Ile Gly Ile
240                 245                 250 gcc ccc tgg gga att gtg gaa aac cag gag gac ctc att gga aga gat       878
Ala Pro Trp Gly Ile Val Glu Asn Gln Glu Asp Leu Ile Gly Arg Asp
255                 260                 265 gtt gtc cgg cca tac cag acc atg tcc aat ccc atg agc aag ctc act       926
Val Val Arg Pro Tyr Gln Thr Met Ser Asn Pro Met Ser Lys Leu Thr
270                 275                 280                 285 gtt ctc aac agc atg cat tcc cac ttc att ctg gct gac aac ggg acc       974
Val Leu Asn Ser Met His Ser His Phe Ile Leu Ala Asp Asn Gly Thr
290                 295                 300 act gga aaa tat gga gca gag gtg aaa ctt cga aga caa ctg gaa aag      1022
Thr Gly Lys Tyr Gly Ala Glu Val Lys Leu Arg Arg Gln Leu Glu Lys
305                 310                 315 cat att tca ctc cag aag ata aac aca aga atc ggt caa ggt gtt cct      1070
His Ile Ser Leu Gln Lys Ile Asn Thr Arg Ile Gly Gln Gly Val Pro
320                 325                 330 gtg gtg gca ctc ata gtg gaa gga gga ccc aat gtg atc tcg att gtt      1118
Val Val Ala Leu Ile Val Glu Gly Gly Pro Asn Val Ile Ser Ile Val
335                 340                 345 ttg gag tac ctt cga gac acc cct ccc gtg cca gtg gtt gtc tgt gat      1166
Leu Glu Tyr Leu Arg Asp Thr Pro Pro Val Pro Val Val Val Cys Asp
350                 355                 360                 365 ggg agt gga cgg gca tcg gac atc ctg gcc ttt ggg cat aaa tac tca      1214
Gly Ser Gly Arg Ala Ser Asp Ile Leu Ala Phe Gly His Lys Tyr Ser
370                 375                 380 gaa gaa ggc gga ctg ata aat gaa tct ttg agg gac cag ctg ttg gtg      1262
Glu Glu Gly Gly Leu Ile Asn Glu Ser Leu Arg Asp Gln Leu Leu Val
385                 390                 395 act ata cag aag act ttc aca tac act cga acc caa gct cag cat ctg      1310
Thr Ile Gln Lys Thr Phe Thr Tyr Thr Arg Thr Gln Ala Gln His Leu
400                 405                 410 ttc atc atc ctc atg gag tgc atg aag aag aag gaa ttg att acg gta      1358
Phe Ile Ile Leu Met Glu Cys Met Lys Lys Lys Glu Leu Ile Thr Val
415                 420                 425 ttt cgg atg gga tca gaa gga cac cag gac att gat ttg gct atc ctg      1406
Phe Arg Met Gly Ser Glu Gly His Gln Asp Ile Asp Leu Ala Ile Leu
430                 435                 440                 445 aca gct tta ctc aaa gga gcc aat gcc tcg gcc cca gac caa ctg agc      1454
Thr Ala Leu Leu Lys Gly Ala Asn Ala Ser Ala Pro Asp Gln Leu Ser
450                 455                 460 tta gct tta gcc tgg aac aga gtc gac atc gct cgc agc cag atc ttt      1502
Leu Ala Leu Ala Trp Asn Arg Val Asp Ile Ala Arg Ser Gln Ile Phe
465                 470                 475 att tac ggg caa cag tgg ccg gtg gga tct ctg gag caa gcc atg ttg      1550
Ile Tyr Gly Gln Gln Trp Pro Val Gly Ser Leu Glu Gln Ala Met Leu
480                 485                 490 gat gcc tta gtt ctg gac aga gtg gat ttt gtg aaa tta ctc ata gag      1598
Asp Ala Leu Val Leu Asp Arg Val Asp Phe Val Lys Leu Leu Ile Glu
495                 500                 505 aat gga gta agc atg cac cgt ttt ctc acc atc tcc aga cta gag gaa      1646
Asn Gly Val Ser Met His Arg Phe Leu Thr Ile Ser Arg Leu Glu Glu
510                 515                 520                 525 ttg tac aat acg aga cat ggg ccc tca aat aca ttg tac cac ttg gtc      1694
Leu Tyr Asn Thr Arg His Gly Pro Ser Asn Thr Leu Tyr His Leu Val
530                 535                 540
```

```
agg gat gtc aaa aag ggg aac ctg ccc cca gac tac aga atc agc ctg      1742
Arg Asp Val Lys Lys Gly Asn Leu Pro Pro Asp Tyr Arg Ile Ser Leu
545                 550                 555 att gac atc ggc ctg gtg atc gag tac ctg atg ggc ggg gct tat cgc      1790
Ile Asp Ile Gly Leu Val Ile Glu Tyr Leu Met Gly Gly Ala Tyr Arg
560                 565                 570 tgc aac tac acg cgc aag cgc ttc cgg acc ctc tac cac aac ctc ttc      1838
Cys Asn Tyr Thr Arg Lys Arg Phe Arg Thr Leu Tyr His Asn Leu Phe
575                 580                 585 ggc ccc aag agg ccc aaa gcc ttg aaa ctg ctg gga atg gag gat gat      1886
Gly Pro Lys Arg Pro Lys Ala Leu Lys Leu Leu Gly Met Glu Asp Asp
590                 595                 600                 605 att ccc ttg agg cga gga aga aag aca acc aag aaa cgt gaa gaa gag      1934
Ile Pro Leu Arg Arg Gly Arg Lys Thr Thr Lys Lys Arg Glu Glu Glu
610                 615                 620 gtg gac att gac ttg gat gat cct gag atc aac cac ttc ccc ttc cct      1982
Val Asp Ile Asp Leu Asp Asp Pro Glu Ile Asn His Phe Pro Phe Pro
625                 630                 635 ttc cat gag ctc atg gtg tgg gct gtt ctc atg aag cgg cag aag atg      2030
Phe His Glu Leu Met Val Trp Ala Val Leu Met Lys Arg Gln Lys Met
640                 645                 650 gcc ctg ttc ttc tgg cag cac ggt gag gag gcc atg gcc aag gcc ctg      2078
Ala Leu Phe Phe Trp Gln His Gly Glu Glu Ala Met Ala Lys Ala Leu
655                 660                 665 gtg gcc tgc aag ctc tgc aaa gcc atg gct cat gag gcc tct gag aac      2126
Val Ala Cys Lys Leu Cys Lys Ala Met Ala His Glu Ala Ser Glu Asn
670                 675                 680                 685 gac atg gtt gac gac att tcc cag gag ctg aat cac aat tcc aga gac      2174
Asp Met Val Asp Asp Ile Ser Gln Glu Leu Asn His Asn Ser Arg Asp
690                 695                 700 ttt ggc cag ctg gct gtg gag ctc ctg gac cag tcc tac aag cag gac      2222
Phe Gly Gln Leu Ala Val Glu Leu Leu Asp Gln Ser Tyr Lys Gln Asp
705                 710                 715 gaa cag ctg gcc atg aaa ctg ctg acg tat gag ctg aag aac tgg agc      2270
Glu Gln Leu Ala Met Lys Leu Leu Thr Tyr Glu Leu Lys Asn Trp Ser
720                 725                 730 aac gcc acg tgc ctg cag ctt gcc gtg gct gcc aaa cac cgc gac ttc      2318
Asn Ala Thr Cys Leu Gln Leu Ala Val Ala Ala Lys His Arg Asp Phe
735                 740                 745 atc gcg cac acg tgc agc cag atg ctg ctc acc gac atg tgg atg ggc      2366
Ile Ala His Thr Cys Ser Gln Met Leu Leu Thr Asp Met Trp Met Gly
750                 755                 760                 765 cgg ctc cgc atg cgc aag aac tca ggc ctc aag gta att ctg gga att      2414
Arg Leu Arg Met Arg Lys Asn Ser Gly Leu Lys Val Ile Leu Gly Ile
770                 775                 780 cta ctt cct cct tca att ctc agc ttg gag ttc aag aac aaa gac gac      2462
Leu Leu Pro Pro Ser Ile Leu Ser Leu Glu Phe Lys Asn Lys Asp Asp
785                 790                 795 atg ccc tat atg tct cag gcc cag gaa atc cac ctc caa gag aag gag      2510
Met Pro Tyr Met Ser Gln Ala Gln Glu Ile His Leu Gln Glu Lys Glu
800                 805                 810 gca gaa gaa cca gag aag ccc aca aag gaa aaa gag gaa gag gac atg      2558
Ala Glu Glu Pro Glu Lys Pro Thr Lys Glu Lys Glu Glu Glu Asp Met
815                 820                 825 gag ctc aca gca atg ttg gga cga aac aac ggg gag tcc tcc agg aag      2606
Glu Leu Thr Ala Met Leu Gly Arg Asn Asn Gly Glu Ser Ser Arg Lys
830                 835                 840                 845 aag gat gaa gag gaa gtt cag agc aag cac cgg tta atc ccc ctc ggc      2654
Lys Asp Glu Glu Glu Val Gln Ser Lys His Arg Leu Ile Pro Leu Gly
```

```
                          -continued
      850              855              860
aga aaa atc tat gaa ttc tac aat gca ccc atc gtg aag ttc tgg ttc    2702
Arg Lys Ile Tyr Glu Phe Tyr Asn Ala Pro Ile Val Lys Phe Trp Phe
865                 870                 875 tac aca ctg gcg tat atc gga tac ctg atg ctc ttc aac tat atc gtg    2750
Tyr Thr Leu Ala Tyr Ile Gly Tyr Leu Met Leu Phe Asn Tyr Ile Val
880                 885                 890 tta gtg aag atg gaa cgc tgg ccg tcc acc cag gaa tgg atc gta atc    2798
Leu Val Lys Met Glu Arg Trp Pro Ser Thr Gln Glu Trp Ile Val Ile
895                 900                 905 tcc tat att ttc acc ctg gga ata gaa aag atg aga gag att ctg atg    2846
Ser Tyr Ile Phe Thr Leu Gly Ile Glu Lys Met Arg Glu Ile Leu Met
910                 915                 920                 925 tca gag cca ggg aag ttg cta cag aaa gtg aag gta tgg ctg cag gag    2894
Ser Glu Pro Gly Lys Leu Leu Gln Lys Val Lys Val Trp Leu Gln Glu
930                 935                 940 tac tgg aat gtc acg gac ctc atc gcc atc ctt ctg ttt tct gtc gga    2942
Tyr Trp Asn Val Thr Asp Leu Ile Ala Ile Leu Leu Phe Ser Val Gly
945                 950                 955 atg atc ctt cgt ctc caa gac cag ccc ttc agg agt gac ggg agg gtc    2990
Met Ile Leu Arg Leu Gln Asp Gln Pro Phe Arg Ser Asp Gly Arg Val
960                 965                 970 atc tac tgc gtg aac atc att tac tgg tat atc cgt ctc cta gac atc    3038
Ile Tyr Cys Val Asn Ile Ile Tyr Trp Tyr Ile Arg Leu Leu Asp Ile
975                 980                 985 ttc ggc gtg aac aag tat ttg ggc ccg tat gta  atg atg att gga aaa   3086
Phe Gly Val Asn Lys Tyr Leu Gly Pro Tyr Val  Met Met Ile Gly Lys
990                 995                 1000                 1005 atg atg ata gac atg  atg tac ttt gtc atc  att atg ctg gtg gtt      3131
Met Met Ile Asp Met  Met Tyr Phe Val Ile  Ile Met Leu Val Val
1010                 1015                 1020 ctg atg agc ttt ggg  gtc gcc agg caa gcc  atc ctt ttt ccc aat      3176
Leu Met Ser Phe Gly  Val Ala Arg Gln Ala  Ile Leu Phe Pro Asn
1025                 1030                 1035 gag gag cca tca tgg  aaa ctg gcc aag aac  atc ttc tac atg ccc      3221
Glu Glu Pro Ser Trp  Lys Leu Ala Lys Asn  Ile Phe Tyr Met Pro
1040                 1045                 1050 tat tgg atg att tat  ggg gaa gtg ttt gcg  gac cag ata gac cct      3266
Tyr Trp Met Ile Tyr  Gly Glu Val Phe Ala  Asp Gln Ile Asp Pro
1055                 1060                 1065 ccc tgt gga cag aat  gag acc cga gag gat  ggt aaa ata atc cag      3311
Pro Cys Gly Gln Asn  Glu Thr Arg Glu Asp  Gly Lys Ile Ile Gln
1070                 1075                 1080 ctg cct ccc tgc aag  aca gga gct tgg atc  gtg ccg gcc atc atg      3356
Leu Pro Pro Cys Lys  Thr Gly Ala Trp Ile  Val Pro Ala Ile Met
1085                 1090                 1095 gcc tgc tac ctc tta  gtg gca aac atc ttg  ctg gtc aac ctc ctc      3401
Ala Cys Tyr Leu Leu  Val Ala Asn Ile Leu  Leu Val Asn Leu Leu
1100                 1105                 1110 att gct gtc ttt aac  aat aca ttt ttt gaa  gta aaa tcg ata tcc      3446
Ile Ala Val Phe Asn  Asn Thr Phe Phe Glu  Val Lys Ser Ile Ser
1115                 1120                 1125 aac caa gtc tgg aag  ttt cag agg tat cag  ctc atc atg act ttc      3491
Asn Gln Val Trp Lys  Phe Gln Arg Tyr Gln  Leu Ile Met Thr Phe
1130                 1135                 1140 cat gaa agg cca gtt  ctg ccc cca cca ctg  atc atc ttc agc cac      3536
His Glu Arg Pro Val  Leu Pro Pro Pro Leu  Ile Ile Phe Ser His
1145                 1150                 1155 atg acc atg ata ttc  cag cac ctg tgc tgc  cga tgg agg aaa cac      3581
```

-continued

| | |
|---|---|
| Met Thr Met Ile Phe Gln His Leu Cys Cys Arg Trp Arg Lys His<br>1160                             1165                     1170 | |
| gag agc gac ccg gat gaa agg gac tac ggc ctg aaa ctc ttc ata<br>Glu Ser Asp Pro Asp Glu Arg Asp Tyr Gly Leu Lys Leu Phe Ile<br>1175                       1180                     1185 | 3626 |
| acc gat gat gag ctc aag aaa gta cat gac ttt gaa gag caa tgc<br>Thr Asp Asp Glu Leu Lys Lys Val His Asp Phe Glu Glu Gln Cys<br>1190                       1195                     1200 | 3671 |
| ata gaa gaa tac ttc aga gaa aag gat gat cgg ttc aac tca tct<br>Ile Glu Glu Tyr Phe Arg Glu Lys Asp Asp Arg Phe Asn Ser Ser<br>1205                       1210                     1215 | 3716 |
| aat gat gag agg ata cgg gtg act tca gaa agg gtg gag aac atg<br>Asn Asp Glu Arg Ile Arg Val Thr Ser Glu Arg Val Glu Asn Met<br>1220                       1225                     1230 | 3761 |
| tct atg cgg ctg gag gaa gtc aac gag aga gag cac tcc atg aag<br>Ser Met Arg Leu Glu Glu Val Asn Glu Arg Glu His Ser Met Lys<br>1235                       1240                     1245 | 3806 |
| gct tca ctc cag acc gtg gac atc cgg ctg gcg cag ctg gaa gac<br>Ala Ser Leu Gln Thr Val Asp Ile Arg Leu Ala Gln Leu Glu Asp<br>1250                       1255                     1260 | 3851 |
| ctt atc ggg cgc atg gcc acg gcc ctg gag cgc ctg aca ggt ctg<br>Leu Ile Gly Arg Met Ala Thr Ala Leu Glu Arg Leu Thr Gly Leu<br>1265                       1270                     1275 | 3896 |
| gag cgg gcc gag tcc aac aaa atc cgc tcg agg acc tcg tca gac<br>Glu Arg Ala Glu Ser Asn Lys Ile Arg Ser Arg Thr Ser Ser Asp<br>1280                       1285                     1290 | 3941 |
| tgc acg gac gcc gcc tac att gtc cgt cag agc agc ttc aac agc<br>Cys Thr Asp Ala Ala Tyr Ile Val Arg Gln Ser Ser Phe Asn Ser<br>1295                       1300                     1305 | 3986 |
| cag gaa ggg aac acc ttc aag ctc caa gag agt ata gac cct gca<br>Gln Glu Gly Asn Thr Phe Lys Leu Gln Glu Ser Ile Asp Pro Ala<br>1310                       1315                     1320 | 4031 |
| ggt gag gag acc atg tcc cca act tct cca acc tta atg ccc cgt<br>Gly Glu Glu Thr Met Ser Pro Thr Ser Pro Thr Leu Met Pro Arg<br>1325                       1330                     1335 | 4076 |
| atg cga agc cat tct ttc tat tca gtc aat atg aaa gac aaa ggt<br>Met Arg Ser His Ser Phe Tyr Ser Val Asn Met Lys Asp Lys Gly<br>1340                       1345                     1350 | 4121 |
| ggt ata gaa aag ttg gaa agt att ttt aaa gaa agg tcc ctg agc<br>Gly Ile Glu Lys Leu Glu Ser Ile Phe Lys Glu Arg Ser Leu Ser<br>1355                       1360                     1365 | 4166 |
| cta cac cgg gct act agt tcc cac tct gta gca aaa gaa ccc aaa<br>Leu His Arg Ala Thr Ser Ser His Ser Val Ala Lys Glu Pro Lys<br>1370                       1375                     1380 | 4211 |
| gct cct gca gcc cct gcc aac acc ttg gcc att gtt cct gat tcc<br>Ala Pro Ala Ala Pro Ala Asn Thr Leu Ala Ile Val Pro Asp Ser<br>1385                       1390                     1395 | 4256 |
| aga aga cca tca tcg tgt ata gac atc tat gtc tct gct atg gat<br>Arg Arg Pro Ser Ser Cys Ile Asp Ile Tyr Val Ser Ala Met Asp<br>1400                       1405                     1410 | 4301 |
| gag ctc cac tgt gat ata gac cct ctg gac aat tcc gtg aac atc<br>Glu Leu His Cys Asp Ile Asp Pro Leu Asp Asn Ser Val Asn Ile<br>1415                       1420                     1425 | 4346 |
| ctt ggg cta ggc gag cca agc ttt tca act cca gta cct tcc aca<br>Leu Gly Leu Gly Glu Pro Ser Phe Ser Thr Pro Val Pro Ser Thr<br>1430                       1435                     1440 | 4391 |
| gcc cct tca agt agt gcc tat gca aca ctt gca ccc aca gac aga<br>Ala Pro Ser Ser Ser Ala Tyr Ala Thr Leu Ala Pro Thr Asp Arg<br>1445                       1450                     1455 | 4436 |

| | | | | |
|---|---|---|---|---|
| cct cca agc cgg agc<br>Pro Pro Ser Arg Ser<br>1460 | att gat ttt gag gac<br>Ile Asp Phe Glu Asp<br>1465 | atc acc tcc atg gac<br>Ile Thr Ser Met Asp<br>1470 | | 4481 |
| act aga tct ttt tct<br>Thr Arg Ser Phe Ser<br>1475 | tca gac tac acc cac<br>Ser Asp Tyr Thr His<br>1480 | ctc cca gaa tgc caa<br>Leu Pro Glu Cys Gln<br>1485 | | 4526 |
| aac ccc tgg gac tca<br>Asn Pro Trp Asp Ser<br>1490 | gag cct ccg atg tac<br>Glu Pro Pro Met Tyr<br>1495 | cac acc att gag cgt<br>His Thr Ile Glu Arg<br>1500 | | 4571 |
| tcc aaa agt agc cgc<br>Ser Lys Ser Ser Arg<br>1505 | tac cta gcc acc aca<br>Tyr Leu Ala Thr Thr<br>1510 | ccc ttt ctt cta gaa<br>Pro Phe Leu Leu Glu<br>1515 | | 4616 |
| gag gct ccc att gtg<br>Glu Ala Pro Ile Val<br>1520 | aaa tct cat agc ttt<br>Lys Ser His Ser Phe<br>1525 | atg ttt tcc ccc tca<br>Met Phe Ser Pro Ser<br>1530 | | 4661 |
| agg agc tat tat gcc<br>Arg Ser Tyr Tyr Ala<br>1535 | aac ttt ggg gtg cct<br>Asn Phe Gly Val Pro<br>1540 | gta aaa aca gca gaa<br>Val Lys Thr Ala Glu<br>1545 | | 4706 |
| tac aca agt att aca<br>Tyr Thr Ser Ile Thr<br>1550 | gac tgt att gac aca<br>Asp Cys Ile Asp Thr<br>1555 | agg tgt gtc aat gcc<br>Arg Cys Val Asn Ala<br>1560 | | 4751 |
| cct caa gca att gcg<br>Pro Gln Ala Ile Ala<br>1565 | gac aga gct gcc ttc<br>Asp Arg Ala Ala Phe<br>1570 | cct gga ggt ctt gga<br>Pro Gly Gly Leu Gly<br>1575 | | 4796 |
| gac aaa gtg gag gac<br>Asp Lys Val Glu Asp<br>1580 | tta act tgc tgc cat<br>Leu Thr Cys Cys His<br>1585 | cca gag cga gaa gca<br>Pro Glu Arg Glu Ala<br>1590 | | 4841 |
| gaa ctg agt cac ccc<br>Glu Leu Ser His Pro<br>1595 | agc tct gac agt gag<br>Ser Ser Asp Ser Glu<br>1600 | gag aat gag gcc aaa<br>Glu Asn Glu Ala Lys<br>1605 | | 4886 |
| ggc cgc aga gcc acc<br>Gly Arg Arg Ala Thr<br>1610 | att gca ata tcc tcc<br>Ile Ala Ile Ser Ser<br>1615 | cag gag ggt gat aac<br>Gln Glu Gly Asp Asn<br>1620 | | 4931 |
| tca gag aga acc ctg<br>Ser Glu Arg Thr Leu<br>1625 | tcc aac aac atc act<br>Ser Asn Asn Ile Thr<br>1630 | gtt ccc aag ata gag<br>Val Pro Lys Ile Glu<br>1635 | | 4976 |
| cgc gcc aac agc tac<br>Arg Ala Asn Ser Tyr<br>1640 | tcg gca gag gag cca<br>Ser Ala Glu Glu Pro<br>1645 | agt gcg cca tat gca<br>Ser Ala Pro Tyr Ala<br>1650 | | 5021 |
| cac acc agg aag agc<br>His Thr Arg Lys Ser<br>1655 | ttc tcc atc agt gac<br>Phe Ser Ile Ser Asp<br>1660 | aaa ctc gac agg cag<br>Lys Leu Asp Arg Gln<br>1665 | | 5066 |
| cgg aac aca gca agc<br>Arg Asn Thr Ala Ser<br>1670 | ctg caa aat ccc ttc<br>Leu Gln Asn Pro Phe<br>1675 | cag aga agc aag tcc<br>Gln Arg Ser Lys Ser<br>1680 | | 5111 |
| tcc aag ccg gag ggc<br>Ser Lys Pro Glu Gly<br>1685 | cga ggg gac agc ctg<br>Arg Gly Asp Ser Leu<br>1690 | tcc atg agg aga ctg<br>Ser Met Arg Arg Leu<br>1695 | | 5156 |
| tcc aga aca tcg gct<br>Ser Arg Thr Ser Ala<br>1700 | ttc caa agc ttt gaa<br>Phe Gln Ser Phe Glu<br>1705 | agc aag cac acc taa<br>Ser Lys His Thr | | 5201 |

<210> SEQ ID NO 2
<211> LENGTH: 1709
<212> TYPE: PRT
<213> ORGANISM: Homo sapiens

<400> SEQUENCE: 2

Met Gly Lys Lys Trp Arg Asp Ala Ala Glu Met Glu Arg Gly Cys Ser
1               5                   10                  15

-continued

```
Asp Arg Glu Asp Asn Ala Glu Ser Arg Arg Ser Arg Ser Ala Ser
 20                  25                  30

Arg Gly Arg Phe Ala Glu Ser Trp Lys Arg Leu Ser Ser Lys Gln Gly
 35                  40                  45

Ser Thr Lys Arg Ser Gly Leu Pro Ser Gln Gln Thr Pro Ala Gln Lys
 50                  55                  60

Ser Trp Ile Glu Arg Ala Phe Tyr Lys Arg Glu Cys Val His Ile Ile
 65                  70                  75                  80

Pro Ser Thr Lys Asp Pro His Arg Cys Cys Cys Gly Arg Leu Ile Gly
 85                  90                  95

Gln His Val Gly Leu Thr Pro Ser Ile Ser Val Leu Gln Asn Glu Lys
100                 105                 110

Asn Glu Ser Arg Leu Ser Arg Asn Asp Ile Gln Ser Glu Lys Trp Ser
115                 120                 125

Ile Ser Lys His Thr Gln Leu Ser Pro Thr Asp Ala Phe Gly Thr Ile
130                 135                 140

Glu Phe Gln Gly Gly Gly His Ser Asn Lys Ala Met Tyr Val Arg Val
145                 150                 155                 160

Ser Phe Asp Thr Lys Pro Asp Leu Leu Leu His Leu Met Thr Lys Glu
165                 170                 175

Trp Gln Leu Glu Leu Pro Lys Leu Leu Ile Ser Val His Gly Gly Leu
180                 185                 190

Gln Asn Phe Glu Leu Gln Pro Lys Leu Lys Gln Val Phe Gly Lys Gly
195                 200                 205

Leu Ile Lys Ala Ala Met Thr Thr Gly Ala Trp Ile Phe Thr Gly Gly
210                 215                 220

Val Asn Thr Gly Val Ile Arg His Val Gly Asp Ala Leu Lys Asp His
225                 230                 235                 240

Ala Ser Lys Ser Arg Gly Lys Ile Cys Thr Ile Gly Ile Ala Pro Trp
245                 250                 255

Gly Ile Val Glu Asn Gln Glu Asp Leu Ile Gly Arg Asp Val Val Arg
260                 265                 270

Pro Tyr Gln Thr Met Ser Asn Pro Met Ser Lys Leu Thr Val Leu Asn
275                 280                 285

Ser Met His Ser His Phe Ile Leu Ala Asp Asn Gly Thr Thr Gly Lys
290                 295                 300

Tyr Gly Ala Glu Val Lys Leu Arg Arg Gln Leu Glu Lys His Ile Ser
305                 310                 315                 320

Leu Gln Lys Ile Asn Thr Arg Ile Gly Gln Gly Val Pro Val Val Ala
325                 330                 335

Leu Ile Val Glu Gly Gly Pro Asn Val Ile Ser Ile Val Leu Glu Tyr
340                 345                 350

Leu Arg Asp Thr Pro Pro Val Pro Val Val Val Cys Asp Gly Ser Gly
355                 360                 365

Arg Ala Ser Asp Ile Leu Ala Phe Gly His Lys Tyr Ser Glu Glu Gly
370                 375                 380

Gly Leu Ile Asn Glu Ser Leu Arg Asp Gln Leu Leu Val Thr Ile Gln
385                 390                 395                 400

Lys Thr Phe Thr Tyr Thr Arg Thr Gln Ala Gln His Leu Phe Ile Ile
405                 410                 415

Leu Met Glu Cys Met Lys Lys Lys Glu Leu Ile Thr Val Phe Arg Met
420                 425                 430

Gly Ser Glu Gly His Gln Asp Ile Asp Leu Ala Ile Leu Thr Ala Leu
```

```
435                 440                 445
Leu Lys Gly Ala Asn Ala Ser Ala Pro Asp Gln Leu Ser Leu Ala Leu
450                 455                 460

Ala Trp Asn Arg Val Asp Ile Ala Arg Ser Gln Ile Phe Ile Tyr Gly
465                 470                 475                 480

Gln Gln Trp Pro Val Gly Ser Leu Glu Gln Ala Met Leu Asp Ala Leu
485                 490                 495

Val Leu Asp Arg Val Asp Phe Val Lys Leu Leu Ile Glu Asn Gly Val
500                 505                 510

Ser Met His Arg Phe Leu Thr Ile Ser Arg Leu Glu Glu Leu Tyr Asn
515                 520                 525

Thr Arg His Gly Pro Ser Asn Thr Leu Tyr His Leu Val Arg Asp Val
530                 535                 540

Lys Lys Gly Asn Leu Pro Pro Asp Tyr Arg Ile Ser Leu Ile Asp Ile
545                 550                 555                 560

Gly Leu Val Ile Glu Tyr Leu Met Gly Gly Ala Tyr Arg Cys Asn Tyr
565                 570                 575

Thr Arg Lys Arg Phe Arg Thr Leu Tyr His Asn Leu Phe Gly Pro Lys
580                 585                 590

Arg Pro Lys Ala Leu Lys Leu Leu Gly Met Glu Asp Asp Ile Pro Leu
595                 600                 605

Arg Arg Gly Arg Lys Thr Thr Lys Lys Arg Glu Glu Glu Val Asp Ile
610                 615                 620

Asp Leu Asp Asp Pro Glu Ile Asn His Phe Pro Phe Pro Phe His Glu
625                 630                 635                 640

Leu Met Val Trp Ala Val Leu Met Lys Arg Gln Lys Met Ala Leu Phe
645                 650                 655

Phe Trp Gln His Gly Glu Glu Ala Met Ala Lys Ala Leu Val Ala Cys
660                 665                 670

Lys Leu Cys Lys Ala Met Ala His Glu Ala Ser Glu Asn Asp Met Val
675                 680                 685

Asp Asp Ile Ser Gln Glu Leu Asn His Asn Ser Arg Asp Phe Gly Gln
690                 695                 700

Leu Ala Val Glu Leu Leu Asp Gln Ser Tyr Lys Gln Asp Glu Gln Leu
705                 710                 715                 720

Ala Met Lys Leu Leu Thr Tyr Glu Leu Lys Asn Trp Ser Asn Ala Thr
725                 730                 735

Cys Leu Gln Leu Ala Val Ala Ala Lys His Arg Asp Phe Ile Ala His
740                 745                 750

Thr Cys Ser Gln Met Leu Leu Thr Asp Met Trp Met Gly Arg Leu Arg
755                 760                 765

Met Arg Lys Asn Ser Gly Leu Lys Val Ile Leu Gly Ile Leu Leu Pro
770                 775                 780

Pro Ser Ile Leu Ser Leu Glu Phe Lys Asn Lys Asp Asp Met Pro Tyr
785                 790                 795                 800

Met Ser Gln Ala Gln Glu Ile His Leu Gln Glu Lys Glu Ala Glu Glu
805                 810                 815

Pro Glu Lys Pro Thr Lys Glu Lys Glu Glu Asp Met Glu Leu Thr
820                 825                 830

Ala Met Leu Gly Arg Asn Asn Gly Glu Ser Ser Arg Lys Lys Asp Glu
835                 840                 845

Glu Glu Val Gln Ser Lys His Arg Leu Ile Pro Leu Gly Arg Lys Ile
850                 855                 860
```

-continued

```
Tyr Glu Phe Tyr Asn Ala Pro Ile Val Lys Phe Trp Phe Tyr Thr Leu
865                 870                 875                 880

Ala Tyr Ile Gly Tyr Leu Met Leu Phe Asn Tyr Ile Val Leu Val Lys
    885                 890                 895

Met Glu Arg Trp Pro Ser Thr Gln Glu Trp Ile Val Ile Ser Tyr Ile
900                 905                 910

Phe Thr Leu Gly Ile Glu Lys Met Arg Glu Ile Leu Met Ser Glu Pro
915                 920                 925

Gly Lys Leu Leu Gln Lys Val Lys Val Trp Leu Gln Glu Tyr Trp Asn
930                 935                 940

Val Thr Asp Leu Ile Ala Ile Leu Leu Phe Ser Val Gly Met Ile Leu
945                 950                 955                 960

Arg Leu Gln Asp Gln Pro Phe Arg Ser Asp Gly Arg Val Ile Tyr Cys
965                 970                 975

Val Asn Ile Ile Tyr Trp Tyr Ile Arg Leu Leu Asp Ile Phe Gly Val
980                 985                 990

Asn Lys Tyr Leu Gly Pro Tyr Val  Met Met Ile Gly Lys  Met Met Ile
995                 1000                1005

Asp Met  Met Tyr Phe Val Ile  Ile Met Leu Val Val  Leu Met Ser
1010                1015                1020

Phe Gly  Val Ala Arg Gln Ala  Ile Leu Phe Pro Asn  Glu Glu Pro
1025                1030                1035

Ser Trp  Lys Leu Ala Lys Asn  Ile Phe Tyr Met Pro  Tyr Trp Met
1040                1045                1050

Ile Tyr  Gly Glu Val Phe Ala  Asp Gln Ile Asp Pro  Pro Cys Gly
1055                1060                1065

Gln Asn  Glu Thr Arg Glu Asp  Gly Lys Ile Ile Gln  Leu Pro Pro
1070                1075                1080

Cys Lys  Thr Gly Ala Trp Ile  Val Pro Ala Ile Met  Ala Cys Tyr
1085                1090                1095

Leu Leu  Val Ala Asn Ile Leu  Leu Val Asn Leu Leu  Ile Ala Val
1100                1105                1110

Phe Asn  Asn Thr Phe Phe Glu  Val Lys Ser Ile Ser  Asn Gln Val
1115                1120                1125

Trp Lys  Phe Gln Arg Tyr Gln  Leu Ile Met Thr Phe  His Glu Arg
1130                1135                1140

Pro Val  Leu Pro Pro Pro Leu  Ile Ile Phe Ser His  Met Thr Met
1145                1150                1155

Ile Phe  Gln His Leu Cys Cys  Arg Trp Arg Lys His  Glu Ser Asp
1160                1165                1170

Pro Asp  Glu Arg Asp Tyr Gly  Leu Lys Leu Phe Ile  Thr Asp Asp
1175                1180                1185

Glu Leu  Lys Lys Val His Asp  Phe Glu Glu Gln Cys  Ile Glu Glu
1190                1195                1200

Tyr Phe  Arg Glu Lys Asp Asp  Arg Phe Asn Ser Ser  Asn Asp Glu
1205                1210                1215

Arg Ile  Arg Val Thr Ser Glu  Arg Val Glu Asn Met  Ser Met Arg
1220                1225                1230

Leu Glu  Glu Val Asn Glu Arg  Glu His Ser Met Lys  Ala Ser Leu
1235                1240                1245

Gln Thr  Val Asp Ile Arg Leu  Ala Gln Leu Glu Asp  Leu Ile Gly
1250                1255                1260
```

-continued

```
Arg Met Ala Thr Ala Leu Glu Arg Leu Thr Gly Leu Glu Arg Ala
1265                1270                1275

Glu Ser Asn Lys Ile Arg Ser Arg Thr Ser Ser Asp Cys Thr Asp
1280                1285                1290

Ala Ala Tyr Ile Val Arg Gln Ser Ser Phe Asn Ser Gln Glu Gly
1295                1300                1305

Asn Thr Phe Lys Leu Gln Glu Ser Ile Asp Pro Ala Gly Glu Glu
1310                1315                1320

Thr Met Ser Pro Thr Ser Pro Thr Leu Met Pro Arg Met Arg Ser
1325                1330                1335

His Ser Phe Tyr Ser Val Asn Met Lys Asp Lys Gly Gly Ile Glu
1340                1345                1350

Lys Leu Glu Ser Ile Phe Lys Glu Arg Ser Leu Ser Leu His Arg
1355                1360                1365

Ala Thr Ser Ser His Ser Val Ala Lys Glu Pro Lys Ala Pro Ala
1370                1375                1380

Ala Pro Ala Asn Thr Leu Ala Ile Val Pro Asp Ser Arg Arg Pro
1385                1390                1395

Ser Ser Cys Ile Asp Ile Tyr Val Ser Ala Met Asp Glu Leu His
1400                1405                1410

Cys Asp Ile Asp Pro Leu Asp Asn Ser Val Asn Ile Leu Gly Leu
1415                1420                1425

Gly Glu Pro Ser Phe Ser Thr Pro Val Pro Ser Thr Ala Pro Ser
1430                1435                1440

Ser Ser Ala Tyr Ala Thr Leu Ala Pro Thr Asp Arg Pro Pro Ser
1445                1450                1455

Arg Ser Ile Asp Phe Glu Asp Ile Thr Ser Met Asp Thr Arg Ser
1460                1465                1470

Phe Ser Ser Asp Tyr Thr His Leu Pro Glu Cys Gln Asn Pro Trp
1475                1480                1485

Asp Ser Glu Pro Pro Met Tyr His Thr Ile Glu Arg Ser Lys Ser
1490                1495                1500

Ser Arg Tyr Leu Ala Thr Thr Pro Phe Leu Leu Glu Glu Ala Pro
1505                1510                1515

Ile Val Lys Ser His Ser Phe Met Phe Ser Pro Ser Arg Ser Tyr
1520                1525                1530

Tyr Ala Asn Phe Gly Val Pro Val Lys Thr Ala Glu Tyr Thr Ser
1535                1540                1545

Ile Thr Asp Cys Ile Asp Thr Arg Cys Val Asn Ala Pro Gln Ala
1550                1555                1560

Ile Ala Asp Arg Ala Ala Phe Pro Gly Gly Leu Gly Asp Lys Val
1565                1570                1575

Glu Asp Leu Thr Cys Cys His Pro Glu Arg Glu Ala Glu Leu Ser
1580                1585                1590

His Pro Ser Ser Asp Ser Glu Glu Asn Glu Ala Lys Gly Arg Arg
1595                1600                1605

Ala Thr Ile Ala Ile Ser Ser Gln Glu Gly Asp Asn Ser Glu Arg
1610                1615                1620

Thr Leu Ser Asn Asn Ile Thr Val Pro Lys Ile Glu Arg Ala Asn
1625                1630                1635

Ser Tyr Ser Ala Glu Glu Pro Ser Ala Pro Tyr Ala His Thr Arg
1640                1645                1650

Lys Ser Phe Ser Ile Ser Asp Lys Leu Asp Arg Gln Arg Asn Thr
```

-continued

```
             1655                1660                1665
Ala Ser  Leu Gln Asn Pro Phe  Gln Arg Ser Lys Ser  Ser Lys Pro
        1670                1675                1680

Glu Gly  Arg Gly Asp Ser Leu  Ser Met Arg Arg Leu  Ser Arg Thr
        1685                1690                1695

Ser Ala  Phe Gln Ser Phe Glu  Ser Lys His Thr
        1700                1705

<210> SEQ ID NO 3
<211> LENGTH: 5237
<212> TYPE: DNA
<213> ORGANISM: Homo sapiens
<220> FEATURE:
<221> NAME/KEY: CDS
<222> LOCATION: (72)..(5234)

<400> SEQUENCE: 3
cgcccgcggc gaggagccag cgagagcgct cggcgctggg ctgtttcccg gccgagggag        60
gcgaacttct c atg ggg aag aag tgg agg gat gcg gcg gaa atg gag cgg       110
            Met Gly Lys Lys Trp Arg Asp Ala Ala Glu Met Glu Arg
            1               5                  10 ggc tgc tcc gac cgc gag gac aac gcg gag agc cgc aga cgc agc cgg        158
Gly Cys Ser Asp Arg Glu Asp Asn Ala Glu Ser Arg Arg Arg Ser Arg
 15                  20                  25 agc gcc agc cgg ggc agg ttt gcc gag tcg tgg aaa agg tta agt tcc        206
Ser Ala Ser Arg Gly Arg Phe Ala Glu Ser Trp Lys Arg Leu Ser Ser
 30                  35                  40                  45 aag cag ggg tcc acc aaa cgc tcg gga ctc ccg tcg cag cag acg ccg        254
Lys Gln Gly Ser Thr Lys Arg Ser Gly Leu Pro Ser Gln Gln Thr Pro
             50                  55                  60 gct cag aaa tcc tgg ata gaa aga gca ttt tat aaa aga gaa tgt gtc        302
Ala Gln Lys Ser Trp Ile Glu Arg Ala Phe Tyr Lys Arg Glu Cys Val
         65                  70                  75 cac atc ata ccc agc acc aaa gac ccc cat agg tgt tgc tgt ggg cgt        350
His Ile Ile Pro Ser Thr Lys Asp Pro His Arg Cys Cys Cys Gly Arg
     80                  85                  90 ctg ata ggc cag cat gtt ggc ctc acc ccc agt atc tcc gtg ctt cag        398
Leu Ile Gly Gln His Val Gly Leu Thr Pro Ser Ile Ser Val Leu Gln
 95                  100                 105 aat gag aaa aat gaa agt cgc ctc tcc cga aat gac atc cag tct gaa        446
Asn Glu Lys Asn Glu Ser Arg Leu Ser Arg Asn Asp Ile Gln Ser Glu
110                 115                 120                 125 aag tgg tcc atc agc aaa cac act caa ctc agc cct acg gat gct ttt        494
Lys Trp Ser Ile Ser Lys His Thr Gln Leu Ser Pro Thr Asp Ala Phe
             130                 135                 140 ggg acc att gag ttc caa gga ggt ggc cat tcc aac aaa gcc atg tat        542
Gly Thr Ile Glu Phe Gln Gly Gly Gly His Ser Asn Lys Ala Met Tyr
         145                 150                 155 gtg cga gta tct ttt gat aca aaa cct gat ctc ctc tta cac ctg atg        590
Val Arg Val Ser Phe Asp Thr Lys Pro Asp Leu Leu Leu His Leu Met
     160                 165                 170 acc aag gaa tgg cag ttg gag ctt ccc aag ctt ctc atc tct gtc cat        638
Thr Lys Glu Trp Gln Leu Glu Leu Pro Lys Leu Leu Ile Ser Val His
 175                 180                 185 ggg ggc ctg cag aac ttt gaa ctc cag cca aaa ctc aag caa gtc ttt        686
Gly Gly Leu Gln Asn Phe Glu Leu Gln Pro Lys Leu Lys Gln Val Phe
190                 195                 200                 205 ggg aaa ggg ctc atc aaa gca gca atg aca act gga gcg tgg ata ttc        734
Gly Lys Gly Leu Ile Lys Ala Ala Met Thr Thr Gly Ala Trp Ile Phe
             210                 215                 220
```

-continued

| | |
|---|---|
| act gga ggg gtt aac aca ggt gtt att cgt cat gtt ggc gat gcc ttg<br>Thr Gly Gly Val Asn Thr Gly Val Ile Arg His Val Gly Asp Ala Leu<br>225                   230                       235 | 782 |
| aag gat cat gcc tct aag tct cga gga aag ata tgc acc ata ggt att<br>Lys Asp His Ala Ser Lys Ser Arg Gly Lys Ile Cys Thr Ile Gly Ile<br>240                  245                     250 | 830 |
| gcc ccc tgg gga att gtg gaa aac cag gag gac ctc att gga aga gat<br>Ala Pro Trp Gly Ile Val Glu Asn Gln Glu Asp Leu Ile Gly Arg Asp<br>255                   260                    265 | 878 |
| gtt gtc cgg cca tac cag acc atg tcc aat ccc atg agc aag ctc act<br>Val Val Arg Pro Tyr Gln Thr Met Ser Asn Pro Met Ser Lys Leu Thr<br>270                 275                   280            285 | 926 |
| gtt ctc aac agc atg cat tcc cac ttc att ctg gct gac aac ggg acc<br>Val Leu Asn Ser Met His Ser His Phe Ile Leu Ala Asp Asn Gly Thr<br>290                 295                   300 | 974 |
| act gga aaa tat gga gca gag gtg aaa ctt cga aga caa ctg gaa aag<br>Thr Gly Lys Tyr Gly Ala Glu Val Lys Leu Arg Arg Gln Leu Glu Lys<br>305                 310                   315 | 1022 |
| cat att tca ctc cag aag ata aac aca aga atc ggt caa ggt gtt cct<br>His Ile Ser Leu Gln Lys Ile Asn Thr Arg Ile Gly Gln Gly Val Pro<br>320                 325                   330 | 1070 |
| gtg gtg gca ctc ata gtg gaa gga gga ccc aat gtg atc tcg att gtt<br>Val Val Ala Leu Ile Val Glu Gly Gly Pro Asn Val Ile Ser Ile Val<br>335                 340                   345 | 1118 |
| ttg gag tac ctt cga gac acc cct ccc gtg cca gtg gtt gtc tgt gat<br>Leu Glu Tyr Leu Arg Asp Thr Pro Pro Val Pro Val Val Val Cys Asp<br>350                 355                   360            365 | 1166 |
| ggg agt gga cgg gca tcg gac atc ctg gcc ttt ggg cat aaa tac tca<br>Gly Ser Gly Arg Ala Ser Asp Ile Leu Ala Phe Gly His Lys Tyr Ser<br>370                 375                   380 | 1214 |
| gaa gaa ggc gga ctg ata aat gaa tct ttg agg gac cag ctg ttg gtg<br>Glu Glu Gly Gly Leu Ile Asn Glu Ser Leu Arg Asp Gln Leu Leu Val<br>385                 390                   395 | 1262 |
| act ata cag aag act ttc aca tac act cga acc caa gct cag cat ctg<br>Thr Ile Gln Lys Thr Phe Thr Tyr Thr Arg Thr Gln Ala Gln His Leu<br>400                 405                   410 | 1310 |
| ttc atc atc ctc atg gag tgc atg aag aag aag gaa ttg att acg gta<br>Phe Ile Ile Leu Met Glu Cys Met Lys Lys Lys Glu Leu Ile Thr Val<br>415                 420                   425 | 1358 |
| ttt cgg atg gga tca gaa gga cac cag gac att gat ttg gct atc ctg<br>Phe Arg Met Gly Ser Glu Gly His Gln Asp Ile Asp Leu Ala Ile Leu<br>430                 435                   440            445 | 1406 |
| aca gct tta ctc aaa gga gcc aat gcc tcg gcc cca gac caa ctg agc<br>Thr Ala Leu Leu Lys Gly Ala Asn Ala Ser Ala Pro Asp Gln Leu Ser<br>450                 455                   460 | 1454 |
| tta gct tta gcc tgg aac aga gtc gac atc gct cgc agc cag atc ttt<br>Leu Ala Leu Ala Trp Asn Arg Val Asp Ile Ala Arg Ser Gln Ile Phe<br>465                 470                   475 | 1502 |
| att tac ggg caa cag tgg ccg gtg gga tct ctg gag caa gcc atg ttg<br>Ile Tyr Gly Gln Gln Trp Pro Val Gly Ser Leu Glu Gln Ala Met Leu<br>480                 485                   490 | 1550 |
| gat gcc tta gtt ctg gac aga gtg gat ttt gtg aaa tta ctc ata gag<br>Asp Ala Leu Val Leu Asp Arg Val Asp Phe Val Lys Leu Leu Ile Glu<br>495                 500                   505 | 1598 |
| aat gga gta agc atg cac cgt ttt ctc acc atc tcc aga cta gag gaa<br>Asn Gly Val Ser Met His Arg Phe Leu Thr Ile Ser Arg Leu Glu Glu<br>510                 515                   520            525 | 1646 |
| ttg tac aat acg aga cat ggg ccc tca aat aca ttg tac cac ttg gtc<br>Leu Tyr Asn Thr Arg His Gly Pro Ser Asn Thr Leu Tyr His Leu Val | 1694 |

-continued

```
                530                 535                 540
agg gat gtc aaa aag cga gag tat cca ggt ttc ggt tgg atc tat ttt    1742
Arg Asp Val Lys Lys Arg Glu Tyr Pro Gly Phe Gly Trp Ile Tyr Phe
545                 550                 555 aag ggg aac ctg ccc cca gac tac aga atc agc ctg att gac atc ggc    1790
Lys Gly Asn Leu Pro Pro Asp Tyr Arg Ile Ser Leu Ile Asp Ile Gly
560                 565                 570 ctg gtg atc gag tac ctg atg ggc ggg gct tat cgc tgc aac tac acg    1838
Leu Val Ile Glu Tyr Leu Met Gly Gly Ala Tyr Arg Cys Asn Tyr Thr
575                 580                 585 cgc aag cgc ttc cgg acc ctc tac cac aac ctc ttc ggc ccc aag agg    1886
Arg Lys Arg Phe Arg Thr Leu Tyr His Asn Leu Phe Gly Pro Lys Arg
590                 595                 600                 605 ccc aaa gcc ttg aaa ctg ctg gga atg gag gat gat att ccc ttg agg    1934
Pro Lys Ala Leu Lys Leu Leu Gly Met Glu Asp Asp Ile Pro Leu Arg
610                 615                 620 cga gga aga aag aca acc aag aaa cgt gaa gaa gag gtg gac att gac    1982
Arg Gly Arg Lys Thr Thr Lys Lys Arg Glu Glu Glu Val Asp Ile Asp
625                 630                 635 ttg gat gat cct gag atc aac cac ttc ccc ttc cct ttc cat gag ctc    2030
Leu Asp Asp Pro Glu Ile Asn His Phe Pro Phe Pro Phe His Glu Leu
640                 645                 650 atg gtg tgg gct gtt ctc atg aag cgg cag aag atg gcc ctg ttc ttc    2078
Met Val Trp Ala Val Leu Met Lys Arg Gln Lys Met Ala Leu Phe Phe
655                 660                 665 tgg cag cac ggt gag gag gcc atg gcc aag gcc ctg gtg gcc tgc aag    2126
Trp Gln His Gly Glu Glu Ala Met Ala Lys Ala Leu Val Ala Cys Lys
670                 675                 680                 685 ctc tgc aaa gcc atg gct cat gag gcc tct gag aac gac atg gtt gac    2174
Leu Cys Lys Ala Met Ala His Glu Ala Ser Glu Asn Asp Met Val Asp
690                 695                 700 gac att tcc cag gag ctg aat cac aat tcc aga gac ttt ggc cag ctg    2222
Asp Ile Ser Gln Glu Leu Asn His Asn Ser Arg Asp Phe Gly Gln Leu
705                 710                 715 gct gtg gag ctc ctg gac cag tcc tac aag cag gac gaa cag ctg gcc    2270
Ala Val Glu Leu Leu Asp Gln Ser Tyr Lys Gln Asp Glu Gln Leu Ala
720                 725                 730 atg aaa ctg ctg acg tat gag ctg aag aac tgg agc aac gcc acg tgc    2318
Met Lys Leu Leu Thr Tyr Glu Leu Lys Asn Trp Ser Asn Ala Thr Cys
735                 740                 745 ctg cag ctt gcc gtg gct gcc aaa cac cgc gac ttc atc gcg cac acg    2366
Leu Gln Leu Ala Val Ala Ala Lys His Arg Asp Phe Ile Ala His Thr
750                 755                 760                 765 tgc agc cag atg ctg ctc acc gac atg tgg atg ggc cgg ctc cgc atg    2414
Cys Ser Gln Met Leu Leu Thr Asp Met Trp Met Gly Arg Leu Arg Met
770                 775                 780 cgc aag aac tca ggc ctc aag gta att ctg gga att cta ctt cct cct    2462
Arg Lys Asn Ser Gly Leu Lys Val Ile Leu Gly Ile Leu Leu Pro Pro
785                 790                 795 tca att ctc agc ttg gag ttc aag aac aaa gac gac atg ccc tat atg    2510
Ser Ile Leu Ser Leu Glu Phe Lys Asn Lys Asp Asp Met Pro Tyr Met
800                 805                 810 tct cag gcc cag gaa atc cac ctc caa gag aag gag gca gaa gaa cca    2558
Ser Gln Ala Gln Glu Ile His Leu Gln Glu Lys Glu Ala Glu Glu Pro
815                 820                 825 gag aag ccc aca aag gaa aaa gag gaa gag gac atg gag ctc aca gca    2606
Glu Lys Pro Thr Lys Glu Lys Glu Glu Glu Asp Met Glu Leu Thr Ala
830                 835                 840                 845 atg ttg gga cga aac aac ggg gag tcc tcc agg aag aag gat gaa gag    2654
```

```
Met Leu Gly Arg Asn Asn Gly Glu Ser Ser Arg Lys Lys Asp Glu Glu
850                 855                 860 gaa gtt cag agc aag cac cgg tta atc ccc ctc ggc aga aaa atc tat       2702
Glu Val Gln Ser Lys His Arg Leu Ile Pro Leu Gly Arg Lys Ile Tyr
865                 870                 875 gaa ttc tac aat gca ccc atc gtg aag ttc tgg ttc tac aca ctg gcg       2750
Glu Phe Tyr Asn Ala Pro Ile Val Lys Phe Trp Phe Tyr Thr Leu Ala
880                 885                 890 tat atc gga tac ctg atg ctc ttc aac tat atc gtg tta gtg aag atg       2798
Tyr Ile Gly Tyr Leu Met Leu Phe Asn Tyr Ile Val Leu Val Lys Met
895                 900                 905 gaa cgc tgg ccg tcc acc cag gaa tgg atc gta atc tcc tat att ttc       2846
Glu Arg Trp Pro Ser Thr Gln Glu Trp Ile Val Ile Ser Tyr Ile Phe
910                 915                 920                 925 acc ctg gga ata gaa aag atg aga gag att ctg atg tca gag cca ggg       2894
Thr Leu Gly Ile Glu Lys Met Arg Glu Ile Leu Met Ser Glu Pro Gly
930                 935                 940 aag ttg cta cag aaa gtg aag gta tgg ctg cag gag tac tgg aat gtc       2942
Lys Leu Leu Gln Lys Val Lys Val Trp Leu Gln Glu Tyr Trp Asn Val
945                 950                 955 acg gac ctc atc gcc atc ctt ctg ttt tct gtc gga atg atc ctt cgt       2990
Thr Asp Leu Ile Ala Ile Leu Leu Phe Ser Val Gly Met Ile Leu Arg
960                 965                 970 ctc caa gac cag ccc ttc agg agt gac ggg agg gtc atc tac tgc gtg       3038
Leu Gln Asp Gln Pro Phe Arg Ser Asp Gly Arg Val Ile Tyr Cys Val
975                 980                 985 aac atc att tac tgg tat atc cgt ctc cta gac atc ttc ggc gtg aac       3086
Asn Ile Ile Tyr Trp Tyr Ile Arg Leu Leu Asp Ile Phe Gly Val Asn
990                 995                 1000                1005 aag tat ttg ggc ccg tat gta atg atg att gga aaa atg atg ata           3131
Lys Tyr Leu Gly Pro Tyr Val Met Met Ile Gly Lys Met Met Ile
1010                1015                1020 gac atg atg tac ttt gtc atc att atg ctg gtg gtt ctg atg agc           3176
Asp Met Met Tyr Phe Val Ile Ile Met Leu Val Val Leu Met Ser
1025                1030                1035 ttt ggg gtc gcc agg caa gcc atc ctt ttt ccc aat gag gag cca           3221
Phe Gly Val Ala Arg Gln Ala Ile Leu Phe Pro Asn Glu Glu Pro
1040                1045                1050 tca tgg aaa ctg gcc aag aac atc ttc tac atg ccc tat tgg atg           3266
Ser Trp Lys Leu Ala Lys Asn Ile Phe Tyr Met Pro Tyr Trp Met
1055                1060                1065 att tat ggg gaa gtg ttt gcg gac cag ata gac cct ccc tgt gga           3311
Ile Tyr Gly Glu Val Phe Ala Asp Gln Ile Asp Pro Pro Cys Gly
1070                1075                1080 cag aat gag acc cga gag gat ggt aaa ata atc cag ctg cct ccc           3356
Gln Asn Glu Thr Arg Glu Asp Gly Lys Ile Ile Gln Leu Pro Pro
1085                1090                1095 tgc aag aca gga gct tgg atc gtg ccg gcc atc atg gcc tgc tac           3401
Cys Lys Thr Gly Ala Trp Ile Val Pro Ala Ile Met Ala Cys Tyr
1100                1105                1110 ctc tta gtg gca aac atc ttg ctg gtc aac ctc ctc att gct gtc           3446
Leu Leu Val Ala Asn Ile Leu Leu Val Asn Leu Leu Ile Ala Val
1115                1120                1125 ttt aac aat aca ttt ttt gaa gta aaa tcg ata tcc aac caa gtc           3491
Phe Asn Asn Thr Phe Phe Glu Val Lys Ser Ile Ser Asn Gln Val
1130                1135                1140 tgg aag ttt cag agg tat cag ctc atc atg act ttc cat gaa agg           3536
Trp Lys Phe Gln Arg Tyr Gln Leu Ile Met Thr Phe His Glu Arg
1145                1150                1155
```

-continued

| | | |
|---|---|---|
| cca gtt ctg ccc cca<br>Pro Val Leu Pro Pro<br>1160 | cca ctg atc atc ttc<br>Pro Leu Ile Ile Phe<br>1165 | agc cac atg acc atg<br>Ser His Met Thr Met<br>1170 | 3581 |
| ata ttc cag cac ctg<br>Ile Phe Gln His Leu<br>1175 | tgc tgc cga tgg agg<br>Cys Cys Arg Trp Arg<br>1180 | aaa cac gag agc gac<br>Lys His Glu Ser Asp<br>1185 | 3626 |
| ccg gat gaa agg gac<br>Pro Asp Glu Arg Asp<br>1190 | tac ggc ctg aaa ctc<br>Tyr Gly Leu Lys Leu<br>1195 | ttc ata acc gat gat<br>Phe Ile Thr Asp Asp<br>1200 | 3671 |
| gag ctc aag aaa gta<br>Glu Leu Lys Lys Val<br>1205 | cat gac ttt gaa gag<br>His Asp Phe Glu Glu<br>1210 | caa tgc ata gaa gaa<br>Gln Cys Ile Glu Glu<br>1215 | 3716 |
| tac ttc aga gaa aag<br>Tyr Phe Arg Glu Lys<br>1220 | gat gat cgg ttc aac<br>Asp Asp Arg Phe Asn<br>1225 | tca tct aat gat gag<br>Ser Ser Asn Asp Glu<br>1230 | 3761 |
| agg ata cgg gtg act<br>Arg Ile Arg Val Thr<br>1235 | tca gaa agg gtg gag<br>Ser Glu Arg Val Glu<br>1240 | aac atg tct atg cgg<br>Asn Met Ser Met Arg<br>1245 | 3806 |
| ctg gag gaa gtc aac<br>Leu Glu Glu Val Asn<br>1250 | gag aga gag cac tcc<br>Glu Arg Glu His Ser<br>1255 | atg aag gct tca ctc<br>Met Lys Ala Ser Leu<br>1260 | 3851 |
| cag acc gtg gac atc<br>Gln Thr Val Asp Ile<br>1265 | cgg ctg gcg cag ctg<br>Arg Leu Ala Gln Leu<br>1270 | gaa gac ctt atc ggg<br>Glu Asp Leu Ile Gly<br>1275 | 3896 |
| cgc atg gcc acg gcc<br>Arg Met Ala Thr Ala<br>1280 | ctg gag cgc ctg aca<br>Leu Glu Arg Leu Thr<br>1285 | ggt ctg gag cgg gcc<br>Gly Leu Glu Arg Ala<br>1290 | 3941 |
| gag tcc aac aaa atc<br>Glu Ser Asn Lys Ile<br>1295 | cgc tcg agg acc tcg<br>Arg Ser Arg Thr Ser<br>1300 | tca gac tgc acg gac<br>Ser Asp Cys Thr Asp<br>1305 | 3986 |
| gcc gcc tac att gtc<br>Ala Ala Tyr Ile Val<br>1310 | cgt cag agc agc ttc<br>Arg Gln Ser Ser Phe<br>1315 | aac agc cag gaa ggg<br>Asn Ser Gln Glu Gly<br>1320 | 4031 |
| aac acc ttc aag ctc<br>Asn Thr Phe Lys Leu<br>1325 | caa gag agt ata gac<br>Gln Glu Ser Ile Asp<br>1330 | cct gca ggt gag gag<br>Pro Ala Gly Glu Glu<br>1335 | 4076 |
| acc atg tcc cca act<br>Thr Met Ser Pro Thr<br>1340 | tct cca acc tta atg<br>Ser Pro Thr Leu Met<br>1345 | ccc cgt atg cga agc<br>Pro Arg Met Arg Ser<br>1350 | 4121 |
| cat tct ttc tat tca<br>His Ser Phe Tyr Ser<br>1355 | gtc aat atg aaa gac<br>Val Asn Met Lys Asp<br>1360 | aaa ggt ggt ata gaa<br>Lys Gly Gly Ile Glu<br>1365 | 4166 |
| aag ttg gaa agt att<br>Lys Leu Glu Ser Ile<br>1370 | ttt aaa gaa agg tcc<br>Phe Lys Glu Arg Ser<br>1375 | ctg agc cta cac cgg<br>Leu Ser Leu His Arg<br>1380 | 4211 |
| gct act agt tcc cac<br>Ala Thr Ser Ser His<br>1385 | tct gta gca aaa gaa<br>Ser Val Ala Lys Glu<br>1390 | ccc aaa gct cct gca<br>Pro Lys Ala Pro Ala<br>1395 | 4256 |
| gcc cct gcc aac acc<br>Ala Pro Ala Asn Thr<br>1400 | ttg gcc att gtt cct<br>Leu Ala Ile Val Pro<br>1405 | gat tcc aga aga cca<br>Asp Ser Arg Arg Pro<br>1410 | 4301 |
| tca tcg tgt ata gac<br>Ser Ser Cys Ile Asp<br>1415 | atc tat gtc tct gct<br>Ile Tyr Val Ser Ala<br>1420 | atg gat gag ctc cac<br>Met Asp Glu Leu His<br>1425 | 4346 |
| tgt gat ata gac cct<br>Cys Asp Ile Asp Pro<br>1430 | ctg gac aat tcc gtg<br>Leu Asp Asn Ser Val<br>1435 | aac atc ctt ggg cta<br>Asn Ile Leu Gly Leu<br>1440 | 4391 |
| ggc gag cca agc ttt<br>Gly Glu Pro Ser Phe<br>1445 | tca act cca gta cct<br>Ser Thr Pro Val Pro<br>1450 | tcc aca gcc cct tca<br>Ser Thr Ala Pro Ser<br>1455 | 4436 |

| | | |
|---|---|---|
| agt agt gcc tat gca<br>Ser Ser Ala Tyr Ala<br>1460 | aca ctt gca ccc aca<br>Thr Leu Ala Pro Thr<br>1465 | gac aga cct cca agc<br>Asp Arg Pro Pro Ser<br>1470 | 4481 |
| cgg agc att gat ttt<br>Arg Ser Ile Asp Phe<br>1475 | gag gac atc acc tcc<br>Glu Asp Ile Thr Ser<br>1480 | atg gac act aga tct<br>Met Asp Thr Arg Ser<br>1485 | 4526 |
| ttt tct tca gac tac<br>Phe Ser Ser Asp Tyr<br>1490 | acc cac ctc cca gaa<br>Thr His Leu Pro Glu<br>1495 | tgc caa aac ccc tgg<br>Cys Gln Asn Pro Trp<br>1500 | 4571 |
| gac tca gag cct ccg<br>Asp Ser Glu Pro Pro<br>1505 | atg tac cac acc att<br>Met Tyr His Thr Ile<br>1510 | gag cgt tcc aaa agt<br>Glu Arg Ser Lys Ser<br>1515 | 4616 |
| agc cgc tac cta gcc<br>Ser Arg Tyr Leu Ala<br>1520 | acc aca ccc ttt ctt<br>Thr Thr Pro Phe Leu<br>1525 | cta gaa gag gct ccc<br>Leu Glu Glu Ala Pro<br>1530 | 4661 |
| att gtg aaa tct cat<br>Ile Val Lys Ser His<br>1535 | agc ttt atg ttt tcc<br>Ser Phe Met Phe Ser<br>1540 | ccc tca agg agc tat<br>Pro Ser Arg Ser Tyr<br>1545 | 4706 |
| tat gcc aac ttt ggg<br>Tyr Ala Asn Phe Gly<br>1550 | gtg cct gta aaa aca<br>Val Pro Val Lys Thr<br>1555 | gca gaa tac aca agt<br>Ala Glu Tyr Thr Ser<br>1560 | 4751 |
| att aca gac tgt att<br>Ile Thr Asp Cys Ile<br>1565 | gac aca agg tgt gtc<br>Asp Thr Arg Cys Val<br>1570 | aat gcc cct caa gca<br>Asn Ala Pro Gln Ala<br>1575 | 4796 |
| att gcg gac aga gct<br>Ile Ala Asp Arg Ala<br>1580 | gcc ttc cct gga ggt<br>Ala Phe Pro Gly Gly<br>1585 | ctt gga gac aaa gtg<br>Leu Gly Asp Lys Val<br>1590 | 4841 |
| gag gac tta act tgc<br>Glu Asp Leu Thr Cys<br>1595 | tgc cat cca gag cga<br>Cys His Pro Glu Arg<br>1600 | gaa gca gaa ctg agt<br>Glu Ala Glu Leu Ser<br>1605 | 4886 |
| cac ccc agc tct gac<br>His Pro Ser Ser Asp<br>1610 | agt gag gag aat gag<br>Ser Glu Glu Asn Glu<br>1615 | gcc aaa ggc cgc aga<br>Ala Lys Gly Arg Arg<br>1620 | 4931 |
| gcc acc att gca ata<br>Ala Thr Ile Ala Ile<br>1625 | tcc tcc cag gag ggt<br>Ser Ser Gln Glu Gly<br>1630 | gat aac tca gag aga<br>Asp Asn Ser Glu Arg<br>1635 | 4976 |
| acc ctg tcc aac aac<br>Thr Leu Ser Asn Asn<br>1640 | atc act gtt ccc aag<br>Ile Thr Val Pro Lys<br>1645 | ata gag cgc gcc aac<br>Ile Glu Arg Ala Asn<br>1650 | 5021 |
| agc tac tcg gca gag<br>Ser Tyr Ser Ala Glu<br>1655 | gag cca agt gcg cca<br>Glu Pro Ser Ala Pro<br>1660 | tat gca cac acc agg<br>Tyr Ala His Thr Arg<br>1665 | 5066 |
| aag agc ttc tcc atc<br>Lys Ser Phe Ser Ile<br>1670 | agt gac aaa ctc gac<br>Ser Asp Lys Leu Asp<br>1675 | agg cag cgg aac aca<br>Arg Gln Arg Asn Thr<br>1680 | 5111 |
| gca agc ctg caa aat<br>Ala Ser Leu Gln Asn<br>1685 | ccc ttc cag aga agc<br>Pro Phe Gln Arg Ser<br>1690 | aag tcc tcc aag ccg<br>Lys Ser Ser Lys Pro<br>1695 | 5156 |
| gag ggc cga ggg gac<br>Glu Gly Arg Gly Asp<br>1700 | agc ctg tcc atg agg<br>Ser Leu Ser Met Arg<br>1705 | aga ctg tcc aga aca<br>Arg Leu Ser Arg Thr<br>1710 | 5201 |
| tcg gct ttc caa agc<br>Ser Ala Phe Gln Ser<br>1715 | ttt gaa agc aag cac<br>Phe Glu Ser Lys His<br>1720 | acc taa<br>Thr | 5237 |

<210> SEQ ID NO 4
<211> LENGTH: 1721
<212> TYPE: PRT
<213> ORGANISM: Homo sapiens -continued

```
<400> SEQUENCE: 4

Met Gly Lys Lys Trp Arg Asp Ala Ala Glu Met Glu Arg Gly Cys Ser
1               5                   10                  15

Asp Arg Glu Asp Asn Ala Glu Ser Arg Arg Ser Arg Ser Ala Ser
        20                  25                  30

Arg Gly Arg Phe Ala Glu Ser Trp Lys Arg Leu Ser Ser Lys Gln Gly
35                  40                  45

Ser Thr Lys Arg Ser Gly Leu Pro Ser Gln Gln Thr Pro Ala Gln Lys
50                  55                  60

Ser Trp Ile Glu Arg Ala Phe Tyr Lys Arg Glu Cys Val His Ile Ile
65                  70                  75                  80

Pro Ser Thr Lys Asp Pro His Arg Cys Cys Gly Arg Leu Ile Gly
85                  90                  95

Gln His Val Gly Leu Thr Pro Ser Ile Ser Val Leu Gln Asn Glu Lys
100                 105                 110

Asn Glu Ser Arg Leu Ser Arg Asn Asp Ile Gln Ser Glu Lys Trp Ser
115                 120                 125

Ile Ser Lys His Thr Gln Leu Ser Pro Thr Asp Ala Phe Gly Thr Ile
130                 135                 140

Glu Phe Gln Gly Gly Gly His Ser Asn Lys Ala Met Tyr Val Arg Val
145                 150                 155                 160

Ser Phe Asp Thr Lys Pro Asp Leu Leu Leu His Leu Met Thr Lys Glu
165                 170                 175

Trp Gln Leu Glu Leu Pro Lys Leu Leu Ile Ser Val His Gly Gly Leu
180                 185                 190

Gln Asn Phe Glu Leu Gln Pro Lys Leu Lys Gln Val Phe Gly Lys Gly
195                 200                 205

Leu Ile Lys Ala Ala Met Thr Thr Gly Ala Trp Ile Phe Thr Gly Gly
210                 215                 220

Val Asn Thr Gly Val Ile Arg His Val Gly Asp Ala Leu Lys Asp His
225                 230                 235                 240

Ala Ser Lys Ser Arg Gly Lys Ile Cys Thr Ile Gly Ile Ala Pro Trp
245                 250                 255

Gly Ile Val Glu Asn Gln Glu Asp Leu Ile Gly Arg Asp Val Val Arg
260                 265                 270

Pro Tyr Gln Thr Met Ser Asn Pro Met Ser Lys Leu Thr Val Leu Asn
275                 280                 285

Ser Met His Ser His Phe Ile Leu Ala Asp Asn Gly Thr Thr Gly Lys
290                 295                 300

Tyr Gly Ala Glu Val Lys Leu Arg Arg Gln Leu Glu Lys His Ile Ser
305                 310                 315                 320

Leu Gln Lys Ile Asn Thr Arg Ile Gly Gln Gly Val Pro Val Val Ala
325                 330                 335

Leu Ile Val Glu Gly Gly Pro Asn Val Ile Ser Ile Val Leu Glu Tyr
340                 345                 350

Leu Arg Asp Thr Pro Pro Val Pro Val Val Cys Asp Gly Ser Gly
355                 360                 365

Arg Ala Ser Asp Ile Leu Ala Phe Gly His Lys Tyr Ser Glu Glu Gly
370                 375                 380

Gly Leu Ile Asn Glu Ser Leu Arg Asp Gln Leu Leu Val Thr Ile Gln
385                 390                 395                 400

Lys Thr Phe Thr Tyr Thr Arg Thr Gln Ala Gln His Leu Phe Ile Ile
405                 410                 415
```

```
Leu Met Glu Cys Met Lys Lys Glu Leu Ile Thr Val Phe Arg Met
420                 425                 430

Gly Ser Glu Gly His Gln Asp Ile Asp Leu Ala Ile Leu Thr Ala Leu
435                 440                 445

Leu Lys Gly Ala Asn Ala Ser Ala Pro Asp Gln Leu Ser Leu Ala Leu
450                 455                 460

Ala Trp Asn Arg Val Asp Ile Ala Arg Ser Gln Ile Phe Ile Tyr Gly
465                 470                 475                 480

Gln Gln Trp Pro Val Gly Ser Leu Glu Gln Ala Met Leu Asp Ala Leu
485                 490                 495

Val Leu Asp Arg Val Asp Phe Val Lys Leu Leu Ile Glu Asn Gly Val
500                 505                 510

Ser Met His Arg Phe Leu Thr Ile Ser Arg Leu Glu Glu Leu Tyr Asn
515                 520                 525

Thr Arg His Gly Pro Ser Asn Thr Leu Tyr His Leu Val Arg Asp Val
530                 535                 540

Lys Lys Arg Glu Tyr Pro Gly Phe Gly Trp Ile Tyr Phe Lys Gly Asn
545                 550                 555                 560

Leu Pro Pro Asp Tyr Arg Ile Ser Leu Ile Asp Ile Gly Leu Val Ile
565                 570                 575

Glu Tyr Leu Met Gly Gly Ala Tyr Arg Cys Asn Tyr Thr Arg Lys Arg
580                 585                 590

Phe Arg Thr Leu Tyr His Asn Leu Phe Gly Pro Lys Arg Pro Lys Ala
595                 600                 605

Leu Lys Leu Leu Gly Met Glu Asp Asp Ile Pro Leu Arg Arg Gly Arg
610                 615                 620

Lys Thr Thr Lys Lys Arg Glu Glu Glu Val Asp Ile Asp Leu Asp Asp
625                 630                 635                 640

Pro Glu Ile Asn His Phe Pro Phe Pro Phe His Glu Leu Met Val Trp
645                 650                 655

Ala Val Leu Met Lys Arg Gln Lys Met Ala Leu Phe Phe Trp Gln His
660                 665                 670

Gly Glu Glu Ala Met Ala Lys Ala Leu Val Ala Cys Lys Leu Cys Lys
675                 680                 685

Ala Met Ala His Glu Ala Ser Glu Asn Asp Met Val Asp Asp Ile Ser
690                 695                 700

Gln Glu Leu Asn His Asn Ser Arg Asp Phe Gly Gln Leu Ala Val Glu
705                 710                 715                 720

Leu Leu Asp Gln Ser Tyr Lys Gln Asp Glu Gln Leu Ala Met Lys Leu
725                 730                 735

Leu Thr Tyr Glu Leu Lys Asn Trp Ser Asn Ala Thr Cys Leu Gln Leu
740                 745                 750

Ala Val Ala Ala Lys His Arg Asp Phe Ile Ala His Thr Cys Ser Gln
755                 760                 765

Met Leu Leu Thr Asp Met Trp Met Gly Arg Leu Arg Met Arg Lys Asn
770                 775                 780

Ser Gly Leu Lys Val Ile Leu Gly Ile Leu Leu Pro Pro Ser Ile Leu
785                 790                 795                 800

Ser Leu Glu Phe Lys Asn Lys Asp Asp Met Pro Tyr Met Ser Gln Ala
805                 810                 815

Gln Glu Ile His Leu Gln Glu Lys Glu Ala Glu Glu Pro Glu Lys Pro
820                 825                 830
```

-continued

```
Thr Lys Glu Lys Glu Glu Asp Met Glu Leu Thr Ala Met Leu Gly
835                 840                 845

Arg Asn Asn Gly Glu Ser Ser Arg Lys Lys Asp Glu Glu Val Gln
850                 855                 860

Ser Lys His Arg Leu Ile Pro Leu Gly Arg Lys Ile Tyr Glu Phe Tyr
865                 870                 875                 880

Asn Ala Pro Ile Val Lys Phe Trp Phe Tyr Thr Leu Ala Tyr Ile Gly
885                 890                 895

Tyr Leu Met Leu Phe Asn Tyr Ile Val Leu Val Lys Met Glu Arg Trp
900                 905                 910

Pro Ser Thr Gln Glu Trp Ile Val Ile Ser Tyr Ile Phe Thr Leu Gly
915                 920                 925

Ile Glu Lys Met Arg Glu Ile Leu Met Ser Glu Pro Gly Lys Leu Leu
930                 935                 940

Gln Lys Val Lys Val Trp Leu Gln Glu Tyr Trp Asn Val Thr Asp Leu
945                 950                 955                 960

Ile Ala Ile Leu Leu Phe Ser Val Gly Met Ile Leu Arg Leu Gln Asp
965                 970                 975

Gln Pro Phe Arg Ser Asp Gly Arg Val Ile Tyr Cys Val Asn Ile Ile
980                 985                 990

Tyr Trp Tyr Ile Arg Leu Leu Asp  Ile Phe Gly Val Asn  Lys Tyr Leu
995                 1000                 1005

Gly Pro  Tyr Val Met Met Ile  Gly Lys Met Met Ile  Asp Met Met
1010                 1015                 1020

Tyr Phe  Val Ile Ile Met Leu  Val Val Leu Met Ser  Phe Gly Val
1025                 1030                 1035

Ala Arg  Gln Ala Ile Leu Phe  Pro Asn Glu Glu Pro  Ser Trp Lys
1040                 1045                 1050

Leu Ala  Lys Asn Ile Phe Tyr  Met Pro Tyr Trp Met  Ile Tyr Gly
1055                 1060                 1065

Glu Val  Phe Ala Asp Gln Ile  Asp Pro Pro Cys Gly  Gln Asn Glu
1070                 1075                 1080

Thr Arg  Glu Asp Gly Lys Ile  Ile Gln Leu Pro Pro  Cys Lys Thr
1085                 1090                 1095

Gly Ala  Trp Ile Val Pro Ala  Ile Met Ala Cys Tyr  Leu Leu Val
1100                 1105                 1110

Ala Asn  Ile Leu Leu Val Asn  Leu Leu Ile Ala Val  Phe Asn Asn
1115                 1120                 1125

Thr Phe  Phe Glu Val Lys Ser  Ile Ser Asn Gln Val  Trp Lys Phe
1130                 1135                 1140

Gln Arg  Tyr Gln Leu Ile Met  Thr Phe His Glu Arg  Pro Val Leu
1145                 1150                 1155

Pro Pro  Pro Leu Ile Ile Phe  Ser His Met Thr Met  Ile Phe Gln
1160                 1165                 1170

His Leu  Cys Cys Arg Trp Arg  Lys His Glu Ser Asp  Pro Asp Glu
1175                 1180                 1185

Arg Asp  Tyr Gly Leu Lys Leu  Phe Ile Thr Asp Asp  Glu Leu Lys
1190                 1195                 1200

Lys Val  His Asp Phe Glu Glu  Gln Cys Ile Glu Glu  Tyr Phe Arg
1205                 1210                 1215

Glu Lys  Asp Asp Arg Phe Asn  Ser Ser Asn Asp Glu  Arg Ile Arg
1220                 1225                 1230

Val Thr  Ser Glu Arg Val Glu  Asn Met Ser Met Arg  Leu Glu Glu
```

-continued

```
        1235                1240                1245

Val Asn Glu Arg Glu His Ser Met Lys Ala Ser Leu Gln Thr Val
1250                1255                1260

Asp Ile Arg Leu Ala Gln Leu Glu Asp Leu Ile Gly Arg Met Ala
1265                1270                1275

Thr Ala Leu Glu Arg Leu Thr Gly Leu Glu Arg Ala Glu Ser Asn
1280                1285                1290

Lys Ile Arg Ser Arg Thr Ser Ser Asp Cys Thr Asp Ala Ala Tyr
1295                1300                1305

Ile Val Arg Gln Ser Ser Phe Asn Ser Gln Glu Gly Asn Thr Phe
1310                1315                1320

Lys Leu Gln Glu Ser Ile Asp Pro Ala Gly Glu Glu Thr Met Ser
1325                1330                1335

Pro Thr Ser Pro Thr Leu Met Pro Arg Met Arg Ser His Ser Phe
1340                1345                1350

Tyr Ser Val Asn Met Lys Asp Lys Gly Gly Ile Glu Lys Leu Glu
1355                1360                1365

Ser Ile Phe Lys Glu Arg Ser Leu Ser Leu His Arg Ala Thr Ser
1370                1375                1380

Ser His Ser Val Ala Lys Glu Pro Lys Ala Pro Ala Ala Pro Ala
1385                1390                1395

Asn Thr Leu Ala Ile Val Pro Asp Ser Arg Arg Pro Ser Ser Cys
1400                1405                1410

Ile Asp Ile Tyr Val Ser Ala Met Asp Glu Leu His Cys Asp Ile
1415                1420                1425

Asp Pro Leu Asp Asn Ser Val Asn Ile Leu Gly Leu Gly Glu Pro
1430                1435                1440

Ser Phe Ser Thr Pro Val Pro Ser Thr Ala Pro Ser Ser Ser Ala
1445                1450                1455

Tyr Ala Thr Leu Ala Pro Thr Asp Arg Pro Pro Ser Arg Ser Ile
1460                1465                1470

Asp Phe Glu Asp Ile Thr Ser Met Asp Thr Arg Ser Phe Ser Ser
1475                1480                1485

Asp Tyr Thr His Leu Pro Glu Cys Gln Asn Pro Trp Asp Ser Glu
1490                1495                1500

Pro Pro Met Tyr His Thr Ile Glu Arg Ser Lys Ser Ser Arg Tyr
1505                1510                1515

Leu Ala Thr Thr Pro Phe Leu Leu Glu Glu Ala Pro Ile Val Lys
1520                1525                1530

Ser His Ser Phe Met Phe Ser Pro Ser Arg Ser Tyr Tyr Ala Asn
1535                1540                1545

Phe Gly Val Pro Val Lys Thr Ala Glu Tyr Thr Ser Ile Thr Asp
1550                1555                1560

Cys Ile Asp Thr Arg Cys Val Asn Ala Pro Gln Ala Ile Ala Asp
1565                1570                1575

Arg Ala Ala Phe Pro Gly Gly Leu Gly Asp Lys Val Glu Asp Leu
1580                1585                1590

Thr Cys Cys His Pro Glu Arg Glu Ala Glu Leu Ser His Pro Ser
1595                1600                1605

Ser Asp Ser Glu Glu Asn Glu Ala Lys Gly Arg Arg Ala Thr Ile
1610                1615                1620

Ala Ile Ser Ser Gln Glu Gly Asp Asn Ser Glu Arg Thr Leu Ser
1625                1630                1635
```

```
Asn Asn Ile Thr Val Pro Lys Ile Glu Arg Ala Asn Ser Tyr Ser
1640                1645                1650

Ala Glu Glu Pro Ser Ala Pro Tyr Ala His Thr Arg Lys Ser Phe
1655                1660                1665

Ser Ile Ser Asp Lys Leu Asp Arg Gln Arg Asn Thr Ala Ser Leu
1670                1675                1680

Gln Asn Pro Phe Gln Arg Ser Lys Ser Ser Lys Pro Glu Gly Arg
1685                1690                1695

Gly Asp Ser Leu Ser Met Arg Arg Leu Ser Arg Thr Ser Ala Phe
1700                1705                1710

Gln Ser Phe Glu Ser Lys His Thr
1715                1720

<210> SEQ ID NO 5
<211> LENGTH: 5237
<212> TYPE: DNA
<213> ORGANISM: Homo sapiens
<220> FEATURE:
<221> NAME/KEY: CDS
<222> LOCATION: (72)..(5234)

<400> SEQUENCE: 5
cgcccgcggc gaggagccag cgagagcgct cggcgctggg ctgtttcccg gccgagggag    60
gcgaacttct c atg ggg aag aag tgg agg gat gcg gcg gaa atg gag cgg   110
            Met Gly Lys Lys Trp Arg Asp Ala Ala Glu Met Glu Arg
            1               5                   10 ggc tgc tcc gac cgc gag gac aac gcg gag agc cgc aga cgc agc cgg   158
Gly Cys Ser Asp Arg Glu Asp Asn Ala Glu Ser Arg Arg Arg Ser Arg
15                  20                  25 agc gcc agc cgg ggc agg ttt gcc gag tcg tgg aaa agg tta agt tcc   206
Ser Ala Ser Arg Gly Arg Phe Ala Glu Ser Trp Lys Arg Leu Ser Ser
30                  35                  40                  45 aag cag ggg tcc acc aaa cgc tcg gga ctc ccg tcg cag cag acg ccg   254
Lys Gln Gly Ser Thr Lys Arg Ser Gly Leu Pro Ser Gln Gln Thr Pro
50                  55                  60 gct cag aaa tcc tgg ata gaa aga gca ttt tat aaa aga gaa tgt gtc   302
Ala Gln Lys Ser Trp Ile Glu Arg Ala Phe Tyr Lys Arg Glu Cys Val
65                  70                  75 cac atc ata ccc agc acc aaa gac ccc cat agg tgt tgc tgt ggg cgt   350
His Ile Ile Pro Ser Thr Lys Asp Pro His Arg Cys Cys Cys Gly Arg
80                  85                  90 ctg ata ggc cag cat gtt ggc ctc acc ccc agt atc tcc gtg ctt cag   398
Leu Ile Gly Gln His Val Gly Leu Thr Pro Ser Ile Ser Val Leu Gln
95                  100                 105 aat gag aaa aat gaa agt cgc ctc tcc cga aat gac atc cag tct gaa   446
Asn Glu Lys Asn Glu Ser Arg Leu Ser Arg Asn Asp Ile Gln Ser Glu
110                 115                 120                 125 aag tgg tcc atc agc aaa cac act caa ctc agc cct acg gat gct ttt   494
Lys Trp Ser Ile Ser Lys His Thr Gln Leu Ser Pro Thr Asp Ala Phe
130                 135                 140 ggg acc att gag ttc caa gga ggt ggc cat tcc aac aaa gcc atg tat   542
Gly Thr Ile Glu Phe Gln Gly Gly Gly His Ser Asn Lys Ala Met Tyr
145                 150                 155 gtg cga gta tct ttt gat aca aaa cct gat ctc ctc tta cac ctg atg   590
Val Arg Val Ser Phe Asp Thr Lys Pro Asp Leu Leu Leu His Leu Met
160                 165                 170 acc aag gaa tgg cag ttg gag ctt ccc aag ctt ctc atc tct gtc cat   638
Thr Lys Glu Trp Gln Leu Glu Leu Pro Lys Leu Leu Ile Ser Val His
175                 180                 185
```

-continued

| | | |
|---|---|---|
| ggg ggc ctg cag aac ttt gaa ctc cag cca aaa ctc aag caa gtc ttt<br>Gly Gly Leu Gln Asn Phe Glu Leu Gln Pro Lys Leu Lys Gln Val Phe<br>190                      195                    200                  205 | 686 |
| ggg aaa ggg ctc atc aaa gca gca atg aca act gga gcg tgg ata ttc<br>Gly Lys Gly Leu Ile Lys Ala Ala Met Thr Thr Gly Ala Trp Ile Phe<br>210                      215                    220 | 734 |
| act gga ggg gtt aac aca ggt gtt att cgt cat gtt ggc gat gcc ttg<br>Thr Gly Gly Val Asn Thr Gly Val Ile Arg His Val Gly Asp Ala Leu<br>225                      230                    235 | 782 |
| aag gat cat gcc tct aag tct cga gga aag ata tgc acc ata ggt att<br>Lys Asp His Ala Ser Lys Ser Arg Gly Lys Ile Cys Thr Ile Gly Ile<br>240                      245                    250 | 830 |
| gcc ccc tgg gga att gtg gaa aac cag gag gac ctc att gga aga gat<br>Ala Pro Trp Gly Ile Val Glu Asn Gln Glu Asp Leu Ile Gly Arg Asp<br>255                      260                    265 | 878 |
| gtt gtc cgg cca tac cag acc atg tcc aat ccc atg agc aag ctc act<br>Val Val Arg Pro Tyr Gln Thr Met Ser Asn Pro Met Ser Lys Leu Thr<br>270                      275                    280                    285 | 926 |
| gtt ctc aac agc atg cat tcc cac ttc att ctg gct gac aac ggg acc<br>Val Leu Asn Ser Met His Ser His Phe Ile Leu Ala Asp Asn Gly Thr<br>290                      295                    300 | 974 |
| act gga aaa tat gga gca gag gtg aaa ctt cga aga caa ctg gaa aag<br>Thr Gly Lys Tyr Gly Ala Glu Val Lys Leu Arg Arg Gln Leu Glu Lys<br>305                      310                    315 | 1022 |
| cat att tca ctc cag aag ata aac aca aga atc ggt caa ggt gtt cct<br>His Ile Ser Leu Gln Lys Ile Asn Thr Arg Ile Gly Gln Gly Val Pro<br>320                      325                    330 | 1070 |
| gtg gtg gca ctc ata gtg gaa gga gga ccc aat gtg atc tcg att gtt<br>Val Val Ala Leu Ile Val Glu Gly Gly Pro Asn Val Ile Ser Ile Val<br>335                      340                    345 | 1118 |
| ttg gag tac ctt cga gac acc cct ccc gtg cca gtg gtt gtc tgt gat<br>Leu Glu Tyr Leu Arg Asp Thr Pro Pro Val Pro Val Val Val Cys Asp<br>350                      355                    360                    365 | 1166 |
| ggg agt gga cgg gca tcg gac atc ctg gcc ttt ggg cat aaa tac tca<br>Gly Ser Gly Arg Ala Ser Asp Ile Leu Ala Phe Gly His Lys Tyr Ser<br>370                      375                    380 | 1214 |
| gaa gaa ggc gga ctg ata aat gaa tct ttg agg gac cag ctg ttg gtg<br>Glu Glu Gly Gly Leu Ile Asn Glu Ser Leu Arg Asp Gln Leu Leu Val<br>385                      390                    395 | 1262 |
| act ata cag aag act ttc aca tac act cga acc caa gct cag cat ctg<br>Thr Ile Gln Lys Thr Phe Thr Tyr Thr Arg Thr Gln Ala Gln His Leu<br>400                      405                    410 | 1310 |
| ttc atc atc ctc atg gag tgc atg aag aag aag gaa ttg att acg gta<br>Phe Ile Ile Leu Met Glu Cys Met Lys Lys Lys Glu Leu Ile Thr Val<br>415                      420                    425 | 1358 |
| ttt cgg atg gga tca gaa gga cac cag gac att gat ttg gct atc ctg<br>Phe Arg Met Gly Ser Glu Gly His Gln Asp Ile Asp Leu Ala Ile Leu<br>430                      435                    440                    445 | 1406 |
| aca gct tta ctc aaa gga gcc aat gcc tcg gcc cca gac caa ctg agc<br>Thr Ala Leu Leu Lys Gly Ala Asn Ala Ser Ala Pro Asp Gln Leu Ser<br>450                      455                    460 | 1454 |
| tta gct tta gcc tgg aac aga gtc gac atc gct cgc agc cag atc ttt<br>Leu Ala Leu Ala Trp Asn Arg Val Asp Ile Ala Arg Ser Gln Ile Phe<br>465                      470                    475 | 1502 |
| att tac ggg caa cag tgg ccg gtg gga tct ctg gag caa gcc atg ttg<br>Ile Tyr Gly Gln Gln Trp Pro Val Gly Ser Leu Glu Gln Ala Met Leu<br>480                      485                    490 | 1550 |
| gat gcc tta gtt ctg gac aga gtg gat ttt gtg aaa tta ctc ata gag<br>Asp Ala Leu Val Leu Asp Arg Val Asp Phe Val Lys Leu Leu Ile Glu | 1598 |

-continued

```
                495                 500                 505
aat gga gta agc atg cac cgt ttt ctc acc atc tcc aga cta gag gaa    1646
Asn Gly Val Ser Met His Arg Phe Leu Thr Ile Ser Arg Leu Glu Glu
510                 515                 520                 525 ttg tac aat acg aga cat ggg ccc tca aat aca ttg tac cac ttg gtc    1694
Leu Tyr Asn Thr Arg His Gly Pro Ser Asn Thr Leu Tyr His Leu Val
530                 535                 540 agg gat gtc aaa aag ggg aac ctg ccc cca gac tac aga atc agc ctg    1742
Arg Asp Val Lys Lys Gly Asn Leu Pro Pro Asp Tyr Arg Ile Ser Leu
545                 550                 555 att gac atc ggc ctg gtg atc gag tac ctg atg ggc ggg gct tat cgc    1790
Ile Asp Ile Gly Leu Val Ile Glu Tyr Leu Met Gly Gly Ala Tyr Arg
560                 565                 570 tgc aac tac acg cgc aag cgc ttc cgg acc ctc tac cac aac ctc ttc    1838
Cys Asn Tyr Thr Arg Lys Arg Phe Arg Thr Leu Tyr His Asn Leu Phe
575                 580                 585 ggc ccc aag agg ccc aaa gcc ttg aaa ctg ctg gga atg gag gat gat    1886
Gly Pro Lys Arg Pro Lys Ala Leu Lys Leu Leu Gly Met Glu Asp Asp
590                 595                 600                 605 att ccc ttg agg cga gga aga aag aca acc aag aaa cgt gaa gaa gag    1934
Ile Pro Leu Arg Arg Gly Arg Lys Thr Thr Lys Lys Arg Glu Glu Glu
610                 615                 620 gtg gac att gac ttg gat gat cct gag atc aac cac ttc ccc ttc cct    1982
Val Asp Ile Asp Leu Asp Asp Pro Glu Ile Asn His Phe Pro Phe Pro
625                 630                 635 ttc cat gag ctc atg gtg tgg gct gtt ctc atg aag cgg cag aag atg    2030
Phe His Glu Leu Met Val Trp Ala Val Leu Met Lys Arg Gln Lys Met
640                 645                 650 gcc ctg ttc ttc tgg cag cac ggt gag gag gcc atg gcc aag gcc ctg    2078
Ala Leu Phe Phe Trp Gln His Gly Glu Glu Ala Met Ala Lys Ala Leu
655                 660                 665 gtg gcc tgc aag ctc tgc aaa gcc atg gct cat gag gcc tct gag aac    2126
Val Ala Cys Lys Leu Cys Lys Ala Met Ala His Glu Ala Ser Glu Asn
670                 675                 680                 685 gac atg gtt gac gac att tcc cag gag ctg aat cac aat tcc aga gac    2174
Asp Met Val Asp Asp Ile Ser Gln Glu Leu Asn His Asn Ser Arg Asp
690                 695                 700 ttt ggc cag ctg gct gtg gag ctc ctg gac cag tcc tac aag cag gac    2222
Phe Gly Gln Leu Ala Val Glu Leu Leu Asp Gln Ser Tyr Lys Gln Asp
705                 710                 715 gaa cag ctg gcc atg aaa ctg ctg acg tat gag ctg aag aac tgg agc    2270
Glu Gln Leu Ala Met Lys Leu Leu Thr Tyr Glu Leu Lys Asn Trp Ser
720                 725                 730 aac gcc acg tgc ctg cag ctt gcc gtg gct gcc aaa cac cgc gac ttc    2318
Asn Ala Thr Cys Leu Gln Leu Ala Val Ala Ala Lys His Arg Asp Phe
735                 740                 745 atc gcg cac acg tgc agc cag atg ctg ctc acc gac atg tgg atg ggc    2366
Ile Ala His Thr Cys Ser Gln Met Leu Leu Thr Asp Met Trp Met Gly
750                 755                 760                 765 cgg ctc cgc atg cgc aag aac tca ggc ctc aag gta att ctg gga att    2414
Arg Leu Arg Met Arg Lys Asn Ser Gly Leu Lys Val Ile Leu Gly Ile
770                 775                 780 cta ctt cct cct tca att ctc agc ttg gag ttc aag aac aaa gac gac    2462
Leu Leu Pro Pro Ser Ile Leu Ser Leu Glu Phe Lys Asn Lys Asp Asp
785                 790                 795 atg ccc tat atg tct cag gcc cag gaa atc cac ctc caa gag aag gag    2510
Met Pro Tyr Met Ser Gln Ala Gln Glu Ile His Leu Gln Glu Lys Glu
800                 805                 810 gca gaa gaa cca gag aag ccc aca aag gaa aaa gag gaa gag gac atg    2558
```

-continued

```
Ala Glu Glu Pro Glu Lys Pro Thr Lys Glu Lys Glu Glu Asp Met
815                 820                 825 gag ctc aca gca atg ttg gga cga aac aac ggg gag tcc tcc agg aag      2606
Glu Leu Thr Ala Met Leu Gly Arg Asn Asn Gly Glu Ser Ser Arg Lys
830                 835                 840                 845 aag gat gaa gag gaa gtt cag agc aag cac cgg tta atc ccc ctc ggc      2654
Lys Asp Glu Glu Glu Val Gln Ser Lys His Arg Leu Ile Pro Leu Gly
        850                 855                 860 aga aaa atc tat gaa ttc tac aat gca ccc atc gtg aag ttc tgg ttc      2702
Arg Lys Ile Tyr Glu Phe Tyr Asn Ala Pro Ile Val Lys Phe Trp Phe
865                 870                 875 tac aca ctg gcg tat atc gga tac ctg atg ctc ttc aac tat atc gtg      2750
Tyr Thr Leu Ala Tyr Ile Gly Tyr Leu Met Leu Phe Asn Tyr Ile Val
880                 885                 890 tta gtg aag atg gaa cgc tgg ccg tcc acc cag gaa tgg atc gta atc      2798
Leu Val Lys Met Glu Arg Trp Pro Ser Thr Gln Glu Trp Ile Val Ile
895                 900                 905 tcc tat att ttc acc ctg gga ata gaa aag atg aga gag att ctg atg      2846
Ser Tyr Ile Phe Thr Leu Gly Ile Glu Lys Met Arg Glu Ile Leu Met
910                 915                 920                 925 tca gag cca ggg aag ttg cta cag aaa gtg aag gta tgg ctg cag gag      2894
Ser Glu Pro Gly Lys Leu Leu Gln Lys Val Lys Val Trp Leu Gln Glu
930                 935                 940 tac tgg aat gtc acg gac ctc atc gcc atc ctt ctg ttt tct gtc gga      2942
Tyr Trp Asn Val Thr Asp Leu Ile Ala Ile Leu Leu Phe Ser Val Gly
945                 950                 955 atg atc ctt cgt ctc caa gac cag ccc ttc agg agt gac ggg agg gtc      2990
Met Ile Leu Arg Leu Gln Asp Gln Pro Phe Arg Ser Asp Gly Arg Val
960                 965                 970 atc tac tgc gtg aac atc att tac tgg tat atc cgt ctc cta gac atc      3038
Ile Tyr Cys Val Asn Ile Ile Tyr Trp Tyr Ile Arg Leu Leu Asp Ile
975                 980                 985 ttc ggc gtg aac aag tat ttg ggc ccg tat gta atg atg att gga aaa      3086
Phe Gly Val Asn Lys Tyr Leu Gly Pro Tyr Val Met Met Ile Gly Lys
990                 995                 1000                1005 atg atg ata gac atg atg tac ttt gtc atc att atg ctg gtg gtt          3131
Met Met Ile Asp Met Met Tyr Phe Val Ile Ile Met Leu Val Val
1010                1015                1020 ctg atg agc ttt ggg gtc gcc agg caa gcc atc ctt ttt ccc aat          3176
Leu Met Ser Phe Gly Val Ala Arg Gln Ala Ile Leu Phe Pro Asn
1025                1030                1035 gag gag cca tca tgg aaa ctg gcc aag aac atc ttc tac atg ccc          3221
Glu Glu Pro Ser Trp Lys Leu Ala Lys Asn Ile Phe Tyr Met Pro
1040                1045                1050 tat tgg atg att tat ggg gaa gtg ttt gcg gac cag ata gac cgt          3266
Tyr Trp Met Ile Tyr Gly Glu Val Phe Ala Asp Gln Ile Asp Arg
1055                1060                1065 aag caa gtt tat gat tct cat aca cca aag tca gct ccc tgt gga          3311
Lys Gln Val Tyr Asp Ser His Thr Pro Lys Ser Ala Pro Cys Gly
1070                1075                1080 cag aat gag acc cga gag gat ggt aaa ata atc cag ctg cct ccc          3356
Gln Asn Glu Thr Arg Glu Asp Gly Lys Ile Ile Gln Leu Pro Pro
1085                1090                1095 tgc aag aca gga gct tgg atc gtg ccg gcc atc atg gcc tgc tac          3401
Cys Lys Thr Gly Ala Trp Ile Val Pro Ala Ile Met Ala Cys Tyr
1100                1105                1110 ctc tta gtg gca aac atc ttg ctg gtc aac ctc ctc att gct gtc          3446
Leu Leu Val Ala Asn Ile Leu Leu Val Asn Leu Leu Ile Ala Val
1115                1120                1125
```

```
                                                  -continued ttt aac aat aca ttt   ttt gaa gta aaa tcg   ata tcc aac caa gtc    3491
Phe Asn Asn Thr Phe   Phe Glu Val Lys Ser   Ile Ser Asn Gln Val
1130                  1135                  1140 tgg aag ttt cag agg   tat cag ctc atc atg   act ttc cat gaa agg    3536
Trp Lys Phe Gln Arg   Tyr Gln Leu Ile Met   Thr Phe His Glu Arg
1145                  1150                  1155 cca gtt ctg ccc cca   cca ctg atc atc ttc   agc cac atg acc atg    3581
Pro Val Leu Pro Pro   Pro Leu Ile Ile Phe   Ser His Met Thr Met
1160                  1165                  1170 ata ttc cag cac ctg   tgc tgc cga tgg agg   aaa cac gag agc gac    3626
Ile Phe Gln His Leu   Cys Cys Arg Trp Arg   Lys His Glu Ser Asp
1175                  1180                  1185 ccg gat gaa agg gac   tac ggc ctg aaa ctc   ttc ata acc gat gat    3671
Pro Asp Glu Arg Asp   Tyr Gly Leu Lys Leu   Phe Ile Thr Asp Asp
1190                  1195                  1200 gag ctc aag aaa gta   cat gac ttt gaa gag   caa tgc ata gaa gaa    3716
Glu Leu Lys Lys Val   His Asp Phe Glu Glu   Gln Cys Ile Glu Glu
1205                  1210                  1215 tac ttc aga gaa aag   gat gat cgg ttc aac   tca tct aat gat gag    3761
Tyr Phe Arg Glu Lys   Asp Asp Arg Phe Asn   Ser Ser Asn Asp Glu
1220                  1225                  1230 agg ata cgg gtg act   tca gaa agg gtg gag   aac atg tct atg cgg    3806
Arg Ile Arg Val Thr   Ser Glu Arg Val Glu   Asn Met Ser Met Arg
1235                  1240                  1245 ctg gag gaa gtc aac   gag aga gag cac tcc   atg aag gct tca ctc    3851
Leu Glu Glu Val Asn   Glu Arg Glu His Ser   Met Lys Ala Ser Leu
1250                  1255                  1260 cag acc gtg gac atc   cgg ctg gcg cag ctg   gaa gac ctt atc ggg    3896
Gln Thr Val Asp Ile   Arg Leu Ala Gln Leu   Glu Asp Leu Ile Gly
1265                  1270                  1275 cgc atg gcc acg gcc   ctg gag cgc ctg aca   ggt ctg gag cgg gcc    3941
Arg Met Ala Thr Ala   Leu Glu Arg Leu Thr   Gly Leu Glu Arg Ala
1280                  1285                  1290 gag tcc aac aaa atc   cgc tcg agg acc tcg   tca gac tgc acg gac    3986
Glu Ser Asn Lys Ile   Arg Ser Arg Thr Ser   Ser Asp Cys Thr Asp
1295                  1300                  1305 gcc gcc tac att gtc   cgt cag agc agc ttc   aac agc cag gaa ggg    4031
Ala Ala Tyr Ile Val   Arg Gln Ser Ser Phe   Asn Ser Gln Glu Gly
1310                  1315                  1320 aac acc ttc aag ctc   caa gag agt ata gac   cct gca ggt gag gag    4076
Asn Thr Phe Lys Leu   Gln Glu Ser Ile Asp   Pro Ala Gly Glu Glu
1325                  1330                  1335 acc atg tcc cca act   tct cca acc tta atg   ccc cgt atg cga agc    4121
Thr Met Ser Pro Thr   Ser Pro Thr Leu Met   Pro Arg Met Arg Ser
1340                  1345                  1350 cat tct ttc tat tca   gtc aat atg aaa gac   aaa ggt ggt ata gaa    4166
His Ser Phe Tyr Ser   Val Asn Met Lys Asp   Lys Gly Gly Ile Glu
1355                  1360                  1365 aag ttg gaa agt att   ttt aaa gaa agg tcc   ctg agc cta cac cgg    4211
Lys Leu Glu Ser Ile   Phe Lys Glu Arg Ser   Leu Ser Leu His Arg
1370                  1375                  1380 gct act agt tcc cac   tct gta gca aaa gaa   ccc aaa gct cct gca    4256
Ala Thr Ser Ser His   Ser Val Ala Lys Glu   Pro Lys Ala Pro Ala
1385                  1390                  1395 gcc cct gcc aac acc   ttg gcc att gtt cct   gat tcc aga aga cca    4301
Ala Pro Ala Asn Thr   Leu Ala Ile Val Pro   Asp Ser Arg Arg Pro
1400                  1405                  1410 tca tcg tgt ata gac   atc tat gtc tct gct   atg gat gag ctc cac    4346
Ser Ser Cys Ile Asp   Ile Tyr Val Ser Ala   Met Asp Glu Leu His
1415                  1420                  1425
```

|     |     |
| --- | --- |
| tgt gat ata gac cct ctg gac aat tcc gtg aac atc ctt ggg cta<br>Cys Asp Ile Asp Pro Leu Asp Asn Ser Val Asn Ile Leu Gly Leu<br>1430                      1435                      1440 | 4391 |
| ggc gag cca agc ttt tca act cca gta cct tcc aca gcc cct tca<br>Gly Glu Pro Ser Phe Ser Thr Pro Val Pro Ser Thr Ala Pro Ser<br>1445                      1450                      1455 | 4436 |
| agt agt gcc tat gca aca ctt gca ccc aca gac aga cct cca agc<br>Ser Ser Ala Tyr Ala Thr Leu Ala Pro Thr Asp Arg Pro Pro Ser<br>1460                      1465                      1470 | 4481 |
| cgg agc att gat ttt gag gac atc acc tcc atg gac act aga tct<br>Arg Ser Ile Asp Phe Glu Asp Ile Thr Ser Met Asp Thr Arg Ser<br>1475                      1480                      1485 | 4526 |
| ttt tct tca gac tac acc cac ctc cca gaa tgc caa aac ccc tgg<br>Phe Ser Ser Asp Tyr Thr His Leu Pro Glu Cys Gln Asn Pro Trp<br>1490                      1495                      1500 | 4571 |
| gac tca gag cct ccg atg tac cac acc att gag cgt tcc aaa agt<br>Asp Ser Glu Pro Pro Met Tyr His Thr Ile Glu Arg Ser Lys Ser<br>1505                      1510                      1515 | 4616 |
| agc cgc tac cta gcc acc aca ccc ttt ctt cta gaa gag gct ccc<br>Ser Arg Tyr Leu Ala Thr Thr Pro Phe Leu Leu Glu Glu Ala Pro<br>1520                      1525                      1530 | 4661 |
| att gtg aaa tct cat agc ttt atg ttt tcc ccc tca agg agc tat<br>Ile Val Lys Ser His Ser Phe Met Phe Ser Pro Ser Arg Ser Tyr<br>1535                      1540                      1545 | 4706 |
| tat gcc aac ttt ggg gtg cct gta aaa aca gca gaa tac aca agt<br>Tyr Ala Asn Phe Gly Val Pro Val Lys Thr Ala Glu Tyr Thr Ser<br>1550                      1555                      1560 | 4751 |
| att aca gac tgt att gac aca agg tgt gtc aat gcc cct caa gca<br>Ile Thr Asp Cys Ile Asp Thr Arg Cys Val Asn Ala Pro Gln Ala<br>1565                      1570                      1575 | 4796 |
| att gcg gac aga gct gcc ttc cct gga ggt ctt gga gac aaa gtg<br>Ile Ala Asp Arg Ala Ala Phe Pro Gly Gly Leu Gly Asp Lys Val<br>1580                      1585                      1590 | 4841 |
| gag gac tta act tgc tgc cat cca gag cga gaa gca gaa ctg agt<br>Glu Asp Leu Thr Cys Cys His Pro Glu Arg Glu Ala Glu Leu Ser<br>1595                      1600                      1605 | 4886 |
| cac ccc agc tct gac agt gag gag aat gag gcc aaa ggc cgc aga<br>His Pro Ser Ser Asp Ser Glu Glu Asn Glu Ala Lys Gly Arg Arg<br>1610                      1615                      1620 | 4931 |
| gcc acc att gca ata tcc tcc cag gag ggt gat aac tca gag aga<br>Ala Thr Ile Ala Ile Ser Ser Gln Glu Gly Asp Asn Ser Glu Arg<br>1625                      1630                      1635 | 4976 |
| acc ctg tcc aac aac atc act gtt ccc aag ata gag cgc gcc aac<br>Thr Leu Ser Asn Asn Ile Thr Val Pro Lys Ile Glu Arg Ala Asn<br>1640                      1645                      1650 | 5021 |
| agc tac tcg gca gag gag cca agt gcg cca tat gca cac acc agg<br>Ser Tyr Ser Ala Glu Glu Pro Ser Ala Pro Tyr Ala His Thr Arg<br>1655                      1660                      1665 | 5066 |
| aag agc ttc tcc atc agt gac aaa ctc gac agg cag cgg aac aca<br>Lys Ser Phe Ser Ile Ser Asp Lys Leu Asp Arg Gln Arg Asn Thr<br>1670                      1675                      1680 | 5111 |
| gca agc ctg caa aat ccc ttc cag aga agc aag tcc tcc aag ccg<br>Ala Ser Leu Gln Asn Pro Phe Gln Arg Ser Lys Ser Ser Lys Pro<br>1685                      1690                      1695 | 5156 |
| gag ggc cga ggg gac agc ctg tcc atg agg aga ctg tcc aga aca<br>Glu Gly Arg Gly Asp Ser Leu Ser Met Arg Arg Leu Ser Arg Thr<br>1700                      1705                      1710 | 5201 |
| tcg gct ttc caa agc ttt gaa agc aag cac acc taa<br>Ser Ala Phe Gln Ser Phe Glu Ser Lys His Thr | 5237 |

-continued

```
1715                1720

<210> SEQ ID NO 6
<211> LENGTH: 1721
<212> TYPE: PRT
<213> ORGANISM: Homo sapiens

<400> SEQUENCE: 6

Met Gly Lys Lys Trp Arg Asp Ala Ala Glu Met Glu Arg Gly Cys Ser
1               5                   10                  15

Asp Arg Glu Asp Asn Ala Glu Ser Arg Arg Ser Arg Ser Ala Ser
20                  25                  30

Arg Gly Arg Phe Ala Glu Ser Trp Lys Arg Leu Ser Ser Lys Gln Gly
35                  40                  45

Ser Thr Lys Arg Ser Gly Leu Pro Ser Gln Gln Thr Pro Ala Gln Lys
50                  55                  60

Ser Trp Ile Glu Arg Ala Phe Tyr Lys Arg Glu Cys Val His Ile Ile
65                  70                  75                  80

Pro Ser Thr Lys Asp Pro His Arg Cys Cys Cys Gly Arg Leu Ile Gly
85                  90                  95

Gln His Val Gly Leu Thr Pro Ser Ile Ser Val Leu Gln Asn Glu Lys
100                 105                 110

Asn Glu Ser Arg Leu Ser Arg Asn Asp Ile Gln Ser Glu Lys Trp Ser
115                 120                 125

Ile Ser Lys His Thr Gln Leu Ser Pro Thr Asp Ala Phe Gly Thr Ile
130                 135                 140

Glu Phe Gln Gly Gly Gly His Ser Asn Lys Ala Met Tyr Val Arg Val
145                 150                 155                 160

Ser Phe Asp Thr Lys Pro Asp Leu Leu Leu His Leu Met Thr Lys Glu
165                 170                 175

Trp Gln Leu Glu Leu Pro Lys Leu Leu Ile Ser Val His Gly Gly Leu
180                 185                 190

Gln Asn Phe Glu Leu Gln Pro Lys Leu Lys Gln Val Phe Gly Lys Gly
195                 200                 205

Leu Ile Lys Ala Ala Met Thr Thr Gly Ala Trp Ile Phe Thr Gly Gly
210                 215                 220

Val Asn Thr Gly Val Ile Arg His Val Gly Asp Ala Leu Lys Asp His
225                 230                 235                 240

Ala Ser Lys Ser Arg Gly Lys Ile Cys Thr Ile Gly Ile Ala Pro Trp
245                 250                 255

Gly Ile Val Glu Asn Gln Glu Asp Leu Ile Gly Arg Asp Val Val Arg
260                 265                 270

Pro Tyr Gln Thr Met Ser Asn Pro Met Ser Lys Leu Thr Val Leu Asn
275                 280                 285

Ser Met His Ser His Phe Ile Leu Ala Asp Asn Gly Thr Thr Gly Lys
290                 295                 300

Tyr Gly Ala Glu Val Lys Leu Arg Arg Gln Leu Glu Lys His Ile Ser
305                 310                 315                 320

Leu Gln Lys Ile Asn Thr Arg Ile Gly Gln Gly Val Pro Val Val Ala
325                 330                 335

Leu Ile Val Glu Gly Gly Pro Asn Val Ile Ser Ile Val Leu Glu Tyr
340                 345                 350

Leu Arg Asp Thr Pro Pro Val Pro Val Val Val Cys Asp Gly Ser Gly
355                 360                 365
```

-continued

```
Arg Ala Ser Asp Ile Leu Ala Phe Gly His Lys Tyr Ser Glu Glu Gly
370                 375                 380

Gly Leu Ile Asn Glu Ser Leu Arg Asp Gln Leu Leu Val Thr Ile Gln
385                 390                 395                 400

Lys Thr Phe Thr Tyr Thr Arg Thr Gln Ala Gln His Leu Phe Ile Ile
405                 410                 415

Leu Met Glu Cys Met Lys Lys Glu Leu Ile Thr Val Phe Arg Met
420                 425                 430

Gly Ser Glu Gly His Gln Asp Ile Asp Leu Ala Ile Leu Thr Ala Leu
435                 440                 445

Leu Lys Gly Ala Asn Ala Ser Ala Pro Asp Gln Leu Ser Leu Ala Leu
450                 455                 460

Ala Trp Asn Arg Val Asp Ile Ala Arg Ser Gln Ile Phe Ile Tyr Gly
465                 470                 475                 480

Gln Gln Trp Pro Val Gly Ser Leu Glu Gln Ala Met Leu Asp Ala Leu
485                 490                 495

Val Leu Asp Arg Val Asp Phe Val Lys Leu Leu Ile Glu Asn Gly Val
500                 505                 510

Ser Met His Arg Phe Leu Thr Ile Ser Arg Leu Glu Glu Leu Tyr Asn
515                 520                 525

Thr Arg His Gly Pro Ser Asn Thr Leu Tyr His Leu Val Arg Asp Val
530                 535                 540

Lys Lys Gly Asn Leu Pro Pro Asp Tyr Arg Ile Ser Leu Ile Asp Ile
545                 550                 555                 560

Gly Leu Val Ile Glu Tyr Leu Met Gly Gly Ala Tyr Arg Cys Asn Tyr
565                 570                 575

Thr Arg Lys Arg Phe Arg Thr Leu Tyr His Asn Leu Phe Gly Pro Lys
580                 585                 590

Arg Pro Lys Ala Leu Lys Leu Leu Gly Met Glu Asp Asp Ile Pro Leu
595                 600                 605

Arg Arg Gly Arg Lys Thr Thr Lys Lys Arg Glu Glu Glu Val Asp Ile
610                 615                 620

Asp Leu Asp Asp Pro Glu Ile Asn His Phe Pro Phe Pro Phe His Glu
625                 630                 635                 640

Leu Met Val Trp Ala Val Leu Met Lys Arg Gln Lys Met Ala Leu Phe
645                 650                 655

Phe Trp Gln His Gly Glu Glu Ala Met Ala Lys Ala Leu Val Ala Cys
660                 665                 670

Lys Leu Cys Lys Ala Met Ala His Glu Ala Ser Glu Asn Asp Met Val
675                 680                 685

Asp Asp Ile Ser Gln Glu Leu Asn His Asn Ser Arg Asp Phe Gly Gln
690                 695                 700

Leu Ala Val Glu Leu Leu Asp Gln Ser Tyr Lys Gln Asp Glu Gln Leu
705                 710                 715                 720

Ala Met Lys Leu Leu Thr Tyr Glu Leu Lys Asn Trp Ser Asn Ala Thr
725                 730                 735

Cys Leu Gln Leu Ala Val Ala Ala Lys His Arg Asp Phe Ile Ala His
740                 745                 750

Thr Cys Ser Gln Met Leu Leu Thr Asp Met Trp Met Gly Arg Leu Arg
755                 760                 765

Met Arg Lys Asn Ser Gly Leu Lys Val Ile Leu Gly Ile Leu Leu Pro
770                 775                 780

Pro Ser Ile Leu Ser Leu Glu Phe Lys Asn Lys Asp Asp Met Pro Tyr
```

-continued

```
                785                 790                 795                 800
Met Ser Gln Ala Gln Glu Ile His Leu Gln Glu Lys Glu Ala Glu Glu
805                 810                 815

Pro Glu Lys Pro Thr Lys Glu Lys Glu Glu Asp Met Glu Leu Thr
820                 825                 830

Ala Met Leu Gly Arg Asn Asn Gly Glu Ser Ser Arg Lys Lys Asp Glu
835                 840                 845

Glu Glu Val Gln Ser Lys His Arg Leu Ile Pro Leu Gly Arg Lys Ile
850                 855                 860

Tyr Glu Phe Tyr Asn Ala Pro Ile Val Lys Phe Trp Phe Tyr Thr Leu
865                 870                 875                 880

Ala Tyr Ile Gly Tyr Leu Met Leu Phe Asn Tyr Ile Val Leu Val Lys
885                 890                 895

Met Glu Arg Trp Pro Ser Thr Gln Glu Trp Ile Val Ile Ser Tyr Ile
900                 905                 910

Phe Thr Leu Gly Ile Glu Lys Met Arg Glu Ile Leu Met Ser Glu Pro
915                 920                 925

Gly Lys Leu Leu Gln Lys Val Lys Val Trp Leu Gln Glu Tyr Trp Asn
930                 935                 940

Val Thr Asp Leu Ile Ala Ile Leu Leu Phe Ser Val Gly Met Ile Leu
945                 950                 955                 960

Arg Leu Gln Asp Gln Pro Phe Arg Ser Asp Gly Arg Val Ile Tyr Cys
965                 970                 975

Val Asn Ile Ile Tyr Trp Tyr Ile Arg Leu Leu Asp Ile Phe Gly Val
980                 985                 990

Asn Lys Tyr Leu Gly Pro Tyr Val Met Met Ile Gly Lys Met Met Ile
995                 1000                1005

Asp Met Met Tyr Phe Val Ile Ile Met Leu Val Val Leu Met Ser
1010                1015                1020

Phe Gly Val Ala Arg Gln Ala Ile Leu Phe Pro Asn Glu Glu Pro
1025                1030                1035

Ser Trp Lys Leu Ala Lys Asn Ile Phe Tyr Met Pro Tyr Trp Met
1040                1045                1050

Ile Tyr Gly Glu Val Phe Ala Asp Gln Ile Asp Arg Lys Gln Val
1055                1060                1065

Tyr Asp Ser His Thr Pro Lys Ser Ala Pro Cys Gly Gln Asn Glu
1070                1075                1080

Thr Arg Glu Asp Gly Lys Ile Ile Gln Leu Pro Pro Cys Lys Thr
1085                1090                1095

Gly Ala Trp Ile Val Pro Ala Ile Met Ala Cys Tyr Leu Leu Val
1100                1105                1110

Ala Asn Ile Leu Leu Val Asn Leu Leu Ile Ala Val Phe Asn Asn
1115                1120                1125

Thr Phe Phe Glu Val Lys Ser Ile Ser Asn Gln Val Trp Lys Phe
1130                1135                1140

Gln Arg Tyr Gln Leu Ile Met Thr Phe His Glu Arg Pro Val Leu
1145                1150                1155

Pro Pro Pro Leu Ile Ile Phe Ser His Met Thr Met Ile Phe Gln
1160                1165                1170

His Leu Cys Cys Arg Trp Arg Lys His Glu Ser Asp Pro Asp Glu
1175                1180                1185

Arg Asp Tyr Gly Leu Lys Leu Phe Ile Thr Asp Asp Glu Leu Lys
1190                1195                1200
```

-continued

```
Lys Val His Asp Phe Glu Glu Gln Cys Ile Glu Glu Tyr Phe Arg
1205                 1210                1215

Glu Lys Asp Asp Arg Phe Asn Ser Ser Asn Asp Glu Arg Ile Arg
1220                 1225                1230

Val Thr Ser Glu Arg Val Glu Asn Met Ser Met Arg Leu Glu Glu
1235                 1240                1245

Val Asn Glu Arg Glu His Ser Met Lys Ala Ser Leu Gln Thr Val
1250                 1255                1260

Asp Ile Arg Leu Ala Gln Leu Glu Asp Leu Ile Gly Arg Met Ala
1265                 1270                1275

Thr Ala Leu Glu Arg Leu Thr Gly Leu Glu Arg Ala Glu Ser Asn
1280                 1285                1290

Lys Ile Arg Ser Arg Thr Ser Ser Asp Cys Thr Asp Ala Ala Tyr
1295                 1300                1305

Ile Val Arg Gln Ser Ser Phe Asn Ser Gln Glu Gly Asn Thr Phe
1310                 1315                1320

Lys Leu Gln Glu Ser Ile Asp Pro Ala Gly Glu Glu Thr Met Ser
1325                 1330                1335

Pro Thr Ser Pro Thr Leu Met Pro Arg Met Arg Ser His Ser Phe
1340                 1345                1350

Tyr Ser Val Asn Met Lys Asp Lys Gly Gly Ile Glu Lys Leu Glu
1355                 1360                1365

Ser Ile Phe Lys Glu Arg Ser Leu Ser Leu His Arg Ala Thr Ser
1370                 1375                1380

Ser His Ser Val Ala Lys Glu Pro Lys Ala Pro Ala Ala Pro Ala
1385                 1390                1395

Asn Thr Leu Ala Ile Val Pro Asp Ser Arg Arg Pro Ser Ser Cys
1400                 1405                1410

Ile Asp Ile Tyr Val Ser Ala Met Asp Glu Leu His Cys Asp Ile
1415                 1420                1425

Asp Pro Leu Asp Asn Ser Val Asn Ile Leu Gly Leu Gly Glu Pro
1430                 1435                1440

Ser Phe Ser Thr Pro Val Pro Ser Thr Ala Pro Ser Ser Ser Ala
1445                 1450                1455

Tyr Ala Thr Leu Ala Pro Thr Asp Arg Pro Pro Ser Arg Ser Ile
1460                 1465                1470

Asp Phe Glu Asp Ile Thr Ser Met Asp Thr Arg Ser Phe Ser Ser
1475                 1480                1485

Asp Tyr Thr His Leu Pro Glu Cys Gln Asn Pro Trp Asp Ser Glu
1490                 1495                1500

Pro Pro Met Tyr His Thr Ile Glu Arg Ser Lys Ser Ser Arg Tyr
1505                 1510                1515

Leu Ala Thr Thr Pro Phe Leu Leu Glu Glu Ala Pro Ile Val Lys
1520                 1525                1530

Ser His Ser Phe Met Phe Ser Pro Ser Arg Ser Tyr Tyr Ala Asn
1535                 1540                1545

Phe Gly Val Pro Val Lys Thr Ala Glu Tyr Thr Ser Ile Thr Asp
1550                 1555                1560

Cys Ile Asp Thr Arg Cys Val Asn Ala Pro Gln Ala Ile Ala Asp
1565                 1570                1575

Arg Ala Ala Phe Pro Gly Gly Leu Gly Asp Lys Val Glu Asp Leu
1580                 1585                1590
```

-continued

```
Thr Cys Cys His Pro Glu Arg Glu Ala Glu Leu Ser His Pro Ser
1595                1600                1605

Ser Asp Ser Glu Glu Asn Glu Ala Lys Gly Arg Arg Ala Thr Ile
1610                1615                1620

Ala Ile Ser Ser Gln Glu Gly Asp Asn Ser Glu Arg Thr Leu Ser
1625                1630                1635

Asn Asn Ile Thr Val Pro Lys Ile Glu Arg Ala Asn Ser Tyr Ser
1640                1645                1650

Ala Glu Glu Pro Ser Ala Pro Tyr Ala His Thr Arg Lys Ser Phe
1655                1660                1665

Ser Ile Ser Asp Lys Leu Asp Arg Gln Arg Asn Thr Ala Ser Leu
1670                1675                1680

Gln Asn Pro Phe Gln Arg Ser Lys Ser Ser Lys Pro Glu Gly Arg
1685                1690                1695

Gly Asp Ser Leu Ser Met Arg Arg Leu Ser Arg Thr Ser Ala Phe
1700                1705                1710

Gln Ser Phe Glu Ser Lys His Thr
1715                1720

<210> SEQ ID NO 7
<211> LENGTH: 5171
<212> TYPE: DNA
<213> ORGANISM: Homo sapiens
<220> FEATURE:
<221> NAME/KEY: CDS
<222> LOCATION: (72)..(5168)

<400> SEQUENCE: 7
cgcccgcggc gaggagccag cgagagcgct cggcgctggg ctgtttcccg gccgagggag      60
gcgaacttct c atg ggg aag aag tgg agg gat gcg gcg gaa atg gag cgg     110
            Met Gly Lys Lys Trp Arg Asp Ala Ala Glu Met Glu Arg
            1               5                   10 ggc tgc tcc gac cgc gag gac aac gcg gag agc cgc aga cgc agc cgg     158
Gly Cys Ser Asp Arg Glu Asp Asn Ala Glu Ser Arg Arg Arg Ser Arg
15                  20                  25 agc gcc agc cgg ggc agg ttt gcc gag tcg tgg aaa agg tta agt tcc     206
Ser Ala Ser Arg Gly Arg Phe Ala Glu Ser Trp Lys Arg Leu Ser Ser
30                  35                  40                  45 aag cag ggg tcc acc aaa cgc tcg gga ctc ccg tcg cag cag acg ccg     254
Lys Gln Gly Ser Thr Lys Arg Ser Gly Leu Pro Ser Gln Gln Thr Pro
50                  55                  60 gct cag aaa tcc tgg ata gaa aga gca ttt tat aaa aga gaa tgt gtc     302
Ala Gln Lys Ser Trp Ile Glu Arg Ala Phe Tyr Lys Arg Glu Cys Val
65                  70                  75 cac atc ata ccc agc acc aaa gac ccc cat agg tgt tgc tgt ggg cgt     350
His Ile Ile Pro Ser Thr Lys Asp Pro His Arg Cys Cys Cys Gly Arg
80                  85                  90 ctg ata ggc cag cat gtt ggc ctc acc ccc agt atc tcc gtg ctt cag     398
Leu Ile Gly Gln His Val Gly Leu Thr Pro Ser Ile Ser Val Leu Gln
95                  100                 105 aat gag aaa aat gaa agt cgc ctc tcc cga aat gac atc cag tct gaa     446
Asn Glu Lys Asn Glu Ser Arg Leu Ser Arg Asn Asp Ile Gln Ser Glu
110                 115                 120                 125 aag tgg tcc atc agc aaa cac act caa ctc agc cct acg gat gct ttt     494
Lys Trp Ser Ile Ser Lys His Thr Gln Leu Ser Pro Thr Asp Ala Phe
130                 135                 140 ggg acc att gag ttc caa gga ggt ggc cat tcc aac aaa gcc atg tat     542
Gly Thr Ile Glu Phe Gln Gly Gly Gly His Ser Asn Lys Ala Met Tyr
145                 150                 155
```

```
gtg cga gta tct ttt gat aca aaa cct gat ctc ctc tta cac ctg atg         590
Val Arg Val Ser Phe Asp Thr Lys Pro Asp Leu Leu Leu His Leu Met
160                 165                 170 acc aag gaa tgg cag ttg gag ctt ccc aag ctt ctc atc tct gtc cat         638
Thr Lys Glu Trp Gln Leu Glu Leu Pro Lys Leu Leu Ile Ser Val His
175                 180                 185 ggg ggc ctg cag aac ttt gaa ctc cag cca aaa ctc aag caa gtc ttt         686
Gly Gly Leu Gln Asn Phe Glu Leu Gln Pro Lys Leu Lys Gln Val Phe
190                 195                 200                 205 ggg aaa ggg ctc atc aaa gca gca atg aca act gga gcg tgg ata ttc         734
Gly Lys Gly Leu Ile Lys Ala Ala Met Thr Thr Gly Ala Trp Ile Phe
210                 215                 220 act gga ggg gtt aac aca ggt gtt att cgt cat gtt ggc gat gcc ttg         782
Thr Gly Gly Val Asn Thr Gly Val Ile Arg His Val Gly Asp Ala Leu
225                 230                 235 aag gat cat gcc tct aag tct cga gga aag ata tgc acc ata ggt att         830
Lys Asp His Ala Ser Lys Ser Arg Gly Lys Ile Cys Thr Ile Gly Ile
240                 245                 250 gcc ccc tgg gga att gtg gaa aac cag gag gac ctc att gga aga gat         878
Ala Pro Trp Gly Ile Val Glu Asn Gln Glu Asp Leu Ile Gly Arg Asp
255                 260                 265 gtt gtc cgg cca tac cag acc atg tcc aat ccc atg agc aag ctc act         926
Val Val Arg Pro Tyr Gln Thr Met Ser Asn Pro Met Ser Lys Leu Thr
270                 275                 280                 285 gtt ctc aac agc atg cat tcc cac ttc att ctg gct gac aac ggg acc         974
Val Leu Asn Ser Met His Ser His Phe Ile Leu Ala Asp Asn Gly Thr
290                 295                 300 act gga aaa tat gga gca gag gtg aaa ctt cga aga caa ctg gaa aag        1022
Thr Gly Lys Tyr Gly Ala Glu Val Lys Leu Arg Arg Gln Leu Glu Lys
305                 310                 315 cat att tca ctc cag aag ata aac aca aga atc ggt caa ggt gtt cct        1070
His Ile Ser Leu Gln Lys Ile Asn Thr Arg Ile Gly Gln Gly Val Pro
320                 325                 330 gtg gtg gca ctc ata gtg gaa gga gga ccc aat gtg atc tcg att gtt        1118
Val Val Ala Leu Ile Val Glu Gly Gly Pro Asn Val Ile Ser Ile Val
335                 340                 345 ttg gag tac ctt cga gac acc cct ccc gtg cca gtg gtt gtc tgt gat        1166
Leu Glu Tyr Leu Arg Asp Thr Pro Pro Val Pro Val Val Val Cys Asp
350                 355                 360                 365 ggg agt gga cgg gca tcg gac atc ctg gcc ttt ggg cat aaa tac tca        1214
Gly Ser Gly Arg Ala Ser Asp Ile Leu Ala Phe Gly His Lys Tyr Ser
370                 375                 380 gaa gaa ggc gga ctg ata aat gaa tct ttg agg gac cag ctg ttg gtg        1262
Glu Glu Gly Gly Leu Ile Asn Glu Ser Leu Arg Asp Gln Leu Leu Val
385                 390                 395 act ata cag aag act ttc aca tac act cga acc caa gct cag cat ctg        1310
Thr Ile Gln Lys Thr Phe Thr Tyr Thr Arg Thr Gln Ala Gln His Leu
400                 405                 410 ttc atc atc ctc atg gag tgc atg aag aag aag gaa ttg att acg gta        1358
Phe Ile Ile Leu Met Glu Cys Met Lys Lys Lys Glu Leu Ile Thr Val
415                 420                 425 ttt cgg atg gga tca gaa gga cac cag gac att gat ttg gct atc ctg        1406
Phe Arg Met Gly Ser Glu Gly His Gln Asp Ile Asp Leu Ala Ile Leu
430                 435                 440                 445 aca gct tta ctc aaa gga gcc aat gcc tcg gcc cca gac caa ctg agc        1454
Thr Ala Leu Leu Lys Gly Ala Asn Ala Ser Ala Pro Asp Gln Leu Ser
450                 455                 460 tta gct tta gcc tgg aac aga gtc gac atc gct cgc agc cag atc ttt        1502
Leu Ala Leu Ala Trp Asn Arg Val Asp Ile Ala Arg Ser Gln Ile Phe
```

-continued

```
            465                 470                 475
att tac ggg caa cag tgg ccg gtg gga tct ctg gag caa gcc atg ttg    1550
Ile Tyr Gly Gln Gln Trp Pro Val Gly Ser Leu Glu Gln Ala Met Leu
480                 485                 490 gat gcc tta gtt ctg gac aga gtg gat ttt gtg aaa tta ctc ata gag    1598
Asp Ala Leu Val Leu Asp Arg Val Asp Phe Val Lys Leu Leu Ile Glu
495                 500                 505 aat gga gta agc atg cac cgt ttt ctc acc atc tcc aga cta gag gaa    1646
Asn Gly Val Ser Met His Arg Phe Leu Thr Ile Ser Arg Leu Glu Glu
510                 515                 520                 525 ttg tac aat acg aga cat ggg ccc tca aat aca ttg tac cac ttg gtc    1694
Leu Tyr Asn Thr Arg His Gly Pro Ser Asn Thr Leu Tyr His Leu Val
530                 535                 540 agg gat gtc aaa aag ggg aac ctg ccc cca gac tac aga atc agc ctg    1742
Arg Asp Val Lys Lys Gly Asn Leu Pro Pro Asp Tyr Arg Ile Ser Leu
545                 550                 555 att gac atc ggc ctg gtg atc gag tac ctg atg ggc ggg gct tat cgc    1790
Ile Asp Ile Gly Leu Val Ile Glu Tyr Leu Met Gly Gly Ala Tyr Arg
560                 565                 570 tgc aac tac acg cgc aag cgc ttc cgg acc ctc tac cac aac ctc ttc    1838
Cys Asn Tyr Thr Arg Lys Arg Phe Arg Thr Leu Tyr His Asn Leu Phe
575                 580                 585 ggc ccc aag agg gat gat att ccc ttg agg cga gga aga aag aca acc    1886
Gly Pro Lys Arg Asp Asp Ile Pro Leu Arg Arg Gly Arg Lys Thr Thr
590                 595                 600                 605 aag aaa cgt gaa gaa gag gtg gac att gac ttg gat gat cct gag atc    1934
Lys Lys Arg Glu Glu Glu Val Asp Ile Asp Leu Asp Asp Pro Glu Ile
610                 615                 620 aac cac ttc ccc ttc cct ttc cat gag ctc atg gtg tgg gct gtt ctc    1982
Asn His Phe Pro Phe Pro Phe His Glu Leu Met Val Trp Ala Val Leu
625                 630                 635 atg aag cgg cag aag atg gcc ctg ttc ttc tgg cag cac ggt gag gag    2030
Met Lys Arg Gln Lys Met Ala Leu Phe Phe Trp Gln His Gly Glu Glu
640                 645                 650 gcc atg gcc aag gcc ctg gtg gcc tgc aag ctc tgc aaa gcc atg gct    2078
Ala Met Ala Lys Ala Leu Val Ala Cys Lys Leu Cys Lys Ala Met Ala
655                 660                 665 cat gag gcc tct gag aac gac atg gtt gac gac att tcc cag gag ctg    2126
His Glu Ala Ser Glu Asn Asp Met Val Asp Asp Ile Ser Gln Glu Leu
670                 675                 680                 685 aat cac aat tcc aga gac ttt ggc cag ctg gct gtg gag ctc ctg gac    2174
Asn His Asn Ser Arg Asp Phe Gly Gln Leu Ala Val Glu Leu Leu Asp
690                 695                 700 cag tcc tac aag cag gac gaa cag ctg gcc atg aaa ctg ctg acg tat    2222
Gln Ser Tyr Lys Gln Asp Glu Gln Leu Ala Met Lys Leu Leu Thr Tyr
705                 710                 715 gag ctg aag aac tgg agc aac gcc acg tgc ctg cag ctt gcc gtg gct    2270
Glu Leu Lys Asn Trp Ser Asn Ala Thr Cys Leu Gln Leu Ala Val Ala
720                 725                 730 gcc aaa cac cgc gac ttc atc gcg cac acg tgc agc cag atg ctg ctc    2318
Ala Lys His Arg Asp Phe Ile Ala His Thr Cys Ser Gln Met Leu Leu
735                 740                 745 acc gac atg tgg atg ggc cgg ctc cgc atg cgc aag aac tca ggc ctc    2366
Thr Asp Met Trp Met Gly Arg Leu Arg Met Arg Lys Asn Ser Gly Leu
750                 755                 760                 765 aag gta att ctg gga att cta ctt cct cct tca att ctc agc ttg gag    2414
Lys Val Ile Leu Gly Ile Leu Leu Pro Pro Ser Ile Leu Ser Leu Glu
770                 775                 780 ttc aag aac aaa gac gac atg ccc tat atg tct cag gcc cag gaa atc    2462
```

```
                Phe Lys Asn Lys Asp Asp Met Pro Tyr Met Ser Gln Ala Gln Glu Ile
                785                 790                 795 cac ctc caa gag aag gag gca gaa gaa cca gag aag ccc aca aag gaa          2510
His Leu Gln Glu Lys Glu Ala Glu Glu Pro Glu Lys Pro Thr Lys Glu
800                 805                 810 aaa gag gaa gag gac atg gag ctc aca gca atg ttg gga cga aac aac          2558
Lys Glu Glu Glu Asp Met Glu Leu Thr Ala Met Leu Gly Arg Asn Asn
815                 820                 825 ggg gag tcc tcc agg aag aag gat gaa gag gaa gtt cag agc aag cac          2606
Gly Glu Ser Ser Arg Lys Lys Asp Glu Glu Glu Val Gln Ser Lys His
830                 835                 840                 845 cgg tta atc ccc ctc ggc aga aaa atc tat gaa ttc tac aat gca ccc          2654
Arg Leu Ile Pro Leu Gly Arg Lys Ile Tyr Glu Phe Tyr Asn Ala Pro
850                 855                 860 atc gtg aag ttc tgg ttc tac aca ctg gcg tat atc gga tac ctg atg          2702
Ile Val Lys Phe Trp Phe Tyr Thr Leu Ala Tyr Ile Gly Tyr Leu Met
865                 870                 875 ctc ttc aac tat atc gtg tta gtg aag atg gaa cgc tgg ccg tcc acc          2750
Leu Phe Asn Tyr Ile Val Leu Val Lys Met Glu Arg Trp Pro Ser Thr
880                 885                 890 cag gaa tgg atc gta atc tcc tat att ttc acc ctg gga ata gaa aag          2798
Gln Glu Trp Ile Val Ile Ser Tyr Ile Phe Thr Leu Gly Ile Glu Lys
895                 900                 905 atg aga gag att ctg atg tca gag cca ggg aag ttg cta cag aaa gtg          2846
Met Arg Glu Ile Leu Met Ser Glu Pro Gly Lys Leu Leu Gln Lys Val
910                 915                 920                 925 aag gta tgg ctg cag gag tac tgg aat gtc acg gac ctc atc gcc atc          2894
Lys Val Trp Leu Gln Glu Tyr Trp Asn Val Thr Asp Leu Ile Ala Ile
930                 935                 940 ctt ctg ttt tct gtc gga atg atc ctt cgt ctc caa gac cag ccc ttc          2942
Leu Leu Phe Ser Val Gly Met Ile Leu Arg Leu Gln Asp Gln Pro Phe
945                 950                 955 agg agt gac ggg agg gtc atc tac tgc gtg aac atc att tac tgg tat          2990
Arg Ser Asp Gly Arg Val Ile Tyr Cys Val Asn Ile Ile Tyr Trp Tyr
960                 965                 970 atc cgt ctc cta gac atc ttc ggc gtg aac aag tat ttg ggc ccg tat          3038
Ile Arg Leu Leu Asp Ile Phe Gly Val Asn Lys Tyr Leu Gly Pro Tyr
975                 980                 985 gta atg atg att gga aaa atg atg ata gac atg  atg tac ttt gtc atc         3086
Val Met Met Ile Gly Lys Met Met Ile Asp Met  Met Tyr Phe Val Ile
990                 995                 1000                1005 att atg ctg gtg gtt  ctg atg agc ttt ggg  gtc gcc agg caa gcc            3131
Ile Met Leu Val Val  Leu Met Ser Phe Gly  Val Ala Arg Gln Ala
1010                 1015                 1020 atc ctt ttt ccc aat  gag gag cca tca tgg  aaa ctg gcc aag aac            3176
Ile Leu Phe Pro Asn  Glu Glu Pro Ser Trp  Lys Leu Ala Lys Asn
1025                 1030                 1035 atc ttc tac atg ccc  tat tgg atg att tat  ggg gaa gtg ttt gcg            3221
Ile Phe Tyr Met Pro  Tyr Trp Met Ile Tyr  Gly Glu Val Phe Ala
1040                 1045                 1050 gac cag ata gac cct  ccc tgt gga cag aat  gag acc cga gag gat            3266
Asp Gln Ile Asp Pro  Pro Cys Gly Gln Asn  Glu Thr Arg Glu Asp
1055                 1060                 1065 ggt aaa ata atc cag  ctg cct ccc tgc aag  aca gga gct tgg atc            3311
Gly Lys Ile Ile Gln  Leu Pro Pro Cys Lys  Thr Gly Ala Trp Ile
1070                 1075                 1080 gtg ccg gcc atc atg  gcc tgc tac ctc tta  gtg gca aac atc ttg            3356
Val Pro Ala Ile Met  Ala Cys Tyr Leu Leu  Val Ala Asn Ile Leu
1085                 1090                 1095
```

-continued

| | |
|---|---|
| ctg gtc aac ctc ctc att gct gtc ttt aac aat aca ttt ttt gaa<br>Leu Val Asn Leu Leu Ile Ala Val Phe Asn Asn Thr Phe Phe Glu<br>1100                             1105                        1110 | 3401 |
| gta aaa tcg ata tcc aac caa gtc tgg aag ttt cag agg tat cag<br>Val Lys Ser Ile Ser Asn Gln Val Trp Lys Phe Gln Arg Tyr Gln<br>1115                             1120                        1125 | 3446 |
| ctc atc atg act ttc cat gaa agg cca gtt ctg ccc cca cca ctg<br>Leu Ile Met Thr Phe His Glu Arg Pro Val Leu Pro Pro Pro Leu<br>1130                             1135                        1140 | 3491 |
| atc atc ttc agc cac atg acc atg ata ttc cag cac ctg tgc tgc<br>Ile Ile Phe Ser His Met Thr Met Ile Phe Gln His Leu Cys Cys<br>1145                             1150                        1155 | 3536 |
| cga tgg agg aaa cac gag agc gac ccg gat gaa agg gac tac ggc<br>Arg Trp Arg Lys His Glu Ser Asp Pro Asp Glu Arg Asp Tyr Gly<br>1160                             1165                        1170 | 3581 |
| ctg aaa ctc ttc ata acc gat gat gag ctc aag aaa gta cat gac<br>Leu Lys Leu Phe Ile Thr Asp Asp Glu Leu Lys Lys Val His Asp<br>1175                             1180                        1185 | 3626 |
| ttt gaa gag caa tgc ata gaa gaa tac ttc aga gaa aag gat gat<br>Phe Glu Glu Gln Cys Ile Glu Glu Tyr Phe Arg Glu Lys Asp Asp<br>1190                             1195                        1200 | 3671 |
| cgg ttc aac tca tct aat gat gag agg ata cgg gtg act tca gaa<br>Arg Phe Asn Ser Ser Asn Asp Glu Arg Ile Arg Val Thr Ser Glu<br>1205                             1210                        1215 | 3716 |
| agg gtg gag aac atg tct atg cgg ctg gag gaa gtc aac gag aga<br>Arg Val Glu Asn Met Ser Met Arg Leu Glu Glu Val Asn Glu Arg<br>1220                             1225                        1230 | 3761 |
| gag cac tcc atg aag gct tca ctc cag acc gtg gac atc cgg ctg<br>Glu His Ser Met Lys Ala Ser Leu Gln Thr Val Asp Ile Arg Leu<br>1235                             1240                        1245 | 3806 |
| gcg cag ctg gaa gac ctt atc ggg cgc atg gcc acg gcc ctg gag<br>Ala Gln Leu Glu Asp Leu Ile Gly Arg Met Ala Thr Ala Leu Glu<br>1250                             1255                        1260 | 3851 |
| cgc ctg aca ggt ctg gag cgg gcc gag tcc aac aaa atc cgc tcg<br>Arg Leu Thr Gly Leu Glu Arg Ala Glu Ser Asn Lys Ile Arg Ser<br>1265                             1270                        1275 | 3896 |
| agg acc tcg tca gac tgc acg gac gcc gcc tac att gtc cgt cag<br>Arg Thr Ser Ser Asp Cys Thr Asp Ala Ala Tyr Ile Val Arg Gln<br>1280                             1285                        1290 | 3941 |
| agc agc ttc aac agc cag gaa ggg aac acc ttc aag ctc caa gag<br>Ser Ser Phe Asn Ser Gln Glu Gly Asn Thr Phe Lys Leu Gln Glu<br>1295                             1300                        1305 | 3986 |
| agt ata gac cct gca ggt gag gag acc atg tcc cca act tct cca<br>Ser Ile Asp Pro Ala Gly Glu Glu Thr Met Ser Pro Thr Ser Pro<br>1310                             1315                        1320 | 4031 |
| acc tta atg ccc cgt atg cga agc cat tct ttc tat tca gtc aat<br>Thr Leu Met Pro Arg Met Arg Ser His Ser Phe Tyr Ser Val Asn<br>1325                             1330                        1335 | 4076 |
| atg aaa gac aaa ggt ggt ata gaa aag ttg gaa agt att ttt aaa<br>Met Lys Asp Lys Gly Gly Ile Glu Lys Leu Glu Ser Ile Phe Lys<br>1340                             1345                        1350 | 4121 |
| gaa agg tcc ctg agc cta cac cgg gct act agt tcc cac tct gta<br>Glu Arg Ser Leu Ser Leu His Arg Ala Thr Ser Ser His Ser Val<br>1355                             1360                        1365 | 4166 |
| gca aaa gaa ccc aaa gct cct gca gcc cct gcc aac acc ttg gcc<br>Ala Lys Glu Pro Lys Ala Pro Ala Ala Pro Ala Asn Thr Leu Ala<br>1370                             1375                        1380 | 4211 |
| att gtt cct gat tcc aga aga cca tca tcg tgt ata gac atc tat<br>Ile Val Pro Asp Ser Arg Arg Pro Ser Ser Cys Ile Asp Ile Tyr<br>1385                             1390                        1395 | 4256 |

-continued

```
gtc tct gct atg gat   gag ctc cac tgt gat   ata gac cct ctg gac    4301
Val Ser Ala Met Asp   Glu Leu His Cys Asp   Ile Asp Pro Leu Asp
1400                  1405                  1410 aat tcc gtg aac atc   ctt ggg cta ggc gag   cca agc ttt tca act    4346
Asn Ser Val Asn Ile   Leu Gly Leu Gly Glu   Pro Ser Phe Ser Thr
1415                  1420                  1425 cca gta cct tcc aca   gcc cct tca agt agt   gcc tat gca aca ctt    4391
Pro Val Pro Ser Thr   Ala Pro Ser Ser Ser   Ala Tyr Ala Thr Leu
1430                  1435                  1440 gca ccc aca gac aga   cct cca agc cgg agc   att gat ttt gag gac    4436
Ala Pro Thr Asp Arg   Pro Pro Ser Arg Ser   Ile Asp Phe Glu Asp
1445                  1450                  1455 atc acc tcc atg gac   act aga tct ttt tct   tca gac tac acc cac    4481
Ile Thr Ser Met Asp   Thr Arg Ser Phe Ser   Ser Asp Tyr Thr His
1460                  1465                  1470 ctc cca gaa tgc caa   aac ccc tgg gac tca   gag cct ccg atg tac    4526
Leu Pro Glu Cys Gln   Asn Pro Trp Asp Ser   Glu Pro Pro Met Tyr
1475                  1480                  1485 cac acc att gag cgt   tcc aaa agt agc cgc   tac cta gcc acc aca    4571
His Thr Ile Glu Arg   Ser Lys Ser Ser Arg   Tyr Leu Ala Thr Thr
1490                  1495                  1500 ccc ttt ctt cta gaa   gag gct ccc att gtg   aaa tct cat agc ttt    4616
Pro Phe Leu Leu Glu   Glu Ala Pro Ile Val   Lys Ser His Ser Phe
1505                  1510                  1515 atg ttt tcc ccc tca   agg agc tat tat gcc   aac ttt ggg gtg cct    4661
Met Phe Ser Pro Ser   Arg Ser Tyr Tyr Ala   Asn Phe Gly Val Pro
1520                  1525                  1530 gta aaa aca gca gaa   tac aca agt att aca   gac tgt att gac aca    4706
Val Lys Thr Ala Glu   Tyr Thr Ser Ile Thr   Asp Cys Ile Asp Thr
1535                  1540                  1545 agg tgt gtc aat gcc   cct caa gca att gcg   gac aga gct gcc ttc    4751
Arg Cys Val Asn Ala   Pro Gln Ala Ile Ala   Asp Arg Ala Ala Phe
1550                  1555                  1560 cct gga ggt ctt gga   gac aaa gtg gag gac   tta act tgc tgc cat    4796
Pro Gly Gly Leu Gly   Asp Lys Val Glu Asp   Leu Thr Cys Cys His
1565                  1570                  1575 cca gag cga gaa gca   gaa ctg agt cac ccc   agc tct gac agt gag    4841
Pro Glu Arg Glu Ala   Glu Leu Ser His Pro   Ser Ser Asp Ser Glu
1580                  1585                  1590 gag aat gag gcc aaa   ggc cgc aga gcc acc   att gca ata tcc tcc    4886
Glu Asn Glu Ala Lys   Gly Arg Arg Ala Thr   Ile Ala Ile Ser Ser
1595                  1600                  1605 cag gag ggt gat aac   tca gag aga acc ctg   tcc aac aac atc act    4931
Gln Glu Gly Asp Asn   Ser Glu Arg Thr Leu   Ser Asn Asn Ile Thr
1610                  1615                  1620 gtt ccc aag ata gag   cgc gcc aac agc tac   tcg gca gag gag cca    4976
Val Pro Lys Ile Glu   Arg Ala Asn Ser Tyr   Ser Ala Glu Glu Pro
1625                  1630                  1635 agt gcg cca tat gca   cac acc agg aag agc   ttc tcc atc agt gac    5021
Ser Ala Pro Tyr Ala   His Thr Arg Lys Ser   Phe Ser Ile Ser Asp
1640                  1645                  1650 aaa ctc gac agg cag   cgg aac aca gca agc   ctg caa aat ccc ttc    5066
Lys Leu Asp Arg Gln   Arg Asn Thr Ala Ser   Leu Gln Asn Pro Phe
1655                  1660                  1665 cag aga agc aag tcc   tcc aag ccg gag ggc   cga ggg gac agc ctg    5111
Gln Arg Ser Lys Ser   Ser Lys Pro Glu Gly   Arg Gly Asp Ser Leu
1670                  1675                  1680 tcc atg agg aga ctg   tcc aga aca tcg gct   ttc caa agc ttt gaa    5156
Ser Met Arg Arg Leu   Ser Arg Thr Ser Ala   Phe Gln Ser Phe Glu
```

-continued

```
                           1685                1690                1695
agc aag cac acc taa                                                         5171
Ser Lys His Thr
```

<210> SEQ ID NO 8
<211> LENGTH: 1699
<212> TYPE: PRT
<213> ORGANISM: Homo sapiens

<400> SEQUENCE: 8

Met Gly Lys Lys Trp Arg Asp Ala Ala Glu Met Glu Arg Gly Cys Ser
1               5                   10                  15

Asp Arg Glu Asp Asn Ala Glu Ser Arg Arg Ser Arg Ser Ala Ser
20                  25                  30

Arg Gly Arg Phe Ala Glu Ser Trp Lys Arg Leu Ser Ser Lys Gln Gly
35                  40                  45

Ser Thr Lys Arg Ser Gly Leu Pro Ser Gln Gln Thr Pro Ala Gln Lys
50                  55                  60

Ser Trp Ile Glu Arg Ala Phe Tyr Lys Arg Glu Cys Val His Ile Ile
65                  70                  75                  80

Pro Ser Thr Lys Asp Pro His Arg Cys Cys Cys Gly Arg Leu Ile Gly
85                  90                  95

Gln His Val Gly Leu Thr Pro Ser Ile Ser Val Leu Gln Asn Glu Lys
100                 105                 110

Asn Glu Ser Arg Leu Ser Arg Asn Asp Ile Gln Ser Glu Lys Trp Ser
115                 120                 125

Ile Ser Lys His Thr Gln Leu Ser Pro Thr Asp Ala Phe Gly Thr Ile
130                 135                 140

Glu Phe Gln Gly Gly Gly His Ser Asn Lys Ala Met Tyr Val Arg Val
145                 150                 155                 160

Ser Phe Asp Thr Lys Pro Asp Leu Leu Leu His Leu Met Thr Lys Glu
165                 170                 175

Trp Gln Leu Glu Leu Pro Lys Leu Leu Ile Ser Val His Gly Gly Leu
180                 185                 190

Gln Asn Phe Glu Leu Gln Pro Lys Leu Lys Gln Val Phe Gly Lys Gly
195                 200                 205

Leu Ile Lys Ala Ala Met Thr Thr Gly Ala Trp Ile Phe Thr Gly Gly
210                 215                 220

Val Asn Thr Gly Val Ile Arg His Val Gly Asp Ala Leu Lys Asp His
225                 230                 235                 240

Ala Ser Lys Ser Arg Gly Lys Ile Cys Thr Ile Gly Ile Ala Pro Trp
245                 250                 255

Gly Ile Val Glu Asn Gln Glu Asp Leu Ile Gly Arg Asp Val Val Arg
260                 265                 270

Pro Tyr Gln Thr Met Ser Asn Pro Met Ser Lys Leu Thr Val Leu Asn
275                 280                 285

Ser Met His Ser His Phe Ile Leu Ala Asp Asn Gly Thr Thr Gly Lys
290                 295                 300

Tyr Gly Ala Glu Val Lys Leu Arg Arg Gln Leu Glu Lys His Ile Ser
305                 310                 315                 320

Leu Gln Lys Ile Asn Thr Arg Ile Gly Gln Gly Val Pro Val Val Ala
325                 330                 335

Leu Ile Val Glu Gly Gly Pro Asn Val Ile Ser Ile Val Leu Glu Tyr
340                 345                 350

```
Leu Arg Asp Thr Pro Pro Val Pro Val Val Cys Asp Gly Ser Gly
355                 360                 365

Arg Ala Ser Asp Ile Leu Ala Phe Gly His Lys Tyr Ser Glu Glu Gly
370                 375                 380

Gly Leu Ile Asn Glu Ser Leu Arg Asp Gln Leu Val Thr Ile Gln
385                 390                 395                 400

Lys Thr Phe Thr Tyr Thr Arg Thr Gln Ala Gln His Leu Phe Ile Ile
405                 410                 415

Leu Met Glu Cys Met Lys Lys Glu Leu Ile Thr Val Phe Arg Met
420                 425                 430

Gly Ser Glu Gly His Gln Asp Ile Asp Leu Ala Ile Leu Thr Ala Leu
435                 440                 445

Leu Lys Gly Ala Asn Ala Ser Ala Pro Asp Gln Leu Ser Leu Ala Leu
450                 455                 460

Ala Trp Asn Arg Val Asp Ile Ala Arg Ser Gln Ile Phe Ile Tyr Gly
465                 470                 475                 480

Gln Gln Trp Pro Val Gly Ser Leu Glu Gln Ala Met Leu Asp Ala Leu
485                 490                 495

Val Leu Asp Arg Val Asp Phe Val Lys Leu Leu Ile Glu Asn Gly Val
500                 505                 510

Ser Met His Arg Phe Leu Thr Ile Ser Arg Leu Glu Glu Leu Tyr Asn
515                 520                 525

Thr Arg His Gly Pro Ser Asn Thr Leu Tyr His Leu Val Arg Asp Val
530                 535                 540

Lys Lys Gly Asn Leu Pro Pro Asp Tyr Arg Ile Ser Leu Ile Asp Ile
545                 550                 555                 560

Gly Leu Val Ile Glu Tyr Leu Met Gly Gly Ala Tyr Arg Cys Asn Tyr
565                 570                 575

Thr Arg Lys Arg Phe Arg Thr Leu Tyr His Asn Leu Phe Gly Pro Lys
580                 585                 590

Arg Asp Asp Ile Pro Leu Arg Arg Gly Arg Lys Thr Thr Lys Lys Arg
595                 600                 605

Glu Glu Glu Val Asp Ile Asp Leu Asp Asp Pro Glu Ile Asn His Phe
610                 615                 620

Pro Phe Pro Phe His Glu Leu Met Val Trp Ala Val Leu Met Lys Arg
625                 630                 635                 640

Gln Lys Met Ala Leu Phe Phe Trp Gln His Gly Glu Glu Ala Met Ala
645                 650                 655

Lys Ala Leu Val Ala Cys Lys Leu Cys Lys Ala Met Ala His Glu Ala
660                 665                 670

Ser Glu Asn Asp Met Val Asp Asp Ile Ser Gln Glu Leu Asn His Asn
675                 680                 685

Ser Arg Asp Phe Gly Gln Leu Ala Val Glu Leu Leu Asp Gln Ser Tyr
690                 695                 700

Lys Gln Asp Glu Gln Leu Ala Met Lys Leu Leu Thr Tyr Glu Leu Lys
705                 710                 715                 720

Asn Trp Ser Asn Ala Thr Cys Leu Gln Leu Ala Val Ala Ala Lys His
725                 730                 735

Arg Asp Phe Ile Ala His Thr Cys Ser Gln Met Leu Leu Thr Asp Met
740                 745                 750

Trp Met Gly Arg Leu Arg Met Arg Lys Asn Ser Gly Leu Lys Val Ile
755                 760                 765

Leu Gly Ile Leu Leu Pro Pro Ser Ile Leu Ser Leu Glu Phe Lys Asn
```

-continued

```
            770                 775                 780
Lys Asp Asp Met Pro Tyr Met Ser Gln Ala Gln Glu Ile His Leu Gln
            785                 790                 795                 800

Glu Lys Glu Ala Glu Glu Pro Glu Lys Pro Thr Lys Glu Lys Glu Glu
            805                 810                 815

Glu Asp Met Glu Leu Thr Ala Met Leu Gly Arg Asn Asn Gly Glu Ser
            820                 825                 830

Ser Arg Lys Lys Asp Glu Glu Val Gln Ser Lys His Arg Leu Ile
            835                 840                 845

Pro Leu Gly Arg Lys Ile Tyr Glu Phe Tyr Asn Ala Pro Ile Val Lys
            850                 855                 860

Phe Trp Phe Tyr Thr Leu Ala Tyr Ile Gly Tyr Leu Met Leu Phe Asn
            865                 870                 875                 880

Tyr Ile Val Leu Val Lys Met Glu Arg Trp Pro Ser Thr Gln Glu Trp
            885                 890                 895

Ile Val Ile Ser Tyr Ile Phe Thr Leu Gly Ile Glu Lys Met Arg Glu
            900                 905                 910

Ile Leu Met Ser Glu Pro Gly Lys Leu Leu Gln Lys Val Lys Val Trp
            915                 920                 925

Leu Gln Glu Tyr Trp Asn Val Thr Asp Leu Ile Ala Ile Leu Leu Phe
            930                 935                 940

Ser Val Gly Met Ile Leu Arg Leu Gln Asp Gln Pro Phe Arg Ser Asp
            945                 950                 955                 960

Gly Arg Val Ile Tyr Cys Val Asn Ile Ile Tyr Trp Tyr Ile Arg Leu
            965                 970                 975

Leu Asp Ile Phe Gly Val Asn Lys Tyr Leu Gly Pro Tyr Val Met Met
            980                 985                 990

Ile Gly Lys Met Met Ile Asp Met  Met Tyr Phe Val Ile  Ile Met Leu
            995                 1000                1005

Val Val  Leu Met Ser Phe Gly  Val Ala Arg Gln Ala  Ile Leu Phe
            1010                1015                1020

Pro Asn  Glu Glu Pro Ser Trp  Lys Leu Ala Lys Asn  Ile Phe Tyr
            1025                1030                1035

Met Pro  Tyr Trp Met Ile Tyr  Gly Glu Val Phe Ala  Asp Gln Ile
            1040                1045                1050

Asp Pro  Pro Cys Gly Gln Asn  Glu Thr Arg Glu Asp  Gly Lys Ile
            1055                1060                1065

Ile Gln  Leu Pro Pro Cys Lys  Thr Gly Ala Trp Ile  Val Pro Ala
            1070                1075                1080

Ile Met  Ala Cys Tyr Leu Leu  Val Ala Asn Ile Leu  Leu Val Asn
            1085                1090                1095

Leu Leu  Ile Ala Val Phe Asn  Asn Thr Phe Phe Glu  Val Lys Ser
            1100                1105                1110

Ile Ser  Asn Gln Val Trp Lys  Phe Gln Arg Tyr Gln  Leu Ile Met
            1115                1120                1125

Thr Phe  His Glu Arg Pro Val  Leu Pro Pro Pro Leu  Ile Ile Phe
            1130                1135                1140

Ser His  Met Thr Met Ile Phe  Gln His Leu Cys Cys  Arg Trp Arg
            1145                1150                1155

Lys His  Glu Ser Asp Pro Asp  Glu Arg Asp Tyr Gly  Leu Lys Leu
            1160                1165                1170

Phe Ile  Thr Asp Asp Glu Leu  Lys Lys Val His Asp  Phe Glu Glu
            1175                1180                1185
```

-continued

```
Gln Cys Ile Glu Glu Tyr Phe Arg Glu Lys Asp Asp Arg Phe Asn
1190                1195                1200

Ser Ser Asn Asp Glu Arg Ile Arg Val Thr Ser Glu Arg Val Glu
1205                1210                1215

Asn Met Ser Met Arg Leu Glu Glu Val Asn Glu Arg Glu His Ser
1220                1225                1230

Met Lys Ala Ser Leu Gln Thr Val Asp Ile Arg Leu Ala Gln Leu
1235                1240                1245

Glu Asp Leu Ile Gly Arg Met Ala Thr Ala Leu Glu Arg Leu Thr
1250                1255                1260

Gly Leu Glu Arg Ala Glu Ser Asn Lys Ile Arg Ser Arg Thr Ser
1265                1270                1275

Ser Asp Cys Thr Asp Ala Ala Tyr Ile Val Arg Gln Ser Ser Phe
1280                1285                1290

Asn Ser Gln Glu Gly Asn Thr Phe Lys Leu Gln Glu Ser Ile Asp
1295                1300                1305

Pro Ala Gly Glu Glu Thr Met Ser Pro Thr Ser Pro Thr Leu Met
1310                1315                1320

Pro Arg Met Arg Ser His Ser Phe Tyr Ser Val Asn Met Lys Asp
1325                1330                1335

Lys Gly Gly Ile Glu Lys Leu Glu Ser Ile Phe Lys Glu Arg Ser
1340                1345                1350

Leu Ser Leu His Arg Ala Thr Ser Ser His Ser Val Ala Lys Glu
1355                1360                1365

Pro Lys Ala Pro Ala Ala Pro Ala Asn Thr Leu Ala Ile Val Pro
1370                1375                1380

Asp Ser Arg Arg Pro Ser Ser Cys Ile Asp Ile Tyr Val Ser Ala
1385                1390                1395

Met Asp Glu Leu His Cys Ile Asp Pro Leu Asp Asn Ser Val
1400                1405                1410

Asn Ile Leu Gly Leu Gly Glu Pro Ser Phe Ser Thr Pro Val Pro
1415                1420                1425

Ser Thr Ala Pro Ser Ser Ser Ala Tyr Ala Thr Leu Ala Pro Thr
1430                1435                1440

Asp Arg Pro Pro Ser Arg Ser Ile Asp Phe Glu Asp Ile Thr Ser
1445                1450                1455

Met Asp Thr Arg Ser Phe Ser Ser Asp Tyr Thr His Leu Pro Glu
1460                1465                1470

Cys Gln Asn Pro Trp Asp Ser Glu Pro Pro Met Tyr His Thr Ile
1475                1480                1485

Glu Arg Ser Lys Ser Ser Arg Tyr Leu Ala Thr Thr Pro Phe Leu
1490                1495                1500

Leu Glu Glu Ala Pro Ile Val Lys Ser His Ser Phe Met Phe Ser
1505                1510                1515

Pro Ser Arg Ser Tyr Tyr Ala Asn Phe Gly Val Pro Val Lys Thr
1520                1525                1530

Ala Glu Tyr Thr Ser Ile Thr Asp Cys Ile Asp Thr Arg Cys Val
1535                1540                1545

Asn Ala Pro Gln Ala Ile Ala Asp Arg Ala Ala Phe Pro Gly Gly
1550                1555                1560

Leu Gly Asp Lys Val Glu Asp Leu Thr Cys Cys His Pro Glu Arg
1565                1570                1575
```

```
Glu Ala   Glu Leu Ser His Pro   Ser Ser Asp Ser Glu   Glu Asn Glu
1580              1585                   1590

Ala Lys   Gly Arg Arg Ala Thr   Ile Ala Ile Ser Ser   Gln Glu Gly
1595              1600                   1605

Asp Asn   Ser Glu Arg Thr Leu   Ser Asn Asn Ile Thr   Val Pro Lys
1610              1615                   1620

Ile Glu   Arg Ala Asn Ser Tyr   Ser Ala Glu Glu Pro   Ser Ala Pro
1625              1630                   1635

Tyr Ala   His Thr Arg Lys Ser   Phe Ser Ile Ser Asp   Lys Leu Asp
1640              1645                   1650

Arg Gln   Arg Asn Thr Ala Ser   Leu Gln Asn Pro Phe   Gln Arg Ser
1655              1660                   1665

Lys Ser   Ser Lys Pro Glu Gly   Arg Gly Asp Ser Leu   Ser Met Arg
1670              1675                   1680

Arg Leu   Ser Arg Thr Ser Ala   Phe Gln Ser Phe Glu   Ser Lys His
1685              1690                   1695

Thr

<210> SEQ ID NO 9
<211> LENGTH: 5207
<212> TYPE: DNA
<213> ORGANISM: Homo sapiens
<220> FEATURE:
<221> NAME/KEY: CDS
<222> LOCATION: (72)..(5204)

<400> SEQUENCE: 9
cgcccgcggc gaggagccag cgagagcgct cggcgctggg ctgtttcccg gccgagggag       60
gcgaacttct c atg ggg aag aag tgg agg gat gcg gcg gaa atg gag cgg      110
            Met Gly Lys Lys Trp Arg Asp Ala Ala Glu Met Glu Arg
            1               5                   10 ggc tgc tcc gac cgc gag gac aac gcg gag agc cgc aga cgc agc cgg       158
Gly Cys Ser Asp Arg Glu Asp Asn Ala Glu Ser Arg Arg Arg Ser Arg
15                  20                  25 agc gcc agc cgg ggc agg ttt gcc gag tcg tgg aaa agg tta agt tcc       206
Ser Ala Ser Arg Gly Arg Phe Ala Glu Ser Trp Lys Arg Leu Ser Ser
30                  35                  40                  45 aag cag ggg tcc acc aaa cgc tcg gga ctc ccg tcg cag cag acg ccg       254
Lys Gln Gly Ser Thr Lys Arg Ser Gly Leu Pro Ser Gln Gln Thr Pro
50                  55                  60 gct cag aaa tcc tgg ata gaa aga gca ttt tat aaa aga gaa tgt gtc       302
Ala Gln Lys Ser Trp Ile Glu Arg Ala Phe Tyr Lys Arg Glu Cys Val
65                  70                  75 cac atc ata ccc agc acc aaa gac ccc cat agg tgt tgc tgt ggg cgt       350
His Ile Ile Pro Ser Thr Lys Asp Pro His Arg Cys Cys Cys Gly Arg
80                  85                  90 ctg ata ggc cag cat gtt ggc ctc acc ccc agt atc tcc gtg ctt cag       398
Leu Ile Gly Gln His Val Gly Leu Thr Pro Ser Ile Ser Val Leu Gln
95                  100                 105 aat gag aaa aat gaa agt cgc ctc tcc cga aat gac atc cag tct gaa       446
Asn Glu Lys Asn Glu Ser Arg Leu Ser Arg Asn Asp Ile Gln Ser Glu
110                 115                 120                 125 aag tgg tcc atc agc aaa cac act caa ctc agc cct acg gat gct ttt       494
Lys Trp Ser Ile Ser Lys His Thr Gln Leu Ser Pro Thr Asp Ala Phe
130                 135                 140 ggg acc att gag ttc caa gga ggt ggc cat tcc aac aaa gcc atg tat       542
Gly Thr Ile Glu Phe Gln Gly Gly Gly His Ser Asn Lys Ala Met Tyr
145                 150                 155
```

-continued

| | |
|---|---|
| gtg cga gta tct ttt gat aca aaa cct gat ctc ctc tta cac ctg atg<br>Val Arg Val Ser Phe Asp Thr Lys Pro Asp Leu Leu Leu His Leu Met<br>160                         165                            170 | 590 |
| acc aag gaa tgg cag ttg gag ctt ccc aag ctt ctc atc tct gtc cat<br>Thr Lys Glu Trp Gln Leu Glu Leu Pro Lys Leu Leu Ile Ser Val His<br>175                         180                            185 | 638 |
| ggg ggc ctg cag aac ttt gaa ctc cag cca aaa ctc aag caa gtc ttt<br>Gly Gly Leu Gln Asn Phe Glu Leu Gln Pro Lys Leu Lys Gln Val Phe<br>190                         195                            200                   205 | 686 |
| ggg aaa ggg ctc atc aaa gca gca atg aca act gga gcg tgg ata ttc<br>Gly Lys Gly Leu Ile Lys Ala Ala Met Thr Thr Gly Ala Trp Ile Phe<br>210                         215                            220 | 734 |
| act gga ggg gtt aac aca ggt gtt att cgt cat gtt ggc gat gcc ttg<br>Thr Gly Gly Val Asn Thr Gly Val Ile Arg His Val Gly Asp Ala Leu<br>225                         230                            235 | 782 |
| aag gat cat gcc tct aag tct cga gga aag ata tgc acc ata ggt att<br>Lys Asp His Ala Ser Lys Ser Arg Gly Lys Ile Cys Thr Ile Gly Ile<br>240                         245                            250 | 830 |
| gcc ccc tgg gga att gtg gaa aac cag gag gac ctc att gga aga gat<br>Ala Pro Trp Gly Ile Val Glu Asn Gln Glu Asp Leu Ile Gly Arg Asp<br>255                         260                            265 | 878 |
| gtt gtc cgg cca tac cag acc atg tcc aat ccc atg agc aag ctc act<br>Val Val Arg Pro Tyr Gln Thr Met Ser Asn Pro Met Ser Lys Leu Thr<br>270                         275                            280                   285 | 926 |
| gtt ctc aac agc atg cat tcc cac ttc att ctg gct gac aac ggg acc<br>Val Leu Asn Ser Met His Ser His Phe Ile Leu Ala Asp Asn Gly Thr<br>290                         295                            300 | 974 |
| act gga aaa tat gga gca gag gtg aaa ctt cga aga caa ctg gaa aag<br>Thr Gly Lys Tyr Gly Ala Glu Val Lys Leu Arg Arg Gln Leu Glu Lys<br>305                         310                            315 | 1022 |
| cat att tca ctc cag aag ata aac aca aga atc ggt caa ggt gtt cct<br>His Ile Ser Leu Gln Lys Ile Asn Thr Arg Ile Gly Gln Gly Val Pro<br>320                         325                            330 | 1070 |
| gtg gtg gca ctc ata gtg gaa gga gga ccc aat gtg atc tcg att gtt<br>Val Val Ala Leu Ile Val Glu Gly Gly Pro Asn Val Ile Ser Ile Val<br>335                         340                            345 | 1118 |
| ttg gag tac ctt cga gac acc cct ccc gtg cca gtg gtt gtc tgt gat<br>Leu Glu Tyr Leu Arg Asp Thr Pro Pro Val Pro Val Val Val Cys Asp<br>350                         355                            360                   365 | 1166 |
| ggg agt gga cgg gca tcg gac atc ctg gcc ttt ggg cat aaa tac tca<br>Gly Ser Gly Arg Ala Ser Asp Ile Leu Ala Phe Gly His Lys Tyr Ser<br>370                         375                            380 | 1214 |
| gaa gaa ggc gga ctg ata aat gaa tct ttg agg gac cag ctg ttg gtg<br>Glu Glu Gly Gly Leu Ile Asn Glu Ser Leu Arg Asp Gln Leu Leu Val<br>385                         390                            395 | 1262 |
| act ata cag aag act ttc aca tac act cga acc caa gct cag cat ctg<br>Thr Ile Gln Lys Thr Phe Thr Tyr Thr Arg Thr Gln Ala Gln His Leu<br>400                         405                            410 | 1310 |
| ttc atc atc ctc atg gag tgc atg aag aag aag gaa ttg att acg gta<br>Phe Ile Ile Leu Met Glu Cys Met Lys Lys Lys Glu Leu Ile Thr Val<br>415                         420                            425 | 1358 |
| ttt cgg atg gga tca gaa gga cac cag gac att gat ttg gct atc ctg<br>Phe Arg Met Gly Ser Glu Gly His Gln Asp Ile Asp Leu Ala Ile Leu<br>430                         435                            440                   445 | 1406 |
| aca gct tta ctc aaa gga gcc aat gcc tcg gcc cca gac caa ctg agc<br>Thr Ala Leu Leu Lys Gly Ala Asn Ala Ser Ala Pro Asp Gln Leu Ser<br>450                         455                            460 | 1454 |
| tta gct tta gcc tgg aac aga gtc gac atc gct cgc agc cag atc ttt<br>Leu Ala Leu Ala Trp Asn Arg Val Asp Ile Ala Arg Ser Gln Ile Phe<br>465                         470                            475 | 1502 |

```
att tac ggg caa cag tgg ccg gtg gga tct ctg gag caa gcc atg ttg      1550
Ile Tyr Gly Gln Gln Trp Pro Val Gly Ser Leu Glu Gln Ala Met Leu
480                 485                 490 gat gcc tta gtt ctg gac aga gtg gat ttt gtg aaa tta ctc ata gag      1598
Asp Ala Leu Val Leu Asp Arg Val Asp Phe Val Lys Leu Leu Ile Glu
495                 500                 505 aat gga gta agc atg cac cgt ttt ctc acc atc tcc aga cta gag gaa      1646
Asn Gly Val Ser Met His Arg Phe Leu Thr Ile Ser Arg Leu Glu Glu
510                 515                 520                 525 ttg tac aat acg aga cat ggg ccc tca aat aca ttg tac cac ttg gtc      1694
Leu Tyr Asn Thr Arg His Gly Pro Ser Asn Thr Leu Tyr His Leu Val
530                 535                 540 agg gat gtc aaa aag cga gag tat cca ggt ttc ggt tgg atc tat ttt      1742
Arg Asp Val Lys Lys Arg Glu Tyr Pro Gly Phe Gly Trp Ile Tyr Phe
545                 550                 555 aag ggg aac ctg ccc cca gac tac aga atc agc ctg att gac atc ggc      1790
Lys Gly Asn Leu Pro Pro Asp Tyr Arg Ile Ser Leu Ile Asp Ile Gly
560                 565                 570 ctg gtg atc gag tac ctg atg ggc ggg gct tat cgc tgc aac tac acg      1838
Leu Val Ile Glu Tyr Leu Met Gly Gly Ala Tyr Arg Cys Asn Tyr Thr
575                 580                 585 cgc aag cgc ttc cgg acc ctc tac cac aac ctc ttc ggc ccc aag agg      1886
Arg Lys Arg Phe Arg Thr Leu Tyr His Asn Leu Phe Gly Pro Lys Arg
590                 595                 600                 605 gat gat att ccc ttg agg cga gga aga aag aca acc aag aaa cgt gaa      1934
Asp Asp Ile Pro Leu Arg Arg Gly Arg Lys Thr Thr Lys Lys Arg Glu
610                 615                 620 gaa gag gtg gac att gac ttg gat gat cct gag atc aac cac ttc ccc      1982
Glu Glu Val Asp Ile Asp Leu Asp Asp Pro Glu Ile Asn His Phe Pro
625                 630                 635 ttc cct ttc cat gag ctc atg gtg tgg gct gtt ctc atg aag cgg cag      2030
Phe Pro Phe His Glu Leu Met Val Trp Ala Val Leu Met Lys Arg Gln
640                 645                 650 aag atg gcc ctg ttc ttc tgg cag cac ggt gag gag gcc atg gcc aag      2078
Lys Met Ala Leu Phe Phe Trp Gln His Gly Glu Glu Ala Met Ala Lys
655                 660                 665 gcc ctg gtg gcc tgc aag ctc tgc aaa gcc atg gct cat gag gcc tct      2126
Ala Leu Val Ala Cys Lys Leu Cys Lys Ala Met Ala His Glu Ala Ser
670                 675                 680                 685 gag aac gac atg gtt gac gac att tcc cag gag ctg aat cac aat tcc      2174
Glu Asn Asp Met Val Asp Asp Ile Ser Gln Glu Leu Asn His Asn Ser
690                 695                 700 aga gac ttt ggc cag ctg gct gtg gag ctc ctg gac cag tcc tac aag      2222
Arg Asp Phe Gly Gln Leu Ala Val Glu Leu Leu Asp Gln Ser Tyr Lys
705                 710                 715 cag gac gaa cag ctg gcc atg aaa ctg ctg acg tat gag ctg aag aac      2270
Gln Asp Glu Gln Leu Ala Met Lys Leu Leu Thr Tyr Glu Leu Lys Asn
720                 725                 730 tgg agc aac gcc acg tgc ctg cag ctt gcc gtg gct gcc aaa cac cgc      2318
Trp Ser Asn Ala Thr Cys Leu Gln Leu Ala Val Ala Ala Lys His Arg
735                 740                 745 gac ttc atc gcg cac acg tgc agc cag atg ctg ctc acc gac atg tgg      2366
Asp Phe Ile Ala His Thr Cys Ser Gln Met Leu Leu Thr Asp Met Trp
750                 755                 760                 765 atg ggc cgg ctc cgc atg cgc aag aac tca ggc ctc aag gta att ctg      2414
Met Gly Arg Leu Arg Met Arg Lys Asn Ser Gly Leu Lys Val Ile Leu
770                 775                 780 gga att cta ctt cct cct tca att ctc agc ttg gag ttc aag aac aaa      2462
Gly Ile Leu Leu Pro Pro Ser Ile Leu Ser Leu Glu Phe Lys Asn Lys
```

-continued

```
                785                 790                 795
gac gac atg ccc tat atg tct cag gcc cag gaa atc cac ctc caa gag   2510
Asp Asp Met Pro Tyr Met Ser Gln Ala Gln Glu Ile His Leu Gln Glu
800                 805                 810 aag gag gca gaa gaa cca gag aag ccc aca aag gaa aaa gag gaa gag   2558
Lys Glu Ala Glu Glu Pro Glu Lys Pro Thr Lys Glu Lys Glu Glu Glu
815                 820                 825 gac atg gag ctc aca gca atg ttg gga cga aac aac ggg gag tcc tcc   2606
Asp Met Glu Leu Thr Ala Met Leu Gly Arg Asn Asn Gly Glu Ser Ser
830                 835                 840                 845 agg aag aag gat gaa gag gaa gtt cag agc aag cac cgg tta atc ccc   2654
Arg Lys Lys Asp Glu Glu Glu Val Gln Ser Lys His Arg Leu Ile Pro
850                 855                 860 ctc ggc aga aaa atc tat gaa ttc tac aat gca ccc atc gtg aag ttc   2702
Leu Gly Arg Lys Ile Tyr Glu Phe Tyr Asn Ala Pro Ile Val Lys Phe
865                 870                 875 tgg ttc tac aca ctg gcg tat atc gga tac ctg atg ctc ttc aac tat   2750
Trp Phe Tyr Thr Leu Ala Tyr Ile Gly Tyr Leu Met Leu Phe Asn Tyr
880                 885                 890 atc gtg tta gtg aag atg gaa cgc tgg ccg tcc acc cag gaa tgg atc   2798
Ile Val Leu Val Lys Met Glu Arg Trp Pro Ser Thr Gln Glu Trp Ile
895                 900                 905 gta atc tcc tat att ttc acc ctg gga ata gaa aag atg aga gag att   2846
Val Ile Ser Tyr Ile Phe Thr Leu Gly Ile Glu Lys Met Arg Glu Ile
910                 915                 920                 925 ctg atg tca gag cca ggg aag ttg cta cag aaa gtg aag gta tgg ctg   2894
Leu Met Ser Glu Pro Gly Lys Leu Leu Gln Lys Val Lys Val Trp Leu
930                 935                 940 cag gag tac tgg aat gtc acg gac ctc atc gcc atc ctt ctg ttt tct   2942
Gln Glu Tyr Trp Asn Val Thr Asp Leu Ile Ala Ile Leu Leu Phe Ser
945                 950                 955 gtc gga atg atc ctt cgt ctc caa gac cag ccc ttc agg agt gac ggg   2990
Val Gly Met Ile Leu Arg Leu Gln Asp Gln Pro Phe Arg Ser Asp Gly
960                 965                 970 agg gtc atc tac tgc gtg aac atc att tac tgg tat atc cgt ctc cta   3038
Arg Val Ile Tyr Cys Val Asn Ile Ile Tyr Trp Tyr Ile Arg Leu Leu
975                 980                 985 gac atc ttc ggc gtg aac aag tat ttg ggc ccg tat gta atg atg att   3086
Asp Ile Phe Gly Val Asn Lys Tyr Leu Gly Pro Tyr Val Met Met Ile
990                 995                 1000                1005 gga aaa atg atg ata   gac atg atg tac ttt   gtc atc att atg ctg      3131
Gly Lys Met Met Ile   Asp Met Met Tyr Phe   Val Ile Ile Met Leu
1010                  1015                  1020 gtg gtt ctg atg agc   ttt ggg gtc gcc agg   caa gcc atc ctt ttt      3176
Val Val Leu Met Ser   Phe Gly Val Ala Arg   Gln Ala Ile Leu Phe
1025                  1030                  1035 ccc aat gag gag cca   tca tgg aaa ctg gcc   aag aac atc ttc tac      3221
Pro Asn Glu Glu Pro   Ser Trp Lys Leu Ala   Lys Asn Ile Phe Tyr
1040                  1045                  1050 atg ccc tat tgg atg   att tat ggg gaa gtg   ttt gcg gac cag ata      3266
Met Pro Tyr Trp Met   Ile Tyr Gly Glu Val   Phe Ala Asp Gln Ile
1055                  1060                  1065 gac cct ccc tgt gga   cag aat gag acc cga   gag gat ggt aaa ata      3311
Asp Pro Pro Cys Gly   Gln Asn Glu Thr Arg   Glu Asp Gly Lys Ile
1070                  1075                  1080 atc cag ctg cct ccc   tgc aag aca gga gct   tgg atc gtg ccg gcc      3356
Ile Gln Leu Pro Pro   Cys Lys Thr Gly Ala   Trp Ile Val Pro Ala
1085                  1090                  1095 atc atg gcc tgc tac   ctc tta gtg gca aac   atc ttg ctg gtc aac      3401
```

| | | |
|---|---|---|
| Ile Met Ala Cys Tyr<br>1100 | Leu Leu Val Ala Asn<br>1105 | Ile Leu Leu Val Asn<br>1110 | |
| ctc ctc att gct gtc<br>Leu Leu Ile Ala Val<br>1115 | ttt aac aat aca ttt<br>Phe Asn Asn Thr Phe<br>1120 | ttt gaa gta aaa tcg<br>Phe Glu Val Lys Ser<br>1125 | 3446 |
| ata tcc aac caa gtc<br>Ile Ser Asn Gln Val<br>1130 | tgg aag ttt cag agg<br>Trp Lys Phe Gln Arg<br>1135 | tat cag ctc atc atg<br>Tyr Gln Leu Ile Met<br>1140 | 3491 |
| act ttc cat gaa agg<br>Thr Phe His Glu Arg<br>1145 | cca gtt ctg ccc cca<br>Pro Val Leu Pro Pro<br>1150 | cca ctg atc atc ttc<br>Pro Leu Ile Ile Phe<br>1155 | 3536 |
| agc cac atg acc atg<br>Ser His Met Thr Met<br>1160 | ata ttc cag cac ctg<br>Ile Phe Gln His Leu<br>1165 | tgc tgc cga tgg agg<br>Cys Cys Arg Trp Arg<br>1170 | 3581 |
| aaa cac gag agc gac<br>Lys His Glu Ser Asp<br>1175 | ccg gat gaa agg gac<br>Pro Asp Glu Arg Asp<br>1180 | tac ggc ctg aaa ctc<br>Tyr Gly Leu Lys Leu<br>1185 | 3626 |
| ttc ata acc gat gat<br>Phe Ile Thr Asp Asp<br>1190 | gag ctc aag aaa gta<br>Glu Leu Lys Lys Val<br>1195 | cat gac ttt gaa gag<br>His Asp Phe Glu Glu<br>1200 | 3671 |
| caa tgc ata gaa gaa<br>Gln Cys Ile Glu Glu<br>1205 | tac ttc aga gaa aag<br>Tyr Phe Arg Glu Lys<br>1210 | gat gat cgg ttc aac<br>Asp Asp Arg Phe Asn<br>1215 | 3716 |
| tca tct aat gat gag<br>Ser Ser Asn Asp Glu<br>1220 | agg ata cgg gtg act<br>Arg Ile Arg Val Thr<br>1225 | tca gaa agg gtg gag<br>Ser Glu Arg Val Glu<br>1230 | 3761 |
| aac atg tct atg cgg<br>Asn Met Ser Met Arg<br>1235 | ctg gag gaa gtc aac<br>Leu Glu Glu Val Asn<br>1240 | gag aga gag cac tcc<br>Glu Arg Glu His Ser<br>1245 | 3806 |
| atg aag gct tca ctc<br>Met Lys Ala Ser Leu<br>1250 | cag acc gtg gac atc<br>Gln Thr Val Asp Ile<br>1255 | cgg ctg gcg cag ctg<br>Arg Leu Ala Gln Leu<br>1260 | 3851 |
| gaa gac ctt atc ggg<br>Glu Asp Leu Ile Gly<br>1265 | cgc atg gcc acg gcc<br>Arg Met Ala Thr Ala<br>1270 | ctg gag cgc ctg aca<br>Leu Glu Arg Leu Thr<br>1275 | 3896 |
| ggt ctg gag cgg gcc<br>Gly Leu Glu Arg Ala<br>1280 | gag tcc aac aaa atc<br>Glu Ser Asn Lys Ile<br>1285 | cgc tcg agg acc tcg<br>Arg Ser Arg Thr Ser<br>1290 | 3941 |
| tca gac tgc acg gac<br>Ser Asp Cys Thr Asp<br>1295 | gcc gcc tac att gtc<br>Ala Ala Tyr Ile Val<br>1300 | cgt cag agc agc ttc<br>Arg Gln Ser Ser Phe<br>1305 | 3986 |
| aac agc cag gaa ggg<br>Asn Ser Gln Glu Gly<br>1310 | aac acc ttc aag ctc<br>Asn Thr Phe Lys Leu<br>1315 | caa gag agt ata gac<br>Gln Glu Ser Ile Asp<br>1320 | 4031 |
| cct gca ggt gag gag<br>Pro Ala Gly Glu Glu<br>1325 | acc atg tcc cca act<br>Thr Met Ser Pro Thr<br>1330 | tct cca acc tta atg<br>Ser Pro Thr Leu Met<br>1335 | 4076 |
| ccc cgt atg cga agc<br>Pro Arg Met Arg Ser<br>1340 | cat tct ttc tat tca<br>His Ser Phe Tyr Ser<br>1345 | gtc aat atg aaa gac<br>Val Asn Met Lys Asp<br>1350 | 4121 |
| aaa ggt ggt ata gaa<br>Lys Gly Gly Ile Glu<br>1355 | aag ttg gaa agt att<br>Lys Leu Glu Ser Ile<br>1360 | ttt aaa gaa agg tcc<br>Phe Lys Glu Arg Ser<br>1365 | 4166 |
| ctg agc cta cac cgg<br>Leu Ser Leu His Arg<br>1370 | gct act agt tcc cac<br>Ala Thr Ser Ser His<br>1375 | tct gta gca aaa gaa<br>Ser Val Ala Lys Glu<br>1380 | 4211 |
| ccc aaa gct cct gca<br>Pro Lys Ala Pro Ala<br>1385 | gcc cct gcc aac acc<br>Ala Pro Ala Asn Thr<br>1390 | ttg gcc att gtt cct<br>Leu Ala Ile Val Pro<br>1395 | 4256 |

-continued

| | | |
|---|---|---|
| gat tcc aga aga cca<br>Asp Ser Arg Arg Pro<br>1400 | tca tcg tgt ata gac<br>Ser Ser Cys Ile Asp<br>1405 | atc tat gtc tct gct<br>Ile Tyr Val Ser Ala<br>1410 | 4301 |
| atg gat gag ctc cac<br>Met Asp Glu Leu His<br>1415 | tgt gat ata gac cct<br>Cys Asp Ile Asp Pro<br>1420 | ctg gac aat tcc gtg<br>Leu Asp Asn Ser Val<br>1425 | 4346 |
| aac atc ctt ggg cta<br>Asn Ile Leu Gly Leu<br>1430 | ggc gag cca agc ttt<br>Gly Glu Pro Ser Phe<br>1435 | tca act cca gta cct<br>Ser Thr Pro Val Pro<br>1440 | 4391 |
| tcc aca gcc cct tca<br>Ser Thr Ala Pro Ser<br>1445 | agt agt gcc tat gca<br>Ser Ser Ala Tyr Ala<br>1450 | aca ctt gca ccc aca<br>Thr Leu Ala Pro Thr<br>1455 | 4436 |
| gac aga cct cca agc<br>Asp Arg Pro Pro Ser<br>1460 | cgg agc att gat ttt<br>Arg Ser Ile Asp Phe<br>1465 | gag gac atc acc tcc<br>Glu Asp Ile Thr Ser<br>1470 | 4481 |
| atg gac act aga tct<br>Met Asp Thr Arg Ser<br>1475 | ttt tct tca gac tac<br>Phe Ser Ser Asp Tyr<br>1480 | acc cac ctc cca gaa<br>Thr His Leu Pro Glu<br>1485 | 4526 |
| tgc caa aac ccc tgg<br>Cys Gln Asn Pro Trp<br>1490 | gac tca gag cct ccg<br>Asp Ser Glu Pro Pro<br>1495 | atg tac cac acc att<br>Met Tyr His Thr Ile<br>1500 | 4571 |
| gag cgt tcc aaa agt<br>Glu Arg Ser Lys Ser<br>1505 | agc cgc tac cta gcc<br>Ser Arg Tyr Leu Ala<br>1510 | acc aca ccc ttt ctt<br>Thr Thr Pro Phe Leu<br>1515 | 4616 |
| cta gaa gag gct ccc<br>Leu Glu Glu Ala Pro<br>1520 | att gtg aaa tct cat<br>Ile Val Lys Ser His<br>1525 | agc ttt atg ttt tcc<br>Ser Phe Met Phe Ser<br>1530 | 4661 |
| ccc tca agg agc tat<br>Pro Ser Arg Ser Tyr<br>1535 | tat gcc aac ttt ggg<br>Tyr Ala Asn Phe Gly<br>1540 | gtg cct gta aaa aca<br>Val Pro Val Lys Thr<br>1545 | 4706 |
| gca gaa tac aca agt<br>Ala Glu Tyr Thr Ser<br>1550 | att aca gac tgt att<br>Ile Thr Asp Cys Ile<br>1555 | gac aca agg tgt gtc<br>Asp Thr Arg Cys Val<br>1560 | 4751 |
| aat gcc cct caa gca<br>Asn Ala Pro Gln Ala<br>1565 | att gcg gac aga gct<br>Ile Ala Asp Arg Ala<br>1570 | gcc ttc cct gga ggt<br>Ala Phe Pro Gly Gly<br>1575 | 4796 |
| ctt gga gac aaa gtg<br>Leu Gly Asp Lys Val<br>1580 | gag gac tta act tgc<br>Glu Asp Leu Thr Cys<br>1585 | tgc cat cca gag cga<br>Cys His Pro Glu Arg<br>1590 | 4841 |
| gaa gca gaa ctg agt<br>Glu Ala Glu Leu Ser<br>1595 | cac ccc agc tct gac<br>His Pro Ser Ser Asp<br>1600 | agt gag gag aat gag<br>Ser Glu Glu Asn Glu<br>1605 | 4886 |
| gcc aaa ggc cgc aga<br>Ala Lys Gly Arg Arg<br>1610 | gcc acc att gca ata<br>Ala Thr Ile Ala Ile<br>1615 | tcc tcc cag gag ggt<br>Ser Ser Gln Glu Gly<br>1620 | 4931 |
| gat aac tca gag aga<br>Asp Asn Ser Glu Arg<br>1625 | acc ctg tcc aac aac<br>Thr Leu Ser Asn Asn<br>1630 | atc act gtt ccc aag<br>Ile Thr Val Pro Lys<br>1635 | 4976 |
| ata gag cgc gcc aac<br>Ile Glu Arg Ala Asn<br>1640 | agc tac tcg gca gag<br>Ser Tyr Ser Ala Glu<br>1645 | gag cca agt gcg cca<br>Glu Pro Ser Ala Pro<br>1650 | 5021 |
| tat gca cac acc agg<br>Tyr Ala His Thr Arg<br>1655 | aag agc ttc tcc atc<br>Lys Ser Phe Ser Ile<br>1660 | agt gac aaa ctc gac<br>Ser Asp Lys Leu Asp<br>1665 | 5066 |
| agg cag cgg aac aca<br>Arg Gln Arg Asn Thr<br>1670 | gca agc ctg caa aat<br>Ala Ser Leu Gln Asn<br>1675 | ccc ttc cag aga agc<br>Pro Phe Gln Arg Ser<br>1680 | 5111 |
| aag tcc tcc aag ccg<br>Lys Ser Ser Lys Pro<br>1685 | gag ggc cga ggg gac<br>Glu Gly Arg Gly Asp<br>1690 | agc ctg tcc atg agg<br>Ser Leu Ser Met Arg<br>1695 | 5156 |

```
aga ctg tcc aga aca tcg gct ttc caa agc ttt gaa agc aag cac    5201
Arg Leu Ser Arg Thr Ser Ala Phe Gln Ser Phe Glu Ser Lys His
1700            1705                1710 acc taa                                                         5207
Thr
```

<210> SEQ ID NO 10
<211> LENGTH: 1711
<212> TYPE: PRT
<213> ORGANISM: Homo sapiens

<400> SEQUENCE: 10

```
Met Gly Lys Lys Trp Arg Asp Ala Ala Glu Met Glu Arg Gly Cys Ser
1               5                   10                  15

Asp Arg Glu Asp Asn Ala Glu Ser Arg Arg Ser Arg Ser Ala Ser
20                  25                  30

Arg Gly Arg Phe Ala Glu Ser Trp Lys Arg Leu Ser Ser Lys Gln Gly
35              40                  45

Ser Thr Lys Arg Ser Gly Leu Pro Ser Gln Gln Thr Pro Ala Gln Lys
50                  55                  60

Ser Trp Ile Glu Arg Ala Phe Tyr Lys Arg Glu Cys Val His Ile Ile
65                  70                  75                  80

Pro Ser Thr Lys Asp Pro His Arg Cys Cys Cys Gly Arg Leu Ile Gly
85                  90                  95

Gln His Val Gly Leu Thr Pro Ser Ile Ser Val Leu Gln Asn Glu Lys
100                 105                 110

Asn Glu Ser Arg Leu Ser Arg Asn Asp Ile Gln Ser Glu Lys Trp Ser
115                 120                 125

Ile Ser Lys His Thr Gln Leu Ser Pro Thr Asp Ala Phe Gly Thr Ile
130                 135                 140

Glu Phe Gln Gly Gly Gly His Ser Asn Lys Ala Met Tyr Val Arg Val
145                 150                 155                 160

Ser Phe Asp Thr Lys Pro Asp Leu Leu Leu His Leu Met Thr Lys Glu
165                 170                 175

Trp Gln Leu Glu Leu Pro Lys Leu Leu Ile Ser Val His Gly Gly Leu
180                 185                 190

Gln Asn Phe Glu Leu Gln Pro Lys Leu Lys Gln Val Phe Gly Lys Gly
195                 200                 205

Leu Ile Lys Ala Ala Met Thr Thr Gly Ala Trp Ile Phe Thr Gly Gly
210                 215                 220

Val Asn Thr Gly Val Ile Arg His Val Gly Asp Ala Leu Lys Asp His
225                 230                 235                 240

Ala Ser Lys Ser Arg Gly Lys Ile Cys Thr Ile Gly Ile Ala Pro Trp
245                 250                 255

Gly Ile Val Glu Asn Gln Glu Asp Leu Ile Gly Arg Asp Val Val Arg
260                 265                 270

Pro Tyr Gln Thr Met Ser Asn Pro Met Ser Lys Leu Thr Val Leu Asn
275                 280                 285

Ser Met His Ser His Phe Ile Leu Ala Asp Asn Gly Thr Thr Gly Lys
290                 295                 300

Tyr Gly Ala Glu Val Lys Leu Arg Arg Gln Leu Glu Lys His Ile Ser
305                 310                 315                 320

Leu Gln Lys Ile Asn Thr Arg Ile Gly Gln Gly Val Pro Val Val Ala
325                 330                 335
```

-continued

```
Leu Ile Val Glu Gly Gly Pro Asn Val Ile Ser Ile Val Leu Glu Tyr
340                 345                 350

Leu Arg Asp Thr Pro Pro Val Pro Val Val Cys Asp Gly Ser Gly
355                 360                 365

Arg Ala Ser Asp Ile Leu Ala Phe Gly His Lys Tyr Ser Glu Glu Gly
370                 375                 380

Gly Leu Ile Asn Glu Ser Leu Arg Asp Gln Leu Leu Val Thr Ile Gln
385                 390                 395                 400

Lys Thr Phe Thr Tyr Thr Arg Thr Gln Ala Gln His Leu Phe Ile Ile
405                 410                 415

Leu Met Glu Cys Met Lys Lys Glu Leu Ile Thr Val Phe Arg Met
420                 425                 430

Gly Ser Glu Gly His Gln Asp Ile Asp Leu Ala Ile Leu Thr Ala Leu
435                 440                 445

Leu Lys Gly Ala Asn Ala Ser Ala Pro Asp Gln Leu Ser Leu Ala Leu
450                 455                 460

Ala Trp Asn Arg Val Asp Ile Ala Arg Ser Gln Ile Phe Ile Tyr Gly
465                 470                 475                 480

Gln Gln Trp Pro Val Gly Ser Leu Glu Gln Ala Met Leu Asp Ala Leu
485                 490                 495

Val Leu Asp Arg Val Asp Phe Val Lys Leu Leu Ile Glu Asn Gly Val
500                 505                 510

Ser Met His Arg Phe Leu Thr Ile Ser Arg Leu Glu Glu Leu Tyr Asn
515                 520                 525

Thr Arg His Gly Pro Ser Asn Thr Leu Tyr His Leu Val Arg Asp Val
530                 535                 540

Lys Lys Arg Glu Tyr Pro Gly Phe Gly Trp Ile Tyr Phe Lys Gly Asn
545                 550                 555                 560

Leu Pro Pro Asp Tyr Arg Ile Ser Leu Ile Asp Ile Gly Leu Val Ile
565                 570                 575

Glu Tyr Leu Met Gly Gly Ala Tyr Arg Cys Asn Tyr Thr Arg Lys Arg
580                 585                 590

Phe Arg Thr Leu Tyr His Asn Leu Phe Gly Pro Lys Arg Asp Asp Ile
595                 600                 605

Pro Leu Arg Arg Gly Arg Lys Thr Thr Lys Arg Glu Glu Glu Val
610                 615                 620

Asp Ile Asp Leu Asp Asp Pro Glu Ile Asn His Phe Pro Phe Pro Phe
625                 630                 635                 640

His Glu Leu Met Val Trp Ala Val Leu Met Lys Arg Gln Lys Met Ala
645                 650                 655

Leu Phe Phe Trp Gln His Gly Glu Glu Ala Met Ala Lys Ala Leu Val
660                 665                 670

Ala Cys Lys Leu Cys Lys Ala Met Ala His Glu Ala Ser Glu Asn Asp
675                 680                 685

Met Val Asp Asp Ile Ser Gln Glu Leu Asn His Asn Ser Arg Asp Phe
690                 695                 700

Gly Gln Leu Ala Val Glu Leu Leu Asp Gln Ser Tyr Lys Gln Asp Glu
705                 710                 715                 720

Gln Leu Ala Met Lys Leu Leu Thr Tyr Glu Leu Lys Asn Trp Ser Asn
725                 730                 735

Ala Thr Cys Leu Gln Leu Ala Val Ala Ala Lys His Arg Asp Phe Ile
740                 745                 750

Ala His Thr Cys Ser Gln Met Leu Leu Thr Asp Met Trp Met Gly Arg
```

-continued

```
            755                 760                 765
Leu Arg Met Arg Lys Asn Ser Gly Leu Lys Val Ile Leu Gly Ile Leu
770                 775                 780

Leu Pro Pro Ser Ile Leu Ser Leu Glu Phe Lys Asn Lys Asp Asp Met
785                 790                 795                 800

Pro Tyr Met Ser Gln Ala Gln Glu Ile His Leu Gln Glu Lys Glu Ala
805                 810                 815

Glu Glu Pro Glu Lys Pro Thr Lys Glu Lys Glu Glu Asp Met Glu
820                 825                 830

Leu Thr Ala Met Leu Gly Arg Asn Asn Gly Glu Ser Ser Arg Lys Lys
835                 840                 845

Asp Glu Glu Val Gln Ser Lys His Arg Leu Ile Pro Leu Gly Arg
850                 855                 860

Lys Ile Tyr Glu Phe Tyr Asn Ala Pro Ile Val Lys Phe Trp Phe Tyr
865                 870                 875                 880

Thr Leu Ala Tyr Ile Gly Tyr Leu Met Leu Phe Asn Tyr Ile Val Leu
885                 890                 895

Val Lys Met Glu Arg Trp Pro Ser Thr Gln Glu Trp Ile Val Ile Ser
900                 905                 910

Tyr Ile Phe Thr Leu Gly Ile Glu Lys Met Arg Glu Ile Leu Met Ser
915                 920                 925

Glu Pro Gly Lys Leu Leu Gln Lys Val Lys Val Trp Leu Gln Glu Tyr
930                 935                 940

Trp Asn Val Thr Asp Leu Ile Ala Ile Leu Leu Phe Ser Val Gly Met
945                 950                 955                 960

Ile Leu Arg Leu Gln Asp Gln Pro Phe Arg Ser Asp Gly Arg Val Ile
965                 970                 975

Tyr Cys Val Asn Ile Ile Tyr Trp Tyr Ile Arg Leu Leu Asp Ile Phe
980                 985                 990

Gly Val Asn Lys Tyr Leu Gly Pro  Tyr Val Met Met Ile  Gly Lys Met
995                 1000                1005

Met Ile  Asp Met Met Tyr Phe  Val Ile Ile Met Leu  Val Val Leu
1010                1015                1020

Met Ser  Phe Gly Val Ala Arg  Gln Ala Ile Leu Phe  Pro Asn Glu
1025                1030                1035

Glu Pro  Ser Trp Lys Leu Ala  Lys Asn Ile Phe Tyr  Met Pro Tyr
1040                1045                1050

Trp Met  Ile Tyr Gly Glu Val  Phe Ala Asp Gln Ile  Asp Pro Pro
1055                1060                1065

Cys Gly  Gln Asn Glu Thr Arg  Glu Asp Gly Lys Ile  Ile Gln Leu
1070                1075                1080

Pro Pro  Cys Lys Thr Gly Ala  Trp Ile Val Pro Ala  Ile Met Ala
1085                1090                1095

Cys Tyr  Leu Leu Val Ala Asn  Ile Leu Leu Val Asn  Leu Leu Ile
1100                1105                1110

Ala Val  Phe Asn Asn Thr Phe  Phe Glu Val Lys Ser  Ile Ser Asn
1115                1120                1125

Gln Val  Trp Lys Phe Gln Arg  Tyr Gln Leu Ile Met  Thr Phe His
1130                1135                1140

Glu Arg  Pro Val Leu Pro Pro  Pro Leu Ile Ile Phe  Ser His Met
1145                1150                1155

Thr Met  Ile Phe Gln His Leu  Cys Cys Arg Trp Arg  Lys His Glu
1160                1165                1170
```

-continued

```
Ser Asp Pro Asp Glu Arg Asp Tyr Gly Leu Lys Leu Phe Ile Thr
1175                1180                1185
Asp Asp Glu Leu Lys Lys Val His Asp Phe Glu Glu Gln Cys Ile
1190                1195                1200
Glu Glu Tyr Phe Arg Glu Lys Asp Asp Arg Phe Asn Ser Ser Asn
1205                1210                1215
Asp Glu Arg Ile Arg Val Thr Ser Glu Arg Val Glu Asn Met Ser
1220                1225                1230
Met Arg Leu Glu Glu Val Asn Glu Arg Glu His Ser Met Lys Ala
1235                1240                1245
Ser Leu Gln Thr Val Asp Ile Arg Leu Ala Gln Leu Glu Asp Leu
1250                1255                1260
Ile Gly Arg Met Ala Thr Ala Leu Glu Arg Leu Thr Gly Leu Glu
1265                1270                1275
Arg Ala Glu Ser Asn Lys Ile Arg Ser Arg Thr Ser Ser Asp Cys
1280                1285                1290
Thr Asp Ala Ala Tyr Ile Val Arg Gln Ser Ser Phe Asn Ser Gln
1295                1300                1305
Glu Gly Asn Thr Phe Lys Leu Gln Glu Ser Ile Asp Pro Ala Gly
1310                1315                1320
Glu Glu Thr Met Ser Pro Thr Ser Pro Thr Leu Met Pro Arg Met
1325                1330                1335
Arg Ser His Ser Phe Tyr Ser Val Asn Met Lys Asp Lys Gly Gly
1340                1345                1350
Ile Glu Lys Leu Glu Ser Ile Phe Lys Glu Arg Ser Leu Ser Leu
1355                1360                1365
His Arg Ala Thr Ser Ser His Ser Val Ala Lys Glu Pro Lys Ala
1370                1375                1380
Pro Ala Ala Pro Ala Asn Thr Leu Ala Ile Val Pro Asp Ser Arg
1385                1390                1395
Arg Pro Ser Ser Cys Ile Asp Ile Tyr Val Ser Ala Met Asp Glu
1400                1405                1410
Leu His Cys Asp Ile Asp Pro Leu Asp Asn Ser Val Asn Ile Leu
1415                1420                1425
Gly Leu Gly Glu Pro Ser Phe Ser Thr Pro Val Pro Ser Thr Ala
1430                1435                1440
Pro Ser Ser Ser Ala Tyr Ala Thr Leu Ala Pro Thr Asp Arg Pro
1445                1450                1455
Pro Ser Arg Ser Ile Asp Phe Glu Asp Ile Thr Ser Met Asp Thr
1460                1465                1470
Arg Ser Phe Ser Ser Asp Tyr Thr His Leu Pro Glu Cys Gln Asn
1475                1480                1485
Pro Trp Asp Ser Glu Pro Pro Met Tyr His Thr Ile Glu Arg Ser
1490                1495                1500
Lys Ser Ser Arg Tyr Leu Ala Thr Thr Pro Phe Leu Leu Glu Glu
1505                1510                1515
Ala Pro Ile Val Lys Ser His Ser Phe Met Phe Ser Pro Ser Arg
1520                1525                1530
Ser Tyr Tyr Ala Asn Phe Gly Val Pro Val Lys Thr Ala Glu Tyr
1535                1540                1545
Thr Ser Ile Thr Asp Cys Ile Asp Thr Arg Cys Val Asn Ala Pro
1550                1555                1560
```

```
Gln Ala  Ile Ala Asp Arg Ala  Ala Phe Pro Gly Gly  Leu Gly Asp
1565              1570                  1575

Lys Val  Glu Asp Leu Thr Cys  Cys His Pro Glu Arg  Glu Ala Glu
1580              1585                  1590

Leu Ser  His Pro Ser Ser Asp  Ser Glu Glu Asn Glu  Ala Lys Gly
1595              1600                  1605

Arg Arg  Ala Thr Ile Ala Ile  Ser Ser Gln Glu Gly  Asp Asn Ser
1610              1615                  1620

Glu Arg  Thr Leu Ser Asn Asn  Ile Thr Val Pro Lys  Ile Glu Arg
1625              1630                  1635

Ala Asn  Ser Tyr Ser Ala Glu  Glu Pro Ser Ala Pro  Tyr Ala His
1640              1645                  1650

Thr Arg  Lys Ser Phe Ser Ile  Ser Asp Lys Leu Asp  Arg Gln Arg
1655              1660                  1665

Asn Thr  Ala Ser Leu Gln Asn  Pro Phe Gln Arg Ser  Lys Ser Ser
1670              1675                  1680

Lys Pro  Glu Gly Arg Gly Asp  Ser Leu Ser Met Arg  Arg Leu Ser
1685              1690                  1695

Arg Thr  Ser Ala Phe Gln Ser  Phe Glu Ser Lys His  Thr
1700              1705                  1710

<210> SEQ ID NO 11
<211> LENGTH: 5276
<212> TYPE: DNA
<213> ORGANISM: Homo sapiens
<220> FEATURE:
<221> NAME/KEY: CDS
<222> LOCATION: (72)..(5273)

<400> SEQUENCE: 11
cgcccgcggc gaggagccag cgagagcgct cggcgctggg ctgtttcccg gccgagggag         60
gcgaacttct c atg ggg aag aag tgg agg gat gcg gcg gaa atg gag cgg        110
            Met Gly Lys Lys Trp Arg Asp Ala Ala Glu Met Glu Arg
            1               5                   10 ggc tgc tcc gac cgc gag gac aac gcg gag agc cgc aga cgc agc cgg         158
Gly Cys Ser Asp Arg Glu Asp Asn Ala Glu Ser Arg Arg Arg Ser Arg
15                  20                  25 agc gcc agc cgg ggc agg ttt gcc gag tcg tgg aaa agg tta agt tcc         206
Ser Ala Ser Arg Gly Arg Phe Ala Glu Ser Trp Lys Arg Leu Ser Ser
30                  35                  40                  45 aag cag ggg tcc acc aaa cgc tcg gga ctc ccg tcg cag cag acg ccg         254
Lys Gln Gly Ser Thr Lys Arg Ser Gly Leu Pro Ser Gln Gln Thr Pro
50                  55                  60 gct cag aaa tcc tgg ata gaa aga gca ttt tat aaa aga gaa tgt gtc         302
Ala Gln Lys Ser Trp Ile Glu Arg Ala Phe Tyr Lys Arg Glu Cys Val
65                  70                  75 cac atc ata ccc agc acc aaa gac ccc cat agg tgt tgc tgt ggg cgt         350
His Ile Ile Pro Ser Thr Lys Asp Pro His Arg Cys Cys Cys Gly Arg
80                  85                  90 ctg ata ggc cag cat gtt ggc ctc acc ccc agt atc tcc gtg ctt cag         398
Leu Ile Gly Gln His Val Gly Leu Thr Pro Ser Ile Ser Val Leu Gln
95                  100                 105 aat gag aaa aat gaa agt cgc ctc tcc cga aat gac atc cag tct gaa         446
Asn Glu Lys Asn Glu Ser Arg Leu Ser Arg Asn Asp Ile Gln Ser Glu
110                 115                 120                 125 aag tgg tcc atc agc aaa cac act caa ctc agc cct acg gat gct ttt         494
Lys Trp Ser Ile Ser Lys His Thr Gln Leu Ser Pro Thr Asp Ala Phe
130                 135                 140
```

-continued

```
ggg acc att gag ttc caa gga ggt ggc cat tcc aac aaa gcc atg tat        542
Gly Thr Ile Glu Phe Gln Gly Gly Gly His Ser Asn Lys Ala Met Tyr
145                 150                 155 gtg cga gta tct ttt gat aca aaa cct gat ctc ctc tta cac ctg atg        590
Val Arg Val Ser Phe Asp Thr Lys Pro Asp Leu Leu Leu His Leu Met
160                 165                 170 acc aag gaa tgg cag ttg gag ctt ccc aag ctt ctc atc tct gtc cat        638
Thr Lys Glu Trp Gln Leu Glu Leu Pro Lys Leu Leu Ile Ser Val His
175                 180                 185 ggg ggc ctg cag aac ttt gaa ctc cag cca aaa ctc aag caa gtc ttt        686
Gly Gly Leu Gln Asn Phe Glu Leu Gln Pro Lys Leu Lys Gln Val Phe
    190                 195                 200                 205 ggg aaa ggg ctc atc aaa gca gca atg aca act gga gcg tgg ata ttc        734
Gly Lys Gly Leu Ile Lys Ala Ala Met Thr Thr Gly Ala Trp Ile Phe
210                 215                 220 act gga ggg gtt aac aca ggt gtt att cgt cat gtt ggc gat gcc ttg        782
Thr Gly Gly Val Asn Thr Gly Val Ile Arg His Val Gly Asp Ala Leu
225                 230                 235 aag gat cat gcc tct aag tct cga gga aag ata tgc acc ata ggt att        830
Lys Asp His Ala Ser Lys Ser Arg Gly Lys Ile Cys Thr Ile Gly Ile
240                 245                 250 gcc ccc tgg gga att gtg gaa aac cag gag gac ctc att gga aga gat        878
Ala Pro Trp Gly Ile Val Glu Asn Gln Glu Asp Leu Ile Gly Arg Asp
255                 260                 265 gtt gtc cgg cca tac cag acc atg tcc aat ccc atg agc aag ctc act        926
Val Val Arg Pro Tyr Gln Thr Met Ser Asn Pro Met Ser Lys Leu Thr
270                 275                 280                 285 gtt ctc aac agc atg cat tcc cac ttc att ctg gct gac aac ggg acc        974
Val Leu Asn Ser Met His Ser His Phe Ile Leu Ala Asp Asn Gly Thr
290                 295                 300 act gga aaa tat gga gca gag gtg aaa ctt cga aga caa ctg gaa aag       1022
Thr Gly Lys Tyr Gly Ala Glu Val Lys Leu Arg Arg Gln Leu Glu Lys
305                 310                 315 cat att tca ctc cag aag ata aac aca aga tgc ctg ccg ttt ttc tct       1070
His Ile Ser Leu Gln Lys Ile Asn Thr Arg Cys Leu Pro Phe Phe Ser
320                 325                 330 ctt gac tcc cgc ttg ttt tat tca ttt tgg ggt agt tgc cag cta gac       1118
Leu Asp Ser Arg Leu Phe Tyr Ser Phe Trp Gly Ser Cys Gln Leu Asp
335                 340                 345 tca gtt gga atc ggt caa ggt gtt cct gtg gtg gca ctc ata gtg gaa       1166
Ser Val Gly Ile Gly Gln Gly Val Pro Val Val Ala Leu Ile Val Glu
350                 355                 360                 365 gga gga ccc aat gtg atc tcg att gtt ttg gag tac ctt cga gac acc       1214
Gly Gly Pro Asn Val Ile Ser Ile Val Leu Glu Tyr Leu Arg Asp Thr
370                 375                 380 cct ccc gtg cca gtg gtt gtc tgt gat ggg agt gga cgg gca tcg gac       1262
Pro Pro Val Pro Val Val Val Cys Asp Gly Ser Gly Arg Ala Ser Asp
385                 390                 395 atc ctg gcc ttt ggg cat aaa tac tca gaa gaa ggc gga ctg ata aat       1310
Ile Leu Ala Phe Gly His Lys Tyr Ser Glu Glu Gly Gly Leu Ile Asn
400                 405                 410 gaa tct ttg agg gac cag ctg ttg gtg act ata cag aag act ttc aca       1358
Glu Ser Leu Arg Asp Gln Leu Leu Val Thr Ile Gln Lys Thr Phe Thr
415                 420                 425 tac act cga acc caa gct cag cat ctg ttc atc atc ctc atg gag tgc       1406
Tyr Thr Arg Thr Gln Ala Gln His Leu Phe Ile Ile Leu Met Glu Cys
430                 435                 440                 445 atg aag aag aag gaa ttg att acg gta ttt cgg atg gga tca gaa gga       1454
Met Lys Lys Lys Glu Leu Ile Thr Val Phe Arg Met Gly Ser Glu Gly
450                 455                 460
```

```
cac cag gac att gat ttg gct atc ctg aca gct tta ctc aaa gga gcc    1502
His Gln Asp Ile Asp Leu Ala Ile Leu Thr Ala Leu Leu Lys Gly Ala
465                 470                 475 aat gcc tcg gcc cca gac caa ctg agc tta gct tta gcc tgg aac aga    1550
Asn Ala Ser Ala Pro Asp Gln Leu Ser Leu Ala Leu Ala Trp Asn Arg
480                 485                 490 gtc gac atc gct cgc agc cag atc ttt att tac ggg caa cag tgg ccg    1598
Val Asp Ile Ala Arg Ser Gln Ile Phe Ile Tyr Gly Gln Gln Trp Pro
495                 500                 505 gtg gga tct ctg gag caa gcc atg ttg gat gcc tta gtt ctg gac aga    1646
Val Gly Ser Leu Glu Gln Ala Met Leu Asp Ala Leu Val Leu Asp Arg
510                 515                 520                 525 gtg gat ttt gtg aaa tta ctc ata gag aat gga gta agc atg cac cgt    1694
Val Asp Phe Val Lys Leu Leu Ile Glu Asn Gly Val Ser Met His Arg
530                 535                 540 ttt ctc acc atc tcc aga cta gag gaa ttg tac aat acg aga cat ggg    1742
Phe Leu Thr Ile Ser Arg Leu Glu Glu Leu Tyr Asn Thr Arg His Gly
545                 550                 555 ccc tca aat aca ttg tac cac ttg gtc agg gat gtc aaa aag ggg aac    1790
Pro Ser Asn Thr Leu Tyr His Leu Val Arg Asp Val Lys Lys Gly Asn
560                 565                 570 ctg ccc cca gac tac aga atc agc ctg att gac atc ggc ctg gtg atc    1838
Leu Pro Pro Asp Tyr Arg Ile Ser Leu Ile Asp Ile Gly Leu Val Ile
575                 580                 585 gag tac ctg atg ggc ggg gct tat cgc tgc aac tac acg cgc aag cgc    1886
Glu Tyr Leu Met Gly Gly Ala Tyr Arg Cys Asn Tyr Thr Arg Lys Arg
590                 595                 600                 605 ttc cgg acc ctc tac cac aac ctc ttc ggc ccc aag agg ccc aaa gcc    1934
Phe Arg Thr Leu Tyr His Asn Leu Phe Gly Pro Lys Arg Pro Lys Ala
610                 615                 620 ttg aaa ctg ctg gga atg gag gat gat att ccc ttg agg cga gga aga    1982
Leu Lys Leu Leu Gly Met Glu Asp Asp Ile Pro Leu Arg Arg Gly Arg
625                 630                 635 aag aca acc aag aaa cgt gaa gaa gag gtg gac att gac ttg gat gat    2030
Lys Thr Thr Lys Lys Arg Glu Glu Glu Val Asp Ile Asp Leu Asp Asp
640                 645                 650 cct gag atc aac cac ttc ccc ttc cct ttc cat gag ctc atg gtg tgg    2078
Pro Glu Ile Asn His Phe Pro Phe Pro Phe His Glu Leu Met Val Trp
655                 660                 665 gct gtt ctc atg aag cgg cag aag atg gcc ctg ttc ttc tgg cag cac    2126
Ala Val Leu Met Lys Arg Gln Lys Met Ala Leu Phe Phe Trp Gln His
670                 675                 680                 685 ggt gag gag gcc atg gcc aag gcc ctg gtg gcc tgc aag ctc tgc aaa    2174
Gly Glu Glu Ala Met Ala Lys Ala Leu Val Ala Cys Lys Leu Cys Lys
690                 695                 700 gcc atg gct cat gag gcc tct gag aac gac atg gtt gac gac att tcc    2222
Ala Met Ala His Glu Ala Ser Glu Asn Asp Met Val Asp Asp Ile Ser
705                 710                 715 cag gag ctg aat cac aat tcc aga gac ttt ggc cag ctg gct gtg gag    2270
Gln Glu Leu Asn His Asn Ser Arg Asp Phe Gly Gln Leu Ala Val Glu
720                 725                 730 ctc ctg gac cag tcc tac aag cag gac gaa cag ctg gcc atg aaa ctg    2318
Leu Leu Asp Gln Ser Tyr Lys Gln Asp Glu Gln Leu Ala Met Lys Leu
735                 740                 745 ctg acg tat gag ctg aag aac tgg agc aac gcc acg tgc ctg cag ctt    2366
Leu Thr Tyr Glu Leu Lys Asn Trp Ser Asn Ala Thr Cys Leu Gln Leu
750                 755                 760                 765 gcc gtg gct gcc aaa cac cgc gac ttc atc gcg cac acg tgc agc cag    2414
Ala Val Ala Ala Lys His Arg Asp Phe Ile Ala His Thr Cys Ser Gln
```

-continued

```
                 770              775               780
atg ctg ctc acc gac atg tgg atg ggc cgg ctc cgc atg cgc aag aac        2462
Met Leu Leu Thr Asp Met Trp Met Gly Arg Leu Arg Met Arg Lys Asn
785                 790               795 tca ggc ctc aag gta att ctg gga att cta ctt cct cct tca att ctc        2510
Ser Gly Leu Lys Val Ile Leu Gly Ile Leu Leu Pro Pro Ser Ile Leu
800                 805               810 agc ttg gag ttc aag aac aaa gac gac atg ccc tat atg tct cag gcc        2558
Ser Leu Glu Phe Lys Asn Lys Asp Asp Met Pro Tyr Met Ser Gln Ala
815                 820               825 cag gaa atc cac ctc caa gag aag gag gca gaa gaa cca gag aag ccc        2606
Gln Glu Ile His Leu Gln Glu Lys Glu Ala Glu Glu Pro Glu Lys Pro
830                 835               840               845 aca aag gaa aaa gag gaa gag gac atg gag ctc aca gca atg ttg gga        2654
Thr Lys Glu Lys Glu Glu Glu Asp Met Glu Leu Thr Ala Met Leu Gly
850                 855               860 cga aac aac ggg gag tcc tcc agg aag aag gat gaa gag gaa gtt cag        2702
Arg Asn Asn Gly Glu Ser Ser Arg Lys Lys Asp Glu Glu Glu Val Gln
865                 870               875 agc aag cac cgg tta atc ccc ctc ggc aga aaa atc tat gaa ttc tac        2750
Ser Lys His Arg Leu Ile Pro Leu Gly Arg Lys Ile Tyr Glu Phe Tyr
880                 885               890 aat gca ccc atc gtg aag ttc tgg ttc tac aca ctg gcg tat atc gga        2798
Asn Ala Pro Ile Val Lys Phe Trp Phe Tyr Thr Leu Ala Tyr Ile Gly
895                 900               905 tac ctg atg ctc ttc aac tat atc gtg tta gtg aag atg gaa cgc tgg        2846
Tyr Leu Met Leu Phe Asn Tyr Ile Val Leu Val Lys Met Glu Arg Trp
910                 915               920               925 ccg tcc acc cag gaa tgg atc gta atc tcc tat att ttc acc ctg gga        2894
Pro Ser Thr Gln Glu Trp Ile Val Ile Ser Tyr Ile Phe Thr Leu Gly
930                 935               940 ata gaa aag atg aga gag att ctg atg tca gag cca ggg aag ttg cta        2942
Ile Glu Lys Met Arg Glu Ile Leu Met Ser Glu Pro Gly Lys Leu Leu
945                 950               955 cag aaa gtg aag gta tgg ctg cag gag tac tgg aat gtc acg gac ctc        2990
Gln Lys Val Lys Val Trp Leu Gln Glu Tyr Trp Asn Val Thr Asp Leu
960                 965               970 atc gcc atc ctt ctg ttt tct gtc gga atg atc ctt cgt ctc caa gac        3038
Ile Ala Ile Leu Leu Phe Ser Val Gly Met Ile Leu Arg Leu Gln Asp
975                 980               985 cag ccc ttc agg agt gac ggg agg gtc atc tac tgc gtg aac atc att        3086
Gln Pro Phe Arg Ser Asp Gly Arg Val Ile Tyr Cys Val Asn Ile Ile
990                 995               1000              1005 tac tgg tat atc cgt  ctc cta gac atc ttc  ggc gtg aac aag tat         3131
Tyr Trp Tyr Ile Arg  Leu Leu Asp Ile Phe  Gly Val Asn Lys Tyr
1010                 1015                 1020 ttg ggc ccg tat gta  atg atg att gga aaa  atg atg ata gac atg         3176
Leu Gly Pro Tyr Val  Met Met Ile Gly Lys  Met Met Ile Asp Met
1025                 1030                 1035 atg tac ttt gtc atc  att atg ctg gtg gtt  ctg atg agc ttt ggg         3221
Met Tyr Phe Val Ile  Ile Met Leu Val Val  Leu Met Ser Phe Gly
1040                 1045                 1050 gtc gcc agg caa gcc  atc ctt ttt ccc aat  gag gag cca tca tgg         3266
Val Ala Arg Gln Ala  Ile Leu Phe Pro Asn  Glu Glu Pro Ser Trp
1055                 1060                 1065 aaa ctg gcc aag aac  atc ttc tac atg ccc  tat tgg atg att tat         3311
Lys Leu Ala Lys Asn  Ile Phe Tyr Met Pro  Tyr Trp Met Ile Tyr
1070                 1075                 1080 ggg gaa gtg ttt gcg  gac cag ata gac cct  ccc tgt gga cag aat         3356
```

```
Gly Glu Val Phe Ala   Asp Gln Ile Asp Pro   Pro Cys Gly Gln Asn
1085                  1090                  1095 gag acc cga gag gat   ggt aaa ata atc cag   ctg cct ccc tgc aag       3401
Glu Thr Arg Glu Asp   Gly Lys Ile Ile Gln   Leu Pro Pro Cys Lys
1100                  1105                  1110 aca gga gct tgg atc   gtg ccg gcc atc atg   gcc tgc tac ctc tta       3446
Thr Gly Ala Trp Ile   Val Pro Ala Ile Met   Ala Cys Tyr Leu Leu
1115                  1120                  1125 gtg gca aac atc ttg   ctg gtc aac ctc ctc   att gct gtc ttt aac       3491
Val Ala Asn Ile Leu   Leu Val Asn Leu Leu   Ile Ala Val Phe Asn
1130                  1135                  1140 aat aca ttt ttt gaa   gta aaa tcg ata tcc   aac caa gtc tgg aag       3536
Asn Thr Phe Phe Glu   Val Lys Ser Ile Ser   Asn Gln Val Trp Lys
1145                  1150                  1155 ttt cag agg tat cag   ctc atc atg act ttc   cat gaa agg cca gtt       3581
Phe Gln Arg Tyr Gln   Leu Ile Met Thr Phe   His Glu Arg Pro Val
1160                  1165                  1170 ctg ccc cca cca ctg   atc atc ttc agc cac   atg acc atg ata ttc       3626
Leu Pro Pro Pro Leu   Ile Ile Phe Ser His   Met Thr Met Ile Phe
1175                  1180                  1185 cag cac ctg tgc tgc   cga tgg agg aaa cac   gag agc gac ccg gat       3671
Gln His Leu Cys Cys   Arg Trp Arg Lys His   Glu Ser Asp Pro Asp
1190                  1195                  1200 gaa agg gac tac ggc   ctg aaa ctc ttc ata   acc gat gat gag ctc       3716
Glu Arg Asp Tyr Gly   Leu Lys Leu Phe Ile   Thr Asp Asp Glu Leu
1205                  1210                  1215 aag aaa gta cat gac   ttt gaa gag caa tgc   ata gaa gaa tac ttc       3761
Lys Lys Val His Asp   Phe Glu Glu Gln Cys   Ile Glu Glu Tyr Phe
1220                  1225                  1230 aga gaa aag gat gat   cgg ttc aac tca tct   aat gat gag agg ata       3806
Arg Glu Lys Asp Asp   Arg Phe Asn Ser Ser   Asn Asp Glu Arg Ile
1235                  1240                  1245 cgg gtg act tca gaa   agg gtg gag aac atg   tct atg cgg ctg gag       3851
Arg Val Thr Ser Glu   Arg Val Glu Asn Met   Ser Met Arg Leu Glu
1250                  1255                  1260 gaa gtc aac gag aga   gag cac tcc atg aag   gct tca ctc cag acc       3896
Glu Val Asn Glu Arg   Glu His Ser Met Lys   Ala Ser Leu Gln Thr
1265                  1270                  1275 gtg gac atc cgg ctg   gcg cag ctg gaa gac   ctt atc ggg cgc atg       3941
Val Asp Ile Arg Leu   Ala Gln Leu Glu Asp   Leu Ile Gly Arg Met
1280                  1285                  1290 gcc acg gcc ctg gag   cgc ctg aca ggt ctg   gag cgg gcc gag tcc       3986
Ala Thr Ala Leu Glu   Arg Leu Thr Gly Leu   Glu Arg Ala Glu Ser
1295                  1300                  1305 aac aaa atc cgc tcg   agg acc tcg tca gac   tgc acg gac gcc gcc       4031
Asn Lys Ile Arg Ser   Arg Thr Ser Ser Asp   Cys Thr Asp Ala Ala
1310                  1315                  1320 tac att gtc cgt cag   agc agc ttc aac agc   cag gaa ggg aac acc       4076
Tyr Ile Val Arg Gln   Ser Ser Phe Asn Ser   Gln Glu Gly Asn Thr
1325                  1330                  1335 ttc aag ctc caa gag   agt ata gac cct gca   ggt gag gag acc atg       4121
Phe Lys Leu Gln Glu   Ser Ile Asp Pro Ala   Gly Glu Glu Thr Met
1340                  1345                  1350 tcc cca act tct cca   acc tta atg ccc cgt   atg cga agc cat tct       4166
Ser Pro Thr Ser Pro   Thr Leu Met Pro Arg   Met Arg Ser His Ser
1355                  1360                  1365 ttc tat tca gtc aat   atg aaa gac aaa ggt   ggt ata gaa aag ttg       4211
Phe Tyr Ser Val Asn   Met Lys Asp Lys Gly   Gly Ile Glu Lys Leu
1370                  1375                  1380
```

```
gaa agt att ttt aaa  gaa agg tcc ctg agc  cta cac cgg gct act            4256
Glu Ser Ile Phe Lys  Glu Arg Ser Leu Ser  Leu His Arg Ala Thr
1385                 1390                 1395 agt tcc cac tct gta  gca aaa gaa ccc aaa  gct cct gca gcc cct            4301
Ser Ser His Ser Val  Ala Lys Glu Pro Lys  Ala Pro Ala Ala Pro
1400                 1405                 1410 gcc aac acc ttg gcc  att gtt cct gat tcc  aga aga cca tca tcg            4346
Ala Asn Thr Leu Ala  Ile Val Pro Asp Ser  Arg Arg Pro Ser Ser
1415                 1420                 1425 tgt ata gac atc tat  gtc tct gct atg gat  gag ctc cac tgt gat            4391
Cys Ile Asp Ile Tyr  Val Ser Ala Met Asp  Glu Leu His Cys Asp
1430                 1435                 1440 ata gac cct ctg gac  aat tcc gtg aac atc  ctt ggg cta ggc gag            4436
Ile Asp Pro Leu Asp  Asn Ser Val Asn Ile  Leu Gly Leu Gly Glu
1445                 1450                 1455 cca agc ttt tca act  cca gta cct tcc aca  gcc cct tca agt agt            4481
Pro Ser Phe Ser Thr  Pro Val Pro Ser Thr  Ala Pro Ser Ser Ser
1460                 1465                 1470 gcc tat gca aca ctt  gca ccc aca gac aga  cct cca agc cgg agc            4526
Ala Tyr Ala Thr Leu  Ala Pro Thr Asp Arg  Pro Pro Ser Arg Ser
1475                 1480                 1485 att gat ttt gag gac  atc acc tcc atg gac  act aga tct ttt tct            4571
Ile Asp Phe Glu Asp  Ile Thr Ser Met Asp  Thr Arg Ser Phe Ser
1490                 1495                 1500 tca gac tac acc cac  ctc cca gaa tgc caa  aac ccc tgg gac tca            4616
Ser Asp Tyr Thr His  Leu Pro Glu Cys Gln  Asn Pro Trp Asp Ser
1505                 1510                 1515 gag cct ccg atg tac  cac acc att gag cgt  tcc aaa agt agc cgc            4661
Glu Pro Pro Met Tyr  His Thr Ile Glu Arg  Ser Lys Ser Ser Arg
1520                 1525                 1530 tac cta gcc acc aca  ccc ttt ctt cta gaa  gag gct ccc att gtg            4706
Tyr Leu Ala Thr Thr  Pro Phe Leu Leu Glu  Glu Ala Pro Ile Val
1535                 1540                 1545 aaa tct cat agc ttt  atg ttt tcc ccc tca  agg agc tat tat gcc            4751
Lys Ser His Ser Phe  Met Phe Ser Pro Ser  Arg Ser Tyr Tyr Ala
1550                 1555                 1560 aac ttt ggg gtg cct  gta aaa aca gca gaa  tac aca agt att aca            4796
Asn Phe Gly Val Pro  Val Lys Thr Ala Glu  Tyr Thr Ser Ile Thr
1565                 1570                 1575 gac tgt att gac aca  agg tgt gtc aat gcc  cct caa gca att gcg            4841
Asp Cys Ile Asp Thr  Arg Cys Val Asn Ala  Pro Gln Ala Ile Ala
1580                 1585                 1590 gac aga gct gcc ttc  cct gga ggt ctt gga  gac aaa gtg gag gac            4886
Asp Arg Ala Ala Phe  Pro Gly Gly Leu Gly  Asp Lys Val Glu Asp
1595                 1600                 1605 tta act tgc tgc cat  cca gag cga gaa gca  gaa ctg agt cac ccc            4931
Leu Thr Cys Cys His  Pro Glu Arg Glu Ala  Glu Leu Ser His Pro
1610                 1615                 1620 agc tct gac agt gag  gag aat gag gcc aaa  ggc cgc aga gcc acc            4976
Ser Ser Asp Ser Glu  Glu Asn Glu Ala Lys  Gly Arg Arg Ala Thr
1625                 1630                 1635 att gca ata tcc tcc  cag gag ggt gat aac  tca gag aga acc ctg            5021
Ile Ala Ile Ser Ser  Gln Glu Gly Asp Asn  Ser Glu Arg Thr Leu
1640                 1645                 1650 tcc aac aac atc act  gtt ccc aag ata gag  cgc gcc aac agc tac            5066
Ser Asn Asn Ile Thr  Val Pro Lys Ile Glu  Arg Ala Asn Ser Tyr
1655                 1660                 1665 tcg gca gag gag cca  agt gcg cca tat gca  cac acc agg aag agc            5111
Ser Ala Glu Glu Pro  Ser Ala Pro Tyr Ala  His Thr Arg Lys Ser
1670                 1675                 1680
```

```
ttc tcc atc agt gac aaa ctc gac agg cag cgg aac aca gca agc         5156
Phe Ser Ile Ser Asp Lys Leu Asp Arg Gln Arg Asn Thr Ala Ser
1685                1690                1695 ctg caa aat ccc ttc cag aga agc aag tcc tcc aag ccg gag ggc         5201
Leu Gln Asn Pro Phe Gln Arg Ser Lys Ser Ser Lys Pro Glu Gly
1700                1705                1710 cga ggg gac agc ctg tcc atg agg aga ctg tcc aga aca tcg gct         5246
Arg Gly Asp Ser Leu Ser Met Arg Arg Leu Ser Arg Thr Ser Ala
1715                1720                1725 ttc caa agc ttt gaa agc aag cac acc taa                             5276
Phe Gln Ser Phe Glu Ser Lys His Thr
1730

<210> SEQ ID NO 12
<211> LENGTH: 1734
<212> TYPE: PRT
<213> ORGANISM: Homo sapiens

<400> SEQUENCE: 12

Met Gly Lys Lys Trp Arg Asp Ala Ala Glu Met Glu Arg Gly Cys Ser
1               5                   10                  15

Asp Arg Glu Asp Asn Ala Glu Ser Arg Arg Ser Arg Ser Ala Ser
20                  25                  30

Arg Gly Arg Phe Ala Glu Ser Trp Lys Arg Leu Ser Ser Lys Gln Gly
35                  40                  45

Ser Thr Lys Arg Ser Gly Leu Pro Ser Gln Gln Thr Pro Ala Gln Lys
50                  55                  60

Ser Trp Ile Glu Arg Ala Phe Tyr Lys Arg Glu Cys Val His Ile Ile
65                  70                  75                  80

Pro Ser Thr Lys Asp Pro His Arg Cys Cys Cys Gly Arg Leu Ile Gly
85                  90                  95

Gln His Val Gly Leu Thr Pro Ser Ile Ser Val Leu Gln Asn Glu Lys
100                 105                 110

Asn Glu Ser Arg Leu Ser Arg Asn Asp Ile Gln Ser Glu Lys Trp Ser
115                 120                 125

Ile Ser Lys His Thr Gln Leu Ser Pro Thr Asp Ala Phe Gly Thr Ile
130                 135                 140

Glu Phe Gln Gly Gly Gly His Ser Asn Lys Ala Met Tyr Val Arg Val
145                 150                 155                 160

Ser Phe Asp Thr Lys Pro Asp Leu Leu Leu His Leu Met Thr Lys Glu
165                 170                 175

Trp Gln Leu Glu Leu Pro Lys Leu Leu Ile Ser Val His Gly Gly Leu
180                 185                 190

Gln Asn Phe Glu Leu Gln Pro Lys Leu Lys Gln Val Phe Gly Lys Gly
195                 200                 205

Leu Ile Lys Ala Ala Met Thr Thr Gly Ala Trp Ile Phe Thr Gly Gly
210                 215                 220

Val Asn Thr Gly Val Ile Arg His Val Gly Asp Ala Leu Lys Asp His
225                 230                 235                 240

Ala Ser Lys Ser Arg Gly Lys Ile Cys Thr Ile Gly Ile Ala Pro Trp
245                 250                 255

Gly Ile Val Glu Asn Gln Glu Asp Leu Ile Gly Arg Asp Val Val Arg
260                 265                 270

Pro Tyr Gln Thr Met Ser Asn Pro Met Ser Lys Leu Thr Val Leu Asn
275                 280                 285
```

```
Ser Met His Ser His Phe Ile Leu Ala Asp Asn Gly Thr Thr Gly Lys
290                 295                 300

Tyr Gly Ala Glu Val Lys Leu Arg Arg Gln Leu Glu Lys His Ile Ser
305                 310                 315                 320

Leu Gln Lys Ile Asn Thr Arg Cys Leu Pro Phe Phe Ser Leu Asp Ser
325                 330                 335

Arg Leu Phe Tyr Ser Phe Trp Gly Ser Cys Gln Leu Asp Ser Val Gly
340                 345                 350

Ile Gly Gln Gly Val Pro Val Ala Leu Ile Val Glu Gly Gly Pro
355                 360                 365

Asn Val Ile Ser Ile Val Leu Glu Tyr Leu Arg Asp Thr Pro Pro Val
370                 375                 380

Pro Val Val Cys Asp Gly Ser Gly Arg Ala Ser Asp Ile Leu Ala
385                 390                 395                 400

Phe Gly His Lys Tyr Ser Glu Glu Gly Gly Leu Ile Asn Glu Ser Leu
405                 410                 415

Arg Asp Gln Leu Leu Val Thr Ile Gln Lys Thr Phe Thr Tyr Thr Arg
420                 425                 430

Thr Gln Ala Gln His Leu Phe Ile Ile Leu Met Glu Cys Met Lys Lys
435                 440                 445

Lys Glu Leu Ile Thr Val Phe Arg Met Gly Ser Glu Gly His Gln Asp
450                 455                 460

Ile Asp Leu Ala Ile Leu Thr Ala Leu Leu Lys Gly Ala Asn Ala Ser
465                 470                 475                 480

Ala Pro Asp Gln Leu Ser Leu Ala Leu Ala Trp Asn Arg Val Asp Ile
485                 490                 495

Ala Arg Ser Gln Ile Phe Ile Tyr Gly Gln Gln Trp Pro Val Gly Ser
500                 505                 510

Leu Glu Gln Ala Met Leu Asp Ala Leu Val Leu Asp Arg Val Asp Phe
515                 520                 525

Val Lys Leu Leu Ile Glu Asn Gly Val Ser Met His Arg Phe Leu Thr
530                 535                 540

Ile Ser Arg Leu Glu Glu Leu Tyr Asn Thr Arg His Gly Pro Ser Asn
545                 550                 555                 560

Thr Leu Tyr His Leu Val Arg Asp Val Lys Lys Gly Asn Leu Pro Pro
565                 570                 575

Asp Tyr Arg Ile Ser Leu Ile Asp Ile Gly Leu Val Ile Glu Tyr Leu
580                 585                 590

Met Gly Gly Ala Tyr Arg Cys Asn Tyr Thr Arg Lys Arg Phe Arg Thr
595                 600                 605

Leu Tyr His Asn Leu Phe Gly Pro Lys Arg Pro Lys Ala Leu Lys Leu
610                 615                 620

Leu Gly Met Glu Asp Asp Ile Pro Leu Arg Arg Gly Arg Lys Thr Thr
625                 630                 635                 640

Lys Lys Arg Glu Glu Glu Val Asp Ile Asp Leu Asp Asp Pro Glu Ile
645                 650                 655

Asn His Phe Pro Phe Pro Phe His Glu Leu Met Val Trp Ala Val Leu
660                 665                 670

Met Lys Arg Gln Lys Met Ala Leu Phe Phe Trp Gln His Gly Glu Glu
675                 680                 685

Ala Met Ala Lys Ala Leu Val Ala Cys Lys Leu Cys Lys Ala Met Ala
690                 695                 700

His Glu Ala Ser Glu Asn Asp Met Val Asp Asp Ile Ser Gln Glu Leu
```

```
                705                 710                 715                 720
Asn His Asn Ser Arg Asp Phe Gly Gln Leu Ala Val Glu Leu Leu Asp
725                 730                 735
Gln Ser Tyr Lys Gln Asp Glu Gln Leu Ala Met Lys Leu Leu Thr Tyr
740                 745                 750
Glu Leu Lys Asn Trp Ser Asn Ala Thr Cys Leu Gln Leu Ala Val Ala
755                 760                 765
Ala Lys His Arg Asp Phe Ile Ala His Thr Cys Ser Gln Met Leu Leu
770                 775                 780
Thr Asp Met Trp Met Gly Arg Leu Arg Met Arg Lys Asn Ser Gly Leu
785                 790                 795                 800
Lys Val Ile Leu Gly Ile Leu Leu Pro Pro Ser Ile Leu Ser Leu Glu
805                 810                 815
Phe Lys Asn Lys Asp Asp Met Pro Tyr Met Ser Gln Ala Gln Glu Ile
820                 825                 830
His Leu Gln Glu Lys Glu Ala Glu Glu Pro Glu Lys Pro Thr Lys Glu
835                 840                 845
Lys Glu Glu Asp Met Glu Leu Thr Ala Met Leu Gly Arg Asn Asn
850                 855                 860
Gly Glu Ser Ser Arg Lys Lys Asp Glu Glu Val Gln Ser Lys His
865                 870                 875                 880
Arg Leu Ile Pro Leu Gly Arg Lys Ile Tyr Glu Phe Tyr Asn Ala Pro
885                 890                 895
Ile Val Lys Phe Trp Phe Tyr Thr Leu Ala Tyr Ile Gly Tyr Leu Met
900                 905                 910
Leu Phe Asn Tyr Ile Val Leu Val Lys Met Glu Arg Trp Pro Ser Thr
915                 920                 925
Gln Glu Trp Ile Val Ile Ser Tyr Ile Phe Thr Leu Gly Ile Glu Lys
930                 935                 940
Met Arg Glu Ile Leu Met Ser Glu Pro Gly Lys Leu Leu Gln Lys Val
945                 950                 955                 960
Lys Val Trp Leu Gln Glu Tyr Trp Asn Val Thr Asp Leu Ile Ala Ile
965                 970                 975
Leu Leu Phe Ser Val Gly Met Ile Leu Arg Leu Gln Asp Gln Pro Phe
980                 985                 990
Arg Ser Asp Gly Arg Val Ile Tyr  Cys Val Asn Ile Ile  Tyr Trp Tyr
995                 1000                1005
Ile Arg  Leu Leu Asp Ile Phe  Gly Val Asn Lys Tyr  Leu Gly Pro
1010                1015                1020
Tyr Val Met Met Ile Gly Lys  Met Met Ile Asp Met  Met Tyr Phe
1025                1030                1035
Val Ile Ile Met Leu Val Val  Leu Met Ser Phe Gly  Val Ala Arg
1040                1045                1050
Gln Ala Ile Leu Phe Pro Asn  Glu Glu Pro Ser Trp  Lys Leu Ala
1055                1060                1065
Lys Asn Ile Phe Tyr Met Pro  Tyr Trp Met Ile Tyr  Gly Glu Val
1070                1075                1080
Phe Ala Asp Gln Ile Asp Pro  Pro Cys Gly Gln Asn  Glu Thr Arg
1085                1090                1095
Glu Asp Gly Lys Ile Ile Gln  Leu Pro Pro Cys Lys  Thr Gly Ala
1100                1105                1110
Trp Ile Val Pro Ala Ile Met  Ala Cys Tyr Leu Leu  Val Ala Asn
1115                1120                1125
```

-continued

```
Ile Leu Leu Val Asn Leu Leu Ile Ala Val Phe Asn Asn Thr Phe
1130                1135                1140

Phe Glu Val Lys Ser Ile Ser Asn Gln Val Trp Lys Phe Gln Arg
1145                1150                1155

Tyr Gln Leu Ile Met Thr Phe His Glu Arg Pro Val Leu Pro Pro
1160                1165                1170

Pro Leu Ile Ile Phe Ser His Met Thr Met Ile Phe Gln His Leu
1175                1180                1185

Cys Cys Arg Trp Arg Lys His Glu Ser Asp Pro Asp Glu Arg Asp
1190                1195                1200

Tyr Gly Leu Lys Leu Phe Ile Thr Asp Asp Glu Leu Lys Lys Val
1205                1210                1215

His Asp Phe Glu Glu Gln Cys Ile Glu Glu Tyr Phe Arg Glu Lys
1220                1225                1230

Asp Asp Arg Phe Asn Ser Ser Asn Asp Glu Arg Ile Arg Val Thr
1235                1240                1245

Ser Glu Arg Val Glu Asn Met Ser Met Arg Leu Glu Glu Val Asn
1250                1255                1260

Glu Arg Glu His Ser Met Lys Ala Ser Leu Gln Thr Val Asp Ile
1265                1270                1275

Arg Leu Ala Gln Leu Glu Asp Leu Ile Gly Arg Met Ala Thr Ala
1280                1285                1290

Leu Glu Arg Leu Thr Gly Leu Glu Arg Ala Glu Ser Asn Lys Ile
1295                1300                1305

Arg Ser Arg Thr Ser Ser Asp Cys Thr Asp Ala Ala Tyr Ile Val
1310                1315                1320

Arg Gln Ser Ser Phe Asn Ser Gln Glu Gly Asn Thr Phe Lys Leu
1325                1330                1335

Gln Glu Ser Ile Asp Pro Ala Gly Glu Glu Thr Met Ser Pro Thr
1340                1345                1350

Ser Pro Thr Leu Met Pro Arg Met Arg Ser His Ser Phe Tyr Ser
1355                1360                1365

Val Asn Met Lys Asp Lys Gly Gly Ile Glu Lys Leu Glu Ser Ile
1370                1375                1380

Phe Lys Glu Arg Ser Leu Ser Leu His Arg Ala Thr Ser Ser His
1385                1390                1395

Ser Val Ala Lys Glu Pro Lys Ala Pro Ala Ala Pro Ala Asn Thr
1400                1405                1410

Leu Ala Ile Val Pro Asp Ser Arg Arg Pro Ser Ser Cys Ile Asp
1415                1420                1425

Ile Tyr Val Ser Ala Met Asp Glu Leu His Cys Asp Ile Asp Pro
1430                1435                1440

Leu Asp Asn Ser Val Asn Ile Leu Gly Leu Gly Glu Pro Ser Phe
1445                1450                1455

Ser Thr Pro Val Pro Ser Thr Ala Pro Ser Ser Ala Tyr Ala
1460                1465                1470

Thr Leu Ala Pro Thr Asp Arg Pro Pro Ser Arg Ser Ile Asp Phe
1475                1480                1485

Glu Asp Ile Thr Ser Met Asp Thr Arg Ser Phe Ser Ser Asp Tyr
1490                1495                1500

Thr His Leu Pro Glu Cys Gln Asn Pro Trp Asp Ser Glu Pro Pro
1505                1510                1515
```

-continued

```
Met Tyr His Thr Ile Glu Arg Ser Lys Ser Ser Arg Tyr Leu Ala
1520                1525                1530

Thr Thr Pro Phe Leu Leu Glu Glu Ala Pro Ile Val Lys Ser His
1535                1540                1545

Ser Phe Met Phe Ser Pro Ser Arg Ser Tyr Tyr Ala Asn Phe Gly
1550                1555                1560

Val Pro Val Lys Thr Ala Glu Tyr Thr Ser Ile Thr Asp Cys Ile
1565                1570                1575

Asp Thr Arg Cys Val Asn Ala Pro Gln Ala Ile Ala Asp Arg Ala
1580                1585                1590

Ala Phe Pro Gly Gly Leu Gly Asp Lys Val Glu Asp Leu Thr Cys
1595                1600                1605

Cys His Pro Glu Arg Glu Ala Glu Leu Ser His Pro Ser Ser Asp
1610                1615                1620

Ser Glu Glu Asn Glu Ala Lys Gly Arg Arg Ala Thr Ile Ala Ile
1625                1630                1635

Ser Ser Gln Glu Gly Asp Asn Ser Glu Arg Thr Leu Ser Asn Asn
1640                1645                1650

Ile Thr Val Pro Lys Ile Glu Arg Ala Asn Ser Tyr Ser Ala Glu
1655                1660                1665

Glu Pro Ser Ala Pro Tyr Ala His Thr Arg Lys Ser Phe Ser Ile
1670                1675                1680

Ser Asp Lys Leu Asp Arg Gln Arg Asn Thr Ala Ser Leu Gln Asn
1685                1690                1695

Pro Phe Gln Arg Ser Lys Ser Ser Lys Pro Glu Gly Arg Gly Asp
1700                1705                1710

Ser Leu Ser Met Arg Arg Leu Ser Arg Thr Ser Ala Phe Gln Ser
1715                1720                1725

Phe Glu Ser Lys His Thr
1730

<210> SEQ ID NO 13
<211> LENGTH: 1533
<212> TYPE: PRT
<213> ORGANISM: Homo sapiens

<400> SEQUENCE: 13

Met Tyr Ile Arg Val Ser Tyr Asp Thr Lys Pro Asp Ser Leu Leu His
1               5                   10                  15

Leu Met Val Lys Asp Trp Gln Leu Glu Leu Pro Lys Leu Leu Ile Ser
20                  25                  30

Val His Gly Gly Leu Gln Asn Phe Glu Met Gln Pro Lys Leu Lys Gln
35                  40                  45

Val Phe Gly Lys Gly Leu Ile Lys Ala Ala Met Thr Thr Gly Ala Trp
50                  55                  60

Ile Phe Thr Gly Gly Val Ser Thr Gly Val Ile Ser His Val Gly Asp
65                  70                  75                  80

Ala Leu Lys Asp His Ser Ser Lys Ser Arg Gly Arg Val Cys Ala Ile
85                  90                  95

Gly Ile Ala Pro Trp Gly Ile Val Glu Asn Lys Glu Asp Leu Val Gly
100                 105                 110

Lys Asp Val Thr Arg Val Tyr Gln Thr Met Ser Asn Pro Leu Ser Lys
115                 120                 125

Leu Ser Val Leu Asn Asn Ser His Thr His Phe Ile Leu Ala Asp Asn
130                 135                 140
```

-continued

```
Gly Thr Leu Gly Lys Tyr Gly Ala Glu Val Lys Leu Arg Arg Leu Leu
145                 150                 155                 160
Glu Lys His Ile Ser Leu Gln Lys Ile Asn Thr Arg Leu Gly Gln Gly
            165                 170                 175
Val Pro Leu Val Gly Leu Val Glu Gly Gly Pro Asn Val Val Ser
180                 185                 190
Ile Val Leu Glu Tyr Leu Gln Glu Glu Pro Ile Pro Val Val Ile
195                 200                 205
Cys Asp Gly Ser Gly Arg Ala Ser Asp Ile Leu Ser Phe Ala His Lys
210                 215                 220
Tyr Cys Glu Glu Gly Ile Ile Asn Glu Ser Leu Arg Glu Gln Leu
225                 230                 235                 240
Leu Val Thr Ile Gln Lys Thr Phe Asn Tyr Asn Lys Ala Gln Ser His
245                 250                 255
Gln Leu Phe Ala Ile Ile Met Glu Cys Met Lys Lys Glu Leu Val
260                 265                 270
Thr Val Phe Arg Met Gly Ser Glu Gly Gln Gln Asp Ile Glu Met Ala
275                 280                 285
Ile Leu Thr Ala Leu Leu Lys Gly Thr Asn Val Ser Ala Pro Asp Gln
290                 295                 300
Leu Ser Leu Ala Leu Ala Trp Asn Arg Val Asp Ile Ala Arg Ser Gln
305                 310                 315                 320
Ile Phe Val Phe Gly Pro His Trp Thr Pro Leu Gly Ser Leu Ala Pro
325                 330                 335
Pro Thr Asp Ser Lys Ala Thr Glu Lys Glu Lys Pro Pro Met Ala
340                 345                 350
Thr Thr Lys Gly Gly Arg Gly Lys Gly Lys Lys Lys Lys Gly Lys
355                 360                 365
Val Lys Glu Glu Val Glu Glu Thr Asp Pro Arg Lys Ile Glu Leu
370                 375                 380
Leu Asn Trp Val Asn Ala Leu Glu Gln Ala Met Leu Asp Ala Leu Val
385                 390                 395                 400
Leu Asp Arg Val Asp Phe Val Lys Leu Leu Ile Glu Asn Gly Val Asn
405                 410                 415
Met Gln His Phe Leu Thr Ile Pro Arg Leu Glu Glu Leu Tyr Asn Thr
420                 425                 430
Arg Leu Gly Pro Pro Asn Thr Leu His Leu Leu Val Arg Asp Val Lys
435                 440                 445
Lys Ser Asn Leu Pro Pro Asp Tyr His Ile Ser Leu Ile Asp Ile Gly
450                 455                 460
Leu Val Leu Glu Tyr Leu Met Gly Gly Ala Tyr Arg Cys Asn Tyr Thr
465                 470                 475                 480
Arg Lys Asn Phe Arg Thr Leu Tyr Asn Asn Leu Phe Gly Pro Lys Arg
485                 490                 495
Pro Lys Ala Leu Lys Leu Leu Gly Met Glu Asp Asp Glu Pro Pro Ala
500                 505                 510
Lys Gly Lys Lys Lys Lys Lys Lys Lys Glu Glu Ile Asp Ile
515                 520                 525
Asp Val Asp Asp Pro Ala Val Ser Arg Phe Gln Tyr Pro Phe His Glu
530                 535                 540
Leu Met Val Trp Ala Val Leu Met Lys Arg Gln Lys Met Ala Val Phe
545                 550                 555                 560
```

-continued

```
Leu Trp Gln Arg Gly Glu Glu Ser Met Ala Lys Ala Leu Val Ala Cys
565                 570                 575
Lys Leu Tyr Lys Ala Met Ala His Glu Ser Ser Glu Ser Asp Leu Val
580                 585                 590
Asp Asp Ile Ser Gln Asp Leu Asp Asn Asn Ser Lys Asp Phe Gly Gln
595                 600                 605
Leu Ala Leu Glu Leu Leu Asp Gln Ser Tyr Lys His Asp Glu Gln Ile
610                 615                 620
Ala Met Lys Leu Leu Thr Tyr Glu Leu Lys Asn Trp Ser Asn Ser Thr
625                 630                 635                 640
Cys Leu Lys Leu Ala Val Ala Ala Lys His Arg Asp Phe Ile Ala His
645                 650                 655
Thr Cys Ser Gln Met Leu Leu Thr Asp Met Trp Met Gly Arg Leu Arg
660                 665                 670
Met Arg Lys Asn Pro Gly Leu Lys Val Ile Met Gly Ile Leu Leu Pro
675                 680                 685
Pro Thr Ile Leu Phe Leu Glu Phe Arg Thr Tyr Asp Asp Phe Ser Tyr
690                 695                 700
Gln Thr Ser Lys Glu Asn Glu Asp Gly Lys Lys Glu Glu Glu Asn
705                 710                 715                 720
Thr Asp Ala Asn Ala Asp Ala Gly Ser Arg Lys Gly Asp Glu Glu Asn
725                 730                 735
Glu His Lys Lys Gln Arg Ser Ile Pro Ile Gly Thr Lys Ile Cys Glu
740                 745                 750
Phe Tyr Asn Ala Pro Ile Val Lys Phe Trp Phe Tyr Thr Ile Ser Tyr
755                 760                 765
Leu Gly Tyr Leu Leu Phe Asn Tyr Val Ile Leu Val Arg Met Asp
770                 775                 780
Gly Trp Pro Ser Leu Gln Glu Trp Ile Val Ser Tyr Ile Val Ser
785                 790                 795                 800
Leu Ala Leu Glu Lys Ile Arg Glu Ile Leu Met Ser Glu Pro Gly Lys
805                 810                 815
Leu Ser Gln Lys Ile Lys Val Trp Leu Gln Glu Tyr Trp Asn Ile Thr
820                 825                 830
Asp Leu Val Ala Ile Ser Thr Phe Met Ile Gly Ala Ile Leu Arg Leu
835                 840                 845
Gln Asn Gln Pro Tyr Met Gly Tyr Gly Arg Val Ile Tyr Cys Val Asp
850                 855                 860
Ile Ile Phe Trp Tyr Ile Arg Val Leu Asp Ile Phe Gly Val Asn Lys
865                 870                 875                 880
Tyr Leu Gly Pro Tyr Val Met Met Ile Gly Lys Met Met Ile Asp Met
885                 890                 895
Leu Tyr Phe Val Val Ile Met Leu Val Val Leu Met Ser Phe Gly Val
900                 905                 910
Ala Arg Gln Ala Ile Leu His Pro Glu Glu Lys Pro Ser Trp Lys Leu
915                 920                 925
Ala Arg Asn Ile Phe Tyr Met Pro Tyr Trp Met Ile Tyr Gly Glu Val
930                 935                 940
Phe Ala Asp Gln Ile Asp Leu Tyr Ala Met Glu Ile Asn Pro Pro Cys
945                 950                 955                 960
Gly Glu Asn Leu Tyr Asp Glu Glu Gly Lys Arg Leu Pro Pro Cys Ile
965                 970                 975
Pro Gly Ala Trp Leu Thr Pro Ala Leu Met Ala Cys Tyr Leu Leu Val
```

-continued

```
            980             985             990
Ala Asn Ile Leu Leu Val Asn Leu  Leu Ile Ala Val Phe  Asn Asn Thr
995             1000            1005

Phe Phe Glu Val Lys Ser Ile  Ser Asn Gln Val Trp  Lys Phe Gln
1010            1015            1020

Arg Tyr Gln Leu Ile Met Thr  Phe His Asp Arg Pro  Val Leu Pro
1025            1030            1035

Pro Pro Met Ile Ile Leu Ser  His Ile Tyr Ile Ile  Ile Met Arg
1040            1045            1050

Leu Ser Gly Arg Cys Arg Lys  Lys Arg Glu Gly Asp  Gln Glu Glu
1055            1060            1065

Arg Asp Arg Gly Leu Lys Leu  Phe Leu Ser Asp Glu  Glu Leu Lys
1070            1075            1080

Arg Leu His Glu Phe Glu Glu  Gln Cys Val Gln Glu  His Phe Arg
1085            1090            1095

Glu Lys Glu Asp Glu Gln Gln  Ser Ser Ser Asp Glu  Arg Ile Arg
1100            1105            1110

Val Thr Ser Glu Arg Val Glu  Asn Met Ser Met Arg  Leu Glu Glu
1115            1120            1125

Ile Asn Glu Arg Glu Thr Phe  Met Lys Thr Ser Leu  Gln Thr Val
1130            1135            1140

Asp Leu Arg Leu Ala Gln Leu  Glu Glu Leu Ser Asn  Arg Met Val
1145            1150            1155

Asn Ala Leu Glu Asn Leu Ala  Gly Ile Asp Arg Ser  Asp Leu Ile
1160            1165            1170

Gln Ala Arg Ser Arg Ala Ser  Ser Glu Cys Glu Ala  Thr Tyr Leu
1175            1180            1185

Leu Arg Gln Ser Ser Ile Asn  Ser Ala Asp Gly Tyr  Ser Leu Tyr
1190            1195            1200

Arg Tyr His Phe Asn Gly Glu  Glu Leu Leu Phe Glu  Asp Thr Ser
1205            1210            1215

Leu Ser Thr Ser Pro Gly Thr  Gly Val Arg Lys Lys  Thr Cys Ser
1220            1225            1230

Phe Arg Ile Lys Glu Glu Lys  Asp Val Lys Thr His  Leu Val Pro
1235            1240            1245

Glu Cys Gln Asn Ser Leu His  Leu Ser Leu Gly Thr  Ser Thr Ser
1250            1255            1260

Ala Thr Pro Asp Gly Ser His  Leu Ala Val Asp Asp  Leu Lys Asn
1265            1270            1275

Ala Glu Glu Ser Lys Leu Gly  Pro Asp Ile Gly Ile  Ser Lys Glu
1280            1285            1290

Asp Asp Glu Arg Gln Thr Asp  Ser Lys Lys Glu Glu  Thr Ile Ser
1295            1300            1305

Pro Ser Leu Asn Lys Thr Asp  Val Ile His Gly Gln  Asp Lys Ser
1310            1315            1320

Asp Val Gln Asn Thr Gln Leu  Thr Val Glu Thr Thr  Asn Ile Glu
1325            1330            1335

Gly Thr Ile Ser Tyr Pro Leu  Glu Glu Thr Lys Ile  Thr Arg Tyr
1340            1345            1350

Phe Pro Asp Glu Thr Ile Asn  Ala Cys Lys Thr Met  Lys Ser Arg
1355            1360            1365

Ser Phe Val Tyr Ser Arg Gly  Arg Lys Leu Val Gly  Gly Val Asn
1370            1375            1380
```

```
Gln Asp Val Glu Tyr Ser Ser Ile Thr Asp Gln Gln Leu Thr Thr
1385                1390                1395

Glu Trp Gln Cys Gln Val Gln Lys Ile Thr Arg Ser His Ser Thr
1400                1405                1410

Asp Ile Pro Tyr Ile Val Ser Glu Ala Ala Val Gln Ala Glu Gln
1415                1420                1425

Lys Glu Gln Phe Ala Asp Met Gln Asp Glu His His Val Ala Glu
1430                1435                1440

Ala Ile Pro Arg Ile Pro Arg Leu Ser Leu Thr Ile Thr Asp Arg
1445                1450                1455

Asn Gly Met Glu Asn Leu Leu Ser Val Lys Pro Asp Gln Thr Leu
1460                1465                1470

Gly Phe Pro Ser Leu Arg Ser Lys Ser Leu His Gly His Pro Arg
1475                1480                1485

Asn Val Lys Ser Ile Gln Gly Lys Leu Asp Arg Ser Gly His Ala
1490                1495                1500

Ser Ser Val Ser Ser Leu Val Ile Val Ser Gly Met Thr Ala Glu
1505                1510                1515

Glu Lys Lys Val Lys Lys Glu Lys Ala Ser Thr Glu Thr Glu Cys
1520                1525                1530

<210> SEQ ID NO 14
<211> LENGTH: 4665
<212> TYPE: DNA
<213> ORGANISM: Homo sapiens
<220> FEATURE:
<221> NAME/KEY: CDS
<222> LOCATION: (1)..(4662)

<400> SEQUENCE: 14 atg tat gtg cga gta tct ttt gat aca aaa cct gat ctc ctc tta cac     48
Met Tyr Val Arg Val Ser Phe Asp Thr Lys Pro Asp Leu Leu Leu His
1               5                   10                  15 ctg atg acc aag gaa tgg cag ttg gag ctt ccc aag ctt ctc atc tct     96
Leu Met Thr Lys Glu Trp Gln Leu Glu Leu Pro Lys Leu Leu Ile Ser
            20                  25                  30 gtc cat ggg ggc ctg cag aac ttt gaa ctc cag cca aaa ctc aag caa    144
Val His Gly Gly Leu Gln Asn Phe Glu Leu Gln Pro Lys Leu Lys Gln
        35                  40                  45 gtc ttt ggg aaa ggg ctc atc aaa gca gca atg aca act gga gcg tgg    192
Val Phe Gly Lys Gly Leu Ile Lys Ala Ala Met Thr Thr Gly Ala Trp
    50                  55                  60 ata ttc act gga ggg gtt aac aca ggt gtt att cgt cat gtt ggc gat    240
Ile Phe Thr Gly Gly Val Asn Thr Gly Val Ile Arg His Val Gly Asp
65                  70                  75                  80 gcc ttg aag gat cat gcc tct aag tct cga gga aag ata tgc acc ata    288
Ala Leu Lys Asp His Ala Ser Lys Ser Arg Gly Lys Ile Cys Thr Ile
                85                  90                  95 ggt att gcc ccc tgg gga att gtg gaa aac cag gag gac ctc att gga    336
Gly Ile Ala Pro Trp Gly Ile Val Glu Asn Gln Glu Asp Leu Ile Gly
            100                 105                 110 aga gat gtt gtc cgg cca tac cag acc atg tcc aat ccc atg agc aag    384
Arg Asp Val Val Arg Pro Tyr Gln Thr Met Ser Asn Pro Met Ser Lys
        115                 120                 125 ctc act gtt ctc aac agc atg cat tcc cac ttc att ctg gct gac aac    432
Leu Thr Val Leu Asn Ser Met His Ser His Phe Ile Leu Ala Asp Asn
    130                 135                 140 ggg acc act gga aaa tat gga gca gag gtg aaa ctt cga aga caa ctg    480
```

```
Gly Thr Thr Gly Lys Tyr Gly Ala Glu Val Lys Leu Arg Arg Gln Leu
145                 150                 155                 160 gaa aag cat att tca ctc cag aag ata aac aca aga atc ggt caa ggt       528
Glu Lys His Ile Ser Leu Gln Lys Ile Asn Thr Arg Ile Gly Gln Gly
165                 170                 175 gtt cct gtg gtg gca ctc ata gtg gaa gga ccc aat gtg atc tcg           576
Val Pro Val Val Ala Leu Ile Val Glu Gly Pro Asn Val Ile Ser
180                 185                 190 att gtt ttg gag tac ctt cga gac acc cct ccc gtg cca gtg gtt gtc       624
Ile Val Leu Glu Tyr Leu Arg Asp Thr Pro Pro Val Pro Val Val Val
195                 200                 205 tgt gat ggg agt gga cgg gca tcg gac atc ctg gcc ttt ggg cat aaa       672
Cys Asp Gly Ser Gly Arg Ala Ser Asp Ile Leu Ala Phe Gly His Lys
210                 215                 220 tac tca gaa gaa ggc gga ctg ata aat gaa tct ttg agg gac cag ctg       720
Tyr Ser Glu Glu Gly Gly Leu Ile Asn Glu Ser Leu Arg Asp Gln Leu
225                 230                 235                 240 ttg gtg act ata cag aag act ttc aca tac act cga acc caa gct cag       768
Leu Val Thr Ile Gln Lys Thr Phe Thr Tyr Thr Arg Thr Gln Ala Gln
245                 250                 255 cat ctg ttc atc atc ctc atg gag tgc atg aag aag aag gaa ttg att       816
His Leu Phe Ile Ile Leu Met Glu Cys Met Lys Lys Lys Glu Leu Ile
260                 265                 270 acg gta ttt cgg atg gga tca gaa gga cac cag gac att gat ttg gct       864
Thr Val Phe Arg Met Gly Ser Glu Gly His Gln Asp Ile Asp Leu Ala
275                 280                 285 atc ctg aca gct tta ctc aaa gga gcc aat gcc tcg gcc cca gac caa       912
Ile Leu Thr Ala Leu Leu Lys Gly Ala Asn Ala Ser Ala Pro Asp Gln
290                 295                 300 ctg agc tta gct tta gcc tgg aac aga gtc gac atc gct cgc agc cag       960
Leu Ser Leu Ala Leu Ala Trp Asn Arg Val Asp Ile Ala Arg Ser Gln
305                 310                 315                 320 atc ttt att tac ggg caa cag tgg ccg gtg gga tct ctg gag caa gcc      1008
Ile Phe Ile Tyr Gly Gln Gln Trp Pro Val Gly Ser Leu Glu Gln Ala
325                 330                 335 atg ttg gat gcc tta gtt ctg gac aga gtg gat ttt gtg aaa tta ctc      1056
Met Leu Asp Ala Leu Val Leu Asp Arg Val Asp Phe Val Lys Leu Leu
340                 345                 350 ata gag aat gga gta agc atg cac cgt ttt ctc acc atc tcc aga cta      1104
Ile Glu Asn Gly Val Ser Met His Arg Phe Leu Thr Ile Ser Arg Leu
355                 360                 365 gag gaa ttg tac aat acg aga cat ggg ccc tca aat aca ttg tac cac      1152
Glu Glu Leu Tyr Asn Thr Arg His Gly Pro Ser Asn Thr Leu Tyr His
370                 375                 380 ttg gtc agg gat gtc aaa aag ggg aac ctg ccc cca gac tac aga atc      1200
Leu Val Arg Asp Val Lys Lys Gly Asn Leu Pro Pro Asp Tyr Arg Ile
385                 390                 395                 400 agc ctg att gac atc ggc ctg gtg atc gag tac ctg atg ggc ggg gct      1248
Ser Leu Ile Asp Ile Gly Leu Val Ile Glu Tyr Leu Met Gly Gly Ala
405                 410                 415 tat cgc tgc aac tac acg cgc aag cgc ttc cgg acc ctc tac cac aac      1296
Tyr Arg Cys Asn Tyr Thr Arg Lys Arg Phe Arg Thr Leu Tyr His Asn
420                 425                 430 ctc ttc ggc ccc aag agg ccc aaa gcc ttg aaa ctg ctg gga atg gag      1344
Leu Phe Gly Pro Lys Arg Pro Lys Ala Leu Lys Leu Leu Gly Met Glu
435                 440                 445 gat gat att ccc ttg agg cga gga aga aag aca acc aag aaa cgt gaa      1392
Asp Asp Ile Pro Leu Arg Arg Gly Arg Lys Thr Thr Lys Lys Arg Glu
450                 455                 460
```

```
gaa gag gtg gac att gac ttg gat gat cct gag atc aac cac ttc ccc    1440
Glu Glu Val Asp Ile Asp Leu Asp Asp Pro Glu Ile Asn His Phe Pro
465                 470                 475                 480 ttc cct ttc cat gag ctc atg gtg tgg gct gtt ctc atg aag cgg cag    1488
Phe Pro Phe His Glu Leu Met Val Trp Ala Val Leu Met Lys Arg Gln
    485                 490                 495 aag atg gcc ctg ttc ttc tgg cag cac ggt gag gag gcc atg gcc aag    1536
Lys Met Ala Leu Phe Phe Trp Gln His Gly Glu Glu Ala Met Ala Lys
500                 505                 510 gcc ctg gtg gcc tgc aag ctc tgc aaa gcc atg gct cat gag gcc tct    1584
Ala Leu Val Ala Cys Lys Leu Cys Lys Ala Met Ala His Glu Ala Ser
515                 520                 525 gag aac gac atg gtt gac gac att tcc cag gag ctg aat cac aat tcc    1632
Glu Asn Asp Met Val Asp Asp Ile Ser Gln Glu Leu Asn His Asn Ser
530                 535                 540 aga gac ttt ggc cag ctg gct gtg gag ctc ctg gac cag tcc tac aag    1680
Arg Asp Phe Gly Gln Leu Ala Val Glu Leu Leu Asp Gln Ser Tyr Lys
545                 550                 555                 560 cag gac gaa cag ctg gcc atg aaa ctg ctg acg tat gag ctg aag aac    1728
Gln Asp Glu Gln Leu Ala Met Lys Leu Leu Thr Tyr Glu Leu Lys Asn
565                 570                 575 tgg agc aac gcc acg tgc ctg cag ctt gcc gtg gct gcc aaa cac cgc    1776
Trp Ser Asn Ala Thr Cys Leu Gln Leu Ala Val Ala Ala Lys His Arg
580                 585                 590 gac ttc atc gcg cac acg tgc agc cag atg ctg ctc acc gac atg tgg    1824
Asp Phe Ile Ala His Thr Cys Ser Gln Met Leu Leu Thr Asp Met Trp
595                 600                 605 atg ggc cgg ctc cgc atg cgc aag aac tca ggc ctc aag gta att ctg    1872
Met Gly Arg Leu Arg Met Arg Lys Asn Ser Gly Leu Lys Val Ile Leu
610                 615                 620 gga att cta ctt cct cct tca att ctc agc ttg gag ttc aag aac aaa    1920
Gly Ile Leu Leu Pro Pro Ser Ile Leu Ser Leu Glu Phe Lys Asn Lys
625                 630                 635                 640 gac gac atg ccc tat atg tct cag gcc cag gaa atc cac ctc caa gag    1968
Asp Asp Met Pro Tyr Met Ser Gln Ala Gln Glu Ile His Leu Gln Glu
645                 650                 655 aag gag gca gaa gaa cca gag aag ccc aca aag gaa aaa gag gaa gag    2016
Lys Glu Ala Glu Glu Pro Glu Lys Pro Thr Lys Glu Lys Glu Glu Glu
660                 665                 670 gac atg gag ctc aca gca atg ttg gga cga aac aac ggg gag tcc tcc    2064
Asp Met Glu Leu Thr Ala Met Leu Gly Arg Asn Asn Gly Glu Ser Ser
675                 680                 685 agg aag aag gat gaa gag gaa gtt cag agc aag cac cgg tta atc ccc    2112
Arg Lys Lys Asp Glu Glu Glu Val Gln Ser Lys His Arg Leu Ile Pro
690                 695                 700 ctc ggc aga aaa atc tat gaa ttc tac aat gca ccc atc gtg aag ttc    2160
Leu Gly Arg Lys Ile Tyr Glu Phe Tyr Asn Ala Pro Ile Val Lys Phe
705                 710                 715                 720 tgg ttc tac aca ctg gcg tat atc gga tac ctg atg ctc ttc aac tat    2208
Trp Phe Tyr Thr Leu Ala Tyr Ile Gly Tyr Leu Met Leu Phe Asn Tyr
725                 730                 735 atc gtg tta gtg aag atg gaa cgc tgg ccg tcc acc cag gaa tgg atc    2256
Ile Val Leu Val Lys Met Glu Arg Trp Pro Ser Thr Gln Glu Trp Ile
740                 745                 750 gta atc tcc tat att ttc acc ctg gga ata gaa aag atg aga gag att    2304
Val Ile Ser Tyr Ile Phe Thr Leu Gly Ile Glu Lys Met Arg Glu Ile
755                 760                 765 ctg atg tca gag cca ggg aag ttg cta cag aaa gtg aag gta tgg ctg    2352
Leu Met Ser Glu Pro Gly Lys Leu Leu Gln Lys Val Lys Val Trp Leu
770                 775                 780
```

| | | |
|---|---|---|
| cag gag tac tgg aat gtc acg gac ctc atc gcc atc ctt ctg ttt tct<br>Gln Glu Tyr Trp Asn Val Thr Asp Leu Ile Ala Ile Leu Leu Phe Ser<br>785                      790                    795                 800 | 2400 |
| gtc gga atg atc ctt cgt ctc caa gac cag ccc ttc agg agt gac ggg<br>Val Gly Met Ile Leu Arg Leu Gln Asp Gln Pro Phe Arg Ser Asp Gly<br>805                    810                  815 | 2448 |
| agg gtc atc tac tgc gtg aac atc att tac tgg tat atc cgt ctc cta<br>Arg Val Ile Tyr Cys Val Asn Ile Ile Tyr Trp Tyr Ile Arg Leu Leu<br>820                    825                  830 | 2496 |
| gac atc ttc ggc gtg aac aag tat ttg ggc ccg tat gta atg atg att<br>Asp Ile Phe Gly Val Asn Lys Tyr Leu Gly Pro Tyr Val Met Met Ile<br>835                    840                  845 | 2544 |
| gga aaa atg atg ata gac atg atg tac ttt gtc atc att atg ctg gtg<br>Gly Lys Met Met Ile Asp Met Met Tyr Phe Val Ile Ile Met Leu Val<br>850                    855                  860 | 2592 |
| gtt ctg atg agc ttt ggg gtc gcc agg caa gcc atc ctt ttt ccc aat<br>Val Leu Met Ser Phe Gly Val Ala Arg Gln Ala Ile Leu Phe Pro Asn<br>865                    870                  875                 880 | 2640 |
| gag gag cca tca tgg aaa ctg gcc aag aac atc ttc tac atg ccc tat<br>Glu Glu Pro Ser Trp Lys Leu Ala Lys Asn Ile Phe Tyr Met Pro Tyr<br>885                    890                  895 | 2688 |
| tgg atg att tat ggg gaa gtg ttt gcg gac cag ata gac cct ccc tgt<br>Trp Met Ile Tyr Gly Glu Val Phe Ala Asp Gln Ile Asp Pro Pro Cys<br>900                    905                  910 | 2736 |
| gga cag aat gag acc cga gag gat ggt aaa ata atc cag ctg cct ccc<br>Gly Gln Asn Glu Thr Arg Glu Asp Gly Lys Ile Ile Gln Leu Pro Pro<br>915                    920                  925 | 2784 |
| tgc aag aca gga gct tgg atc gtg ccg gcc atc atg gcc tgc tac ctc<br>Cys Lys Thr Gly Ala Trp Ile Val Pro Ala Ile Met Ala Cys Tyr Leu<br>930                    935                  940 | 2832 |
| tta gtg gca aac atc ttg ctg gtc aac ctc ctc att gct gtc ttt aac<br>Leu Val Ala Asn Ile Leu Leu Val Asn Leu Leu Ile Ala Val Phe Asn<br>945                    950                  955                 960 | 2880 |
| aat aca ttt ttt gaa gta aaa tcg ata tcc aac caa gtc tgg aag ttt<br>Asn Thr Phe Phe Glu Val Lys Ser Ile Ser Asn Gln Val Trp Lys Phe<br>965                    970                  975 | 2928 |
| cag agg tat cag ctc atc atg act ttc cat gaa agg cca gtt ctg ccc<br>Gln Arg Tyr Gln Leu Ile Met Thr Phe His Glu Arg Pro Val Leu Pro<br>980                    985                  990 | 2976 |
| cca cca ctg atc atc ttc agc cac atg acc atg ata ttc cag cac ctg<br>Pro Pro Leu Ile Ile Phe Ser His Met Thr Met Ile Phe Gln His Leu<br>995                    1000                1005 | 3024 |
| tgc tgc cga tgg agg aaa cac gag agc gac ccg gat gaa agg gac<br>Cys Cys Arg Trp Arg Lys His Glu Ser Asp Pro Asp Glu Arg Asp<br>1010               1015              1020 | 3069 |
| tac ggc ctg aaa ctc ttc ata acc gat gat gag ctc aag aaa gta<br>Tyr Gly Leu Lys Leu Phe Ile Thr Asp Asp Glu Leu Lys Lys Val<br>1025              1030              1035 | 3114 |
| cat gac ttt gaa gag caa tgc ata gaa gaa tac ttc aga gaa aag<br>His Asp Phe Glu Glu Gln Cys Ile Glu Glu Tyr Phe Arg Glu Lys<br>1040              1045              1050 | 3159 |
| gat gat cgg ttc aac tca tct aat gat gag agg ata cgg gtg act<br>Asp Asp Arg Phe Asn Ser Ser Asn Asp Glu Arg Ile Arg Val Thr<br>1055              1060              1065 | 3204 |
| tca gaa agg gtg gag aac atg tct atg cgg ctg gag gaa gtc aac<br>Ser Glu Arg Val Glu Asn Met Ser Met Arg Leu Glu Glu Val Asn<br>1070              1075              1080 | 3249 |
| gag aga gag cac tcc atg aag gct tca ctc cag acc gtg gac atc<br>Glu Arg Glu His Ser Met Lys Ala Ser Leu Gln Thr Val Asp Ile | 3294 |

-continued

| | | | | | | | | |
|---|---|---|---|---|---|---|---|---|
| 1085 | | | 1090 | | | 1095 | | |

| | | | | | | | | | |
|---|---|---|---|---|---|---|---|---|---|
| cgg ctg<br>Arg Leu<br>1100 | gcg cag<br>Ala Gln | ctg gaa gac<br>Leu Glu Asp<br>1105 | ctt atc ggg<br>Leu Ile Gly | cgc atg<br>Arg Met<br>1110 | gcc acg gcc<br>Ala Thr Ala | | | | 3339 |
| ctg gag<br>Leu Glu<br>1115 | cgc ctg<br>Arg Leu | aca ggt ctg<br>Thr Gly Leu<br>1120 | gag cgg gcc<br>Glu Arg Ala | gag tcc<br>Glu Ser<br>1125 | aac aaa atc<br>Asn Lys Ile | | | | 3384 |
| cgc tcg<br>Arg Ser<br>1130 | agg acc<br>Arg Thr | tcg tca gac<br>Ser Ser Asp<br>1135 | tgc acg gac<br>Cys Thr Asp | gcc gcc<br>Ala Ala<br>1140 | tac att gtc<br>Tyr Ile Val | | | | 3429 |
| cgt cag<br>Arg Gln<br>1145 | agc agc<br>Ser Ser | ttc aac agc<br>Phe Asn Ser<br>1150 | cag gaa ggg<br>Gln Glu Gly | aac acc<br>Asn Thr<br>1155 | ttc aag ctc<br>Phe Lys Leu | | | | 3474 |
| caa gag<br>Gln Glu<br>1160 | agt ata<br>Ser Ile | gac cct gca<br>Asp Pro Ala<br>1165 | ggt gag gag<br>Gly Glu Glu | acc atg<br>Thr Met<br>1170 | tcc cca act<br>Ser Pro Thr | | | | 3519 |
| tct cca<br>Ser Pro<br>1175 | acc tta<br>Thr Leu | atg ccc cgt<br>Met Pro Arg<br>1180 | atg cga agc<br>Met Arg Ser | cat tct<br>His Ser<br>1185 | ttc tat tca<br>Phe Tyr Ser | | | | 3564 |
| gtc aat<br>Val Asn<br>1190 | atg aaa<br>Met Lys | gac aaa ggt<br>Asp Lys Gly<br>1195 | ggt ata gaa<br>Gly Ile Glu | aag ttg<br>Lys Leu<br>1200 | gaa agt att<br>Glu Ser Ile | | | | 3609 |
| ttt aaa<br>Phe Lys<br>1205 | gaa agg<br>Glu Arg | tcc ctg agc<br>Ser Leu Ser<br>1210 | cta cac cgg<br>Leu His Arg | gct act<br>Ala Thr<br>1215 | agt tcc cac<br>Ser Ser His | | | | 3654 |
| tct gta<br>Ser Val<br>1220 | gca aaa<br>Ala Lys | gaa ccc aaa<br>Glu Pro Lys<br>1225 | gct cct gca<br>Ala Pro Ala | gcc cct<br>Ala Pro<br>1230 | gcc aac acc<br>Ala Asn Thr | | | | 3699 |
| ttg gcc<br>Leu Ala<br>1235 | att gtt<br>Ile Val | cct gat tcc<br>Pro Asp Ser<br>1240 | aga aga cca<br>Arg Arg Pro | tca tcg<br>Ser Ser<br>1245 | tgt ata gac<br>Cys Ile Asp | | | | 3744 |
| atc tat<br>Ile Tyr<br>1250 | gtc tct<br>Val Ser | gct atg gat<br>Ala Met Asp<br>1255 | gag ctc cac<br>Glu Leu His | tgt gat<br>Cys Asp<br>1260 | ata gac cct<br>Ile Asp Pro | | | | 3789 |
| ctg gac<br>Leu Asp<br>1265 | aat tcc<br>Asn Ser | gtg aac atc<br>Val Asn Ile<br>1270 | ctt ggg cta<br>Leu Gly Leu | ggc gag<br>Gly Glu<br>1275 | cca agc ttt<br>Pro Ser Phe | | | | 3834 |
| tca act<br>Ser Thr<br>1280 | cca gta<br>Pro Val | cct tcc aca<br>Pro Ser Thr<br>1285 | gcc cct tca<br>Ala Pro Ser | agt agt<br>Ser Ser<br>1290 | gcc tat gca<br>Ala Tyr Ala | | | | 3879 |
| aca ctt<br>Thr Leu<br>1295 | gca ccc<br>Ala Pro | aca gac aga<br>Thr Asp Arg<br>1300 | cct cca agc<br>Pro Pro Ser | cgg agc<br>Arg Ser<br>1305 | att gat ttt<br>Ile Asp Phe | | | | 3924 |
| gag gac<br>Glu Asp<br>1310 | atc acc<br>Ile Thr | tcc atg gac<br>Ser Met Asp<br>1315 | act aga tct<br>Thr Arg Ser | ttt tct<br>Phe Ser<br>1320 | tca gac tac<br>Ser Asp Tyr | | | | 3969 |
| acc cac<br>Thr His<br>1325 | ctc cca<br>Leu Pro | gaa tgc caa<br>Glu Cys Gln<br>1330 | aac ccc tgg<br>Asn Pro Trp | gac tca<br>Asp Ser<br>1335 | gag cct ccg<br>Glu Pro Pro | | | | 4014 |
| atg tac<br>Met Tyr<br>1340 | cac acc<br>His Thr | att gag cgt<br>Ile Glu Arg<br>1345 | tcc aaa agt<br>Ser Lys Ser | agc cgc<br>Ser Arg<br>1350 | tac cta gcc<br>Tyr Leu Ala | | | | 4059 |
| acc aca<br>Thr Thr<br>1355 | ccc ttt<br>Pro Phe | ctt cta gaa<br>Leu Leu Glu<br>1360 | gag gct ccc<br>Glu Ala Pro | att gtg<br>Ile Val<br>1365 | aaa tct cat<br>Lys Ser His | | | | 4104 |
| agc ttt<br>Ser Phe<br>1370 | atg ttt<br>Met Phe | tcc ccc tca<br>Ser Pro Ser<br>1375 | agg agc tat<br>Arg Ser Tyr | tat gcc<br>Tyr Ala<br>1380 | aac ttt ggg<br>Asn Phe Gly | | | | 4149 |
| gtg cct<br>Val Pro | gta aaa<br>Val Lys | aca gca gaa<br>Thr Ala Glu | tac aca agt<br>Tyr Thr Ser | att aca<br>Ile Thr | gac tgt att<br>Asp Cys Ile | | | | 4194 |

```
Val Pro Val Lys Thr Ala Glu Tyr Thr Ser Ile Thr Asp Cys Ile
1385                1390                1395 gac aca agg tgt gtc aat gcc cct caa gca att gcg gac aga gct         4239
Asp Thr Arg Cys Val Asn Ala Pro Gln Ala Ile Ala Asp Arg Ala
1400                1405                1410 gcc ttc cct gga ggt ctt gga gac aaa gtg gag gac tta act tgc         4284
Ala Phe Pro Gly Gly Leu Gly Asp Lys Val Glu Asp Leu Thr Cys
1415                1420                1425 tgc cat cca gag cga gaa gca gaa ctg agt cac ccc agc tct gac         4329
Cys His Pro Glu Arg Glu Ala Glu Leu Ser His Pro Ser Ser Asp
1430                1435                1440 agt gag gag aat gag gcc aaa ggc cgc aga gcc acc att gca ata         4374
Ser Glu Glu Asn Glu Ala Lys Gly Arg Arg Ala Thr Ile Ala Ile
1445                1450                1455 tcc tcc cag gag ggt gat aac tca gag aga acc ctg tcc aac aac         4419
Ser Ser Gln Glu Gly Asp Asn Ser Glu Arg Thr Leu Ser Asn Asn
1460                1465                1470 atc act gtt ccc aag ata gag cgc gcc aac agc tac tcg gca gag         4464
Ile Thr Val Pro Lys Ile Glu Arg Ala Asn Ser Tyr Ser Ala Glu
1475                1480                1485 gag cca agt gcg cca tat gca cac acc agg aag agc ttc tcc atc         4509
Glu Pro Ser Ala Pro Tyr Ala His Thr Arg Lys Ser Phe Ser Ile
1490                1495                1500 agt gac aaa ctc gac agg cag cgg aac aca gca agc ctg caa aat         4554
Ser Asp Lys Leu Asp Arg Gln Arg Asn Thr Ala Ser Leu Gln Asn
1505                1510                1515 ccc ttc cag aga agc aag tcc tcc aag ccg gag ggc cga ggg gac         4599
Pro Phe Gln Arg Ser Lys Ser Ser Lys Pro Glu Gly Arg Gly Asp
1520                1525                1530 agc ctg tcc atg agg aga ctg tcc aga aca tcg gct ttc caa agc         4644
Ser Leu Ser Met Arg Arg Leu Ser Arg Thr Ser Ala Phe Gln Ser
1535                1540                1545 ttt gaa agc aag cac acc taa                                         4665
Phe Glu Ser Lys His Thr
1550

<210> SEQ ID NO 15
<211> LENGTH: 1554
<212> TYPE: PRT
<213> ORGANISM: Homo sapiens

<400> SEQUENCE: 15

Met Tyr Val Arg Val Ser Phe Asp Thr Lys Pro Asp Leu Leu His
1               5                   10                  15

Leu Met Thr Lys Glu Trp Gln Leu Glu Leu Pro Lys Leu Leu Ile Ser
20                  25                  30

Val His Gly Gly Leu Gln Asn Phe Glu Leu Gln Pro Lys Leu Lys Gln
35                  40                  45

Val Phe Gly Lys Gly Leu Ile Lys Ala Ala Met Thr Thr Gly Ala Trp
50                  55                  60

Ile Phe Thr Gly Gly Val Asn Thr Gly Val Ile Arg His Val Gly Asp
65                  70                  75                  80

Ala Leu Lys Asp His Ala Ser Lys Ser Arg Gly Lys Ile Cys Thr Ile
85                  90                  95

Gly Ile Ala Pro Trp Gly Ile Val Glu Asn Gln Glu Asp Leu Ile Gly
100                 105                 110

Arg Asp Val Val Arg Pro Tyr Gln Thr Met Ser Asn Pro Met Ser Lys
115                 120                 125
```

-continued

```
Leu Thr Val Leu Asn Ser Met His Ser His Phe Ile Leu Ala Asp Asn
130                 135                 140

Gly Thr Thr Gly Lys Tyr Gly Ala Glu Val Lys Leu Arg Arg Gln Leu
145                 150                 155                 160

Glu Lys His Ile Ser Leu Gln Lys Ile Asn Thr Arg Ile Gly Gln Gly
165                 170                 175

Val Pro Val Val Ala Leu Ile Val Glu Gly Pro Asn Val Ile Ser
180                 185                 190

Ile Val Leu Glu Tyr Leu Arg Asp Thr Pro Val Pro Val Val Val
195                 200                 205

Cys Asp Gly Ser Gly Arg Ala Ser Asp Ile Leu Ala Phe Gly His Lys
210                 215                 220

Tyr Ser Glu Glu Gly Leu Ile Asn Glu Ser Leu Arg Asp Gln Leu
225                 230                 235                 240

Leu Val Thr Ile Gln Lys Thr Phe Thr Tyr Thr Arg Thr Gln Ala Gln
245                 250                 255

His Leu Phe Ile Ile Leu Met Glu Cys Met Lys Lys Lys Glu Leu Ile
260                 265                 270

Thr Val Phe Arg Met Gly Ser Glu Gly His Gln Asp Ile Asp Leu Ala
275                 280                 285

Ile Leu Thr Ala Leu Leu Lys Gly Ala Asn Ala Ser Ala Pro Asp Gln
290                 295                 300

Leu Ser Leu Ala Leu Ala Trp Asn Arg Val Asp Ile Ala Arg Ser Gln
305                 310                 315                 320

Ile Phe Ile Tyr Gly Gln Gln Trp Pro Val Gly Ser Leu Glu Gln Ala
325                 330                 335

Met Leu Asp Ala Leu Val Leu Asp Arg Val Asp Phe Val Lys Leu Leu
340                 345                 350

Ile Glu Asn Gly Val Ser Met His Arg Phe Leu Thr Ile Ser Arg Leu
355                 360                 365

Glu Glu Leu Tyr Asn Thr Arg His Gly Pro Ser Asn Thr Leu Tyr His
370                 375                 380

Leu Val Arg Asp Val Lys Lys Gly Asn Leu Pro Pro Asp Tyr Arg Ile
385                 390                 395                 400

Ser Leu Ile Asp Ile Gly Leu Val Ile Glu Tyr Leu Met Gly Gly Ala
405                 410                 415

Tyr Arg Cys Asn Tyr Thr Arg Lys Arg Phe Arg Thr Leu Tyr His Asn
420                 425                 430

Leu Phe Gly Pro Lys Arg Pro Lys Ala Leu Lys Leu Leu Gly Met Glu
435                 440                 445

Asp Asp Ile Pro Leu Arg Arg Gly Arg Lys Thr Thr Lys Lys Arg Glu
450                 455                 460

Glu Glu Val Asp Ile Asp Leu Asp Asp Pro Glu Ile Asn His Phe Pro
465                 470                 475                 480

Phe Pro Phe His Glu Leu Met Val Trp Ala Val Leu Met Lys Arg Gln
485                 490                 495

Lys Met Ala Leu Phe Phe Trp Gln His Gly Glu Glu Ala Met Ala Lys
500                 505                 510

Ala Leu Val Ala Cys Lys Leu Cys Lys Ala Met Ala His Glu Ala Ser
515                 520                 525

Glu Asn Asp Met Val Asp Asp Ile Ser Gln Glu Leu Asn His Asn Ser
530                 535                 540

Arg Asp Phe Gly Gln Leu Ala Val Glu Leu Leu Asp Gln Ser Tyr Lys
```

-continued

```
            545                 550                 555                 560
Gln Asp Glu Gln Leu Ala Met Lys Leu Leu Thr Tyr Glu Leu Lys Asn
565                 570                 575
Trp Ser Asn Ala Thr Cys Leu Gln Leu Ala Val Ala Ala Lys His Arg
580                 585                 590
Asp Phe Ile Ala His Thr Cys Ser Gln Met Leu Leu Thr Asp Met Trp
595                 600                 605
Met Gly Arg Leu Arg Met Arg Lys Asn Ser Gly Leu Lys Val Ile Leu
610                 615                 620
Gly Ile Leu Leu Pro Ser Ile Leu Ser Leu Glu Phe Lys Asn Lys
625                 630                 635                 640
Asp Asp Met Pro Tyr Met Ser Gln Ala Gln Glu Ile His Leu Gln Glu
645                 650                 655
Lys Glu Ala Glu Glu Pro Glu Lys Pro Thr Lys Glu Lys Glu Glu Glu
660                 665                 670
Asp Met Glu Leu Thr Ala Met Leu Gly Arg Asn Asn Gly Glu Ser Ser
675                 680                 685
Arg Lys Lys Asp Glu Glu Val Gln Ser Lys His Arg Leu Ile Pro
690                 695                 700
Leu Gly Arg Lys Ile Tyr Glu Phe Tyr Asn Ala Pro Ile Val Lys Phe
705                 710                 715                 720
Trp Phe Tyr Thr Leu Ala Tyr Ile Gly Tyr Leu Met Leu Phe Asn Tyr
725                 730                 735
Ile Val Leu Val Lys Met Glu Arg Trp Pro Ser Thr Gln Glu Trp Ile
740                 745                 750
Val Ile Ser Tyr Ile Phe Thr Leu Gly Ile Glu Lys Met Arg Glu Ile
755                 760                 765
Leu Met Ser Glu Pro Gly Lys Leu Leu Gln Lys Val Lys Val Trp Leu
770                 775                 780
Gln Glu Tyr Trp Asn Val Thr Asp Leu Ile Ala Ile Leu Leu Phe Ser
785                 790                 795                 800
Val Gly Met Ile Leu Arg Leu Gln Asp Gln Pro Phe Arg Ser Asp Gly
805                 810                 815
Arg Val Ile Tyr Cys Val Asn Ile Ile Tyr Trp Tyr Ile Arg Leu Leu
820                 825                 830
Asp Ile Phe Gly Val Asn Lys Tyr Leu Gly Pro Tyr Val Met Met Ile
835                 840                 845
Gly Lys Met Met Ile Asp Met Met Tyr Phe Val Ile Ile Met Leu Val
850                 855                 860
Val Leu Met Ser Phe Gly Val Ala Arg Gln Ala Ile Leu Phe Pro Asn
865                 870                 875                 880
Glu Glu Pro Ser Trp Lys Leu Ala Lys Asn Ile Phe Tyr Met Pro Tyr
885                 890                 895
Trp Met Ile Tyr Gly Glu Val Phe Ala Asp Gln Ile Asp Pro Pro Cys
900                 905                 910
Gly Gln Asn Glu Thr Arg Glu Asp Gly Lys Ile Ile Gln Leu Pro Pro
915                 920                 925
Cys Lys Thr Gly Ala Trp Ile Val Pro Ala Ile Met Ala Cys Tyr Leu
930                 935                 940
Leu Val Ala Asn Ile Leu Leu Val Asn Leu Leu Ile Ala Val Phe Asn
945                 950                 955                 960
Asn Thr Phe Phe Glu Val Lys Ser Ile Ser Asn Gln Val Trp Lys Phe
965                 970                 975
```

-continued

```
Gln Arg Tyr Gln Leu Ile Met Thr Phe His Glu Arg Pro Val Leu Pro
980                 985                 990

Pro Pro Leu Ile Ile Phe Ser His  Met Thr Met Ile Phe  Gln His Leu
995                 1000                1005

Cys Cys Arg Trp Arg Lys His Glu Ser Asp Pro Asp  Glu Arg Asp
1010                1015                1020

Tyr Gly Leu Lys Leu Phe Ile Thr Asp Asp Glu Leu  Lys Lys Val
1025                1030                1035

His Asp Phe Glu Glu Gln Cys Ile Glu Glu Tyr Phe  Arg Glu Lys
1040                1045                1050

Asp Asp Arg Phe Asn Ser Ser Asn Asp Glu Arg Ile  Arg Val Thr
1055                1060                1065

Ser Glu Arg Val Glu Asn Met Ser Met Arg Leu Glu  Glu Val Asn
1070                1075                1080

Glu Arg Glu His Ser Met Lys Ala Ser Leu Gln Thr  Val Asp Ile
1085                1090                1095

Arg Leu Ala Gln Leu Glu Asp Leu Ile Gly Arg Met  Ala Thr Ala
1100                1105                1110

Leu Glu Arg Leu Thr Gly Leu Glu Arg Ala Glu Ser  Asn Lys Ile
1115                1120                1125

Arg Ser Arg Thr Ser Ser Asp Cys Thr Asp Ala Ala  Tyr Ile Val
1130                1135                1140

Arg Gln Ser Ser Phe Asn Ser Gln Glu Gly Asn Thr  Phe Lys Leu
1145                1150                1155

Gln Glu Ser Ile Asp Pro Ala Gly Glu Glu Thr Met  Ser Pro Thr
1160                1165                1170

Ser Pro Thr Leu Met Pro Arg Met Arg Ser His Ser  Phe Tyr Ser
1175                1180                1185

Val Asn Met Lys Asp Lys Gly Gly Ile Glu Lys Leu  Glu Ser Ile
1190                1195                1200

Phe Lys Glu Arg Ser Leu Ser Leu His Arg Ala Thr  Ser Ser His
1205                1210                1215

Ser Val Ala Lys Glu Pro Lys Ala Pro Ala Ala Pro  Ala Asn Thr
1220                1225                1230

Leu Ala Ile Val Pro Asp Ser Arg Arg Pro Ser Ser  Cys Ile Asp
1235                1240                1245

Ile Tyr Val Ser Ala Met Asp Glu Leu His Cys Asp  Ile Asp Pro
1250                1255                1260

Leu Asp Asn Ser Val Asn Ile Leu Gly Leu Gly Glu  Pro Ser Phe
1265                1270                1275

Ser Thr Pro Val Pro Ser Thr Ala Pro Ser Ser Ser  Ala Tyr Ala
1280                1285                1290

Thr Leu Ala Pro Thr Asp Arg Pro Pro Ser Arg Ser  Ile Asp Phe
1295                1300                1305

Glu Asp Ile Thr Ser Met Asp Thr Arg Ser Phe Ser  Ser Asp Tyr
1310                1315                1320

Thr His Leu Pro Glu Cys Gln Asn Pro Trp Asp Ser  Glu Pro Pro
1325                1330                1335

Met Tyr His Thr Ile Glu Arg Ser Lys Ser Ser Arg  Tyr Leu Ala
1340                1345                1350

Thr Thr Pro Phe Leu Leu Glu Glu Ala Pro Ile Val  Lys Ser His
1355                1360                1365
```

```
Ser Phe Met Phe Ser Pro Arg Ser Tyr Tyr Ala Asn Phe Gly
1370                1375                1380

Val Pro Val Lys Thr Ala Glu Tyr Thr Ser Ile Thr Asp Cys Ile
1385                1390                1395

Asp Thr Arg Cys Val Asn Ala Pro Gln Ala Ile Ala Asp Arg Ala
1400                1405                1410

Ala Phe Pro Gly Gly Leu Gly Asp Lys Val Glu Asp Leu Thr Cys
1415                1420                1425

Cys His Pro Glu Arg Glu Ala Glu Leu Ser His Pro Ser Ser Asp
1430                1435                1440

Ser Glu Glu Asn Glu Ala Lys Gly Arg Arg Ala Thr Ile Ala Ile
1445                1450                1455

Ser Ser Gln Glu Gly Asp Asn Ser Glu Arg Thr Leu Ser Asn Asn
1460                1465                1470

Ile Thr Val Pro Lys Ile Glu Arg Ala Asn Ser Tyr Ser Ala Glu
1475                1480                1485

Glu Pro Ser Ala Pro Tyr Ala His Thr Arg Lys Ser Phe Ser Ile
1490                1495                1500

Ser Asp Lys Leu Asp Arg Gln Arg Asn Thr Ala Ser Leu Gln Asn
1505                1510                1515

Pro Phe Gln Arg Ser Lys Ser Ser Lys Pro Glu Gly Arg Gly Asp
1520                1525                1530

Ser Leu Ser Met Arg Arg Leu Ser Arg Thr Ser Ala Phe Gln Ser
1535                1540                1545

Phe Glu Ser Lys His Thr
1550
```

<210> SEQ ID NO 16
<211> LENGTH: 8
<212> TYPE: PRT
<213> ORGANISM: bacteriophage T7

<400> SEQUENCE: 16

```
Asp Tyr Lys Asp Asp Asp Asp Lys
1               5
```

<210> SEQ ID NO 17
<211> LENGTH: 1566
<212> TYPE: PRT
<213> ORGANISM: Homo sapiens

<400> SEQUENCE: 17

```
Met Tyr Val Arg Val Ser Phe Asp Thr Lys Pro Asp Leu Leu Leu His
1               5                   10                  15

Leu Met Thr Lys Glu Trp Gln Leu Glu Leu Pro Lys Leu Leu Ile Ser
20                  25                  30

Val His Gly Gly Leu Gln Asn Phe Glu Leu Gln Pro Lys Leu Lys Gln
35                  40                  45

Val Phe Gly Lys Gly Leu Ile Lys Ala Ala Met Thr Thr Gly Ala Trp
50                  55                  60

Ile Phe Thr Gly Gly Val Asn Thr Gly Val Ile Arg His Val Gly Asp
65                  70                  75                  80

Ala Leu Lys Asp His Ala Ser Lys Ser Arg Gly Lys Ile Cys Thr Ile
85                  90                  95

Gly Ile Ala Pro Trp Gly Ile Val Glu Asn Gln Glu Asp Leu Ile Gly
100                 105                 110
```

-continued

```
Arg Asp Val Val Arg Pro Tyr Gln Thr Met Ser Asn Pro Met Ser Lys
115                 120                 125

Leu Thr Val Leu Asn Ser Met His Ser His Phe Ile Leu Ala Asp Asn
130                 135                 140

Gly Thr Thr Gly Lys Tyr Gly Ala Glu Val Lys Leu Arg Arg Gln Leu
145                 150                 155                 160

Glu Lys His Ile Ser Leu Gln Lys Ile Asn Thr Arg Ile Gly Gln Gly
165                 170                 175

Val Pro Val Val Ala Leu Ile Val Glu Gly Gly Pro Asn Val Ile Ser
180                 185                 190

Ile Val Leu Glu Tyr Leu Arg Asp Thr Pro Pro Val Pro Val Val Val
195                 200                 205

Cys Asp Gly Ser Gly Arg Ala Ser Asp Ile Leu Ala Phe Gly His Lys
210                 215                 220

Tyr Ser Glu Glu Gly Gly Leu Ile Asn Glu Ser Leu Arg Asp Gln Leu
225                 230                 235                 240

Leu Val Thr Ile Gln Lys Thr Phe Thr Tyr Thr Arg Thr Gln Ala Gln
245                 250                 255

His Leu Phe Ile Ile Leu Met Glu Cys Met Lys Lys Lys Glu Leu Ile
260                 265                 270

Thr Val Phe Arg Met Gly Ser Glu Gly His Gln Asp Ile Asp Leu Ala
275                 280                 285

Ile Leu Thr Ala Leu Leu Lys Gly Ala Asn Ala Ser Ala Pro Asp Gln
290                 295                 300

Leu Ser Leu Ala Leu Ala Trp Asn Arg Val Asp Ile Ala Arg Ser Gln
305                 310                 315                 320

Ile Phe Ile Tyr Gly Gln Gln Trp Pro Val Gly Ser Leu Glu Gln Ala
325                 330                 335

Met Leu Asp Ala Leu Val Leu Asp Arg Val Asp Phe Val Lys Leu Leu
340                 345                 350

Ile Glu Asn Gly Val Ser Met His Arg Phe Leu Thr Ile Ser Arg Leu
355                 360                 365

Glu Glu Leu Tyr Asn Thr Arg His Gly Pro Ser Asn Thr Leu Tyr His
370                 375                 380

Leu Val Arg Asp Val Lys Lys Arg Glu Tyr Pro Gly Phe Gly Trp Ile
385                 390                 395                 400

Tyr Phe Lys Gly Asn Leu Pro Pro Asp Tyr Arg Ile Ser Leu Ile Asp
405                 410                 415

Ile Gly Leu Val Ile Glu Tyr Leu Met Gly Gly Ala Tyr Arg Cys Asn
420                 425                 430

Tyr Thr Arg Lys Arg Phe Arg Thr Leu Tyr His Asn Leu Phe Gly Pro
435                 440                 445

Lys Arg Pro Lys Ala Leu Lys Leu Leu Gly Met Glu Asp Asp Ile Pro
450                 455                 460

Leu Arg Arg Gly Arg Lys Thr Thr Lys Lys Arg Glu Glu Val Asp
465                 470                 475                 480

Ile Asp Leu Asp Asp Pro Glu Ile Asn His Phe Pro Phe Pro Phe His
485                 490                 495

Glu Leu Met Val Trp Ala Val Leu Met Lys Arg Gln Lys Met Ala Leu
500                 505                 510

Phe Phe Trp Gln His Gly Glu Glu Ala Met Ala Lys Ala Leu Val Ala
515                 520                 525

Cys Lys Leu Cys Lys Ala Met Ala His Glu Ala Ser Glu Asn Asp Met
```

-continued

```
               530                 535                 540
Val Asp Asp Ile Ser Gln Glu Leu Asn His Asn Ser Arg Asp Phe Gly
545                 550                 555                 560
Gln Leu Ala Val Glu Leu Leu Asp Gln Ser Tyr Lys Gln Asp Glu Gln
                565                 570                 575
Leu Ala Met Lys Leu Leu Thr Tyr Glu Leu Lys Asn Trp Ser Asn Ala
580                 585                 590
Thr Cys Leu Gln Leu Ala Val Ala Lys His Arg Asp Phe Ile Ala
595                 600                 605
His Thr Cys Ser Gln Met Leu Leu Thr Asp Met Trp Met Gly Arg Leu
610                 615                 620
Arg Met Arg Lys Asn Ser Gly Leu Lys Val Ile Leu Gly Ile Leu Leu
625                 630                 635                 640
Pro Pro Ser Ile Leu Ser Leu Glu Phe Lys Asn Lys Asp Asp Met Pro
645                 650                 655
Tyr Met Ser Gln Ala Gln Glu Ile His Leu Gln Glu Lys Glu Ala Glu
660                 665                 670
Glu Pro Glu Lys Pro Thr Lys Glu Lys Glu Glu Asp Met Glu Leu
675                 680                 685
Thr Ala Met Leu Gly Arg Asn Asn Gly Glu Ser Ser Arg Lys Lys Asp
690                 695                 700
Glu Glu Glu Val Gln Ser Lys His Arg Leu Ile Pro Leu Gly Arg Lys
705                 710                 715                 720
Ile Tyr Glu Phe Tyr Asn Ala Pro Ile Val Lys Phe Trp Phe Tyr Thr
725                 730                 735
Leu Ala Tyr Ile Gly Tyr Leu Met Leu Phe Asn Tyr Ile Val Leu Val
740                 745                 750
Lys Met Glu Arg Trp Pro Ser Thr Gln Glu Trp Ile Val Ile Ser Tyr
755                 760                 765
Ile Phe Thr Leu Gly Ile Glu Lys Met Arg Glu Ile Leu Met Ser Glu
770                 775                 780
Pro Gly Lys Leu Leu Gln Lys Val Lys Val Trp Leu Gln Glu Tyr Trp
785                 790                 795                 800
Asn Val Thr Asp Leu Ile Ala Ile Leu Leu Phe Ser Val Gly Met Ile
805                 810                 815
Leu Arg Leu Gln Asp Gln Pro Phe Arg Ser Asp Gly Arg Val Ile Tyr
820                 825                 830
Cys Val Asn Ile Ile Tyr Trp Tyr Ile Arg Leu Leu Asp Ile Phe Gly
835                 840                 845
Val Asn Lys Tyr Leu Gly Pro Tyr Val Met Met Ile Gly Lys Met Met
850                 855                 860
Ile Asp Met Met Tyr Phe Val Ile Ile Met Leu Val Val Leu Met Ser
865                 870                 875                 880
Phe Gly Val Ala Arg Gln Ala Ile Leu Phe Pro Asn Glu Glu Pro Ser
885                 890                 895
Trp Lys Leu Ala Lys Asn Ile Phe Tyr Met Pro Tyr Trp Met Ile Tyr
900                 905                 910
Gly Glu Val Phe Ala Asp Gln Ile Asp Pro Pro Cys Gly Gln Asn Glu
915                 920                 925
Thr Arg Glu Asp Gly Lys Ile Ile Gln Leu Pro Pro Cys Lys Thr Gly
930                 935                 940
Ala Trp Ile Val Pro Ala Ile Met Ala Cys Tyr Leu Leu Val Ala Asn
945                 950                 955                 960
```

-continued

```
Ile Leu Leu Val Asn Leu Leu Ile Ala Val Phe Asn Asn Thr Phe Phe
965                 970                 975

Glu Val Lys Ser Ile Ser Asn Gln Val Trp Lys Phe Gln Arg Tyr Gln
980                 985                 990

Leu Ile Met Thr Phe His Glu Arg Pro Val Leu Pro Pro Pro Leu Ile
995                 1000                1005

Ile Phe Ser His Met Thr Met Ile Phe Gln His Leu Cys Cys Arg
    1010                1015                1020

Trp Arg Lys His Glu Ser Asp Pro Asp Glu Arg Asp Tyr Gly Leu
    1025                1030                1035

Lys Leu Phe Ile Thr Asp Asp Glu Leu Lys Lys Val His Asp Phe
    1040                1045                1050

Glu Glu Gln Cys Ile Glu Glu Tyr Phe Arg Glu Lys Asp Asp Arg
    1055                1060                1065

Phe Asn Ser Ser Asn Asp Glu Arg Ile Arg Val Thr Ser Glu Arg
    1070                1075                1080

Val Glu Asn Met Ser Met Arg Leu Glu Glu Val Asn Glu Arg Glu
    1085                1090                1095

His Ser Met Lys Ala Ser Leu Gln Thr Val Asp Ile Arg Leu Ala
    1100                1105                1110

Gln Leu Glu Asp Leu Ile Gly Arg Met Ala Thr Ala Leu Glu Arg
    1115                1120                1125

Leu Thr Gly Leu Glu Arg Ala Glu Ser Asn Lys Ile Arg Ser Arg
    1130                1135                1140

Thr Ser Ser Asp Cys Thr Asp Ala Ala Tyr Ile Val Arg Gln Ser
    1145                1150                1155

Ser Phe Asn Ser Gln Glu Gly Asn Thr Phe Lys Leu Gln Glu Ser
    1160                1165                1170

Ile Asp Pro Ala Gly Glu Glu Thr Met Ser Pro Thr Ser Pro Thr
    1175                1180                1185

Leu Met Pro Arg Met Arg Ser His Ser Phe Tyr Ser Val Asn Met
    1190                1195                1200

Lys Asp Lys Gly Gly Ile Glu Lys Leu Glu Ser Ile Phe Lys Glu
    1205                1210                1215

Arg Ser Leu Ser Leu His Arg Ala Thr Ser Ser His Ser Val Ala
    1220                1225                1230

Lys Glu Pro Lys Ala Pro Ala Ala Pro Ala Asn Thr Leu Ala Ile
    1235                1240                1245

Val Pro Asp Ser Arg Arg Pro Ser Ser Cys Ile Asp Ile Tyr Val
    1250                1255                1260

Ser Ala Met Asp Glu Leu His Cys Asp Ile Asp Pro Leu Asp Asn
    1265                1270                1275

Ser Val Asn Ile Leu Gly Leu Gly Glu Pro Ser Phe Ser Thr Pro
    1280                1285                1290

Val Pro Ser Thr Ala Pro Ser Ser Ser Ala Tyr Ala Thr Leu Ala
    1295                1300                1305

Pro Thr Asp Arg Pro Pro Ser Arg Ser Ile Asp Phe Glu Asp Ile
    1310                1315                1320

Thr Ser Met Asp Thr Arg Ser Phe Ser Ser Asp Tyr Thr His Leu
    1325                1330                1335

Pro Glu Cys Gln Asn Pro Trp Asp Ser Glu Pro Pro Met Tyr His
    1340                1345                1350
```

```
Thr Ile Glu Arg Ser Lys Ser     Ser Arg Tyr     Leu Ala Thr Thr Pro
1355            1360                 1365

Phe Leu Leu Glu Glu Ala Pro     Ile Val Lys     Ser His Ser Phe Met
1370            1375                 1380

Phe Ser Pro Ser Arg Ser Tyr     Tyr Ala Asn     Phe Gly Val Pro Val
1385            1390                 1395

Lys Thr Ala Glu Tyr Thr Ser     Ile Thr Asp     Cys Ile Asp Thr Arg
1400            1405                 1410

Cys Val Asn Ala Pro Gln Ala     Ile Ala Asp     Arg Ala Ala Phe Pro
1415            1420                 1425

Gly Gly Leu Gly Asp Lys Val     Glu Asp Leu     Thr Cys Cys His Pro
1430            1435                 1440

Glu Arg Glu Ala Glu Leu Ser     His Pro Ser     Ser Asp Ser Glu Glu
1445            1450                 1455

Asn Glu Ala Lys Gly Arg Arg     Ala Thr Ile     Ala Ile Ser Ser Gln
1460            1465                 1470

Glu Gly Asp Asn Ser Glu Arg     Thr Leu Ser     Asn Asn Ile Thr Val
1475            1480                 1485

Pro Lys Ile Glu Arg Ala Asn     Ser Tyr Ser     Ala Glu Glu Pro Ser
1490            1495                 1500

Ala Pro Tyr Ala His Thr Arg     Lys Ser Phe     Ser Ile Ser Asp Lys
1505            1510                 1515

Leu Asp Arg Gln Arg Asn Thr     Ala Ser Leu     Gln Asn Pro Phe Gln
1520            1525                 1530

Arg Ser Lys Ser Ser Lys Pro     Glu Gly Arg     Gly Asp Ser Leu Ser
1535            1540                 1545

Met Arg Arg Leu Ser Arg Thr     Ser Ala Phe     Gln Ser Phe Glu Ser
1550            1555                 1560

Lys His Thr
1565

<210> SEQ ID NO 18
<211> LENGTH: 1566
<212> TYPE: PRT
<213> ORGANISM: Homo sapiens

<400> SEQUENCE: 18

Met Tyr Val Arg Val Ser Phe     Asp Thr Lys     Pro Asp Leu Leu His
1               5                    10                  15

Leu Met Thr Lys Glu Trp Gln     Leu Glu Leu     Pro Lys Leu Leu Ile Ser
20              25                   30

Val His Gly Gly Leu Gln Asn     Phe Glu Leu     Gln Pro Lys Leu Lys Gln
35              40                   45

Val Phe Gly Lys Gly Leu Ile     Lys Ala Ala     Met Thr Thr Gly Ala Trp
50              55                   60

Ile Phe Thr Gly Gly Val Asn     Thr Gly Val     Ile Arg His Val Gly Asp
65              70                   75                  80

Ala Leu Lys Asp His Ala Ser     Lys Ser Arg     Gly Lys Ile Cys Thr Ile
85              90                   95

Gly Ile Ala Pro Trp Gly Ile     Val Glu Asn     Gln Glu Asp Leu Ile Gly
100             105                  110

Arg Asp Val Val Arg Pro Tyr     Gln Thr Met     Ser Asn Pro Met Ser Lys
115             120                  125

Leu Thr Val Leu Asn Ser Met     His Ser His     Phe Ile Leu Ala Asp Asn
130             135                  140
```

```
Gly Thr Thr Gly Lys Tyr Gly Ala Glu Val Lys Leu Arg Arg Gln Leu
145                 150                 155                 160

Glu Lys His Ile Ser Leu Gln Lys Ile Asn Thr Arg Ile Gly Gln Gly
165                 170                 175

Val Pro Val Val Ala Leu Ile Val Glu Gly Gly Pro Asn Val Ile Ser
180                 185                 190

Ile Val Leu Glu Tyr Leu Arg Asp Thr Pro Val Pro Val Val Val
195                 200                 205

Cys Asp Gly Ser Gly Arg Ala Ser Asp Ile Leu Ala Phe Gly His Lys
210                 215                 220

Tyr Ser Glu Glu Gly Gly Leu Ile Asn Glu Ser Leu Arg Asp Gln Leu
225                 230                 235                 240

Leu Val Thr Ile Gln Lys Thr Phe Thr Tyr Thr Arg Thr Gln Ala Gln
245                 250                 255

His Leu Phe Ile Ile Leu Met Glu Cys Met Lys Lys Lys Glu Leu Ile
260                 265                 270

Thr Val Phe Arg Met Gly Ser Glu Gly His Gln Asp Ile Asp Leu Ala
275                 280                 285

Ile Leu Thr Ala Leu Leu Lys Gly Ala Asn Ala Ser Ala Pro Asp Gln
290                 295                 300

Leu Ser Leu Ala Leu Ala Trp Asn Arg Val Asp Ile Ala Arg Ser Gln
305                 310                 315                 320

Ile Phe Ile Tyr Gly Gln Gln Trp Pro Val Gly Ser Leu Glu Gln Ala
325                 330                 335

Met Leu Asp Ala Leu Val Leu Asp Arg Val Asp Phe Val Lys Leu Leu
340                 345                 350

Ile Glu Asn Gly Val Ser Met His Arg Phe Leu Thr Ile Ser Arg Leu
355                 360                 365

Glu Glu Leu Tyr Asn Thr Arg His Gly Pro Ser Asn Thr Leu Tyr His
370                 375                 380

Leu Val Arg Asp Val Lys Lys Gly Asn Leu Pro Pro Asp Tyr Arg Ile
385                 390                 395                 400

Ser Leu Ile Asp Ile Gly Leu Val Ile Glu Tyr Leu Met Gly Gly Ala
405                 410                 415

Tyr Arg Cys Asn Tyr Thr Arg Lys Arg Phe Arg Thr Leu Tyr His Asn
420                 425                 430

Leu Phe Gly Pro Lys Arg Pro Lys Ala Leu Lys Leu Leu Gly Met Glu
435                 440                 445

Asp Asp Ile Pro Leu Arg Arg Gly Arg Lys Thr Thr Lys Lys Arg Glu
450                 455                 460

Glu Glu Val Asp Ile Asp Leu Asp Asp Pro Glu Ile Asn His Phe Pro
465                 470                 475                 480

Phe Pro Phe His Glu Leu Met Val Trp Ala Val Leu Met Lys Arg Gln
485                 490                 495

Lys Met Ala Leu Phe Phe Trp Gln His Gly Glu Glu Ala Met Ala Lys
500                 505                 510

Ala Leu Val Ala Cys Lys Leu Cys Lys Ala Met Ala His Glu Ala Ser
515                 520                 525

Glu Asn Asp Met Val Asp Asp Ile Ser Gln Glu Leu Asn His Asn Ser
530                 535                 540

Arg Asp Phe Gly Gln Leu Ala Val Glu Leu Leu Asp Gln Ser Tyr Lys
545                 550                 555                 560
```

-continued

```
Gln Asp Glu Gln Leu Ala Met Lys Leu Leu Thr Tyr Glu Leu Lys Asn
565                 570                 575
Trp Ser Asn Ala Thr Cys Leu Gln Leu Ala Val Ala Ala Lys His Arg
580                 585                 590
Asp Phe Ile Ala His Thr Cys Ser Gln Met Leu Leu Thr Asp Met Trp
595                 600                 605
Met Gly Arg Leu Arg Met Arg Lys Asn Ser Gly Leu Lys Val Ile Leu
610                 615                 620
Gly Ile Leu Leu Pro Pro Ser Ile Leu Ser Leu Glu Phe Lys Asn Lys
625                 630                 635                 640
Asp Asp Met Pro Tyr Met Ser Gln Ala Gln Glu Ile His Leu Gln Glu
645                 650                 655
Lys Glu Ala Glu Glu Pro Glu Lys Pro Thr Lys Glu Lys Glu Glu Glu
660                 665                 670
Asp Met Glu Leu Thr Ala Met Leu Gly Arg Asn Asn Gly Glu Ser Ser
675                 680                 685
Arg Lys Lys Asp Glu Glu Val Gln Ser Lys His Arg Leu Ile Pro
690                 695                 700
Leu Gly Arg Lys Ile Tyr Glu Phe Tyr Asn Ala Pro Ile Val Lys Phe
705                 710                 715                 720
Trp Phe Tyr Thr Leu Ala Tyr Ile Gly Tyr Leu Met Leu Phe Asn Tyr
725                 730                 735
Ile Val Leu Val Lys Met Glu Arg Trp Pro Ser Thr Gln Glu Trp Ile
740                 745                 750
Val Ile Ser Tyr Ile Phe Thr Leu Gly Ile Glu Lys Met Arg Glu Ile
755                 760                 765
Leu Met Ser Glu Pro Gly Lys Leu Leu Gln Lys Val Lys Val Trp Leu
770                 775                 780
Gln Glu Tyr Trp Asn Val Thr Asp Leu Ile Ala Ile Leu Leu Phe Ser
785                 790                 795                 800
Val Gly Met Ile Leu Arg Leu Gln Asp Gln Pro Phe Arg Ser Asp Gly
805                 810                 815
Arg Val Ile Tyr Cys Val Asn Ile Ile Tyr Trp Tyr Ile Arg Leu Leu
820                 825                 830
Asp Ile Phe Gly Val Asn Lys Tyr Leu Gly Pro Tyr Val Met Met Ile
835                 840                 845
Gly Lys Met Met Ile Asp Met Met Tyr Phe Val Ile Ile Met Leu Val
850                 855                 860
Val Leu Met Ser Phe Gly Val Ala Arg Gln Ala Ile Leu Phe Pro Asn
865                 870                 875                 880
Glu Glu Pro Ser Trp Lys Leu Ala Lys Asn Ile Phe Tyr Met Pro Tyr
885                 890                 895
Trp Met Ile Tyr Gly Glu Val Phe Ala Asp Gln Ile Asp Arg Lys Gln
900                 905                 910
Val Tyr Asp Ser His Thr Pro Lys Ser Ala Pro Cys Gly Gln Asn Glu
915                 920                 925
Thr Arg Glu Asp Gly Lys Ile Ile Gln Leu Pro Pro Cys Lys Thr Gly
930                 935                 940
Ala Trp Ile Val Pro Ala Ile Met Ala Cys Tyr Leu Leu Val Ala Asn
945                 950                 955                 960
Ile Leu Leu Val Asn Leu Leu Ile Ala Val Phe Asn Asn Thr Phe Phe
965                 970                 975
Glu Val Lys Ser Ile Ser Asn Gln Val Trp Lys Phe Gln Arg Tyr Gln
```

-continued

```
            980             985             990
Leu Ile Met Thr Phe His Glu Arg  Pro Val Leu Pro  Pro Leu Ile
995             1000            1005
Ile Phe Ser His Met Thr Met  Ile Phe Gln His Leu  Cys Cys Arg
1010            1015            1020
Trp Arg Lys His Glu Ser Asp  Pro Asp Glu Arg Asp  Tyr Gly Leu
1025            1030            1035
Lys Leu Phe Ile Thr Asp Asp  Glu Leu Lys Lys Val  His Asp Phe
1040            1045            1050
Glu Glu Gln Cys Ile Glu Glu  Tyr Phe Arg Glu Lys  Asp Asp Arg
1055            1060            1065
Phe Asn Ser Ser Asn Asp Glu  Arg Ile Arg Val Thr  Ser Glu Arg
1070            1075            1080
Val Glu Asn Met Ser Met Arg  Leu Glu Glu Val Asn  Glu Arg Glu
1085            1090            1095
His Ser Met Lys Ala Ser Leu  Gln Thr Val Asp Ile  Arg Leu Ala
1100            1105            1110
Gln Leu Glu Asp Leu Ile Gly  Arg Met Ala Thr Ala  Leu Glu Arg
1115            1120            1125
Leu Thr Gly Leu Glu Arg Ala  Glu Ser Asn Lys Ile  Arg Ser Arg
1130            1135            1140
Thr Ser Ser Asp Cys Thr Asp  Ala Ala Tyr Ile Val  Arg Gln Ser
1145            1150            1155
Ser Phe Asn Ser Gln Glu Gly  Asn Thr Phe Lys Leu  Gln Glu Ser
1160            1165            1170
Ile Asp Pro Ala Gly Glu Glu  Thr Met Ser Pro Thr  Ser Pro Thr
1175            1180            1185
Leu Met Pro Arg Met Arg Ser  His Ser Phe Tyr Ser  Val Asn Met
1190            1195            1200
Lys Asp Lys Gly Gly Ile Glu  Lys Leu Glu Ser Ile  Phe Lys Glu
1205            1210            1215
Arg Ser Leu Ser Leu His Arg  Ala Thr Ser Ser His  Ser Val Ala
1220            1225            1230
Lys Glu Pro Lys Ala Pro Ala  Ala Pro Ala Asn Thr  Leu Ala Ile
1235            1240            1245
Val Pro Asp Ser Arg Arg Pro  Ser Ser Cys Ile Asp  Ile Tyr Val
1250            1255            1260
Ser Ala Met Asp Glu Leu His  Cys Asp Ile Asp Pro  Leu Asp Asn
1265            1270            1275
Ser Val Asn Ile Leu Gly Leu  Gly Glu Pro Ser Phe  Ser Thr Pro
1280            1285            1290
Val Pro Ser Thr Ala Pro Ser  Ser Ser Ala Tyr Ala  Thr Leu Ala
1295            1300            1305
Pro Thr Asp Arg Pro Pro Ser  Arg Ser Ile Asp Phe  Glu Asp Ile
1310            1315            1320
Thr Ser Met Asp Thr Arg Ser  Phe Ser Ser Asp Tyr  Thr His Leu
1325            1330            1335
Pro Glu Cys Gln Asn Pro Trp  Asp Ser Glu Pro Pro  Met Tyr His
1340            1345            1350
Thr Ile Glu Arg Ser Lys Ser  Ser Arg Tyr Leu Ala  Thr Thr Pro
1355            1360            1365
Phe Leu Leu Glu Glu Ala Pro  Ile Val Lys Ser His  Ser Phe Met
1370            1375            1380
```

-continued

Phe Ser Pro Ser Arg Ser Tyr Tyr Ala Asn Phe Gly Val Pro Val
1385                1390                1395

Lys Thr Ala Glu Tyr Thr Ser Ile Thr Asp Cys Ile Asp Thr Arg
1400                1405                1410

Cys Val Asn Ala Pro Gln Ala Ile Ala Asp Arg Ala Ala Phe Pro
1415                1420                1425

Gly Gly Leu Gly Asp Lys Val Glu Asp Leu Thr Cys Cys His Pro
1430                1435                1440

Glu Arg Glu Ala Glu Leu Ser His Pro Ser Ser Asp Ser Glu Glu
1445                1450                1455

Asn Glu Ala Lys Gly Arg Arg Ala Thr Ile Ala Ile Ser Ser Gln
1460                1465                1470

Glu Gly Asp Asn Ser Glu Arg Thr Leu Ser Asn Asn Ile Thr Val
1475                1480                1485

Pro Lys Ile Glu Arg Ala Asn Ser Tyr Ser Ala Glu Glu Pro Ser
1490                1495                1500

Ala Pro Tyr Ala His Thr Arg Lys Ser Phe Ser Ile Ser Asp Lys
1505                1510                1515

Leu Asp Arg Gln Arg Asn Thr Ala Ser Leu Gln Asn Pro Phe Gln
1520                1525                1530

Arg Ser Lys Ser Ser Lys Pro Glu Gly Arg Gly Asp Ser Leu Ser
1535                1540                1545

Met Arg Arg Leu Ser Arg Thr Ser Ala Phe Gln Ser Phe Glu Ser
1550                1555                1560

Lys His Thr
1565

<210> SEQ ID NO 19
<211> LENGTH: 1544
<212> TYPE: PRT
<213> ORGANISM: Homo sapiens

<400> SEQUENCE: 19

Met Tyr Val Arg Val Ser Phe Asp Thr Lys Pro Asp Leu Leu Leu His
1               5                   10                  15

Leu Met Thr Lys Glu Trp Gln Leu Glu Leu Pro Lys Leu Leu Ile Ser
20                  25                  30

Val His Gly Gly Leu Gln Asn Phe Glu Leu Gln Pro Lys Leu Lys Gln
35                  40                  45

Val Phe Gly Lys Gly Leu Ile Lys Ala Ala Met Thr Thr Gly Ala Trp
50                  55                  60

Ile Phe Thr Gly Gly Val Asn Thr Gly Val Ile Arg His Val Gly Asp
65                  70                  75                  80

Ala Leu Lys Asp His Ala Ser Lys Ser Arg Gly Lys Ile Cys Thr Ile
85                  90                  95

Gly Ile Ala Pro Trp Gly Ile Val Glu Asn Gln Glu Asp Leu Ile Gly
100                 105                 110

Arg Asp Val Val Arg Pro Tyr Gln Thr Met Ser Asn Pro Met Ser Lys
115                 120                 125

Leu Thr Val Leu Asn Ser Met His Ser His Phe Ile Leu Ala Asp Asn
130                 135                 140

Gly Thr Thr Gly Lys Tyr Gly Ala Glu Val Lys Leu Arg Arg Gln Leu
145                 150                 155                 160

Glu Lys His Ile Ser Leu Gln Lys Ile Asn Thr Arg Ile Gly Gln Gly

-continued

```
            165                 170                 175
Val Pro Val Val Ala Leu Ile Val Glu Gly Gly Pro Asn Val Ile Ser
        180                 185                 190
Ile Val Leu Glu Tyr Leu Arg Asp Thr Pro Val Pro Val Val Val
195                 200                 205
Cys Asp Gly Ser Gly Arg Ala Ser Asp Ile Leu Ala Phe Gly His Lys
210                 215                 220
Tyr Ser Glu Glu Gly Gly Leu Ile Asn Glu Ser Leu Arg Asp Gln Leu
225                 230                 235                 240
Leu Val Thr Ile Gln Lys Thr Phe Thr Tyr Thr Arg Thr Gln Ala Gln
245                 250                 255
His Leu Phe Ile Ile Leu Met Glu Cys Met Lys Lys Lys Glu Leu Ile
260                 265                 270
Thr Val Phe Arg Met Gly Ser Glu Gly His Gln Asp Ile Asp Leu Ala
275                 280                 285
Ile Leu Thr Ala Leu Leu Lys Gly Ala Asn Ala Ser Ala Pro Asp Gln
290                 295                 300
Leu Ser Leu Ala Leu Ala Trp Asn Arg Val Asp Ile Ala Arg Ser Gln
305                 310                 315                 320
Ile Phe Ile Tyr Gly Gln Gln Trp Pro Val Gly Ser Leu Glu Gln Ala
325                 330                 335
Met Leu Asp Ala Leu Val Leu Asp Arg Val Asp Phe Val Lys Leu Leu
340                 345                 350
Ile Glu Asn Gly Val Ser Met His Arg Phe Leu Thr Ile Ser Arg Leu
355                 360                 365
Glu Glu Leu Tyr Asn Thr Arg His Gly Pro Ser Asn Thr Leu Tyr His
370                 375                 380
Leu Val Arg Asp Val Lys Lys Gly Asn Leu Pro Pro Asp Tyr Arg Ile
385                 390                 395                 400
Ser Leu Ile Asp Ile Gly Leu Val Ile Glu Tyr Leu Met Gly Gly Ala
405                 410                 415
Tyr Arg Cys Asn Tyr Thr Arg Lys Arg Phe Arg Thr Leu Tyr His Asn
420                 425                 430
Leu Phe Gly Pro Lys Arg Asp Asp Ile Pro Leu Arg Arg Gly Arg Lys
435                 440                 445
Thr Thr Lys Lys Arg Glu Glu Val Asp Ile Asp Leu Asp Asp Pro
450                 455                 460
Glu Ile Asn His Phe Pro Phe Pro Phe His Glu Leu Met Val Trp Ala
465                 470                 475                 480
Val Leu Met Lys Arg Gln Lys Met Ala Leu Phe Phe Trp Gln His Gly
485                 490                 495
Glu Glu Ala Met Ala Lys Ala Leu Val Ala Cys Lys Leu Cys Lys Ala
500                 505                 510
Met Ala His Glu Ala Ser Glu Asn Asp Met Val Asp Asp Ile Ser Gln
515                 520                 525
Glu Leu Asn His Asn Ser Arg Asp Phe Gly Gln Leu Ala Val Glu Leu
530                 535                 540
Leu Asp Gln Ser Tyr Lys Gln Asp Glu Gln Leu Ala Met Lys Leu Leu
545                 550                 555                 560
Thr Tyr Glu Leu Lys Asn Trp Ser Asn Ala Thr Cys Leu Gln Leu Ala
565                 570                 575
Val Ala Ala Lys His Arg Asp Phe Ile Ala His Thr Cys Ser Gln Met
580                 585                 590
```

-continued

```
Leu Leu Thr Asp Met Trp Met Gly Arg Leu Arg Met Arg Lys Asn Ser
595                 600                 605
Gly Leu Lys Val Ile Leu Gly Ile Leu Leu Pro Pro Ser Ile Leu Ser
610                 615                 620
Leu Glu Phe Lys Asn Lys Asp Asp Met Pro Tyr Met Ser Gln Ala Gln
625                 630                 635                 640
Glu Ile His Leu Gln Glu Lys Glu Ala Glu Pro Glu Lys Pro Thr
645                 650                 655
Lys Glu Lys Glu Glu Asp Met Glu Leu Thr Ala Met Leu Gly Arg
660                 665                 670
Asn Asn Gly Glu Ser Ser Arg Lys Lys Asp Glu Glu Val Gln Ser
675                 680                 685
Lys His Arg Leu Ile Pro Leu Gly Arg Lys Ile Tyr Glu Phe Tyr Asn
690                 695                 700
Ala Pro Ile Val Lys Phe Trp Phe Tyr Thr Leu Ala Tyr Ile Gly Tyr
705                 710                 715                 720
Leu Met Leu Phe Asn Tyr Ile Val Leu Val Lys Met Glu Arg Trp Pro
725                 730                 735
Ser Thr Gln Glu Trp Ile Val Ile Ser Tyr Ile Phe Thr Leu Gly Ile
740                 745                 750
Glu Lys Met Arg Glu Ile Leu Met Ser Glu Pro Gly Lys Leu Leu Gln
755                 760                 765
Lys Val Lys Val Trp Leu Gln Glu Tyr Trp Asn Val Thr Asp Leu Ile
770                 775                 780
Ala Ile Leu Leu Phe Ser Val Gly Met Ile Leu Arg Leu Gln Asp Gln
785                 790                 795                 800
Pro Phe Arg Ser Asp Gly Arg Val Ile Tyr Cys Val Asn Ile Ile Tyr
805                 810                 815
Trp Tyr Ile Arg Leu Leu Asp Ile Phe Gly Val Asn Lys Tyr Leu Gly
820                 825                 830
Pro Tyr Val Met Met Ile Gly Lys Met Met Ile Asp Met Met Tyr Phe
835                 840                 845
Val Ile Ile Met Leu Val Val Leu Met Ser Phe Gly Val Ala Arg Gln
850                 855                 860
Ala Ile Leu Phe Pro Asn Glu Glu Pro Ser Trp Lys Leu Ala Lys Asn
865                 870                 875                 880
Ile Phe Tyr Met Pro Tyr Trp Met Ile Tyr Gly Glu Val Phe Ala Asp
885                 890                 895
Gln Ile Asp Pro Pro Cys Gly Gln Asn Glu Thr Arg Glu Asp Gly Lys
900                 905                 910
Ile Ile Gln Leu Pro Pro Cys Lys Thr Gly Ala Trp Ile Val Pro Ala
915                 920                 925
Ile Met Ala Cys Tyr Leu Leu Val Ala Asn Ile Leu Leu Val Asn Leu
930                 935                 940
Leu Ile Ala Val Phe Asn Asn Thr Phe Phe Glu Val Lys Ser Ile Ser
945                 950                 955                 960
Asn Gln Val Trp Lys Phe Gln Arg Tyr Gln Leu Ile Met Thr Phe His
965                 970                 975
Glu Arg Pro Val Leu Pro Pro Pro Leu Ile Ile Phe Ser His Met Thr
980                 985                 990
Met Ile Phe Gln His Leu Cys Cys Arg Trp Arg Lys His Glu Ser Asp
995                 1000                1005
```

```
Pro Asp Glu Arg Asp Tyr Gly Leu Lys Leu Phe Ile Thr Asp Asp
1010                1015                1020

Glu Leu Lys Lys Val His Asp Phe Glu Gln Cys Ile Glu Glu
1025                1030                1035

Tyr Phe Arg Glu Lys Asp Asp Arg Phe Asn Ser Ser Asn Asp Glu
1040                1045                1050

Arg Ile Arg Val Thr Ser Glu Arg Val Glu Asn Met Ser Met Arg
1055                1060                1065

Leu Glu Glu Val Asn Glu Arg Glu His Ser Met Lys Ala Ser Leu
1070                1075                1080

Gln Thr Val Asp Ile Arg Leu Ala Gln Leu Glu Asp Leu Ile Gly
1085                1090                1095

Arg Met Ala Thr Ala Leu Glu Arg Leu Thr Gly Leu Glu Arg Ala
1100                1105                1110

Glu Ser Asn Lys Ile Arg Ser Arg Thr Ser Ser Asp Cys Thr Asp
1115                1120                1125

Ala Ala Tyr Ile Val Arg Gln Ser Ser Phe Asn Ser Gln Glu Gly
1130                1135                1140

Asn Thr Phe Lys Leu Gln Glu Ser Ile Asp Pro Ala Gly Glu Glu
1145                1150                1155

Thr Met Ser Pro Thr Ser Pro Thr Leu Met Pro Arg Met Arg Ser
1160                1165                1170

His Ser Phe Tyr Ser Val Asn Met Lys Asp Lys Gly Gly Ile Glu
1175                1180                1185

Lys Leu Glu Ser Ile Phe Lys Glu Arg Ser Leu Ser Leu His Arg
1190                1195                1200

Ala Thr Ser Ser His Ser Val Ala Lys Glu Pro Lys Ala Pro Ala
1205                1210                1215

Ala Pro Ala Asn Thr Leu Ala Ile Val Pro Asp Ser Arg Arg Pro
1220                1225                1230

Ser Ser Cys Ile Asp Ile Tyr Val Ser Ala Met Asp Glu Leu His
1235                1240                1245

Cys Asp Ile Asp Pro Leu Asp Asn Ser Val Asn Ile Leu Gly Leu
1250                1255                1260

Gly Glu Pro Ser Phe Ser Thr Pro Val Pro Ser Thr Ala Pro Ser
1265                1270                1275

Ser Ser Ala Tyr Ala Thr Leu Ala Pro Thr Asp Arg Pro Pro Ser
1280                1285                1290

Arg Ser Ile Asp Phe Glu Asp Ile Thr Ser Met Asp Thr Arg Ser
1295                1300                1305

Phe Ser Ser Asp Tyr Thr His Leu Pro Glu Cys Gln Asn Pro Trp
1310                1315                1320

Asp Ser Glu Pro Pro Met Tyr His Thr Ile Glu Arg Ser Lys Ser
1325                1330                1335

Ser Arg Tyr Leu Ala Thr Thr Pro Phe Leu Leu Glu Glu Ala Pro
1340                1345                1350

Ile Val Lys Ser His Ser Phe Met Phe Ser Pro Ser Arg Ser Tyr
1355                1360                1365

Tyr Ala Asn Phe Gly Val Pro Val Lys Thr Ala Glu Tyr Thr Ser
1370                1375                1380

Ile Thr Asp Cys Ile Asp Thr Arg Cys Val Asn Ala Pro Gln Ala
1385                1390                1395

Ile Ala Asp Arg Ala Ala Phe Pro Gly Gly Leu Gly Asp Lys Val
```

-continued

```
              1400                1405                1410
Glu Asp Leu Thr Cys Cys His Pro Glu Arg Glu Ala Glu Leu Ser
1415                1420                1425

His Pro Ser Ser Asp Ser Glu Glu Asn Glu Ala Lys Gly Arg Arg
1430                1435                1440

Ala Thr Ile Ala Ile Ser Ser Gln Glu Gly Asp Asn Ser Glu Arg
1445                1450                1455

Thr Leu Ser Asn Asn Ile Thr Val Pro Lys Ile Glu Arg Ala Asn
1460                1465                1470

Ser Tyr Ser Ala Glu Glu Pro Ser Ala Pro Tyr Ala His Thr Arg
1475                1480                1485

Lys Ser Phe Ser Ile Ser Asp Lys Leu Asp Arg Gln Arg Asn Thr
1490                1495                1500

Ala Ser Leu Gln Asn Pro Phe Gln Arg Ser Lys Ser Ser Lys Pro
1505                1510                1515

Glu Gly Arg Gly Asp Ser Leu Ser Met Arg Arg Leu Ser Arg Thr
1520                1525                1530

Ser Ala Phe Gln Ser Phe Glu Ser Lys His Thr
1535                1540

<210> SEQ ID NO 20
<211> LENGTH: 1556
<212> TYPE: PRT
<213> ORGANISM: Homo sapiens

<400> SEQUENCE: 20

Met Tyr Val Arg Val Ser Phe Asp Thr Lys Pro Asp Leu Leu Leu His
1               5                   10                  15

Leu Met Thr Lys Glu Trp Gln Leu Glu Leu Pro Lys Leu Leu Ile Ser
            20                  25                  30

Val His Gly Gly Leu Gln Asn Phe Glu Leu Gln Pro Lys Leu Lys Gln
        35                  40                  45

Val Phe Gly Lys Gly Leu Ile Lys Ala Ala Met Thr Thr Gly Ala Trp
    50                  55                  60

Ile Phe Thr Gly Gly Val Asn Thr Gly Val Ile Arg His Val Gly Asp
65                  70                  75                  80

Ala Leu Lys Asp His Ala Ser Lys Ser Arg Gly Lys Ile Cys Thr Ile
                85                  90                  95

Gly Ile Ala Pro Trp Gly Ile Val Glu Asn Gln Glu Asp Leu Ile Gly
            100                 105                 110

Arg Asp Val Val Arg Pro Tyr Gln Thr Met Ser Asn Pro Met Ser Lys
        115                 120                 125

Leu Thr Val Leu Asn Ser Met His Ser His Phe Ile Leu Ala Asp Asn
    130                 135                 140

Gly Thr Thr Gly Lys Tyr Gly Ala Glu Val Lys Leu Arg Arg Gln Leu
145                 150                 155                 160

Glu Lys His Ile Ser Leu Gln Lys Ile Asn Thr Arg Ile Gly Gln Gly
                165                 170                 175

Val Pro Val Val Ala Leu Ile Val Glu Gly Gly Pro Asn Val Ile Ser
            180                 185                 190

Ile Val Leu Glu Tyr Leu Arg Asp Thr Pro Pro Val Pro Val Val Val
        195                 200                 205

Cys Asp Gly Ser Gly Arg Ala Ser Asp Ile Leu Ala Phe Gly His Lys
    210                 215                 220
```

-continued

```
Tyr Ser Glu Glu Gly Gly Leu Ile Asn Glu Ser Leu Arg Asp Gln Leu
225                 230                 235                 240

Leu Val Thr Ile Gln Lys Thr Phe Thr Tyr Thr Arg Thr Gln Ala Gln
        245                 250                 255

His Leu Phe Ile Ile Leu Met Glu Cys Met Lys Lys Lys Glu Leu Ile
260                 265                 270

Thr Val Phe Arg Met Gly Ser Glu Gly His Gln Asp Ile Asp Leu Ala
275                 280                 285

Ile Leu Thr Ala Leu Leu Lys Gly Ala Asn Ala Ser Ala Pro Asp Gln
290                 295                 300

Leu Ser Leu Ala Leu Ala Trp Asn Arg Val Asp Ile Ala Arg Ser Gln
305                 310                 315                 320

Ile Phe Ile Tyr Gly Gln Gln Trp Pro Val Gly Ser Leu Glu Gln Ala
325                 330                 335

Met Leu Asp Ala Leu Val Leu Asp Arg Val Asp Phe Val Lys Leu Leu
340                 345                 350

Ile Glu Asn Gly Val Ser Met His Arg Phe Leu Thr Ile Ser Arg Leu
355                 360                 365

Glu Glu Leu Tyr Asn Thr Arg His Gly Pro Ser Asn Thr Leu Tyr His
370                 375                 380

Leu Val Arg Asp Val Lys Lys Arg Glu Tyr Pro Gly Phe Gly Trp Ile
385                 390                 395                 400

Tyr Phe Lys Gly Asn Leu Pro Pro Asp Tyr Arg Ile Ser Leu Ile Asp
405                 410                 415

Ile Gly Leu Val Ile Glu Tyr Leu Met Gly Gly Ala Tyr Arg Cys Asn
420                 425                 430

Tyr Thr Arg Lys Arg Phe Arg Thr Leu Tyr His Asn Leu Phe Gly Pro
435                 440                 445

Lys Arg Asp Asp Ile Pro Leu Arg Arg Gly Arg Lys Thr Thr Lys Lys
450                 455                 460

Arg Glu Glu Glu Val Asp Ile Asp Leu Asp Asp Pro Glu Ile Asn His
465                 470                 475                 480

Phe Pro Phe Pro Phe His Glu Leu Met Val Trp Ala Val Leu Met Lys
485                 490                 495

Arg Gln Lys Met Ala Leu Phe Phe Trp Gln His Gly Glu Glu Ala Met
500                 505                 510

Ala Lys Ala Leu Val Ala Cys Lys Leu Cys Lys Ala Met Ala His Glu
515                 520                 525

Ala Ser Glu Asn Asp Met Val Asp Asp Ile Ser Gln Glu Leu Asn His
530                 535                 540

Asn Ser Arg Asp Phe Gly Gln Leu Ala Val Glu Leu Leu Asp Gln Ser
545                 550                 555                 560

Tyr Lys Gln Asp Glu Gln Leu Ala Met Lys Leu Leu Thr Tyr Glu Leu
565                 570                 575

Lys Asn Trp Ser Asn Ala Thr Cys Leu Gln Leu Ala Val Ala Ala Lys
580                 585                 590

His Arg Asp Phe Ile Ala His Thr Cys Ser Gln Met Leu Leu Thr Asp
595                 600                 605

Met Trp Met Gly Arg Leu Arg Met Arg Lys Asn Ser Gly Leu Lys Val
610                 615                 620

Ile Leu Gly Ile Leu Leu Pro Pro Ser Ile Leu Ser Leu Glu Phe Lys
625                 630                 635                 640

Asn Lys Asp Asp Met Pro Tyr Met Ser Gln Ala Gln Glu Ile His Leu
```

-continued

```
            645                 650                 655
Gln Glu Lys Glu Ala Glu Pro Glu Lys Thr Lys Glu Lys Glu
660                 665                 670
Glu Glu Asp Met Glu Leu Thr Ala Met Leu Gly Arg Asn Asn Gly Glu
675                 680                 685
Ser Ser Arg Lys Lys Asp Glu Glu Val Gln Ser Lys His Arg Leu
690                 695                 700
Ile Pro Leu Gly Arg Lys Ile Tyr Glu Phe Tyr Asn Ala Pro Ile Val
705                 710                 715                 720
Lys Phe Trp Phe Tyr Thr Leu Ala Tyr Ile Gly Tyr Leu Met Leu Phe
725                 730                 735
Asn Tyr Ile Val Leu Val Lys Met Glu Arg Trp Pro Ser Thr Gln Glu
740                 745                 750
Trp Ile Val Ile Ser Tyr Ile Phe Thr Leu Gly Ile Glu Lys Met Arg
755                 760                 765
Glu Ile Leu Met Ser Glu Pro Gly Lys Leu Leu Gln Lys Val Lys Val
770                 775                 780
Trp Leu Gln Glu Tyr Trp Asn Val Thr Asp Leu Ile Ala Ile Leu Leu
785                 790                 795                 800
Phe Ser Val Gly Met Ile Leu Arg Leu Gln Asp Gln Pro Phe Arg Ser
805                 810                 815
Asp Gly Arg Val Ile Tyr Cys Val Asn Ile Ile Tyr Trp Tyr Ile Arg
820                 825                 830
Leu Leu Asp Ile Phe Gly Val Asn Lys Tyr Leu Gly Pro Tyr Val Met
835                 840                 845
Met Ile Gly Lys Met Met Ile Asp Met Met Tyr Phe Val Ile Ile Met
850                 855                 860
Leu Val Val Leu Met Ser Phe Gly Val Ala Arg Gln Ala Ile Leu Phe
865                 870                 875                 880
Pro Asn Glu Glu Pro Ser Trp Lys Leu Ala Lys Asn Ile Phe Tyr Met
885                 890                 895
Pro Tyr Trp Met Ile Tyr Gly Glu Val Phe Ala Asp Gln Ile Asp Pro
900                 905                 910
Pro Cys Gly Gln Asn Glu Thr Arg Glu Asp Gly Lys Ile Ile Gln Leu
915                 920                 925
Pro Pro Cys Lys Thr Gly Ala Trp Ile Val Pro Ala Ile Met Ala Cys
930                 935                 940
Tyr Leu Leu Val Ala Asn Ile Leu Leu Val Asn Leu Leu Ile Ala Val
945                 950                 955                 960
Phe Asn Asn Thr Phe Phe Glu Val Lys Ser Ile Ser Asn Gln Val Trp
965                 970                 975
Lys Phe Gln Arg Tyr Gln Leu Ile Met Thr Phe His Glu Arg Pro Val
980                 985                 990
Leu Pro Pro Pro Leu Ile Ile Phe Ser His Met Thr Met Ile Phe Gln
995                 1000                1005
His Leu Cys Cys Arg Trp Arg Lys His Glu Ser Asp Pro Asp Glu
1010                1015                1020
Arg Asp Tyr Gly Leu Lys Leu Phe Ile Thr Asp Asp Glu Leu Lys
1025                1030                1035
Lys Val His Asp Phe Glu Glu Gln Cys Ile Glu Glu Tyr Phe Arg
1040                1045                1050
Glu Lys Asp Asp Arg Phe Asn Ser Ser Asn Asp Glu Arg Ile Arg
1055                1060                1065
```

-continued

| | | | | | | | | | | |
|---|---|---|---|---|---|---|---|---|---|---|
| Val Thr | Ser | Glu | Arg | Val Glu | Asn | Met | Ser | Met Arg | Leu Glu Glu | |
| 1070 | | | | 1075 | | | | 1080 | | |
| Val Asn | Glu | Arg | Glu | His Ser | Met | Lys | Ala | Ser Leu | Gln Thr Val | |
| 1085 | | | | 1090 | | | | 1095 | | |
| Asp Ile | Arg | Leu | Ala | Gln Leu | Glu | Asp | Leu | Ile Gly | Arg Met Ala | |
| 1100 | | | | 1105 | | | | 1110 | | |
| Thr Ala | Leu | Glu | Arg | Leu Thr | Gly | Leu | Glu | Arg Ala | Glu Ser Asn | |
| 1115 | | | | 1120 | | | | 1125 | | |
| Lys Ile | Arg | Ser | Arg | Thr Ser | Ser | Asp | Cys | Thr Asp | Ala Ala Tyr | |
| 1130 | | | | 1135 | | | | 1140 | | |
| Ile Val | Arg | Gln | Ser | Ser Phe | Asn | Ser | Gln | Glu Gly | Asn Thr Phe | |
| 1145 | | | | 1150 | | | | 1155 | | |
| Lys Leu | Gln | Glu | Ser | Ile Asp | Pro | Ala | Gly | Glu Glu | Thr Met Ser | |
| 1160 | | | | 1165 | | | | 1170 | | |
| Pro Thr | Ser | Pro | Thr | Leu Met | Pro | Arg | Met | Arg Ser | His Ser Phe | |
| 1175 | | | | 1180 | | | | 1185 | | |
| Tyr Ser | Val | Asn | Met | Lys Asp | Lys | Gly | Gly | Ile Glu | Lys Leu Glu | |
| 1190 | | | | 1195 | | | | 1200 | | |
| Ser Ile | Phe | Lys | Glu | Arg Ser | Leu | Ser | Leu | His Arg | Ala Thr Ser | |
| 1205 | | | | 1210 | | | | 1215 | | |
| Ser His | Ser | Val | Ala | Lys Glu | Pro | Lys | Ala | Pro Ala | Ala Pro Ala | |
| 1220 | | | | 1225 | | | | 1230 | | |
| Asn Thr | Leu | Ala | Ile | Val Pro | Asp | Ser | Arg | Arg Pro | Ser Ser Cys | |
| 1235 | | | | 1240 | | | | 1245 | | |
| Ile Asp | Ile | Tyr | Val | Ser Ala | Met | Asp | Glu | Leu His | Cys Asp Ile | |
| 1250 | | | | 1255 | | | | 1260 | | |
| Asp Pro | Leu | Asp | Asn | Ser Val | Asn | Ile | Leu | Gly Leu | Gly Glu Pro | |
| 1265 | | | | 1270 | | | | 1275 | | |
| Ser Phe | Ser | Thr | Pro | Val Pro | Ser | Thr | Ala | Pro Ser | Ser Ser Ala | |
| 1280 | | | | 1285 | | | | 1290 | | |
| Tyr Ala | Thr | Leu | Ala | Pro Thr | Asp | Arg | Pro | Pro Ser | Arg Ser Ile | |
| 1295 | | | | 1300 | | | | 1305 | | |
| Asp Phe | Glu | Asp | Ile | Thr Ser | Met | Asp | Thr | Arg Ser | Phe Ser Ser | |
| 1310 | | | | 1315 | | | | 1320 | | |
| Asp Tyr | Thr | His | Leu | Pro Glu | Cys | Gln | Asn | Pro Trp | Asp Ser Glu | |
| 1325 | | | | 1330 | | | | 1335 | | |
| Pro Pro | Met | Tyr | His | Thr Ile | Glu | Arg | Ser | Lys Ser | Ser Arg Tyr | |
| 1340 | | | | 1345 | | | | 1350 | | |
| Leu Ala | Thr | Thr | Pro | Phe Leu | Leu | Glu | Glu | Ala Pro | Ile Val Lys | |
| 1355 | | | | 1360 | | | | 1365 | | |
| Ser His | Ser | Phe | Met | Phe Ser | Pro | Ser | Arg | Ser Tyr | Tyr Ala Asn | |
| 1370 | | | | 1375 | | | | 1380 | | |
| Phe Gly | Val | Pro | Val | Lys Thr | Ala | Glu | Tyr | Thr Ser | Ile Thr Asp | |
| 1385 | | | | 1390 | | | | 1395 | | |
| Cys Ile | Asp | Thr | Arg | Cys Val | Asn | Ala | Pro | Gln Ala | Ile Ala Asp | |
| 1400 | | | | 1405 | | | | 1410 | | |
| Arg Ala | Ala | Phe | Pro | Gly Gly | Leu | Gly | Asp | Lys Val | Glu Asp Leu | |
| 1415 | | | | 1420 | | | | 1425 | | |
| Thr Cys | Cys | His | Pro | Glu Arg | Glu | Ala | Gly | Leu Ser | His Pro Ser | |
| 1430 | | | | 1435 | | | | 1440 | | |
| Ser Asp | Ser | Glu | Glu | Asn Glu | Ala | Lys | Gly | Arg Arg | Ala Thr Ile | |
| 1445 | | | | 1450 | | | | 1455 | | |

-continued

```
Ala Ile Ser Ser Gln Glu Gly Asp Asn Ser Glu Arg Thr Leu Ser
1460                1465                1470

Asn Asn Ile Thr Val Pro Lys Ile Glu Arg Ala Asn Ser Tyr Ser
1475                1480                1485

Ala Glu Glu Pro Ser Ala Pro Tyr Ala His Thr Arg Lys Ser Phe
1490                1495                1500

Ser Ile Ser Asp Lys Leu Asp Arg Gln Arg Asn Thr Ala Ser Leu
1505                1510                1515

Gln Asn Pro Phe Gln Arg Ser Lys Ser Ser Lys Pro Glu Gly Arg
1520                1525                1530

Gly Asp Ser Leu Ser Met Arg Arg Leu Ser Arg Thr Ser Ala Phe
1535                1540                1545

Gln Ser Phe Glu Ser Lys His Thr
1550                1555

<210> SEQ ID NO 21
<211> LENGTH: 1579
<212> TYPE: PRT
<213> ORGANISM: Homo sapiens

<400> SEQUENCE: 21

Met Tyr Val Arg Val Ser Phe Asp Thr Lys Pro Asp Leu Leu Leu His
1               5                   10                  15

Leu Met Thr Lys Glu Trp Gln Leu Glu Leu Pro Lys Leu Leu Ile Ser
            20                  25                  30

Val His Gly Gly Leu Gln Asn Phe Glu Leu Gln Pro Lys Leu Lys Gln
        35                  40                  45

Val Phe Gly Lys Gly Leu Ile Lys Ala Ala Met Thr Thr Gly Ala Trp
    50                  55                  60

Ile Phe Thr Gly Gly Val Asn Thr Gly Val Ile Arg His Val Gly Asp
65                  70                  75                  80

Ala Leu Lys Asp His Ala Ser Lys Ser Arg Gly Lys Ile Cys Thr Ile
                85                  90                  95

Gly Ile Ala Pro Trp Gly Ile Val Glu Asn Gln Glu Asp Leu Ile Gly
            100                 105                 110

Arg Asp Val Val Arg Pro Tyr Gln Thr Met Ser Asn Pro Met Ser Lys
        115                 120                 125

Leu Thr Val Leu Asn Ser Met His Ser His Phe Ile Leu Ala Asp Asn
    130                 135                 140

Gly Thr Thr Gly Lys Tyr Gly Ala Glu Val Lys Leu Arg Arg Gln Leu
145                 150                 155                 160

Glu Lys His Ile Ser Leu Gln Lys Ile Asn Thr Arg Cys Leu Pro Phe
                165                 170                 175

Phe Ser Leu Asp Ser Arg Leu Phe Tyr Ser Phe Trp Gly Ser Cys Gln
            180                 185                 190

Leu Asp Ser Val Gly Ile Gly Gln Gly Val Pro Val Val Ala Leu Ile
        195                 200                 205

Val Glu Gly Gly Pro Asn Val Ile Ser Ile Val Leu Glu Tyr Leu Arg
    210                 215                 220

Asp Thr Pro Pro Val Pro Val Val Cys Asp Gly Ser Gly Arg Ala
225                 230                 235                 240

Ser Asp Ile Leu Ala Phe Gly His Lys Tyr Ser Glu Glu Gly Gly Leu
                245                 250                 255

Ile Asn Glu Ser Leu Arg Asp Gln Leu Leu Val Thr Ile Gln Lys Thr
            260                 265                 270
```

```
Phe Thr Tyr Thr Arg Thr Gln Ala Gln His Leu Phe Ile Ile Leu Met
275                 280                 285

Glu Cys Met Lys Lys Lys Glu Leu Ile Thr Val Phe Arg Met Gly Ser
290                 295                 300

Glu Gly His Gln Asp Ile Asp Leu Ala Ile Leu Thr Ala Leu Leu Lys
305                 310                 315                 320

Gly Ala Asn Ala Ser Ala Pro Asp Gln Leu Ser Leu Ala Leu Ala Trp
325                 330                 335

Asn Arg Val Asp Ile Ala Arg Ser Gln Ile Phe Ile Tyr Gly Gln Gln
340                 345                 350

Trp Pro Val Gly Ser Leu Glu Gln Ala Met Leu Asp Ala Leu Val Leu
355                 360                 365

Asp Arg Val Asp Phe Val Lys Leu Leu Ile Glu Asn Gly Val Ser Met
370                 375                 380

His Arg Phe Leu Thr Ile Ser Arg Leu Glu Glu Leu Tyr Asn Thr Arg
385                 390                 395                 400

His Gly Pro Ser Asn Thr Leu Tyr His Leu Val Arg Asp Val Lys Lys
405                 410                 415

Gly Asn Leu Pro Pro Asp Tyr Arg Ile Ser Leu Ile Asp Ile Gly Leu
420                 425                 430

Val Ile Glu Tyr Leu Met Gly Gly Ala Tyr Arg Cys Asn Tyr Thr Arg
435                 440                 445

Lys Arg Phe Arg Thr Leu Tyr His Asn Leu Phe Gly Pro Lys Arg Pro
450                 455                 460

Lys Ala Leu Lys Leu Leu Gly Met Glu Asp Asp Ile Pro Leu Arg Arg
465                 470                 475                 480

Gly Arg Lys Thr Thr Lys Lys Arg Glu Glu Glu Val Asp Ile Asp Leu
485                 490                 495

Asp Asp Pro Glu Ile Asn His Phe Pro Phe Pro Phe His Glu Leu Met
500                 505                 510

Val Trp Ala Val Leu Met Lys Arg Gln Lys Met Ala Leu Phe Phe Trp
515                 520                 525

Gln His Gly Glu Glu Ala Met Ala Lys Ala Leu Val Ala Cys Lys Leu
530                 535                 540

Cys Lys Ala Met Ala His Glu Ala Ser Glu Asn Asp Met Val Asp Asp
545                 550                 555                 560

Ile Ser Gln Glu Leu Asn His Asn Ser Arg Asp Phe Gly Gln Leu Ala
565                 570                 575

Val Glu Leu Leu Asp Gln Ser Tyr Lys Gln Asp Glu Gln Leu Ala Met
580                 585                 590

Lys Leu Leu Thr Tyr Glu Leu Lys Asn Trp Ser Asn Ala Thr Cys Leu
595                 600                 605

Gln Leu Ala Val Ala Ala Lys His Arg Asp Phe Ile Ala His Thr Cys
610                 615                 620

Ser Gln Met Leu Leu Thr Asp Met Trp Met Gly Arg Leu Arg Met Arg
625                 630                 635                 640

Lys Asn Ser Gly Leu Lys Val Ile Leu Gly Ile Leu Leu Pro Pro Ser
645                 650                 655

Ile Leu Ser Leu Glu Phe Lys Asn Lys Asp Asp Met Pro Tyr Met Ser
660                 665                 670

Gln Ala Gln Glu Ile His Leu Gln Glu Lys Glu Ala Glu Glu Pro Glu
675                 680                 685
```

```
Lys Pro Thr Lys Glu Lys Glu Glu Asp Met Glu Leu Thr Ala Met
690             695             700

Leu Gly Arg Asn Asn Gly Glu Ser Ser Arg Lys Lys Asp Glu Glu
705             710             715             720

Val Gln Ser Lys His Arg Leu Ile Pro Leu Gly Arg Lys Ile Tyr Glu
725             730             735

Phe Tyr Asn Ala Pro Ile Val Lys Phe Trp Phe Tyr Thr Leu Ala Tyr
740             745             750

Ile Gly Tyr Leu Met Leu Phe Asn Tyr Ile Val Leu Val Lys Met Glu
755             760             765

Arg Trp Pro Ser Thr Gln Glu Trp Ile Val Ile Ser Tyr Ile Phe Thr
770             775             780

Leu Gly Ile Glu Lys Met Arg Glu Ile Leu Met Ser Glu Pro Gly Lys
785             790             795             800

Leu Leu Gln Lys Val Lys Val Trp Leu Gln Glu Tyr Trp Asn Val Thr
805             810             815

Asp Leu Ile Ala Ile Leu Leu Phe Ser Val Gly Met Ile Leu Arg Leu
820             825             830

Gln Asp Gln Pro Phe Arg Ser Asp Gly Arg Val Ile Tyr Cys Val Asn
835             840             845

Ile Ile Tyr Trp Tyr Ile Arg Leu Leu Asp Ile Phe Gly Val Asn Lys
850             855             860

Tyr Leu Gly Pro Tyr Val Met Met Ile Gly Lys Met Met Ile Asp Met
865             870             875             880

Met Tyr Phe Val Ile Ile Met Leu Val Val Leu Met Ser Phe Gly Val
885             890             895

Ala Arg Gln Ala Ile Leu Phe Pro Asn Glu Glu Pro Ser Trp Lys Leu
900             905             910

Ala Lys Asn Ile Phe Tyr Met Pro Tyr Trp Met Ile Tyr Gly Glu Val
915             920             925

Phe Ala Asp Gln Ile Asp Pro Pro Cys Gly Gln Asn Glu Thr Arg Glu
930             935             940

Asp Gly Lys Ile Ile Gln Leu Pro Pro Cys Lys Thr Gly Ala Trp Ile
945             950             955             960

Val Pro Ala Ile Met Ala Cys Tyr Leu Leu Val Ala Asn Ile Leu Leu
965             970             975

Val Asn Leu Leu Ile Ala Val Phe Asn Asn Thr Phe Phe Glu Val Lys
980             985             990

Ser Ile Ser Asn Gln Val Trp Lys Phe Gln Arg Tyr Gln Leu Ile Met
995             1000            1005

Thr Phe His Glu Arg Pro Val Leu Pro Pro Pro Leu Ile Ile Phe
1010            1015            1020

Ser His Met Thr Met Ile Phe Gln His Leu Cys Cys Arg Trp Arg
1025            1030            1035

Lys His Glu Ser Asp Pro Asp Glu Arg Asp Tyr Gly Leu Lys Leu
1040            1045            1050

Phe Ile Thr Asp Asp Glu Leu Lys Lys Val His Asp Phe Glu Glu
1055            1060            1065

Gln Cys Ile Glu Glu Tyr Phe Arg Glu Lys Asp Asp Arg Phe Asn
1070            1075            1080

Ser Ser Asn Asp Glu Arg Ile Arg Val Thr Ser Glu Arg Val Glu
1085            1090            1095

Asn Met Ser Met Arg Leu Glu Glu Val Asn Glu Arg Glu His Ser
```

-continued

```
                1100                1105                1110
Met Lys Ala Ser Leu Gln Thr Val Asp Ile Arg Leu Ala Gln Leu
1115                1120                1125

Glu Asp Leu Ile Gly Arg Met Ala Thr Ala Leu Glu Arg Leu Thr
1130                1135                1140

Gly Leu Glu Arg Ala Glu Ser Asn Lys Ile Arg Ser Arg Thr Ser
1145                1150                1155

Ser Asp Cys Thr Asp Ala Ala Tyr Ile Val Arg Gln Ser Ser Phe
1160                1165                1170

Asn Ser Gln Glu Gly Asn Thr Phe Lys Leu Gln Glu Ser Ile Asp
1175                1180                1185

Pro Ala Gly Glu Glu Thr Met Ser Pro Thr Ser Pro Thr Leu Met
1190                1195                1200

Pro Arg Met Arg Ser His Ser Phe Tyr Ser Val Asn Met Lys Asp
1205                1210                1215

Lys Gly Gly Ile Glu Lys Leu Glu Ser Ile Phe Lys Glu Arg Ser
1220                1225                1230

Leu Ser Leu His Arg Ala Thr Ser Ser His Ser Val Ala Lys Glu
1235                1240                1245

Pro Lys Ala Pro Ala Ala Pro Ala Asn Thr Leu Ala Ile Val Pro
1250                1255                1260

Asp Ser Arg Arg Pro Ser Ser Cys Ile Asp Ile Tyr Val Ser Ala
1265                1270                1275

Met Asp Glu Leu His Cys Asp Ile Asp Pro Leu Asp Asn Ser Val
1280                1285                1290

Asn Ile Leu Gly Leu Gly Glu Pro Ser Phe Ser Thr Pro Val Pro
1295                1300                1305

Ser Thr Ala Pro Ser Ser Ser Ala Tyr Ala Thr Leu Ala Pro Thr
1310                1315                1320

Asp Arg Pro Pro Ser Arg Ser Ile Asp Phe Glu Asp Ile Thr Ser
1325                1330                1335

Met Asp Thr Arg Ser Phe Ser Ser Asp Tyr Thr His Leu Pro Glu
1340                1345                1350

Cys Gln Asn Pro Trp Asp Ser Glu Pro Pro Met Tyr His Thr Ile
1355                1360                1365

Glu Arg Ser Lys Ser Ser Arg Tyr Leu Ala Thr Thr Pro Phe Leu
1370                1375                1380

Leu Glu Glu Ala Pro Ile Val Lys Ser His Ser Phe Met Phe Ser
1385                1390                1395

Pro Ser Arg Ser Tyr Tyr Ala Asn Phe Gly Val Pro Val Lys Thr
1400                1405                1410

Ala Glu Tyr Thr Ser Ile Thr Asp Cys Ile Asp Thr Arg Cys Val
1415                1420                1425

Asn Ala Pro Gln Ala Ile Ala Asp Arg Ala Ala Phe Pro Gly Gly
1430                1435                1440

Leu Gly Asp Lys Val Glu Asp Leu Thr Cys Cys His Pro Glu Arg
1445                1450                1455

Glu Ala Glu Leu Ser His Pro Ser Ser Asp Ser Glu Glu Asn Glu
1460                1465                1470

Ala Lys Gly Arg Arg Ala Thr Ile Ala Ile Ser Ser Gln Glu Gly
1475                1480                1485

Asp Asn Ser Glu Arg Thr Leu Ser Asn Asn Ile Thr Val Pro Lys
1490                1495                1500
```

```
Ile Glu  Arg Ala Asn Ser Tyr  Ser Ala Glu Pro  Ser Ala Pro
1505               1510              1515

Tyr Ala  His Thr Arg Lys Ser  Phe Ser Ile Ser Asp  Lys Leu Asp
1520               1525              1530

Arg Gln  Arg Asn Thr Ala Ser  Leu Gln Asn Pro Phe  Gln Arg Ser
1535               1540              1545

Lys Ser  Ser Lys Pro Glu Gly  Arg Gly Asp Ser Leu  Ser Met Arg
1550               1555              1560

Arg Leu  Ser Arg Thr Ser Ala  Phe Gln Ser Phe Glu  Ser Lys His
1565               1570              1575

Thr

<210> SEQ ID NO 22
<211> LENGTH: 18
<212> TYPE: PRT
<213> ORGANISM: Homo sapiens

<400> SEQUENCE: 22

Leu Lys Val Ile Leu Gly Ile Leu Leu Pro Pro Ser Ile Leu Ser Leu
1               5                   10                  15

Glu Phe

<210> SEQ ID NO 23
<211> LENGTH: 18
<212> TYPE: PRT
<213> ORGANISM: Homo sapiens

<400> SEQUENCE: 23

Ile Val Lys Phe Trp Phe Tyr Thr Leu Ala Tyr Ile Gly Tyr Leu Met
1               5                   10                  15

Leu Phe

<210> SEQ ID NO 24
<211> LENGTH: 14
<212> TYPE: PRT
<213> ORGANISM: Homo sapiens

<400> SEQUENCE: 24

Val Thr Asp Leu Ile Ala Ile Leu Leu Phe Ser Val Gly Met
1               5                   10

<210> SEQ ID NO 25
<211> LENGTH: 18
<212> TYPE: PRT
<213> ORGANISM: Homo sapiens

<400> SEQUENCE: 25

Arg Val Ile Tyr Cys Val Asn Ile Ile Tyr Trp Tyr Ile Arg Leu Leu
1               5                   10                  15

Asp Ile

<210> SEQ ID NO 26
<211> LENGTH: 18
<212> TYPE: PRT
<213> ORGANISM: Homo sapiens

<400> SEQUENCE: 26

Met Met Ile Asp Met Met Tyr Phe Val Ile Ile Met Leu Val Val Leu
1               5                   10                  15
```

Met Ser

```
<210> SEQ ID NO 27
<211> LENGTH: 21
<212> TYPE: PRT
<213> ORGANISM: Homo sapiens

<400> SEQUENCE: 27
```

Ala Ile Met Ala Cys Tyr Leu Leu Val Ala Asn Ile Leu Leu Val Asn
1               5                   10                  15

Leu Leu Ile Ala Val
        20

```
<210> SEQ ID NO 28
<211> LENGTH: 79
<212> TYPE: PRT
<213> ORGANISM: Homo sapiens

<400> SEQUENCE: 28
```

Lys Asn Lys Asp Asp Met Pro Tyr Met Ser Gln Ala Gln Glu Ile His
1               5                   10                  15

Leu Gln Glu Lys Glu Ala Glu Glu Pro Lys Pro Thr Lys Glu Lys
        20                  25                  30

Glu Glu Glu Asp Met Glu Leu Thr Ala Met Leu Gly Arg Asn Asn Gly
35                  40                  45

Glu Ser Ser Arg Lys Lys Asp Glu Glu Val Gln Ser Lys His Arg
50                  55                  60

Leu Ile Pro Leu Gly Arg Lys Ile Tyr Glu Phe Tyr Asn Ala Pro
65                  70                  75

```
<210> SEQ ID NO 29
<211> LENGTH: 55
<212> TYPE: PRT
<213> ORGANISM: Homo sapiens

<400> SEQUENCE: 29
```

Asn Tyr Ile Val Leu Val Lys Met Glu Arg Trp Pro Ser Thr Gln Glu
1               5                   10                  15

Trp Ile Val Ile Ser Tyr Ile Phe Thr Leu Gly Ile Glu Lys Met Arg
        20                  25                  30

Glu Ile Leu Met Ser Glu Pro Gly Lys Leu Leu Gln Lys Val Lys Val
35                  40                  45

Trp Leu Gln Glu Tyr Trp Asn
50                  55

```
<210> SEQ ID NO 30
<211> LENGTH: 13
<212> TYPE: PRT
<213> ORGANISM: Homo sapiens

<400> SEQUENCE: 30
```

Ile Leu Arg Leu Gln Asp Gln Pro Phe Arg Ser Asp Gly
1               5                   10

```
<210> SEQ ID NO 31
<211> LENGTH: 16
<212> TYPE: PRT
<213> ORGANISM: Homo sapiens

<400> SEQUENCE: 31
```

Phe Gly Val Asn Lys Tyr Leu Gly Pro Tyr Val Met Met Ile Gly Lys

-continued

<210> SEQ ID NO 32
<211> LENGTH: 69
<212> TYPE: PRT
<213> ORGANISM: Homo sapiens

<400> SEQUENCE: 32

Phe Gly Val Ala Arg Gln Ala Ile Leu Phe Pro Asn Glu Glu Pro Ser
1               5                   10                  15

Trp Lys Leu Ala Lys Asn Ile Phe Tyr Met Pro Tyr Trp Met Ile Tyr
            20                  25                  30

Gly Glu Val Phe Ala Asp Gln Ile Asp Pro Pro Cys Gly Gln Asn Glu
        35                  40                  45

Thr Arg Glu Asp Gly Lys Ile Ile Gln Leu Pro Pro Cys Lys Thr Gly
    50                  55                  60

Ala Trp Ile Val Pro
65

<210> SEQ ID NO 33
<211> LENGTH: 6
<212> TYPE: PRT
<213> ORGANISM: Homo sapiens

<400> SEQUENCE: 33

Val Trp Lys Phe Gln Arg
1               5

<210> SEQ ID NO 34
<211> LENGTH: 212
<212> TYPE: PRT
<213> ORGANISM: Homo sapiens

<400> SEQUENCE: 34

Thr Gln Glu Trp Ile Val Ile Ser Tyr Ile Phe Thr Leu Gly Ile Glu
1               5                   10                  15

Lys Met Arg Glu Ile Leu Met Ser Glu Pro Gly Lys Leu Leu Gln Lys
            20                  25                  30

Val Lys Val Trp Leu Gln Glu Tyr Trp Asn Val Thr Asp Leu Ile Ala
        35                  40                  45

Ile Leu Leu Phe Ser Val Gly Met Ile Leu Arg Leu Gln Asp Gln Pro
    50                  55                  60

Phe Arg Ser Asp Gly Arg Val Ile Tyr Cys Val Asn Ile Ile Tyr Trp
65                  70                  75                  80

Tyr Ile Arg Leu Leu Asp Ile Phe Gly Val Asn Lys Tyr Leu Gly Pro
                85                  90                  95

Tyr Val Met Met Ile Gly Lys Met Met Ile Asp Met Met Tyr Phe Val
            100                 105                 110

Ile Ile Met Leu Val Val Leu Met Ser Phe Gly Val Ala Arg Gln Ala
        115                 120                 125

Ile Leu Phe Pro Asn Glu Glu Pro Ser Trp Lys Leu Ala Lys Asn Ile
    130                 135                 140

Phe Tyr Met Pro Tyr Trp Met Ile Tyr Gly Glu Val Phe Ala Asp Gln
145                 150                 155                 160

Ile Asp Pro Pro Cys Gly Gln Asn Glu Thr Arg Glu Asp Gly Lys Ile
                165                 170                 175

Ile Gln Leu Pro Pro Cys Lys Thr Gly Ala Trp Ile Val Pro Ala Ile
            180                 185                 190

```
Met Ala Cys Tyr Leu Leu Val Ala Asn Ile Leu Leu Val Asn Leu Leu
195                 200                 205

Ile Ala Val Phe
210

<210> SEQ ID NO 35
<211> LENGTH: 56
<212> TYPE: PRT
<213> ORGANISM: Homo sapiens

<400> SEQUENCE: 35

Glu Arg Ile Arg Val Thr Ser Glu Arg Val Glu Asn Met Ser Met Arg
1               5                   10                  15

Leu Glu Glu Val Asn Arg Glu His Ser Met Lys Ala Ser Leu Gln
20                  25                  30

Thr Val Asp Ile Arg Leu Ala Gln Leu Glu Asp Leu Ile Gly Arg Met
35                  40                  45

Ala Thr Ala Leu Glu Arg Leu Thr
50                  55

<210> SEQ ID NO 36
<211> LENGTH: 18
<212> TYPE: PRT
<213> ORGANISM: Homo sapiens

<400> SEQUENCE: 36

Leu Lys Val Ile Leu Gly Ile Leu Leu Pro Pro Ser Ile Leu Ser Leu
1               5                   10                  15

Glu Phe

<210> SEQ ID NO 37
<211> LENGTH: 18
<212> TYPE: PRT
<213> ORGANISM: Homo sapiens

<400> SEQUENCE: 37

Ile Val Lys Phe Trp Phe Tyr Thr Leu Ala Tyr Ile Gly Tyr Leu Met
1               5                   10                  15

Leu Phe

<210> SEQ ID NO 38
<211> LENGTH: 14
<212> TYPE: PRT
<213> ORGANISM: Homo sapiens

<400> SEQUENCE: 38

Val Thr Asp Leu Ile Ala Ile Leu Leu Phe Ser Val Gly Met
1               5                   10

<210> SEQ ID NO 39
<211> LENGTH: 18
<212> TYPE: PRT
<213> ORGANISM: Homo sapiens

<400> SEQUENCE: 39

Arg Val Ile Tyr Cys Val Asn Ile Ile Tyr Trp Tyr Ile Arg Leu Leu
1               5                   10                  15

Asp Ile

<210> SEQ ID NO 40
```

```
<211> LENGTH: 18
<212> TYPE: PRT
<213> ORGANISM: Homo sapiens

<400> SEQUENCE: 40

Met Met Ile Asp Met Met Tyr Phe Val Ile Ile Met Leu Val Val Leu
1               5                   10                  15

Met Ser

<210> SEQ ID NO 41
<211> LENGTH: 21
<212> TYPE: PRT
<213> ORGANISM: Homo sapiens

<400> SEQUENCE: 41

Ala Ile Met Ala Cys Tyr Leu Leu Val Ala Asn Ile Leu Leu Val Asn
1               5                   10                  15

Leu Leu Ile Ala Val
            20

<210> SEQ ID NO 42
<211> LENGTH: 79
<212> TYPE: PRT
<213> ORGANISM: Homo sapiens

<400> SEQUENCE: 42

Lys Asn Lys Asp Asp Met Pro Tyr Met Ser Gln Ala Gln Glu Ile His
1               5                   10                  15

Leu Gln Glu Lys Glu Ala Glu Glu Pro Glu Lys Pro Thr Lys Glu Lys
            20                  25                  30

Glu Glu Glu Asp Met Glu Leu Thr Ala Met Leu Gly Arg Asn Asn Gly
        35                  40                  45

Glu Ser Ser Arg Lys Lys Asp Glu Glu Val Gln Ser Lys His Arg
    50                  55                  60

Leu Ile Pro Leu Gly Arg Lys Ile Tyr Glu Phe Tyr Asn Ala Pro
65                  70                  75

<210> SEQ ID NO 43
<211> LENGTH: 55
<212> TYPE: PRT
<213> ORGANISM: Homo sapiens

<400> SEQUENCE: 43

Asn Tyr Ile Val Leu Val Lys Met Glu Arg Trp Pro Ser Thr Gln Glu
1               5                   10                  15

Trp Ile Val Ile Ser Tyr Ile Phe Thr Leu Gly Ile Glu Lys Met Arg
            20                  25                  30

Glu Ile Leu Met Ser Glu Pro Gly Lys Leu Leu Gln Lys Val Lys Val
        35                  40                  45

Trp Leu Gln Glu Tyr Trp Asn
    50                  55

<210> SEQ ID NO 44
<211> LENGTH: 13
<212> TYPE: PRT
<213> ORGANISM: Homo sapiens

<400> SEQUENCE: 44

Ile Leu Arg Leu Gln Asp Gln Pro Phe Arg Ser Asp Gly
1               5                   10
```

<210> SEQ ID NO 45
<211> LENGTH: 16
<212> TYPE: PRT
<213> ORGANISM: Homo sapiens

<400> SEQUENCE: 45

Phe Gly Val Asn Lys Tyr Leu Gly Pro Tyr Val Met Met Ile Gly Lys
1               5                   10                  15

<210> SEQ ID NO 46
<211> LENGTH: 69
<212> TYPE: PRT
<213> ORGANISM: Homo sapiens

<400> SEQUENCE: 46

Phe Gly Val Ala Arg Gln Ala Ile Leu Phe Pro Asn Glu Glu Pro Ser
1               5                   10                  15

Trp Lys Leu Ala Lys Asn Ile Phe Tyr Met Pro Tyr Trp Met Ile Tyr
            20                  25                  30

Gly Glu Val Phe Ala Asp Gln Ile Asp Pro Pro Cys Gly Gln Asn Glu
        35                  40                  45

Thr Arg Glu Asp Gly Lys Ile Ile Gln Leu Pro Pro Cys Lys Thr Gly
    50                  55                  60

Ala Trp Ile Val Pro
65

<210> SEQ ID NO 47
<211> LENGTH: 6
<212> TYPE: PRT
<213> ORGANISM: Homo sapiens

<400> SEQUENCE: 47

Val Trp Lys Phe Gln Arg
1               5

<210> SEQ ID NO 48
<211> LENGTH: 212
<212> TYPE: PRT
<213> ORGANISM: Homo sapiens

<400> SEQUENCE: 48

Thr Gln Glu Trp Ile Val Ile Ser Tyr Ile Phe Thr Leu Gly Ile Glu
1               5                   10                  15

Lys Met Arg Glu Ile Leu Met Ser Glu Pro Gly Lys Leu Leu Gln Lys
            20                  25                  30

Val Lys Val Trp Leu Gln Glu Tyr Trp Asn Val Thr Asp Leu Ile Ala
        35                  40                  45

Ile Leu Leu Phe Ser Val Gly Met Ile Leu Arg Leu Gln Asp Gln Pro
    50                  55                  60

Phe Arg Ser Asp Gly Arg Val Ile Tyr Cys Val Asn Ile Ile Tyr Trp
65                  70                  75                  80

Tyr Ile Arg Leu Leu Asp Ile Phe Gly Val Asn Lys Tyr Leu Gly Pro
                85                  90                  95

Tyr Val Met Met Ile Gly Lys Met Met Ile Asp Met Met Tyr Phe Val
            100                 105                 110

Ile Ile Met Leu Val Val Leu Met Ser Phe Gly Val Ala Arg Gln Ala
        115                 120                 125

Ile Leu Phe Pro Asn Glu Glu Pro Ser Trp Lys Leu Ala Lys Asn Ile
    130                 135                 140

```
Phe Tyr Met Pro Tyr Trp Met Ile Tyr Gly Glu Val Phe Ala Asp Gln
145                 150                 155                 160

Ile Asp Pro Pro Cys Gly Gln Asn Glu Thr Arg Glu Asp Gly Lys Ile
165                 170                 175

Ile Gln Leu Pro Pro Cys Lys Thr Gly Ala Trp Ile Val Pro Ala Ile
            180                 185                 190

Met Ala Cys Tyr Leu Leu Val Ala Asn Ile Leu Leu Val Asn Leu Leu
195                 200                 205

Ile Ala Val Phe
210

<210> SEQ ID NO 49
<211> LENGTH: 55
<212> TYPE: PRT
<213> ORGANISM: Homo sapiens

<400> SEQUENCE: 49

Glu Arg Ile Arg Val Thr Ser Glu Arg Val Glu Asn Met Ser Met Arg
1               5                   10                  15

Leu Glu Glu Val Asn Glu Arg Glu His Ser Met Lys Ala Ser Leu Gln
            20                  25                  30

Thr Val Asp Ile Arg Leu Ala Gln Leu Glu Asp Leu Ile Gly Arg Met
        35                  40                  45

Ala Thr Ala Leu Glu Arg Leu
50                  55

<210> SEQ ID NO 50
<211> LENGTH: 18
<212> TYPE: PRT
<213> ORGANISM: Homo sapiens

<400> SEQUENCE: 50

Leu Lys Val Ile Leu Gly Ile Leu Leu Pro Pro Ser Ile Leu Ser Leu
1               5                   10                  15

Glu Phe

<210> SEQ ID NO 51
<211> LENGTH: 18
<212> TYPE: PRT
<213> ORGANISM: Homo sapiens

<400> SEQUENCE: 51

Ile Val Lys Phe Trp Phe Tyr Thr Leu Ala Tyr Ile Gly Tyr Leu Met
1               5                   10                  15

Leu Phe

<210> SEQ ID NO 52
<211> LENGTH: 14
<212> TYPE: PRT
<213> ORGANISM: Homo sapiens

<400> SEQUENCE: 52

Val Thr Asp Leu Ile Ala Ile Leu Leu Phe Ser Val Gly Met
1               5                   10

<210> SEQ ID NO 53
<211> LENGTH: 18
<212> TYPE: PRT
<213> ORGANISM: Homo sapiens
```

```
<400> SEQUENCE: 53

Arg Val Ile Tyr Cys Val Asn Ile Ile Tyr Trp Tyr Ile Arg Leu Leu
1               5                   10                  15

Asp Ile

<210> SEQ ID NO 54
<211> LENGTH: 18
<212> TYPE: PRT
<213> ORGANISM: Homo sapiens

<400> SEQUENCE: 54

Met Met Ile Asp Met Met Tyr Phe Val Ile Met Leu Val Val Leu
1               5                   10                  15

Met Ser

<210> SEQ ID NO 55
<211> LENGTH: 21
<212> TYPE: PRT
<213> ORGANISM: Homo sapiens

<400> SEQUENCE: 55

Ala Ile Met Ala Cys Tyr Leu Leu Val Ala Asn Ile Leu Leu Val Asn
1               5                   10                  15

Leu Leu Ile Ala Val
20

<210> SEQ ID NO 56
<211> LENGTH: 79
<212> TYPE: PRT
<213> ORGANISM: Homo sapiens

<400> SEQUENCE: 56

Lys Asn Lys Asp Asp Met Pro Tyr Met Ser Gln Ala Gln Glu Ile His
1               5                   10                  15

Leu Gln Glu Lys Glu Ala Glu Pro Glu Lys Pro Thr Lys Glu Lys
20                  25                  30

Glu Glu Glu Asp Met Glu Leu Thr Ala Met Leu Gly Arg Asn Asn Gly
35                  40                  45

Glu Ser Ser Arg Lys Lys Asp Glu Glu Glu Val Gln Ser Lys His Arg
50                  55                  60

Leu Ile Pro Leu Gly Arg Lys Ile Tyr Glu Phe Tyr Asn Ala Pro
65                  70                  75

<210> SEQ ID NO 57
<211> LENGTH: 55
<212> TYPE: PRT
<213> ORGANISM: Homo sapiens

<400> SEQUENCE: 57

Asn Tyr Ile Val Leu Val Lys Met Glu Arg Trp Pro Ser Thr Gln Glu
1               5                   10                  15

Trp Ile Val Ile Ser Tyr Ile Phe Thr Leu Gly Ile Glu Lys Met Arg
20                  25                  30

Glu Ile Leu Met Ser Glu Pro Gly Lys Leu Leu Gln Lys Val Lys Val
35                  40                  45

Trp Leu Gln Glu Tyr Trp Asn
50                  55

<210> SEQ ID NO 58
```

```
<211> LENGTH: 13
<212> TYPE: PRT
<213> ORGANISM: Homo sapiens

<400> SEQUENCE: 58

Ile Leu Arg Leu Gln Asp Gln Pro Phe Arg Ser Asp Gly
1               5                  10

<210> SEQ ID NO 59
<211> LENGTH: 16
<212> TYPE: PRT
<213> ORGANISM: Homo sapiens

<400> SEQUENCE: 59

Phe Gly Val Asn Lys Tyr Leu Gly Pro Tyr Val Met Met Ile Gly Lys
1               5                  10                  15

<210> SEQ ID NO 60
<211> LENGTH: 81
<212> TYPE: PRT
<213> ORGANISM: Homo sapiens

<400> SEQUENCE: 60

Phe Gly Val Ala Arg Gln Ala Ile Leu Phe Pro Asn Glu Glu Pro Ser
1               5                  10                  15

Trp Lys Leu Ala Lys Asn Ile Phe Tyr Met Pro Tyr Trp Met Ile Tyr
            20                  25                  30

Gly Glu Val Phe Ala Asp Gln Ile Asp Arg Lys Gln Val Tyr Asp Ser
        35                  40                  45

His Thr Pro Lys Ser Ala Pro Cys Gly Gln Asn Glu Thr Arg Glu Asp
    50                  55                  60

Gly Lys Ile Ile Gln Leu Pro Pro Cys Lys Thr Gly Ala Trp Ile Val
65                  70                  75                  80

Pro

<210> SEQ ID NO 61
<211> LENGTH: 6
<212> TYPE: PRT
<213> ORGANISM: Homo sapiens

<400> SEQUENCE: 61

Val Trp Lys Phe Gln Arg
1               5

<210> SEQ ID NO 62
<211> LENGTH: 212
<212> TYPE: PRT
<213> ORGANISM: Homo sapiens

<400> SEQUENCE: 62

Leu Gly Ile Glu Lys Met Arg Glu Ile Leu Met Ser Glu Pro Gly Lys
1               5                  10                  15

Leu Leu Gln Lys Val Lys Val Trp Leu Gln Glu Tyr Trp Asn Val Thr
            20                  25                  30

Asp Leu Ile Ala Ile Leu Leu Phe Ser Val Gly Met Ile Leu Arg Leu
        35                  40                  45

Gln Asp Gln Pro Phe Arg Ser Asp Gly Arg Val Ile Tyr Cys Val Asn
    50                  55                  60

Ile Ile Tyr Trp Tyr Ile Arg Leu Leu Asp Ile Phe Gly Val Asn Lys
65                  70                  75                  80
```

```
Tyr Leu Gly Pro Tyr Val Met Met Ile Gly Lys Met Met Ile Asp Met
 85                  90                  95

Met Tyr Phe Val Ile Ile Met Leu Val Val Leu Met Ser Phe Gly Val
100                 105                 110

Ala Arg Gln Ala Ile Leu Phe Pro Asn Glu Glu Pro Ser Trp Lys Leu
115                 120                 125

Ala Lys Asn Ile Phe Tyr Met Pro Tyr Trp Met Ile Tyr Gly Glu Val
130                 135                 140

Phe Ala Asp Gln Ile Asp Arg Lys Gln Val Tyr Asp Ser His Thr Pro
145                 150                 155                 160

Lys Ser Ala Pro Cys Gly Gln Asn Glu Thr Arg Glu Asp Gly Lys Ile
165                 170                 175

Ile Gln Leu Pro Pro Cys Lys Thr Gly Ala Trp Ile Val Pro Ala Ile
180                 185                 190

Met Ala Cys Tyr Leu Leu Val Ala Asn Ile Leu Leu Val Asn Leu Leu
195                 200                 205

Ile Ala Val Phe
210

<210> SEQ ID NO 63
<211> LENGTH: 55
<212> TYPE: PRT
<213> ORGANISM: Homo sapiens

<400> SEQUENCE: 63

Glu Arg Ile Arg Val Thr Ser Glu Arg Val Glu Asn Met Ser Met Arg
  1               5                  10                  15

Leu Glu Glu Val Asn Glu Arg Glu His Ser Met Lys Ala Ser Leu Gln
 20                  25                  30

Thr Val Asp Ile Arg Leu Ala Gln Leu Glu Asp Leu Ile Gly Arg Met
 35                  40                  45

Ala Thr Ala Leu Glu Arg Leu
 50                  55

<210> SEQ ID NO 64
<211> LENGTH: 18
<212> TYPE: PRT
<213> ORGANISM: Homo sapiens

<400> SEQUENCE: 64

Leu Lys Val Ile Leu Gly Ile Leu Leu Pro Pro Ser Ile Leu Ser Leu
  1               5                  10                  15

Glu Phe

<210> SEQ ID NO 65
<211> LENGTH: 18
<212> TYPE: PRT
<213> ORGANISM: Homo sapiens

<400> SEQUENCE: 65

Ile Val Lys Phe Trp Phe Tyr Thr Leu Ala Tyr Ile Gly Tyr Leu Met
  1               5                  10                  15

Leu Phe

<210> SEQ ID NO 66
<211> LENGTH: 14
<212> TYPE: PRT
<213> ORGANISM: Homo sapiens
```

-continued

```
<400> SEQUENCE: 66

Val Thr Asp Leu Ile Ala Ile Leu Leu Phe Ser Val Gly Met
1               5                   10

<210> SEQ ID NO 67
<211> LENGTH: 18
<212> TYPE: PRT
<213> ORGANISM: Homo sapiens

<400> SEQUENCE: 67

Arg Val Ile Tyr Cys Val Asn Ile Ile Tyr Trp Tyr Ile Arg Leu Leu
1               5                   10                  15

Asp Ile

<210> SEQ ID NO 68
<211> LENGTH: 18
<212> TYPE: PRT
<213> ORGANISM: Homo sapiens

<400> SEQUENCE: 68

Met Met Ile Asp Met Met Tyr Phe Val Ile Ile Met Leu Val Val Leu
1               5                   10                  15

Met Ser

<210> SEQ ID NO 69
<211> LENGTH: 21
<212> TYPE: PRT
<213> ORGANISM: Homo sapiens

<400> SEQUENCE: 69

Ala Ile Met Ala Cys Tyr Leu Leu Val Ala Asn Ile Leu Leu Val Asn
1               5                   10                  15

Leu Leu Ile Ala Val
            20

<210> SEQ ID NO 70
<211> LENGTH: 79
<212> TYPE: PRT
<213> ORGANISM: Homo sapiens

<400> SEQUENCE: 70

Lys Asn Lys Asp Asp Met Pro Tyr Met Ser Gln Ala Gln Glu Ile His
1               5                   10                  15

Leu Gln Glu Lys Glu Ala Glu Glu Pro Glu Lys Pro Thr Lys Glu Lys
            20                  25                  30

Glu Glu Glu Asp Met Glu Leu Thr Ala Met Leu Gly Arg Asn Asn Gly
        35                  40                  45

Glu Ser Ser Arg Lys Lys Asp Glu Glu Val Gln Ser Lys His Arg
    50                  55                  60

Leu Ile Pro Leu Gly Arg Lys Ile Tyr Glu Phe Tyr Asn Ala Pro
65                  70                  75

<210> SEQ ID NO 71
<211> LENGTH: 56
<212> TYPE: PRT
<213> ORGANISM: Homo sapiens

<400> SEQUENCE: 71

Phe Asn Tyr Ile Val Leu Val Lys Met Glu Arg Trp Pro Ser Thr Gln
1               5                   10                  15
```

-continued

```
Glu Trp Ile Val Ile Ser Tyr Ile Phe Thr Leu Gly Ile Glu Lys Met
 20                  25                  30

Arg Glu Ile Leu Met Ser Glu Pro Gly Lys Leu Leu Gln Lys Val Lys
 35                  40                  45

Val Trp Leu Gln Glu Tyr Trp Asn
 50                  55

<210> SEQ ID NO 72
<211> LENGTH: 13
<212> TYPE: PRT
<213> ORGANISM: Homo sapiens

<400> SEQUENCE: 72

Ile Leu Arg Leu Gln Asp Gln Pro Phe Arg Ser Asp Gly
 1               5                  10

<210> SEQ ID NO 73
<211> LENGTH: 16
<212> TYPE: PRT
<213> ORGANISM: Homo sapiens

<400> SEQUENCE: 73

Phe Gly Val Asn Lys Tyr Leu Gly Pro Tyr Val Met Met Ile Gly Lys
 1               5                  10                  15

<210> SEQ ID NO 74
<211> LENGTH: 69
<212> TYPE: PRT
<213> ORGANISM: Homo sapiens

<400> SEQUENCE: 74

Phe Gly Val Ala Arg Gln Ala Ile Leu Phe Pro Asn Glu Glu Pro Ser
 1               5                  10                  15

Trp Lys Leu Ala Lys Asn Ile Phe Tyr Met Pro Tyr Trp Met Ile Tyr
 20                  25                  30

Gly Glu Val Phe Ala Asp Gln Ile Asp Pro Pro Cys Gly Gln Asn Glu
 35                  40                  45

Thr Arg Glu Asp Gly Lys Ile Ile Gln Leu Pro Pro Cys Lys Thr Gly
 50                  55                  60

Ala Trp Ile Val Pro
 65

<210> SEQ ID NO 75
<211> LENGTH: 6
<212> TYPE: PRT
<213> ORGANISM: Homo sapiens

<400> SEQUENCE: 75

Val Trp Lys Phe Gln Arg
 1               5

<210> SEQ ID NO 76
<211> LENGTH: 212
<212> TYPE: PRT
<213> ORGANISM: Homo sapiens

<400> SEQUENCE: 76

Thr Gln Glu Trp Ile Val Ile Ser Tyr Ile Phe Thr Leu Gly Ile Glu
 1               5                  10                  15

Lys Met Arg Glu Ile Leu Met Ser Glu Pro Gly Lys Leu Leu Gln Lys
 20                  25                  30
```

```
Val Lys Val Trp Leu Gln Glu Tyr Trp Asn Val Thr Asp Leu Ile Ala
 35                  40                  45

Ile Leu Leu Phe Ser Val Gly Met Ile Leu Arg Leu Gln Asp Gln Pro
 50                  55                  60

Phe Arg Ser Asp Gly Arg Val Ile Tyr Cys Val Asn Ile Ile Tyr Trp
 65                  70                  75                  80

Tyr Ile Arg Leu Leu Asp Ile Phe Gly Val Asn Lys Tyr Leu Gly Pro
             85                  90                  95

Tyr Val Met Met Ile Gly Lys Met Met Ile Asp Met Met Tyr Phe Val
100                 105                 110

Ile Ile Met Leu Val Val Leu Met Ser Phe Gly Val Ala Arg Gln Ala
115                 120                 125

Ile Leu Phe Pro Asn Glu Glu Pro Ser Trp Lys Leu Ala Lys Asn Ile
130                 135                 140

Phe Tyr Met Pro Tyr Trp Met Ile Tyr Gly Glu Val Phe Ala Asp Gln
145                 150                 155                 160

Ile Asp Pro Pro Cys Gly Gln Asn Glu Thr Arg Glu Asp Gly Lys Ile
            165                 170                 175

Ile Gln Leu Pro Pro Cys Lys Thr Gly Ala Trp Ile Val Pro Ala Ile
180                 185                 190

Met Ala Cys Tyr Leu Leu Val Ala Asn Ile Leu Leu Val Asn Leu Leu
195                 200                 205

Ile Ala Val Phe
210

<210> SEQ ID NO 77
<211> LENGTH: 55
<212> TYPE: PRT
<213> ORGANISM: Homo sapiens

<400> SEQUENCE: 77

Glu Arg Ile Arg Val Thr Ser Glu Arg Val Glu Asn Met Ser Met Arg
  1               5                  10                  15

Leu Glu Glu Val Asn Glu Arg Glu His Ser Met Lys Ala Ser Leu Gln
 20                  25                  30

Thr Val Asp Ile Arg Leu Ala Gln Leu Glu Asp Leu Ile Gly Arg Met
 35                  40                  45

Ala Thr Ala Leu Glu Arg Leu
 50                  55

<210> SEQ ID NO 78
<211> LENGTH: 18
<212> TYPE: PRT
<213> ORGANISM: Homo sapiens

<400> SEQUENCE: 78

Leu Lys Val Ile Leu Gly Ile Leu Leu Pro Pro Ser Ile Leu Ser Leu
  1               5                  10                  15

Glu Phe

<210> SEQ ID NO 79
<211> LENGTH: 18
<212> TYPE: PRT
<213> ORGANISM: Homo sapiens

<400> SEQUENCE: 79

Ile Val Lys Phe Trp Phe Tyr Thr Leu Ala Tyr Ile Gly Tyr Leu Met
  1               5                  10                  15
```

Leu Phe

<210> SEQ ID NO 80
<211> LENGTH: 14
<212> TYPE: PRT
<213> ORGANISM: Homo sapiens

<400> SEQUENCE: 80

Val Thr Asp Leu Ile Ala Ile Leu Leu Phe Ser Val Gly Met
1               5                   10

<210> SEQ ID NO 81
<211> LENGTH: 18
<212> TYPE: PRT
<213> ORGANISM: Homo sapiens

<400> SEQUENCE: 81

Arg Val Ile Tyr Cys Val Asn Ile Ile Tyr Trp Tyr Ile Arg Leu Leu
1               5                   10                  15

Asp Ile

<210> SEQ ID NO 82
<211> LENGTH: 18
<212> TYPE: PRT
<213> ORGANISM: Homo sapiens

<400> SEQUENCE: 82

Met Met Ile Asp Met Met Tyr Phe Val Ile Ile Met Leu Val Val Leu
1               5                   10                  15

Met Ser

<210> SEQ ID NO 83
<211> LENGTH: 21
<212> TYPE: PRT
<213> ORGANISM: Homo sapiens

<400> SEQUENCE: 83

Ala Ile Met Ala Cys Tyr Leu Leu Val Ala Asn Ile Leu Leu Val Asn
1               5                   10                  15

Leu Leu Ile Ala Val
20

<210> SEQ ID NO 84
<211> LENGTH: 79
<212> TYPE: PRT
<213> ORGANISM: Homo sapiens

<400> SEQUENCE: 84

Lys Asn Lys Asp Asp Met Pro Tyr Met Ser Gln Ala Gln Glu Ile His
1               5                   10                  15

Leu Gln Glu Lys Glu Ala Glu Glu Pro Glu Lys Pro Thr Lys Glu Lys
            20                  25                  30

Glu Glu Glu Asp Met Glu Leu Thr Ala Met Leu Gly Arg Asn Asn Gly
    35                  40                  45

Glu Ser Ser Arg Lys Lys Asp Glu Glu Val Gln Ser Lys His Arg
50                  55                  60

Leu Ile Pro Leu Gly Arg Lys Ile Tyr Glu Phe Tyr Asn Ala Pro
65                  70                  75

<210> SEQ ID NO 85

-continued

<211> LENGTH: 55
<212> TYPE: PRT
<213> ORGANISM: Homo sapiens

<400> SEQUENCE: 85

Asn Tyr Ile Val Leu Val Lys Met Glu Arg Trp Pro Ser Thr Gln Glu
1               5                   10                  15

Trp Ile Val Ile Ser Tyr Ile Phe Thr Leu Gly Ile Glu Lys Met Arg
            20                  25                  30

Glu Ile Leu Met Ser Glu Pro Gly Lys Leu Leu Gln Lys Val Lys Val
        35                  40                  45

Trp Leu Gln Glu Tyr Trp Asn
    50                  55

<210> SEQ ID NO 86
<211> LENGTH: 13
<212> TYPE: PRT
<213> ORGANISM: Homo sapiens

<400> SEQUENCE: 86

Ile Leu Arg Leu Gln Asp Gln Pro Phe Arg Ser Asp Gly
1               5                   10

<210> SEQ ID NO 87
<211> LENGTH: 16
<212> TYPE: PRT
<213> ORGANISM: Homo sapiens

<400> SEQUENCE: 87

Phe Gly Val Asn Lys Tyr Leu Gly Pro Tyr Val Met Met Ile Gly Lys
1               5                   10                  15

<210> SEQ ID NO 88
<211> LENGTH: 69
<212> TYPE: PRT
<213> ORGANISM: Homo sapiens

<400> SEQUENCE: 88

Phe Gly Val Ala Arg Gln Ala Ile Leu Phe Pro Asn Glu Glu Pro Ser
1               5                   10                  15

Trp Lys Leu Ala Lys Asn Ile Phe Tyr Met Pro Tyr Trp Met Ile Tyr
            20                  25                  30

Gly Glu Val Phe Ala Asp Gln Ile Asp Pro Pro Cys Gly Gln Asn Glu
        35                  40                  45

Thr Arg Glu Asp Gly Lys Ile Ile Gln Leu Pro Pro Cys Lys Thr Gly
    50                  55                  60

Ala Trp Ile Val Pro
65

<210> SEQ ID NO 89
<211> LENGTH: 6
<212> TYPE: PRT
<213> ORGANISM: Homo sapiens

<400> SEQUENCE: 89

Val Trp Lys Phe Gln Arg
1               5

<210> SEQ ID NO 90
<211> LENGTH: 212
<212> TYPE: PRT
<213> ORGANISM: Homo sapiens

```
<400> SEQUENCE: 90

Thr Gln Glu Trp Ile Val Ile Ser Tyr Ile Phe Thr Leu Gly Ile Glu
1               5                   10                  15

Lys Met Arg Glu Ile Leu Met Ser Glu Pro Gly Lys Leu Leu Gln Lys
            20                  25                  30

Val Lys Val Trp Leu Gln Glu Tyr Trp Asn Val Thr Asp Leu Ile Ala
        35                  40                  45

Ile Leu Leu Phe Ser Val Gly Met Ile Leu Arg Leu Gln Asp Gln Pro
50                  55                  60

Phe Arg Ser Asp Gly Arg Val Ile Tyr Cys Val Asn Ile Ile Tyr Trp
65                  70                  75                  80

Tyr Ile Arg Leu Leu Asp Ile Phe Gly Val Asn Lys Tyr Leu Gly Pro
            85                  90                  95

Tyr Val Met Met Ile Gly Lys Met Met Ile Asp Met Met Tyr Phe Val
        100                 105                 110

Ile Ile Met Leu Val Val Leu Met Ser Phe Gly Val Ala Arg Gln Ala
115                 120                 125

Ile Leu Phe Pro Asn Glu Glu Pro Ser Trp Lys Leu Ala Lys Asn Ile
130                 135                 140

Phe Tyr Met Pro Tyr Trp Met Ile Tyr Gly Glu Val Phe Ala Asp Gln
145                 150                 155                 160

Ile Asp Pro Pro Cys Gly Gln Asn Glu Thr Arg Glu Asp Gly Lys Ile
            165                 170                 175

Ile Gln Leu Pro Pro Cys Lys Thr Gly Ala Trp Ile Val Pro Ala Ile
        180                 185                 190

Met Ala Cys Tyr Leu Leu Val Ala Asn Ile Leu Leu Val Asn Leu Leu
195                 200                 205

Ile Ala Val Phe
210

<210> SEQ ID NO 91
<211> LENGTH: 55
<212> TYPE: PRT
<213> ORGANISM: Homo sapiens

<400> SEQUENCE: 91

Glu Arg Ile Arg Val Thr Ser Glu Arg Val Glu Asn Met Ser Met Arg
1               5                   10                  15

Leu Glu Glu Val Asn Glu Arg Glu His Ser Met Lys Ala Ser Leu Gln
            20                  25                  30

Thr Val Asp Ile Arg Leu Ala Gln Leu Glu Asp Leu Ile Gly Arg Met
        35                  40                  45

Ala Thr Ala Leu Glu Arg Leu
50                  55

<210> SEQ ID NO 92
<211> LENGTH: 18
<212> TYPE: PRT
<213> ORGANISM: Homo sapiens

<400> SEQUENCE: 92

Leu Lys Val Ile Leu Gly Ile Leu Leu Pro Pro Ser Ile Leu Ser Leu
1               5                   10                  15

Glu Phe
```

```
<210> SEQ ID NO 93
<211> LENGTH: 18
<212> TYPE: PRT
<213> ORGANISM: Homo sapiens

<400> SEQUENCE: 93

Ile Val Lys Phe Trp Phe Tyr Thr Leu Ala Tyr Ile Gly Tyr Leu Met
1               5                   10                  15
Leu Phe

<210> SEQ ID NO 94
<211> LENGTH: 14
<212> TYPE: PRT
<213> ORGANISM: Homo sapiens

<400> SEQUENCE: 94

Val Thr Asp Leu Ile Ala Ile Leu Leu Phe Ser Val Gly Met
1               5                   10

<210> SEQ ID NO 95
<211> LENGTH: 18
<212> TYPE: PRT
<213> ORGANISM: Homo sapiens

<400> SEQUENCE: 95

Arg Val Ile Tyr Cys Val Asn Ile Ile Tyr Trp Tyr Ile Arg Leu Leu
1               5                   10                  15
Asp Ile

<210> SEQ ID NO 96
<211> LENGTH: 18
<212> TYPE: PRT
<213> ORGANISM: Homo sapiens

<400> SEQUENCE: 96

Met Met Ile Asp Met Met Tyr Phe Val Ile Met Leu Val Val Leu
1               5                   10                  15
Met Ser

<210> SEQ ID NO 97
<211> LENGTH: 21
<212> TYPE: PRT
<213> ORGANISM: Homo sapiens

<400> SEQUENCE: 97

Ala Ile Met Ala Cys Tyr Leu Leu Val Ala Asn Ile Leu Leu Val Asn
1               5                   10                  15
Leu Leu Ile Ala Val
20

<210> SEQ ID NO 98
<211> LENGTH: 79
<212> TYPE: PRT
<213> ORGANISM: Homo sapiens

<400> SEQUENCE: 98

Lys Asn Lys Asp Asp Met Pro Tyr Met Ser Gln Ala Gln Glu Ile His
1               5                   10                  15
Leu Gln Glu Lys Glu Ala Glu Pro Glu Lys Pro Thr Lys Glu Lys
20                  25                  30
Glu Glu Glu Asp Met Glu Leu Thr Ala Met Leu Gly Arg Asn Asn Gly
35                  40                  45
```

-continued

```
Glu Ser Ser Arg Lys Lys Asp Glu Glu Val Gln Ser Lys His Arg
 50              55                  60

Leu Ile Pro Leu Gly Arg Lys Ile Tyr Glu Phe Tyr Asn Ala Pro
 65                  70                  75

<210> SEQ ID NO 99
<211> LENGTH: 55
<212> TYPE: PRT
<213> ORGANISM: Homo sapiens

<400> SEQUENCE: 99

Asn Tyr Ile Val Leu Val Lys Met Glu Arg Trp Pro Ser Thr Gln Glu
 1               5                  10                  15

Trp Ile Val Ile Ser Tyr Ile Phe Thr Leu Gly Ile Glu Lys Met Arg
             20                  25                  30

Glu Ile Leu Met Ser Glu Pro Gly Lys Leu Leu Gln Lys Val Lys Val
         35                  40                  45

Trp Leu Gln Glu Tyr Trp Asn
 50                  55

<210> SEQ ID NO 100
<211> LENGTH: 13
<212> TYPE: PRT
<213> ORGANISM: Homo sapiens

<400> SEQUENCE: 100

Ile Leu Arg Leu Gln Asp Gln Pro Phe Arg Ser Asp Gly
 1               5                  10

<210> SEQ ID NO 101
<211> LENGTH: 16
<212> TYPE: PRT
<213> ORGANISM: Homo sapiens

<400> SEQUENCE: 101

Phe Gly Val Asn Lys Tyr Leu Gly Pro Tyr Val Met Met Ile Gly Lys
 1               5                  10                  15

<210> SEQ ID NO 102
<211> LENGTH: 69
<212> TYPE: PRT
<213> ORGANISM: Homo sapiens

<400> SEQUENCE: 102

Phe Gly Val Ala Arg Gln Ala Ile Leu Phe Pro Asn Glu Glu Pro Ser
 1               5                  10                  15

Trp Lys Leu Ala Lys Asn Ile Phe Tyr Met Pro Tyr Trp Met Ile Tyr
             20                  25                  30

Gly Glu Val Phe Ala Asp Gln Ile Asp Pro Pro Cys Gly Gln Asn Glu
         35                  40                  45

Thr Arg Glu Asp Gly Lys Ile Ile Gln Leu Pro Pro Cys Lys Thr Gly
     50                  55                  60

Ala Trp Ile Val Pro
 65

<210> SEQ ID NO 103
<211> LENGTH: 6
<212> TYPE: PRT
<213> ORGANISM: Homo sapiens

<400> SEQUENCE: 103
```

```
Val Trp Lys Phe Gln Arg
1               5
```

<210> SEQ ID NO 104
<211> LENGTH: 212
<212> TYPE: PRT
<213> ORGANISM: Homo sapiens

<400> SEQUENCE: 104

```
Thr Gln Glu Trp Ile Val Ile Ser Tyr Ile Phe Thr Leu Gly Ile Glu
1               5                   10                  15

Lys Met Arg Glu Ile Leu Met Ser Glu Pro Gly Lys Leu Leu Gln Lys
            20                  25                  30

Val Lys Val Trp Leu Gln Glu Tyr Trp Asn Val Thr Asp Leu Ile Ala
        35                  40                  45

Ile Leu Leu Phe Ser Val Gly Met Ile Leu Arg Leu Gln Asp Gln Pro
    50                  55                  60

Phe Arg Ser Asp Gly Arg Val Ile Tyr Cys Val Asn Ile Ile Tyr Trp
65                  70                  75                  80

Tyr Ile Arg Leu Leu Asp Ile Phe Gly Val Asn Lys Tyr Leu Gly Pro
                85                  90                  95

Tyr Val Met Met Ile Gly Lys Met Met Ile Asp Met Met Tyr Phe Val
            100                 105                 110

Ile Ile Met Leu Val Val Leu Met Ser Phe Gly Val Ala Arg Gln Ala
        115                 120                 125

Ile Leu Phe Pro Asn Glu Glu Pro Ser Trp Lys Leu Ala Lys Asn Ile
    130                 135                 140

Phe Tyr Met Pro Tyr Trp Met Ile Tyr Gly Glu Val Phe Ala Asp Gln
145                 150                 155                 160

Ile Asp Pro Pro Cys Gly Gln Asn Glu Thr Arg Glu Asp Gly Lys Ile
                165                 170                 175

Ile Gln Leu Pro Pro Cys Lys Thr Gly Ala Trp Ile Val Pro Ala Ile
            180                 185                 190

Met Ala Cys Tyr Leu Leu Val Ala Asn Ile Leu Leu Val Asn Leu Leu
        195                 200                 205

Ile Ala Val Phe
210
```

<210> SEQ ID NO 105
<211> LENGTH: 55
<212> TYPE: PRT
<213> ORGANISM: Homo sapiens

<400> SEQUENCE: 105

```
Glu Arg Ile Arg Val Thr Ser Glu Arg Val Glu Asn Met Ser Met Arg
1               5                   10                  15

Leu Glu Glu Val Asn Glu Arg Glu His Ser Met Lys Ala Ser Leu Gln
            20                  25                  30

Thr Val Asp Ile Arg Leu Ala Gln Leu Glu Asp Leu Ile Gly Arg Met
        35                  40                  45

Ala Thr Ala Leu Glu Arg Leu
    50                  55
```

<210> SEQ ID NO 106
<211> LENGTH: 4470
<212> TYPE: DNA
<213> ORGANISM: Homo sapiens

<400> SEQUENCE: 106

```
cgcccgcggc gaggagccag cgagagcgct cggcgctggg ctgtttcccg gccgagggag      60
gcgaacttct catggggaag aagtggaggg atgcggcgga aatggagcgg ggctgctccg     120
accgcgagga caacgcggag agccgcagac gcagccggag cgccagccgg ggcaggtttg     180
ccgagtcgtg gaaaaggtta agttccaagc agggtccac caaacgctcg ggactcccgt      240
cgcagcagac gccggctcag aaatcctgga tagaaagagc attttataaa agagaatgtg     300
tccacatcat acccagcacc aaagaccccc ataggtgttg ctgtgggcgt ctgataggcc     360
agcatgttgg cctcaccccc agtatctccg tgcttcagaa tgagaaaaat gaaagtcgcc     420
tctcccgaaa tgcatccag tctgaaaagt ggtccatcag caaacacact caactcagcc      480
ctacggatgc ttttgggacc attgagttcc aaggaggtgg ccattccaac aaagccatgt     540
atgtgcgagt atcttttgat acaaaacctg atctcctctt acacctgatg accaaggaat     600
ggcagttgga gcttcccaag cttctcatct ctgtccatgg gggcctgcag aactttgaac     660
tccagccaaa actcaagcaa gtctttggga aagggctcat caaagcagca atgacaactg     720
gagcgtggat attcactgga ggggttaaca caggtgttat tcgtcatgtt ggcgatgcct     780
tgaaggatca tgcctctaag tctcgaggaa agatatgcac cataggtatt gcccctggg      840
gaattgtgga aaaccaggag gacctcattg aagagatgt tgtccggcca taccagacca      900
tgtccaatcc catgagcaag ctcactgttc tcaacagcat gcattccac ttcattctgg      960
ctgacaacgg gaccactgga aaatatggag cagaggtgaa acttcgaaga caactggaaa    1020
agcatatttc actccagaag ataaacacaa gtaagtagcg gttgttccca ctggcatggc    1080
tcgtaggagg tatgctgaaa gtgaataact ttaagtacac catgcagcaa tgtaataaaa    1140
acttgagcaa gttttaaaca tgaaccatta tttctaccgg gccagagctt agaatgagag    1200
gaagccatcc agaggagaac aattggaggc gtaagaagta attacacaat tagtgactcc    1260
agcttatgta tcatgtgtga aaaattcaac tccatctggg gtatgtgtat gcagataagc    1320
tttctcttca gacttttcct tcatcatctg catggtactc caaggagaaa agtttctatt    1380
tattaagctc ttttggtgg ctaaacagaa aagcaaaaga atcagatttt gatcttagca     1440
ccgatctggc tgtgcaaagg catttcaaag aaattgaaca ttcactctct aagctaaagc    1500
atcatgtgaa aatgtttcta tttattaagc tttttttggt ggctaaacag aaatgtttct    1560
atttattaag agacaatgtt tctatttatt aagcttttt tggtggctaa acagaaaagc     1620
aaaagaatca gattttgaac ttagcaacga tctagctgtg caaaggcatt tcaaagaaat    1680
tgaacattca ctctctaagc taaagcatca tgtgaaacta tcttcatgaa attttaattg    1740
tctgaatttt aagtatgtac tcattgtctc tagatacata tggatttaga tatagataga    1800
tgtatatgtg aaccacatag tacatagtta cgctaatatt atctcttaag cgcataggaa    1860
tctctatttg ctgtatttat tgtgtaaaca tttgttttaa ctgtgaaagg tagcatcatc    1920
aaaacagcaa tgctccccag atcactaagt ggcttgcatt taaatgcaat ttaggtatga    1980
aagcaatcta ccgtcccgcc tcacaaaata aaattctatt tgttttata aagtaacagg     2040
tgaggatgca tggcaagctc aaactttgtg gtaattagat gtcccatcag ggaaactttg    2100
atctaattga ttgaaattcc aaagtctaca gttccaaaga acaaaagatt cccttttggct   2160
agatgagttt tcagaggttc tatgtactgt gattcaactt ttccaaatga ctttccctt    2220
ctctagattt ttctctgcac ctgtcccaaa tgggtcttca ttgccatcgc caccttcctc    2280
```

-continued

```
caaaaacagg gatgttagat ttatcagacc acagcttctc cttcctacac tctcttttct      2340
ggtcccacct tttagggact gctactgttt aagtgtcatg tttcatggtt tcatattttt      2400
cacagtgaaa cctgaaataa taaattttgt cctaggtctg aaataaaaat tatattacga      2460
aatttccttc ccaaactgtc tttggaaaga agaaacacaa gtgttattat cccaaggtga      2520
acatcttctg gaaacaaaaa gagtagaaaa gactagaaaa tatacagaga ccagcagaga      2580
tcaaatgtaa caaagcactg tgatcaatgg gtggtaggtt ttactgtaaa tactaaaatt      2640
gagttccatt acagtacttg atagaatggg caaatgttat gtaatcagtg ttatctattt      2700
aggttttat aagctgcagc atgactttct gtacaccatc aagttaagaa cgagagctta      2760
aataggactg agctagaagc tgaagaggat aagagcaagg aaacaaggaa taaattcagg      2820
gtcaagttca gtacttggta ataagacaaa atcggtccag agaggcaaag catgtcattg      2880
tggcaggccc tggtggcagc tgggctggtt agccagtagt gtgggtagca ggcctaggga      2940
tgtgttcgtg taagttacac acccagcaaa ggggatggga gctggagtta aaaccccagc      3000
cagagcctag gttttagtca aactttggca ccttccagaa tgcctagagg aaggggggttc     3060
cttttcctaa ttgatcatcc cagagggagt acccttttgc aatgtacgtg cctgaagggg     3120
tgactttctt cagaaatggg agagctgctg catatatgga tggcactgca ggggaagtcc     3180
agggaggctc atggacagtg gcctggcctc cctgaggagc agaggccaac agcacgcagc     3240
tgaagagcag ggcacggtgg atggtcagca tgtcaggaat gctggaggag tcaccacccg     3300
atactagtcc ttgggtagat catcagggac acatcacatt ccatttatgg aaacaccaaa     3360
cctttgctag attatcaagg caggtagtgg cacatgggca cttgacaagc aggggcccgt     3420
caggagtcta gagtacaaag gagggagag gcacggatcc aggtaccacg ggacttactt      3480
ttgggactgt atttgtggct tcatagagac ccacaggctc ctcttccagt gaatatatta     3540
ataattaaat ggtaagagga gagttataaa agcccaagag aaattctgaa gtcacaggaa     3600
gtaaaaaggc ccaaggtaag gaatttgtgc atgagctgta gtgaatgtca agagttagct     3660
cctatagcag ttctaccct gaacttaata gtggtagggt gaccaacttg tctcagtttg      3720
cctgggactt tgttaggttt agccgtgaaa gtcccaaatc cctgggcccc ctcagtctgg     3780
gcaaactgag ataatgggtc gccctacaag agagtgactc ataagtcatt aggtcaactt     3840
ccctcattac tgtactcagc ccccaaagtc ggatggagca gcaagctcct tagagggtag     3900
ggagtgaccc aggctctttg aagtaggtaa agcaggacct ttgaggtctc cattcaatta     3960
acagcaaaaa atgctcactg agaacacaaa ggcctctaga acagcactga caaagacaca     4020
aagacaggca aaagcggac ctggtcttaa catgaaaaac ggcagaagaa tacaaacctt      4080
taatgcaatc ctcagtcagc aatttagaac agcaaatcta ctttctaaca tggacacttt     4140
gtggttcttc ctttaaaa taaaatttta tggccgggca cagtggctca cacctgtaat       4200
cccagcactt tgggaggccg aggcaggtgg atcacgatgt caggagttcg agaccagcct     4260
ggccaacatg gtgaaacccc gtctctacta aaaatacaaa aattagctgg gcatggtggc     4320
gggtgcctgt aatcccagct actcgggaga ctgaggcagg agaattgttt gaaccctgga     4380
ggcggaagtt gcagtgagcc gagaccatgc cattgcactc cagcctgggc gacagagcag     4440
gactccatct caaaaaaaaa aaaaaaaaa                                       4470
```

<210> SEQ ID NO 107
<211> LENGTH: 534
<212> TYPE: DNA
<213> ORGANISM: Homo sapiens

```
<400> SEQUENCE: 107
cccgcggcga ggagccagcg agagcgctcg gcgctgggct gtttcccggc cgagggaggc    60
gaacttctca tggggaagaa gtggagggat cggcgcgaaa tggagcgggg ctgctccgac   120
cgcgaggaca acgcggagag ccgcagacgc agccggagcg ccagccgggg caggtttgcc   180
gagtcgtgga aaaggttaag ttccaagcag gggtccacca aacgctcggg actcccgtcg   240
cagcagacgc cggctcagaa atcctggata gaaagagcat tttataaaag agaatgtgtc   300
cacatcatac ccagcaccaa agaccccat aggtgttgct gtgggcgtct gataggccag    360
catgttggcc tcaccccag tatctccgtg cttcagaatg agaaaatga agtcgcctc      420
tcccgaaatg acatccagtc tgaaaagtgg tccatcagca aacacactca actcagccct   480
acggatgctt ttgggaccat tgagttccaa ggaggtggcc attccaacaa agcc          534
```

<210> SEQ ID NO 108
<211> LENGTH: 733
<212> TYPE: DNA
<213> ORGANISM: homo sapiens

```
<400> SEQUENCE: 108
gggatccgga gcccaaatct tctgacaaaa ctcacacatg cccaccgtgc ccagcacctg    60
aattcgaggg tgcaccgtca gtcttcctct tccccccaaa acccaaggac accctcatga   120
tctcccggac tcctgaggtc acatgcgtgg tggtggacgt aagccacgaa gaccctgagg   180
tcaagttcaa ctggtacgtg gacggcgtgg aggtgcataa tgccaagaca aagccgcggg   240
aggagcagta caacagcacg taccgtgtgg tcagcgtcct caccgtcctg caccaggact   300
ggctgaatgg caaggagtac aagtgcaagg tctccaacaa agcctccca accccccatcg   360
agaaaaccat ctccaaagcc aaagggcagc ccgagaacc acaggtgtac accctgcccc    420
catcccggga tgagctgacc aagaaccagg tcagcctgac ctgcctggtc aaaggcttct   480
atccaagcga catcgccgtg gagtgggaga gcaatgggca gccggagaac aactacaaga   540
ccacgcctcc cgtgctggac tccgacggct ccttcttcct ctacagcaag ctcaccgtgg   600
acaagagcag gtggcagcag gggaacgtct tctcatgctc cgtgatgcat gaggctctgc   660
acaaccacta cacgcagaag agcctctccc tgtctccggg taaatgagtg cgacggccgc   720
gactctagag gat                                                      733
```

<210> SEQ ID NO 109
<211> LENGTH: 20
<212> TYPE: DNA
<213> ORGANISM: Homo sapiens

```
<400> SEQUENCE: 109
cgcagctgga agaccttatc                                                20
```

<210> SEQ ID NO 110
<211> LENGTH: 20
<212> TYPE: DNA
<213> ORGANISM: Homo sapiens

```
<400> SEQUENCE: 110
aagctgctct gacggacaat                                                20
```

<210> SEQ ID NO 111
<211> LENGTH: 24
<212> TYPE: DNA

<210> SEQ ID NO 111
<211> LENGTH: 24
<212> TYPE: DNA
<213> ORGANISM: Homo sapiens

<400> SEQUENCE: 111
gaaggacacc aggacattga tttg                                           24

<210> SEQ ID NO 112
<211> LENGTH: 24
<212> TYPE: DNA
<213> ORGANISM: Homo sapiens

<400> SEQUENCE: 112
agggaagggg aagtggttga tctc                                           24

<210> SEQ ID NO 113
<211> LENGTH: 23
<212> TYPE: DNA
<213> ORGANISM: Homo sapiens

<400> SEQUENCE: 113
gcttagcttt agcctggaac aga                                            23

<210> SEQ ID NO 114
<211> LENGTH: 21
<212> TYPE: DNA
<213> ORGANISM: Homo sapiens

<400> SEQUENCE: 114
gccactgttg cccgtaaata a                                              21

<210> SEQ ID NO 115
<211> LENGTH: 21
<212> TYPE: DNA
<213> ORGANISM: Homo sapiens

<400> SEQUENCE: 115
tcgacatcgc tcgcagccag a                                              21

<210> SEQ ID NO 116
<211> LENGTH: 20
<212> TYPE: DNA
<213> ORGANISM: Homo sapiens

<400> SEQUENCE: 116
ccacctgatg ggcatgttct                                                20

<210> SEQ ID NO 117
<211> LENGTH: 21
<212> TYPE: DNA
<213> ORGANISM: Homo sapiens

<400> SEQUENCE: 117
cggcttgcca tcaaagacat a                                              21

<210> SEQ ID NO 118
<211> LENGTH: 22
<212> TYPE: DNA
<213> ORGANISM: Homo sapiens

<400> SEQUENCE: 118
ccgcaccatt cgcatgatgg ag                                             22

<210> SEQ ID NO 119
<211> LENGTH: 26

```
<212> TYPE: DNA
<213> ORGANISM: Artificial Sequence
<220> FEATURE:
<223> OTHER INFORMATION: Synthesized Oligonucleotide.

<400> SEQUENCE: 119
ccauggacag agaugagaag cuuggu                                              26

<210> SEQ ID NO 120
<211> LENGTH: 26
<212> TYPE: DNA
<213> ORGANISM: Artificial Sequence
<220> FEATURE:
<223> OTHER INFORMATION: Synthesized Oligonucleotide.

<400> SEQUENCE: 120 agugucccg uugucagcca gaaugu                                               26

<210> SEQ ID NO 121
<211> LENGTH: 26
<212> TYPE: DNA
<213> ORGANISM: Artificial Sequence
<220> FEATURE:
<223> OTHER INFORMATION: Synthesized Oligonucleotide.

<400> SEQUENCE: 121
ccuuccacua ugagugccac cacagu                                              26

<210> SEQ ID NO 122
<211> LENGTH: 26
<212> TYPE: DNA
<213> ORGANISM: Artificial Sequence
<220> FEATURE:
<223> OTHER INFORMATION: Synthesized Oligonucleotide.

<400> SEQUENCE: 122
guguccuucu gaucccaucc gaaauu                                              26

<210> SEQ ID NO 123
<211> LENGTH: 26
<212> TYPE: DNA
<213> ORGANISM: Artificial Sequence
<220> FEATURE:
<223> OTHER INFORMATION: Synthesized Oligonucleotide.

<400> SEQUENCE: 123
ugguauggcc ggacaacauc ucuucu                                              26

<210> SEQ ID NO 124
<211> LENGTH: 21
<212> TYPE: DNA
<213> ORGANISM: Homo sapiens

<400> SEQUENCE: 124
cagctggaag accttatcgg g                                                   21

<210> SEQ ID NO 125
<211> LENGTH: 24
<212> TYPE: DNA
<213> ORGANISM: Homo sapiens

<400> SEQUENCE: 125
tgggaggtgg gtgtagtctg aaga                                                24

<210> SEQ ID NO 126
```

```
<211> LENGTH: 39
<212> TYPE: DNA
<213> ORGANISM: Homo sapiens

<400> SEQUENCE: 126
gcagcagcgg ccgcctcaag gtaattctgg gaattctac                    39

<210> SEQ ID NO 127
<211> LENGTH: 37
<212> TYPE: DNA
<213> ORGANISM: Homo sapiens

<400> SEQUENCE: 127
gcagcagtcg acggtgtgct tgctttcaaa gctttgg                      37

<210> SEQ ID NO 128
<211> LENGTH: 36
<212> TYPE: DNA
<213> ORGANISM: Homo sapiens

<400> SEQUENCE: 128
gcagcagcgg ccgcatgtat gtgcgagtat cttttg                       36

<210> SEQ ID NO 129
<211> LENGTH: 37
<212> TYPE: DNA
<213> ORGANISM: Homo sapiens

<400> SEQUENCE: 129
gcagcagtcg acgttaaaga cagcaatgag gaggttg                      37

<210> SEQ ID NO 130
<211> LENGTH: 36
<212> TYPE: DNA
<213> ORGANISM: Homo sapiens

<400> SEQUENCE: 130
gcagcagcgg ccgcatgtat gtgcgagtat cttttg                       36

<210> SEQ ID NO 131
<211> LENGTH: 37
<212> TYPE: DNA
<213> ORGANISM: Homo sapiens

<400> SEQUENCE: 131
gcagcagtcg acattagatg agttgaaccg atcatcc                      37

<210> SEQ ID NO 132
<211> LENGTH: 23
<212> TYPE: DNA
<213> ORGANISM: Homo sapiens

<400> SEQUENCE: 132
caggtgcagc tggtgcagtc tgg                                     23

<210> SEQ ID NO 133
<211> LENGTH: 23
<212> TYPE: DNA
<213> ORGANISM: Homo sapiens

<400> SEQUENCE: 133
caggtcaact taagggagtc tgg                                     23
```

<210> SEQ ID NO 134
<211> LENGTH: 23
<212> TYPE: DNA
<213> ORGANISM: Homo sapiens

<400> SEQUENCE: 134
gaggtgcagc tggtggagtc tgg					23

<210> SEQ ID NO 135
<211> LENGTH: 23
<212> TYPE: DNA
<213> ORGANISM: Homo sapiens

<400> SEQUENCE: 135
caggtgcagc tgcaggagtc ggg					23

<210> SEQ ID NO 136
<211> LENGTH: 23
<212> TYPE: DNA
<213> ORGANISM: Homo sapiens

<400> SEQUENCE: 136
gaggtgcagc tgttgcagtc tgc					23

<210> SEQ ID NO 137
<211> LENGTH: 23
<212> TYPE: DNA
<213> ORGANISM: Homo sapiens

<400> SEQUENCE: 137
caggtacagc tgcagcagtc agg					23

<210> SEQ ID NO 138
<211> LENGTH: 24
<212> TYPE: DNA
<213> ORGANISM: Homo sapiens

<400> SEQUENCE: 138
tgaggagacg gtgaccaggg tgcc					24

<210> SEQ ID NO 139
<211> LENGTH: 24
<212> TYPE: DNA
<213> ORGANISM: Homo sapiens

<400> SEQUENCE: 139
tgaagagacg gtgaccattg tccc					24

<210> SEQ ID NO 140
<211> LENGTH: 24
<212> TYPE: DNA
<213> ORGANISM: Homo sapiens

<400> SEQUENCE: 140
tgaggagacg gtgaccaggg ttcc					24

<210> SEQ ID NO 141
<211> LENGTH: 24
<212> TYPE: DNA
<213> ORGANISM: Homo sapiens

<400> SEQUENCE: 141
tgaggagacg gtgaccgtgg tccc					24

```
<210> SEQ ID NO 142
<211> LENGTH: 23
<212> TYPE: DNA
<213> ORGANISM: Homo sapiens

<400> SEQUENCE: 142
gacatccaga tgacccagtc tcc                                              23

<210> SEQ ID NO 143
<211> LENGTH: 23
<212> TYPE: DNA
<213> ORGANISM: Homo sapiens

<400> SEQUENCE: 143
gatgttgtga tgactcagtc tcc                                              23

<210> SEQ ID NO 144
<211> LENGTH: 23
<212> TYPE: DNA
<213> ORGANISM: Homo sapiens

<400> SEQUENCE: 144
gatattgtga tgactcagtc tcc                                              23

<210> SEQ ID NO 145
<211> LENGTH: 23
<212> TYPE: DNA
<213> ORGANISM: Homo sapiens

<400> SEQUENCE: 145
gaaattgtgt tgacgcagtc tcc                                              23

<210> SEQ ID NO 146
<211> LENGTH: 23
<212> TYPE: DNA
<213> ORGANISM: Homo sapiens

<400> SEQUENCE: 146
gacatcgtga tgacccagtc tcc                                              23

<210> SEQ ID NO 147
<211> LENGTH: 23
<212> TYPE: DNA
<213> ORGANISM: Homo sapiens

<400> SEQUENCE: 147
gaaacgacac tcacgcagtc tcc                                              23

<210> SEQ ID NO 148
<211> LENGTH: 23
<212> TYPE: DNA
<213> ORGANISM: Homo sapiens

<400> SEQUENCE: 148
gaaattgtgc tgactcagtc tcc                                              23

<210> SEQ ID NO 149
<211> LENGTH: 23
<212> TYPE: DNA
<213> ORGANISM: Homo sapiens

<400> SEQUENCE: 149
cagtctgtgt tgacgcagcc gcc                                              23
```

```
<210> SEQ ID NO 150
<211> LENGTH: 23
<212> TYPE: DNA
<213> ORGANISM: Homo sapiens

<400> SEQUENCE: 150
cagtctgccc tgactcagcc tgc                                           23

<210> SEQ ID NO 151
<211> LENGTH: 23
<212> TYPE: DNA
<213> ORGANISM: Homo sapiens

<400> SEQUENCE: 151
tcctatgtgc tgactcagcc acc                                           23

<210> SEQ ID NO 152
<211> LENGTH: 23
<212> TYPE: DNA
<213> ORGANISM: Homo sapiens

<400> SEQUENCE: 152
tcttctgagc tgactcagga ccc                                           23

<210> SEQ ID NO 153
<211> LENGTH: 23
<212> TYPE: DNA
<213> ORGANISM: Homo sapiens

<400> SEQUENCE: 153
cacgttatac tgactcaacc gcc                                           23

<210> SEQ ID NO 154
<211> LENGTH: 23
<212> TYPE: DNA
<213> ORGANISM: Homo sapiens

<400> SEQUENCE: 154
caggctgtgc tcactcagcc gtc                                           23

<210> SEQ ID NO 155
<211> LENGTH: 23
<212> TYPE: DNA
<213> ORGANISM: Homo sapiens

<400> SEQUENCE: 155
aattttatgc tgactcagcc cca                                           23

<210> SEQ ID NO 156
<211> LENGTH: 24
<212> TYPE: DNA
<213> ORGANISM: Homo sapiens

<400> SEQUENCE: 156
acgtttgatt tccaccttgg tccc                                          24

<210> SEQ ID NO 157
<211> LENGTH: 24
<212> TYPE: DNA
<213> ORGANISM: Homo sapiens

<400> SEQUENCE: 157
```

-continued acgtttgatc tccagcttgg tccc                                                24

<210> SEQ ID NO 158
<211> LENGTH: 24
<212> TYPE: DNA
<213> ORGANISM: Homo sapiens

<400> SEQUENCE: 158
acgtttgata tccactttgg tccc                                                24

<210> SEQ ID NO 159
<211> LENGTH: 24
<212> TYPE: DNA
<213> ORGANISM: Homo sapiens

<400> SEQUENCE: 159
acgtttgatc tccaccttgg tccc                                                24

<210> SEQ ID NO 160
<211> LENGTH: 24
<212> TYPE: DNA
<213> ORGANISM: Homo sapiens

<400> SEQUENCE: 160
acgtttaatc tccagtcgtg tccc                                                24

<210> SEQ ID NO 161
<211> LENGTH: 23
<212> TYPE: DNA
<213> ORGANISM: Homo sapiens

<400> SEQUENCE: 161
cagtctgtgt tgacgcagcc gcc                                                 23

<210> SEQ ID NO 162
<211> LENGTH: 23
<212> TYPE: DNA
<213> ORGANISM: Homo sapiens

<400> SEQUENCE: 162
cagtctgccc tgactcagcc tgc                                                 23

<210> SEQ ID NO 163
<211> LENGTH: 23
<212> TYPE: DNA
<213> ORGANISM: Homo sapiens

<400> SEQUENCE: 163
tcctatgtgc tgactcagcc acc                                                 23

<210> SEQ ID NO 164
<211> LENGTH: 23
<212> TYPE: DNA
<213> ORGANISM: Homo sapiens

<400> SEQUENCE: 164
tcttctgagc tgactcagga ccc                                                 23

<210> SEQ ID NO 165
<211> LENGTH: 23
<212> TYPE: DNA
<213> ORGANISM: Homo sapiens

<400> SEQUENCE: 165

```
cacgttatac tgactcaacc gcc                                          23

<210> SEQ ID NO 166
<211> LENGTH: 23
<212> TYPE: DNA
<213> ORGANISM: Homo sapiens

<400> SEQUENCE: 166
caggctgtgc tcactcagcc gtc                                          23

<210> SEQ ID NO 167
<211> LENGTH: 23
<212> TYPE: DNA
<213> ORGANISM: Homo sapiens

<400> SEQUENCE: 167
aattttatgc tgactcagcc cca                                          23

<210> SEQ ID NO 168
<211> LENGTH: 6
<212> TYPE: PRT
<213> ORGANISM: Artificial Sequence
<220> FEATURE:
<223> OTHER INFORMATION: Consensus TRP Sequence.
<220> FEATURE:
<221> NAME/KEY: MISC_FEATURE
<222> LOCATION: (1)..(1)
<223> OTHER INFORMATION: wherein "X" equals any naturally occuring amino
      acid.
<220> FEATURE:
<221> NAME/KEY: MISC_FEATURE
<222> LOCATION: (5)..(5)
<223> OTHER INFORMATION: wherein "X" equals any naturally occuring amino
      acid.

<400> SEQUENCE: 168

Xaa Trp Lys Phe Xaa Arg
1               5

<210> SEQ ID NO 169
<211> LENGTH: 25
<212> TYPE: DNA
<213> ORGANISM: Homo sapiens

<400> SEQUENCE: 169
atggggaaga agtggaggga tgcgg                                        25

<210> SEQ ID NO 170
<211> LENGTH: 25
<212> TYPE: DNA
<213> ORGANISM: Homo sapiens

<400> SEQUENCE: 170
gctcagaaat cctggataga aagag                                        25

<210> SEQ ID NO 171
<211> LENGTH: 27
<212> TYPE: DNA
<213> ORGANISM: Homo sapiens

<400> SEQUENCE: 171
tgtatcaaaa gatactcgca catacat                                      27
```